US008048878B2

(12) United States Patent
Kimura et al.

(10) Patent No.: US 8,048,878 B2
(45) Date of Patent: Nov. 1, 2011

(54) TWO CYCLIC CINNAMIDE COMPOUND

(75) Inventors: Teiji Kimura, Tsukuba (JP); Koki Kawano, Tsukuba (JP); Eriko Doi, Tsukuba (JP); Noritaka Kitazawa, Tsukuba (JP); Mamoru Takaishi, Tsukuba (JP); Koichi Ito, Tsukuba (JP); Toshihiko Kaneko, Tsukuba (JP); Takeo Sasaki, Tsukuba (JP); Takehiko Miyagawa, Tsukuba (JP); Hiroaki Hagiwara, Tsukuba (JP); Yu Yoshida, Tsukuba (JP)

(73) Assignee: Eisai R&D Management Co., Ltd., Tokyo (JP)

( * ) Notice: Subject to any disclaimer, the term of this patent is extended or adjusted under 35 U.S.C. 154(b) by 200 days.

(21) Appl. No.: 12/403,565

(22) Filed: Mar. 13, 2009

(65) Prior Publication Data
US 2009/0181945 A1 Jul. 16, 2009

(30) Foreign Application Priority Data

Nov. 24, 2005 (JP) ................................. 2005-337963
Jul. 28, 2006 (JP) ................................. 2006-205538

(51) Int. Cl.
C07D 491/02 (2006.01)
C07D 265/36 (2006.01)
C07D 498/02 (2006.01)
C07D 295/00 (2006.01)
A61K 31/535 (2006.01)
A61K 31/50 (2006.01)
A61K 31/44 (2006.01)
A01N 43/60 (2006.01)

(52) U.S. Cl. ...................... 514/230.5; 514/249; 514/299; 546/121; 544/105; 544/349

(58) Field of Classification Search .................. 514/249, 514/230.5, 299; 546/121; 544/105, 349
See application file for complete search history.

(56) References Cited

U.S. PATENT DOCUMENTS

| 4,910,200 | A | 3/1990 | Curtze et al. |
| 5,281,626 | A | 1/1994 | Oinuma et al. |
| 5,563,162 | A | 10/1996 | Oku et al. |
| 5,985,856 | A | 11/1999 | Stella et al. |
| 6,235,728 | B1 | 5/2001 | Golik et al. |
| 6,306,870 | B1 | 10/2001 | Bombrun |
| 7,053,087 | B1 | 5/2006 | Beatch et al. |
| 7,138,414 | B2 | 11/2006 | Schoenafinger et al. |
| 7,300,936 | B2 | 11/2007 | Parker et al. |
| 7,314,940 | B2 | 1/2008 | Graczyk et al. |
| 7,618,960 | B2 | 11/2009 | Kimura et al. |
| 7,667,041 | B2 | 2/2010 | Kimura et al. |
| 7,687,640 | B2 | 3/2010 | Kimura et al. |
| 7,737,141 | B2 * | 6/2010 | Kimura et al. ............. 514/232.2 |
| 7,880,009 | B2 | 2/2011 | Kimura et al. |
| 7,923,563 | B2 | 4/2011 | Kushida et al. |

| 2001/0051642 | A1 | 12/2001 | Ahn et al. |
| 2002/0128263 | A1 | 9/2002 | Mutel et al. |
| 2003/0195201 | A1 | 10/2003 | Bo et al. |
| 2003/0208082 | A1 | 11/2003 | Mutel et al. |
| 2003/0225070 | A1 | 12/2003 | Mutel et al. |
| 2004/0034096 | A1 | 2/2004 | Jolidon et al. |
| 2004/0038969 | A1 | 2/2004 | Doherty et al. |
| 2004/0063770 | A1 | 4/2004 | Ahn et al. |
| 2004/0087798 | A1 | 5/2004 | Yamada |
| 2004/0127494 | A1 | 7/2004 | Parker et al. |
| 2004/0127555 | A1 | 7/2004 | Snow et al. |
| 2004/0152743 | A1 | 8/2004 | Schoenafinger et al. |
| 2004/0192743 | A1 | 9/2004 | Mjalli et al. |

(Continued)

FOREIGN PATENT DOCUMENTS

CN 1668593 A 9/2005

(Continued)

OTHER PUBLICATIONS

Rafii et al., BioMed Center, 7:7, (2009), pp. 1-4.*
Hardy et al., Science, vol. 297, (2002), pp. 353-356.*
http://downsyndrome.about.com/od/medicalissuesinds/a/DSAlzheimers_ro.htm.*
http://www.sciencedaily.com/releases/2010/01/100115182639.htm.*

(Continued)

Primary Examiner — D M Seaman
Assistant Examiner — Niloofar Rahmani
(74) Attorney, Agent, or Firm — Birch, Stewart, Kolasch & Birch, LLP

(57) ABSTRACT

The present invention relates to a novel two cyclic cinnamide compound and a pharmaceutical agent comprising the compound as an active ingredient. The two cyclic cinnamide compound represented by the general formula (I):

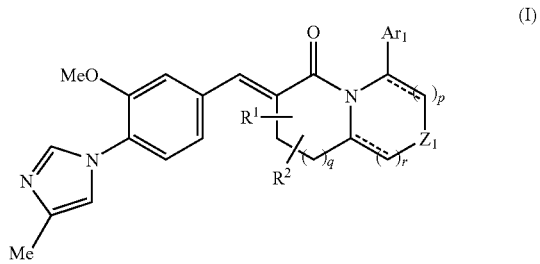

wherein ---- represents a single bond or a double bond; $Ar_1$ represents a phenyl group or pyridinyl group that may be substituted with 1 to 3 substituents; $R^1$ and $R^2$ each represent a C1-6 alkyl group, a hydroxyl group, or the like; $Z_1$ represents a methylene group or vinylene group, which may be substituted with 1 or 2 substituents selected from Substituent Group A1, an oxygen atom, or an imino group that may be substituted with a substituent selected from Substituent Group A1; and p, q, and r each represent an integer of 0 to 2, which has an effect of reducing Aβ40 and Aβ42 production, and thus is particularly useful as a prophylactic or therapeutic agent for a neurodegenerative disease caused by Aβ such as Alzheimer's disease or Down's syndrome.

14 Claims, No Drawings

U.S. PATENT DOCUMENTS

| | | |
|---|---|---|
| 2004/0235864 A1 | 11/2004 | Graczyk et al. |
| 2005/0070538 A1 | 3/2005 | Cheng et al. |
| 2005/0131043 A1 | 6/2005 | Mutel et al. |
| 2005/0187277 A1 | 8/2005 | Mjalli et al. |
| 2006/0004013 A1 | 1/2006 | Kimura et al. |
| 2007/0117798 A1 | 5/2007 | Kimura et al. |
| 2007/0117839 A1 | 5/2007 | Kimura et al. |
| 2007/0219181 A1 | 9/2007 | Kimura et al. |
| 2007/0249833 A1 | 10/2007 | Cheng et al. |
| 2008/0070902 A1 | 3/2008 | Kimura et al. |
| 2008/0085894 A1 | 4/2008 | Parker et al. |
| 2008/0096892 A1 | 4/2008 | Cheng et al. |
| 2008/0280948 A1 | 11/2008 | Baumann et al. |
| 2009/0048213 A1 | 2/2009 | Kimura et al. |
| 2009/0048448 A1 | 2/2009 | Kushida et al. |
| 2009/0203916 A1 | 8/2009 | Kushida et al. |
| 2009/0270623 A1 | 10/2009 | Shimomura et al. |

FOREIGN PATENT DOCUMENTS

| | | |
|---|---|---|
| DE | 3541716 A1 | 5/1987 |
| EP | 0219756 | 4/1987 |
| EP | 0 270 091 A1 | 6/1988 |
| EP | 0 589 491 A1 | 3/1994 |
| EP | 1 264 820 | 12/2002 |
| EP | 0 973 768 B1 | 7/2003 |
| EP | 1 757 591 A1 | 2/2007 |
| EP | 1 808-432 A1 | 7/2007 |
| EP | 1 953 151 A1 | 8/2008 |
| EP | 1 953 158 A1 | 8/2008 |
| EP | 1 992 618 A1 | 11/2008 |
| GE | P 2006 3920 B | 5/2006 |
| JP | 60-174781 A | 9/1985 |
| JP | 3-206042 A | 9/1991 |
| JP | 7-2780 A | 1/1995 |
| JP | 8283219 | 10/1996 |
| JP | 10-510512 A | 10/1998 |
| JP | 11-228548 A | 8/1999 |
| JP | 3176365 B2 | 4/2001 |
| JP | 2001-508767 A | 7/2001 |
| JP | 2001-527083 A | 12/2001 |
| JP | 2003-206280 A | 7/2003 |
| JP | 2004-520292 A | 7/2004 |
| JP | 2004-531519 A | 10/2004 |
| JP | 2005-518371 A | 6/2005 |
| JP | 2005-526807 A | 9/2005 |
| JP | 2005-531596 A | 10/2005 |
| JP | 2005-533092 A | 11/2005 |
| JP | 2006-502247 A | 1/2006 |
| JP | 2006-518738 A | 8/2006 |
| JP | 2007-504282 T | 3/2007 |
| JP | 2007-523903 A | 8/2007 |
| RU | 2001126135 A | 7/2003 |
| SG | 145500 | 9/2007 |
| TW | 379224 B | 1/2000 |
| TW | 200400824 | 1/2004 |
| WO | WO 87/02587 A1 | 5/1987 |
| WO | WO-91/12237 A1 | 8/1991 |
| WO | WO 95/21832 A1 | 8/1995 |
| WO | WO-96/10559 A1 | 4/1996 |
| WO | WO-97/43287 | 11/1997 |
| WO | WO-98/03166 A1 | 1/1998 |
| WO | WO-98/24785 A1 | 6/1998 |
| WO | WO-00/07993 A1 | 2/2000 |
| WO | WO-00/50391 A1 | 8/2000 |
| WO | WO-00/51981 A1 | 9/2000 |
| WO | WO-01/68585 A1 | 9/2001 |
| WO | WO-01/81312 A2 | 11/2001 |
| WO | WO 03/022273 A1 | 3/2003 |
| WO | WO 03/027081 A2 | 4/2003 |
| WO | WO-03/053912 A1 | 7/2003 |
| WO | WO 03/062206 A2 | 7/2003 |
| WO | WO-03/082292 A1 | 10/2003 |
| WO | WO-03/101927 A1 | 12/2003 |
| WO | WO 2004/002478 A1 | 1/2004 |
| WO | WO-2004/007429 | 1/2004 |
| WO | WO-2004/007455 A1 | 1/2004 |
| WO | WO-2005/020921 A2 | 3/2005 |
| WO | WO-2005/063754 A1 | 7/2005 |
| WO | WO 2005/072731 A1 | 8/2005 |
| WO | WO-2005/115990 A1 | 12/2005 |
| WO | WO 2006/018662 A2 | 2/2006 |
| WO | WO-2006/046575 A1 | 5/2006 |
| WO | WO-2006/112550 A2 | 10/2006 |
| WO | WO-2007/034282 A2 | 3/2007 |
| WO | WO-2007/060810 A1 | 5/2007 |
| WO | WO-2007/102580 A1 | 9/2007 |
| WO | WO-2008/013213 A1 | 1/2008 |
| WO | WO-2008/097538 A1 | 8/2008 |
| WO | WO 2008/137102 A2 | 11/2008 |
| WO | WO-2008/137139 A1 | 11/2008 |
| WO | WO-2008/156580 A1 | 12/2008 |
| WO | WO-2009/020580 A1 | 2/2009 |

OTHER PUBLICATIONS

Yuesong Gong et al.; Proceeding National Academy of Science, vol. 100, No. 18, pp. 10417-10422, Sep. 2, 2003.
Christoph Hock et al.; Neuron, vol. 38, No. 4, pp. 547-554, May 22, 2003.
Joseph T. Jarrett et al.; Biochemistry; vol. 32, No. 18, pp. 4693-4697, May 11, 1993.
George G. Glenner et al.; Biochemical and Biophysical Research Communications; vol. 120, No. 3, pp. 885-890, May 16, 1984.
Colin L. Masters et al.; Proceeding National Academy of Science; vol. 82, No. 12, pp. 4245-4249, Jun. 1985.
Gunnar K. Gouras et al.; American Journal of Pathology, vol. 156, No. 1, pp. 15-20, Jan. 2000.
D. Scheuner et al.; Nature Medicine, vol. 2, No. 8, pp. 864-870, Aug. 1996.
Mark S. Forman et al.; The Journal of Biological Chemistry; vol. 272, No. 51, pp. 32247-32253, Dec. 19, 1997.
Mark S. Shearman et al.; Biochemistry; vol. 39, No. 30, pp. 8698-8704, 2000.
Huw D. Lewis et al.; Biochemistry, vol. 42, No. 24, pp. 7580-7586, 2003.
Thomas A. Lanz et al., The Journal of Pharmacology and Experimental Therapeutics; vol. 39, No. 1, pp. 49-55, 2004.
Gwendolyn T. Wong et al.; The Journal of Biological Chemistry, vol. 279, No. 13, pp. 12876-12882, Mar. 26, 2004.
John P. Blass; Journal of Neuroscience Research, vol. 66, No. 1, pp. 851-856, 2001.
Genevieve Evin et al.; NeuroReport; vol. 13, No. 5, pp. 719-723, Apr. 16, 2002.
Osamu Yasuhara et al.; Neuroscience Letters, vol. 171, Nos. 1 and 2, pp. 63-66, 1994.
Jan T. Teller et al.; Nature Medicine, vol. 2, No. 1, pp. 93-95, Jan. 1996.
Takahiko Tokuda et al.; Annals Neurology, vol. 41, No. 2, pp. 271-273, Feb. 1997.
Yorihide Hayashi et al.; Brain Research; vol. 789, No. 2, pp. 307-314, 1998.
Helene Barelli et al.; Molecular Medicine, vol. 3, No. 10, pp. 695-707, Oct. 1997.
Michael E. Calhoun et al.; Proceeding National Academy of Science, vol. 96, No. 24, pp. 14088-14093, Nov. 23, 1999.
B. Dermaut et al.; Brain, vol. 124, No. 12, pp. 2383-2392, 2001.
P. Cras et al.; Acta Neuropathol, vol. 96, No. 3, pp. 253-260, 1998.
Martin C. Herzig et al.; Nature Neuroscience, vol. 7, No. 9, pp. 954-960, Sep. 2004.
Sjoerd G. Van Duinen at al.; Proceeding National Academy of Science, vol. 84, No. 16, pp. 5991-5994, Aug. 1987.
Efrat Levy et al.; Science, vol. 248, No. 4959, pp. 1124-1126, 1990.
Simon M. Laws et al.; Neurobiology of Aging, vol. 23, No. 1, pp. 55-58, 2002.
E. Vaucher et al.; Experimental Neurology, vol. 175, No. 2, pp. 398-406, 2002.
Dave Morgan et al.; Nature, vol. 408, No. 6815, pp. 982-985, Dec. 2000.
Paula M. Moran et al.; Proceeding National Academy of Science, vol. 92, No. 12, pp. 5341-5345, 2002.
Milla Koistinaho et al.; Proceeding National Academy of Science, vol. 99, No. 3, pp. 1610-1615, Feb. 5, 2002.

Fangyi Zhang et al.; The Journal of Neuroscience, vol. 17, No. 20, pp. 7655-7661, Oct. 15, 2997.
Marcin Sadowski et al.; Neurochemical Research, vol. 29, No. 6, pp. 1257-1266, Jun. 2004.
S. O'Riordan et al.; Neurology, vol. 59, No. 7, pp. 1108-1110, Oct. 2002.
Jochen Gehrmann et al.; Glia; vol. 15, No. 2, pp. 141-151, 1995.
Wanda F. Reynolds et al.; Experimental Neurology, vol. 155, No. 1, pp. 31-41, 1999.
Douglas H. Smith et al.; NeuroMolecular Medicine, vol. 4, No. 1 and 2, pp. 59-72, 2003.
Miho Matsubara-Tsutsui et al.; American Journal of Medical Genetics, vol. 114, No. 3, pp. 292-298, 2002.
Marina D. Kirkitadze et al.; Journal of Neuroscience Research, vol. 69, No. 5, pp. 567-577, 2002.
Bernd O. Evert et al.; The Journal of Neuroscience, vol. 21, No. 15, pp. 5389-5396, Aug. 1, 2001.
D.M.A. Mann et al.; Neuroscience Letters, vol. 109, No. 1 and 2, pp. 68-75, 1990.
James Primavera et al.; Journal of Alzheimer's Disease, vol. 1, No. 3, pp. 183-193, 1999.
Benoit I. Giasson et al.; NeuroMolecular Medicine, vol. 4, No. 1 and 2, pp. 49-58, 2003.
Eliezer Masliah et al.; Proceeding National Academy of Science; vol. 98, No. 21, pp. 12245-12250, Oct. 9, 2001.
Marta Barrachina et al.; Neurochemistry International; vol. 46, No. 3, pp. 253-260, 2005.
M.L. Schmidt et al.; Acta Neuropathol, vol. 95, No. 2, pp. 117-122, 1998.
H. Ito et al.; Neuropathology and Applied Neurobiology, vol. 17, No. 5, pp. 365-373, 1991.
S.M. Rosso et al.; Annals of the New York Academy of Science, vol. 920, pp. 115-119, 2000.
M. Tolnay et al.; Neuropathology and Applied Neurobiology, vol. 25, No. 4, pp. 295-305, 1999.
Lee-Way Jin et al.; American Journal of Pathology, vol. 164, No. 3, pp. 975-985, Mar. 2004.
Shoichi Sasaki et al.; Acta Neuropathol, vol. 97, No. 5, pp. 463-468, 1999.
A. Tamaoka et al.; Journal of Neurology, vol. 247, No. 8, pp. 633-635, 2000.
Ronald L. Hamilton et al.; Acta Neuropathol, vol. 107, No. 6, pp. 515-522, 2004.
Bradley J. Turner et al.; Neurochemical Research, vol. 29, No. 12, pp. 2281-2286, 2004.
Roy O. Weller; Journal of Neuropathology and Experimental Neurology, vol. 57, No. 10, pp. 885-894, Oct. 1998.
Gerald D. Silverberg et al.; Lancet Neurology, vol. 2, No. 8, pp. 506-511, Aug. 2003.
Roy O. Weller et al.; Annals of the New York Academy of Science, vol. 903, pp. 110-117, 2000.
H. Y. Yow et al.; Neuropathology and Applied Neurobiology; vol. 28, p. 149, 2002.
Roy O. Weller et al.; Annals of the New York Academy of Science, vol. 977, pp. 162-168, 2002.
Margaret J. Smith et al.; Annals of Neurology, vol. 49, No. 1, pp. 125-129, 2001.
Richard Crook et al.; Nature Medicine, vol. 4, No. 4, pp. 452-455, Apr. 1998.
Craig S. Atwood, Brain Research Review; vol. 43, No. 1, pp. 164-178, 2003.
Jonathan D. Lowenson et al.; Trends in Cardiovascular Medicine, vol. 4, No. 1, pp. 3-8, 1994.
Andrew B. Singleton et al.; vol. 123, No. 12, pp. 2467-2474, 2000.
W.F. Gattaz et al.; Journal of Neural Transmission, vol. 111, No. 5, pp. 591-601, 2004.
A. Assini et al.; Neurology, vol. 63, No. 5, pp. 828-831, 2004.
Guido R. Y. DeMeyer et al.; Circulation Research, vol. 90, No. 11, pp. 1197-1204, 2002.
Masahiko Kato et al., Chem. Pharm. Bull., 42 (12), 2546-2555 (1994).
Guiroy et al., Acta Neuropathol (991) 82:87-92.
Ross, J. Med. Chem., 1973, vol. 16, No. 4, 347-352.
Official Action dated Jul. 4, 2008, which issued in corresponding Russian Patent Application No. 2006146070.
Official Action issued on Nov. 14, 2008, in corresponding Russian Patent Application No. 2006146070.
T. A. Comery, The Journal of Neuroscience, Sep. 28, 2005, 25(39): 8898-8902.
T. A. Comery et al., Society for Neuroscience Annual Meeting (2003), Abstracts, Program No. 525.21.
Varnes et al., Bioorganic & Medicinal Chemistry Letter, vol. 14, No. 7, 2004, pp. 1645-1649.
Stark et al., Pharmazie, vol. 52, No. 6, 1997, pp. 419-429.
Kajbaf et al., Journal of Chromatography, vol. 575, No. 1, 1992, pp. 75-85.
Marcus et al., Cancer Research, vol. 45, No. 1, Jan. 1985, pp. 112-115.
Yale et al., Journal of Medicinal Chemistry, 1966. vol. 9. No. 1, pp. 42-46.
S. M. Catalano et al., "The Role of Amyloid-Beta Derived Diffusible Ligands (ADDLs) in Alzheimer's Disease," Current Tosics in Medicinal Chemistry, vol. 6, 597-608 (2006).
Search Report issued May 27, 2009, in connection with Georgia Patent Application No. AP 2006 010709 (with English translation).
International Search Report for International Appl. No. PCT/JP2008/053887, mailed Sep. 19, 2008.
Office Action from Russian Patent Appl. No. 2008125426/04(030920), date Jun. 1, 2009.
Office Action from U.S. Appl. No. 11/715,440, dated Jul. 16, 2009.
Office Action from U.S. Appl. No. 12/200,731, dated Jul. 30, 2009.
English abstract of GEP 20084571 B, published Jul. 10, 2008.
Search Report issued on Oct. 1, 2009, in connection with Georgian Patent Application No. AP 2007 010893.
Official Action issued Jan. 22, 2010, in Peruvian Patent Application No. 001480-2006.
Office Action issued Jan. 19, 2010, in copending U.S. Appl. No. 11/596,723.
Brocchini et al., "Preparation of piperazinedione-derivative inhibitors of plasminogen activator inhibitor," Database CA [Online] Chemical Abstracts Service, Columbus, Ohio, US, XP002574973, retrieved from STN, Database accession No. 1995:994197, Abstract.
Database Crossfire Beilstein, Beilstein Institut Zur Foerderung Der Chemischen Wissenschaften, Frankfurt Am Main, DE, XP002574972, Database accession No. 4617764, Abstract.
Supplementary European Search Report dated Apr. 7, 2010 for corresponding European Application No. 05743758.4.
European Search Report issued Aug. 4, 2010, in corresponding European Patent Application No. 06822806.3.
Honig et al., "From bench to clinic and back: Perspective on the 1st IQPC Translational Research Conference," Journal of Translational Medicine 2004, vol. 2, No. 44.
Office Action issued Jan. 11, 2011, in copending U.S. Appl. No. 12/522,281.
Office Action issued Jan. 24, 2011, in copending U.S. Appl. No. 12/301,428.
Office Action issued Nov. 12, 2010, in Chinese Patent Application No. 200780018090.5 (with English translation).
Schafer et al., "Failure is an option: learning from unsuccessful proof-of-concept trials," Drug Discovery Today 2008, vol. 13, Nos. 21/22, pp. 913-916.
Extended European Search Report, dated Jan. 26, 2011, for European Application No. 07743622.8.
US Office Action, dated Feb. 15, 2011, for U.S. Appl. No. 12/301,421.
Written Opinion issued Jan. 27, 2011, in Singapore Patent Application No. 201000682-3.
Cooper et al., "1,4-Dihydropyridines as antagonists of platelet activating factor. 1. Synethesis and structure-activity realtionships of 2-(4-heterocyclyl)phenyl derivatives," J. Med. Chem. (1992), vol. 35, pp. 3115-3129.
Davey et al., "Novel compounds posessing potent cAMP and cGMP phosphodiesterase inhibitory activity. Synthesis and cardiovascular effects of a series of . . . ," J. Med. Chem. (1991) vol. 34, pp. 2671-2677.

Erhardt et al., "Cardiotonic Agents. 5. Fragments from the heterocycle-phenyl-imidazole pharmacophore," J. Med. Chem. (1989) vol. 32, pp. 1173-1176.

European Search Report issued May 17, 2011, in European Patent Application No. 10177579.9.

Higaki et al., "A Combinatorial Approach to the Identification of Dipeptide Aldehyde Inhibitors of Beta-Amyloid Production," J. Med. Chem. 1999, vol. 42, pp. 3889-3898.

Kimura et al., CAPLUS Accession No. 2005:1290311 (2005).

Mano et al., "Novel imidazole compounds as a new series of potent, orally active inhibitors of 5-Lipoxygenase," Bioorganic and Medicinal Chemistry (2003), vol. 11, pp. 3879-3887.

Meciarova et al., "Ultrasound effect on the aromatic nucleophilic substitution reactions on some haloarenes," Ultrasonics Sonochemistry (2003) vol. 10, pp. 265-270.

Office Action issued Apr. 20, 2011, in Chinese Patent Application No. 200880006622.8 (with English translation).

Office Action issued Jun. 10, 2011, in copending U.S. Appl. No. 12/093,929.

Office Action issued Jun. 21, 2011, in copending U.S. Appl. No. 12/093,287.

Office Action issued May 12, 2011, in European Patent Application No. 05 743 758.4.

Office Action issued May 24, 2010, in Japanese Patent Application No. 2007-306088 (with English translation).

Search Report and Substantive Examination Report issued in May, 2011, in El Salvador Patent Application No. 2913/08, with English translation.

Sitkina et al., "Direct N-arylation of 5-membered heterocyclic nitrogen rings," Chemistry of Heterocyclic Compounds (1966) vol. 2, No. 1, pp. 143-145.

Office Action issued May 11, 2011, in Australian Patent Application No. 2006317468.

Office Action issued May 20, 2011 in Chinese Patent Application No. 200680043648.0 (with English translation).

Office Action issued May 9, 2011, in Australian Patent Application No. 2007223158.

* cited by examiner

TWO CYCLIC CINNAMIDE COMPOUND

CROSS REFERENCE TO RELATED APPLICATIONS

The present application is a 37 CFR §1.53(b) continuation of U.S. application Ser. No. 11/594,150 filed Nov. 8, 2006, which claims priority on Japanese Application Nos. 2005-337963 filed on Nov. 24, 2005, and 2006-205538 filed Jul. 28, 2006, and U.S. Provisional Application No. 60/833,768 filed on Jul. 28, 2006. The entire contents of each of these applications are hereby incorporated by reference.

BACKGROUND OF THE INVENTION (1) Field of the Invention

The present invention relates to a two cyclic cinnamide compound and a pharmaceutical agent comprising the compound as an active ingredient. More specifically, the present invention relates to a nonpeptidic two cyclic cinnamide compound and an amyloid-β (hereinafter referred to as Aβ) production inhibitor which comprises the compound as an active ingredient and is particularly effective for treatment of a neurodegenerative disease caused by Aβ such as Alzheimer's disease or Down's syndrome.

(2) Description of Related Art

Alzheimer's disease is a disease characterized by degeneration and loss of neurons as well as formation of senile plaques and neurofibrillary degeneration. Currently, Alzheimer's disease is treated only with symptomatic treatment using a symptom improving agent typified by an acetylcholinesterase inhibitor, and a fundamental remedy to inhibit progression of the disease has not yet-been developed. It is necessary to develop a method for controlling the cause of the onset of pathology in order to create a fundamental remedy for Alzheimer's disease.

It is assumed that Aβ-proteins as metabolites of amyloid precursor proteins (hereinafter referred to as APP) are highly involved in degeneration and loss of neurons and onset of symptoms of dementia (see Klein W L, and seven others, Alzheimer's disease-affected brain: Presence of oligomeric Aβ ligands (ADDLs) suggests a molecular basis for reversible memory loss, Proceding National Academy of Science USA 2003, Sep. 2; 100(18), p. 10417-10422; and Nitsch R M, and sixteen others, Antibodies against β-amyloid slow cognitive decline in Alzheimer's disease, Neuron, 2003, May 22; 38, p. 547-554, for example). An Aβ-protein has, as main components, Aβ40 consisting of 40 amino acids and Aβ42 in which the number of amino acids is increased by two at the C-terminal. The Aβ40 and Aβ42 are known to have high aggregability (see Jarrett J T, and two others, The carboxy terminus of the β amyloid protein is critical for the seeding of amyloid formation: Implications for the pathogenesis of Alzheimer's disease, Biochemistry, 1993, 32(18), p. 4693-4697, for example) and to be main components of senile plaques (see Jarrett J T, and two others, The carboxy terminus of the β amyloid protein is critical for the seeding of amyloid formation: Implications for the pathogenesis of Alzheimer's disease, Biochemistry, 1993, 32(18), p. 4693-4697; Glenner G G, and one other, Alzheimer's disease: initial report of the purification and characterization of a novel cerebrovascular amyloid protein, Biochemical and biophysical research communications, 1984, May 16, 120(3), p. 885-890; and Masters C L, and five others, Amyloid plaque core protein in Alzheimer disease and Down syndrome, Proceding National Academy of Science USA, 1985, June, 82(12), p. 4245-4249, for example). Further, it is known that the Aβ40 and Aβ42 are increased by mutation in APP and presenilin genes which is observed in familial Alzheimer's disease (see Gouras G K, and eleven others, Intraneuronal Aβ42 accumulation in human brain, American Journal of Pathology, 2000, January, 156(1), p. 15-20; Scheuner D, and twenty others, Secreted amyloid α-protein similar to that in the senile plaques of Alzheimer's disease is increased in vivo by the presenilin 1 and 2 and APP mutations linked to familial Alzheimer's disease, Nature Medicine, 1996, August, 2(8), p. 864-870; and Forman M S, and four others, Differential effects of the swedish mutant amyloid precursor protein on β-amyloid accumulation and secretion in neurons and nonneuronal cells, The Journal of Biological Chemistry, 1997, Dec. 19, 272(51), p. 32247-32253, for example). Accordingly, a compound that reduces production of Aβ40 and Aβ42 has been expected as a progression inhibitor or prophylactic agent for Alzheimer's disease.

Aβ is produced by cleaving APP by β-secretase and subsequently by γ-secretase. For this reason, attempts have been made to create γ-secretase and β-secretase inhibitors in order to reduce Aβ production. Many of these secretase inhibitors already known are, for example, peptides and peptide mimetics such as L-685,458 (see Shearman M S, and nine others, L-685,458, an Aspartyl Protease Transition State Mimic, Is a Potent Inhibitor of Amyloid β-Protein Precursor γ-Secretase Activity, Biochemistry, 2000, Aug. 1, 39(30), p. 8698-8704, for example) and LY-411575 (see Shearman M S, and six others, Catalytic Site-Directed γ-Secretase Complex Inhibitors Do Not Discriminate Pharmacologically between Notch S3 and β-APP Cleavages, Biochemistry, 2003, Jun. 24, 42(24), p. 7580-7586; Lanz T A, and three others, Studies of Aβ pharmacodynamics in the brain, cerebrospinal fluid, and plasma in young (plaque-free) Tg2576 mice using the γ-secretase inhibitor N2-[(2S)-2-(3,5-difluorophenyl)-2-hydroxyethanoyl]-N1-[(7S)-5-methyl-6-oxo-6,7-dihydro-5H-dibenzo[b,d]azepin-7-yl]-L-alaninamide (LY-411575), The journal of pharmacology and experimental therapeutics, 2004, April, 309(1), p. 49-55; and Wong G T, and twelve others, Chronic treatment with the γ-secretase inhibitor LY-411,575 inhibits β-amyloid peptide production and alters lymphopoiesis and intestinal cell differentiation, The journal of biological chemistry, 2004, Mar. 26, 279(13), p. 12876-12882, for example).

BRIEF SUMMARY OF THE INVENTION

As described above, a compound that inhibits production of Aβ40 and Aβ42 from APP has been expected as a therapeutic or prophylactic agent for a disease caused by Aβ which is typified by Alzheimer's disease. However, a nonpeptidic compound having high efficacy which inhibits production of Aβ40 and Aβ42 has not yet been known. Accordingly, there is a need for a novel low-molecular-weight compound that inhibits production of Aβ40 and Aβ42.

As a result of extensive studies, the present inventors have found a nonpeptidic two cyclic cinnamide compound that inhibits production of Aβ40 and Aβ42 from APP for the first time, and thus found a prophylactic or therapeutic agent for a disease caused by Aβ which is typified by Alzheimer's disease. This finding has led to the accomplishment of the present invention.

Specifically, the present invention relates to
1) A compound represented by the formula (I):

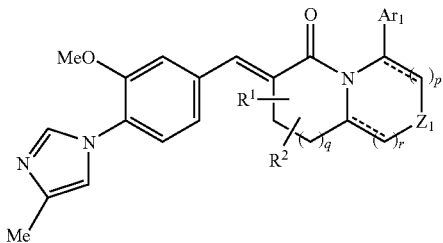

or a pharmacologically acceptable salt thereof,
wherein ---- represents a single bond or a double bond; $Ar_1$ represents a phenyl group that may be substituted with 1 to 3 substituents selected from Substituent Group A1 or a pyridinyl group that may be substituted with 1 to 3 substituents selected from Substituent Group A1; $R^1$ and $R^2$ are the same or different and each represent a group selected from the following Substituent Group A1; $Z_1$ represents a methylene group or vinylene group, which may be substituted with 1 or 2 substituents selected from Substituent Group A1, an oxygen atom, or an imino group that may be substituted with a substituent selected from Substituent Group A1; and p, q, and r are the same or different and represent an integer of 0 to 2;
Substituent Group A1: (1) a halogen atom, (2) a hydroxyl group, (3) a cyano group, (4) a C3-8 cycloalkyl group, (5) a C3-8 cycloalkoxy group, (6) a C1-6 alkyl group, wherein the C1-6 alkyl group may be substituted with 1 to 3 substituents selected from the group consisting of a halogen atom, hydroxyl group, cyano group, C3-8 cycloalkyl group, C1-6 alkoxy group, and C3-8 cycloalkoxy group, (7) a C1-6 alkoxy group, wherein the C1-6 alkoxy group may be substituted with 1 to 3 substituents selected from the group consisting of a halogen atom, hydroxyl group, cyano group, C3-8 cycloalkyl group, and C3-8 cycloalkoxy group, (8) an amino group that may be substituted with one or two C1-6 alkyl groups, wherein the C1-6 alkyl groups may be substituted with 1 to 3 halogen atoms, (9) a carbamoyl group that may be substituted with one or two C1-6 alkyl groups, wherein the C1-6 alkyl groups may be substituted with 1 to 3 halogen atoms, (10) a carboxyl group, (11) a C1-6 alkoxycarbonyl group, wherein the C1-6 alkoxy group may be substituted with 1 to 3 substituents selected from the group consisting of a halogen atom, hydroxyl group, cyano group, C3-8 cycloalkyl group, and C3-8 cycloalkoxy group), (12) a C1-6 acyl group and (13) C1-6 alkylsulfonyl group;
2) The compound or pharmacologically acceptable salt thereof according to 1) above, wherein the compound is represented by the formula (II):

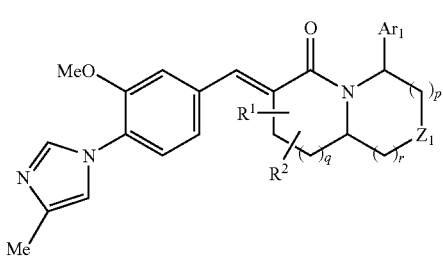

wherein $Ar_1$ represents a phenyl group that may be substituted with 1 to 3 substituents selected from Substituent Group A1 or a pyridinyl group that may be substituted with 1 to 3 substituents selected from Substituent Group A1; $R^1$ and $R^2$ are the same or different and each represent a group selected from the following Substituent Group A1; $Z_1$ represents a methylene group or vinylene group, which may be substituted with 1 or 2 substituents selected from Substituent Group A1, an oxygen atom, or an imino group that may be substituted with a substituent selected from Substituent Group A1; and p, q, and r are the same or different and represent an integer of 0 to 2;
Substituent Group A1: (1) a halogen atom, (2) a hydroxyl group, (3) a cyano group, (4) a C3-8 cycloalkyl group, (5) a C3-8 cycloalkoxy group, (6) a C1-6 alkyl group, wherein the C1-6 alkyl group may be substituted with 1 to 3 substituents selected from the group consisting of a halogen atom, hydroxyl group, cyano group, C3-8 cycloalkyl group, C1-6 alkoxy group, and C3-8 cycloalkoxy group, (7) a C1-6 alkoxy group, wherein the C1-6 alkoxy group may be substituted with 1 to 3 substituents selected from the group consisting of a halogen atom, hydroxyl group, cyano group, C3-8 cycloalkyl group, and C3-8 cycloalkoxy group, (8) an amino group that may be substituted with one or two C1-6 alkyl groups, wherein the C1-6 alkyl groups may be substituted with 1 to 3 halogen atoms, (9) a carbamoyl group that may be substituted with one or two C1-6 alkyl groups, wherein the C1-6 alkyl groups may be substituted with 1 to 3 halogen atoms, (10) a carboxyl group, (11) a C1-6 alkoxycarbonyl group, wherein the C1-6 alkoxy group may be substituted with 1 to 3 substituents selected from the group consisting of a halogen atom, hydroxyl group, cyano group, C3-8 cycloalkyl group and C3-8 cycloalkoxy group, (12) a C1-6 acyl group and (13) C1-6 alkylsulfonyl group);
3) The compound or pharmacologically acceptable salt thereof according to 1) or 2) above, wherein $Z_1$ represents a methylene group, wherein the methylene group may be substituted with 1 or 2 substituents selected from the group consisting of a C1-6 alkyl group, hydroxyl group, and halogen atom;
4) The compound or pharmacologically acceptable salt thereof according to 3) above, wherein $Z_1$ represents a methylene group that may be substituted with 1 or 2 substituents selected from the group consisting of a C1-6 alkyl group and hydroxyl group;
5) The compound or pharmacologically acceptable salt thereof according to 1) or 2) above, wherein $Z_1$ represents a methylene group, wherein the methylene group may be substituted with 1 or 2 substituents selected from the group consisting of a C1-6 alkyl group, hydroxyl group, and halogen atom; and p, q, and r each represent 1;
6) The compound or pharmacologically acceptable salt thereof according to 5) above, wherein $Z_1$ represents a methylene group, wherein the methylene group may be substituted with 1 or 2 substituents selected from the group consisting of a C1-6 alkyl group and hydroxyl group; and p, q, and r each represent 1;
7) The compound or pharmacologically acceptable salt thereof according to 1) or 2) above, wherein $Z_1$ represents a methylene group, wherein the methylene group may be substituted with 1 or 2 substituents selected from the group consisting of a C1-6 alkyl group, hydroxyl group, and halogen atom; p and q each represent 1; and r represents 0;
8) The compound or pharmacologically acceptable salt thereof according to 7) above, wherein $Z_1$ represents a methylene group, wherein the methylene group may be substituted with 1 or 2 substituents selected from the group consisting of a C1-6 alkyl group and hydroxyl group; p and q each represent 1; and r represents 0;
9) The compound or pharmacologically acceptable salt thereof according to 1) or 2) above, wherein $Z_1$ represents an oxygen atom; and p, q, and r each represent 1;
10) The compound or pharmacologically acceptable salt thereof according to 1) or 2) above, wherein $Z_1$ represents a methylene group, wherein the methylene group may be substituted with 1 or 2 substituents selected from the group consisting of a C1-6 alkyl group, halogen atom, and hydroxyl group; p represents 1; and q and r each represent 0;
11). The compound or pharmacologically acceptable salt thereof according to 10) above, wherein $Z_1$ represents a methylene group, wherein the methylene group may be substituted with 1 or 2 substituents selected from the group consisting of a C1-6 alkyl group and hydroxyl group; p represents 1; and q and r each represent 0;
12) The compound or pharmacologically acceptable salt thereof according to 1) or 2) above, wherein $Z_1$ represents a methylene group, wherein the methylene group may be substituted with 1 or 2 substituents selected from the group consisting of a C1-6 alkyl group, halogen atom, and hydroxyl group; p and r each represent 1; and q represents 0;
13) The compound or pharmacologically acceptable salt thereof according to 12) above, wherein $Z_1$ represents a methylene group, wherein the methylene group may be substituted with 1 or 2 substituents selected from the group consisting of a C1-6 alkyl group and hydroxyl group; p and r each represent 1; and q represents 0;
14) The compound or pharmacologically acceptable salt thereof according to 1) or 2) above, wherein $Z_1$ represents a methylene group, wherein the methylene group may be substituted with 1 or 2 substituents selected from the group consisting of a C1-6 alkyl group, halogen atom, and hydroxyl group; p represents 1; q represents 2; and r represents 0;
15) The compound or pharmacologically acceptable salt thereof according to 14) above, wherein $Z_1$ represents a methylene group, wherein the methylene group may be substituted with 1 or 2 substituents selected from the group consisting of a C1-6 alkyl group and hydroxyl group; p represents 1; q represents 2; and r represents 0;
16) The compound or pharmacologically acceptable salt thereof according to 1) or 2) above, wherein $Z_1$ represents a methylene group, wherein the methylene group may be substituted with 1 or 2 substituents selected from the group consisting of a C1-6 alkyl group, halogen atom, and hydroxyl group; p and r each represent 1; and q represents 2;
17) The compound or pharmacologically acceptable salt thereof according to 16) above, wherein $Z_1$ represents a methylene group, wherein the methylene group may be substituted with 1 or 2 substituents selected from the group consisting of a C1-6 alkyl group and hydroxyl group; p and r each represent 1; and q represents 2;
18) The compound or pharmacologically acceptable salt thereof according to 1) or 2) above, wherein $Z_1$ represents a vinylene group, wherein the vinylene group may be substituted with one or two C1-6 alkyl groups or halogen atoms; p represents 0; and q and r each represent 1;
19) The compound or pharmacologically acceptable salt thereof according to 18), wherein $Z_1$ represents a vinylene group, wherein the vinylene group may be substituted with one or two C1-6 alkyl groups; p represents 0; and q and r each represent 1;
20) The compound or pharmacologically acceptable salt thereof according to 1) or 2) above, wherein $Z_1$ represents a vinylene group, wherein the vinylene group may be substituted with one or two C1-6 alkyl groups or halogen atoms; p and q each represent 1; and r represents 0;
21) The compound or pharmacologically acceptable salt thereof according to 20) above, wherein $Z_1$ represents a vinylene group, wherein the vinylene group may be substituted with one or two C1-6 alkyl groups; p and q each represent 1; and r represents 0;
22) The compound or pharmacologically acceptable salt thereof according to 1) or 2) above, wherein $Ar_1$ represents a phenyl group substituted with 1 to 3 halogen atoms;
23) The compound or pharmacologically acceptable salt thereof according to 22) above, wherein $Ar_1$ represents a phenyl group substituted with 1 to 3 fluorine atoms or chlorine atoms;
24) The compound or pharmacologically acceptable salt thereof according to 7) or 8) above, wherein $Ar_1$ represents a phenyl group substituted with 2 or 3 halogen atoms;
25) The compound or pharmacologically acceptable salt thereof according to any of 2), 22), 23), and 24) above, wherein $Ar_1$ represents a phenyl group substituted with a fluorine atom;
26) The compound or pharmacologically acceptable salt thereof according to 1) or 2) above, wherein $R^1$ and $R^2$ are the same or different and each represent a substituent selected from the group consisting of a C1-6 alkyl group, halogen atom, and hydroxyl group;
27) The compound or pharmacologically acceptable salt thereof according to 1) or 2) above, wherein the compound is selected from the following group:
1) (E)-(3S)-(3,4,5-trifluorophenyl)-6-[3-methoxy-4-(4-methyl-1H-imidazol-1-yl)benzylidene]-(9R)-hexahydroindolizin-5-one,
2) (E)-(3R)-(3,4,5-trifluorophenyl)-6-[3-methoxy-4-(4-methyl-1H-imidazol-1-yl)benzylidene]-(9R)-hexahydroindolizin-5-one,
3) (E)-(3S)-(3,4,5-trifluorophenyl)-6-[3-methoxy-4-(4-methyl-1H-imidazol-1-yl)benzylidene]-(9S)-hexahydroindolizin-5-one,
4) (E)-(3R)-(3,4,5-trifluorophenyl)-6-[3-methoxy-4-(4-methyl-1H-imidazol-1-yl)benzylidene]-(9S)-hexahydroindolizin-5-one,
5) (E)-(3R)-(3,4-difluorophenyl)-6-[3-methoxy-4-(4-methyl-1H-imidazol-1-yl)benzylidene]-(9R)-hexahydroindolizin-5-one,
6) (E)-(3S)-(3,4-difluorophenyl)-6-[3-methoxy-4-(4-methyl-1H-imidazol-1-yl)benzylidene]-(9S)-hexahydroindolizin-5-one,
7) (E)-(6R,9aS)-6-(4-fluorophenyl)-3-[3-methoxy-4-(4-methyl-1H-imidazol-1-yl)benzylidene]octahydroquinolizin-4-one,
8) (E)-(6S,9aR)-6-(4-fluorophenyl)-3-[3-methoxy-4-(4-methyl-1H-imidazol-1-yl)benzylidene]octahydroquinolizin-4-one,
9) (E)-(6S,8S,9aR)-6-phenyl-8-hydroxy-3-[3-methoxy-4-(4-methyl-1H-imidazol-1-yl)benzylidene]octahydroquinolizin-4-one,
10) (E)-(6R,8R,9aS)-6-phenyl-8-hydroxy-3-[3-methoxy-4-(4-methyl-1H-imidazol-1-yl)benzylidene]octahydroquinolizin-4-one,
11) (E)-(6S,8S,9aR)-6-(4-fluorophenyl)-8-hydroxy-3-[3-methoxy-4-(4-methyl-1H-imidazol-1-yl)benzylidene]octahydroquinolizin-4-one,
12) (E)-(6R,8R,9aS)-6-(4-fluorophenyl)-8-hydroxy-3-[3-methoxy-4-(4-methyl-1H-imidazol-1-yl)benzylidene]octahydroquinolizin-4-one, 13) (E)-(6S,9aS)-6-(3,4,5-trifluorophenyl)-3-[3-methoxy-4-(4-methyl-1H-imidazol-1-yl)benzylidene]octahydroquinolizin-4-one,
14) (E)-(6R,9aR)-6-(3,4,5-trifluorophenyl)-3-[3-methoxy-4-(4-methyl-1H-imidazol-1-yl)benzylidene]octahydroquinolizin-4-one,
15) (E)-(6S,8S,9aR)-6-(3,4,5-trifluorophenyl)-8-hydroxy-3-[3-methoxy-4-(4-methyl-1H-imidazol-1-yl)benzylidene]octahydroquinolizin-4-one,
16) (E)-(6R,8R,9aS)-6-(3,4,5-trifluorophenyl)-8-hydroxy-3-[3-methoxy-4-(4-methyl-1H-imidazol-1-yl)benzylidene]octahydroquinolizin-4-one,
17) (E)-(6S,8R,9aR)-6-(3,4,5-trifluorophenyl)-8-hydroxy-3-[3-methoxy-4-(4-methyl-1H-imidazol-1-yl)benzylidene]octahydroquinolizin-4-one,
18) (E)-(6R,8S,9aS)-6-(3,4,5-trifluorophenyl)-8-hydroxy-3-[3-methoxy-4-(4-methyl-1H-imidazol-1-yl)benzylidene]octahydroquinolizin-4-one,
19) (E)-(6S,9aS)-6-(4-fluorophenyl)-3-[3-methoxy-4-(4-methyl-1H-imidazol-1-yl)benzylidene]octahydroquinolizin-4-one,
20) (E)-(6R,9aR)-6-(4-fluorophenyl)-3-[3-methoxy-4-(4-methyl-1H-imidazol-1-yl)benzylidene]octahydroquinolizin-4-one,
21) (E)-(5S)-(4-fluorophenyl)-2-[3-methoxy-4-(4-methyl-1H-imidazol-1-yl)benzylidene]-(8aS)-hexahydroindolizin-3-one,
22) (E)-(5R)-(4-fluorophenyl)-2-[3-methoxy-4-(4-methyl-1H-imidazol-1-yl)benzylidene]-(8aR)-hexahydroindolizin-3-one,
23) (E)-(5S)-(3,4-difluorophenyl)-2-[3-methoxy-4-(4-methyl-1H-imidazol-1-yl)benzylidene]-(8aS)-hexahydroindolizin-3-one,
24) (E)-(5R)-(3,4-difluorophenyl)-2-[3-methoxy-4-(4-methyl-1H-imidazol-1-yl)benzylidene]-(8aR)-hexahydroindolizin-3-one,
25) (Z)-(5S)-(3,4-difluorophenyl)-2-[3-methoxy-4-(4-methyl-1H-imidazol-1-yl)benzylidene]-(8aS)-hexahydroindolizin-3-one,
26) (Z)-(5R)-(3,4-difluorophenyl)-2-[3-methoxy-4-(4-methyl-1H-imidazol-1-yl)benzylidene]-(8aR)-hexahydroindolizin-3-one,
27) (E)-(5R,8aS)-5-(4-fluorophenyl)-2-[3-methoxy-4-(4-methyl-1H-imidazol-1-yl)benzylidene]hexahydroindolizin-3-one,
28) (E)-(5S,8aR)-5-(4-fluorophenyl)-2-[3-methoxy-4-(4-methyl-1H-imidazol-1-yl)benzylidene]hexahydroindolizin-3-one,
29) (E)-(6R,9aS)-3-[3-methoxy-4-(4-methyl-1H-imidazol-1-yl)benzylidene]-6-(4-methoxyphenyl)octahydroquinolizin-4-one,
30) (E)-(6S,9aR)-3-[3-methoxy-4-(4-methyl-1H-imidazol-1-yl)benzylidene]-6-(4-methoxyphenyl)octahydroquinolizin-4-one,
31) (E)-(4S,10aS)-4-(4-fluorophenyl)-7-[3-methoxy-4-(4-methyl-1H-imidazol-1-yl)benzylidene]octahydropyrido[1,2-a]azepin-6-one,
32) (E)-(4R,10aR)-4-(4-fluorophenyl)-7-[3-methoxy-4-(4-methyl-1H-imidazol-1-yl)benzylidene]octahydropyrido[1,2-a]azepin-6-one,
33) (E)-(5R,7aS)-5-(3,4-difluorophenyl)-2-[3-methoxy-4-(4-methyl-1H-imidazol-1-yl)benzylidene]hexahydropyrrolidin-3-one,
34) (E)-(3R,9aR)-3-(3,4-difluorophenyl)-6-[3-methoxy-4-(4-methyl-1H-imidazol-1-yl)benzylidene]octahydropyrrolo[1,2-a]azepin-5-one,
35) methyl (E)-4-{(4S*,9aR*)-7-[3-methoxy-4-(4-methyl-1H-imidazol-1-yl)benzylidene]-6-oxooctahydroquinolizin-4-yl}benzoate,
36) (E)-(6S*,9aR*)-6-(4-hydroxymethylphenyl)-3-[3-methoxy-4-(4-methyl-1H-imidazol-1-yl)benzylidene]octahydroquinolizin-4-one,
37) (E)-(6S*,9aR*)-6-(4-cyanophenyl)-3-[3-methoxy-4-(4-methyl-1H-imidazol-1-yl)benzylidene]octahydroquinolizin-4-one,
38) (E)-4-{(4S*,9aR*)-7-[3-methoxy-4-(4-methyl-1H-imidazol-1-yl)benzylidene]-6-oxooctahydroquinolizin-4-yl}benzoic acid,
39) (E)-(6S*,9aR*)-6-(4-aminophenyl)-3-[3-methoxy-4-(4-methyl-1H-imidazol-1-yl)benzylidene]octahydroquinolizin-4-one,
40) (E)-4-{(4S*,9aR*)-7-[3-methoxy-4-(4-methyl-1H-imidazol-1-yl)benzylidene]-6-oxooctahydroquinolizin-4-yl}-N,N-dimethylbenzamide,
41) (E)-(6S,9aR)-6-(3-fluorophenyl)-3-[3-methoxy-4-(4-methyl-1H-imidazol-1-yl)benzylidene]octahydroquinolizin-4-one,
42) (E)-(6R,9aS)-6-(3-fluorophenyl)-3-[3-methoxy-4-(4-methyl-1H-imidazol-1-yl)benzylidene]octahydroquinolizin-4-one,
43) (E)-(6S,9aR)-6-(2-fluorophenyl)-3-[3-methoxy-4-(4-methyl-1H-imidazol-1-yl)benzylidene]octahydroquinolizin-4-one,
44) (E)-(6R,9aS)-6-(2-fluorophenyl)-3-[3-methoxy-4-(4-methyl-1H-imidazol-1-yl)benzylidene]octahydroquinolizin-4-one,
45) (E)-(6S,8R,9aR)-6-(4-fluorophenyl)-8-hydroxy-3-[3-methoxy-4-(4-methyl-1H-imidazol-1-yl)benzylidene]-8-methyl-octahydroquinolizin-4-one,
46) (E)-(6R,8S,9aS)-6-(4-fluorophenyl)-8-hydroxy-3-[3-methoxy-4-(4-methyl-1H-imidazol-1-yl)benzylidene]-8-methyl-octahydroquinolizin-4-one,
47) (E)-(6S,8R,9aR)-6-(4-fluorophenyl)-8-hydroxy-3-[3-methoxy-4-(4-methyl-1H-imidazol-1-yl)benzylidene]-8-methyloctahydroquinolizin-4-one,
48) (E)-(6R,8S,9aS)-6-(4-fluorophenyl)-8-hydroxy-3-[3-methoxy-4-(4-methyl-1H-imidazol-1-yl)benzylidene]-8-methyloctahydroquinolizin-4-one,
49) (E)-(6S,9aR)-6-(4-fluorophenyl)-3-[3-methoxy-4-(4-methyl-1H-imidazol-1-yl)benzylidene]-8-methyl-1,2,3,6,9,9a-hexahydroquinolizin-4-one,
50) (E)-(6R,9aS)-6-(4-fluorophenyl)-3-[3-methoxy-4-(4-methyl-1H-imidazol-1-yl)benzylidene]-8-methyl-1,2,3,6,9,9a-hexahydroquinolizin-4-one,
51) (E)-(6S,8S,9aR)-6-(4-fluorophenyl)-8-hydroxy-3-[3-methoxy-4-(4-methyl-1H-imidazol-1-yl)benzylidene]-8-methyloctahydroquinolizin-4-one,
52) (E)-(6R,8R,9aS)-6-(4-fluorophenyl)-8-hydroxy-3-[3-methoxy-4-(4-methyl-1H-imidazol-1-yl)benzylidene]-8-methyloctahydroquinolizin-4-one,
53) (E)-(4R,9aS)-7-[3-methoxy-4-(4-methylimidazol-1-yl)benzylidene]-4-phenylhexahydropyrido[2,1-c][1,4]oxazin-6-one,
54) (E)-(5S,7aR)-5-(3,4-difluorophenyl)-2-[3-methoxy-4-(4-methyl-1H-imidazol-1-yl)benzylidene]hexahydropyrrolidin-3-one,
55) (E)-(3S,9aS)-3-(3,4-difluorophenyl)-6-[3-methoxy-4-(4-methyl-1H-imidazol-1-yl)benzylidene]octahydropyrrolo[1,2-a]azepin-5-one,
56) (E)-(3S,8aS)-3-(4-chlorophenyl)-6-[3-methoxy-4-(4-methyl-1H-imidazol-1-yl)benzylidene]hexahydroindolizin-5-one, 57) (E)-(3S,8aS)-3-(2,4,5-trifluorophenyl)-6-[3-methoxy-4-(4-methyl-1H-imidazol-1-yl)benzylidene]hexahydroindolizin-5-one,
58) (E)-(3S,8aS)-3-(2,3,4-trifluorophenyl)-6-[3-methoxy-4-(4-methyl-1H-imidazol-1-yl)benzylidene]hexahydroindolizin-5-one,
59) (E)-(3S,8aS)-3-(2,5-difluorophenyl)-6-[3-methoxy-4-(4-methyl-1H-imidazol-1-yl)benzylidene]hexahydroindolizin-5-one,
60) (E)-(3S,8aS)-3-(3-fluorophenyl)-6-[3-methoxy-4-(4-methyl-1H-imidazol-1-yl)benzylidene]hexahydroindolizin-5-one,
61) (E)-(3S,8aS)-3-(2,6-difluoropyridin-3-yl)-6-[3-methoxy-4-(4-methyl-1H-imidazol-1-yl)benzylidene]hexahydroindolizin-5-one,
62) (E)-(3S,8aS)-3-(2,4-difluorophenyl)-6-[3-methoxy-4-(4-methyl-1H-imidazol-1-yl)benzylidene]hexahydroindolizin-5-one,
63) (E)-(3S,8aS)-3-(3-chlorophenyl)-6-[3-methoxy-4-(4-methyl-1H-imidazol-1-yl)benzylidene]hexahydroindolizin-5-one,
64) (E)-(3S,8aS)-3-(3,5-difluorophenyl)-6-[3-methoxy-4-(4-methyl-1H-imidazol-1-yl)benzylidene]hexahydroindolizin-5-one,
65) (E)-(6S,9aS)-6-(3,4-difluorophenyl)-3-[3-methoxy-4-(4-methyl-1H-imidazol-1-yl)benzylidene]octahydroquinolizin-4-one,
66) (E)-(6R,9aR)-6-(3,4-difluorophenyl)-3-[3-methoxy-4-(4-methyl-1H-imidazol-1-yl)benzylidene]octahydroquinolizin-4-one,
67) (E)-(6S,9aS)-6-(4-chlorophenyl)-3-[3-methoxy-4-(4-methyl-1H-imidazol-1-yl)benzylidene]octahydroquinolizin-4-one,
68) (E)-(6R,9aR)-6-(4-chlorophenyl)-3-[3-methoxy-4-(4-methyl-1H-imidazol-1-yl)benzylidene]octahydroquinolizin-4-one,
69) (E)-(S)-6-(3,4,5-trifluorophenyl)-3-[3-methoxy-4-(4-methyl-1H-imidazol-1-yl)benzylidene]-1,2,3,8,9,9a-hexahydroquinolizin-4-one,
70) (E)-(R)-6-(3,4,5-trifluorophenyl)-3-[3-methoxy-4-(4-methyl-1H-imidazol-1-yl)benzylidene]-1,2,3,8,9,9a-hexahydroquinolizin-4-one,
71) (E)-(6S,8S,9aR)-8-fluoro-3-[3-methoxy-4-(4-methyl-1H-imidazol-1-yl)benzylidene]-6-(3,4,5-trifluorophenyl)octahydroquinolizin-4-one,
72) (E)-(6S,8R,9aR)-8-methoxy-3-[3-methoxy-4-(4-methyl-1H-imidazol-1-yl)benzylidene]-6-(3,4,5-trifluorophenyl)octahydroquinolizin-4-one,
73) (E)-(R)-4-(4-fluorophenyl)-7-[3-methoxy-4-(4-methyl-1H-imidazol-1-yl)benzylidene]-3,4,8,9-tetrahydro-7H-pyrido[2,1-c][1,4]oxazin-6-one,
74) (E)-(S)-4-(4-fluorophenyl)-7-[3-methoxy-4-(4-methyl-1H-imidazol-1-yl)benzylidene]-3,4,8,9-tetrahydro-7H-pyrido[2,1-c][1,4]oxazin-6-one,
75) (E)-(4R,9aR)-4-(4-fluorophenyl)-7-[3-methoxy-4-(4-methyl-1H-imidazol-1-yl)benzylidene]hexahydropyrido[2,1-c][1,4]oxazin-6-one,
76) (E)-(4S,9aS)-4-(4-fluorophenyl)-7-[3-methoxy-4-(4-methyl-1H-imidazol-1-yl)benzylidene]hexahydropyrido[2,1-c][1,4]oxazin-6-one,
77) (E)-(6S,8R,9aR)-8-fluoro-3-[3-methoxy-4-(4-methyl-1H-imidazol-1-yl)benzylidene]-6-(3,4,5-trifluorophenyl)octahydroquinolizin-4-one,
78) (E)-(6S,9aR)-3-[3-methoxy-4-(4-methyl-1H-imidazol-1-yl)benzylidene]-6-(3,4,5-trifluorophenyl)-1,2,3,6,9,9a-hexahydroquinolizin-4-one,
79) (E)-(6S,9aR)-3-[3-methoxy-4-(4-methyl-1H-imidazol-1-yl)benzylidene]-6-(3,4,5-trifluorophenyl)-1,2,3,6,7,9a-hexahydroquinolizin-4-one,
80) (E)-(4R,9aR)-7-[3-methoxy-4-(4-methyl-1H-imidazol-1-yl)benzylidene]-4-(3,4,5-trifluorophenyl)hexahydropyrido[2,1-c][1,4]oxazin-6-one,
81) (E)-(4S,9aS)-7-[3-methoxy-4-(4-methyl-1H-imidazol-1-yl)benzylidene]-4-(3,4,5-trifluorophenyl)hexahydropyrido[2,1-c][1,4]oxazin-6-one,
82) (E)-(4S,9aR)-7-[3-methoxy-4-(4-methyl-1H-imidazol-1-yl)benzylidene]-4-(3,4,5-trifluorophenyl)hexahydropyrido[2,1-c][1,4]oxazin-6-one,
83) (E)-(4R,9aR)-7-[3-methoxy-4-(4-methyl-1H-imidazol-1-yl)benzylidene]-4-(3,4,5-trifluorophenyl)hexahydropyrido[2,1-c][1,4]oxazin-6-one,
84) (E)-(6R,7S,9aR)-7-hydroxy-3-[3-methoxy-4-(4-methyl-1H-imidazol-1-yl)benzylidene]-6-(3,4,5-trifluorophenyl)octahydroquinolizin-4-one,
85) (E)-(6S,7R,9aS)-7-hydroxy-3-[3-methoxy-4-(4-methyl-1H-imidazol-1-yl)benzylidene]-6-(3,4,5-trifluorophenyl)octahydroquinolizin-4-one,
86) (E)-(6R,7R,9aR)-7-hydroxy-3-[3-methoxy-4-(4-methyl-1H-imidazol-1-yl)benzylidene]-6-(3,4,5-trifluorophenyl)octahydroquinolizin-4-one,
87) (E)-(6S,7S,9aS)-7-hydroxy-3-[3-methoxy-4-(4-methyl-1H-imidazol-1-yl)benzylidene]-6-(3,4,5-trifluorophenyl)octahydroquinolizin-4-one,
88) (E)-(6S,9aR)-6-(4-fluorophenyl)-3-[3-methoxy-4-(4-methyl-1H-imidazol-1-yl)benzylidene]-1,2,3,6,9,9a-hexahydroquinolizin-4-one,
89) (3S,8aS)-6-{1-[3-methoxy-4-(4-methyl-1H-imidazol-1-yl)phenyl]-(E)-methylidene}-3-(2,4,6-trifluorophenyl)hexahydroindolizin-5-one,
90) (6S,9aR)-6-(3,4-difluorophenyl)-3-{1-[3-methoxy-4-(4-methyl-1H-imidazol-1-yl)phenyl]-(E)-methylidene}octahydroquinolizin-4-one,
91) (6S,9aR)-6-(3,4,5-trifluorophenyl)-3-{1-[3-methoxy-4-(4-methyl-1H-imidazol-1-yl)phenyl]-(E)-methylidene}octahydroquinolizin-4-one,
92) (6S,9aR)-6-(4-chlorophenyl)-3-{1'-[3-methoxy-4-(4-methyl-1H-imidazol-1-yl)phenyl]-(E)-methylidene}octahydroquinolizin-4-one,
93) (E)-(3S,8aS)-3-(2,3-difluorophenyl)-6-[3-methoxy-4-(4-methyl-1H-imidazol-1-yl)benzylidene]hexahydroindolizin-5-one,
94) (4R,9aS)-4-(4-fluorophenyl)-7-{1-[3-methoxy-4-(4-methyl-1H-imidazol-1-yl)phenyl]-(E)-methylidene}hexahydropyrido[2,1-c][1,4]oxazin-6-one,
95) (4R,9aS)-4-(3,4-difluorophenyl)-7-{1-[3-methoxy-4-(4-methyl-1H-imidazol-1-yl)phenyl]-(E)-methylidene}hexahydropyrido[2,1-c][1,4]oxazin-6-one,
96) (4R,9aS)-4-(4-chlorophenyl)-7-{1-[3-methoxy-4-(4-methyl-1H-imidazol-1-yl)phenyl]-(E)-methylidene}hexahydropyrido[2,1-c][1,4]oxazin-6-one,
97) methyl (4S,9aR)-7-{1-[3-methoxy-4-(4-methyl-1H-imidazol-1-yl)phenyl]-(E)-methylidene}-6-oxo-4-(3,4,5-trifluorophenyl)octahydropyrido[1,2-a]pyrazine-2-carboxylate,
98) methyl (4R,9aS)-7-{1-[3-methoxy-4-(4-methyl-1H-imidazol-1-yl)phenyl]-(E)-methylidene}-6-oxo-4-(3,4,5-trifluorophenyl)octahydropyrido[1,2-a]pyrazine-2-carboxylate,
99) methyl (4R,9aR)-7-{1-[3-methoxy-4-(4-methyl-1H-imidazol-1-yl)phenyl]-(E)-methylidene}-6-oxo-4-(3,4,5-trifluorophenyl)octahydropyrido[1,2-a]pyrazine-2-carboxylate, 100) methyl (4S,9aS)-7-{1-[3-methoxy-4-(4-methyl-1H-imidazol-1-yl)phenyl]-(E)-methylidene}-6-oxo-4-(3,4,5-trifluorophenyl)octahydropyrido[1,2-a]pyrazine-2-carboxylate, 101) (4R,9aS)-7-{1-[3-methoxy-4-(4-methyl-1H-imidazol-1-yl)phenyl]-(E)-methylidene}-4-(3,4,5-trifluorophenyl)octahydropyrido[1,2-a]pyrazin-6-one, 102) (4S,9aR)-7-{1-[3-methoxy-4-(4-methyl-1H-imidazol-1-yl)phenyl]-(E)-methylidene}-4-(3,4,5-trifluorophenyl)octahydropyrido[1,2-a]pyrazin-6-one, 103) (4S,9aS)-7-{1-[3-methoxy-4-(4-methyl-1H-imidazol-1-yl)phenyl]-(E)-methylidene}-4-(3,4,5-trifluorophenyl)octahydropyrido[1,2-a]pyrazin-6-one, 104) (4R,9aR)-7-{1-[3-methoxy-4-(4-methyl-1H-imidazol-1-yl)phenyl]-(E)-methylidene}-4-(3,4,5-trifluorophenyl)octahydropyrido[1,2-a]pyrazin-6-one, 105) (4S,9aR)-2-ethyl-7 {1-[3-methoxy-4-(4-methyl-1H-imidazol-1-yl)phenyl]-(E)-methylidene}-4-(3,4,5-trifluorophenyl)octahydropyrido[1,2-a]pyrazin-6-one, 106) (4R,9aS)-2-ethyl-7-{1-[3-methoxy-4-(4-methyl-1H-imidazol-1-yl)phenyl]-(E)-methylidene}-4-(3,4,5-trifluorophenyl)octahydropyrido[1,2-a]pyrazin-6-one, 107) (4R,9aR)-2-ethyl-7-{1-[3-methoxy-4-(4-methyl-1H-imidazol-1-yl)phenyl]-(E)-methylidene}-4-(3,4,5-trifluorophenyl)octahydropyrido[1,2-a]pyrazin-6-one, 108) (4S,9aS)-2-ethyl-7-{1-[3-methoxy-4-(4-methyl-1H-imidazol-1-yl)phenyl]-(E)-methylidene}-4-(3,4,5-trifluorophenyl)octahydropyrido[1,2-a]pyrazin-6-one, 109) (4S,9aR)-7-{1-[3-methoxy-4-(4-methyl-1H-imidazol-1-yl)phenyl]-(E)-methylidene}-2-methyl-4-(3,4,5-trifluorophenyl)octahydropyrido[1,2-a]pyrazin-6-one, 110) (4R,9aS)-7-{1-[3-methoxy-4-(4-methyl-1H-imidazol-1-yl)phenyl]-(E)-methylidene}-2-methyl-4-(3,4,5-trifluorophenyl)octahydropyrido[1,2-a]pyrazin-6-one, 111) (4S,9aR)-7-{1-[3-methoxy-4-(4-methyl-1H-imidazol-1-yl)phenyl]-(E)-methylidene}-2-propyl-4-(3,4,5-trifluorophenyl)octahydropyrido[1,2-a]pyrazin-6-one, 112) (4R,9aS)-7-{1-[3-methoxy-4-(4-methyl-1H-imidazol-1-yl)phenyl]-(E)-methylidene}-2-propyl-4-(3,4,5-trifluorophenyl)octahydropyrido[1,2-a]pyrazin-6-one, 113) (4R*,9aS*)-2-acetyl-7-{1-[3-methoxy-4-(4-methyl-1H-imidazol-1-yl)phenyl]-(E)-methylidene}-4-(3,4,5-trifluorophenyl)octahydropyrido[1,2-a]pyrazin-6-one, 114) (4R*,9aS*)-2-methanesulfonyl-7-{1-[3-methoxy-4-(4-methyl-1H-imidazol-1-yl)phenyl]-(E)-methylidene}-4-(3,4,5-trifluorophenyl)octahydropyrido[1,2-a]pyrazin-6-one, and 115) (4R*,9aS*)-7-{1-[3-methoxy-4-(4-methyl-1H-imidazol-1-yl)phenyl]-(E)-methylidene}-6-oxo-4-(3,4,5-trifluorophenyl)octahydropyrido[1,2-a]pyrazine-2-carboxylic acid dimethylamide;

28) A pharmaceutical agent comprising the compound or pharmacologically acceptable salt thereof according to any of 1) to 27) above as an active ingredient;

29) The pharmaceutical agent according to 28 above), which is a prophylactic or therapeutic agent for a disease caused by amyloid-β; and 30) The pharmaceutical agent according to 29) above, wherein the disease caused by amyloid-β is Alzheimer's disease, senile dementia, Down's syndrome, or amyloidosis.

DETAILED DESCRIPTION OF THE INVENTION

Meanings of symbols, terms, and the like used in the present specification will be explained, and the present invention will be described in detail below.

In the present specification, a structural formula of a compound may represent a certain isomer for convenience. However, the present invention includes all isomers and isomer mixtures such as geometric isomers which can be generated from the structure of a compound, optical isomers based on asymmetric carbon, stereoisomers, and tautomers. The present invention is not limited to the description of a chemical formula for convenience, and may include any one of the isomers or mixtures thereof. Accordingly, the compound of the present invention may have an asymmetric carbon atom in the molecule, and exist as an optically active compound or racemate, and the present invention includes each of the optically active compound and the racemate without limitations. Although crystal polymorphs of the compound may be present, the compound is not limited thereto as well and may be present as a single crystal form or a mixture of single crystal forms. The compound may be an anhydride or hydrate.

The "disease caused by Aβ" refers to a wide variety of diseases such as Alzheimer's disease (see Klein W L, and seven others, Alzheimer's disease-affected brain: Presence of oligomeric Aβ ligands (ADDLs) suggests a molecular basis for reversible memory loss, Proceding National Academy of Science USA, 2003, Sep. 2, 100(18), p. 10417-10422; Nitsch R M, and sixteen others, Antibodies against β-amyloid slow cognitive decline in Alzheimer's disease, Neuron, 2003, May 22, 38(4), p. 547-554; Jarrett J T, and two others, The carboxy terminus of the β amyloid protein is critical for the seeding of amyloid formation: Implications for the pathogenesis of Alzheimer's disease, Biochemistry, 1993, May 11, 32(18), p. 4693-4697; Glenner G G, and one other, Alzheimer's disease: initial report of the purification and characterization of a novel cerebrovascular amyloid protein, Biochemical and biophysical research communications, 1984, May 16, 120(3), p. 885-890; Masters C L, and six others, Amyloid plaque core protein in Alzheimer disease and Down syndrome, Proceding National Academy of Science USA, 1985, June, 82(12), p. 4245-4249; Gouras G K, and eleven others, Intraneuronal Aβ42 accumulation in human brain, American journal of pathology, 2000, January, 156(1), p. 15-20; Scheuner D, and twenty others, Secreted amyloid β-protein similar to that in the senile plaques of Alzheimer's disease is increased in vivo by the presenilin 1 and 2 and APP mutations linked to familial Alzheimer's disease, Nature Medicine, 1996, August, 2(8), p. 864-870; and Forman M S, and four others, Differential effects of the swedish mutant amyloid precursor protein on β-amyloid accumulation and secretion in neurons and non-neuronal cells, The journal of biological chemistry, 1997, Dec. 19, 272(51), p. 32247-32253, for example), senile dementia (see Blass J P, Brain metabolism and brain disease: Is metabolic deficiency the proximate cause of Alzheimer dementia? Journal of Neuroscience Research, 2001, Dec. 1, 66(5), p. 851-856, for example), frontotemporal dementia (see Evin G, and eleven others, Alternative transcripts of presenilin-1 associated with frontotemporal dementia, Neuroreport, 2002, Apr. 16, 13(5), p. 719-723, for example), Pick's disease (see Yasuhara O, and three others, Accumulation of amyloid precursor protein in brain lesions of patients with Pick disease, Neuroscience Letters, 1994, Apr. 25, 171 (1-2), p. 63-66, for example), Down's syndrome (see Teller J K, and ten others, Presence of soluble amyloid β-peptide precedes amyloid plaque formation in Down's syndrome, Nature Medicine, 1996, January, 2(1), p. 93-95; and Tokuda T, and six others, Plasma levels of amyloid β proteins Aβ1-40 and Aβ1-42(43) are elevated in Down's syndrome, Annals of Neurology, 1997, February, 41(2), p. 271-273, for example), cerebral angiopathy (see Hayashi Y, and nine others, Evidence for presenilin-1 involvement in amyloid angiopathy in the Alzheimer's disease-affected brain, Brain Research, 1998, Apr. 13, 789(2), p. 307-314; Barelli H, and fifteen others, Characterization of new polyclonal antibodies specific for 40 and 42 amino acid-long amyloid β peptides: their use to examine the cell biology of presenilins and the immunohistochemistry of sporadic Alzheimer's disease and cerebral amyloid angiopathy cases, Molecular Medicine, 1997, October, 3(10), p. 695-707; Calhoun M E, and ten others, Neuronal overexpression of mutant amyloid precursor protein results in prominent deposition of cerebrovascular amyloid, Proceding National Academy of Science USA, 1999, Nov. 23, 96(24), p. 14088-14093; and Dermaut B, and ten others, Cerebral amyloid angiopathy is a pathogenic lesion in Alzheimer's Disease due to a novel presenilin-1 mutation, Brain, 2001, December, 124(12), p. 2383-2392, for example), hereditary cerebral hemorrhage with amyloidosis (Dutch type) (see Cras P, and nine others, Presenile Alzheimer dementia characterized by amyloid angiopathy and large amyloid core type senile plaques in the APP 692Ala->Gly mutation, Acta Neuropathologica (Berl), 1998, September, 96(3), p. 253-260; Herzig M C, and fourteen others, Aβ is targeted to the vasculature in a mouse model of hereditary cerebral hemorrhage with amyloidosis, Nature Neuroscience, 2004, September, 7(9), p. 954-960; van Duinen S G, and five others, Hereditary cerebral hemorrhage with amyloidosis in patients of Dutch origin is related to Alzheimer disease, Proceding National Academy of Science USA, 1987, August, 84(16), p. 5991-5994; and Levy E, and eight others, Mutation of the Alzheimer's disease amyloid gene in hereditary cerebral hemorrhage, Dutch type, Science, 1990, Jun. 1, 248(4959), p. 1124-1126, for example), cognitive impairment (see Laws S M, and seven others, Association between the presenilin-1 mutation Glu318Gly and complaints of memory impairment, Neurobiology of Aging, 2002, January-February, 23(1), p. 55-58, for example), memory disorder and learning disability (see Vaucher E, and five others, Object recognition memory and cholinergic parameters in mice expressing human presenilin 1 transgenes, Experimental Neurology, 2002 June, 175(2), p. 398-406; Morgan D, and fourteen others, Aβ peptide vaccination prevents memory loss in an animal model of Alzheimer's disease, Nature, 2000 Dec. 21-28, 408(6815), p. 982-985; and Moran P M, and three others, Age-related learning deficits in transgenic mice expressing the 751-amino acid isoform of human β-amyloid precursor protein, Proceding National Academy of Science USA, 1995, Jun. 6, 92(12), p. 5341-5345, for example), amyloidosis, cerebral ischemia (see Laws S M, and seven others, Association between the presenilin-1 mutation Glu318Gly and complaints of memory impairment, Neurobiology of Aging, 2002, January-February, 23(1), p. 55-58; Koistinaho M, and ten others, β-amyloid precursor protein transgenic mice that harbor diffuse Aβ deposits but do not form plaques show increased ischemic vulnerability: Role of inflammation, Proceding National Academy of Science USA, 2002, Feb. 5, 99(3), p. 1610-1615; and Zhang F, and four others, Increased susceptibility to ischemic brain damage in transgenic mice overexpressing the amyloid precursor protein, The journal of neuroscience, 1997, Oct. 15, 17(20), p. 7655-7661, for example), vascular dementia (see Sadowski M, and six others, Links between the pathology of Alzheimer's disease and vascular dementia, Neurochemical Research, 2004, June, 29(6), p. 1257-1266, for example), opthalmoplegia (see O'Riordan S, and seven others, Presenilin-1 mutation (E280G), spastic paraparesis, and cranial MRI white-matter abnormalities, Neurology, 2002, Oct. 8, 59(7), p. 1108-1110, for example), multiple sclerosis (see Gehrmann J, and four others, Amyloid precursor protein (APP) expression in multiple sclerosis lesions, Glia, 1995, October, 15(2), p. 141-51; and Reynolds W F, and six others, Myeloperoxidase polymorphism is associated with gender specific risk for Alzheimer's disease, Experimental Neurology, 1999, January, 155 (1), p. 31-41, for example), head injury, cranial trauma (see Smith D H, and four others, Protein accumulation in traumatic brain injury, NeuroMolecular Medicine, 2003, 4(1-2), p. 59-72, for example), apraxia (see Matsubara-Tsutsui M, and seven others, Molecular evidence of presenilin 1 mutation in familial early onset dementia, American journal of Medical Genetics, 2002, Apr. 8, 114(3), p. 292-298, for example), prion disease, familial amyloid neuropathy, triplet repeat disease (see Kirkitadze M D, and two others, Paradigm shifts in Alzheimer's disease and other neurodegenerative disorders: the emerging role of oligomeric assemblies, Journal of Neuroscience Research, 2002, Sep. 1, 69(5), p. 567-577; Evert B O, and eight others, Inflammatory genes are upreglulated in expanded ataxin-3-expressing cell lines and spinocerebellar ataxia type 3 brains, The Journal of Neuroscience, 2001, Aug. 1, 21(15), p. 5389-5396; and Mann D M, and one other, Deposition of amyloid (A4) protein within the brains of persons with dementing disorders other than Alzheimer's disease and Down's syndrome, Neuroscience Letters, 1990, Feb. 5, 109(1-2), p. 68-75, for example), Parkinson's disease (see Primavera J, and four others, Brain accumulation of amyloid-β in Non-Alzheimer Neurodegeneration, Journal of Alzheimer's Disease, 1999, October, 1(3), p. 183-193, for example), Lewy body dementia (see Giasson B I, and two others, Interactions of amyloidogenic proteins. NeuroMolecular Medicine, 2003, 4(1-2), p. 49-58; Masliah E, and six others, β-amyloid peptides enhance α-synuclein accumulation and neuronal deficits in a transgenic mouse model linking Alzheimer's disease and Parkinson's disease, Proceding National Academy of Science USA, 2001, Oct. 9, 98(21), p. 12245-12250; Barrachina M, and six others, Amyloid-β deposition in the cerebral cortex in Dementia with Lewy bodies is accompanied by a relative increase in AβPP mRNA isoforms containing the Kunitz protease inhibitor, Neurochemistry International, 2005, February, 46(3), p. 253-260; and Primavera J, and four others, Brain accumulation of amyloid-β in Non-Alzheimer Neurodegeneration, Journal of Alzheimer's Disease, 1999, October, 1(3), p. 183-193, for example), parkinsonism-dementia complex (see Schmidt M L, and six others, Amyloid plaques in Guam amyotrophic lateral sclerosis/parkinsonism-dementia complex contain species of Aβ similar to those found in the amyloid plaques of Alzheimer's disease and pathological aging, Acta Neuropathologica (Berl), 1998, February, 95(2), p. 117-122; and Ito H, and three others, Demonstration of β amyloid protein-containing neurofibrillary tangles in parkinsonism-dementia complex on Guam, Neuropathology and applied neurobiology, 1991, October, 17(5), p. 365-373, for example), fronto-temporal dementia and parkinsonism linked to chromosome 17 (see Rosso S M, and three others, Coexistent tau and amyloid pathology in hereditary frontotemporal dementia with tau mutations, Annals of the New York academy of sciences, 2000, 920, p. 115-119, for example), dementia with argyrophilic grains (see Tolnay M, and four others, Low amyloid (Aβ) plaque load and relative predominance of diffuse plaques distinguish argyrophilic grain disease from Alzheimer's disease, Neuropathology and applied neurobiology, 1999, August, 25(4), p. 295-305, for example), Niemann-Pick disease (see Jin L W, and three others, Intracellular accumulation of amyloidogenic fragments of amyloid-β precursor protein in neurons with Niemann-Pick type C defects is associated with endosomal abnormalities, American Journal of Pathology, 2004, March, 164(3), p. 975-985, for example), amyotrophic lateral sclerosis (see Sasaki S, and one other, Immunoreactivity of β-amyloid precursor protein in amyotrophic lateral sclerosis, Acta Neuropathologica (Berl), 1999, May, 97(5), p. 463-468; Tamaoka A, and four others, Increased amyloid β protein in the skin of patients with amyotrophic lateral sclerosis, Journal of neurology, 2000, August, 247(8), p. 633-635; Hamilton R L, and one other, Alzheimer disease pathology in amyotrophic lateral sclerosis, Acta Neuropathologica, 2004, June, 107(6), p. 515-522; and Turner B J, and six others, Brain β-amyloid accumulation in transgenic mice expressing mutant superoxide dismutase 1, Neurochemical Research, 2004, December, 29(12), p. 2281-2286, for example), hydrocephalus (see Weller R O, Pathology of cerebrospinal fluid and interstitial fluid of the CNS: Significance for Alzheimer disease, prion disorders and multiple sclerosis, Journal of Neuropathology and Experimental Neurology, 1998, October, 57(10), p. 885-894; Silverberg G D, and four others, Alzheimer's disease, normal-pressure hydrocephalus, and senescent changes in CSF circulatory physiology: a hypothesis, Lancet neurology, 2003, August, 2(8), p. 506-511; Weller R O, and three others, Cerebral amyloid angiopathy: Accumulation of Aβ in interstitial fluid drainage pathways in Alzheimer's disease, Annals of the New York academy of sciences, 2000, April, 903, p. 110-117; Yow H Y, and one other, A role for cerebrovascular disease in determining the pattern of β-amyloid deposition in Alzheimer's disease, Neurology and applied neurobiology, 2002, 28, p. 149; and Weller R O, and four others, Cerebrovasculardisease is a major factor in the failure of elimination of Aβ from the aging human brain, Annals of the New York academy of sciences, 2002, November, 977, p. 162-168, for example), paraparesis (see O'Riordan S, and seven others, Presenilin-1 mutation (E280G), spastic paraparesis, and cranial MRI white-matter abnormalities, Neurology, 2002, Oct. 8, 59(7), p. 1108-1110; Matsubara-Tsutsui M, and seven others, Molecular evidence of presenilin 1 mutation in familial early onset dementia, American journal of Medical Genetics, 2002, Apr. 8, 114(3), p. 292-298; Smith M J, and eleven others, Variable phenotype of Alzheimer's disease with spastic paraparesis, Annals of Neurology, 2001, 49(1), p. 125-129; and Crook R, and seventeen others, A variant of Alzheimer's disease with spastic pararesis and unusual plaques due to deletion of exon 9 of presenilin 1, Nature Medicine, 1998, April; 4(4), p. 452-455, for example), progressive supranuclear palsy (see Barrachina M, and six others, Amyloid-β deposition in the cerebral cortex in Dementia with Lewy bodies is accompanied by a relative increase in AβPP mRNA isoforms containing the Kunitz protease inhibitor, Neurochemistry International, 2005, February, 46(3), p. 253-260; and Primavera J, and four others, Brain accumulation of amyloid-β in Non-Alzheimer Neurodegeneration, Journal of Alzheimer's Disease, 1999, October, 1(3), p. 183-193, for example), intracerebral hemorrhage (see Atwood C S, and three others, Cerebrovascular requirement for sealant, anticoagulant and remodeling molecules that allow for the maintenance of vascular integrity and blood supply, Brain Research Reviews, 2003, September, 43(1), p. 164-78; and Lowenson J D, and two others, Protein aging: Extracellular amyloid formation and intracellular repair, Trends in cardiovascular medicine, 1994, 4(1), p. 3-8, for example), convulsion (see Singleton A B, and thirteen others, Pathology of early-onset Alzheimer's disease cases bearing the Thr113-114ins presenilin-1 mutation, Brain, 2000, December, 123 (Pt12), p. 2467-2474, for example), mild cognitive impairment (see Gattaz W F, and four others, Platelet phospholipase A2 activity in Alzheimer's disease and mild cognitive impairment, Journal of Neural Transmission, 2004, May, 111(5), p. 591-601; and Assini A, and fourteen others, Plasma levels of amyloid β-protein 42 are increased in women with mild cognitive impairment, Neurology, 2004, Sep. 14, 63(5), p. 828-831, for example), and arteriosclerosis (see De Meyer G R, and eight others, Platelet phagocytosis and processing of β-amyloid precursor protein as a mechanism of macrophage activation in atherosclerosis, Circulation Reserach, 2002, Jun. 14, 90(11), p. 1197-1204, for example).

The "C1-6 alkyl group" used herein refers to a linear or branched alkyl group having 1 to 6 carbon atoms. Preferable examples of the group include linear or branched alkyl groups such as a methyl group, ethyl group, n-propyl group, i-propyl group, n-butyl group, i-butyl group, tert-butyl group, n-pentyl group, i-pentyl group, neopentyl group, n-hexyl group, 1-methylpropyl group, 1,2-dimethylpropyl group, 1-ethylpropyl group, 1-methyl-2-ethylpropyl group, 1-ethyl-2-methylpropyl group, 1,1,2-trimethylpropyl group, 1-methylbutyl group, 2-methylbutyl group, 1,1-dimethylbutyl group, 2,2-dimethylbutyl group, 2-ethylbutyl group, 1,3-dimethylbutyl group, 2-methylpentyl group, and 3-methylpentyl group.

The "C1-6 acyl group" refers to an alkyl group having 1 to 6 carbon atoms in which one hydrogen atom is substituted with a carbonyl group. Preferable examples of the group include an acetyl group, propionyl group, and butyryl group.

The "halogen atom" refers to a fluorine atom, chlorine atom, bromine atom, iodine atom, or the like, and is preferably a fluorine atom, chlorine atom, or bromine atom.

The "C3-8 cycloalkyl group" refers to a cyclic alkyl group having 3 to 8 carbon atoms. Preferable examples of the group include a cyclopropyl group, cyclobutyl group, cyclopentyl group, cyclohexyl group, cycloheptyl group, and cyclooctyl group.

The "C3-8 cycloalkoxy group" refers to a cyclic alkyl group having 3 to 8 carbon atoms in which one hydrogen atom is substituted with an oxygen atom. Preferable examples of the group include a cyclopropoxy group, cyclobutoxy group, cyclopentoxy group, cyclohexoxy group, cycloheptyloxy group, and cyclooctyloxy group.

The "C1-6 alkoxy group" refers to an alkyl group having 1 to 6 carbon atoms in which a hydrogen atom is substituted with an oxygen atom. Preferable examples of the group include a methoxy group, ethoxy group, n-propoxy group, i-propoxy group, n-butoxy group, i-butoxy group, sec-butoxy group, tert-butoxy group, n-pentoxy group, i-pentoxy group, sec-pentoxy group, tert-pentoxy group, n-hexoxy group, i-hexoxy group, 1,2-dimethylpropoxy group, 2-ethylpropoxy group, 1-methyl-2-ethylpropoxy group, 1-ethyl-2-methylpropoxy group, 1,1,2-trimethylpropoxy group, 1,1-dimethylbutoxy group, 2,2-dimethylbutoxy group, 2-ethylbutoxy group, 1,3-dimethylbutoxy group, 2-methylpentoxy group, 3-methylpentoxy group, and hexyloxy group.

The "C1-6 alkoxycarbonyl group" refers to a so-called ester group in which a carbonyl group is bonded to a C1-6 alkoxy group. Preferable examples of the group include a methoxycarbonyl group, ethoxycarbonyl group, n-propoxycarbonyl group, i-propoxycarbonyl group, n-butoxycarbonyl group, i-butoxycarbonyl group, n-pentoxycarbonyl group, and n-hexoxycarbonyl group.

The "C1-6 alklysulfonyl group" refers to an alkyl group having 1 to 6 carbon atoms in which one hydrogen atom is substituted with a sulfur atom. Preferable examples of the group include methylsulfonyl group, ethylsulfonyl group, n-propylsulfonyl group, i-propylsulfonyl group, n-butylsulfonyl group, i-butylsulfonyl group, tertially butylsulfonyl group, n-pentylsulfonyl group, i-pentylsulfonyl group, neopentylsulfonyl group, n-hexylsulfonyl group, and 1-methylpropylsulfonyl group.

The "methylene group that may be substituted with 1 or 2 substituents selected from Subsituent Group A1" may be, for example, a group of any of the formulas:

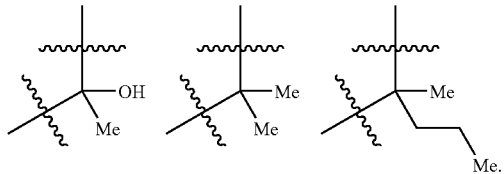

In addition to the above, the group may be another methylene group that may be substituted with 1 or 2 substituents selected from Substituent Group A1.

The "vinylene group that may be substituted with 1 or 2 substituents selected from Subsituent Group A1" may be, for example, a group of the formula:

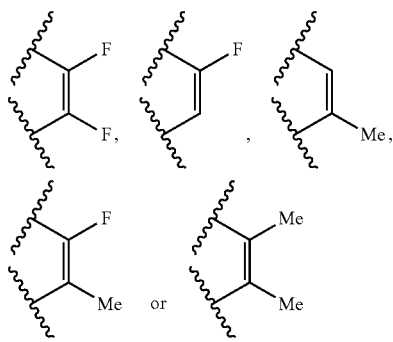

In addition to the above, the group may be another vinylene group that may be substituted with 1 or 2 substituents selected from Substituent Group A1.

The "imino group that may be substituent with a substituent selected from Substituent Group A1" may be, for example, a group of the formula:

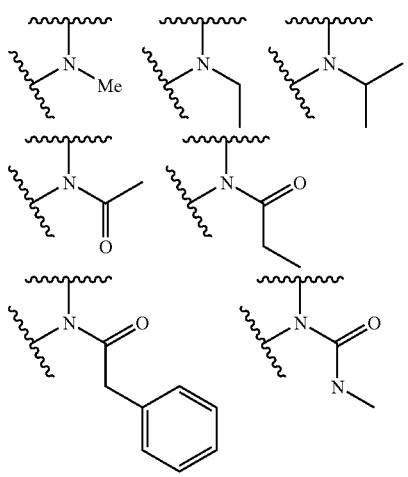

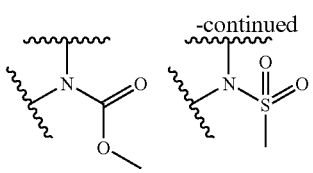

Preferable examples of the "C1-6 alkyl group wherein the C1-6 alkyl group may be substituted with 1 to 3 substituents selected from the group consisting of a halogen atom, hydroxyl group, cyano group, C3-8 cycloalkyl group, C1-6 alkoxy group, and C3-8 cycloalkoxy group" in Substituent Group A1 include a methyl group, trifluoromethyl group, hydroxymethyl group, cyanomethyl group, ethyl group, 2-hydroxyethyl group, n-propyl group, i-propyl group, 3-hydroxy-n-propyl group, tert-butyl group, n-pentyl group, i-pentyl group, neopentyl group, n-hexyl group, 1-methylpropyl group, 1,2-dimethylpropyl group, 1-ethylpropyl group, 1-methyl-2-ethylpropyl group, 1-ethyl-2-methylpropyl group, 1,1,2-trimethylpropyl group, 1-methylbutyl group, 2,2-dimethylbutyl group, 2-ethylbutyl group, 2-methylpentyl group, and 3-methylpentyl group.

Examples of the "C1-6 alkoxy group wherein the C1-6 alkoxy group may be substituted with 1 to 3 substituents selected from the group consisting of a halogen atom, hydroxyl group, cyano group, C3-8 cycloalkyl group, and C3-8 cycloalkoxy group" include a methoxy group, trifluoromethoxy group, hydroxymethoxy group, cyanomethoxy group, ethoxy group, 2-hydroxyethoxy group, n-propoxy group, i-propoxy group, 3-hydroxy-n-propoxy group, tert-butoxy group, n-pentoxy group, i-pentoxy group, neopentoxy group, n-hexoxy group, 1-methylpropoxy group, 1,2-dimethylpropoxy group, 1-ethylpropoxy group, 1-methyl-2-ethylpropoxy group, 1-ethyl-2-methylpropoxy group, 1,1,2-trimethylpropoxy group, 1-methylbutoxy group, 2,2-dimethylbutoxy group, 2-ethylbutoxy group, 2-methylpentoxy group, and 3-methylpentoxy group.

The "amino group that may be substituted with one or two C1-6 alkyl groups wherein the C1-6 alkyl groups may be substituted with 1 to 3 halogen atoms" refers to an amino group in which one or two hydrogen atoms are substituted with one or two C1-6 alkyl groups that may be substituted with 1 to 3 halogen atoms. Preferable examples of the group include a methylamino group, trifluoromethylamino group, dimethylamino group, ethylamino group, diethylamino group, n-propylamino group, i-propylamino group, 3-hydroxy-n-propylamino group, tert-butylamino group, n-pentylamino group, i-pentylamino group, neopentylamino group, n-hexylamino group, 1-methylpropylamino group, 1,2-dimethylpropylamino group, 1-ethylpropylamino group, 1-methyl-2-ethylpropylamino group, 1-ethyl-2-methylpropylamino group, 1,1,2-trimethylpropylamino group, 1-methylbutylamino group, 2,2-dimethylbutylamino group, 2-ethylbutylamino group, 2-methylpentylamino group, difluoromethylamino group, fluoromethylamino group, 2,2,2-trifluoroethylamino group, 2,2-difluoroethylamino group and 3-methylpentylamino group.

The "carbamoyl group that may be substituted with one or two C1-6 alkyl groups wherein the C1-6 alkyl groups may be substituted with 1 to 3 halogen atoms" refers to a carbamoyl group in which one or two hydrogen atoms are substituted with one or two alkyl groups having 1 to 6 carbon atoms. Preferable examples of the group include a methylcarbamoyl group, dimethylcarbamoyl group, ethylcarbamoyl group, diethylcarbamoyl group, n-propylcarbamoyl group, trifluoromethylcarbamoyl group, and di-n-propylcarbamoyl group.

Preferable examples of the "C1-6 alkoxycarbonyl group wherein the C1-6 alkoxy group may be substituted with 1 to 3 substituents selected from the group consisting of a halogen atom, hydroxyl group, cyano group, C3-8 cycloalkyl group, and C3-8 cycloalkoxy group" include a methoxycarbonyl group, trifluoromethoxycarbonyl group, hydroxymethoxycarbonyl group, cyanomethoxycarbonyl group, ethoxycarbonyl group, 2-hydroxyethoxycarbonyl group, n-propoxycarbonyl group, i-propoxycarbonyl group, 3-hydroxy-n-propoxycarbonyl group, tert-butoxycarbonyl group, n-pentoxy carbonyl group, i-pentoxycarbonyl group, neopentoxycarbonyl group, n-hexoxycarbonyl group, 1-methylpropoxycarbonyl group, 1,2-dimethylpropoxycarbonyl group, 1-ethylpropoxycarbonyl group, 1-methyl-2-ethylpropoxycarbonyl group, 1-ethyl-2-methylpropoxycarbonyl group, 1,1,2-trimethylpropoxycarbonyl group, 1-methylbutoxycarbonyl group, 2,2-dimethylbutoxycarbonyl group, 2-ethylbutoxycarbonyl group, 2-methylpentoxycarbonyl group, and 3-methylpentoxycarbonyl group. The "C1-6 alkylsulfonyl group" refers to sulfonyl group with linear or branched alkyl group having 1 to 6 carbon atoms. Preferable examples of the group include linear or branched alkylsulfonyl group such as a methansulfonyl group, ethylmethylsulfonyl group, n-propylsulfonyl group, i-propylsulfonyl group, n-butylsulfonyl group, i-butylsulfonyl group, ter-butylsulfonyl group, n-pentyl sulfonyl group, i-pentyl sulfonyl group, neopentyl sulfonyl group, n-hexylsulfonyl group, 1-methylpropylsulfonyl group, and so on.

In the present specification, there are no specific limitations to the "pharmacologically acceptable salt" insofar as it is a pharmacologically acceptable salt formed with a compound of the general formula (I) or (II) that is a prophylactic or therapeutic agent for a disease caused by Aβ. Preferable specific examples of the salt include hydrogen halides (such as hydrofluorides, hydrochlorides, hydrobromides, and hydroiodides), inorganic acid salts (such as sulfates, nitrates, perchlorates, phosphates, carbonates, and bicarbonates), organic carboxylates (such as acetates, oxalates, maleates, tartrates, fumarates, and citrates), organic sulfonates (such as methanesulfonates, trifluoromethanesulfonates, ethanesulfonates, benzenesulfonates, toluenesulfonates, and camphorsulfonates), amino acid salts (such as aspartates and glutamates), quaternary amine salts, alkali metal salts (such as sodium salts and potassium salts), and alkali earth metal salts (such as magnesium salts and calcium salts).

Next, the compound of the formula (I) or (II) of the present invention will be described.

In the compound of the formula (I) or (II) or pharmacologically acceptable salt thereof, $Ar_1$ is preferably a phenyl group that may be substituted with 1 to 3 substituents selected from Substituent Group A1 or a pyridinyl group that may be substituted with 1 to 3 substituents selected from Substituent Group A1, $Ar_1$ is more preferably a phenyl group substituted with 1 to 3 halogen atoms, and $Ar_1$ is most preferably a phenyl group substituted with 1 to 3 fluorine atoms or chlorine atoms.

In the compound of the formula (I) or (II) or pharmacologically acceptable salt thereof, $R^1$ and $R^2$ are preferably a hydrogen atom; a halogen atom; a hydroxyl group; a cyano group; a C3-8 cycloalkyl group; a C3-8 cycloalkoxy group; a C1-6 alkyl group, wherein the C1-6 alkyl group may be substituted with 1 to 3 substituents selected from the group consisting of a halogen atom, hydroxyl group, cyano group, C3-8 cycloalkyl group, C1-6 alkoxy group, and C3-8 cycloalkoxy group; a C1-6 alkoxy group, wherein the C1-6 alkoxy group may be substituted with 1 to 3 substituents selected from the group consisting of a halogen atom, hydroxyl group, cyano group, C3-8 cycloalkyl group, and C3-8 cycloalkoxy group; an amino group, wherein the amino group may be substituted with one or two C1-6 alkyl groups that are appropriately substituted with 1 to 3 halogen atoms; a carbamoyl group, wherein the carbamoyl group may be substituted with one or two C1-6 alkyl groups that are appropriately substituted with 1 to 3 halogen atoms; a carboxyl group; or a C1-6 alkoxycarbonyl group, wherein the C1-6 alkoxy group may be substituted with 1 to 3 substituents selected from the group consisting of a halogen atom, hydroxyl group, cyano group, C3-8 cycloalkyl group, and C3-8 cycloalkoxy group.

In the compound of the formula (I) or (II) or pharmacologically acceptable salt thereof, more preferably, $R^1$ and $R^2$ are the same or different and each represent hydrogen atom, a C1-6 alkyl group, halogen atom, or hydroxyl group.

In the compound of the formula (I) or (II) or pharmacologically acceptable salt thereof, $Z_1$ is preferably a methylene group that may be substituted with 1 or 2 substituents selected from Substituent Group A1, and $Z_1$ is more preferably a methylene group, wherein the methylene group may be substituted with 1 or 2 substituents selected from the group consisting of a C1-6 alkyl group, hydroxyl group, and halogen atom.

In the compound of the formula (I) or (II) or pharmacologically acceptable salt thereof, preferably, $Z_1$ represents a methylene group, wherein the methylene group may be substituted with 1 or 2 substituents selected from the group consisting of a C1-6 alkyl group, hydroxyl group, and halogen atom; and p, q, and r each represent 1.

In the compound of the formula (I) or pharmacologically acceptable salt thereof, preferably, $Z_1$ represents a methylene group, wherein the methylene group may be substituted with 1 or 2 substituents selected from the group consisting of a C1-6 alkyl group, hydroxyl group, and halogen atom; p and q each represent 1; and r represents 0.

In the compound of the formula (I) or (II) or pharmacologically acceptable salt thereof, preferably, $Z_1$ represents an oxygen atom; and p, q, and r each represent 1.

In the compound of the formula (I) or pharmacologically acceptable salt thereof, preferably, $Z_1$ represents a methylene group, wherein the methylene group may be substituted with 1 or 2 substituents selected from the group consisting of a C1-6 alkyl group, halogen atom, and hydroxyl group; p represents 1; and q and r each represent 0.

In the compound of the formula (I) or (II) or pharmacologically acceptable salt thereof, preferably, $Z_1$ represents a methylene group, wherein the methylene group may be substituted with 1 or 2 substituents selected from the group consisting of a C1-6 alkyl group, halogen atom, and hydroxyl group; p and r each represent 1; and q represents 0.

In the compound of the formula (I) or (II) or pharmacologically acceptable salt thereof, preferably, $Z_1$ represents a methylene group, wherein the methylene group may be substituted with 1 or 2 substituents selected from the group consisting of a C1-6 alkyl group, halogen atom, and hydroxyl group; p represents 1; q represents 2; and r represents 0.

In the compound of the formula (I) or (II) or pharmacologically acceptable salt thereof, preferably, $Z_1$ represents a methylene group, wherein the methylene group may be substituted with 1 or 2 substituents selected from the group consisting of a C1-6 alkyl group, halogen atom, and hydroxyl group; p and r each represent 1; and q represents 2.

In the compound of the formula (I) or (II) or pharmacologically acceptable salt thereof, preferably, $Z_1$ represents a vinylene group, wherein the vinylene group may be substituted with one or two C1-6 alkyl groups or halogen atoms; p represents 0; and q and r each represent 1.

In the compound of the formula (I) or (II) or pharmacologically acceptable salt thereof, preferably, $Z_1$ represents a vinylene group, wherein the vinylene group may be substituted with one or two C1-6 alkyl groups or halogen atoms; p and q each represent 1; and r represents 0.

In particular, a compound selected from the following group or a pharmacologically acceptable salt thereof is particularly suitable, for example, and is useful as a therapeutic or prophylactic agent for a disease such as Alzheimer's disease, senile dementia, Down's syndrome, or amyloidosis.

1) (E)-(3S)-(3,4,5-trifluorophenyl)-6-[3-methoxy-4-(4-methyl-1H-imidazol-1-yl)benzylidene]-(9R)-hexahydroindolizin-5-one,
2) (E)-(3R)-(3,4,5-trifluorophenyl)-6-[3-methoxy-4-(4-methyl-1H-imidazol-1-yl)benzylidene]-(9R)-hexahydroindolizin-5-one,
3) (E)-(3S)-(3,4,5-trifluorophenyl)-6-[3-methoxy-4-(4-methyl-1H-imidazol-1-yl)benzylidene]-(9S)-hexahydroindolizin-5-one,
4) (E)-(3R)-(3,4,5-trifluorophenyl)-6-[3-methoxy-4-(4-methyl-1H-imidazol-1-yl)benzylidene]-(9S)-hexahydroindolizin-5-one,
5) (E)-(3R)-(3,4-difluorophenyl)-6-[3-methoxy-4-(4-methyl-1H-imidazol-1-yl)benzylidene]-(9R)-hexahydroindolizin-5-one,
6) (E)-(3S)-(3,4-difluorophenyl)-6-[3-methoxy-4-(4-methyl-1H-imidazol-1-yl)benzylidene]-(9S)-hexahydroindolizin-5-one,
7) (E)-(6R,9aS)-6-(4-fluorophenyl)-3-[3-methoxy-4-(4-methyl-1H-imidazol-1-yl)benzylidene]octahydroquinolizin-4-one,
8) (E)-(6S,9aR)-6-(4-fluorophenyl)-3-[3-methoxy-4-(4-methyl-1H-imidazol-1-yl)benzylidene]octahydroquinolizin-4-one,
9) (E)-(6S,8S,9aR)-6-phenyl-8-hydroxy-3-[3-methoxy-4-(4-methyl-1H-imidazol-1-yl)benzylidene]octahydroquinolizin-4-one,
10) (E)-(6R,8R,9aS)-6-phenyl-8-hydroxy-3-[3-methoxy-4-(4-methyl-1H-imidazol-1-yl)benzylidene]octahydroquinolizin-4-one,
11) (E)-(6S,8S,9aR)-6-(4-fluorophenyl)-8-hydroxy-3-[3-methoxy-4-(4-methyl-1H-imidazol-1-yl)benzylidene]octahydroquinolizin-4-one,
12) (E)-(6R,8R,9aS)-6-(4-fluorophenyl)-8-hydroxy-3-[3-methoxy-4-(4-methyl-1H-imidazol-1-yl)benzylidene]octahydroquinolizin-4-one,
13) (E)-(6S,9aS)-6-(3,4,5-trifluorophenyl)-3-[3-methoxy-4-(4-methyl-1H-imidazol-1-yl)benzylidene]octahydroquinolizin-4-one,
14) (E)-(6R,9aR)-6-(3,4,5-trifluorophenyl)-3-[3-methoxy-4-(4-methyl-1H-imidazol-1-yl)benzylidene]octahydroquinolizin-4-one,
15) (E)-(6S,8S,9aR)-6-(3,4,5-trifluorophenyl)-8-hydroxy-3-[3-methoxy-4-(4-methyl-1H-imidazol-1-yl)benzylidene]octahydroquinolizin-4-one,
16) (E)-(6R,8R,9aS)-6-(3,4,5-trifluorophenyl)-8-hydroxy-3-[3-methoxy-4-(4-methyl-1H-imidazol-1-yl)benzylidene]octahydroquinolizin-4-one,
17) (E)-(6S,8R,9aR)-6-(3,4,5-trifluorophenyl)-8-hydroxy-3-[3-methoxy-4-(4-methyl-1H-imidazol-1-yl)benzylidene]octahydroquinolizin-4-one,
18) (E)-(6R,8S,9aS)-6-(3,4,5-trifluorophenyl)-8-hydroxy-3-[3-methoxy-4-(4-methyl-1H-imidazol-1-yl)benzylidene]octahydroquinolizin-4-one,
19) (E)-(6S,9aS)-6-(4-fluorophenyl)-3-[3-methoxy-4-(4-methyl-1H-imidazol-1-yl)benzylidene]octahydroquinolizin-4-one,
20) (E)-(6R,9aR)-6-(4-fluorophenyl)-3-[3-methoxy-4-(4-methyl-1H-imidazol-1-yl)benzylidene]octahydroquinolizin-4-one,
21) (E)-(5S)-(4-fluorophenyl)-2-[3-methoxy-4-(4-methyl-1H-imidazol-1-yl)benzylidene]-(8aS)-hexahydroindolizin-3-one,
22) (E)-(5R)-(4-fluorophenyl)-2-[3-methoxy-4-(4-methyl-1H-imidazol-1-yl)benzylidene]-(8aR)-hexahydroindolizin-3-one,
23) (E)-(5S)-(3,4-difluorophenyl)-2-[3-methoxy-4-(4-methyl-1H-imidazol-1-yl)benzylidene]-(8aS)-hexahydroindolizin-3-one,
24) (E)-(5R)-(3,4-difluorophenyl)-2-[3-methoxy-4-(4-methyl-1H-imidazol-1-yl)benzylidene]-(8aR)-hexahydroindolizin-3-one,
25) (Z)-(5S)-(3,4-difluorophenyl)-2-[3-methoxy-4-(4-methyl-1H-imidazol-1-yl)benzylidene]-(8aS)-hexahydroindolizin-3-one,
26) (Z)-(5R)-(3,4-difluorophenyl)-2-[3-methoxy-4-(4-methyl-1H-imidazol-1-yl)benzylidene]-(8aR)-hexahydroindolizin-3-one,
27) (E)-(5R,8aS)-5-(4-fluorophenyl)-2-[3-methoxy-4-(4-methyl-1H-imidazol-1-yl)benzylidene]hexahydroindolizin-3-one,
28) (E)-(5S,8aR)-5-(4-fluorophenyl)-2-[3-methoxy-4-(4-methyl-1H-imidazol-1-yl)benzylidene]hexahydroindolizin-3-one,
29) (E)-(6R,9aS)-3-[3-methoxy-4-(4-methyl-1H-imidazol-1-yl)benzylidene]-6-(4-methoxyphenyl)octahydroquinolizin-4-one,
30) (E)-(6S,9aR)-3-[3-methoxy-4-(4-methyl-1H-imidazol-1-yl)benzylidene]-6-(4-methoxyphenyl)octahydroquinolizin-4-one,
31) (E)-(4S,10aS)-4-(4-fluorophenyl)-7-[3-methoxy-4-(4-methyl-1H-imidazol-1-yl)benzylidene]octahydropyrido[1,2-a]azepin-6-one,
32) (E)-(4R,10aR)-4-(4-fluorophenyl)-7-[3-methoxy-4-(4-methyl-1H-imidazol-1-yl)benzylidene]octahydropyrido[1,2-a]azepin-6-one,
33) (E)-(5R,7aS)-5-(3,4-difluorophenyl)-2-[3-methoxy-4-(4-methyl-1H-imidazol-1-yl)benzylidene]hexahydropyrrolidin-3-one,
34) (E)-(3R,9aR)-3-(3,4-difluorophenyl)-6-[3-methoxy-4-(4-methyl-1H-imidazol-1-yl)benzylidene]octahydropyrrolo[1,2-a]azepin-5-one,
35) methyl (E)-4-{(4S*,9aR*)-7-[3-methoxy-4-(4-methyl-1-imidazol-1-yl)benzylidene]-6-oxooctahydroquinolizin-4-yl}benzoate,
36) (E)-(6S*,9aR*)-6-(4-hydroxymethylphenyl)-3-[3-methoxy-4-(4-methyl-1H-imidazol-1-yl)benzylidene]octahydroquinolizin-4-one, 37) (E)-(6S*,9aR*)-6-(4-cyanophenyl)-3-[3-methoxy-4-(4-methyl-1H-imidazol-1-yl)benzylidene]octahydroquinolizin-4-one,
38) (E)-4-{(4S*,9aR*)-7-[3-methoxy-4-(4-methyl-1H-imidazol-1-yl)benzylidene]-6-oxooctahydroquinolizin-4-yl}benzoic acid,
39) (E)-(6S*,9aR*)-6-(4-aminophenyl)-3-[3-methoxy-4-(4-methyl-1H-imidazol-1-yl)benzylidene]octahydroquinolizin-4-one,
40) (E)-4-{(4S*,9aR*)-7-[3-methoxy-4-(4-methyl-1H-imidazol-1-yl)benzylidene]-6-oxooctahydroquinolizin-4-yl}-N,N-dimethylbenzamide,
41) (E)-(6S,9aR)-6-(3-fluorophenyl)-3-[3-methoxy-4-(4-methyl-1H-imidazol-1-yl)benzylidene]octahydroquinolizin-4-one,
42) (E)-(6R,9aS)-6-(3-fluorophenyl)-3-[3-methoxy-4-(4-methyl-1H-imidazol-1-yl)benzylidene]octahydroquinolizin-4-one,
43) (E)-(6S,9aR)-6-(2-fluorophenyl)-3-[3-methoxy-4-(4-methyl-1H-imidazol-1-yl)benzylidene]octahydroquinolizin-4-one,
44) (E)-(6R,9aS)-6-(2-fluorophenyl)-3-[3-methoxy-4-(4-methyl-1H-imidazol-1-yl)benzylidene]octahydroquinolizin-4-one,
45) (E)-(6S,8R,9aR)-6-(4-fluorophenyl)-8-hydroxy-3-[3-methoxy-4-(4-methyl-1H-imidazol-1-yl)benzylidene]-8-methyl-octahydroquinolizin-4-one,
46) (E)-(6R,8S,9aS)-6-(4-fluorophenyl)-8-hydroxy-3-[3-methoxy-4-(4-methyl-1H-imidazol-1-yl)benzylidene]-8-methyl-octahydroquinolizin-4-one,
47) (E)-(6S,8R,9aR)-6-(4-fluorophenyl)-8-hydroxy-3-[3-methoxy-4-(4-methyl-1H-imidazol-1-yl)benzylidene]-8-methyloctahydroquinolizin-4-one,
48) (E)-(6R,8S,9aS)-6-(4-fluorophenyl)-8-hydroxy-3-[3-methoxy-4-(4-methyl-1H-imidazol-1-yl)benzylidene]-8-methyloctahydroquinolizin-4-one,
49) (E)-(6S,9aR)-6-(4-fluorophenyl)-3-[3-methoxy-4-(4-methyl-1H-imidazol-1-yl)benzylidene]-8-methyl-1,2,3,6,9,9a-hexahydroquinolizin-4-one,
50) (E)-(6R,9aS)-6-(4-fluorophenyl)-3-[3-methoxy-4-(4-methyl-1H-imidazol-1-yl)benzylidene]-8-methyl-1,2,3,6,9,9a-hexahydroquinolizin-4-one,
51) (E)-(6S,8S,9aR)-6-(4-fluorophenyl)-8-hydroxy-3-[3-methoxy-4-(4-methyl-1H-imidazol-1-yl)benzylidene]-8-methyloctahydroquinolizin-4-one,
52) (E)-(6R,8R,9aS)-6-(4-fluorophenyl)-8-hydroxy-3-[3-methoxy-4-(4-methyl-1H-imidazol-1-yl)benzylidene]-8-methyloctahydroquinolizin-4-one,
53) (E)-(4R,9aS)-7-[3-methoxy-4-(4-methylimidazol-1-yl)benzylidene]-4-phenylhexahydropyrido[2,1-c][1,4]oxazin-6-one,
54) (E)-(5S,7aR)-5-(3,4-difluorophenyl)-2-[3-methoxy-4-(4-methyl-1H-imidazol-1-yl)benzylidene]hexahydropyrrolidin-3-one,
55) (E)-(3S,9aS)-3-(3,4-difluorophenyl)-6-[3-methoxy-4-(4-methyl-1H-imidazol-1-yl)benzylidene]octahydropyrrolo[1,2-a]azepin-5-one,
56) (E)-(3S,8aS)-3-(4-chlorophenyl)-6-[3-methoxy-4-(4-methyl-1H-imidazol-1-yl)benzylidene]hexahydroindolizin-5-one,
57) (E)-(3S,8aS)-3-(2,4,5-trifluorophenyl)-6-[3-methoxy-4-(4-methyl-1H-imidazol-1-yl)benzylidene]hexahydroindolizin-5-one,
58) (E)-(3S,8aS)-3-(2,3,4-trifluorophenyl)-6-[3-methoxy-4-(4-methyl-1H-imidazol-1-yl)benzylidene]hexahydroindolizin-5-one,
59) (E)-(3S,8aS)-3-(2,5-difluorophenyl)-6-[3-methoxy-4-(4-methyl-1H-imidazol-1-yl)benzylidene]hexahydroindolizin-5-one,
60) (E)-(3S,8aS)-3-(3-fluorophenyl)-6-[3-methoxy-4-(4-methyl-1H-imidazol-1-yl)benzylidene]hexahydroindolizin-5-one,
61) (E)-(3S,8aS)-3-(2,6-difluoropyridin-3-yl)-6-[3-methoxy-4-(4-methyl-1H-imidazol-1-yl)benzylidene]hexahydroindolizin-5-one,
62) (E)-(3S,8aS)-3-(2,4-difluorophenyl)-6-[3-methoxy-4-(4-methyl-1H-imidazol-1-yl)benzylidene]hexahydroindolizin-5-one,
63) (E)-(3S,8aS)-3-(3-chlorophenyl)-6-[3-methoxy-4-(4-methyl-1H-imidazol-1-yl)benzylidene]hexahydroindolizin-5-one,
64) (E)-(3S,8aS)-3-(3,5-difluorophenyl)-6-[3-methoxy-4-(4-methyl-1H-imidazol-1-yl)benzylidene]hexahydroindolizin-5-one,
65) (E)-(6S,9aS)-6-(3,4-difluorophenyl)-3-[3-methoxy-4-(4-methyl-1H-imidazol-1-yl)benzylidene]octahydroquinolizin-4-one,
66) (E)-(6R,9aR)-6-(3,4-difluorophenyl)-3-[3-methoxy-4-(4-methyl-1H-imidazol-1-yl)benzylidene]octahydroquinolizin-4-one,
67) (E)-(6S,9aS)-6-(4-chlorophenyl)-3-[3-methoxy-4-(4-methyl-1H-imidazol-1-yl)benzylidene]octahydroquinolizin-4-one,
68) (E)-(6R,9aR)-6-(4-chlorophenyl)-3-[3-methoxy-4-(4-methyl-1H-imidazol-1-yl)benzylidene]octahydroquinolizin-4-one,
69) (E)-(S)-6-(3,4,5-trifluorophenyl)-3-[3-methoxy-4-(4-methyl-1H-imidazol-1-yl)benzylidene]-1,2,3,8,9,9a-hexahydroquinolizin-4-one,
70) (E)-(R)-6-(3,4,5-trifluorophenyl)-3-[3-methoxy-4-(4-methyl-1H-imidazol-1-yl)benzylidene]-1,2,3,8,9,9a-hexahydroquinolizin-4-one,
71) (E)-(6S,8S,9aR)-8-fluoro-3-[3-methoxy-4-(4-methyl-1H-imidazol-1-yl)benzylidene]-6-(3,4,5-trifluorophenyl)octahydroquinolizin-4-one,
72) (E)-(6S,8R,9aR)-8-methoxy-3-[3-methoxy-4-(4-methyl-1H-imidazol-1-yl)benzylidene]-6-(3,4,5-trifluorophenyl)octahydroquinolizin-4-one,
73) (E)-(R)-4-(4-fluorophenyl)-7-[3-methoxy-4-(4-methyl-1H-imidazol-1-yl)benzylidene]-3,4,8,9-tetrahydro-7H-pyrido[2,1-c][1,4]oxazin-6-one,
74) (E)-(S)-4-(4-fluorophenyl)-7-[3-methoxy-4-(4-methyl-1H-imidazol-1-yl)benzylidene]-3,4,8,9-tetrahydro-7H-pyrido[2,1-c][1,4]oxazin-6-one,
75) (E)-(4R,9aR)-4-(4-fluorophenyl)-7-[3-methoxy-4-(4-methyl-1H-imidazol-1-yl)benzylidene]hexahydropyrido[2,1-c][1,4]oxazin-6-one,
76) (E)-(4S,9aS)-4-(4-fluorophenyl)-7-[3-methoxy-4-(4-methyl-1H-imidazol-1-yl)benzylidene]hexahydropyrido[2,1-c][1,4]oxazin-6-one,
77) (E)-(6S,8R,9aR)-8-fluoro-3-[3-methoxy-4-(4-methyl-1H-imidazol-1-yl)benzylidene]-6-(3,4,5-trifluorophenyl)octahydroquinolizin-4-one,
78) (E)-(6S,9aR)-3-[3-methoxy-4-(4-methyl-1H-imidazol-1-yl)benzylidene]-6-(3,4,5-trifluorophenyl)-1,2,3,6,9,9a-hexahydroquinolizin-4-one,
79) (E)-(6S,9aR)-3-[3-methoxy-4-(4-methyl-1H-imidazol-1-yl)benzylidene]-6-(3,4,5-trifluorophenyl)-1,2,3,6,7,9a-hexahydroquinolizin-4-one,
80) (E)-(4R,9aR)-7-[3-methoxy-4-(4-methyl-1H-imidazol-1-yl)benzylidene]-4-(3,4,5-trifluorophenyl)hexahydropyrido[2,1-c][1,4]oxazin-6-one, 81) (E)-(4S,9aS)-7-[3-methoxy-4-(4-methyl-1H-imidazol-1-yl)benzylidene]-4-(3,4,5-trifluorophenyl)hexahydropyrido[2,1-c][1,4]oxazin-6-one,
82) (E)-(4S,9aR)-7-[3-methoxy-4-(4-methyl-1H-imidazol-1-yl)benzylidene]-4-(3,4,5-trifluorophenyl)hexahydropyrido[2,1-c][1,4]oxazin-6-one,
83) (E)-(4R,9aS)-7-[3-methoxy-4-(4-methyl-1H-imidazol-1-yl)benzylidene]-4-(3,4,5-trifluorophenyl)hexahydropyrido[2,1-c][1,4]oxazin-6-one,
84) (E)-(6R,7S,9aR)-7-hydroxy-3-[3-methoxy-4-(4-methyl-1H-imidazol-1-yl)benzylidene]-6-(3,4,5-trifluorophenyl)octahydroquinolizin-4-one,
85) (E)-(6S,7R,9aS)-7-hydroxy-3-[3-methoxy-4-(4-methyl-1H-imidazol-1-yl)benzylidene]-6-(3,4,5-trifluorophenyl)octahydroquinolizin-4-one,
86) (E)-(6R,7R,9aR)-7-hydroxy-3-[3-methoxy-4-(4-methyl-1H-imidazol-1-yl)benzylidene]-6-(3,4,5-trifluorophenyl)octahydroquinolizin-4-one,
87) (E)-(6S,7S,9aS)-7-hydroxy-3-[3-methoxy-4-(4-methyl-1H-imidazol-1-yl)benzylidene]-6-(3,4,5-trifluorophenyl)octahydroquinolizin-4-one,
88) (E)-(6S,9aR)-6-(4-fluorophenyl)-3-[3-methoxy-4-(4-methyl-1H-imidazol-1-yl)benzylidene]-1,2,3,6,9,9a-hexahydroquinolizin-4-one,
89) (3S,8aS)-6-{1-[3-methoxy-4-(4-methyl-1H-imidazol-1-yl)phenyl]-(E)-methylidene}-3-(2,4,6-trifluorophenyl)hexahydroindolizin-5-one,
90) (6S,9aR)-6-(3,4-difluorophenyl)-3-{1-[3-methoxy-4-(4-methyl-1H-imidazol-1-yl)phenyl]-(E)-methylidene}octahydroquinolizin-4-one,
91) (6S,9aR)-6-(3,4,5-trifluorophenyl)-3-{1-[3-methoxy-4-(4-methyl-1H-imidazol-1-yl)phenyl]-(E)-methylidene}octahydroquinolizin-4-one,
92) (6S,9aR)-6-(4-chlorophenyl)-3-{1-[3-methoxy-4-(4-methyl-1H-imidazol-1-yl)phenyl]-(E)-methylidene}octahydroquinolizin-4-one,
93) (E)-(3S,8aS)-3-(2,3-difluorophenyl)-6-[3-methoxy-4-(4-methyl-1H-imidazol-1-yl)benzylidene]hexahydroindolizin-5-one,
94) (4R,9aS)-4-(4-fluorophenyl)-7-{1-[3-methoxy-4-(4-methyl-1H-imidazol-1-yl)phenyl]-(E)-methylidene}hexahydropyrido[2,1-c][1,4]oxazin-6-one,
95) (4R,9aS)-4-(3,4-difluorophenyl)-7-{1-[3-methoxy-4-(4-methyl-1H-imidazol-1-yl)phenyl]-(E)-methylidene}hexahydropyrido[2,1-c][1,4]oxazin-6-one,
96) (4R,9aS)-4-(4-chlorophenyl)-7-{1-[3-methoxy-4-(4-methyl-1H-imidazol-1-yl)phenyl]-(E)-methylidene}hexahydropyrido[2,1-c][1,4]oxazin-6-one,
97) methyl (4S,9aR)-7-{1-[3-methoxy-4-(4-methyl-1H-imidazol-1-yl)phenyl]-(E)-methylidene}-6-oxo-4-(3,4,5-trifluorophenyl)octahydropyrido[1,2-a]pyrazine-2-carboxylate,
98) methyl (4R,9aS)-7-{1-[3-methoxy-4-(4-methyl-1H-imidazol-1-yl)phenyl]-(E)-methylidene}-6-oxo-4-(3,4,5-trifluorophenyl)octahydropyrido[1,2-a]pyrazine-2-carboxylate,
99) methyl (4R,9aR)-7-{1-[3-methoxy-4-(4-methyl-1H-imidazol-1-yl)phenyl]-(E)-methylidene}-6-oxo-4-(3,4,5-trifluorophenyl)octahydropyrido[1,2-a]pyrazine-2-carboxylate,
100) methyl (4S,9aS)-7-{1-[3-methoxy-4-(4-methyl-1H-imidazol-1-yl)phenyl]-(E)-methylidene}-6-oxo-4-(3,4,5-trifluorophenyl)octahydropyrido[1,2-a]pyrazine-2-carboxylate,
101) (4R,9aS)-7-{1-[3-methoxy-4-(4-methyl-1H-imidazol-1-yl)phenyl]-(E)-methylidene}-4-(3,4,5-trifluorophenyl)octahydropyrido[1,2-a]pyrazin-6-one,
102) (4S,9aR)-7-{1-[3-methoxy-4-(4-methyl-1H-imidazol-1-yl)phenyl]-(E)-methylidene}-4-(3,4,5-trifluorophenyl)octahydropyrido[1,2-a]pyrazin-6-one,
103) (4S,9aS)-7-{1-[3-methoxy-4-(4-methyl-1H-imidazol-1-yl)phenyl]-(E)-methylidene}-4-(3,4,5-trifluorophenyl)octahydropyrido[1,2-a]pyrazin-6-one,
104) (4R,9aR)-7-{1-[3-methoxy-4-(4-methyl-1H-imidazol-1-yl)phenyl]-(E)-methylidene}-4-(3,4,5-trifluorophenyl)octahydropyrido[1,2-a]pyrazin-6-one,
105) (4S,9aR)-2-ethyl-7-{1-[3-methoxy-4-(4-methyl-1H-imidazol-1-yl)phenyl]-(E)-methylidene}-4-(3,4,5-trifluorophenyl)octahydropyrido[1,2-a]pyrazin-6-one,
106) (4R,9aS)-2-ethyl-7-{1-[3-methoxy-4-(4-methyl-1H-imidazol-1-yl)phenyl]-(E)-methylidene}-4-(3,4,5-trifluorophenyl)octahydropyrido[1,2-a]pyrazin-6-one,
107) (4R,9aS)-2-ethyl-7-{1-[3-methoxy-4-(4-methyl-1H-imidazol-1-yl)phenyl]-(E)-methylidene}-4-(3,4,5-trifluorophenyl)octahydropyrido[1,2-a]pyrazin-6-one,
108) (4S,9aS)-2-ethyl-7-{1-[3-methoxy-4-(4-methyl-1H-imidazol-1-yl)phenyl]-(E)-methylidene}-4-(3,4,5-trifluorophenyl)octahydropyrido[1,2-a]pyrazin-6-one,
109) (4S,9aR)-7-{1-[3-methoxy-4-(4-methyl-1H-imidazol-1-yl)phenyl]-(E)-methylidene}-2-methyl-4-(3,4,5-trifluorophenyl)octahydropyrido[1,2-a]pyrazin-6-one,
110) (4R,9aS)-7-{1-[3-methoxy-4-(4-methyl-1H-imidazol-1-yl)phenyl]-(E)-methylidene}-2-methyl-4-(3,4,5-trifluorophenyl)octahydropyrido[1,2-a]pyrazin-6-one,
111) (4S,9aR)-7-{1-[3-methoxy-4-(4-methyl-1H-imidazol-1-yl)phenyl]-(E)-methylidene}-2-propyl-4-(3,4,5-trifluorophenyl)octahydropyrido[1,2-a]pyrazin-6-one,
112) (4R,9aS)-7-{1-[3-methoxy-4-(4-methyl-1H-imidazol-1-yl)phenyl]-(E)-methylidene}-2-propyl-4-(3,4,5-trifluorophenyl)octahydropyrido[1,2-a]pyrazin-6-one,
113) (4R*,9aS*)-2-acetyl-7-{1-[3-methoxy-4-(4-methyl-1H-imidazol-1-yl)phenyl]-(E)-methylidene}-4-(3,4,5-trifluorophenyl)octahydropyrido[1,2-a]pyrazin-6-one,
114) (4R*,9aS*)-2-methanesulfonyl-7-{1-[3-methoxy-4-(4-methyl-1H-imidazol-1-yl)phenyl]-(E)-methylidene}-4-(3,4,5-trifluorophenyl)octahydropyrido[1,2-a]pyrazin-6-one, and
115) (4R*,9aS*)-7-{1-[3-methoxy-4-(4-methyl-1H-imidazol-1-yl)phenyl]-(E)-methylidene}-6-oxo-4-(3,4,5-trifluorophenyl)octahydropyrido[1,2-a]pyrazine-2-carboxylic acid dimethylamide.

Preferable embodiments of the compound of the general formula (I) are as described above. The pharmaceutically active ingredient of the present invention is not limited to compounds specifically described in the present specification, and any embodiment may be arbitrarily selected within the definition of the compound of the general formula (I).

Methods for preparing the compound of the general formula (I) of the present invention will be described below.

The compound represented by the general formula (I):

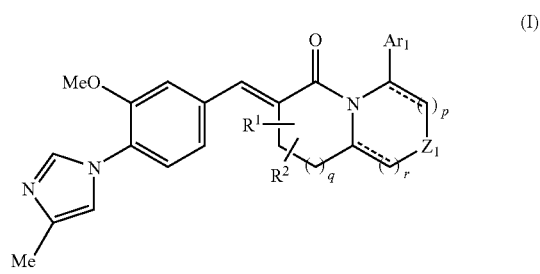

(I)

wherein ---- represents a single bond or a double bond; and $Ar_1, Z_1, R^1, R^2$, p, q, and r are as defined above, is synthesized according to a method such as the following General Preparation Method 1 to General Preparation Method 4, for example. It is obvious that, in order to prepare the compound of the present invention conveniently, the method comprises a protection reaction step and a deprotection reaction step appropriately, using a protecting group known to a person skilled in the art which is suitably selected for each step (see T. Greene et al., "Protective Groups in Organic Synthesis", John Wiley & Sons, Inc., New York, 1981).

General Preparation Method 1

Typically used General Preparation Method 1 for the compound of the general formula (I) of the present invention will be described below.

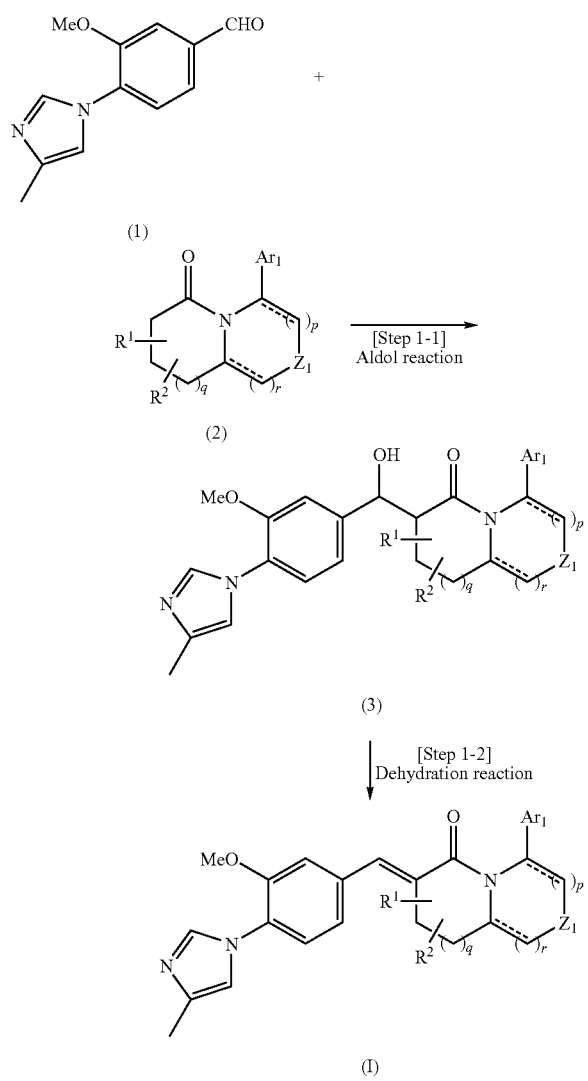

In the formula, ---- represents a single bond or a double bond; and $Ar_1, Z_1, R^1, R^2$, p, q, and r are as defined above.

The above General Production Method 1 is an example of a method for preparing the compound of the general formula (I) comprising converting an aldehyde compound (1) and a lactam compound (2) into an aldol adduct (3) by aldol reaction in Step 1-1 and then dehydrating the adduct.

Preparation of Compound of General Formula (I)

The compound of the general formula (I) can be prepared from an aldol adduct (3) according to Step 1-2. Specifically, the dehydration reaction in Step 1-2 varies according to the starting material and is not specifically limited insofar as the conditions are similar to those in this reaction. A known method described in many documents may be used for the reaction (see Jikken Kagaku Koza (Courses in Experimental Chemistry), vol. 19, Yuki Gosei (Organic Synthesis) [I], edited by The Chemical Society of Japan, Maruzen Co., Ltd., June 1992, p. 194-226, for example). Preferable examples of the method include i) a method of treating an aldol adduct (3) with preferably 0.1 to 100.0 equivalents of an acid, for example (see Jikken Kagaku Koza (Courses in Experimental Chemistry), vol. 19, Yuki Gosei (Organic Synthesis) [I], edited by The Chemical Society of Japan, Maruzen Co., Ltd., June 1992, p. 194-196, for example); and ii) a method of converting an alcohol group of an aldol adduct (3) into a leaving group such as an acetyl group, carboxylate group, sulfonate group, or halogen atom, and then treating the adduct with preferably 1.0 to 10.0 equivalents of a base, for example (see Jikken Kagaku Koza (Courses in Experimental Chemistry), vol. 19, Yuki Gosei (Organic Synthesis) [I], edited by The Chemical Society of Japan, Maruzen Co., Ltd., June 1992, p. 198-205, for example).

In the method i), the acid, solvent, and temperature conditions used vary according to the starting material and are not specifically limited. Preferable examples of the acid used include hydrochloric acid, sulfuric acid, phosphoric acid, potassium hydrogen sulfide, oxalic acid, p-toluenesulfonic acid, a boron trifluoride-ether complex, thionyl chloride, and alumina oxide. The method may be performed without a solvent, or with a solvent or a mixture thereof that does not inhibit the reaction and allows the starting material to be dissolved therein to a certain extent. Preferable examples of the solvent used include nonpolar solvents such as toluene and benzene; polar solvents such as acetone, dimethyl sulfoxide, and hexamethylphosphoramide; halogenated solvents such as chloroform and methylene chloride; and water. In addition, a combination of an acid with an organic base such as pyridine may preferably improve the reaction rate and reaction yield in some cases, for example. The reaction temperature must be a temperature that can complete the reaction without promoting formation of an undesirable by-product, and is preferably room temperature to 200° C., for example. Under preferable reaction conditions, the reaction is preferably completed in 1 to 24 hours, for example, and the progress of the reaction can be monitored by a known chromatography technique. An undesirable by-product can be removed by a technique known to a person skilled in the art such as a conventional chromatography technique, extraction, or/and crystallization.

Preferable examples of the leaving group in the method ii) include an acetyl group, methanesulfonate group, p-toluenesulfonate group, chlorine atom, bromine atom, and iodine atom. The method of conversion into such a leaving group varies according to the starting material and is not specifically limited. A method known to a person skilled in the art may be used as such a conversion method. Preferably 1.0 to 10.0 equivalents of an acetylating agent such as acetyl chloride or acetic anhydride; a sulfonating agent such as methanesulfonyl chloride or p-toluenesulfonyl chloride; or a halogenating agent such as thionyl chloride, for example, may be used preferably in a halogenated solvent such as methylene chloride or chloroform; a nonpolar solvent such as toluene or benzene; an ether solvent such as tetrahydrofuran or ethylene glycol dimethyl ether; or a mixed solvent thereof, for example. The target product may be efficiently obtained when using a base such as preferably pyridine or triethylamine in an amount of preferably 1.0 to 10.0 equivalents, for example, or as a reaction solvent in this step. The reaction temperature must be a temperature that can complete the reaction without promoting formation of an undesirable by-product, and is preferably −78 to 100° C., for example. Under preferable reaction conditions, the reaction is preferably completed in 1 to 24 hours, for example, and the progress of the reaction can be monitored by a known chromatography technique. An undesirable by-product can be removed by a technique known to a person skilled in the art such as a conventional chromatography technique, extraction, or/and crystallization. In the leaving reaction as the second step, preferably 1.0 to 10.0 equivalents of an organic base such as diazabicycloundecene, pyridine, 4-dimethyaminopyridine or triethylamine; a quaternary ammonium salt such as tetrabutylammonium hydroxide; an alkali metal salt such as sodium methoxide or potassium tert-butoxide; an alkali metal hydroxide such as sodium hydroxide; an alkali metal carbonate such as lithium carbonate or potassium carbonate; or an organic metal reagent such as lithium diisopropylamide, for example, is preferably used as a base preferably in a halogenated solvent such as methylene chloride or chloroform; a nonpolar solvent such as toluene or benzene; a polar solvent such as acetonitrile, dimethylformamide, or dimethyl sulfoxide; an ether solvent such as tetrahydrofuran or ethylene glycol dimethyl ether; or a mixed solvent thereof, for example. An organic base such as pyridine may also be used as a solvent. The reaction temperature must be a temperature that can complete the reaction without promoting formation of an undesirable by-product, and is preferably −78 to 100° C., for example. Under preferable reaction conditions, the reaction is preferably completed in 1 to 24 hours, for example, and the progress of the reaction can be monitored by a known chromatography technique. An undesirable by-product can be removed by a technique known to a person skilled in the art such as a conventional chromatography technique, extraction, or/and crystallization.

Preparation of Aldol Adduct (3)

The aldol adduct (3) can be prepared from an aldehyde compound (1) and 1.0 to 5.0 equivalents of a lactam compound (2) with respect to the aldehyde compound (1) according to Step 1-1, for example. Specifically, the aldol reaction in Step 1-1 varies according to the starting material and is not specifically limited insofar as the conditions are similar to those in this reaction. A method known to a person skilled in the art may be used for the reaction (see Jikken Kagaku Koza (Courses in Experimental Chemistry), vol. 20, Yuki Gosei (Organic Synthesis) [II], edited by The Chemical Society of Japan, Maruzen Co., Ltd., July 1992, p. 94-100, for example). Preferable examples of the method include i) a method of converting a lactam compound (2) into an alkali metal enolate by preferably 1.0 to 5.0 equivalents of a base, for example (preferably lithium diisopropylamide, butyl lithium, sodium amide, sodium hydride, sodium methoxide, or potassium tert-butoxide, for example) and then reacting the enolate with an aldehyde compound (1) (see Jikken Kagaku Koza (Courses in Experimental Chemistry), vol. 20, Yuki Gosei (Organic Synthesis) [II], edited by The Chemical Society of Japan, Maruzen Co., Ltd., July 1992, p. 97-98, for example); and ii) a method of converting a lactam compound (2) into an alkali metal enolate by preferably 1.0 to 5.0 equivalents of a base, for example (preferably lithium diisopropylamide, butyl lithium, sodium amide, sodium hydride, sodium methoxide, or potassium tert-butoxide, for example), reacting the enolate with a silicon halide reagent (preferably trimethylchlorosilane or tert-butyldimethylchlorosilane, for example) to once prepare silyl enol ether, and then reacting the ether with an aldehyde compound (1) in the presence of preferably 0.05 to 5.0 equivalents of a Lewis acid, for example (preferably titanium tetrachloride or boron trifluoride, for example) (see Jikken Kagaku Koza (Courses in Experimental Chemistry), vol. 20, Yuki Gosei (Organic Synthesis) [II], edited by The Chemical Society of Japan, Maruzen Co., Ltd., July 1992, p. 96-97, for example). The solvent and reaction temperature used vary according to the starting material and are not specifically limited. As a solvent that does not inhibit the reaction and allows the starting material to be dissolved therein to a certain extent, an ether solvent such as tetrahydrofuran, 1,4-dioxane, or diethyl ether; a halogenated solvent such as methylene chloride, 1,2-dichloroethane, or chloroform; a nonpolar solvent such as toluene or benzene; or a mixed solvent thereof may be preferably used, for example. The reaction temperature must be a temperature that can complete the reaction without promoting formation of an undesirable by-product, and is preferably −78° C. to room temperature, for example. Under preferable reaction conditions, the reaction is preferably completed in 0.5 to 24 hours, for example, and the progress of the reaction can be monitored by a known chromatography technique. An undesirable by-product can be removed by a technique known to a person skilled in the art such as a conventional chromatography technique, extraction, or/and crystallization.

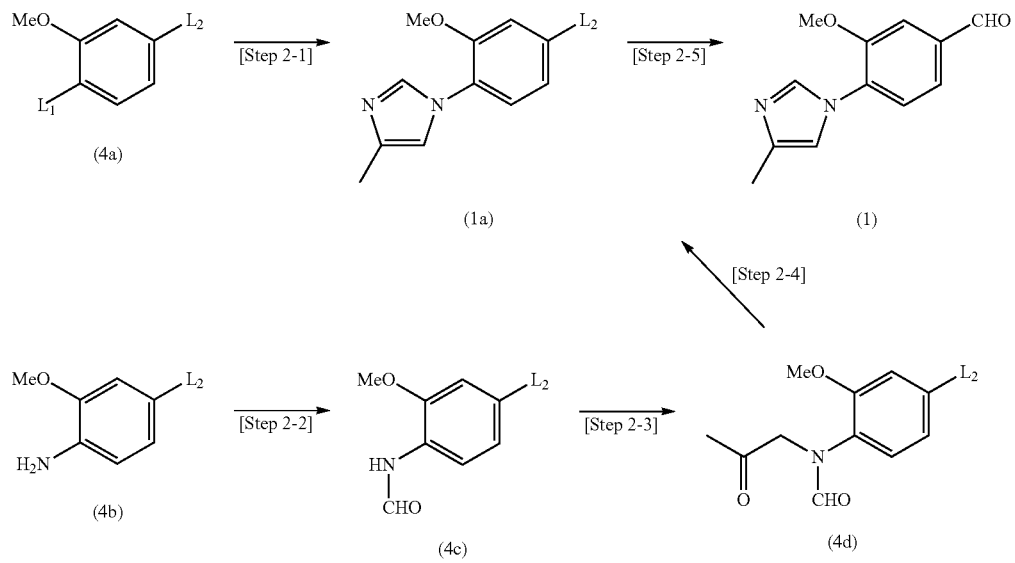

In the formula, $L_1$ represents a fluorine atom, a chlorine atom, a bromine atom, an iodine atom, a sulfonate group such as a triflate group, a trialkyltin group, a boronic acid group, a boronate group, or the like; and $L_2$ represents an alkyl ester group such as a methyl ester group, an aldehyde group, a cyano group, or the like.

Preparation of Aldehyde Compound (1)

The aldehyde compound (1) can be prepared from a compound (1a) as a starting material according to Step 2-5. Specifically, Step 2-5 varies according to the starting material and is not specifically limited insofar as the conditions are similar to those in this reaction. A method known to a person skilled in the art may be used for the reaction. For example, i) when $L_2$ is an alkyl ester group, a reduction reaction described in many known documents may be used (see Jikken Kagaku Koza (Courses in Experimental Chemistry), vol. 26, Yuki Gosei (Organic Synthesis) [VIII], edited by The Chemical Society of Japan, Maruzen Co., Ltd., April 1992, p. 159-266, for example). Preferably, the desired aldehyde compound (1) can be obtained by a reduction method using 1.0 to 10.0 equivalents of a metal hydride such as diisobutylaluminum hydride, for example. More preferably, the desired aldehyde compound (1) can be efficiently obtained by a reduction method using 1.0 to 10.0 equivalents of an aluminum hydride complex such as lithium aluminum hydride or sodium bis(2-methoxyethoxy)aluminum hydride with respect to a compound (1a) in the presence of 1.0 to 10.0 equivalents of an amine with respect to a reducing agent, for example (see T. Abe et al., "Tetrahedron", 2001, vol. 57, p. 2701-2710, for example). For example, ii) when $L_2$ is a cyano group, a reduction reaction described in many known documents may be used (see Jikken Kagaku Koza (Courses in Experimental Chemistry), vol. 26, Yuki Gosei (Organic Synthesis) [VIII], edited by The Chemical Society of Japan, Maruzen Co., Ltd., April 1992, p. 159-266, for example). Preferably, the desired aldehyde compound (1) can be obtained by a reduction method using 1.0 to 10.0 equivalents of a metal hydride such as sodium bis(2-methoxyethoxy)aluminum hydride or diisobutylaluminum hydride, for example (see Jikken Kagaku Koza (Courses in Experimental Chemistry), vol. 26, Yuki Gosei (Organic Synthesis) [VIII], edited by The Chemical Society of Japan, Maruzen Co., Ltd., April 1992, p. 231, for example). Alternatively, for example, iii) the desired aldehyde compound (1) can be efficiently obtained by reducing a compound (1a) to an alcohol compound using a technique known to a person skilled in the art (see Jikken Kagaku Koza (Courses in Experimental Chemistry), vol. 26, Yuki Gosei (Organic Synthesis) [VIII], edited by The Chemical Society of Japan, Maruzen Co., Ltd., April 1992, p. 159-266, for example), and then oxidizing the alcohol compound to an aldehyde compound (1) (see Jikken Kagaku Koza (Courses in Experimental Chemistry), vol. 23, Yuki Gosei (Organic Synthesis) [V], edited by The Chemical Society of Japan, Maruzen Co., Ltd., October 1991, p. 1-550, for example).

The base used in the reduction reaction varies according to the starting material and is not specifically limited. A secondary amine may be used as a base. Preferably, the desired aldehyde compound (1) can be efficiently obtained when using 1.0 to 10.0 equivalents of a linear or cyclic secondary alkylamine such as diethylamine or pyrrolidine with respect to a reducing agent, for example. The solvent used varies according to the starting material and is not specifically limited. As a solvent that does not inhibit the reaction and allows the starting material to be dissolved therein to a certain extent, an ether solvent such as tetrahydrofuran, 1,4-dioxane, or diethyl ether; a nonpolar solvent such as toluene or benzene; or a mixed solvent thereof may be preferably used, for example. The reaction temperature must be a temperature that can complete the reaction without promoting formation of an undesirable by-product, and is preferably −78° C. to room temperature, for example. Under preferable reaction conditions, the reaction is preferably completed in 1 to 24 hours, for example, and the progress of the reaction can be monitored by a known chromatography technique. An undesirable by-product can be removed by a technique known to a person skilled in the art such as a conventional chromatography technique, extraction, or/and crystallization.

The oxidizing agent, solvent, and reaction temperature used in the oxidation reaction vary according to the starting material and are not specifically limited. Preferable examples of the oxidizing agent include chromic acid oxidizing agents such as chromium oxide and dichromic acid; active manganese dioxide; dimethyl sulfoxide; periodic acid oxidizing agents such as Dess-Martin periodinane; and a mixture of an organic amine N-oxide such as 4-methylmorpholine N-oxide with tetrapropylammonium perruthenate (see Jikken Kagaku Koza (Courses in Experimental Chemistry), vol. 21, Yuki Gosei (Organic Synthesis) [III], edited by The Chemical Society of Japan, Maruzen Co., Ltd., February 1991, p. 2-23, for example). 1.0 to 50.0 equivalents of the oxidizing agent is preferably used with respect to the compound, for example. As a solvent that does not inhibit the reaction and allows the starting material to be dissolved therein to a certain extent, an ether solvent such as tetrahydrofuran, 1,4-dioxane, or diethyl ether; a halogenated solvent such as methylene chloride, 1,2-dichloroethane, or chloroform; a nonpolar solvent such as toluene or benzene; or a mixed solvent thereof may be preferably used, for example. The reaction temperature must be a temperature that can complete the reaction without promoting formation of an undesirable by-product, and is preferably −78° C. to 100° C., for example. Under preferable reaction conditions, the reaction is preferably completed in 1 to 24 hours, for example, and the progress of the reaction can be monitored by a known chromatography technique. An undesirable by-product can be removed by a technique known to a person skilled in the art such as a conventional chromatography technique, extraction, or/and crystallization.

Preparation of Compound (1a)

The compound (1a) can be prepared from i) a compound (4a) as a starting material according to Step 2-1, for example. Alternatively, the compound (1a) can be prepared from ii) a compound (4d) as a starting material according to Step 2-4.

In the method i), Step 2-1 varies according to the starting material and is not specifically limited insofar as the conditions are similar to those in this reaction. A method known to a person skilled in the art may be used for the reaction. For example, a compound (4a) and 4-methylimidazole are preferably subjected to coupling reaction under neutral or basic conditions (see D. D. Davey et al., "J. Med. Chem.", 1991, vol. 39, p. 2671-2677). Specifically, 1.0 to 5.0 equivalents of the compound (4a) is preferably used with respect to 4-methylimidazole, for example. Preferably, the reaction may efficiently proceed in some cases when 1.0 to 5.0 equivalents of a base is used, for example. Preferable examples of the base include sodium hydride, sodium hydroxide, potassium hydroxide, potassium carbonate, sodium carbonate, cesium carbonate, barium carbonate, and organic bases such as pyridine. The solvent used in this reaction varies according to the starting material, and is not specifically limited insofar as the solvent does not inhibit the reaction and allows the starting material to be dissolved therein to a certain extent. Preferable examples of the solvent include tetrahydrofuran, dimethyl sulfoxide, N,N-dimethylformamide, N-methylpyrrolidine, and acetonitrile. An organic base may also be used as a solvent. The reaction temperature must be a temperature that can complete the reaction without promoting formation of an undesirable by-product, and is preferably 50° C. to 200° C., for example. Under preferable reaction conditions, the reaction is preferably completed in 1 to 24 hours, for example, and the progress of the reaction can be monitored by a known chromatography technique. An undesirable by-product can be removed by a technique known to a person skilled in the art such as a conventional chromatography technique or/and crystallization.

In the method ii), Step 2-4 varies according to the starting material and is not specifically limited insofar as the conditions are similar to those in this reaction. A method known to a person skilled in the art may be used for the reaction (see Chemical & Pharmaceutical Bulletin, 1986, vol. 34, p. 3111, for example). Preferably, the desired compound (1a) can be obtained by heating a compound (4d) and 1.0 to 100.0 equivalents of ammonia or an ammonium salt with respect to the compound (4d), for example. The solvent and reaction temperature used vary according to the starting material and are not specifically limited. As a solvent that does not inhibit the reaction and allows the starting material to be dissolved therein to a certain extent, an ether solvent such as tetrahydrofuran, 1,4-dioxane, or diethyl ether; a halogenated solvent such as methylene chloride, 1,2-dichloroethane, or chloroform; an alcohol solvent such as ethanol or methanol; a polar solvent such as dimethylformamide or N-methylpyrrolidone; a nonpolar solvent such as toluene; an organic acid such as acetic acid; or a mixed solvent thereof may be preferably used, for example. More preferably, the compound (1a) can be efficiently obtained by using 5.0 to 20.0 equivalents of ammonium acetate in an acetic acid solvent, for example. The reaction temperature must be a temperature that can complete the reaction without promoting formation of an undesirable by-product, and is preferably room temperature to 200° C., for example. Under preferable reaction conditions, the reaction is preferably completed in 1 to 24 hours, for example, and the progress of the reaction can be monitored by a known chromatography technique. An undesirable by-product can be removed by a technique known to a person skilled in the art such as a conventional chromatography technique, extraction, or/and crystallization.

Preparation of Compound (4a)

The compound (4a) is commercially available or can be obtained by a technique known to a person skilled in the art. If not commercially available, the preferable compound (4a), wherein $L_1$ represents a fluorine atom, chlorine atom, or bromine atom, can be obtained by oxidizing a corresponding methyl compound or alcohol compound by an oxidation reaction known to a person skilled in the art; by reducing a corresponding ester compound by a known reduction reaction, or by methylating a corresponding phenol compound.

Preparation of Compound (4d)

The compound (4d) can be prepared from a compound (4c) as a starting material according to Step 2-3, for example. Specifically, Step 2-3 varies according to the starting material and is not specifically limited insofar as the conditions are similar to those in this reaction. A method known to a person skilled in the art may be used for the reaction (see Helvetica Chimica Acta, 1998, vol. 81, p. 1038). Preferably, the compound (4d) can be obtained by stirring a compound (4c) and 1.0 to 10.0 equivalents of 2-halogenated acetone (preferably 2-chloroacetone, 2-bromoacetone, or 2-iodoacetone, for example) with respect to the compound (4c) in the presence of 1.0 to 10.0 equivalents of a base with respect to the compound (4c), for example. Preferable examples of the base used include alkali metal hydrides (preferably sodium hydride and lithium hydride, for example), alkali metal salts (preferably potassium carbonate, sodium carbonate, and cesium carbonate, for example), and metal alkoxides (preferably sodium methoxide and tert-butyl potassium, for example). The solvent and reaction temperature used vary according to the starting material and are not specifically limited. As a solvent that does not inhibit the reaction and allows the starting material to be dissolved therein to a certain extent, an ether solvent such as tetrahydrofuran, 1,4-dioxane, or diethyl ether; a halogenated solvent such as methylene chloride, 1,2-dichloroethane, or chloroform; a polar solvent such as dimethylformamide or N-methylpyrrolidone; a nonpolar solvent such as toluene or benzene; or a mixture thereof may be preferably used, for example. The reaction temperature must be a temperature that can complete the reaction without promoting formation of an undesirable by-product, and is preferably room temperature to 200° C., for example. Under preferable reaction conditions, the reaction is preferably completed in 1 to 24 hours, for example, and the progress of the reaction can be monitored by a known chromatography technique. An undesirable by-product can be removed by a technique known to a person skilled in the art such as a conventional chromatography technique, extraction, or/and crystallization.

Preparation of Compound (4c)

The compound (4c) can be prepared from a compound (4b) as a starting material according to Step 2-2, for example. Specifically, the desired formylamide compound (4c) can be preferably obtained by a method of heating under reflux a compound (4b) in 10.0 to 100.0 equivalents of formic acid with respect to the compound (4b), or by a method of using formic acid and a dehydration condensation agent (an acid anhydride or dicyclohexylcarbodiimide, for example) for a compound (4b), for example. Preferably, the compound (4c) can be efficiently obtained by using 1 to 20 equivalents of formic acid with respect to the compound (4b) and 1 to 3 equivalents of a dehydration condensation agent with respect to the compound (4b), for example. The solvent used varies according to the starting material and is not specifically limited. As a solvent that does not inhibit the reaction and allows the starting material to be dissolved therein to a certain extent, an ether solvent such as tetrahydrofuran, 1,4-dioxane, or diethyl ether; a halogenated solvent such as methylene chloride, 1,2-dichloroethane, or chloroform; a polar solvent such as dimethylformamide or N-methylpyrrolidone; a nonpolar solvent such as toluene or benzene; or a mixture thereof may be preferably used, for example. The reaction temperature must be a temperature that can complete the reaction without promoting formation of an undesirable by-product, and is preferably room temperature to 100° C., for example. Under preferable reaction conditions, the reaction is preferably completed in 1 to 24 hours, for example, and the progress of the reaction can be monitored by a known chromatography technique. An undesirable by-product can be removed by a technique known to a person skilled in the art such as a conventional chromatography technique, extraction, or/and crystallization.

Preparation of Compound (4b)

The compound (4b) is commercially available or can be prepared by a method known to a person skilled in the art. If not commercially available, the compound (4b) can be prepared by methylating a corresponding nitrophenol compound by a method known to a person skilled in the art, and then reducing the nitroanisole compound.

Preparation of lactam compound (2)

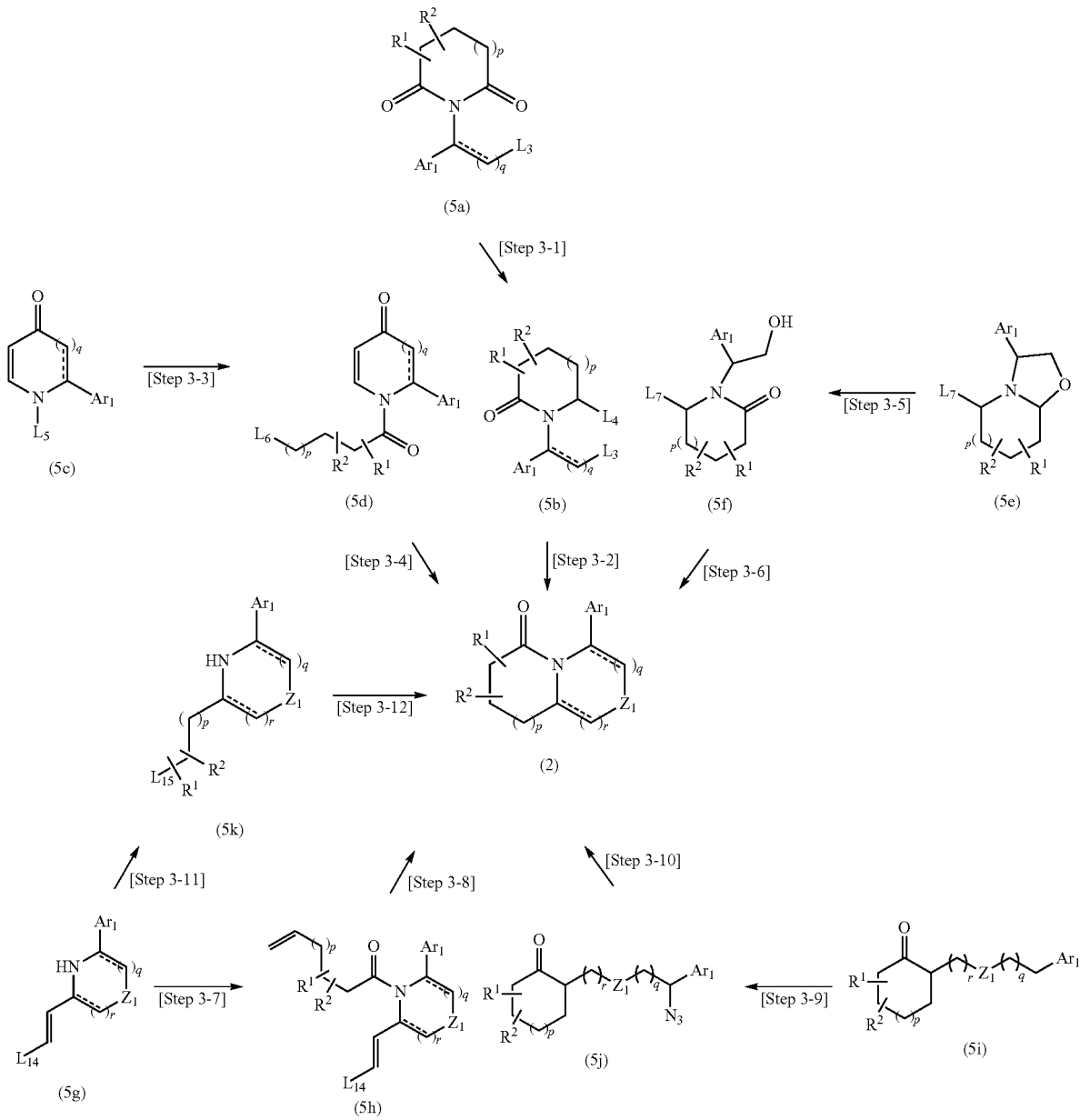

In the formula, ----represents a single bond or a double bond; $Ar_1$, $Z_1$, $R^1$, $R^2$, p, q, and r are as defined above; $L_3$ represents an alkyl ester group such as a methyl ester group or ethyl ester group, or an alkyl ketone group, aryl ketone group, or aralkyl ketone group such as an acetyl group, benzoyl group, or aryl methyl ketone group; $L_4$ represents an alkoxy group such as a methoxy group or ethoxy group; $L_5$ represents a carbamate protecting group such as a methyl carbamate group, benzyl carbamate group, or tert-butyl carbamate group, or an amide protecting group such as an acetyl group; $L_6$ represents a halogen atom such as a bromine atom or iodine atom; $L_7$ represents a nitrile group, an alkyl ester group such as a methyl ester group, or an alkyl ketone group such as an acetyl group; $L_{14}$ represents a hydrogen atom, an alkyl group such as a methyl group or ethyl group, a phenyl group that may be substituted with 1 to 3 substituents selected from the above Substituent Group A1, an ester group such as a methyl ester group or ethyl ester group, a phosphate group such as dimethyl phosphate or diethyl phosphate, an alkylsulfonyl group such as a methylsulfonyl group, an arylsulfonyl group such as a phenylsulfonyl group, or the like; and $L_{15}$ represents an alkyl ketone group such as an acetyl group, an aryl ketone group such as a benzoyl group, a formyl group, an alkyl ester group such as a methyl ester group or ethyl ester group, or an aryl ester group such as a phenyl ester group.

The above reaction formula shows an example of a method for preparing the lactam compound (2). Specifically, the formula shows (i) a method for preparing the lactam compound (2) comprising converting an imide compound (5a) as a starting material that is commercially available or prepared using a method known to a person skilled in the art (see Tetrahedron: Asymmetry, 1998, vol. 9, p. 4361, for example) into an alkoxylactam compound (5b) according to Step 3-1, and then continuously performing carbon Prolongation reaction and cyclization reaction in Step 3-2; (ii) a method for preparing the lactam compound (2) comprising converting a 4-pyridone compound (5c) as a starting material that is commercially available or prepared using a method known to a person skilled in the art (see Tetrahedron Letters, 1986, vol. 27, p. 4549, for example) into an acylated compound (5d) according to Step 3-3, and then performing cyclization reaction in Step 3-4; (iii) a method for preparing the lactam compound (2) comprising converting an oxazolidine compound (5e) as a starting material that is commercially available or prepared using a method known to a person skilled in the art (see European Journal of Organic Chemistry, 2004, vol. 23, p. 4823, for example) into an amide alcohol compound (5f) according to Step 3-5, and then performing cyclization reaction in Step 3-6; (iv) a method for preparing the lactam compound (2) comprising converting a vinyl group substituted cyclic amine compound (5g) as a starting material that is commercially available or prepared using a method known to a person skilled in the art (see Tetrahedron Letters, 1998, vol. 39, p. 5421, and Tetrahedron Letters, 2004, vol. 45, p. 4895, for example) into an acylated compound (5h) according to Step 3-7, and then performing cyclization reaction in Step 3-8; (v) a method for preparing the lactam compound (2) comprising converting a cycloalkyl ketone compound (51) as a starting material that is commercially available or prepared using a method known to a person skilled in the art (see The Journal of Organic Chemistry, 2001, vol. 66, p. 886, for example) into an azide compound (5j) according to Step 3-9, and then performing cyclization reaction in Step 3-10; or (vi) a method for preparing the lactam compound (2) comprising converting a vinyl group substituted cyclic amine compound (5g) as a starting material into a compound (5k) according to Step 3-11, and then performing cyclization reaction in Step 3-12.

Conversion of Imide Compound (5a) into Alkoxylactam Compound (5b)

Partial reduction of an imide group in Step 3-1 varies according to the starting material and can be performed by a method known to a person skilled in the art insofar as the conditions are similar to those in this reaction. Preferably, the desired alkoxylactam compound (5b) can be obtained by reacting an imide compound (5a) with 1.0 to 5.0 equivalents of sodium borohydride with respect to the imide compound (5a) in an alcohol solvent such as methanol (see Jikken Kagaku Koza (Courses in Experimental Chemistry), vol. 26, Yuki Gosei (Organic Synthesis) [VIII], edited by The Chemical Society of Japan, Maruzen Co., Ltd., April 1992, p. 207-237, for example) or reacting an imide compound (5a) with 1.0 to 5.0 equivalents of borane with respect to the imide compound (5a) in an ether solvent such as tetrahydrofuran (see Jikken Kagaku Koza (Courses in Experimental Chemistry), vol. 26, Yuki Gosei (Organic Synthesis) [VIII], edited by The Chemical Society of Japan, Maruzen Co., Ltd., April 1992, p. 237-248, for example); and then performing reaction in an alcohol solvent such as methanol in the presence of 0.1 to 10.0 equivalents of an inorganic acid such as sulfuric acid with respect to the imide compound (5a), for example. Alternatively, the desired alkoxylactam compound (5b) can be preferably obtained in one step by stirring an imide compound (5a) and 1.0 to 5.0 equivalents of sodium borohydride with respect to the imide compound (5a) in an alcohol solvent such as methanol in the presence of 0.1 to 5.0 equivalents of an inorganic acid such as sulfuric acid with respect to the imide compound (5a), for example (see Tetrahedron: Asymmetry, 1998, vol. 9, p. 4361, for example). The reaction temperature must be a temperature that can complete the reaction without promoting formation of an undesirable by-product, and is preferably −78° C. to 100° C., for example. Under preferable reaction conditions, the reaction is preferably completed in 1 to 24 hours, for example, and the progress of the reaction can be monitored by a known chromatography technique. An undesirable by-product can be removed by a technique known to a person skilled in the art such as a conventional chromatography technique, extraction, or/and crystallization.

Conversion of Alkoxylactam Compound (5b) into Lactam Compound (2)

In Step 3-2, the desired lactam compound (2) can be obtained by reacting $L_3$ of the alkoxylactam compound (5b) with a Wittig reagent (see Jikken Kagaku Koza (Courses in Experimental Chemistry), vol. 25, Yuki Gosei (Organic Synthesis) [VII], edited by The Chemical Society of Japan, Maruzen Co., Ltd., September 1991, p. 254-262, for example), a Grignard reagent (see Jikken Kagaku Koza (Courses in Experimental Chemistry), vol. 25, Yuki Gosei (Organic Synthesis) [VII], edited by The Chemical Society of Japan, Maruzen Co., Ltd., September 1991, p. 59-72, for example), or an alkyl lithium reagent (see Jikken Kagaku Koza (Courses in Experimental Chemistry), vol. 25, Yuki Gosei (Organic Synthesis) [VII], edited by The Chemical Society of Japan, Maruzen Co., Ltd., September 1991, p. 9-51, for example) to derive an olefin derivative therefrom, and then reacting the derivative with an acid such as hydrochloric acid. Preferably, the desired lactam compound (2) can be obtained in a high yield by stirring the alkoxylactam compound (5b) and 1.0 to 10.0 equivalents of a Grignard reagent such as trimethylsilylmethylmagnesium chloride with respect to the alkoxylactam compound (5b) in an ether solvent such as tetrahydrofuran in the presence of 1.0 to 10.0 equivalents of cerium chloride with respect to the alkoxylactam compound (5b); and then reacting the solution with an inorganic acid such as hydrochloric acid, for example (see Tetrahedron: Asymmetry, 1998, vol. 9, p. 4361, for example). The reaction temperature must be a temperature that can complete the reaction without promoting formation of an undesirable by-product, and is preferably −78° C. to 100° C., for example. Under preferable reaction conditions, the reaction is preferably completed in 1 to 24 hours, for example, and the progress of the reaction can be monitored by a known chromatography technique. An undesirable by-product can be removed by a technique known to a person skilled in the art such as a conventional chromatography technique, extraction, or/and crystallization.

Conversion of 4-Pyridone Compound (5c) into Acylated Compound (5d)

Step 3-3 consists of deprotection reaction of an amine moiety and subsequent amidation reaction. As deprotection reaction of a compound (5c), a deprotection reaction described in many known documents may be used (see T. W. Green, "Protective Groups in Organic Synthesis", John Wiley & Sons, Inc., 1981, for example). In this reaction, the amine compound may be obtained from a corresponding carbamate compound (preferably a tert-butyl carbamate compound, benzyl carbamate compound, or 9-fluorenylmethyl carbamate compound, for example) or from a corresponding amide compound (preferably a formamide compound, acetamide compound, trifluoroacetamide compound, for example). This deprotection reaction varies according to the starting material and is not specifically limited insofar as the conditions are similar to those in this reaction. A known method may be used for the reaction. Under preferable reaction conditions, the reaction is preferably completed in 1 to 24 hours, for example, and the progress of the reaction can be monitored by a known chromatography technique. An undesirable by-product can be removed by a technique known to a person skilled in the art such as a conventional chromatography technique or/and crystallization. The amidation reaction varies according to the starting material and is not specifically limited insofar as the conditions are similar to those in this reaction. A known method described in many documents may be used for the reaction (see Shin Jikken Kagaku Koza (New Courses in Experimental Chemistry), vol. 14, Yuki Kagobutsu No Gosei To Hannou (Synthesis and Reaction of Organic Compounds) [II], edited by The Chemical Society of Japan, Maruzen Co., Ltd., February 1978, p. 1136-1162, for example). Preferable examples of the method include i) a method of reacting the amine compound with 1.0 to 5.0 equivalents of an acid halide compound with respect to the amine compound (see Shin Jikken Kagaku Koza (New Courses in Experimental Chemistry), vol. 14, Yuki Kagobutsu No Gosei To Hannou (Synthesis and Reaction of Organic Compounds) [II], edited by The Chemical Society of Japan, Maruzen Co., Ltd., February 1978, p. 1142-1145, for example); and ii) a method of reacting the amine compound with 1.0 to 5.0 equivalents of a carboxylic acid compound with respect to the amine compound using 1.0 to 5.0 equivalents of a condensing agent with respect to the amine compound (see "Yukikagaku Jikken No Tebiki (Introduction to Organic Chemistry Experiments) [4]", Kagaku-Dojin Publishing Company, Inc., September 1990, p. 27-52, for example).

In the method i), the base used varies according to the starting material and is not specifically limited. The base is preferably 1.0 to 100.0 equivalents of pyridine, triethylamine, N,N-diisopropylethylamine, lutidine, quinoline, or isoquinoline with respect to the amine compound, for example. The solvent used is not specifically limited insofar as the solvent does not inhibit the reaction and allows the starting material to be dissolved therein to a certain extent. Preferable examples of the solvent include tetrahydrofuran and 1,4-dioxane. A base may be used as a solvent. Alternatively, it is possible to use a two-layer partition system consisting of a base that is an alkali solution, preferably a sodium hydroxide or potassium hydroxide solution, for example, and a halogenated solvent such as methylene chloride or 1,2-dichloroethane. The reaction temperature must be a temperature that can complete the reaction without promoting formation of an undesirable by-product, and is preferably ice-cold temperature to 100° C., for example. Under preferable reaction conditions, the reaction is preferably completed in 1 to 24 hours, for example, and the progress of the reaction can be monitored by a known chromatography technique. An undesirable by-product can be removed by a technique known to a person skilled in the art such as a conventional chromatography technique or/and crystallization.

In the method ii), the condensing agent used varies according to the starting material and is not specifically limited. For example, 1.0 to 2.0 equivalents of 1,3-dicyclohexylcarbodiimide, 1-ethyl-3-(3'-dimethylaminopropyl)carbodiimide, benzotriazol-1-yloxytris(dimethylamino)phosphonium hexafluorophosphate, diethyl cyanophosphonate, or bis(2-oxo-3-oxazolidinyl)phosphinic chloride may be appropriately used with respect to the carboxylic acid used. Preferably, 1.0 to 2.0 equivalents of N-hydroxysuccinimide or N-hydroxybenzotriazole may be added with respect to the carboxylic acid compound used in order to make the reaction efficiently proceed, for example. This reaction is preferably performed in the presence of a solvent from the viewpoint of operativity and stirring efficiency. The solvent used varies according to the starting material and the condensing agent used, and is not specifically limited insofar as the solvent does not inhibit the reaction and allows the starting material to be dissolved therein to a certain extent. Preferable examples of the solvent that can be used include halogenated solvents such as methylene chloride and 1,2-dichloroethane, and polar solvents such as tetrahydrofuran and N,N-dimethylformamide. The reaction temperature must be a temperature that can complete the reaction without promoting formation of an undesirable by-product, and is preferably ice-cold temperature to 100° C., for example. Under preferable reaction conditions, the reaction is preferably completed in 1 to 24 hours, for example, and the progress of the reaction can be monitored by a known chromatography technique. An undesirable by-product can be removed by a technique known to a person skilled in the art such as a conventional chromatography technique or/and crystallization.

Conversion of Acylated Compound (5d) into Lactam Compound (2)

Step 3-4 is cyclization reaction through radical formation. Specifically, for example, the desired lactam compound (2) can be preferably obtained in a high yield by reacting the compound (5d) with preferably 1.0 to 2.0 equivalents of an alkyltin reagent such as tributyltin with respect to the compound (5d), for example, in a nonpolar solvent such as toluene in the presence of preferably 0.1 to 1.0 equivalent of a radical initiator such as 2,2-azobis(isobutyronitrile) with respect to the compound (5d), for example. The reaction temperature must be a temperature that can complete the reaction without promoting formation of an undesirable by-product, and is preferably 50° C. to 150° C., for example. Under preferable reaction conditions, the reaction is preferably completed in 1 to 24 hours, for example, and the progress of the reaction can be monitored by a known chromatography technique. An undesirable by-product can be removed by a technique known to a person skilled in the art such as a conventional chromatography technique or/and crystallization. After cyclization, $Z_1$ may be converted in various manners using a ketone group as a scaffold by a method known to a person skilled in the art such as reduction reaction (see Jikken Kagaku Koza (Courses in Experimental Chemistry), vol. 26, Yuki Gosei (Organic Synthesis) [VIII], edited by The Chemical Society of Japan, Maruzen Co., Ltd., April 1992, p. 159-266, for example), addition reaction (see Jikken Kagaku Koza (Courses in Experimental Chemistry), vol. 25, Yuki Gosei (Organic Synthesis) [VII], edited by The Chemical Society of Japan, Maruzen Co., Ltd., September 1991, p. 9-72, for example), or addition dehydration reaction (see Jikken Kagaku Koza (Courses in Experimental Chemistry), vol. 19, Yuki Gosei (Organic Synthesis) [I], edited by The Chemical Society of Japan, Maruzen Co., Ltd., June 1992, p. 57-85, for example).

Conversion of Oxazolidine Compound (5e) into Amide Alcohol Compound (5f)

Step 3-5 is oxidative cleavage reaction of an oxazolidine ring which derives an amide alcohol compound (5f) from a compound (5e). Specifically, the desired amide alcohol compound (5f) can be preferably obtained in a high yield by reacting a compound (5e) with 2.0 to 10.0 equivalents of potassium permanganate with respect to the compound (5e) in an aqueous solvent such as a mixture of water with acetone, for example (see European Journal of Organic Chemistry, 2004, vol. 23, p. 4823, for example), or the compound (5f) can be preferably obtained by reacting a compound (5e) with 1.0 to 10.0 equivalents of bromine with respect to the compound (5e) in a halogenated solvent such as methylene chloride, for example (see Synlett, 1994, vol. 2, p. 143, for example). The solvent used in this step varies according to the starting material and the oxidizing agent used, and is not specifically limited insofar as the solvent does not inhibit the reaction and allows the starting material to be dissolved therein to a certain extent. The reaction temperature must be a temperature that can complete the reaction without promoting formation of an undesirable by-product, and is preferably ice-cold temperature to 100° C., for example. Under preferable reaction conditions, the reaction is preferably completed in 1 to 24 hours, for example, and the progress of the reaction can be monitored by a known chromatography technique. An undesirable by-product can be removed by a technique known to a person skilled in the art such as a conventional chromatography technique or/and crystallization.

Conversion of Amide Alcohol Compound (5f) into Lactam Compound (2)

Step 3-6 consists of conversion of $L_7$ of the amide alcohol compound (5f) into an alcohol or amine and subsequent cyclization reaction. Specifically, the conversion of $L_7$ of the amide alcohol compound (5f) into an alcohol varies according to the starting material, and can be performed by a method known to a person skilled in the art insofar as the conditions are similar to those in this reaction (see Jikken Kagaku Koza (Courses in Experimental Chemistry), vol. 20, Yuki Gosei (Organic Synthesis) [II], edited by The Chemical Society of Japan, Maruzen Co., Ltd., July 1992, p. 1-30, for example). The conversion of $L_7$ of the amide alcohol compound (5f) into an amine varies according to the starting material, and can be performed by a method known to a person skilled in the art insofar as the conditions are similar to those in this reaction (see Jikken Kagaku Koza (Courses in Experimental Chemistry), vol. 20, Yuki Gosei (Organic Synthesis) [II], edited by The Chemical Society of Japan, Maruzen Co., Ltd., July 1992, p. 279-318, for example). The cyclization reaction of the alcohol compound or the amine compound varies according to the starting material, and can be performed by a method known to a person skilled in the art insofar as the conditions are similar to those in this reaction (see Journal of Fluorine Chemistry, 1997, vol. 2, p. 119, or Scientia Pharmaceutica, 1996, vol. 64, p. 3, for example). Preferably, the lactam compound (2) can be obtained in a high yield by heating the alcohol compound in a solvent or without a solvent in the presence of 0.1 to 10 equivalents of an organic acid such as p-toluenesulfonic acid or camphorsulfonic acid or an inorganic acid such as sulfuric acid or hydrochloric acid with respect to the alcohol compound, for example. The cyclization reaction of the amine compound varies according to the starting material, and can be performed by a method known to a person skilled in the art insofar as the conditions are similar to those in this reaction (see Petrochemia, 1990, vol. 30, p. 56; WO 2003/076386; or Tetrahedron Letters, 1982, vol. 23, p. 229, for example). Preferably, the lactam compound (2) can be obtained in a high yield by stirring the amine compound in a solvent such as tetrahydrofuran, toluene, methylene chloride, or dimethylformamide in the presence of 0.1 to 1.0 equivalents of an organic metal such as tetrakistriphenylphosphine palladium or tristriphenylphosphine ruthenium with respect to the amine compound, for example. Obviously, the solvent used in this step varies according to the starting material and the reagent used, and is not specifically limited insofar as the solvent does not inhibit the reaction and allows the starting material to be dissolved therein to a certain extent. The reaction temperature must be a temperature that can complete the reaction without promoting formation of an undesirable by-product, and is preferably ice-cold temperature to 100° C., for example. Under preferable reaction conditions, the reaction is preferably completed in 1 to 24 hours, for example, and the progress of the reaction can be monitored by a known chromatography technique. An undesirable by-product can be removed by a technique known to a person skilled in the art such as a conventional chromatography technique or/and crystallization.

Conversion of Vinyl Group Substituted Cyclic Amine Compound (5g) into Acylated Compound (5h)

The acylated compound (5h) can be prepared from a vinyl group substituted cyclic amine compound (5g) as a starting material in Step 3-7. Specifically, Step 3-7 is performed by the same method as in Step 3-3.

Conversion of Acylated Compound (5h) into Lactam Compound (2)

Step 3-8 consists of ring closing metathesis reaction and subsequent double bond modification reaction. The ring closing metathesis reaction varies according to the starting material and can be performed by a method known to a person skilled in the art insofar as the conditions are similar to those in this reaction (see Comprehensive Organometallic Chemistry, 1982, vol. 8, p. 499, or Angewandte Chemie International Edition, 2000, vol. 39, p. 3012, for example). Preferably, the double bond modification reaction may be performed by, for example, i) catalytic hydrogenation (see Jikken Kagaku Koza (Courses in Experimental Chemistry), vol. 26, Yuki Gosei (Organic Synthesis) [VIII], edited by The Chemical Society of Japan, Maruzen Co., Ltd., April 1992, p. 251-266, for example); ii) hydroboration (see Jikken Kagaku Koza (Courses in Experimental Chemistry), vol. 25, Yuki Gosei (Organic Synthesis) [VII], edited by The Chemical Society of Japan, Maruzen Co., Ltd., September 1991, p. 83-134, for example); or iii) oxidation of a carbon-carbon double bond (see Jikken Kagaku Koza (Courses in Experimental Chemistry), vol. 23, Yuki Gosei (Organic Synthesis) [V], edited by The Chemical Society of Japan, Maruzen Co., Ltd., October 1991, p. 237-267, for example).

The ring closing metathesis reaction is preferably a method of stirring the acylated compound (5h) in a solvent in the presence of 0.01 to 0.2 equivalent of a metal catalyst with respect to the acylated compound (5h), for example. Preferable examples of the solvent used include halogenated solvents such as methylene chloride and chloroform; ether solvents such as tetrahydrofuran, 1,4-dioxane, 1,2-dimethoxyethane; nonpolar solvents such as benzene, toluene, and xylene; and mixed solvents thereof. The metal catalyst used varies according to the starting material and the solvent. Preferable examples of the metal catalyst used include ruthenium catalysts such as bis(tricyclohexylphosphine)benzylidene ruthenium (IV) dichloride, benzylidene [1,3-bis(2,4,6-trimethylphenyl)-2-imidazolidinylidene] dichloro(tricyclohexylphosphine) ruthenium (IV), and [1,3-bis(2,4,6-trimethylphenyl)-2-imidazolidinylidene]dichloro (o-isopropoxyphenylmethylidene)ruthenium (IV); and molybdenum catalysts such as 2,6-diisopropylphenylimidoneophylidene biphen molybdenum (VI) and 2,6-diisopropylphenylimidoneophylidene molybdenum (VI) bis (hexafluoro-tert-butoxide). The reaction temperature must be a temperature that can complete the reaction without promoting formation of an undesirable by-product, and is preferably room temperature to 100° C., for example. Under preferable reaction conditions, the reaction is preferably completed in 1 to 24 hours, for example, and the progress of the reaction can be monitored by a known chromatography technique. An undesirable by-product can be removed by a technique known to a person skilled in the art such as a conventional chromatography technique, extraction, or/and crystallization.

Conversion of Cycloalkyl Ketone Compound (5i) into Azide Compound (5i)

Step 3-9 consists of i) halogenation reaction at the α-position of an aromatic ring (—$\underline{CH_2}$—$Ar_1$) and ii) subsequent azide introduction reaction.

The halogenation reaction i) varies according to the starting material and can be performed by a method known to a person skilled in the art insofar as the conditions are similar to those in this reaction (see Jikken Kagaku Koza (Courses in Experimental Chemistry), vol. 19, Yuki Gosei (Organic Synthesis) [I], edited by The Chemical Society of Japan, Maruzen Co., Ltd., June 1992, p. 422-458, for example). Preferable examples of the method include a method of stirring a cycloalkyl ketone compound (51) and 1.0 to 2.0 equivalents of a halogenating agent with respect to the cycloalkyl ketone compound (5i) in a solvent. Preferable examples of the halogenating agent used include N-bromosuccinimide and bromine. In addition, the reaction may be remarkably promoted by adding preferably 0.01 to 0.5 equivalent of a radical initiator such as benzoyl peroxide or 2,2-azobisisobutyronitrile with respect to the cycloalkyl ketone compound (5i), for example, or by adding preferably 0.01 to 0.5 equivalent of an acid catalyst such as hydrobromic acid with respect to the cycloalkyl ketone compound (5i), for example. The solvent used varies according to the starting material, and is not specifically limited insofar as the solvent does not inhibit the reaction and allows the starting material to be dissolved therein to a certain extent. Preferable examples of the solvent include carbon tetrachloride and benzene. The reaction temperature must be a temperature that can complete the reaction without promoting formation of an undesirable by-product, and is preferably room temperature to 150° C., for example. Under preferable reaction conditions, the reaction is preferably completed in 1 to 24 hours, for example, and the progress of the reaction can be monitored by a known chromatography technique. An undesirable by-product can be removed by a technique known to a person skilled in the art such as a conventional chromatography technique, extraction, or/and crystallization.

The azidation reaction ii) varies according to the starting material and can be performed by a method known to a person skilled in the art insofar as the conditions are similar to those in this reaction (see Jikken Kagaku Koza (Courses in Experimental Chemistry), vol. 20, Yuki Gosei (Organic Synthesis) [II], edited by The Chemical Society of Japan, Maruzen Co., Ltd., July 1992, p. 415-420, for example). Preferably, the halogenated compound and 1.0 to 5.0 equivalents of an azidating agent with respect to the halogenated compound are stirred in a solvent, for example. Preferable examples of the azidating agent used include sodium azide and trimethylsilyl azide. Preferably, the reaction may be remarkably promoted by using 0.1 to 5.0 equivalents of a quaternary amine salt such as tetrabutylammonium fluoride with respect to the azidating agent used, for example. The solvent used varies according to the starting material, and is not specifically limited insofar as the solvent does not inhibit the reaction and allows the starting material to be dissolved therein to a certain extent. Preferable examples of the solvent used include ether solvents such as tetrahydrofuran and dioxane; halogenated solvents such as chloroform and methylene chloride; nonpolar solvents such as benzene and toluene; and polar solvents such as acetone, acetonitrile, dimethylformamide, and N-methylpyrrolidine. The reaction temperature must be a temperature that can complete the reaction without promoting formation of an undesirable by-product, and is preferably room temperature to 150° C., for example. Under preferable reaction conditions, the reaction is preferably completed in 1 to 24 hours, for example, and the progress of the reaction can be monitored by a known chromatography technique. An undesirable by-product can be removed by a technique known to a person skilled in the art such as a conventional chromatography technique, extraction, or/and crystallization.

Conversion of Azide Compound (5i) into Lactam Compound (2)

Step 3-10 is a method for preparing the lactam compound (2) comprising stirring an azide compound (5j) in a solvent in the presence of 1.0 to 10.0 equivalents of an acid with respect to the azide compound (5j) to cause rearrangement reaction. Specifically, this step varies according to the starting material and can be performed by a method known to a person skilled in the art insofar as the conditions are similar to those in this reaction (see The Journal of Organic Chemistry, 2001, vol. 66, p. 886, for example). Preferable examples of the acid used include trifluoromethanesulfonic acid, trifluoroacetic acid, sulfuric acid, and hydrochloric acid. Although the acid may be used as a solvent, this reaction is preferably performed in the presence of a separate solvent from the viewpoint of operativity and stirring efficiency. The solvent used varies according to the starting material, and is not specifically limited insofar as the solvent does not inhibit the reaction and allows the starting material to be dissolved therein to a certain extent. Preferable examples of the solvent include halogenated solvents such as chloroform and methylene chloride; and nonpolar solvents such as benzene and toluene. The reaction temperature must be a temperature that can complete the reaction without promoting formation of an undesirable by-product, and is preferably −78° C. to 50° C., for example. Under preferable reaction conditions, the reaction is preferably completed in 1 to 24 hours, for example, and the progress of the reaction can be monitored by a known chromatography technique. An undesirable by-product can be removed by a technique known to a person skilled in the art such as a conventional chromatography technique, extraction, or/and crystallization.

Conversion of Vinyl Group Substituted Cyclic Amine Compound (5g) into Compound (5k)

The compound (5k) can be prepared from the vinyl group substituted cyclic amine compound (5g) as a starting material in Step 3-11. Step 3-11 consists of double bond reduction reaction and subsequent carbon prolongation reaction.

A method described in many known documents may be used for the double bond reduction reaction. Preferable examples of the method include i) catalytic hydrogenation reaction (see Jikken Kagaku Koza (Courses in Experimental Chemistry), vol. 26, Yuki Gosei (Organic Synthesis) [VIII], edited by The Chemical Society of Japan, Maruzen Co., Ltd., April 1992, p. 251-266, for example); and ii) reduction using a metal and metal salt (see Jikken Kagaku Koza (Courses in Experimental Chemistry), vol. 26, Yuki Gosei (Organic Synthesis) [VIII], edited by The Chemical Society of Japan, Maruzen Co., Ltd., April 1992, p. 165-1856, for example).

Examples of the method i) include a method of stirring the compound (5g) together with a hydrogen source in a solvent in the presence of 0.01 to 0.5 equivalent of a metal catalyst with respect to the compound (5g). The metal catalyst used varies according to the starting material and is not specifically limited. Preferable examples of the catalyst include palladium-carbon, rhodium-carbon, ruthenium-carbon, palladium hydroxide, platinum oxide, Raney nickel, and a Wilkinson catalyst. The hydrogen source varies according to the starting material and the metal catalyst used, and is not specifically limited. Preferable examples of the hydrogen source include hydrogen gas, formic acid, ammonium formate, and cyclohexadiene. The solvent used varies according to the starting material and the metal catalyst, and is not specifically limited. Preferable examples of the solvent include methanol, ethanol, ethyl acetate, toluene, THF, 1,4-dioxane, chloroform, methylene chloride, water, and a mixture thereof. An organic acid, inorganic acid, or organic base may be appropriately added in order to make the reaction efficiently proceed. The reaction temperature must be a temperature that can complete the reaction without promoting formation of an undesirable by-product, and is preferably room temperature to 150° C., for example. Under preferable reaction conditions, the reaction is preferably completed in 1 to 24 hours, for example, and the progress of the reaction can be monitored by a known chromatography technique. An undesirable by-product can be removed by a technique known to a person skilled in the art such as a conventional chromatography technique, extraction, or/and crystallization.

Examples of the method ii) include a method of stirring the compound (5g) in a solvent in the presence of 1.0 to 10.0 equivalents of a metal or metal salt with respect to the compound (5g). The metal or metal salt used varies according to the starting material and is not specifically limited. Preferable examples of the metal or metal salt include alkali metals such as lithium and sodium; alkali earth metals such as magnesium and calcium; and salts thereof. The solvent used varies according to the starting material and the metal used, and is not specifically limited. Preferable examples of the solvent include ammonia, methanol, ethanol, tert-butanol, tetrahydrofuran, 1,4-dioxane, diethyl ether, water, and a mixture thereof. The reaction temperature must be a temperature that can complete the reaction without promoting formation of an undesirable by-product, and is preferably −78° C. to 100° C., for example. Under preferable reaction conditions, the reaction is preferably completed in 1 to 24 hours, for example, and the progress of the reaction can be monitored by a known chromatography technique. An undesirable by-product can be removed by a technique known to a person skilled in the art such as a conventional chromatography technique, extraction, or/and crystallization.

A method described in many known documents may be used for the carbon prolongation reaction subsequent to the double bond reduction. Preferable examples of the method include i) Wittig reaction, ii) Horner-Emmons reaction, and iii) Peterson reaction (see Jikken Kagaku Koza (Courses in Experimental Chemistry), vol. 19, Yuki Gosei (Organic Synthesis) [1], edited by The Chemical Society of Japan, Maruzen Co., Ltd., June 1992, p. 57-85, for example).

Preferable examples of the Wittig reaction include a method of stirring in a solvent an aldehyde compound derived from the compound (5g) and 1.0 to 3.0 equivalents of a known Wittig reagent with respect to the aldehyde compound in the presence of 1.0 to 5.0 equivalents of a base with respect to the aldehyde compound. The solvent used varies according to the starting material and the base used, and is not specifically limited insofar as the solvent does not inhibit the reaction and allows the starting material to be dissolved therein to a certain extent. Preferable examples of the solvent include polar solvents such as nitromethane, acetonitrile, 1-methyl-2-pyrrolidone, N,N-dimethylformamide, and dimethyl sulfoxide; ether solvents such as tetrahydrofuran, 1,4-dioxane, and 1,2-dimethoxyethane; nonpolar solvents such as benzene, toluene, and xylene; alcohol solvents such as ethanol and methanol; halogenated solvents such as chloroform and methylene chloride; water; and mixed solvents thereof. The base used varies according to the starting material and the solvent. Preferable examples of the base include alkali metal hydroxides such as sodium hydroxide and lithium hydroxide; alkali metal carbonates such as sodium carbonate; alkali metal salts of alcohols such as sodium methoxide and potassium tert-butoxide; organic bases such as triethylamine, pyridine, and diazabicyclononene; organic metals such as butyl lithium and lithium diisobutylamide; and alkali metal hydrides such as sodium hydride. The reaction temperature must be a temperature that can complete the reaction without promoting formation of an undesirable by-product, and is preferably −78 to 150° C., for example. Under preferable reaction conditions, the reaction is preferably completed in 1 to 24 hours, for example, and the progress of the reaction can be monitored by a known chromatography technique. An undesirable by-product can be removed by a technique known to a person skilled in the art such as a conventional chromatography technique, extraction, or/and crystallization.

Preferable examples of the Horner-Emmons reaction include a method of stirring in a solvent an aldehyde compound derived from the compound (5g) and 1.0 to 3.0 equivalents of a known Horner-Emmons reagent with respect to the aldehyde compound in the presence of 1.0 to 5.0 equivalents of a base with respect to the aldehyde compound. The solvent used varies according to the starting material and the base used, and is not specifically limited insofar as the solvent does not inhibit the reaction and allows the starting material to be dissolved therein to a certain extent. Preferable examples of the solvent include polar solvents such as 1-methyl-2-pyrrolidone, N,N-dimethylformamide, and dimethyl sulfoxide; ether solvents such as tetrahydrofuran, 1,4-dioxane, and 1,2-dimethoxyethane; nonpolar solvents such as benzene, toluene, and xylene; alcohol solvents such as ethanol and methanol; water; and mixed solvents thereof. The base used varies according to the starting material and the solvent. Preferable examples of the base include alkali metal hydroxides such as sodium hydroxide and lithium hydroxide; alkali metal carbonates such as sodium carbonate; alkali metal salts of alcohols such as sodium methoxide and potassium tert-butoxide; organic bases such as triethylamine, pyridine, and diazabicyclononene; organic metals such as butyl lithium and lithium diisobutylamide; alkali metal hydrides such as sodium hydride; and alkali metal ammonium salts such as sodium amide. The reaction temperature must be a temperature that can complete the reaction without promoting formation of an undesirable by-product, and is preferably −78 to 150° C., for example. Under preferable reaction conditions, the reaction is preferably completed in 1 to 24 hours, for example, and the progress of the reaction can be monitored by a known chromatography technique. An undesirable by-product can be removed by a technique known to a person skilled in the art such as a conventional chromatography technique, extraction, or/and crystallization.

Preferable examples of the Peterson reaction include a method of stirring in a solvent an aldehyde compound derived from the compound (5g) and 1.0 to 3.0 equivalents of a known Peterson reagent with respect to the aldehyde compound in the presence of 1.0 to 5.0 equivalents of a base with respect to the aldehyde compound. The solvent used varies according to the starting material and the base used, and is not specifically limited insofar as the solvent does not inhibit the reaction and allows the starting material to be dissolved therein to a certain extent. Preferable examples of the solvent include polar solvents such as 1-methyl-2-pyrrolidone, N,N-dimethylformamide, and dimethyl sulfoxide; ether solvents such as tetrahydrofuran, 1,4-dioxane, and 1,2-dimethoxyethane; nonpolar solvents such as benzene, toluene, and xylene; alcohol solvents such as ethanol and methanol; water; and mixed solvents thereof. The base used varies according to the starting material and the solvent. Preferable examples of the base include alkali metal hydroxides such as sodium hydroxide and lithium hydroxide; alkali metal carbonates such as sodium carbonate; alkali metal salts of alcohols such as sodium methoxide and potassium tert-butoxide; organic bases such as triethylamine, pyridine, and diazabicyclononene; organic metals such as butyl lithium and lithium diisobutylamide; alkali metal hydrides such as sodium hydride; and alkali metal ammonium salts such as sodium amide. The reaction temperature must be a temperature that can complete the reaction without promoting formation of an undesirable by-product, and is preferably −78 to 150° C., for example. Under preferable reaction conditions, the reaction is preferably completed in 1 to 24 hours, for example, and the progress of the reaction can be monitored by a known chromatography technique. An undesirable by-product can be removed by a technique known to a person skilled in the art such as a conventional chromatography technique, extraction, or/and crystallization.

Conversion of Compound (5k) into Lactam Compound (2)

The lactam compound (2) can be prepared from the compound (5k) as a starting material by intramolecular amidation reaction according to Step 3-12. Specifically, Step 3-12 is performed by the same method as in Step 3-3.

General Preparation Method 2

Typically used General Preparation Method 2 for the compound of the general formula (I) of the present invention will be described below.

the conditions are similar to those in this reaction. A known method described in many documents may be used for the reaction. Preferable examples of the method include Wittig reaction, Horner-Emmons reaction, Peterson reaction (see Jikken Kagaku Koza (Courses in Experimental Chemistry), vol. 19, Yuki Gosei (Organic Synthesis) [I], edited by The Chemical Society of Japan, Maruzen Co., Ltd., June 1992, p. 57-85, for example), and Knoevegagel reaction.

Preferable examples of the Wittig reaction include a method of stirring in a solvent a compound (6), wherein $L_8$ is a phosphonium salt, preferably 0.5 to 2.0 equivalents of an aldehyde compound (1) with respect to the compound (6), for example, and preferably 1.0 to 5.0 equivalents of a base with respect to the compound (6), for example. This reaction may be a method of first treating a compound (6) and a base to form a phosphonium ylide and then adding an aldehyde compound (1) to the ylide; or a method of adding a base in the presence of a compound (6) and an aldehyde compound (1). The solvent used varies according to the starting material and the base used, and is not specifically limited insofar as the solvent does not inhibit the reaction and allows the starting material to be dissolved therein to a certain extent. Preferable examples of the solvent include polar solvents such as nitromethane, acetonitrile, 1-methyl-2-pyrrolidone, N,N-dimethylformamide, and dimethyl sulfoxide; ether solvents such as tetrahydrofuran, 1,4-dioxane, and 1,2-dimethoxyethane; nonpolar

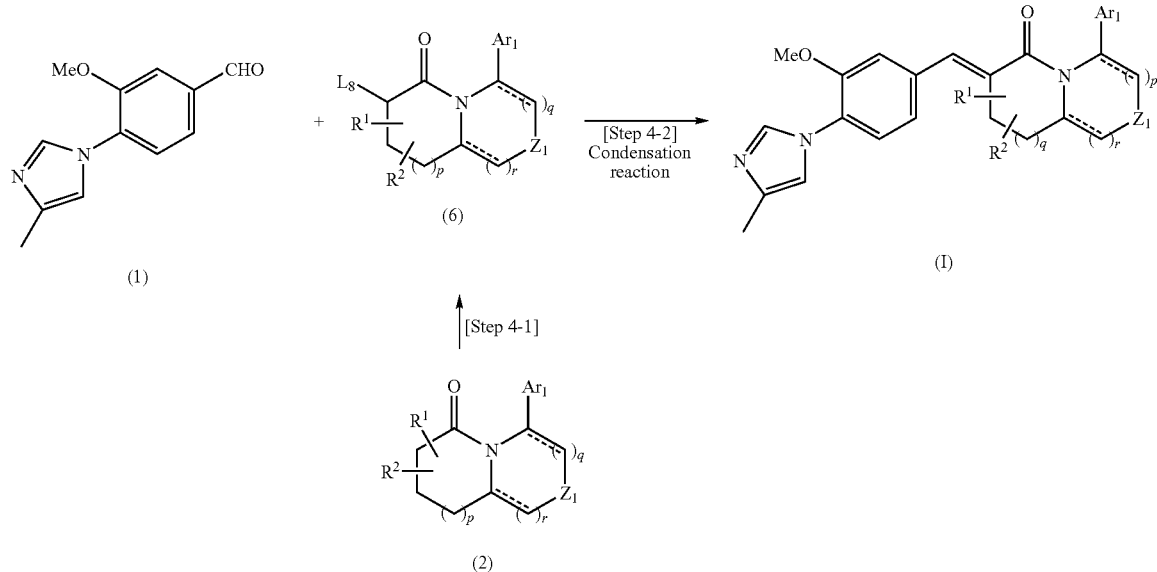

In the formula, ---- represents a single bond or a double bond; $Ar_1$, $Z_1$, $R^1$, $R^2$, p, q, and r are as defined above; and $L_8$ represents a phosphite group such as a diethylphosphonyl group, a phosphonium salt such as triphenylphosphonium bromide, a silyl group such as a trimethylsilyl group, an ester group such as a methyl ester group or ethyl ester group, or a carboxyl group.

The above General Preparation Method 2 is an example of a method for preparing the compound of the general formula (I) comprising introducing a leaving group $L_8$ into a lactam compound (2) according to Step 4-1 and then condensing the compound with an aldehyde compound (1) according to Step 4-2.

Preparation of Compound of General Formula (I)

The condensation reaction of Step 4-2 varies according to the starting material and is not specifically limited insofar as solvents such as benzene, toluene, and xylene; alcohol solvents such as ethanol and methanol; halogenated solvents such as chloroform and methylene chloride; water; and mixed solvents thereof. The base used varies according to the starting material and the solvent. Preferable examples of the base include alkali metal hydroxides such as sodium hydroxide and lithium hydroxide; alkali metal carbonates such as sodium carbonate; alkali metal salts of alcohols such as sodium methoxide and potassium tert-butoxide; organic bases such as triethylamine, pyridine, and diazabicyclononene; organic metals such as butyl lithium and lithium diisobutylamide; and alkali metal hydrides such as sodium hydride. The reaction temperature must be a temperature that can complete the reaction without promoting formation of an undesirable by-product, and is preferably −78 to 150° C., for example. Under preferable reaction conditions, the reaction is preferably completed in 1 to 24 hours, for example, and the progress of the reaction can be monitored by a known chromatography technique. An undesirable by-product can be removed by a technique known to a person skilled in the art such as a conventional chromatography technique, extraction, or/and crystallization.

Preferable examples of the Horner-Emmons reaction include a method of stirring in a solvent a compound (6), wherein $L_8$ is a phosphite group, preferably 0.5 to 2.0 equivalents of an aldehyde compound (1) with respect to the compound (6), for example, and preferably 1.0 to 5.0 equivalents of a base with respect to the compound (6), for example. This reaction may be a method of first treating a compound (6) and a base to form a carbanion and then adding an aldehyde compound (1) to the carbanion; or a method of adding a base in the presence of a compound (6) and an aldehyde compound (1). The solvent used varies according to the starting material and the base used, and is not specifically limited insofar as the solvent does not inhibit the reaction and allows the starting material to be dissolved therein to a certain extent. Preferable examples of the solvent include polar solvents such as 1-methyl-2-pyrrolidone, N,N-dimethylformamide, and dimethyl sulfoxide; ether solvents such as tetrahydrofuran, 1,4-dioxane, and 1,2-dimethoxyethane; nonpolar solvents such as benzene, toluene, and xylene; alcohol solvents such as ethanol and methanol; water; and mixed solvents thereof. The base used varies according to the starting material and the solvent. Preferable examples of the base include alkali metal hydroxides such as sodium hydroxide and lithium hydroxide; alkali metal carbonates such as sodium carbonate; alkali metal salts of alcohols such as sodium methoxide and potassium tert-butoxide; organic bases such as triethylamine, pyridine, and diazabicyclononene; organic metals such as butyl lithium and lithium diisobutylamide; alkali metal hydrides such as sodium hydride; and alkali metal ammonium salts such as sodium amide. The reaction temperature must be a temperature that can complete the reaction without promoting formation of an undesirable by-product, and is preferably −78 to 150° C., for example. Under preferable reaction conditions, the reaction is preferably completed in 1 to 24 hours, for example, and the progress of the reaction can be monitored by a known chromatography technique. An undesirable by-product can be removed by a technique known to a person skilled in the art such as a conventional chromatography technique, extraction, or/and crystallization.

Preferable examples of the Peterson reaction include a method of stirring in a solvent a compound (6), wherein $L_8$ is a silyl group, preferably 0.5 to 2.0 equivalents of an aldehyde compound (1) with respect to the compound (6), for example, and preferably 1.0 to 5.0 equivalents of a base with respect to the compound (6), for example. This reaction may be a method of first treating a compound (6) and a base to form a carbanion and then adding an aldehyde compound (1) to the carbanion; or a method of adding a base in the presence of a compound (6) and an aldehyde compound (1). The solvent used varies according to the starting material and the base used, and is not specifically limited insofar as the solvent does not inhibit the reaction and allows the starting material to be dissolved therein to a certain extent. Preferable examples of the solvent include polar solvents such as 1-methyl-2-pyrrolidone, N,N-dimethylformamide, and dimethyl sulfoxide; ether solvents such as tetrahydrofuran, 1,4-dioxane, and 1,2-dimethoxyethane; nonpolar solvents such as benzene, toluene, and xylene; alcohol solvents such as ethanol and methanol; water; and mixed solvents thereof. The base used varies according to the starting material and the solvent. Preferable examples of the base include alkali metal hydroxides such as sodium hydroxide and lithium hydroxide; alkali metal carbonates such as sodium carbonate; alkali metal salts of alcohols such as sodium methoxide and potassium tert-butoxide; organic bases such as triethylamine, pyridine, and diazabicyclononene; organic metals such as butyl lithium and lithium diisobutylamide; alkali metal hydrides such as sodium hydride; and alkali metal ammonium salts such as sodium amide. The reaction temperature must be a temperature that can complete the reaction without promoting formation of an undesirable by-product, and is preferably −78 to 150° C., for example. Under preferable reaction conditions, the reaction is preferably completed in 1 to 24 hours, for example, and the progress of the reaction can be monitored by a known chromatography technique. An undesirable by-product can be removed by a technique known to a person skilled in the art such as a conventional chromatography technique, extraction, or/and crystallization.

Preferable examples of the Knoevegagel reaction include a method of stirring in a solvent a compound (6), wherein $L_8$ is an ester group or carboxyl group, preferably 0.5 to 2.0 equivalents of an aldehyde compound (1) with respect to the compound (6), for example, and preferably 1.0 to 5.0 equivalents of a base with respect to the compound (6), for example. This reaction may be a method of first treating a compound (6) and a base to form a carbanion and then adding an aldehyde compound (1) to the carbanion; or a method of adding a base in the presence of a compound (6) and an aldehyde compound (1). The solvent used varies according to the starting material and the base used, and is not specifically limited insofar as the solvent does not inhibit the reaction and allows the starting material to be dissolved therein to a certain extent. Preferable examples of the solvent include polar solvents such as 1-methyl-2-pyrrolidone, N,N-dimethylformamide, and dimethyl sulfoxide; ether solvents such as tetrahydrofuran, 1,4-dioxane, and 1,2-dimethoxyethane; nonpolar solvents such as benzene, toluene, and xylene; alcohol solvents such as ethanol and methanol; water; and mixed solvents thereof. The base used varies according to the starting material and the solvent. Preferable examples of the base include alkali metal hydroxides such as sodium hydroxide and lithium hydroxide; alkali metal carbonates such as sodium carbonate; alkali metal salts of alcohols such as sodium methoxide and potassium tert-butoxide; organic bases such as triethylamine, pyridine, and diazabicyclononene; organic metals such as butyl lithium and lithium diisobutylamide; alkali metal hydrides such as sodium hydride; and alkali metal ammonium salts such as sodium amide. The reaction temperature must be a temperature that can complete the reaction without promoting formation of an undesirable by-product, and is preferably −78 to 150° C., for example. Under preferable reaction conditions, the reaction is preferably completed in 1 to 24 hours, for example, and the progress of the reaction can be monitored by a known chromatography technique. An undesirable by-product can be removed by a technique known to a person skilled in the art such as a conventional chromatography technique, extraction, or/and crystallization.

Preparation of Compound (6)

The compound (6) can be prepared from a lactam compound (2) as a starting material according to Step 4-1. Preferably, for example, i) the Wittig reagent (6), wherein $L_8$ is a phosphonium salt, can be prepared by halogenating a lactam compound (2) by a method known to a person skilled in the art (see Jikken Kagaku Koza (Courses in Experimental Chemistry), vol. 19, Yuki Gosei (Organic Synthesis) [I], edited by The Chemical Society of Japan, Maruzen Co., Ltd., June 1992, p. 430-438, for example), and then reacting the compound with an organic phosphine compound such as triphenylphosphine (see Organic Reaction, 1965, vol. 14, p. 270, for example). ii) The Horner-Emmons reagent (6), wherein $L_8$ is a phosphite, can be prepared by halogenating a lactam compound (2) by a method known to a person skilled in the art (see Jikken Kagaku Koza (Courses in Experimental Chemistry), vol. 19, Yuki Gosei (Organic Synthesis) [I], edited by The Chemical Society of Japan, Maruzen Co., Ltd., June 1992, p. 430-438, for example), and then reacting the compound with an alkyl phosphinite by Arbuzov reaction (see Chemical Review, 1981, vol. 81, p. 415, for example) or with a metal phosphonite by Becker reaction (see Journal of the American Chemical Society, 1945, vol. 67, p. 1180, for example). Alternatively, the Horner-Emmons reagent can be prepared from a lactam compound (2) and a chlorophosphate in the presence of a base (see The Journal of Organic Chemistry, 1989, vol. 54, p. 4750, for example). iii) The Peterson reagent (6), wherein $L_8$ is a silyl group, can be prepared from a lactam compound (2) and a trialkylsilyl chloride in the presence of a base (see Journal of Organometallic Chemistry, 1983, vol. 248, p. 51, for example). iv) The ester compound or carboxylic acid compound, wherein $L_8$ is an ester group or carboxyl group, can be prepared from a lactam compound (2) and a carbonic diester, a halogenated carbonate, or carbon dioxide in the presence of a base (see Jikken Kagaku Koza (Courses in Experimental Chemistry), vol. 22, Yuki Gosei (Organic Synthesis) [IV], edited by The Chemical Society of Japan, Maruzen Co., Ltd., June 1992, p. 14-30 and p. 54-71, for example).

General Preparation Method 3

Typically used General Preparation Method 3 for the compound of the general formula (I) of the present invention will be described below.

5-5 through Step 5-4, converting the compound (7) into an amide compound (8) by condensation reaction with an amine compound (16) in Step 5-2, and then subjecting the amide compound (8) to ring closing metathesis reaction and subsequent double bond modification reaction in Step 5-3; or ii) a method for preparing the compound of the general formula (I) comprising deriving a compound (9) from an aldehyde compound (1) according to Step 5-4, converting the compound (9) into an amide compound (10) in Step 5-6, and then subjecting the amide compound (10) to Heck reaction and subsequent double bond modification reaction in Step 5-7.

Preparation of Compound of General Formula (I)

In the method i), the compound of the general formula (I) can be prepared from an amide compound (8) according to Step 5-3. Step 5-3 consists of ring closing metathesis reaction and subsequent double bond modification reaction. Specifically, the first-stage ring closing metathesis reaction varies according to the starting material and can be performed by a method known to a person skilled in the art insofar as the conditions are similar to those in this reaction (see Comprehensive Organometallic Chemistry, 1982, vol. 8, p. 499, or Angewandte Chemie International Edition, 2000, vol. 39, p. 3012, for example). The second-stage double bond modification reaction may be performed by, for example, i) catalytic hydrogenation (see Jikken Kagaku Koza (Courses in Experimental Chemistry), vol. 26, Yuki Gosei (Organic Synthesis) [VIII], edited by The Chemical Society of Japan, Maruzen Co., Ltd., April 1992, p. 251-266, for example); ii) hydroboration (see Jikken Kagaku Koza (Courses in Experimental Chemistry), vol. 25, Yuki Gosei (Organic Synthesis) [VII],

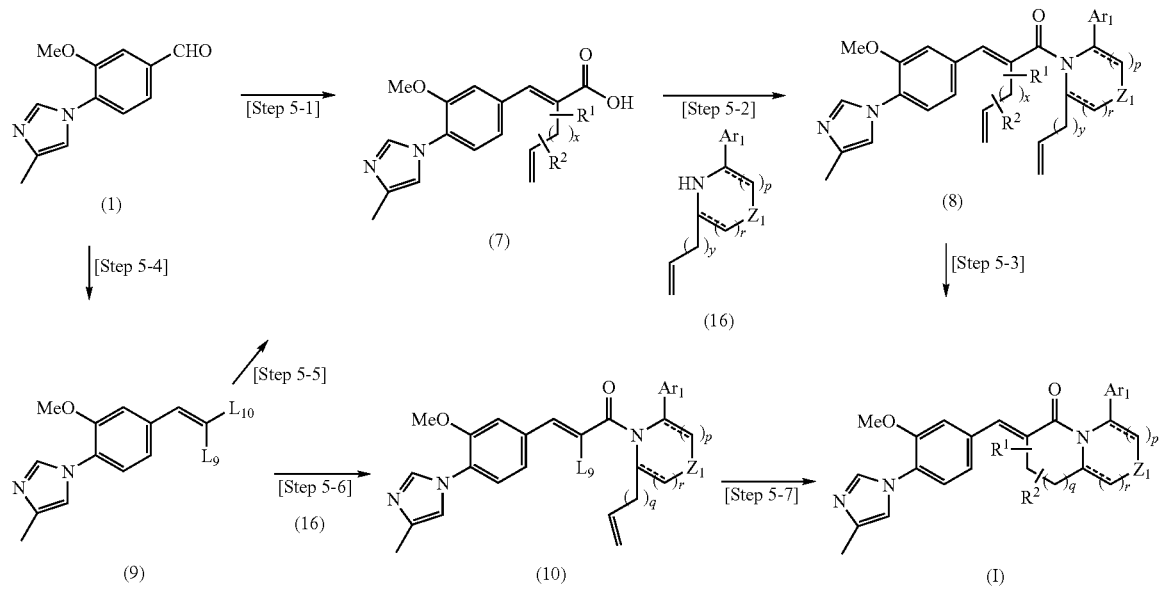

In the formula, ---- represents a single bond or a double bond; $Ar_1$, $Z_1$, $R^1$, $R^2$, p, q, and r are as defined above; x and y each represent an integer of 0 to 2; $L_9$ represents a halogen atom such as chlorine, bromine, or iodine, or a sulfonate group such as a triflate group; and $L_{10}$ represents an ester group such as a methyl ester group or ethyl ester group, or carboxylic acid.

The above General Preparation Method 3 is an example of i) a method for preparing the compound of the general formula (I) comprising deriving a compound (7) from an aldehyde compound (1) according to Step 5-1 or according to Step edited by The Chemical Society of Japan, Maruzen Co., Ltd., September 1991, p. 83-134, for example); or iii) oxidation of a carbon-carbon double bond (see Jikken Kagaku Koza (Courses in Experimental Chemistry), vol. 23, Yuki Gosei (Organic Synthesis) [V], edited by The Chemical Society of Japan, Maruzen Co., Ltd., October 1991, p. 237-267, for example).

Preferably, the ring closing metathesis reaction is a method of performing intramolecular cyclization reaction by stirring an amide compound (8) in a solvent in the presence of 0.01 to 0.2 equivalent of a metal catalyst with respect to the amide compound (8). Preferable examples of the solvent used include halogenated solvents such as methylene chloride and chloroform; ether solvents such as tetrahydrofuran, 1,4-dioxane, 1,2-dimethoxyethane; nonpolar solvents such as benzene, toluene, and xylene; and mixed solvents thereof. The metal catalyst used varies according to the starting material and the solvent. Preferable examples of the metal catalyst used include ruthenium catalysts such as bis(tricyclohexylphosphine)benzylidene ruthenium (IV) dichloride, benzylidene[1,3-bis(2,4,6-trimethylphenyl)-2-imidazolidinylidene]dichloro(tricyclohexylphosphine) ruthenium (IV), and [1,3-bis(2,4,6-trimethylphenyl)-2-imidazolidinylidene]dichloro(o-isopropoxyphenylmethylidene)ruthenium (IV); and molybdenum catalysts such as 2,6-diisopropylphenylimidoneophylidene biphen molybdenum (VI) and 2,6-diisopropylphenylimidoneophylidene molybdenum (VI) bis(hexafluoro-tert-butoxide). The reaction temperature must be a temperature that can complete the reaction without promoting formation of an undesirable by-product, and is preferably room temperature to 100° C., for example. Under preferable reaction conditions, the reaction is preferably completed in 1 to 24 hours, for example, and the progress of the reaction can be monitored by a known chromatography technique. An undesirable by-product can be removed by a technique known to a person skilled in the art such as a conventional chromatography technique, extraction, or/and crystallization.

The double bond modification reaction is preferably catalytic hydrogenation, for example, in which the cyclized compound obtained by the ring closing metathesis reaction is reduced in a hydrogen stream preferably at 1 to 10 atm, for example, in the presence of preferably 0.01 to 0.2 equivalent of a metal catalyst with respect to the cyclized compound, for example. This reaction is preferably performed in the presence of a solvent from the viewpoint of operativity and stirring efficiency. Preferable examples of the solvent used include alcohol solvents such as ethanol and methanol; halogenated solvents such as methylene chloride and chloroform; ether solvents such as tetrahydrofuran, 1,4-dioxane, 1,2-dimethoxyethane; nonpolar solvents such as benzene, toluene, and xylene; polar solvents such as ethyl acetate and acetonitrile; and mixed solvents thereof. The metal catalyst used varies according to the starting material and the solvent. Preferable examples of the catalyst include platinum, platinum oxide, platinum black, Raney nickel, and palladium-carbon. The reaction temperature must be a temperature that can complete the reaction without promoting formation of an undesirable by-product, and is preferably room temperature to 100° C., for example. Under preferable reaction conditions, the reaction is preferably completed in 1 to 24 hours, for example, and the progress of the reaction can be monitored by a known chromatography technique. An undesirable by-product can be removed by a technique known to a person skilled in the art such as a conventional chromatography technique, extraction, or/and crystallization.

In the method ii), the compound of the general formula (I) can be prepared from an amide compound (10) according to Step 5-7. Specifically, Step 5-7 consists of Heck reaction and subsequent double bond modification reaction. Specifically, the first-stage Heck reaction varies according to the starting material and can be performed by a method known to a person skilled in the art insofar as the conditions are similar to those in this reaction (see Jikken Kagaku Koza (Courses in Experimental Chemistry), vol. 19, Yuki Gosei (Organic Synthesis) [I], edited by The Chemical Society of Japan, Maruzen Co., Ltd., June 1992, p. 123-132, for example). The second-stage double bond modification reaction may be performed by, for example, i) catalytic hydrogenation (see Jikken Kagaku Koza (Courses in Experimental Chemistry), vol. 26, Yuki Gosei (Organic Synthesis) [VIII], edited by The Chemical Society of Japan, Maruzen Co., Ltd., April 1992, p. 251-266, for example); ii) hydroboration (see Jikken Kagaku Koza (Courses in Experimental Chemistry), vol. 25, Yuki Gosei (Organic Synthesis) [VII], edited by The Chemical Society of Japan, Maruzen Co., Ltd., September 1991, p. 83-134, for example); or iii) oxidation of a carbon-carbon double bond (see Jikken Kagaku Koza (Courses in Experimental Chemistry), vol. 23, Yuki Gosei (Organic Synthesis) [V], edited by The Chemical Society of Japan, Maruzen Co., Ltd., October 1991, p. 237-267, for example).

Preferable examples of the Heck reaction include a method of stirring a compound (10) in a solvent in the presence of 0.01 to 0.2 equivalent of a transition metal catalyst with respect to the compound (10). The solvent used varies according to the starting material and the transition metal catalyst used, and is not specifically limited insofar as the solvent does not inhibit the reaction and allows the starting material to be dissolved therein to a certain extent. Preferable examples of the solvent include acetonitrile, tetrahydrofuran, 1,4-dioxane, 1,2-dimethoxyethane, benzene, toluene, xylene, 1-methyl-2-pyrrolidone, and N,N-dimethylformamide. The reaction temperature must be a temperature that can complete the coupling reaction, and is preferably room temperature to 150° C., for example. This reaction is performed preferably in an inert gas atmosphere, and more preferably in a nitrogen or argon atmosphere. The transition metal catalyst is preferably a palladium complex, for example, and more preferably a known palladium complex such as palladium (II) acetate, dichlorobis(triphenylphosphine)palladium (II), tetrakis(triphenylphosphine)palladium (0), or tris(dibenzylideneacetone)dipalladium (0). In addition, it is preferable to appropriately add preferably 1.0 to 5.0 equivalents of a phosphorus ligand (preferably triphenylphosphine, tri-o-tolylphosphine, tri-tert-butylphosphine, or 2-(di-tert-butylphosphino)biphenyl, for example) with respect to the transition metal catalyst used, for example, in order to make the reaction efficiently proceed. A preferable result may be obtained in the presence of a base, and the base used is not specifically limited insofar as the base is used in a coupling reaction similar to this reaction. The base is preferably 0.1 to 5.0 equivalents of triethylamine, N,N-diisopropylethylamine, N,N-dicyclohexylmethylamine, or tetrabutylammonium chloride with respect to the compound (10), for example. Under preferable reaction conditions, the reaction is preferably completed in 1 to 24 hours, for example, and the progress of the reaction can be monitored by a known chromatography technique.

Preparation of Amide Compound (8)

The amidation reaction in Step 5-2 varies according to the starting material and is not specifically limited insofar as the conditions are similar to those in this reaction. A known method described in many documents may be used for the reaction (see Shin Jikken Kagaku Koza (New Courses in Experimental Chemistry), vol. 14, Yuki Kagobutsu No Gosei To Hannou (Synthesis and Reaction of Organic Compounds) [II], edited by The Chemical Society of Japan, Maruzen Co., Ltd., February 1978, p. 1136-1162, for example). Preferable examples of the method include i) a method of converting a compound (7) into an acid halide and reacting the acid halide with an amine compound (16) under basic conditions (see Shin Jikken Kagaku Koza (New Courses in Experimental Chemistry), vol. 14, Yuki Kagobutsu No Gosei To Hannou (Synthesis and Reaction of Organic Compounds) [II], edited by The Chemical Society of Japan, Maruzen Co., Ltd., February 1978, p. 1142-1145, for example); and ii) a method of reacting a compound (7) with an amine compound (16) using a condensing agent (see "Yukikagaku Jikken No Tebiki (Introduction to Organic Chemistry Experiments) [4]", Kagaku-Dojin Publishing Company, Inc., September 1990, p. 27-52, for example).

Preferable examples of the reaction of converting a compound (7) into an acid halide in the method i) include a method of stirring a compound (7) in a solvent in the presence of 1.0 to 10.0 equivalents of a halogenating agent with respect to the compound (7). The halogenating agent used varies according to the starting material and is not specifically limited. Preferable examples of the halogenating agent include thionyl chloride, phosphorus pentachloride, and oxalyl chloride. The solvent used is not specifically limited insofar as the solvent does not inhibit the reaction and allows the starting material to be dissolved therein to a certain extent. Preferable examples of the solvent include methylene chloride, chloroform, and toluene. The reaction may efficiently proceed when 0.1 to 1.0 equivalent of an organic base such as pyridine, dimethylformamide, or the like is appropriately added with respect to the compound (7). The reaction temperature must be a temperature that can complete the reaction without promoting formation of an undesirable by-product, and is preferably ice-cold temperature to 150° C., for example. Under preferable reaction conditions, the reaction is preferably completed in 1 to 24 hours, for example, and the progress of the reaction can be monitored by a known chromatography technique. An undesirable by-product can be removed by a technique known to a person skilled in the art such as a conventional chromatography technique or/and crystallization.

Preferable examples of the subsequent coupling reaction include a method of stirring the acid halide and 1.0 to 5.0 equivalents of an amine compound (16) with respect to the acid halide in a solvent in the presence of 1.0 to 100.0 equivalents of a base with respect to the acid halide. The base used varies according to the starting material and is not specifically limited. Preferable examples of the base include pyridine, triethylamine, N,N-diisopropylethylamine, lutidine, quinoline, and isoquinoline. The solvent used is not specifically limited insofar as the solvent does not inhibit the reaction and allows the starting material to be dissolved therein to a certain extent. Preferable examples of the solvent include methylene chloride, chloroform, toluene, tetrahydrofuran, and 1,4-dioxane. A base may be used as a solvent. Alternatively, it is possible to use a two-layer partition system consisting of a base that is an alkali solution, preferably a sodium hydroxide or potassium hydroxide solution, for example, and a halogenated solvent such as methylene chloride or 1,2-dichloroethane. The reaction temperature must be a temperature that can complete the reaction without promoting formation of an undesirable by-product, and is preferably ice-cold temperature to 100° C., for example. Under preferable reaction conditions, the reaction is preferably completed in 1 to 24 hours, for example, and the progress of the reaction can be monitored by a known chromatography technique. An undesirable by-product can be removed by a technique known to a person skilled in the art such as a conventional chromatography technique or/and crystallization.

Preferable examples of the method ii) include a method of stirring in a solvent a compound (7) and 1.0 to 5.0 equivalents of an amine compound (16) with respect to the compound (7) in the presence of 1.0 to 5.0 equivalents of a condensing agent with respect to the compound (7). The condensing agent used varies according to the starting material and is not specifically limited. Preferable examples of the condensing agent include 1,3-dicyclohexylcarbodiimide, 1-ethyl-3-(3'-dimethylaminopropyl)carbodiimide, benzotriazol-1-yloxytris(dimethylamino)phosphonium hexafluorophosphate, diethyl cyanophosphonate, and bis(2-oxo-3-oxazolidinyl)phosphinic chloride. Preferably, 1.0 to 2.0 equivalents of N-hydroxysuccinimide or N-hydroxybenzotriazole may be added with respect to the compound (7) in order to make the reaction efficiently proceed, for example. This reaction is preferably performed in the presence of a solvent from the viewpoint of operativity and stirring efficiency. The solvent used varies according to the starting material and the condensing agent used, and is not specifically limited insofar as the solvent does not inhibit the reaction and allows the starting material to be dissolved therein to a certain extent. Preferable examples of the solvent used include halogenated solvents such as methylene chloride and 1,2-dichloroethane, and polar solvents such as tetrahydrofuran and N,N-dimethylformamide. The reaction temperature must be a temperature that can complete the reaction without promoting formation of an undesirable by-product, and is preferably ice-cold temperature to 100° C., for example. Under preferable reaction conditions, the reaction is preferably completed in 1 to 24 hours, for example, and the progress of the reaction can be monitored by a known chromatography technique. An undesirable by-product can be removed by a technique known to a person skilled in the art such as a conventional chromatography technique or/and crystallization.

Preparation of Amine Compound (16)

The amine compound (16) is commercially available or can be prepared by a method known to a person skilled in the art (see Tetrahedron Letters, 1998, vol. 39, p. 5421, for example).

Preparation of Compound (7)

The compound (7) can be prepared i) from an aldehyde compound (1) according to Step 5-1, or ii) by deriving a compound (9), wherein $L_{10}$ represents an ester group, from an aldehyde compound (1) according to Step 5-4 and then subjecting the compound (9) to Step 5-5.

[Conversion of Aldehyde Compound (1) into Compound (7)]

Step 5-1 consists of a first stage of deriving a cinnamate compound from an aldehyde compound (1) and a subsequent second stage of hydrolyzing the ester group into a carboxylic acid group. The cinnamate compound can be prepared from an aldehyde compound (1) and any of various Horner-Emmons reagents by a method known to a person skilled in the art (see W. S. Wadsworth, Jr., Organic Reactions, 1997, vol. 25, p. 73, for example). Preferably, for example, the compound (7) can be obtained in a high yield by using an aldehyde compound (1), preferably 1.0 to 2.0 equivalents of the Horner-Emmons reagent, for example, and preferably 1.0 to 5.0 equivalents of a base, for example. The Horner-Emmons reagent can be prepared by a method known to a person skilled in the art. For example, the Horner-Emmons reagent can be prepared by alkylation of commercially available trialkylphosphonoacetic acid (see Synthetic Communication, 1991, vol. 22, p. 2391, for example), Arbuzov reaction using an alkylphosphinite of α-halogenoacetic acid derivative (see Chemical Review, 1981, vol. 81, p. 415, for example), or Becker reaction using a metal phosphonite (see Journal of the American Chemical Society, 1945, vol. 67, p. 1180, for example). Preferable examples of the solvent used include polar solvents such as 1-methyl-2-pyrrolidone, N,N-dimethylformamide, and dimethyl sulfoxide; ether solvents such as tetrahydrofuran, 1,4-dioxane, and 1,2-dimethoxyethane; nonpolar solvents such as benzene, toluene, and xylene; alcohol solvents such as ethanol and methanol; water; and mixed solvents thereof. The base used varies according to the starting material and the solvent. Preferable examples of the base include alkali metal hydroxides such as sodium hydroxide and lithium hydroxide; alkali metal carbonates such as sodium carbonate; alkali metal salts of alcohols such as sodium methoxide and potassium tert-butoxide; organic bases such as triethylamine, pyridine, and diazabicyclononene; organic metals such as butyl lithium and lithium diisobutylamide; alkali metal hydrides such as sodium hydride; and alkali metal ammonium salts such as sodium amide. The reaction temperature must be a temperature that can complete the reaction without promoting formation of an undesirable by-product, and is preferably −78 to 150° C., for example. Under preferable reaction conditions, the reaction is preferably completed in 1 to 24 hours, for example, and the progress of the reaction can be monitored by a known chromatography technique. An undesirable by-product can be removed by a technique known to a person skilled in the art such as a conventional chromatography technique, extraction, or/and crystallization. A known deprotection method known to a person skilled in the art may be used for hydrolysis reaction to obtain a compound (7) from the cinnamate compound as a starting material (see T. W. Green, "Protective Groups in Organic Synthesis", John Wiley & Sons, Inc., 1981, p. 154-186).

Conversion of Compound (9) into Compound (7)

The compound (7) can be prepared by coupling a compound (9) as a starting material with a corresponding alkene compound according to Step 5-5. Specifically, a method known to a person skilled in the art may be used for the coupling reaction in Step 5-5. Preferable examples of the method include Heck reaction (see R. F. Heck, "Org. Reactions.", 1982, vol. 27, p. 345, for example), Suzuki reaction (see A. Suzuki, "Chem. Rev.", 1995, vol. 95, p. 2457, for example), and Stille coupling reaction (see J. K. Stille, "Angew. Chem. Int. Ed. Engl.", 1986, vol. 25, p. 508, for example).

In the Heck reaction, a halide or a triflate compound (9), for example, is preferably coupled with preferably 1.0 to 5.0 equivalents of an alkene compound with respect to the compound (9), for example, in the presence of preferably 0.01 to 0.2 equivalent of a transition metal catalyst with respect to the compound (9), for example. This reaction is preferably performed in the presence of a solvent from the viewpoint of operativity and stirring efficiency. The solvent used varies according to the starting material and the transition metal catalyst used, and is not specifically limited insofar as the solvent does not inhibit the reaction and allows the starting material to be dissolved therein to a certain extent. Preferable examples of the solvent include acetonitrile, tetrahydrofuran, 1,4-dioxane, 1,2-dimethoxyethane, benzene, toluene, xylene, 1-methyl-2-pyrrolidone, and N,N-dimethylformamide. The reaction temperature must be a temperature that can complete the coupling reaction, and is preferably room temperature to 150° C., for example. This reaction is performed preferably in an inert gas atmosphere, and more preferably in a nitrogen or argon atmosphere. The transition metal catalyst is preferably a palladium complex, for example, and more preferably a known palladium complex such as palladium (II) acetate, dichlorobis(triphenylphosphine)palladium (II), tetrakis(triphenylphosphine)palladium (0), or tris(dibenzylideneacetone)dipalladium (0). In addition, a phosphorus ligand (preferably triphenylphosphine, tri-o-tolylphosphine, tri-tert-butylphosphine, or 2-(di-tert-butylphosphino)biphenyl, for example) may be appropriately added in order to make the reaction efficiently proceed. A preferable result may be obtained in the presence of a base, and the base used is not specifically limited insofar as the base is used in a coupling reaction similar to this reaction. Preferable examples of the base include triethylamine, N,N-diisopropylethylamine, N,N-dicyclohexylmethylamine, and tetrabutylammonium chloride. Under preferable reaction conditions, the reaction is preferably completed in 1 to 24 hours, for example, and the progress of the reaction can be monitored by a known chromatography technique.

In the Suzuki reaction, a halide or a triflate compound (9), for example, is preferably coupled with preferably 1.0 to 5.0 equivalents of a boronic acid compound or a boronate compound with respect to the compound (9), for example, in the presence of preferably 0.01 to 0.5 equivalent of a transition metal catalyst with respect to the compound (9), for example. This reaction is preferably performed in the presence of a solvent from the viewpoint of operativity and stirring efficiency. The solvent used varies according to the starting material and the transition metal catalyst used, and is not specifically limited insofar as the solvent does not inhibit the reaction and allows the starting material to be dissolved therein to a certain extent. Preferable examples of the solvent include acetonitrile, tetrahydrofuran, 1,4-dioxane, 1,2-dimethoxyethane, benzene, toluene, xylene, 1-methyl-2-pyrrolidone, N,N-dimethylformamide, water, and a mixed solvent thereof. The reaction temperature must be a temperature that can complete the coupling reaction, and is preferably room temperature to 200° C., for example. This reaction is performed preferably in an inert gas atmosphere, and more preferably in a nitrogen or argon atmosphere. The transition metal catalyst is preferably a known palladium complex, and more preferably a known palladium complex such as palladium (II) acetate, dichlorobis(triphenylphosphine)palladium (II), tetrakis(triphenylphosphine)palladium (0), or tris(dibenzylideneacetone)dipalladium (0). In addition, a phosphorus ligand (preferably triphenylphosphine, tri-o-tolylphosphine, tricyclohexylphosphine, or tri-tert-butylphosphine, for example) may be appropriately added in order to make the reaction efficiently proceed. A quaternary ammonium salt, preferably tetrabutylammonium chloride or tetrabutylammonium bromide, for example, may also be appropriately added in order to make the reaction efficiently proceed. In this reaction, a preferable result may be obtained in the presence of a base. The base used at this time varies according to the starting material and the solvent used, and is not specifically limited. Preferable examples of the base include sodium hydroxide, barium hydroxide, potassium fluoride, cesium fluoride, sodium carbonate, potassium carbonate, cesium carbonate, and potassium phosphate. Under preferable reaction conditions, the reaction is preferably completed in 1 to 24 hours, for example, and the progress of the reaction can be monitored by a known chromatography technique.

In the Stille coupling reaction, a halide or a triflate compound (9) is coupled with preferably 1.0 to 10.0 equivalents of a trialkyltin compound with respect to the compound (9), for example, in the presence of preferably 0.01 to 0.2 equivalent of a transition metal catalyst with respect to the compound (9), for example. In addition, preferably 0.1 to 5.0 equivalents of copper (I) halide or/and lithium chloride may be appropriately added with respect to the compound (9), for example, in order to make the reaction efficiently proceed. Preferable examples of the solvent used in this reaction include toluene, xylene, N,N-dimethylformamide, N,N-dimethylacetamide, 1-methyl-2-pyrrolidone, and dimethyl sulfoxide. The reaction temperature must be a temperature that can complete the coupling reaction, and is preferably room temperature to 100° C., for example. The transition metal catalyst used is a palladium complex, preferably a known palladium complex such as palladium (II) acetate, dichlorobis(triphenylphosphine) palladium (II), tetrakis(triphenylphosphine)palladium (0), or tris(dibenzylideneacetone)dipalladium (0), for example, and more preferably tetrakis(triphenylphosphine)palladium (0) or tris(dibenzylideneacetone)dipalladium (0), for example. This reaction is performed preferably in an inert gas atmosphere, and more preferably in a nitrogen or argon atmosphere. Under preferable reaction conditions, the reaction is preferably completed in 1 to 24 hours, for example, and the progress of the reaction can be monitored by a known chromatography technique.

Conversion of Compound (1) into Compound (9)

The compound (9) can be prepared by reacting the compound (1) as a starting material with halogenated phosphonoacetic acid in Horner-Emmons reaction according to Step 5-4 (see Organic Letter, 2000, vol. 2, p. 1975, for example).

Conversion of Compound (9) into Compound (10)

The compound (10) can be prepared from the compound (9) as a starting material according to Step 5-6. Step 5-6 and preparation of the amine compound used are the same as in the above Step 5-2.

General Preparation Method 4

Typically used General Preparation Method 4 for the compound of the general formula (I) of the present invention will be described below.

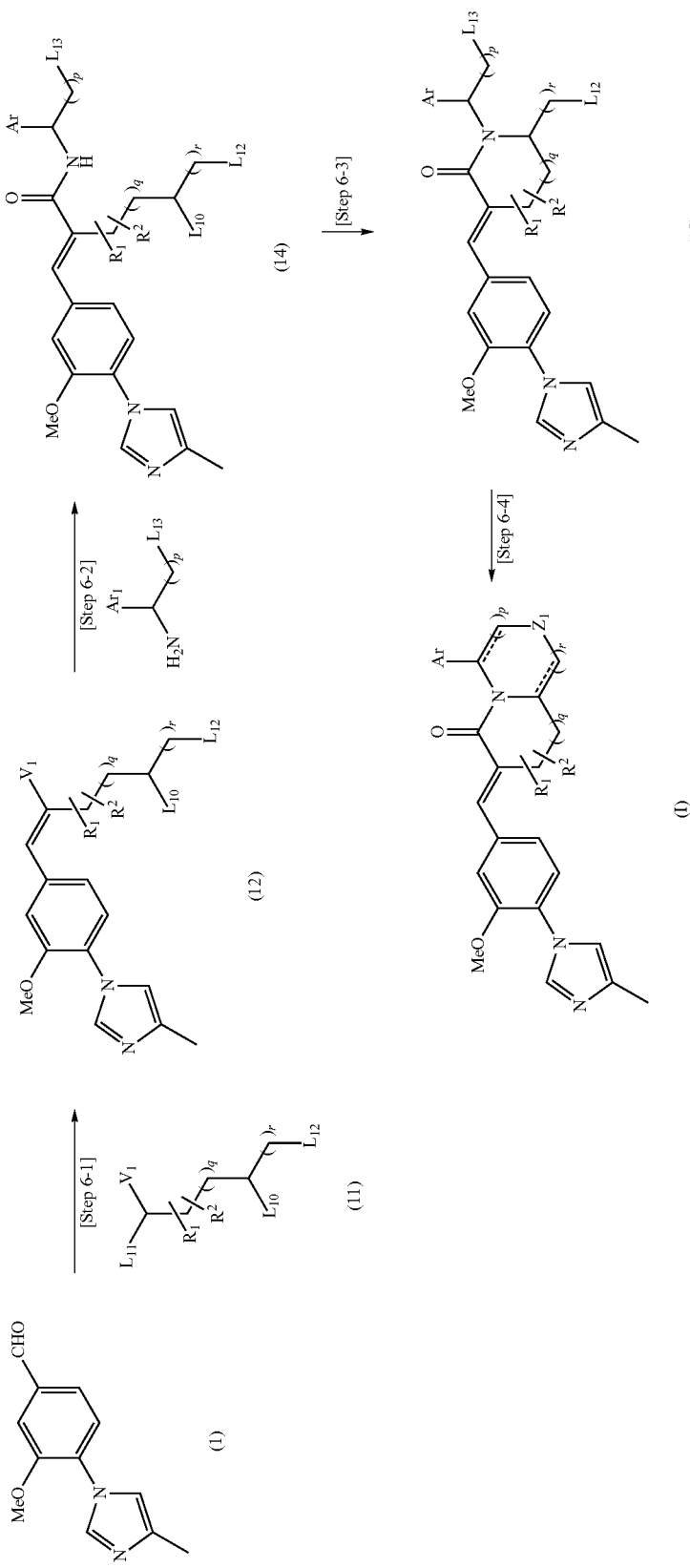

In the formula, ---- represents a single bond or a double bond; $Ar_1$, $Z_1$, $R^1$, $R^2$, p, q, and r are as defined above; $L_{10}$ represents a halogen atom such as a chlorine atom or bromine atom, or a sulfonate group such as a mesyl group or tosyl group; $L_{11}$ represents a phosphite group such as a diethylphosphonyl group; $L_{12}$ and $L_{13}$ each represent a hydroxyl group, a hydroxyl group having a protecting group, an amino group, or an amino group having a protecting group; and $V_1$ represents an ester group such as a methyl ester group or ethyl ester group, or a carboxylic acid group.

The above General Preparation Method 4 is an example of a method for preparing the compound of the general formula (I) comprising deriving a compound (12) from an aldehyde compound (1) and a Horner-Emmons reagent (11) according to Step 6-1, subjecting the compound (12) to amidation reaction according to Step 6-2, forming a lactam ring according to Step 6-3, and finally subjecting the lactam compound (15) to second cyclization reaction in Step 6-4.

Preparation of Compound of General Formula (I)

The compound of the general formula (I) can be prepared from a lactam compound (15) according to Step 6-4. Step 6-4 consists of deprotection reaction of alcohol groups or amine groups in $L_{12}$ and $L_{13}$ of a compound (15) and subsequent cyclization reaction. A deprotection reaction described in many known documents may be used (see T. W. Green, "Protective Groups in Organic Synthesis", John Wiley & Sons, Inc., 1981). The cyclization reaction varies according to the starting material and is not specifically limited insofar as the conditions are similar to those in this reaction. A method known to a person skilled in the art may be used for the reaction. Preferable examples of the method include i) a method of forming a cyclic ether from a diol (see Journal of Fluorine Chemistry, 1997, vol. 2, p. 119, or Scientia Pharmaceutica, 1996, vol. 64, p. 3, for example); and ii) a method of forming a cyclic amine from an aminoalcohol (see Petrochemia, 1990, vol. 30, p. 56; WO 2003/076386; or Tetrahedron Letters, 1982, vol. 23, p. 229, for example). More preferably, for example, the compound of the general formula (I) can be obtained in a high yield by heating the deprotected compound in a solvent or without a solvent in the presence of 0.1 to 10 equivalents of an organic acid such as p-toluenesulfonic acid or camphorsulfonic acid or an inorganic acid such as sulfuric acid or hydrochloric acid with respect to the deprotected compound, or by heating the deprotected compound in the presence of 0.1 to 1.0 equivalent of an organic metal such as tetrakistriphenylphosphine palladium or tristriphenylphosphine ruthenium with respect to the deprotected compound. The solvent used in this step varies according to the starting material and the reagent used, and is not specifically limited insofar as the solvent does not inhibit the reaction and allows the starting material to be dissolved therein to a certain extent. Preferable examples of the solvent include methylene chloride, chloroform, 1,4-dioxane, 1,2-dimethoxyethane, dimethyl sulfoxide, toluene, tetrahydrofuran, dimethylformamide, ethanol, methanol, water, and a mixed solvent thereof. The reaction temperature must be a temperature that can complete the reaction without promoting formation of an undesirable by-product, and is preferably ice-cold temperature to 100° C., for example. Under preferable reaction conditions, the reaction is preferably completed in 1 to 24 hours, for example, and the progress of the reaction can be monitored by a known chromatography technique. An undesirable by-product can be removed by a technique known to a person skilled in the art such as a conventional chromatography technique or/and crystallization.

Preparation of Lactam Compound (15)

The lactam compound (15) can be prepared from a cinnamide compound (14) as a starting material by cyclization reaction that involves leaving of $L_{10}$ of the cinnamide compound (14) according to Step 6-3. Specifically, for example, the desired lactam compound (15) can be obtained in a high yield by treating a compound (14) with 1.0 to 5.0 equivalents of a base with respect to the compound (14), for example. This reaction is preferably performed in the presence of a solvent from the viewpoint of operativity and stirring efficiency. The solvent used varies according to the starting material and the base used, and is not specifically limited insofar as the solvent does not inhibit the reaction and allows the starting material to be dissolved therein to a certain extent. Preferable examples of the solvent include polar solvents such as 1-methyl-2-pyrrolidone, N,N-dimethylformamide, and dimethyl sulfoxide; ether solvents such as tetrahydrofuran, 1,4-dioxane, and 1,2-dimethoxyethane; nonpolar solvents such as benzene, toluene, and xylene; alcohol solvents such as ethanol and methanol; water; and mixed solvents thereof. The base used varies according to the starting material and the solvent. Preferable examples of the base include alkali metal hydroxides such as sodium hydroxide and lithium hydroxide; alkali metal carbonates such as sodium carbonate; alkali metal salts of alcohols such as sodium methoxide and potassium tert-butoxide; organic bases such as triethylamine, pyridine, and diazabicyclononene; organic metals such as butyl lithium and lithium diisobutylamide; alkali metal hydrides such as sodium hydride; and alkali metal ammonium salts such as sodium amide. The reaction temperature must be a temperature that can complete the reaction without promoting formation of an undesirable by-product, and is preferably −78 to 150° C., for example. Under preferable reaction conditions, the reaction is preferably completed in 1 to 24 hours, for example, and the progress of the reaction can be monitored by a known chromatography technique. An undesirable by-product can be removed by a technique known to a person skilled in the art such as a conventional chromatography technique, extraction, or/and crystallization.

Preparation of Cinnamide Compound (14)

The cinnamide compound (14) can be prepared from a compound (12) and preferably 1.0 to 5.0 equivalents of an amine compound (13) with respect to the compound (12), for example, according to amidation reaction in Step 6-2. The amidation reaction varies according to the starting material and is not specifically limited insofar as the conditions are similar to those in this reaction. A known method described in many documents may be used for the reaction (see Shin Jikken Kagaku Koza (New Courses in Experimental Chemistry), vol. 14, Yuki Kagobutsu No Gosei To Hannou (Synthesis and Reaction of Organic Compounds) [H], edited by The Chemical Society of Japan, Maruzen Co., Ltd., February 1978, p. 1136-1162, for example). Preferable examples of the method include i) a method of converting a compound (12) into an acid halide and reacting the acid halide with an amine compound (13) under basic conditions (see Shin Jikken Kagaku Koza (New Courses in Experimental Chemistry), vol. 14, Yuki Kagobutsu No Gosei To Hannou (Synthesis and Reaction of Organic Compounds) [II], edited by The Chemical Society of Japan, Maruzen Co., Ltd., February 1978, p. 1142-1145, for example); and ii) a method of reacting a compound (12) with an amine compound (13) using a condensing (see "Yukikagaku Jikken No Tebiki (Introduction to Organic Chemistry Experiments) [4]", Kagaku-Dojin Publishing Company, Inc., September 1990, p. 27-52, for example).

Preferable examples of the reaction of converting a compound (12) into an acid halide in the method i) include a method of stirring a compound (12) in a solvent in the presence of 1.0 to 10.0 equivalents of a halogenating agent with respect to the compound (12). The halogenating agent used varies according to the starting material and is not specifically limited. Preferable examples of the halogenating agent include thionyl chloride, phosphorus pentachloride, and oxalyl chloride. The solvent used is not specifically limited insofar as the solvent does not inhibit the reaction and allows the starting material to be dissolved therein to a certain extent. Preferable examples of the solvent include methylene chloride, chloroform, and toluene. The reaction may efficiently proceed when 0.1 to 1.0 equivalent of an organic base such as pyridine, dimethylformamide, or the like is appropriately added with respect to the compound (12). The reaction temperature must be a temperature that can complete the reaction without promoting formation of an undesirable by-product, and is preferably ice-cold temperature to 150° C., for example. Under preferable reaction conditions, the reaction is preferably completed in 1 to 24 hours, for example, and the progress of the reaction can be monitored by a known chromatography technique. An undesirable by-product can be removed by a technique known to a person skilled in the art such as a conventional chromatography technique or/and crystallization.

Preferable examples of the subsequent coupling reaction include a method of stirring in a solvent the acid halide and 1.0 to 5.0 equivalents of an amine compound (13) with respect to the acid halide in the presence of 1.0 to 100.0 equivalents of a base with respect to the acid halide. The base used varies according to the starting material and is not specifically limited. Preferable examples of the base include pyridine, triethylamine, N,N-diisopropylethylamine, lutidine, quinoline, and isoquinoline. The solvent used is not specifically limited insofar as the solvent does not inhibit the reaction and allows the starting material to be dissolved therein to a certain extent. Preferable examples of the solvent include methylene chloride, chloroform, toluene, tetrahydrofuran, and 1,4-dioxane. A base may be used as a solvent. Alternatively, it is possible to use a two-layer partition system consisting of a base that is an alkali solution, preferably a sodium hydroxide or potassium hydroxide solution, for example, and a halogenated solvent such as methylene chloride or 1,2-dichloroethane. The reaction temperature must be a temperature that can complete the reaction without promoting formation of an undesirable by-product, and is preferably ice-cold temperature to 100° C., for example. Under preferable reaction conditions, the reaction is preferably completed in 1 to 24 hours, for example, and the progress of the reaction can be monitored by a known chromatography technique. An undesirable by-product can be removed by a technique known to a person skilled in the art such as a conventional chromatography technique or/and crystallization.

Preferable examples of the method ii) include a method of stirring in a solvent a compound (12) and 1.0 to 5.0 equivalents of an amine compound (13) with respect to the compound (12) in the presence of 1.0 to 5.0 equivalents of a condensing agent with respect to the compound (12). The condensing agent used varies according to the starting material and is not specifically limited. Preferable examples of the condensing agent include 1,3-dicyclohexylcarbodiimide, 1-ethyl-3-(3'-dimethylaminopropyl)carbodiimide, benzotriazol-1-yloxytris(dimethylamino)phosphonium hexafluorophosphate, diethyl cyanophosphonate, and bis(2-oxo-3-oxazolidinyl)phosphinic chloride. Preferably, 1.0 to 2.0 equivalents of N-hydroxysuccinimide or N-hydroxybenzotriazole may be added with respect to the compound (12) in order to make the reaction efficiently proceed, for example. This reaction is preferably performed in the presence of a solvent from the viewpoint of operativity and stirring efficiency. The solvent used varies according to the starting material and the condensing agent used, and is not specifically limited insofar as the solvent does not inhibit the reaction and allows the starting material to be dissolved therein to a certain extent. Preferable examples of the solvent that can be used include halogenated solvents such as methylene chloride and 1,2-dichloroethane, and polar solvents such as tetrahydrofuran and N,N-dimethylformamide. The reaction temperature must be a temperature that can complete the reaction without promoting formation of an undesirable by-product, and is preferably ice-cold temperature to 100° C., for example. Under preferable reaction conditions, the reaction is preferably completed in 1 to 24 hours, for example, and the progress of the reaction can be monitored by a known chromatography technique. An undesirable by-product can be removed by a technique known to a person skilled in the art such as a conventional chromatography technique or/and crystallization.

Preparation of Amine Compound (13)

The amine compound (13) is commercially available or can be prepared by a method known to a person skilled in the art. If not commercially available, the amine compound (13) can be prepared by converting a corresponding aldehyde group into a vinyl group and then aminohydroxylating the compound (see Journal of the American Chemical Society, 2001, vol. 123, p. 1862, for example).

Preparation of Compound (12)

Step 6-1 consists of a step of synthesizing a cinnamate compound by condensation reaction of an aldehyde compound (1) with a Horner-Emmons reagent (11) and a subsequent step of deprotecting an ester group into carboxylic acid. Specifically, in the Horner-Emmons reaction, the cinnamate compound can be prepared from an aldehyde compound (1) as a starting material by a method known to a person skilled in the art (see Jikken Kagaku Koza (Courses in Experimental Chemistry), vol. 19, Yuki Gosei (Organic Synthesis) [I], edited by The Chemical Society of Japan, Maruzen Co., Ltd., June 1992, p. 57-85, for example). Preferably, the desired cinnamate compound can be obtained by reacting an aldehyde compound (1) with preferably 1.0 to 5.0 equivalents of a Horner-Emmons reagent (11) with respect to the aldehyde compound (1), for example, in the presence of preferably 1.0 to 5.0 equivalents of a base with respect to the aldehyde compound (1), for example. The solvent used varies according to the starting material and the reagent used and is not specifically limited. Preferable examples of the solvent include polar solvents such as 1-methyl-2-pyrrolidone, N,N-dimethylformamide, and dimethyl sulfoxide; ether solvents such as tetrahydrofuran, 1,4-dioxane, and 1,2-dimethoxyethane; nonpolar solvents such as benzene, toluene, and xylene; alcohol solvents such as ethanol and methanol; water; and mixed solvents thereof. The base used varies according to the starting material and the solvent. Preferable examples of the base include alkali metal hydroxides such as sodium hydroxide and lithium hydroxide; alkali metal carbonates such as sodium carbonate; alkali metal salts of alcohols such as sodium methoxide and potassium tert-butoxide; organic bases such as triethylamine, pyridine, and diazabicyclononene; organic metals such as butyl lithium and lithium diisobutylamide; alkali metal hydrides such as sodium hydride; and alkali metal ammonium salts such as sodium amide. The reaction temperature must be a temperature that can complete the reaction without promoting formation of an undesirable by-product, and is preferably −78 to 150° C., for example. Under preferable reaction conditions, the reaction is preferably completed in 1 to 24 hours, for example, and the progress of the reaction can be monitored by a known chromatography technique. An undesirable by-product can be removed by a technique known to a person skilled in the art such as a conventional chromatography technique, extraction, or/and crystallization. A known deprotection method known to a person skilled in the art may be used for hydrolysis reaction to obtain a compound (12) from the cinnamate compound as a starting material (see T. W. Green, "Protective Groups in Organic Synthesis", John Wiley & Sons, Inc., 1981, p. 154-186). Preferably, for example, the compound (12) can be obtained in a high yield by reacting the cinnamate compound preferably in an alcohol solvent such as methanol or ethanol, for example, in the presence of preferably 1.0 to 50.0 equivalents of an alkali metal hydroxide such as sodium hydroxide or potassium hydroxide with respect to the cinnamate compound, for example.

Preparation of Compound (11)

The compound (11) is commercially available or can be prepared by a method known to a person skilled in the art if not commercially available. For example, the compound (11) can be prepared by alkylation of commercially available trialkylphosphonoacetic acid (see Synthetic Communication, 1991, vol. 22, p. 2391, for example), Arbuzov reaction using an alkylphosphinite of α-halogenoacetic acid derivative (see Chemical Review, 1981, vol. 81, p. 415, for example), or Becker reaction using a metal phosphonite (see Journal of the American Chemical Society, 1945, vol. 67, p. 1180, for example. The compound of the general formula (I) or (II) or pharmacologically acceptable salt thereof according to the present invention has an effect of reducing Aβ42 production. Accordingly, the present invention can particularly provide a therapeutic or prophylactic agent for a neurodegenerative disease caused by Aβ such as Alzheimer's disease or Down's syndrome.

Compounds included in the present invention exhibit excellent pharmaceutical utility, for example, in vitro activity, in vivo activity, solubility, stability, pharmacokinetics, and reduction in toxicity.

The therapeutic or prophylactic agent of the present invention can be prepared by a conventional method. Preferable examples of the dosage form include tablets, powders, fine granules, granules, coated tablets, capsules, syrups, troches, inhalants, suppositories, injections, ointments, ophthalmic solutions, ophthalmic ointments, nasal drops, ear drops, cataplasms, and lotions. The therapeutic or prophylactic agent can be prepared by using ingredients typically used such as an excipient, a binder, a lubricant, a colorant, and a corrective, and ingredients used where necessary such as a stabilizer, an emulsifier, an absorbefacient, a surfactant, a pH adjuster, a preservative, and an antioxidant, and can be prepared by blending ingredients generally used as materials for a pharmaceutical preparation. Examples of such ingredients include animal and vegetable oils such as soybean oil, beef tallow, and synthetic glyceride; hydrocarbons such as liquid paraffin, squalane, and solid paraffin; ester oils such as octyldodecyl myristate and isopropyl myristate; higher alcohols such as cetostearyl alcohol and behenyl alcohol; a silicone resin; silicone oil; surfactants such as polyoxyethylene fatty acid ester, sorbitan fatty acid ester, glycerin fatty acid ester, polyoxyethylene sorbitan fatty acid ester, polyoxyethylene hydrogenated castor oil, and a polyoxyethylene-polyoxypropylene block copolymer; water-soluble polymers such as hydroxyethylcellulose, polyacrytic acid, a carboxyvinyl polymer, polyethylene glycol, polyvinylpyrrolidone, and methylcellulose; lower alcohols such as ethanol and isopropanol; polyhydric alcohols such as glycerin, propylene glycol, dipropylene glycol, and sorbitol; sugars such as glucose and sucrose; inorganic powders such as silicic anhydride, magnesium aluminum silicate, and aluminum silicate; and purified water. Examples of the excipient used include lactose, corn starch, saccharose, glucose, mannitol, sorbitol, crystalline cellulose, and silicon dioxide. Examples of the binder used include polyvinyl alcohol, polyvinyl ether, methylcellulose, ethylcellulose, gum arabic, tragacanth, gelatin, shellac, hydroxypropylmethylcellulose, hydroxypropylcellulose, polyvinylpyrrolidone, a polypropylene glycol-polyoxyethylene block copolymer, and meglumine. Examples of the disintegrator used include starch, agar, gelatin powder, crystalline cellulose, calcium carbonate, sodium bicarbonate, calcium citrate, dextrin, pectin, and carboxymethylcellulose calcium. Examples of the lubricant used include magnesium stearate, talc, polyethylene glycol, silica, and hydrogenated vegetable oil. Examples of the colorant used include those that are permitted to be added to pharmaceuticals. Examples of the corrective used include cocoa powder, menthol, empasm, mentha oil, borneol, and cinnamon powder.

For example, an oral preparation is prepared by adding an active ingredient compound or a salt thereof or a hydrate of the compound or salt, an excipient, and, where necessary, a binder, a disintegrator, a lubricant, a colorant, and a corrective, for example, and then forming the mixture into powder, fine granules, granules, tablets, coated tablets, or capsules, for example, by a conventional method. It is obvious that tablets or granules may be appropriately coated, for example, sugar coated, where necessary. A syrup or an injection preparation is prepared by adding a pH adjuster, a solubilizer, and an isotonizing agent, for example, and a solubilizing aid, a stabilizer, and the like where necessary by a conventional method. An external preparation may be prepared by any conventional method without specific limitations. As a base material, any of various materials usually used for a pharmaceutical, a quasi drug, a cosmetic, or the like may be used. Examples of the base material include materials such as animal and vegetable oils, mineral oils, ester oils, waxes, higher alcohols, fatty acids, silicone oils, surfactants, phospholipids, alcohols, polyhydric alcohols, water-soluble polymers, clay minerals, and purified water. A pH adjuster, an antioxidant, a chelator, a preservative and fungicide, a colorant, a flavor, or the like may be added where necessary. Further, an ingredient having a differentiation inducing effect such as a blood flow enhancer, a bactericide, an antiphlogistic, a cell activator, vitamin, amino acid, a humectant, or a keratolytic agent may be blended where necessary. The dose of the therapeutic or prophylactic agent of the present invention varies according to the degree of symptoms, age, sex, body weight, mode of administration, type of salt, and specific type of disease, for example. Typically, the compound of the formula (I) or pharmacologically acceptable salt thereof is orally administered to an adult at 30 μg to 10 g, preferably 100 μg to 5 g, and more preferably 100 μg to 1 g per day, or is administered to an adult by injection at about 30 μg to 1 g, preferably 100 μg to 500 mg, and more preferably 100 μg to 30 mg per day, in a single dose or multiple doses, respectively.

The present invention will now be described in detail with reference to examples and test examples. However, the examples and test examples are provided only for illustration purposes. The prophylactic or therapeutic agent for a disease caused by Aβ according to the present invention is not limited to the following specific examples in any case. A person skilled in the art can fully implement the present invention by making various modifications to not only the following examples and test examples but also the claims of the present specification, and such modifications are within the scope of the claims of the present specification.

The following abbreviations are used in the following examples.
DMF: N,N-dimethylformamide
THF: Tetrahydrofuran
LAH: Lithium aluminum hydride
EDC: 1-Ethyl-3-(3-dimethylaminopropyl)carbodiimide hydrochloride
HOBT: 1-Hydroxybenzotriazole
IPEA: Diisopropylethylamine
TEA: Triethylamine
DPPA: Diphenylphosphorylazide
CDI: N,N'-carbonyldiimidazole
TBAF: Tetrabutylammonium fluoride
PYBOP: Benzotriazol-1-yloxytris(pyrrolidino)phosphonium hexafluorophosphate
DBU: 1,8-Diazabicyclo[5.4.0]undec-7-ene
DAST: Diethylaminosulfur trifluoride
DMSO: Dimethysulfoxide
DIBAL-H: Diisobutylaluminum hydride
Dess-Martin reagent: Dess-Martin periodinane
DME: 1,2-Dimethoxyethane
TBSCl: tert-Butyldimethylsilyl chloride
DMAP: 4-Dimethylaminopyridine
AIBN: 2,2'-Azobis(isobutyronitrile)
NMP: 1-Methyl-2-pyrrolidinone
LDA: Lithium diisopropylamide
TBSOTf: tert-Butyldimethylsilyl trifluoromethanesulfonate
BOPCl: Bis(2-oxo-3-oxazolidinyl)phosphinic chloride
Grubbs catalyst 2nd generation: Tricyclohexylphosphine[1,3-bis(2,4,6-trimethylphenyl)-4,5-dihydroimidazol-2-ylidene][benzylidene]ruthenium (IV) dichloride
TMED: N,N,N',N'-tetramethylethylenediamine
TMSI: Iodotrimethylsilane
mCPBA: m-Chloroperbenzoic acid Chromatography was performed using BW-300 manufactured by Fuji Silysia Chemical Ltd. as a carrier unless otherwise specified.
LC-MS: High performance liquid chromatography for preparative isolation of a target compound using mass spectroscopy. As an elution solvent, a 10% to 99% linear gradient system of water containing 0.1% trifluoroacetic acid and acetonitrile containing 0.1% trifluoroacetic acid was used.

Examples 1, 2, 3, and 4

Synthesis of (E)-(3S)-(3,4,5-trifluorophenyl)-6-[3-methoxy-4-(4-methyl-1H-imidazol-1-yl)benzylidene]-(9R)-hexahydroindolizin-5-one, (E)-(3R)-(3,4,5-trifluorophenyl)-6-[3-methoxy-4-(4-methyl-1H-imidazol-1-yl)benzylidene]-(9R)-hexahydroindolizin-5-one, (E)-(3S)-(3,4,5-trifluorophenyl)-6-[3-methoxy-4-(4-methyl-1H-imidazol-1-yl)benzylidene]-(9S)-hexahydroindolizin-5-one, and (E)-(3R)-(3,4,5-trifluorophenyl)-6-[3-methoxy-4-(4-methyl-1H-imidazol-1-yl)benzylidene]-(9S)-hexahydroindolizin-5-one

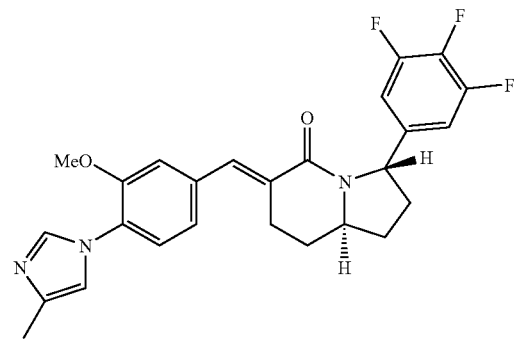

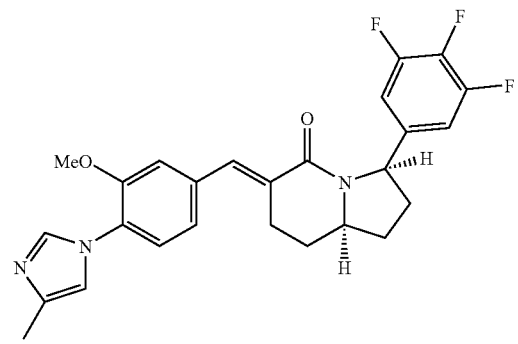

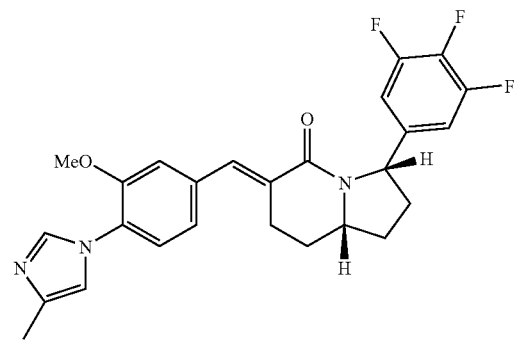

-continued

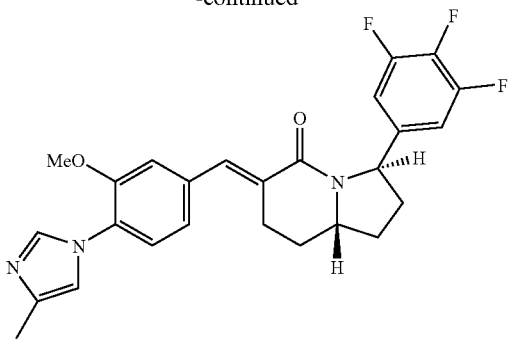

Synthesis of methyl 3-methoxy-4-nitrobenzoate

Methyl iodide (463 g) was added dropwise to a mixture of 3-hydroxy-4-nitrobenzoic acid (199 g) with potassium carbonate (450 g) in DMF (1 L) at room temperature. The reaction solution was stirred at room temperature overnight, and then methyl iodide (230 g) was added to the reaction solution. The reaction solution was further stirred at room temperature for six hours. The reaction solution was added to ice water, and the precipitated solid was collected by filtration. The resulting solid was dried at 50° C. overnight to obtain 178 g of the title compound. The property values corresponded to the reported values (CAS #5081-37-8).

Synthesis of methyl 4-amino-3-methoxybenzoate

10% palladium-carbon (containing 50% water, 15 g) was added to a solution of methyl 3-methoxy-4-nitrobenzoate (150 g) in methanol (600 mL) and THF (300 mL), and the reaction solution was stirred at a hydrogen pressure of 0.9 MPa at 50° C. to 64° C. for 6.5 hours. The reaction solution was left to cool to room temperature and then filtered through celite. The resulting filtrate was concentrated under reduced pressure to obtain 134 g of the title compound. The property values corresponded to the reported values (CAS #41608-64-4).

Synthesis of methyl 4-formylamino-3-methoxybenzoate

Acetic anhydride (268 mL) was added dropwise to formic acid (401 mL) at room temperature, and the reaction solution was stirred at room temperature for 40 minutes. A solution of methyl 4-amino-3-methoxybenzoate (134 g) in THF (600 mL) was added dropwise to the reaction solution at room temperature, and the reaction solution was stirred for one hour. 3.8 L of ice water was added to the reaction solution, and the precipitated solid was filtered and further washed with water (2 L). The resulting solid was dried at 50° C. overnight to obtain 111 g of the title compound. The property values corresponded to the reported values (CAS #700834-18-0).

Synthesis of methyl 4-[formyl-(2-oxopropyl)amino]-3-methoxybenzoate

Chloroacetone (84.5 mL) was added dropwise to a mixture of methyl 4-formylamino-3-methoxybenzoate (111 g), cesium carbonate (346 g), and potassium iodide (8.78 g) in DMF (497 mL) at room temperature, and the reaction solution was stirred for three hours. Cesium carbonate (173 g) and chloroacetone (42.0 mL) were added to the reaction solution, which was then stirred at room temperature for two hours. Ice water and ethyl acetate were added to the reaction solution, and the organic layer was separated. Ethyl acetate was added to the aqueous layer, and the organic layer was separated. The organic layers were combined and washed with water and brine in this order. The resulting organic layers were dried over anhydrous magnesium sulfate and then concentrated under reduced pressure. The residue was diluted with toluene, and the solution was concentrated under reduced pressure. tert-Butyl methyl ether and heptane were added to the resulting residue, and the precipitated solid was collected by filtration and washed with a solution of 50% tert-butyl methyl ether in heptane. The resulting solid was air-dried overnight to obtain 118 g of the title compound.

$^1$H-NMR (CDCl$_3$) δ(ppm): 2.19 (s, 3H), 3.91 (s, 3H), 3.94 (s, 3H), 4.49 (s, 2H), 7.31 (d, J=8.0 Hz, 1H), 7.63 (d, J=2.0 Hz, 1H), 7.69 (dd, J=8.0, 2.0 Hz, 1H), 8.33 (s, 1H).

Synthesis of methyl 3-methoxy-4-(4-methyl-1H-imidazol-1-yl)benzoate

A solution of methyl 4-[formyl-(2-oxopropyl)amino]-3-methoxybenzoate (118 g) and ammonium acetate (172 g) in acetic acid (255 mL) was heated and stirred at 140° C. for one hour. After the reaction was completed, the reaction solution was neutralized with aqueous ammonia under ice-cooling. Ethyl acetate was added to the reaction solution, and the organic layer was separated. The resulting organic layer was dried over anhydrous magnesium sulfate and then filtered on a silica gel pad, and the filtrate was concentrated under reduced pressure. tert-Butyl methyl ether and heptane were added to the residue, and the precipitated solid was collected by filtration and washed with a solution of 50% tert-butyl methyl ether in heptane. The resulting solid was air-dried overnight to obtain 68.4 g of the title compound. Further, the crystallization mother liquor was concentrated under reduced pressure, and the residue was purified by silica gel column chromatography (elution solvent: heptane-ethyl acetate system) to obtain 22.3 g of the title compound.

$^1$H-NMR (CDCl$_3$) δ(ppm): 2.30 (s, 3H), 3.94 (s, 3H), 3.96 (s, 3H), 6.98 (brs, 1H), 7.32 (d, J=8.4 Hz, 1H), 7.71-7.73 (m, 2H), 7.79 (brs, 1H).

Synthesis of 3-methoxy-4-(4-methyl-1H-imidazol-1-yl)benzaldehyde

A solution of pyrrolidine (18 mL) in THF (45 mL) was added dropwise to a solution of sodium bis(2-methoxyethoxy)aluminum hydride (65% solution in toluene, 56 mL) in THF (60 mL) at −5° C. or less over 15 minutes. The reaction solution was stirred at room temperature for one hour. Then, a suspension of tert-butoxide (2.10 g) in THF (15 mL) was added dropwise to the reaction solution at room temperature, and the reaction solution was stirred for 15 minutes. The above reaction solution was added dropwise to a solution of methyl 3-methoxy-4-(4-methyl-1H-imidazol-1-yl)benzoate (20 g) in THF (50 mL) under ice-cooling over 30 minutes. The reaction solution was stirred at room temperature for two hours, and then a 5 N sodium hydroxide solution (150 mL) was added dropwise to the reaction solution. Ethyl acetate was added to the reaction solution, and the organic layer was separated. The organic layer was washed with a saturated ammonium chloride solution and brine in this order. The organic layer was dried over anhydrous magnesium sulfate and filtered on a silica gel pad, and then the filtrate was concentrated under reduced pressure. The residue was diluted with ethyl acetate, and the precipitated solid was collected by filtration. The resulting solid was air-dried overnight to obtain 7.10 g of the title compound. Further, the crystallization mother liquor was concentrated under reduced pressure, and the residue was purified by silica gel column chromatography (elution solvent: heptane-ethyl acetate-2-propanol system) to obtain 2.65 g of the title compound.

$^1$H-NMR (CDCl$_3$) δ(ppm): 2.31 (s, 3H), 3.97 (s, 3H), 7.02 (brs, 1H), 7.44 (d, J=8.0 Hz, 1H), 7.55 (dd, J=1.6 Hz, 8.0 Hz, 1H), 7.58 (d, J=1.6 Hz, 1H), 7.84 (brs, 1H), 10.00 (s, 1H).

Synthesis of (E)-(3S)-(3,4,5-trifluorophenyl)-6-[3-methoxy-4-(4-methyl-1H-imidazol-1-yl)benzylidene]-(9R)-hexahydroindolizin-5-one, (E)-(3R)-(3,4,5-trifluorophenyl)-6-[3-methoxy-4-(4-methyl-1H-imidazol-1-yl)benzylidene]-(9R)-hexahydroindolizin-5-one, (E)-(3S)-(3,4,5-trifluorophenyl)-6-[3-methoxy-4-(4-methyl-1H-imidazol-1-yl)benzylidene]-(9S)-hexahydroindolizin-5-one, and (E)-(3R)-(3,4,5-trifluorophenyl)-6-[3-methoxy-4-(4-methyl-1H-imidazol-1-yl)benzylidene]-(9S)-hexahydroindolizin-5-one LDA (1.5 M solution in cyclohexane, 0.14 mL) was added to a solution of 3-(3,4,5-trifluorophenyl)-9-hexahydroindolizin-5-one (36 mg) synthesized according to the method described in The Journal of Organic Chemistry, 2001, vol. 66, p. 886 in THF (2 mL) at −78° C., and the reaction solution was stirred at −78° C. for one hour. A solution of 3-methoxy-4-(4-methyl-1H-imidazol-1-yl)benzaldehyde (36 mg) in THF (1 mL) was added to the reaction solution at −78° C. The reaction solution was stirred at −78° C. for one hour, and then 2 N aqueous hydrochloric acid and a toluene-THF (2:1) mixed solution were added to the reaction solution. The reaction solution was heated to room temperature, and the organic layer was separated. The resulting organic layer was washed with brine and then dried over magnesium sulfate and concentrated under reduced pressure to obtain 67 mg of a crude aldol adduct. Thionyl chloride (0.02 mL) was added to a solution of the resulting crude aldol adduct (67 mg) in DME (3 mL), and the reaction solution was stirred at room temperature for one hour. A 2 N sodium hydroxide solution and a toluene-THF mixed solution (2:1) were added to the reaction solution, and the organic layer was separated. The resulting organic layer was washed with brine, and then dried over magnesium sulfate and concentrated under reduced pressure. Sodium methoxide (5.2 M solution in methanol, 0.04 mL) was added to a solution of the resulting residue in THF (3 mL), and the reaction solution was stirred at room temperature for one hour. Ethyl acetate and brine were added to the reaction solution, and the organic layer was separated. The resulting organic layer was dried over magnesium sulfate and concentrated under reduced pressure. The residue was purified by silica gel column chromatography (carrier: Chromatorex NH; elution solvent: ethyl acetate) to obtain an isomer mixture of the title compound. The isomer mixture was separated by CHIRALPAK™ AD-H manufactured by Daicel Chemical Industries, Ltd. (2 cm×25 cm; mobile phase: ethanol) to obtain the title optically active compound with a retention time of 6 minutes (3.8 mg; >99% ee), the title optically active compound with a retention time of 7 minutes (2.0 mg; >99% ee), the title optically active compound with a retention time of 9 minutes (2.1 mg; >99% ee), and the title optically active compound with a retention time of 11 minutes (3.8 mg; >99% ee).

The property values of the title optically active compound with a retention time of 6 minutes (Example 1) are as follows.

$^1$H-NMR (CDCl$_3$) δ(ppm): 1.42-1.85 (m, 3H), 2.21-2.36 (m, 5H), 2.45-2.53 (m, 1H), 2.70 (tt, J=14.4, 3.2 Hz, 1H), 3.11 (dt, J=16.0, 2.8 Hz, 1H), 3.85 (s, 3H), 3.88-3.99 (m, 1H), 5.10 (t, J=8.0 Hz, 1H), 6.88 (dd, J=8.0, 6.0 Hz, 2H), 6.93 (s, 1H), 7.01 (brs, 1H), 7.04 (brd, J=8.0 Hz, 1H), 7.25 (d, J=8.0 Hz, 1H), 7.72 (d, J=2.4 Hz, 1H), 7.81 (s, 1H).

The property values of the title optically active compound with a retention time of 7 minutes (Example 2) are as follows.

$^1$H-NMR (CDCl$_3$) δ(ppm): 1.65-1.87 (m, 3H), 2.06-2.14 (m, 1H), 2.30-2.39 (m, 5H), 2.69-2.80 (m, 1H), 3.15 (brt, J=16.8 Hz, 1H), 3.76-3.85 (m, 1H), 3.86 (s, 3H), 5.10 (d, J=8.8 Hz, 1H), 6.79 (dd, J=8.4, 6.4 Hz, 2H), 6.95 (s, 1H), 7.05 (brs, 1H), 7.08 (brd, J=8.0 Hz, 1H), 7.26 (d, J=8.0 Hz, 1H), 7.74 (brs, 1H), 7.85 (s, 1H).

The property values of the title optically active compound with a retention time of 9 minutes (Example 3) are as follows.

$^1$H-NMR (CDCl$_3$) δ(ppm): 1.65-1.87 (m, 3H), 2.06-2.14 (m, 1H), 2.30-2.39 (m, 5H), 2.69-2.80 (m, 1H), 3.15 (brt, J=16.8 Hz, 1H), 3.76-3.85 (m, 1H), 3.86 (s, 3H), 5.10 (d, J=8.8 Hz, 1H), 6.79 (dd, J=8.4, 6.4 Hz, 2H), 6.95 (s, 1H), 7.05 (brs, 1H), 7.08 (brd, J=8.0 Hz, 1H), 7.26 (d, J=8.0 Hz, 1H), 7.74 (brs, 1H), 7.85 (s, 1H).

The property values of the title optically active compound with a retention time of 11 minutes (Example 4) are as follows.

$^1$H-NMR (CDCl$_3$) δ(ppm): 1.42-1.85 (m, 3H), 2.21-2.36 (m, 5H), 2.45-2.53 (m, 1H), 2.70 (tt, J=14.4, 3.2 Hz, 1H), 3.11 (dt, J=16.0, 2.8 Hz, 1H), 3.85 (s, 3H), 3.88-3.99 (m, 1H), 5.10 (t, J=8.0 Hz, 1H), 6.88 (dd, J=8.0, 6.0 Hz, 2H), 6.93 (s, 1H), 7.01 (brs, 1H), 7.04 (brd, J=8.0 Hz, 1H), 7.25 (d, J=8.0 Hz, 1H), 7.72 (d, J=2.4 Hz, 1H), 7.81 (s, 1H).

(E)-(3S)-(3,4,5-trifluorophenyl)-6-[3-methoxy-4-(4-methyl-1H-imidazol-1-yl)benzylidene]-(9S)-hexahydroindolizin-5-one was also separately synthesized by the following method.

Synthesis of ethyl (2R,5S)-5-(3,4,5-trifluorophenyl) pyrrolidine-2-carboxylate

To a solution of (R)-5-oxopyrrolidine-1,2-dicarboxylic acid 1-tert-butyl ester 2-ethyl ester (CAS No. 128811-48-3; 4.1 g) in THF (100 mL), 3,4,5-trifluorophenylmagnesium bromide (0.35 M solution in diethyl ether; 55 mL) was added dropwise at −40° C. over 20 minutes, and the reaction solution was stirred at −40° C. for five hours. Saturated aqueous ammonium chloride and ethyl acetate were added to the solution. The reaction solution was heated to room temperature, and the organic layer was separated. The resulting organic layer was washed with brine, dried over anhydrous magnesium sulfate, and then concentrated under reduced pressure. The residue was purified by silica gel column chromatography (heptane->heptane:ethyl acetate=1:1) to obtain 4.8 g of ethyl (R)-2-tert-butoxycarbonylamino-5-oxo-5-(3,4,5-trifluorophenyl)pentanoate. A solution of 4 N hydrochloric acid in ethyl acetate (30 mL) was added to a solution of the resulting ethyl (R)-2-tert-butoxycarbonylamino-5-oxo-5-(3,4,5-trifluorophenyl)pentanoate in ethyl acetate (30 mL), and the solution was stirred for 16 hours. The reaction solution was concentrated under reduced pressure. Ethyl acetate and saturated sodium bicarbonate water were added to the residue, and the organic layer was separated. The resulting organic layer was dried over anhydrous magnesium sulfate and then concentrated under reduced pressure. 10% palladium-carbon (100 mg) was added to a solution of the residue in ethyl acetate (50 mL), and the reaction solution was stirred in a hydrogen atmosphere at 1 atm for six hours. The reaction solution was filtered through celite, and the filtrate was concentrated under reduced pressure to obtain 2.91 g of the title compound. The property value of the compound is as follows.

ESI-MS; m/z 274 [M⁺+H].

¹H-NMR (CDCl₃) δ(ppm): 1.31 (t, J=6.8 Hz, 3H), 1.57-1.70 (m, 1H), 2.04-2.22 (m, 3H), 3.93 (dd, J=8.0, 5.2 Hz, 1H), 4.17-4.27 (m, 3H) 7.13 (dd, J=8.8, 6.4 Hz, 2H).

Synthesis of [(2R,5S)-5-(3,4,5-trifluorophenyl)pyrrolidin-2-yl]methanol

LAH (483 mg) was added to a solution of ethyl (2R,5S)-5-(3,4,5-trifluorophenyl)pyrrolidine-2-carboxylate (2.91 g) in THF (50 mL) at −15° C. over one hour. The reaction solution was stirred at −15° C. for 19 hours. Water (0.5 mL), a 5 N sodium hydroxide solution (0.5 mL), and water (1.5 mL) were sequentially added to the reaction solution, and the mixture was stirred at room temperature for 30 minutes. The reaction solution was filtered through celite, and the filtrate was concentrated under reduced pressure to obtain 2.4 g of the title compound. The property values of the compound are as follows.

ESI-MS; m/z 232 [M⁺+H].

¹H-NMR (CDCl₃)₆(ppm): 1.51-1.63 (m, 1H), 1.66-1.77 (m, 1H), 1.89-2.00 (m, 1H), 2.10-2.20 (m, 1H), 3.43 (dd, J=10.0, 5.6 Hz, 1H), 3.47-3.55 (m, 1H), 3.64 (dd, J=10.0, 3.6 Hz, 1H), 4.23 (t, J=8.0 Hz, 1H), 7.02 (t, J=8.0 Hz, 2H).

Synthesis of ethyl (E)-3-[(2R,5S)-1-(3-butenoyl)-5-(3,4,5-trifluorophenyl)pyrrolidin-2-yl]acrylate Triethylamine (1.95 mL) and BOPCl (2.85 g) were added to a solution of [(2R,5S)-5-(3,4,5-trifluorophenyl)pyrrolidin-2-yl]methanol (2.17 g) and vinylacetic acid (0.67 mL) in THF (50 mL), and the reaction solution was stirred at room temperature for 12 hours. A toluene-THF (1:1) mixed solution and 1 N aqueous hydrochloric acid were added to the reaction solution, and the organic layer was separated. The resulting organic layer was washed with a 1 N sodium hydroxide solution, dried over anhydrous magnesium sulfate, and then concentrated under reduced pressure.

A solution of DMSO (1.17 g) in methylene chloride (5 mL) was added dropwise to a solution of oxalyl chloride (1.77 g) in methylene chloride (15 mL) at −78° C., and the reaction solution was stirred at the same temperature for 20 minutes. A solution of the above residue in dichloromethane (10 mL) was added dropwise to the reaction solution at −78° C., and the reaction solution was stirred at the same temperature for 70 minutes. Triethylamine (6.5 mL) was added dropwise to the solution, and the reaction solution was stirred at −78° C. for one hour. A toluene-THF (1:1) mixed solution and a saturated ammonium chloride solution were added to the reaction solution. The mixture was returned to room temperature, and the organic layer was separated. The resulting organic layer was washed with 1 N aqueous hydrochloric acid, saturated sodium bicarbonate water, and brine in this order, dried over anhydrous magnesium sulfate, and then concentrated under reduced pressure.

Triethylphosphonoacetic acid (3.7 mL) was added to a suspension of sodium hydride (containing 60% mineral oil, 746 mg) in THF (70 mL) at 0° C., and the reaction solution was stirred at the same temperature for one hour. A solution of the above residue in THF (30 mL) was added to the reaction solution, which was then stirred at room temperature for one hour. Ethyl acetate and a saturated ammonium chloride solution were added to the reaction solution, and the organic layer was separated. The resulting organic layer was dried over anhydrous magnesium sulfate and then concentrated under reduced pressure. The residue was purified by silica gel column chromatography (heptane->heptane:ethyl acetate=1:1) to obtain 1.33 g of the title compound. The property value of the compound is as follows.

ESI-MS; m/z 368 [M⁺+H].

Synthesis of (3S,8aR)-3-(3,4,5-trifluorophenyl)-2,3,6,8a-tetrahydro-1H-indolizin-5-one A solution of ethyl (E)-3-[(2R,5S)-1-(3-butenoyl)-5-(3,4,5-trifluorophenyl)pyrrolidin-2-yl]acrylate (1.33 g) and Grubbs catalyst 2nd generation (153 mg) in methylene chloride (60 mL) was heated under reflux for two hours. The reaction solution was left to cool to room temperature. Then, triethylamine (0.5 mL) was added to the reaction solution, and the mixture was stirred for one hour. The reaction solution was concentrated under reduced pressure, and the residue was purified by silica gel column chromatography (heptane:ethyl acetate=1:1->ethyl acetate) to obtain 680 mg of the title compound. The property values of the compound are as follows.

ESI-MS; m/z 268 [M⁺+H].

¹H-NMR (CDCl₃) δ(ppm): 1.74-1.86 (m, 2H), 2.10-2.18 (m, 1H), 2.29-2.42 (m, 1H), 2.95-3.00 (m, 2H) 4.22-4.32 (m, 1H), 5.01 (d, J=9.2 Hz, 1H), 5.98-6.05 (m, 1H), 6.07-6.32 (m, 1H), 6.67-6.76 (m, 2H).

Synthesis of (3S,8aR)-3-(3,4,5-trifluorophenyl) hexahydroindolizin-5-one

Platinum oxide (100 mg) was added to a solution of (3S,8aR)-3-(3,4,5-trifluorophenyl)-2,3,6,8a-tetrahydro-1H-indolizin-5-one (680 mg) in methanol (20 mL), and the reaction solution was stirred in a hydrogen atmosphere at 1 atm at room temperature for 2.5 hours. The reaction solution was filtered through celite, and the filtrate was concentrated under reduced pressure to obtain 684 mg of the title compound. The property value of the compound is as follows.

ESI-MS; m/z 270 [M⁺+H].

¹H-NMR (CDCl₃) δ(ppm): 1.52-1.88 (m, 4H), 2.00-2.10 (m, 2H), 2.18-2.48 (m, 4H), 3.54-3.64 (m, 1H), 4.99 (d, J=9.2, Hz, 1H), 6.74 (dd, J=8.4, 6.4 Hz, 2H).

Synthesis of (E)-(3S)-(3,4,5-trifluorophenyl)-6-[3-methoxy-4-(4-methyl-1H-imidazol-1-yl)benzylidene]-(9S)-hexahydroindolizin-5-one Iodotrimethylsilane (0.54 mL) was added dropwise to a solution of (3S,8aR)-3-(3,4,5-trifluorophenyl)hexahydroindolizin-5-one (684 mg) and N,N,N',N'-tetramethylethylenediamine (1.34 mL) in methylene chloride (15 mL) at 0° C., and the reaction solution was stirred at 0° C. for 30 minutes. Iodine (967 mg) was added to the reaction solution at 0° C., and the reaction solution was stirred at 0° C. for one hour. A saturated sodium thiosulfate solution and ethyl acetate were added to the reaction solution. The mixture was returned to room temperature, and then the organic layer was separated. The resulting organic layer was washed with brine, dried over anhydrous magnesium sulfate, and then concentrated under reduced pressure. A solution of the residue in triethyl phosphite (5 mL) was stirred at 120° C. for one hour. The reaction solution was left to cool to room temperature and concentrated under reduced pressure. To a solution of the residue in THF (15 mL) and ethanol (3 mL), 3-methoxy-4-(4-methyl-1H-imidazol-1-yl)benzaldehyde (549 mg) and lithium hydroxide monohydrate (319 mg) were added, and the reaction solution was stirred at room temperature for 15 hours. Ethyl acetate and brine were added to the reaction solution, and the organic layer was separated. The resulting organic layer was dried over anhydrous magnesium sulfate and then concentrated under reduced pressure. The residue was purified by silica gel column chromatography (carrier: Chromatorex NH; elution solvent: heptane:ethyl acetate=1:1->ethyl acetate->ethyl acetate:methanol=9:1) to obtain 762 mg of the title compound.

Examples 5 and 6

Synthesis of (E)-(3R)-(3,4-difluorophenyl)-6-[3-methoxy-4-(4-methyl-1H-imidazol-1-yl)benzylidene]-(9R)-hexahydroindolizin-5-one and (E)-(3S)-(3,4-difluorophenyl)-6-[3-methoxy-4-(4-methyl-1H-imidazol-1-yl)benzylidene]-(9S)-hexahydroindolizin-5-one

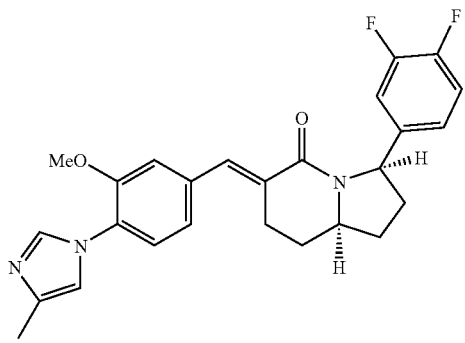

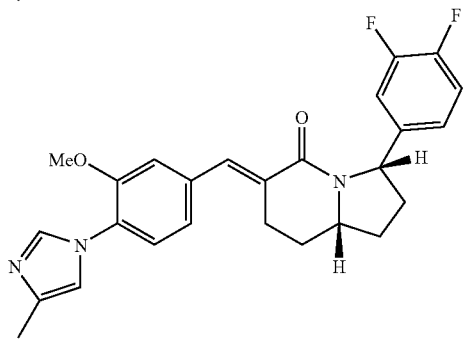

LDA (1.5 M solution in cyclohexane, 3.6 mL) was added to a solution of 3-(3,4-difluorophenyl)-9-hexahydroindolizin-5-one (900 mg) synthesized according to the method described in The Journal of Organic Chemistry, 2001, vol. 66, p. 886 in THF (20 mL) at −78° C., and the reaction solution was stirred at −78° C. for one hour. A solution of 3-methoxy-4-(4-methyl-1H-imidazol-1-yl)benzaldehyde (774 mg) in THF (5 mL) was added to the reaction solution at −78° C. The reaction solution was stirred at −78° C. for one hour, and then 2 N aqueous hydrochloric acid and a toluene-THF (2:1) mixed solution were added to the reaction solution. The reaction solution was heated to room temperature, and the organic layer was separated. The resulting organic layer was washed with brine and then dried over magnesium sulfate and concentrated under reduced pressure to obtain 1.67 g of a crude aldol adduct. Thionyl chloride (0.52 mL) was added to a solution of the resulting crude aldol adduct (1.67 g) in DME (30 mL) at 0° C., and the reaction solution was stirred at room temperature for one hour. A 2 N sodium hydroxide solution and a toluene-THF mixed solution (2:1) were added to the reaction solution at 0° C., and the organic layer was separated. The resulting organic layer was washed with brine, and then dried over magnesium sulfate and concentrated under reduced pressure. Sodium methoxide (5.2 M solution in methanol, 1.1 mL) was added to a solution of the resulting residue in THF (30 mL), and the reaction solution was stirred at room temperature for one hour. Ethyl acetate and brine were added to the reaction solution, and the organic layer was separated. The resulting organic layer was dried over magnesium sulfate and concentrated under reduced pressure. The residue was purified by silica gel column chromatography (carrier: Chromatorex NH; elution solvent: ethyl acetate) to obtain 430 mg of a racemate of the title compound.

The racemate (43 mg) was separated by CHIRALPAK™ AD-H manufactured by Daicel Chemical Industries, Ltd. (2 cm×25 cm; mobile phase: ethanol) to obtain the title optically active compound with a short retention time (9.6 mg; >99% ee) and the title optically active compound with a long retention time (7.3 mg; >99% ee).

The property values of the title optically active compound with a short retention time (Example 5) are as follows.

$^1$H-NMR (CDCl$_3$) δ(ppm): 1.70-1.86 (m, 3H), 2.05-2.12 (m, 1H), 2.29-2.38 (m, 5H), 2.69-2.80 (m, 1H), 3.16 (dt, J=16.8, 2.0 Hz, 1H), 3.76-3.84 (m, 1H), 3.85 (s, 3H), 5.16 (d, J=9.2 Hz, 1H), 6.89-6.99 (m, 3H), 7.04 (d, J=1.2 Hz, 1H), 7.07 (dd, J=8.0, 1.2 Hz, 1H), 7.10 (dd, J=10.0, 8.0 Hz, 1H), 7.25 (d, J=8.0 Hz, 1H), 7.75 (brs, 2H).

The property values of the title optically active compound with a long retention time (Example 6) are as follows.

$^1$H-NMR (CDCl$_3$) δ(ppm): 1.70-1.86 (m, 3H), 2.05-2.12 (m, 1H), 2.29-2.38 (m, 5H), 2.69-2.80 (m, 1H), 3.16 (dt, J=16.8, 2.0 Hz, 1H), 3.76-3.84 (m, 1H), 3.85 (s, 3H), 5.16 (d, J=9.2 Hz, 1H), 6.89-6.99 (m, 3H), 7.04 (d, J=1.2 Hz, 1H), 7.07 (dd, J=8.0, 1.2 Hz, 1H), 7.10 (dd, J=10.0, 8.0 Hz, 1H), 7.25 (d, J=8.0 Hz, 1H), 7.75 (brs, 2H).

Examples 7 and 8

Synthesis of (E)-(6R,9aS)-6-(4-fluorophenyl)-3-[3-methoxy-4-(4-methyl-1H-imidazol-1-yl)benzylidene]octahydroquinolizin-4-one and (E)-(6S,9aR)-6-(4-fluorophenyl)-3-[3-methoxy-4-(4-methyl-1H-imidazol-1-yl)benzylidene]octahydroquinolizin-4-one

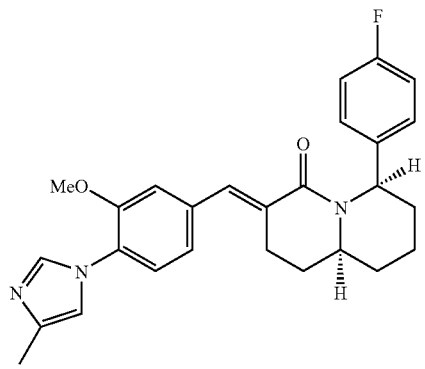

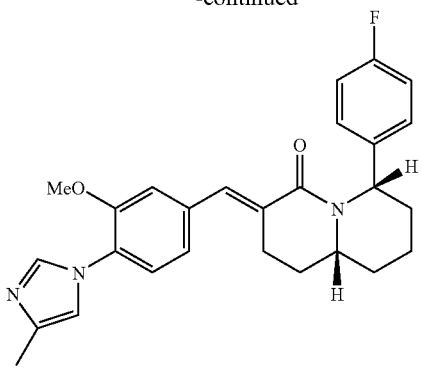

Synthesis of 1-(4-fluorophenyl)hepta-5,6-dienyl-1-amine 2.65 g of the title compound was obtained from (4-fluorobenzyl)-(4-fluorobenzylidene)amine (3 g) and 6-iodohexa-1,2-diene (2.97 g) according to the method described in Journal of the American Chemical Society, 2003, vol. 125, p. 11956. The property values of the compound are as follows.
$^1$H-NMR (CDCl$_3$) δ(ppm): 1.25-1.37 (m, 1H), 1.39-1.50 (m, 1H), 1.63-1.75 (m, 2H), 1.95-2.04 (m, 2H), 3.88 (t, J=6.8 Hz, H), 4.63 (dt, J=6.8, 2.8 Hz, 2H), 5.04 (quintet, J=6.8 Hz, 1H), 6.99 (t, J=8.8 Hz, 2H), 7.26 (dd, J=8.8, 5.6 Hz, 2H).

Synthesis of (2R*,6S*)-2-(4-fluorophenyl)-6-vinylpiperidine

Acetic acid (0.74 mL) was added to a solution of an allylpalladium chloride dimer (472 mg) and 1,1'-bis(diphenylphosphino)ferrocene (1.43 g) in THF (200 mL), and the reaction solution was stirred at room temperature for 10 minutes. A solution of 1-(4-fluorophenyl)hepta-5,6-dienyl-1-amine (2.65 g) in THF (50 mL) was added to the reaction solution, which was then stirred at 70° C. for 1.5 hours. The reaction solution was left to cool to room temperature. Then, diethyl ether and 1 N aqueous hydrochloric acid were added to the reaction solution, and the aqueous layer was separated. The resulting aqueous layer was washed with diethyl ether, and then a 5 N sodium hydroxide solution was added to the aqueous layer until the pH was adjusted to 11 or less. Chloroform was added to the aqueous layer, and the organic layer was separated. The resulting organic layer was dried over magnesium sulfate and concentrated under reduced pressure to obtain 2.4 g of the title compound. The property values of the compound are as follows.
ESI-MS; m/z 206 [M$^+$+H]. $^1$H-NMR (CDCl$_3$) δ(ppm): 1.24-1.60 (m, 3H), 1.67-1.77 (m, 2H), 1.88-1.95 (m, 1H), 3.24-3.30 (m, 1H), 3.67 (dd, J=11.2, 2.8 Hz, 1H), 5.01 (brd, J=10.4 Hz, 1H), 5.17 (brd, J=16.8 Hz, 1H), 5.88 (ddd, J=16.8, 10.4, 6.4 Hz, 1H), 6.98 (t, J=8.8 Hz, 2H), 7.35 (dd, J=8.8, 5.6 Hz, 2H).

Synthesis of 1-[(2R*,6S*)-2-(4-fluorophenyl)-6-vinylpiperidin-1-yl]-3-buten-1-one Diethyl cyanophosphonate (2.1 mL) was added to a solution of (2R*,6S*)-2-(4-fluorophenyl)-6-vinylpiperidine (934 mg), vinylacetic acid (1.15 mL), and triethylamine (3.82 mL) in DMF (10 mL), and the reaction solution was stirred at room temperature for six hours. Ethyl acetate and 1 N aqueous hydrochloric acid were added to the reaction solution, and the organic layer was separated. The resulting organic layer was washed with saturated sodium bicarbonate water, dried over magnesium sulfate, and then concentrated under reduced pressure. The residue was purified by silica gel column chromatography (elution solvent: heptane->heptane:ethyl acetate=1:1) to obtain 744 mg of the title compound. The property values of the compound are as follows.
$^1$H-NMR (CDCl$_3$) δ(ppm): 1.58-1.65 (m, 2H), 1.75-1.92 (m, 3H), 2.40-2.47 (m, 1H), 3.24 (d, J=6.4 Hz, 2H) 4.81 (d, J=10.4 Hz, 2H), 5.00 (d, J=17.2 Hz, 1H), 5.14 (d, J=15.6 Hz, 1H), 5.18 (d, J=13.2 Hz, 1H), 5.39-5.50 (m, 1H), 5.58-5.78 (m, 1H), 5.97-6.09 (m, 1H), 6.96 (t, J=8.8 Hz, 2H), 7.26 (dd, J=8.8, 5.6 Hz, 2H).

Synthesis of (6R*,9aS*)-6-(4-fluorophenyl)-3,6,7,8,9,9a-hexahydroquinolizin-4-one A solution of 1-[(2R*,6S*)-2-(4-fluorophenyl)-6-vinylpiperidin-1-yl]-3-buten-1-one (744 mg) and tricyclohexylphosphine[1,3-bis(2,4,6-trimethylphenyl)-4,5-dihydroimidazol-2-ylidene][benzylidene]ruthenium (IV) dichloride (116 mg) in methylene chloride (250 mL) was heated under reflux for two hours. The reaction solution was left to cool to room temperature and then concentrated. The residue was purified by silica gel column chromatography (elution solvent: heptane:ethyl acetate=4:1->ethyl acetate) to obtain 550 mg of the title compound. The property values of the compound are as follows.
$^1$H-NMR (CDCl$_3$) δ(ppm): 1.39-1.53 (m, 1H), 1.60-1.75 (m, 2H), 1.84-1.94 (m, 1H), 1.97-2.06 (m, 1H), 2.19-2.30 (m, 1H), 2.92-3.10 (m, 2H), 4.26-4.36 (m, 1H), 5.29 (t, J=3.6 Hz, 1H), 5.67 (brd, J=10.0 Hz, 1H), 5.83-5.88 (m, 1H), 6.96 (t, J=7.2 Hz, 2H), 7.16 (dd, J=7.2, 5.6 Hz, 2H).

Synthesis of (6R*,9aS*)-6-(4-fluorophenyl)octahydroquinolizin-4-one

Platinum oxide (10 mg) was added to a solution of (6R*,9aS*)-6-(4-fluorophenyl)-3,6,7,8,9,9a-hexahydroquinolizin-4-one (550 mg) in methanol (5 mL), and the reaction solution was stirred in a hydrogen stream at room temperature for three hours. The reaction solution was filtered through celite, and the filtrate was concentrated under reduced pressure to obtain 550 mg of the title compound. The property values of the compound are as follows.
$^1$H-NMR (CDCl$_3$) δ(ppm): 1.30-1.42 (m, 1H), 1.45-1.53 (m, 3H), 1.67-1.86 (m, 2H), 1.93-2.00 (m, 2H), 2.01-2.08 (m, 1H), 2.14-2.25 (m, 1H), 2.42-2.58 (m, 2H), 3.58-3.66 (m, 1H), 5.37 (t, J=3.2 Hz, 1H), 6.96 (t, J=8.8 HZ, 2H), 7.14 (dd, J=8.8, 5.6 Hz, 2H).

Synthesis of (E)-(6S*,9aR*)-6-(4-fluorophenyl)-3-[3-methoxy-4-(4-methyl-1H-imidazol-1-yl)benzylidene]octahydroquinolizin-4-one LDA (1.5 M solution in THF, 0.6 mL) was added to a solution of (6R*,9aS*)-6-(4-fluorophenyl)octahydroquinolizin-4-one (133 mg) in THF (7 mL) at −78° C. The reaction solution was stirred at −78° C. for one hour, and then a solution of 3-methoxy-4-(4-methyl-1H-imidazol-1-yl)benzaldehyde (116 mg) in THF (3 mL) was added to the reaction solution. The reaction solution was further stirred at −78° C. for one hour and 20 minutes, and ethyl acetate and a saturated ammonium chloride solution were added to the reaction solution. The mixture was returned to room temperature, and the organic layer was separated. The resulting organic layer was dried over magnesium sulfate and then concentrated under reduced pressure to obtain 249 mg of a crude aldol adduct. Thionyl chloride (0.08 mL) was added to a solution of the crude aldol adduct (249 mg) in methylene chloride (5 mL), and the reaction solution was stirred at room temperature for one hour. The reaction solution was cooled to 0° C., and chloroform and a 2 N sodium hydroxide solution were added to the reaction solution. The reaction solution was stirred for 10 minutes, and the organic layer was separated. The resulting organic layer was washed with brine, dried over magnesium sulfate, and then concentrated under reduced pressure. Sodium methoxide (5.2 M solution in methanol, 0.16 mL) was added to a solution of the residue in THF (5 mL), and the reaction solution was stirred at room temperature for 30 minutes. Ethyl acetate and brine were added to the reaction solution, and the organic layer was separated. The resulting organic layer was dried over magnesium sulfate and then concentrated under reduced pressure. The residue was purified by silica gel column chromatography (carrier: Chromatorex NH; elution solvent: ethyl acetate->ethyl acetate:methanol=5:1) to obtain 127 mg of the title compound. The property values of the compound are as follows.

ESI-MS; m/z 446 [M⁺+H]. ¹H-NMR (CDCl₃) δ(ppm): 1.34-1.45 (m, 1H), 1.49-1.78 (m, 4H), 2.00-2.07 (m, 1H), 2.17-2.28 (m, 2H), 2.34 (s, 3H), 2.66-2.77 (m, 1H), 3.06-3.14 (m, 1H), 3.76-3.84 (m, 1H), 3.86 (s, 3H), 5.52 (brs, 1H), 6.94 (brs, 1H), 7.00 (t, J=8.8 Hz, 2H), 7.03 (d, J=1.6 Hz, 1H), 7.05 (dd, J=9.6, 1.6 Hz, 1H), 7.21 (dd, J=8.8, 5.6 Hz, 2H), 7.25 (d, J=9.6 Hz, 1H), 7.80 (brd, J=2.4 Hz, 1H), 7.83 (brs, 1H).

Synthesis of (E)-(6R,9aS)-6-(4-fluorophenyl)-3-[3-methoxy-4-(4-methyl-1H-imidazol-1-yl)benzylidene]octahydroquinolizin-4-one and (E)-(6S,9aR)-6-(4-fluorophenyl)-3-[3-methoxy-4-(4-methyl-1H-imidazol-1-yl)benzylidene]octahydroquinolizin-4-one The racemate (E)-(6S*,9aR*)-6-(4-fluorophenyl)-3-[3-methoxy-4-(4-methyl-1H-imidazol-1-yl)benzylidene]octahydroquinolizin-4-one obtained above (127 mg) was separated by CHIRALPAK™ AD-H manufactured by Daicel Chemical Industries, Ltd. (2 cm×25 cm; mobile phase: ethanol) to obtain the title optically active compound with a retention time of 13 minutes (49 mg; >99% ee) and the title optically active compound with a retention time of 20 minutes (41 mg; >99% ee).

The property values of the title optically active compound with a retention time of 13 minutes (Example 7) are as follows.

ESI-MS; m/z 446 [M⁺+H]. ¹H-NMR (CDCl₃) δ(ppm): 1.34-1.45 (m, 1H), 1.49-1.78 (m, 4H), 2.00-2.07 (m, 1H), 2.17-2.28 (m, 2H), 2.34 (s, 3H), 2.66-2.77 (m, 1H), 3.06-3.14 (m, 1H), 3.76-3.84 (m, 1H), 3.86 (s, 3H), 5.52 (brs, 1H), 6.94 (brs, 1H), 7.00 (t, J=8.8 Hz, 2H), 7.03 (d, J=1.6 Hz, 1H), 7.05 (dd, J=9.6, 1.6 Hz, 1H), 7.21 (dd, J=8.8, 5.6 Hz, 2H), 7.25 (d, J=9.6 Hz, 1H), 7.80 (brd, J=2.4 Hz, 1H), 7.83 (brs, 1H):

The property values of the title optically active compound with a retention time of 20 minutes (Example 8) are as follows.

ESI-MS; m/z 446 [M⁺+H]. ¹H-NMR (CDCl₃) δ(ppm): 1.34-1.45 (m, 1H), 1.49-1.78 (m, 4H), 2.00-2.07 (m, 1H), 2.17-2.28 (m, 2H), 2.34 (s, 3H), 2.66-2.77 (m, 1H), 3.06-3.14 (m, 1H), 3.76-3.84 (m, 1H), 3.86 (s, 3H), 5.52 (brs, 1H), 6.94 (brs, 1H), 7.00 (t, J=8.8 Hz, 2H), 7.03 (d, J=1.6 Hz, 1H), 7.05 (dd, J=9.6, 1.6 Hz, 1H), 7.21 (dd, J=8.8, 5.6 Hz, 2H), 7.25 (d, J=9.6 Hz, 1H), 7.80 (brd, J=2.4 Hz, 1H), 7.83 (brs, 1H).

Examples 9 and 10

Synthesis of (E)-(6S,8S,9aR)-6-phenyl-8-hydroxy-3-[3-methoxy-4-(4-methyl-1H-imidazol-1-yl)benzylidene]octahydroquinolizin-4-one and (E)-(6R,8R,9aS)-6-phenyl-8-hydroxy-3-[3-methoxy-4-(4-methyl-1H-imidazol-1-yl)benzylidene]octahydroquinolizin-4-one

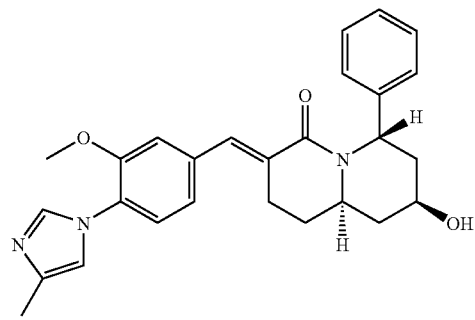

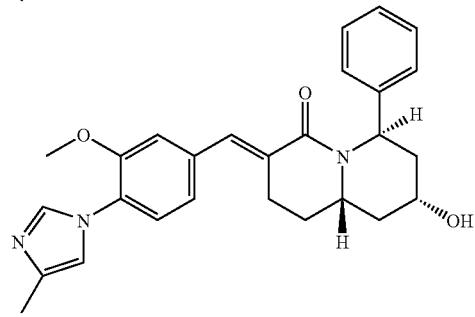

Synthesis of (6S*,9aR*)-8-hydroxy-6-phenyloctahydroquinolizin-4-one

A solution of (4S*,9aR*)-4-phenylhexahydroquinolizine-2,6-dione that is a known compound described in a document (CAS No. 149526-09-0, 93.4 mg) in methanol (5.0 mL) was cooled to 0° C. Sodium borohydride (21.8 mg) was added to the reaction solution, which was then stirred for 30 minutes. Water and ethyl acetate were added to the reaction solution, and the organic layer was separated. The resulting organic layer was washed with brine, dried over anhydrous magnesium sulfate, and then concentrated under reduced pressure to obtain 95.2 mg of a crude alcohol compound. The property values of the compound are as follows.

¹H-NMR (CDCl₃) δ(ppm): 1.75-1.80 (m, 3H), 1.80-2.00 (m, 2H), 2.04-2.18 (m, 2H), 2.45-2.76 (m, 3H), 3.40-3.42 (m, ¼H), 3.89-3.98 (m, 1H), 4.20-4.24 (m, ¾H), 6.05-6.06 (m, ¾H), 6.26-6.28 (m, ¼H), 7.20-7.32 (m, 3H), 7.32-7.37 (m, 2H).

Synthesis of (6S*,8S*,9aR*)-8-(tert-butyldimethylsilanyloxy)-6-phenyloctahydroquinolizin-4-one A solution of (6S*,9aR*)-8-hydroxy-6-phenyloctahydroquinolizin-4-one (96.4 mg) in DMF (5.0 mL) was cooled to 0° C. Imidazole (80.3 mg), TBSCl (88.9 mg), and DMAP (4.8 mg) were sequentially added to the reaction solution, which was then stirred at room temperature overnight. Saturated sodium bicarbonate water and ethyl acetate were added to the reaction solution, and the organic layer was separated. The resulting organic layer was washed with brine, dried over anhydrous magnesium sulfate, and then concentrated under reduced pressure. The residue was purified by silica gel column chromatography (elution solvent: heptane-ethyl acetate system) to obtain 77 mg of the title compound. The property values of the compound are as follows.

$^1$H-NMR (CDCl$_3$) δ(ppm): 0.00 (s, 3H), 0.06 (s, 3H), 0.77 (s, 9H), 1.67-1.79 (m, 1H), 1.81-1.88 (m, 1H), 1.92-2.08 (m, 2H), 2.12-2.22 (m, 2H), 2.52-2.72 (m, 4H), 4.08-4.15 (m, 1H), 4.26-4.30 (m, 1H), 6.10 (dd, J=6.8, 2.4 Hz, 1H), 7.24-7.28 (m, 1R), 7.32-7.41 (m, 4H).

Synthesis of (E)-(6S*,8S*,9aR*)-8-(tert-butyldimethylsilanyloxy)-6-phenyl-3-[3-methoxy-4-(4-methyl-1H-imidazol-1-yl)benzylidene]octahydroquinolizin-4-one LDA (1.5 M solution in THF, 185 µL) was added to a solution of (6S*,8S*,9aR*)-8-(tert-butyldimethylsilanyloxy)-6-phenyloctahydroquinolizin-4-one (54 mg) in THF (2.0 mL) at 0° C. The reaction solution was stirred at 0° C. for one hour, and then a solution of 3-methoxy-4-(4-methyl-1H-imidazol-1-yl)benzaldehyde (30.0 mg) in THF (1.0 mL) was added to the reaction solution. The reaction solution was further stirred at 0° C. for 1.5 hours. Water and ethyl acetate were added to the reaction solution, and the organic layer was separated. The resulting organic layer was dried over magnesium sulfate and then concentrated under reduced pressure. The residue was purified by silica gel column chromatography (elution solvent: heptane-ethyl acetate system) to obtain 60.8 mg of an alcohol compound. A solution of the resulting alcohol compound (60.8 mg) in methylene chloride (3.0 mL) was cooled to 0° C. Triethylamine (44.3 µL) and methanesulfonyl chloride (12.3 µL) were added to the reaction solution, which was then stirred at room temperature for 30 minutes. Triethylamine (162 µL) and methanesulfonyl chloride (61.5 µL) were added to the reaction solution, which was then stirred overnight to complete the reaction. Water and ethyl acetate were added to the reaction solution, and the organic layer was separated. The resulting organic layer was dried over magnesium sulfate and then concentrated under reduced pressure. The residue was purified by silica gel column chromatography (elution solvent: heptane-ethyl acetate system) to obtain a mesyl compound. Sodium methoxide (11.5 mg) was added to a solution of the resulting mesyl compound in THF (2.0 mL), and the reaction solution was stirred at room temperature for six hours and 40 minutes. Water and ethyl acetate were added to the reaction solution, and the organic layer was separated. The resulting organic layer was washed with brine, dried over anhydrous magnesium sulfate, and then concentrated under reduced pressure. The residue was purified by silica gel column chromatography (carrier: Chromatorex NH; elution solvent: heptane-ethyl acetate system->ethyl acetate-methanol system) to obtain 36.0 mg of the title compound. The property values of the compound are as follows.

$^1$H-NMR (CDCl$_3$) δ(ppm): 0.00 (s, 3H), 0.06 (s, 3H), 0.77 (s, 9H), 1.72-1.84 (m, 2H), 1.91-1.98 (m, 1H), 2.14-2.28 (m, 2H), 2.42 (s, 3H), 2.53-2.57 (m, 1H), 2.89-3.06 (m, 2H), 3.97 (s, 3H), 4.18-4.25 (m, 1H), 4.28-4.32 (m, 1H), 6.15 (dd, J=7.2, 3.2 Hz, 1H), 7.04 (dd, J=1.2 Hz, 1H), 7.11-7.14 (m, 2H), 7.24-7.28 (m, 1H), 7.35-7.39 (m, 5H), 7.86 (d, J=1.2 Hz, 1H), 7.90 (brs, 1H).

Synthesis of (E)-(6S*,8S*,9aR*)-6-phenyl-8-hydroxy-3-[3-methoxy-4-(4-methyl-1H-imidazol-1-yl)benzylidene]octahydroquinolizin-4-one TBAF (1.0 M solution in THF, 194 µL) was added to a solution of (E)-(6S*,8S*,9aR*)-8-(tert-butyldimethylsilanyloxy)-6-phenyl-3-[3-methoxy-4-(4-methyl-1H-imidazol-1-yl)benzylidene]octahydroquinolizin-4-one (36.0 mg) in THF (mL), and the reaction solution was stirred at room temperature overnight. A saturated ammonium chloride solution and ethyl acetate were added to the reaction solution, and the organic layer was separated. The resulting organic layer was washed with brine, dried over anhydrous magnesium sulfate, and then concentrated under reduced pressure. The residue was purified by silica gel column chromatography (carrier: Chromatorex NH; elution solvent: heptane-ethyl acetate system->ethyl acetate-methanol system) to obtain 13.3 mg of the title compound. The property values of the compound are as follows.

$^1$H-NMR (CDCl$_3$) δ(ppm): 1.68-1.92 (m, 3H), 2.08-2.16 (m, 1H), 2.21-2.27 (m, 1H), 2.32 (s, 3H), 2.58-2.65 (m, 1H), 2.80-2.87 (m, 1H), 2.91-2.98 (m, 1H), 3.87 (s, 3H), 4.04-4.12 (m, 1H), 4.24-4.28 (m, 1H), 6.12 (dd, J=6.8, 2.4 Hz, 1H), 6.95 (s, 1H), 7.02-7.05 (m, 2H), 7.23-7.39 (m, 6H), 7.77 (s, 1H), 7.82 (s, 1H)

Synthesis of (E)-(6S,8S,9aR)-6-phenyl-8-hydroxy-3-[3-methoxy-4-(4-methyl-1H-imidazol-1-yl)benzylidene]octahydroquinolizin-4-one and (E)-(6R,8R,9aS)-6-phenyl-8-hydroxy-3-[3-methoxy-4-(4-methyl-1H-imidazol-1-yl)benzylidene]octahydroquinolizin-4-one The racemate (E)-(6S*,8S*,9aR*)-6-phenyl-8-hydroxy-3-[3-methoxy-4-(4-methyl-1H-imidazol-1-yl)benzylidene]octahydroquinolizin-4-one obtained above (12.0 mg) was separated by CHIRALPAK™ AD-H manufactured by Daicel Chemical Industries, Ltd. (2 cm×25 cm; mobile phase: ethanol) to obtain the title optically active compound with a retention time of 5.1 minutes (3.3 mg; >99% ee) and the title optically active compound with a retention time of 12.7 minutes (4.1 mg; >99% ee).

The property values of the title optically active compound with a retention time of 5.1 minutes (Example 9) are as follows.

$^1$H-NMR (CDCl$_3$) δ(ppm): 1.68-1.92 (m, 3H), 2.08-2.16 (m, 1H), 2.21-2.27 (m, 1H), 2.32 (s, 3H), 2.58-2.65 (m, 1H), 2.80-2.87 (m, 1H), 2.91-2.98 (m, 1H), 3.87 (s, 3H), 4.04-4.12 (m, 1H), 4.24-4.28 (m, 1H), 6.12 (dd, J=6.8, 2.4 Hz, 1H), 6.95 (s, 1H), 7.02-7.05 (m, 2H), 7.23-7.39 (m, 6H), 7.77 (s, 1H), 7.82 (s, 1H)

The property values of the title optically active compound with a retention time of 12.7 minutes (Example 10) are as follows.

$^1$H-NMR (CDCl$_3$) δ(ppm): 1.68-1.92 (m, 3H), 2.08-2.16 (m, 1H), 2.21-2.27 (m, 1H), 2.32 (s, 3H), 2.58-2.65 (m, 1H), 2.80-2.87 (m, 1H), 2.91-2.98 (m, 1H), 3.87 (s, 3H), 4.04-4.12 (m, 1H), 4.24-4.28 (m, 1H), 6.12 (dd, J=6.8, 2.4 Hz, 1H), 6.95 (s, 1H), 7.02-7.05 (m, 2H), 7.23-7.39 (m, 6H), 7.77 (s, 1H), 7.82 (s, 1H)

Examples 11 and 12

Synthesis of (E)-(6S,8S,9aR)-6-(4-fluorophenyl)-8-hydroxy-3-[3-methoxy-4-(4-methyl-1H-imidazol-1-yl)benzylidene]octahydroquinolizin-4-one and (E)-(6R,8R,9aS)-6-(4-fluorophenyl)-8-hydroxy-3-[3-methoxy-4-(4-methyl-1H-imidazol-1-yl)benzylidene]octahydroquinolizin-4-one

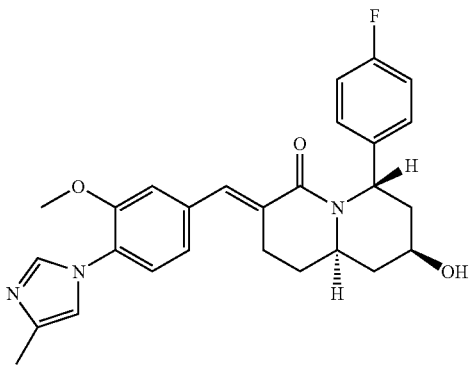

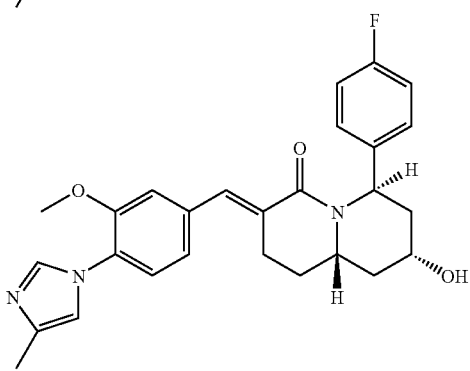

Synthesis of 1-(4-bromobutyryl)-2-(4-fluorophenyl)-2,3-dihydro-1H-pyridin-4-one 6.66 g of the title compound was obtained from 4-methoxypyridine (2.0 mL), 4-fluorophenylmagnesium bromide (1.0 M solution in THF, 20.7 mL), and 4-bromobutyryl chloride (2.4 mL) according to the method described in Tetrahedron Letters, 1986, vol. 27, p. 4549-4552. The property values of the compound are as follows.

$^1$H-NMR (CDCl$_3$) δ(ppm): 2.20-2.32 (m, 2H), 2.79-2.86 (m, 3H), 3.10-3.16 (m, 1H), 3.47-3.55 (m, 2H), 5.47 (brd, J=8.0 Hz, 1H), 6.00 (brs, 1H), 6.99-7.03 (m, 2H), 7.18-7.21 (m, 2H), 7.75 (brs, 1H).

Synthesis of (4S*,9aR*)-4-(4-fluorophenyl)hexahydroquinolizine-2,6-dione 1.05 g of the title compound was obtained from 1-(4-bromobutyryl)-2-(4-fluorophenyl)-2,3-dihydro-1H-pyridin-4-one (2.0 g), tributyltin hydride (1.87 mL), and AIBN (386 mg) according to the method described in The Journal of Organic Chemistry, 1993, vol. 58, p. 4198-4199. The property values of the compound are as follows.

$^1$H-NMR (CDCl$_3$) δ(ppm): 1.58-1.82 (m, 2H), 1.85-2.01 (m, 2H), 2.34-2.39 (m, 1H), 2.45-2.56 (m, 3H), 2.80 (dd, J=15.6, 7.2 Hz, 1H), 2.97-3.01 (m, 1H), 3.49-3.56 (m, 1H), 6.54 (brd, J=7.2 Hz, 1H), 6.99-7.03 (m, 2H), 7.21-7.24 (m, 2H).

Synthesis of (6S*,9aR*)-6-(4-fluorophenyl)-8-hydroxyoctahydroquinolizin-4-one

A solution of (4S*,9aR*)-4-(4-fluorophenyl)hexahydroquinolizine-2,6-dione (790 mg) in methanol (20 mL) was cooled to 0° C. Sodium borohydride (149 mg) was added to the reaction solution, which was then stirred for two hours and 15 minutes. Water and ethyl acetate were added to the reaction solution, and the organic layer was separated. The resulting organic layer was washed with brine, dried over anhydrous magnesium sulfate, and then concentrated under reduced pressure to obtain 760 mg of a crude alcohol compound. The property values of the compound are as follows.

$^1$H-NMR (CDCl$_3$) δ(ppm): 1.52-2.15 (m, 7H), 2.44-2.69 (m, 3H), 3.30-3.36 (m, ⅓H), 3.86-3.94 (m, 1H), 4.22 (brs, ⅔H), 5.99-6.00 (brd, J=6.4 Hz, ⅔H), 6.22-6.23 (brd, J=6.4 Hz, ⅓H), 7.00-7.04 (m, ⁴⁄₃H), 7.15-7.18 (m, ⅔H), 7.22-7.27 (m, 2H).

Synthesis of (6S*,8S*,9aR*)-8-(tert-butyldimethylsilanyloxy)-6-(4-fluorophenyl)octahydroquinolizin-4-one and (6S*,8R*,9aR*)-8-(tert-butyldimethylsilanyloxy)-6-(4-fluorophenyl)octahydroquinolizin-4-one A solution of (6S*,9aR*)-6-(4-fluorophenyl)-8-hydroxyoctahydroquinolizin-4-one (203 mg) in DMF (5.0 mL) was cooled to 0° C. Imidazole (262 mg), TBSCl (291 mg), and DMAP (9.42 mg) were sequentially added to the reaction solution, which was then stirred at room temperature for two hours. Saturated sodium bicarbonate water and ethyl acetate were added to the reaction solution, and the organic layer was separated. The resulting organic layer was washed with brine, dried over anhydrous magnesium sulfate, and then concentrated under reduced pressure. The residue was purified by silica gel column chromatography (elution solvent: heptane-ethyl acetate system) to obtain 183 mg of (6S*,8S*,9aR*)-8-(tert-butyldimethylsilanyloxy)-6-(4-fluorophenyl)octahydroquinolizin-4-one and 31.8 mg of (6S*,8R*,9aR*)-8-(tert-butyldimethylsilanyloxy)-6-(4-fluorophenyl)octahydroquinolizin-4-one.

The property values of (6S*,8S*,9aR*)-8-(tert-butyldimethylsilanyloxy)-6-(4-fluorophenyl)octahydroquinolizin-4-one are as follows.

$^1$H-NMR (CDCl$_3$) δ(ppm): 0.00 (s, 3H), 0.05 (s, 3H), 0.76 (s, 9H), 1.65-1.75 (m, 2H), 1.75-1.85 (m, 1H), 1.85-2.08 (m, 2H), 2.08-2.20 (m, 2H), 2.41-2.52 (m, 1H), 2.52-2.70 (m, 2H), 4.01-4.06 (m, 1H), 4.26-4.27 (m, 1H), 6.04 (brd, J=6.4 Hz, 1H), 7.03-7.08 (m, 2H), 7.27-7.31 (m, 2H).

The property values of (6S*,8R*,9aR*)-8-(tert-butyldimethylsilanyloxy)-6-(4-fluorophenyl)octahydroquinolizin-4-one are as follows.

$^1$H-NMR (CDCl$_3$) δ(ppm): 0.04 (s, 3H), 0.07 (s, 3H), 0.88 (s, 9H), 1.57-1.63 (m, 1H), 1.70-1.82 (m, 4H), 1.86-1.99 (m, 2H), 2.43-2.60 (m, 3H), 3.29-3.35 (m, 1H), 3.80-3.88 (m, 1H), 6.17-6.19 (m, 1H), 7.01-7.06 (m, 2H), 7.13-7.16 (m, 2H).

Synthesis of (E)-(6S*,8S*,9aR*)-8-(tert-butyldimethylsilanyloxy)-6-(4-fluorophenyl)-3-[3-methoxy-4-(4-methyl-1H-imidazol-1-yl)benzylidene]octahydroquinolizin-4-one LDA (1.5 M solution in THF, 1.11 mL) was added to a solution of (6S*,8S*,9aR*)-8-(tert-butyldimethylsilanyloxy)-6-(4-fluorophenyl)octahydroquinolizin-4-one (298 mg) in THF (5.0 mL) at 0° C. The reaction solution was stirred at 0° C. for one hour, and then a solution of 3-methoxy-4-(4-methyl-1H-imidazol-1-yl)benzaldehyde (179 mg) in THF (3 mL) was added to the reaction solution. The reaction solution was further stirred at 0° C. for 40 minutes. Water and ethyl acetate were added to the reaction solution, and the organic layer was separated. The resulting organic layer was dried over magnesium sulfate and then concentrated under reduced pressure to obtain 443 mg of a crude aldol adduct. A solution of the crude aldol adduct (443 mg) in methylene chloride (7 mL) was cooled to 0° C. Triethylamine (416 μL) and methanesulfonyl chloride (115 μL) were added to the reaction solution, which was then stirred at room temperature for 5.5 hours. Saturated sodium bicarbonate water and ethyl acetate were added to the reaction solution, and the organic layer was separated. The resulting organic layer was washed with brine and then dried over magnesium sulfate and concentrated under reduced pressure to obtain a crude mesyl compound. Sodium methoxide (121 mg) and methanol (1.0 mL) were added to a solution of the crude mesyl compound in THF, and the reaction solution was stirred at room temperature for two hours. Water and ethyl acetate were added to the reaction solution, and the organic layer was separated. The resulting organic layer was washed with brine, dried over anhydrous magnesium sulfate, and then concentrated under reduced pressure. The residue was purified by silica gel column chromatography (carrier: Chromatorex NH; elution solvent: heptane-ethyl acetate system->ethyl acetate-methanol system) to obtain 330 mg of the title compound. The property values of the compound are as follows.

$^1$H-NMR (CDCl$_3$) δ(ppm): 0.00 (s, 3H), 0.05 (s, 3H), 0.77 (s, 9H), 1.75-1.96 (m, 3H), 2.12 (s, 3H), 2.12-2.24 (m, 2H), 2.44-2.52 (m, 1H), 2.84-3.02 (m, 2H), 3.97 (s, 3H), 4.11-4.20 (m, 1H), 4.26-4.32 (m, 1H), 6.08-6.12 (m, 1H), 7.03-7.18 (m, 7H), 7.22-7.40 (m, 2H), 7.87 (s, 1H).

Synthesis of (E)-(6S*,8S*,9aR*)-6-(4-fluorophenyl)-8-hydroxy-3-[3-methoxy-4-(4-methyl-1H-imidazol-1-yl)benzylidene]octahydroquinolizin-4-one TBAF (1.0 M solution in THF, 1.15 mL) was added to a solution of (E)-(6S*,8S*,9aR*)-8-(tert-butyldimethylsilanyloxy)-6-(4-fluorophenyl)-3-[3-methoxy-4-(4-methyl-1H-imidazol-1-yl)benzylidene]octahydroquinolizin-4-one (330 mg) in THF (5.0 mL), and the reaction solution was stirred at room temperature overnight. A saturated ammonium chloride solution and ethyl acetate were added to the reaction solution, and the organic layer was separated. The resulting organic layer was washed with brine, dried over anhydrous magnesium sulfate, and then concentrated under reduced pressure. The residue was purified by silica gel column chromatography (carrier: Chromatorex NH; elution solvent: heptane-ethyl acetate system->ethyl acetate-methanol system) to obtain 232 mg of the title compound. The property values of the compound are as follows.

$^1$H-NMR (CDCl$_3$) δ(ppm): 1.75-1.96 (m, 3H), 2.07-2.15 (m, 1H), 2.17-2.27 (m, 1H), 2.34 (s, 3H), 2.52-2.56 (m, 1H), 2.78-2.84 (m, 1H), 2.88-2.96 (m, 1H), 3.88 (s, 3H), 4.01-4.08 (m, 1H), 4.26-4.30 (m, 1H), 6.04-6.10 (m, 1H), 6.96 (s, 1H), 7.00-7.06 (m, 4H), 7.16-7.34 (m, 3H), 7.82 (s, 1H), 7.82-7.84 (m, 1H).

Synthesis of (E)-(6S,8S,9aR)-6-(4-fluorophenyl)-8-hydroxy-3-[3-methoxy-4-(4-methyl-1H-imidazol-1-yl)benzylidene]octahydroquinolizin-4-one and (E)-(6R,8R,9aS)-6-(4-fluorophenyl)-8-hydroxy-3-[3-methoxy-4-(4-methyl-1H-imidazol-1-yl)benzylidene]octahydroquinolizin-4-one The racemate (E)-(6S*,8S*,9aR*)-6-(4-fluorophenyl)-8-hydroxy-3-[3-methoxy-4-(4-methyl-1H-imidazol-1-yl)benzylidene]octahydroquinolizin-4-one obtained above (232 mg) was separated by CHIRALPAK™ AD-H manufactured by Daicel Chemical Industries, Ltd. (2 cm×25 cm; mobile phase: ethanol) to obtain the title optically active compound with a retention time of 5.0 minutes (89 mg; >99% ee) and the title optically active compound with a retention time of 9.7 minutes (89 mg; >99% ee).

The property values of the title optically active compound with a retention time of 5.0 minutes (Example 11) are as follows.

$^1$H-NMR (CDCl$_3$) δ(ppm): $^1$H-NMR (CDCl$_3$) δ(ppm): 1.75-1.96 (m, 3H), 2.07-2.15 (m, 1H), 2.17-2.27 (m, 1H), 2.34 (s, 3H), 2.52-2.56 (m, 1H), 2.78-2.84 (m, 1H), 2.88-2.96 (m, 1H), 3.88 (s, 3H), 4.01-4.08 (m, 1H), 4.26-4.30 (m, 1H), 6.04-6.10 (m, 1H), 6.96 (s, 1H), 7.00-7.06 (m, 4H), 7.16-7.34 (m, 3H), 7.82 (s, 1H), 7.82-7.84 (m, 1H).

The property values of the title optically active compound with a retention time of 9.7 minutes (Example 12) are as follows.

$^1$H-NMR (CDCl$_3$) δ(ppm):

$^1$H-NMR (CDCl$_3$) δ(ppm): 1.75-1.96 (m, 3H), 2.07-2.15 (m, 1H), 2.17-2.27 (m, 1H), 2.34 (s, 3H), 2.52-2.56 (m, 1H), 2.78-2.84 (m, 1H), 2.88-2.96 (m, 1H), 3.88 (s, 3H), 4.01-4.08 (m, 1H), 4.26-4.30 (m, 1H), 6.04-6.10 (m, 1H), 6.96 (s, 1H), 7.00-7.06 (m, 4H), 7.16-7.34 (m, 3H), 7.82 (s, 1H), 7.82-7.84 (m, 1H).

Examples 13 and 14

Synthesis of (E)-(6S,9aS)-6-(3,4,5-trifluorophenyl)-3-[3-methoxy-4-(4-methyl-1H-imidazol-1-yl)benzylidene]octahydroquinolizin-4-one and (E)-(6R,9aR)-6-(3,4,5-trifluorophenyl)-3-[3-methoxy-4-(4-methyl-1H-imidazol-1-yl)benzylidene]octahydroquinolizin-4-one

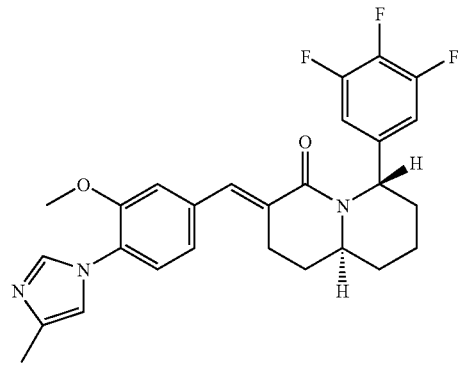

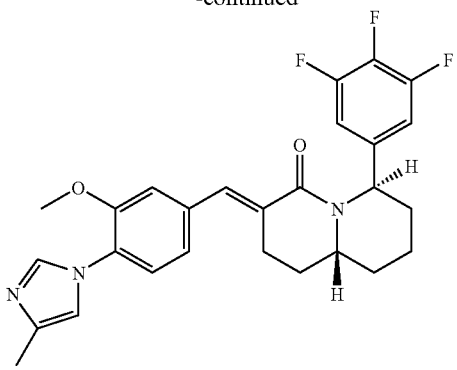

Synthesis of 1-(4-bromobutyryl)-2-(3,4,5-trifluorophenyl)-2,3-dihydro-1H-pyridin-4-one 1.02 g of the title compound was obtained from 4-methoxypyridine (1.52 mL), 3,4,5-trifluorophenylmagnesium bromide (0.3 M solution in THF, 50 mL), and 4-bromobutyryl chloride (1.74 mL) according to the method described in Tetrahedron Letters, 1986, vol. 27, p. 4549-4552. The property values of the compound are as follows.

$^1$H-NMR (CDCl$_3$) δ(ppm): 2.24-2.31 (m, 2H), 2.77-2.88 (m, 3H), 3.06-3.18 (m, 1H), 3.51-3.55 (m, 2H), 5.48 (brd, J=8.0 Hz, 1H), 5.98 (brs, 1H), 6.82-6.90 (m, 2H), 7.72 (brs, 1H).

Synthesis of (6S*,9aR*)-4-(3,4,5-trifluorophenyl)hexahydroquinolizine-2,6-dione 331 mg of the title compound was obtained from 1-(4-bromobutyryl)-2-(3,4,5-trifluorophenyl)-2,3-dihydro-1H-pyridin-4-one (1.15 g), tributyltin hydride (973 μL), and AIBN (201 mg) according to the method described in The Journal of Organic Chemistry, 1993, vol. 58, p. 4198-4199. The property values of the compound are as follows.

$^1$H-NMR (CDCl$_3$) δ(ppm): 1.61-1.69 (m, 1H), 1.72-1.82 (m, 1H), 1.87-1.97 (m, 1H), 1.99-2.07 (m, 1H), 2.23-2.31 (m, 1H), 2.39 (ddd, J=14.8, 3.2, 1.6 Hz, 1H), 2.47-2.57 (m, 2H), 2.81 (ddd, J=15.2, 7.2, 0.8 Hz, 1H), 2.92 (ddd, J=15.2, 2.4, 1.6 Hz, 1H), 3.52-3.59 (m, 1H), 6.45 (brd, J=7.2 Hz, 1H), 6.88-6.92 (m, 2H).

Synthesis of (6S*,9aR*)-8-hydroxy-6-(3,4,5-trifluorophenyl)octahydroquinolizin-4-one A solution of (6S*,9aR*)-4-(3,4,5-trifluorophenyl)hexahydroquinolizine-2,6-dione (331 mg) in methanol (10 mL) was cooled to 0° C. Sodium borohydride (64.1 mg) was added to the reaction solution, which was then stirred for one hour. Water and ethyl acetate were added to the reaction solution, and the organic layer was separated. The resulting organic layer was washed with brine, dried over anhydrous magnesium sulfate, and then concentrated under reduced pressure to obtain 340 mg of a crude alcohol compound. The property values of the compound are as follows.

$^1$H-NMR (CDCl$_3$) δ(ppm): 1.57-1.64 (m, 1H), 1.70-2.00 (m, 3H), 2.00-2.12 (m, 1H), 2.20-2.60 (m, 5H), 3.28-3.35 (m, ½H), 3.81-3.89 (m, 1H), 4.23-4.26 (m, ½H), 5.91 (brd, J=6.4 Hz, ½H), 6.15 (brd, J=4.8 Hz, ½H), 6.80-6.94 (m, 2H).

Synthesis of (6S*,9aR*)-6-(3,4,5-trifluorophenyl)octahydroquinolizin-4-one

A solution of (6S*,9aR*)-8-hydroxy-6-(3,4,5-trifluorophenyl)octahydroquinolizin-4-one (161 mg) in methylene chloride (5 mL) was cooled to 0° C. Triethylamine (450 μL) and methanesulfonyl chloride (125 μL) were added to the reaction solution, which was then stirred at room temperature for 4.5 hours. Water and ethyl acetate were added to the reaction solution, and the organic layer was separated. The resulting organic layer was washed with brine, dried over anhydrous magnesium sulfate, and then concentrated under reduced pressure to obtain 203 mg of a crude mesyl compound. Sodium borohydride (204 mg) was added to a solution of the resulting crude mesyl compound (203 mg) in NMP (5.0 mL), and the reaction solution was heated to 100° C. and stirred for 2.5 hours. The reaction solution was returned to room temperature. Then, water and ethyl acetate were added to the reaction solution, and the organic layer was separated. The resulting organic layer was washed with brine, dried over anhydrous magnesium sulfate, and then concentrated under reduced pressure. The residue was purified by silica gel column chromatography (elution solvent: heptane-ethyl acetate system) to obtain 79 mg of the title compound. The property values of the compound are as follows.

$^1$H-NMR (CDCl$_3$) δ(ppm): 1.38-2.00 (m, 6H), 2.10-2.22 (m, 1H), 2.25-2.34 (m, 1H), 2.42-2.62 (m, 2H), 2.74-2.80 (m, 1H), 3.19-3.30 (m, 2H), 6.00-6.05 (brs, 1H), 6.79-6.83 (m, 2H).

Synthesis of (E)-(6S*,9aS*)-6-(3,4,5-trifluorophenyl)-3-[3-methoxy-4-(4-methyl-1H-imidazol-1-yl)benzylidene]octahydroquinolizin-4-one LDA (1.5 M solution in THF, 372 μL) was added to a solution of (6S*,9aR*)-6-(3,4,5-trifluorophenyl)octahydroquinolizin-4-one (79 mg) in THF (2.0 mL) at 0° C. The reaction solution was stirred at 0° C. for one hour, and then a solution of 3-methoxy-4-(4-methyl-1H-imidazol-1-yl)benzaldehyde (66.4 mg) in THF (1 mL) was added to the reaction solution. The reaction solution was further stirred at 0° C. for 30 minutes. Water and ethyl acetate were added to the reaction solution, and the organic layer was separated. The resulting organic layer was dried over magnesium sulfate and then concentrated under reduced pressure to obtain 88 mg of a crude aldol adduct. A solution of the crude aldol adduct (88 mg) in methylene chloride (3.0 mL) was cooled to 0° C. Triethylamine (147 μL) and methanesulfonyl chloride (40.9 μL) were added to the reaction solution, which was then stirred at room temperature for 2.5 hours. Sodium methoxide (28% solution in methanol, 102 mL) and ethanol (1.0 mL) were added to the reaction solution, which was then stirred at room temperature for 40 minutes. Water and ethyl acetate were added to the reaction solution, and the organic layer was separated. The resulting organic layer was washed with brine, dried over anhydrous magnesium sulfate, and then concentrated under reduced pressure. The residue was purified by silica gel column chromatography (elution solvent: heptane-ethyl acetate system->ethyl acetate-methanol system) to obtain 72 mg of a mixture of the crude aldol adduct with the title compound. 72 mg of the resulting mixture was re-dissolved in methylene chloride (3.0 mL), and the reaction solution was cooled to 0° C. Triethylamine (147 μL) and methanesulfonyl chloride (61.3 μL) were added to the reaction solution, which was then stirred at room temperature for four hours and 15 minutes. Sodium methoxide (28% solution in methanol, 102 mL) and ethanol (1.0 mL) were added to the reaction solution, which was then stirred at room temperature for two hours and 15 minutes. Water and ethyl acetate were added to the reaction solution, and the organic layer was separated. The resulting organic layer was washed with brine, dried over anhydrous magnesium sulfate, and then concentrated under reduced pressure. The residue was purified by silica gel column chromatography (elution solvent: heptane-ethyl acetate system->ethyl acetate-methanol system) to obtain 54.0 mg of the title compound. The property values of the compound are as follows.

$^1$H-NMR (CDCl$_3$) δ(ppm): 1.51-1.80 (m, 5H), 1.88-2.06 (m, 2H), 2.26-2.34 (m, 1H), 2.33 (s, 3H), 2.69-2.76 (m, 1H), 2.86-2.96 (m, 1H), 3.40-3.46 (m, 1H), 3.88 (s, 3H), 6.12-6.16 (brs, 1H), 6.86-6.91 (m, 2H), 6.96 (brs, 1H), 7.03-7.05 (m, 2H), 7.26-7.30 (m, 1H), 7.78-7.84 (brs, 1H), 7.83 (s, 1H).

Synthesis of (E)-(6S,9aS)-6-(3,4,5-trifluorophenyl)-3-[3-methoxy-4-(4-methyl-1H-imidazol-1-yl)benzylidene]octahydroquinolizin-4-one and (E)-(6R,9aR)-6-(3,4,5-trifluorophenyl)-3-[3-methoxy-4-(4-methyl-1H-imidazol-1-yl)benzylidene]octahydroquinolizin-4-one The racemate (E)-(6S*,9aS*)-6-(3,4,5-trifluorophenyl)-3-[3-methoxy-4-(4-methyl-1H-imidazol-1-yl)benzylidene]octahydroquinolizin-4-one obtained above (54 mg) was separated by CHIRALPAK™ AD-H manufactured by Daicel Chemical Industries, Ltd. (2 cm×25 cm; mobile phase: hexane:ethanol=50:50) to obtain the title optically active compound with a retention time of 6.6 minutes (18.6 mg; >99% ee) and the title optically active compound with a retention time of 7.8 minutes (21.0 mg; >95% ee).

The property values of the title optically active compound with a retention time of 6.6 minutes (Example 13) are as follows.

$^1$H-NMR (CDCl$_3$) δ(ppm): 1.51-1.80 (m, 5H), 1.88-2.06 (m, 2H), 2.26-2.34 (m, 1H), 2.33 (s, 3H), 2.69-2.76 (m, 1H), 2.86-2.96 (m, 1H), 3.40-3.46 (m, 1H), 3.88 (s, 3H), 6.12-6.16 (brs, 1H), 6.86-6.91 (m, 2H), 6.96 (brs, 1H), 7.03-7.05 (m, 2H), 7.26-7.30 (m, 1H), 7.78-7.84 (brs, 1H), 7.83 (s, 1H).

The property values of the title optically active compound with a retention time of 7.8 minutes (Example 14) are as follows.

$^1$H-NMR (CDCl$_3$) δ(ppm): 1.51-1.80 (m, 5H), 1.88-2.06 (m, 2H), 2.26-2.34 (m, 1H), 2.33 (s, 3H), 2.69-2.76 (m, 1H), 2.86-2.96 (m, 1H), 3.40-3.46 (m, 1H), 3.88 (s, 3H), 6.12-6.16 (brs, 1H), 6.86-6.91 (m, 2H), 6.96 (brs, 1H), 7.03-7.05 (m, 2H), 7.26-7.30 (m, 1H), 7.78-7.84 (brs, 1H), 7.83 (s, 1H).

Examples 15 and 16

Synthesis of (E)-(6S,8S,9aR)-6-(3,4,5-trifluorophenyl)-8-hydroxy-3-[3-methoxy-4-(4-methyl-1H-imidazol-1-yl)benzylidene]octahydroquinolizin-4-one and (E)-(6R,8R,9aS)-6-(3,4,5-trifluorophenyl)-8-hydroxy-3-[3-methoxy-4-(4-methyl-1H-imidazol-1-yl)benzylidene]octahydroquinolizin-4-one

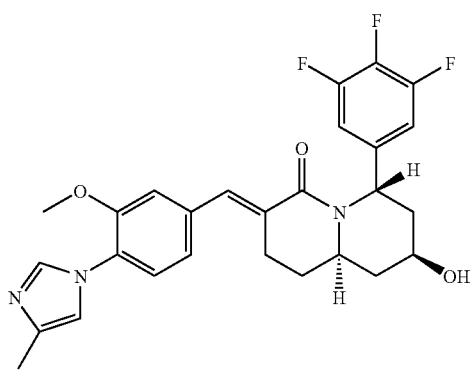

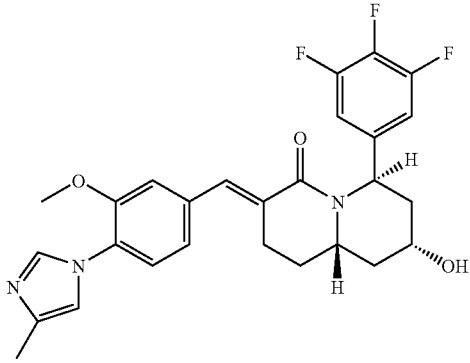

Synthesis of 1-(4-bromobutyryl)-2-(3,4,5-trifluorophenyl)-2,3-dihydro-1H-pyridin-4-one 1.02 g of the title compound was obtained from 4-methoxypyridine (1.52 mL), 3,4,5-trifluorophenylmagnesium bromide (0.3 M solution in THF, 50 mL), and 4-bromobutyryl chloride (1.74 mL) according to the method described in Tetrahedron Letters, 1986, vol. 27, p. 4549-4552. The property values of the compound are as follows.

$^1$H-NMR (CDCl$_3$) δ(ppm): 2.24-2.31 (m, 2H), 2.77-2.88 (m, 3H), 3.06-3.18 (m, 1H), 3.51-3.55 (m, 2H), 5.48 (brd, J=8.0 Hz, 1H), 5.98 (brs, 1H), 6.82-6.90 (m, 2H), 7.72 (brs, 1H).

Synthesis of (6S*,9aR*)-4-(3,4,5-trifluorophenyl)hexahydroquinolizine-2,6-dione 331 mg of the title compound was obtained from 1-(4-bromobutyryl)-2-(3,4,5-trifluorophenyl)-2,3-dihydro-1H-pyridin-4-one (1.15 g), tributyltin hydride (973 µL), and AIBN (201 mg) according to the method described in The Journal of Organic Chemistry, 1993, vol. 58, p. 4198-4199. The property values of the compound are as follows.

$^1$H-NMR (CDCl$_3$) δ(ppm): 1.61-1.69 (m, 1H), 1.72-1.82 (m, 1H), 1.87-1.97 (m, 1H), 1.99-2.07 (m, 1H), 2.23-2.31 (m, 1H), 2.39 (ddd, J=14.8, 3.2, 1.6 Hz, 1H), 2.47-2.57 (m, 2H), 2.81 (ddd, J=15.2, 7.2, 0.8 Hz, 1H), 2.92 (ddd, J=15.2, 2.4, 1.6 Hz, 1H), 3.52-3.59 (m, 1H), 6.45 (brd, J=7.2 Hz, 1H), 6.88-6.92 (m, 2H).

Synthesis of (6S*,9aR*)-8-hydroxy-6-(3,4,5-trifluorophenyl)octahydroquinolizin-4-one A solution of (6S*,9aR*)-4-(3,4,5-trifluorophenyl)hexahydroquinolizine-2,6-dione (331 mg) in methanol (10 mL) was cooled to 0° C. Sodium borohydride (64.1 mg) was added to the reaction solution, which was then stirred for one hour. Water and ethyl acetate were added to the reaction solution, and the organic layer was separated. The resulting organic layer was washed with brine, dried over anhydrous magnesium sulfate, and then concentrated under reduced pressure to obtain 340 mg of a crude alcohol compound. The property values of the compound are as follows.

$^1$H-NMR (CDCl$_3$) δ(ppm): 1.57-1.64 (m, 1H), 1.70-2.00 (m, 3H), 2.00-2.12 (m, 1H), 2.20-2.60 (m, 5H), 3.28-3.35 (m, ½H), 3.81-3.89 (m, 1H), 4.23-4.26 (m, ½H), 5.91 (brd, J=6.4 Hz, ½H), 6.15 (brd, J=4.8 Hz, ½H), 6.80-6.94 (m, 2H).

Synthesis of (6S*,8S*,9aR*)-8-(tert-butyldimethylsilanylox)-6-(3,4,5-fluorophenyl)octahydroquinolizin-4-one and (6S*,8R*,9aR*)-8-(tert-butyldimethylsilanyloxy)-6-(3,4,5-fluorophenyl)octahydroquinolizin-4-one A solution of (6S*,9aR*)-8-hydroxy-6-(3,4,5-trifluorophenyl)octahydroquinolizin-4-one (171 mg) in DMF (5.0 mL) was cooled to 0° C. Imidazole (233 mg), TBSCl (258 mg), and DMAP (6.98 mg) were sequentially added to the reaction solution, which was then stirred at room temperature for 4.5 hours. Water and ethyl acetate were added to the reaction solution, and the organic layer was separated. The resulting organic layer was washed with brine, dried over anhydrous magnesium sulfate, and then concentrated under reduced pressure. The residue was purified by silica gel column chromatography (elution solvent: heptane-ethyl acetate system) to obtain 103 mg of (6S*,8S*,9aR*)-8-(tert-butyldimethylsilanyloxy)-6-(3,4,5-fluorophenyl)octahydroquinolizin-4-one and 60.5 mg of (6S*,8R*,9aR*)-8-(tert-butyldimethylsilanyloxy)-6-(3,4,5-fluorophenyl)octahydroquinolizin-4-one.

The property values of (6S*,8S*,9aR*)-8-(tert-butyldimethylsilanyloxy)-6-(3,4,5-fluorophenyl)octahydroquinolizin-4-one are as follows.
$^1$H-NMR (CDCl$_3$) δ(ppm): 0.00 (s, 3H), 0.03 (s, 3H), 0.75 (s, 9H), 1.61-1.74 (m, 2H), 1.74-1.80 (m, 1H), 1.82-2.02 (m, 2H), 2.07-2.14 (m, 2H), 2.35-2.40 (m, 1H), 2.53 (ddd, J=12.4, 8.8, 5.6 Hz, 1H), 2.60-2.67 (m, 1H), 3.90-3.96 (m, 1H), 4.23-4.26 (m, 1H), 5.99 (brd, J=7.2 Hz, 1H), 6.84-6.93 (m, 2H)

The property values of (6S*,8R*,9aR*)-8-(tert-butyldimethylsilanyloxy)-6-(3,4,5-fluorophenyl)octahydroquinolizin-4-one are as follows.
$^1$H-NMR (CDCl$_3$) δ(ppm): 0.00 (s, 3H), 0.03 (s, 3H), 0.84 (s, 9H), 1.38-1.47 (m, 1H), 1.53-1.60 (m, 2H), 1.67-1.80 (m, 2H), 1.82-1.99 (m, 2H), 2.33-2.38 (m, 1H), 2.40-2.48 (m, 1H), 2.48-2.56 (m, 1H), 3.22-3.29 (m, 1H), 3.68-3.76 (m, 1H), 6.06 (brs, 1H), 6.72-6.76 (m, 2H).

Synthesis of (E)-(6S,8S*,9aR*)-8-(tert-butyldimethylsilanyloxy)-6-(3,4,5-trifluorophenyl)-3-[3-methoxy-4-(4-methyl-1H-imidazol-1-yl)benzylidene]octahydroquinolizin-4-one LDA (1.5 M solution in THF, 332 µL) was added to a solution of (6S*,8S*,9aR*)-8-(tert-butyldimethylsilanyloxy)-6-(3,4,5-fluorophenyl)octahydroquinolizin-4-one (59.2 mg) in THF (2.0 mL) at 0° C. The reaction solution was stirred at 0° C. for one hour, and then a solution of 3-methoxy-4-(4-methyl-1H-imidazol-1-yl)benzaldehyde (59.2 mg) in THF (1 mL) was added to the reaction solution. The reaction solution was further stirred at 0° C. for 30 minutes. Water and ethyl acetate were added to the reaction solution, and the organic layer was separated. The resulting organic layer was dried over magnesium sulfate and then concentrated under reduced pressure to obtain 139 mg of a crude aldol adduct. A solution of the crude aldol adduct (139 mg) in methylene chloride (3.0 mL) was cooled to 0° C. Triethylamine (185 µL) and methanesulfonyl chloride (51.3 µL) were added to the reaction solution, which was then stirred at room temperature for two hours and 10 minutes. Sodium methoxide (28% solution in methanol, 128 mg) and ethanol (1.0 mL) were added to the reaction solution, which was then stirred at room temperature for 40 minutes. Water and ethyl acetate were added to the reaction solution, and the organic layer was separated. The resulting organic layer was washed with brine, dried over anhydrous magnesium sulfate, and then concentrated under reduced pressure. The residue was purified by silica gel column chromatography (elution solvent: heptane-ethyl acetate system->ethyl acetate-methanol system) to obtain 61 mg of a mixture of the crude aldol adduct with the title compound. 61 mg of the resulting mixture was re-dissolved in methylene chloride (3.0 mL), and the reaction solution was cooled to 0° C. Triethylamine (147 µL) and methanesulfonyl chloride (51.3 µL) were added to the reaction solution, which was then stirred at room temperature for four hours and 15 minutes. Sodium methoxide (28% solution in methanol, 128 mg) and ethanol (1.0 mL) were added to the reaction solution, which was then stirred at room temperature for two hours and 15 minutes. Water and ethyl acetate were added to the reaction solution, and the organic layer was separated. The resulting organic layer was washed with brine, dried over anhydrous magnesium sulfate, and then concentrated under reduced pressure. The residue was purified by silica gel column chromatography (elution solvent: heptane-ethyl acetate system->ethyl acetate-methanol system) to obtain 44.1 mg of the title compound. The property values of the compound are as follows.
$^1$H-NMR (CDCl$_3$) δ(ppm): 0.00 (s, 3H), 0.03 (s, 3H), 0.75 (s, 9H), 1.68-1.78 (m, 2H), 1.78-1.87 (m, 1H), 2.08-2.20 (m, 2H), 2.38 (s, 3H), 2.38-2.41 (m, 1H), 2.82-2.88 (m, 1H), 2.93-3.00 (m, 1H), 3.92 (s, 3H), 4.02-4.07 (m, 1H), 4.25-4.29 (m, 1H), 6.05 (brd, J=7.2 Hz, 1H), 6.95-7.00 (m, 3H), 7.04-7.09 (m, 2H), 7.30-7.36 (m, 1H), 7.80-7.88 (m, 2H).

Synthesis of (E)-(6S*,8S*,9aR*)-6-(3,4,5-trifluorophenyl)-8-hydroxy-3-[3-methoxy-4-(4-methyl-1H-imidazol-1-yl)benzylidene]octahydroquinolizin-4-one TBAF (1.0 M solution in THF, 144 µL) was added to a solution of (E)-(6S*,8S*,9aR*)-8-(tert-butyldimethylsilanyloxy)-6-(3,4,5-trifluorophenyl)-3-[3-methoxy-4-(4-methyl-1H-imidazol-1-yl)benzylidene]octahydroquinolizin-4-one (44.1 mg) in THF (1.0 mL), and the reaction solution was stirred at room temperature overnight. A saturated ammonium chloride solution and ethyl acetate were added to the reaction solution, and the organic layer was separated. The resulting organic layer was washed with brine, dried over anhydrous magnesium sulfate, and then concentrated under reduced pressure. The residue was purified by silica gel column chromatography (carrier: Chromatorex NH; elution solvent: heptane-ethyl acetate system->ethyl acetate-methanol system) to obtain 25.4 mg of the title compound. The property values of the compound are as follows.
$^1$H-NMR (CDCl$_3$) δ(ppm): 1.67-1.84 (m, 2H), 1.84-1.94 (m, 1H), 2.07-2.20 (m, 2H), 2.41 (s, 3H), 2.41-2.48 (m, 1H), 2.76-2.86 (m, 1H), 2.86-2.96 (m, 1H), 3.88 (s, 3H), 3.97-4.05 (m, 1H), 4.29-4.34 (m, 1H), 5.98-6.04 (m, 1H), 6.94-7.06 (m, 5H), 7.26-7.30 (m, 1H), 7.78 (s, 1H), 7.81 (s, 1H).

Synthesis of (E)-(6S,8S,9aR)-6-(3,4,5-trifluorophenyl)-8-hydroxy-3-[3-methoxy-4-(4-methyl-1H-imidazol-1-yl)benzylidene]octahydroquinolizin-4-one and (E)-(6R,8R,9aS)-6-(3,4,5-trifluorophenyl)-8-hydroxy-3-[3-methoxy-4-(4-methyl-1H-imidazol-1-yl)benzylidene]octahydroquinolizin-4-one The racemate (E)-(6S*,8S*,9aR*)-6-(3,4,5-trifluorophenyl)-8-hydroxy-3-[3-methoxy-4-(4-methyl-1H-imidazol-1-yl)benzylidene]octahydroquinolizin-4-one obtained above (25.4 mg) was separated by CHIRALPAK™ AD-H manufactured by Daicel Chemical Industries, Ltd. (2 cm×25 cm;

mobile phase: ethanol) to obtain the title optically active compound with a retention time of 4.4 minutes (13.3 mg; >99% ee) and the title optically active compound with a retention time of 5.2 minutes (12.1 mg; >97% ee).

The property values of the title optically active compound with a retention time of 4.4 minutes (Example 15) are as follows.

$^1$H-NMR (CDCl$_3$) δ(ppm): 1.67-1.84 (m, 2H), 1.84-1.94 (m, 1H), 2.07-2.20 (m, 2H), 2.41 (s, 3H), 2.41-2.48 (m, 1H), 2.76-2.86 (m, 1H), 2.86-2.96 (m, 1H), 3.88 (s, 3H), 3.97-4.05 (m, 1H), 4.29-4.34 (m, 1H), 5.98-6.04 (m, 1H), 6.94-7.06 (m, 5H), 7.26-7.30 (m, 1H), 7.78 (s, 1H), 7.81 (s, 1H).

The property values of the title optically active compound with a retention time of 5.2 minutes (Example 16) are as follows.

$^1$H-NMR (CDCl$_3$) δ(ppm): 1.67-1.84 (m, 2H), 1.84-1.94 (m, 1H), 2.07-2.20 (m, 2H), 2.41 (s, 3H), 2.41-2.48 (m, 1H), 2.76-2.86 (m, 1H), 2.86-2.96 (m, 1H), 3.88 (s, 3H), 3.97-4.05 (m, 1H), 4.29-4.34 (m, 1H), 5.98-6.04 (m, 1H), 6.94-7.06 (m, 5H), 7.26-7.30 (m, 1H), 7.78 (s, 1H), 7.81 (s, 1H).

Examples 17 and 18

Synthesis of (E)-(6S,8R,9aR)-6-(3,4,5-trifluorophenyl)-8-hydroxy-3-[3-methoxy-4-(4-methyl-1H-imidazol-1-yl)benzylidene]octahydroquinolizin-4-one and (E)-(6R,8S,9aS)-6-(3,4,5-trifluorophenyl)-8-hydroxy-3-[3-methoxy-4-(4-methyl-1H-imidazol-1-yl)benzylidene]octahydroquinolizin-4-one

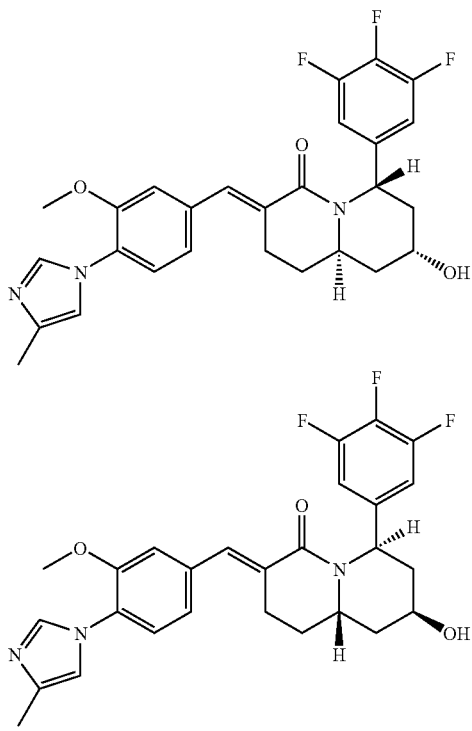

Synthesis of 1-(4-bromobutyryl)-2-(3,4,5-trifluorophenyl)-2,3-dihydro-1H-pyridin-4-one 1.02 g of the title compound was obtained from 4-methoxypyridine (1.52 mL), 3,4,5-trifluorophenylmagnesium bromide (0.3 M solution in THF, 50 mL), and 4-bromobutyryl chloride (1.74 mL) according to the method described in Tetrahedron Letters, 1986, vol. 27, p. 4549-4552. The property values of the compound are as follows.

$^1$H-NMR (CDCl$_3$) δ(ppm): 2.24-2.31 (m, 2H), 2.77-2.88 (m, 3H), 3.06-3.18 (m, 1H), 3.51-3.55 (m, 2H), 5.48 (brd, J=8.0 Hz, 1H), 5.98 (brs, 1H), 6.82-6.90 (m, 2H), 7.72 (brs, 1H).

Synthesis of (6S*,9aR*)-4-(3,4,5-trifluorophenyl)hexahydroquinolizine-2,6-dione 331 mg of the title compound was obtained from 1-(4-bromobutyryl)-2-(3,4,5-trifluorophenyl)-2,3-dihydro-1H-pyridin-4-one (1.15 g), tributyltin hydride (973 μL), and AIBN (201 mg) according to the method described in The Journal of Organic Chemistry, 1993, vol. 58, p. 4198-4199. The property values of the compound are as follows.

$^1$H-NMR (CDCl$_3$) δ(ppm): 1.61-1.69 (m, 1H), 1.72-1.82 (m, 1H), 1.87-1.97 (m, 1H), 1.99-2.07 (m, 1H), 2.23-2.31 (m, 1H), 2.39 (ddd, J=14.8, 3.2, 1.6 Hz, 1H), 2.47-2.57 (m, 2H), 2.81 (ddd, J=15.2, 7.2, 0.8 Hz, 1H), 2.92 (ddd, J=15.2, 2.4, 1.6 Hz, 1H), 3.52-3.59 (m, 1H), 6.45 (brd, J=7.2 Hz, 1H), 6.88-6.92 (m, 2H).

Synthesis of (6S*,9aR*)-8-hydroxy-6-(3,4,5-trifluorophenyl)octahydroquinolizin-4-one A solution of (6S*,9aR*)-4-(3,4,5-trifluorophenyl)hexahydroquinolizine-2,6-dione (331 mg) in methanol (10 mL) was cooled to 0° C. Sodium borohydride (64.1 mg) was added to the reaction solution, which was then stirred for one hour. Water and ethyl acetate were added to the reaction solution, and the organic layer was separated. The resulting organic layer was washed with brine, dried over anhydrous magnesium sulfate, and then concentrated under reduced pressure to obtain 340 mg of a crude alcohol compound. The property values of the compound are as follows.

$^1$H-NMR (CDCl$_3$) δ(ppm): 1.57-1.64 (m, 1H), 1.70-2.00 (m, 3H), 2.00-2.12 (m, 1H), 2.20-2.60 (m, 5H), 3.28-3.35 (m, ½H), 3.81-3.89 (m, 1H), 4.23-4.26 (m, ½H), 5.91 (brd, J=6.4 Hz, ½H), 6.15 (brd, J=4.8 Hz, ½H), 6.80-6.94 (m, 2H).

Synthesis of (6S*,8S*,9aR*)-8-(tert-butyldimethylsilanyloxy)-6-(3,4,5-fluorophenyl)octahydroquinolizin-4-one and (6S*,8R*,9aR*)-8-(tert-butyldimethylsilanyloxy)-6-(3,4,5-fluorophenyl)octahydroquinolizin-4-one A solution of (6S*,9aR*)-8-hydroxy-6-(3,4,5-trifluorophenyl)octahydroquinolizin-4-one (171 mg) in DMF (5.0 mL) was cooled to 0° C. Imidazole (233 mg), TBSCl (258 mg), and DMAP (6.98 mg) were sequentially added to the reaction solution, which was then stirred at room temperature for 4.5 hours. Water and ethyl acetate were added to the reaction solution, and the organic layer was separated. The resulting organic layer was washed with brine, dried over anhydrous magnesium sulfate, and then concentrated under reduced pressure. The residue was purified by silica gel column chromatography (elution solvent: heptane-ethyl acetate system) to obtain 103 mg of (6S*,8S*,9aR*)-8-(tert-butyldimethylsilanyloxy)-6-(3,4,5-fluorophenyl)octahydroquinolizin-4-one and 60.5 mg of (6S*,8R*,9aR*)-8-(tert-butyldimethylsilanyloxy)-6-(3,4,5-fluorophenyl)octahydroquinolizin-4-one.

The property values of (6S*,8S*,9aR*)-8-(tert-butyldimethylsilanyloxy)-6-(3,4,5-fluorophenyl)octahydroquinolizin-4-one are as follows.

$^1$H-NMR (CDCl$_3$) δ(ppm): 0.00 (s, 3H), 0.03 (s, 3H), 0.75 (s, 9H), 1.61-1.74 (m, 2H), 1.74-1.80 (m, 1H), 1.82-2.02 (m, 2H), 2.07-2.14 (m, 2H), 2.35-2.40 (m, 1H), 2.53 (ddd, J=12.4, 8.8, 5.6 Hz, 1H), 2.60-2.67 (m, 1H), 3.90-3.96 (m, 1H), 4.23-4.26 (m, 1H), 5.99 (brd, J=7.2 Hz, 1H), 6.84-6.93 (m, 2H)

The property values of (6S*,8R*,9aR*)-8-(tert-butyldimethylsilanyloxy)-6-(3,4,5-fluorophenyl)octahydroquinolizin-4-one are as follows.

$^1$H-NMR (CDCl$_3$) δ(ppm): 0.00 (s, 3H), 0.03 (s, 3H), 0.84 (s, 9H), 1.38-1.47 (m, 1H), 1.53-1.60 (m, 2H), 1.67-1.80 (m, 2H), 1.82-1.99 (m, 2H), 2.33-2.38 (m, 1H), 2.40-2.48 (m, 1H), 2.48-2.56 (m, 1H), 3.22-3.29 (m, 1H), 3.68-3.76 (m, 1H), 6.06 (brs, 1H), 6.72-6.76 (m, 2H).

(E)-(6S*,8R*,9aR*)-8-(tert-butyldimethylsilanyloxy)-6-(3,4,5-trifluorophenyl)-3-[3-methoxy-4-(4-methyl-1H-imidazol-1-yl)benzylidene]octahydroquinolizin-4-one LDA (1.5 M solution in THF, 153 μL) was added to a solution of (6S*,8R*,9aR*)-8-(tert-butyldimethylsilanyloxy)-6-(3,4,5-fluorophenyl)octahydroquinolizin-4-one (47.7 mg) in THF (2.0 mL) at 0° C. The reaction solution was stirred at 0° C. for one hour, and then a solution of 3-methoxy-4-(4-methyl-1H-imidazol-1-yl)benzaldehyde (24.9 mg) in THF (1 mL) was added to the reaction solution. The reaction solution was further stirred at 0° C. for 30 minutes. Water and ethyl acetate were added to the reaction solution, and the organic layer was separated. The resulting organic layer was dried over magnesium sulfate and then concentrated under reduced pressure to obtain 27.2 mg of a crude aldol adduct. A solution of the crude aldol adduct (27.2 mg) in methylene chloride (1.0 mL) was cooled to 0° C. Triethylamine (48.2 μL) and methanesulfonyl chloride (13.4 μL) were added to the reaction solution, which was then stirred at room temperature for five hours. Sodium methoxide (28% solution in methanol, 50 mg) and ethanol (1.0 mL) were added to the reaction solution, which was then stirred at room temperature for 1.5 hours. Water and ethyl acetate were added to the reaction solution, and the organic layer was separated. The resulting organic layer was washed with brine, dried over anhydrous magnesium sulfate, and then concentrated under reduced pressure. The residue was purified by silica gel column chromatography (elution solvent: heptane-ethyl acetate system->ethyl acetate-methanol system) to obtain 21.0 mg of the title compound. The property values of the compound are as follows.

$^1$H-NMR (CDCl$_3$) δ(ppm): 0.06 (s, 3H), 0.09 (s, 3H), 0.89 (s, 9H), 1.54-1.64 (m, 1H), 1.64-1.74 (m, 1H), 1.80-1.92 (m, 2H), 2.00-2.10 (m, 1H), 2.33 (s, 3H), 2.42-2.50 (m, 1H), 2.72-2.80 (m, 1H), 2.88-2.98 (m, 1H), 3.41-3.48 (m, 1H), 3.81-3.90 (m, 1H), 3.88 (s, 3H), 6.20-6.23 (m, 1H), 6.82-6.90 (m, 2H), 6.95 (brs, 1H), 7.02-7.06 (m, 2H), 7.26-7.30 (m, 1H), 7.81 (brs, 1H), 7.84 (s, 1H).

Synthesis of (E)-(6S*,8R*,9aR*)-6-(3,4,5-trifluorophenyl)-8-hydroxy-3-[3-methoxy-4-(4-methyl-1H-imidazol-1-yl)benzylidene]octahydroquinolizin-4-one TBAF (1.0 M solution in THF, 68.6 μL) was added to a solution of (E)-(6S*,8R*,9aR*)-8-(tert-butyldimethylsilanyloxy)-6-(3,4,5-trifluorophenyl)-3-[3-methoxy-4-(4-methyl-1H-imidazol-1-yl)benzylidene]octahydroquinolizin-4-one (21.0 mg) in THF (1.0 mL), and the reaction solution was stirred at room temperature overnight. A saturated ammonium chloride solution and ethyl acetate were added to the reaction solution, and the organic layer was separated. The resulting organic layer was washed with brine, dried over anhydrous magnesium sulfate, and then concentrated under reduced pressure. The residue was purified by silica gel column chromatography (carrier: Chromatorex NH; elution solvent: heptane-ethyl acetate system->ethyl acetate-methanol system) to obtain 11.5 mg of the title compound. The property values of the compound are as follows.

$^1$H-NMR (CDCl$_3$) δ(ppm): 1.50-1.61 (m, 1H), 1.68-1.90 (m, 3H), 1.98-2.12 (m, 1H), 2.34 (s, 3H), 2.56-2.64 (m, 1H), 2.72-2.80 (m, 1H), 2.88-3.00 (m, 1H), 3.45-3.51 (m, 1H), 3.81-3.96 (m, 1H), 3.89 (s, 3H), 6.26-6.30 (m, 1H), 6.88-6.92 (m, 2H), 6.96 (dd, J=1.2, 1.2 Hz, 1H), 7.03-7.06 (m, 2H), 7.28-7.30 (m, 1H), 7.83-7.85 (m, 2H).

Synthesis of (E)-(6S,8R,9aR)-6-(3,4,5-trifluorophenyl)-8-hydroxy-3-[3-methoxy-4-(4-methyl-1H-imidazol-1-yl)benzylidene]octahydroquinolizin-4-one and (E)-(6R,8S,9aS)-6-(3,4,5-trifluorophenyl)-8-hydroxy-3-[3-methoxy-4-(4-methyl-1H-imidazol-1-yl)benzylidene]octahydroquinolizin-4-one The racemate (E)-(6S*,8R*,9aR*)-6-(3,4,5-trifluorophenyl)-8-hydroxy-3-[3-methoxy-4-(4-methyl-1H-imidazol-1-yl)benzylidene]octahydroquinolizin-4-one obtained above (11.5 mg) was separated by CHIRALPAK™ AD-H manufactured by Daicel Chemical Industries, Ltd. (2 cm×25 cm; mobile phase: ethanol) to obtain the title optically active compound with a retention time of 4.8 minutes (4.9 mg; >99% ee) and the title optically active compound with a retention time of 6.0 minutes (4.4 mg; >99% ee).

The property values of the title optically active compound with a retention time of 4.8 minutes (Example 17) are as follows.

$^1$H-NMR (CDCl$_3$) δ(ppm): 1.50-1.61 (m, 1H), 1.68-1.90 (m, 3H), 1.98-2.12 (m, 1H), 2.34 (s, 3H), 2.56-2.64 (m, 1H), 2.72-2.80 (m, 1H), 2.88-3.00 (m, 1H), 3.45-3.51 (m, 1H), 3.81-3.96 (m, 1H), 3.89 (s, 3H), 6.26-6.30 (m, 1H), 6.88-6.92 (m, 2H), 6.96 (dd, J=1.2, 1.2 Hz, 1H), 7.03-7.06 (m, 2H), 7.28-7.30 (m, 1H), 7.83-7.85 (m, 2H).

The property values of the title optically active compound with a retention time of 6.0 minutes (Example 18) are as follows.

$^1$H-NMR (CDCl$_3$) δ(ppm): 1.50-1.61 (m, 1H), 1.68-1.90 (m, 3H), 1.98-2.12 (m, 1H), 2.34 (s, 3H), 2.56-2.64 (m, 1H), 2.72-2.80 (m, 1H), 2.88-3.00 (m, 1H), 3.45-3.51 (m, 1H), 3.81-3.96 (m, 1H), 3.89 (s, 3H), 6.26-6.30 (m, 1H), 6.88-6.92

(m, 2H), 6.96 (dd, J=1.2, 1.2 Hz, 1H), 7.03-7.06 (m, 2H), 7.28-7.30 (m, 1H), 7.83-7.85 (m, 2H).

Examples 19 and 20

Synthesis of (E)-(6S,9aS)-6-(4-fluorophenyl)-3-[3-methoxy-4-(4-methyl-1H-imidazol-1-yl)benzylidene]octahydroquinolizin-4-one and (E)-(6R,9aR)-6-(4-fluorophenyl)-3-[3-methoxy-4-(4-methyl-1H-imidazol-1-yl)benzylidene]octahydroquinolizin-4-one

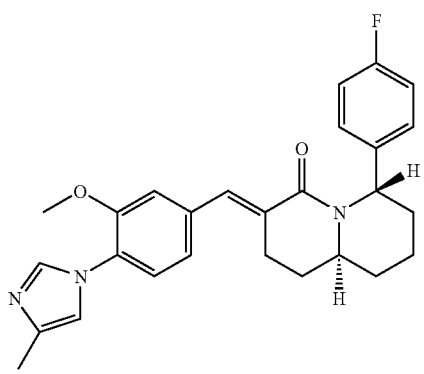

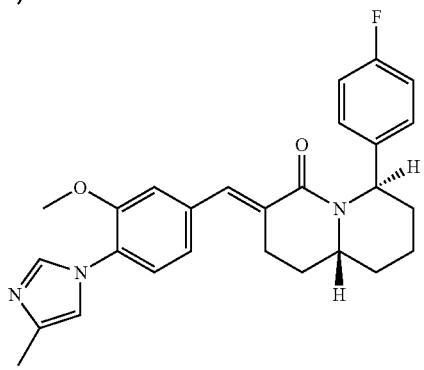

Synthesis of 1-(4-bromobutyryl)-2-(4-fluorophenyl)-2,3-dihydro-1H-pyridin-4-one 6.66 g of the title compound was obtained from 4-methoxypyridine (2.0 mL), 4-fluorophenylmagnesium bromide (1.0 M solution in THF, 20.7 mL), and 4-bromobutyryl chloride (2.4 mL) according to the method described in Tetrahedron Letters, 1986, vol. 27, p. 4549-4552. The property values of the compound are as follows.

$^1$H-NMR (CDCl$_3$) δ(ppm): 2.20-2.32 (m, 2H), 2.79-2.86 (m, 3H), 3.10-3.16 (m, 1H), 3.47-3.55 (m, 2H), 5.47 (brd, J=8.0 Hz, 1H), 6.00 (brs, 1H), 6.99-7.03 (m, 2H), 7.18-7.21 (m, 2H), 7.75 (brs, 1H).

Synthesis of (4S*,9aR*)-4-(4-fluorophenyl)hexahydroquinolizine-2,6-dione 1.05 g of the title compound was obtained from 1-(4-bromobutyryl)-2-(4-fluorophenyl)-2,3-dihydro-1H-pyridin-4-one (2.0 g), tributyltin hydride (1.87 mL), and AIBN (386 mg) according to the method described in The Journal of Organic Chemistry, 1993, vol. 58, p. 4198-4199. The property values of the compound are as follows.

$^1$H-NMR (CDCl$_3$) δ(ppm): 1.58-1.82 (m, 2H), 1.85-2.01 (m, 2H), 2.34-2.39 (m, 1H), 2.45-2.56 (m, 3H), 2.80 (dd, J=15.6, 7.2 Hz, 1H), 2.97-3.01 (m, 1H), 3.49-3.56 (m, 1H), 6.54 (brd, J=7.2 Hz, 1H), 6.99-7.03 (m, 2H), 7.21-7.24 (m, 2H).

Synthesis of (6S*,9aR*)-6-(4-fluorophenyl)-8-hydroxyoctahydroquinolizin-4-one

A solution of (4S*,9aR*)-4-(4-fluorophenyl)hexahydroquinolizine-2,6-dione (790 mg) in methanol (20 μL) was cooled to 0° C. Sodium borohydride (149 mg) was added to the reaction solution, which was then stirred for two hours and 15 minutes. Water and ethyl acetate were added to the reaction solution, and the organic layer was separated. The resulting organic layer was washed with brine, dried over anhydrous magnesium sulfate, and then concentrated under reduced pressure to obtain 760 mg of a crude alcohol compound. The property values of the compound are as follows.

$^1$H-NMR (CDCl$_3$) δ(ppm): 1.52-2.15 (m, 7H), 2.44-2.69 (m, 3H), 3.30-3.36 (m, ⅓H), 3.86-3.94 (m, 1H), 4.22 (brs, ⅔H), 5.99-6.00 (brd, J=6.4 Hz, ⅔H), 6.22-6.23 (brd, J=6.4 Hz, ⅓H), 7.00-7.04 (m, 4/3H), 7.15-7.18 (m, ⅔H), 7.22-7.27 (m, 2H).

Synthesis of (6S*,9aS*)-6-(4-fluorophenyl)octahydroquinolizin-4-one

A solution of (6S*,9aR*)-6-(4-fluorophenyl)-8-hydroxyoctahydroquinolizin-4-one (760 mg) in methylene chloride (10 mL) was cooled to 0° C. Triethylamine (2.42 mL) and methanesulfonyl chloride (671 μL) were added to the reaction solution, which was then stirred at room temperature for two hours. Water and ethyl acetate were added to the reaction solution, and the organic layer was separated. The resulting organic layer was washed with brine, dried over anhydrous magnesium sulfate, and then concentrated under reduced pressure to obtain 1.12 g of a crude mesyl compound. Sodium borohydride (547 mg) was added to a solution of the resulting crude mesyl compound (1.12 g) in NMP (10 mL), and the reaction solution was heated to 100° C. and stirred for two hours and 20 minutes. The reaction solution was returned to room temperature. Then, water and ethyl acetate were added to the reaction solution, and the organic layer was separated. The resulting organic layer was washed with brine, dried over anhydrous magnesium sulfate, and then concentrated under reduced pressure. The residue was purified by silica gel column chromatography (elution solvent: heptane-ethyl acetate system) to obtain 500 mg of the title compound. The property values of the compound are as follows.

$^1$H-NMR (CDCl$_3$) δ(ppm): 1.40-1.80 (m, 6H), 1.80-2.00 (m, 3H), 2.32-2.41 (m, 1H), 2.41-2.60 (m, 2H), 3.27-3.33 (m, 1H), 6.08-6.10 (m, 1H), 6.98-7.05 (m, 2H), 7.15-7.18 (m, 2H).

Synthesis of (E)-(6S*,9aS*)-6-(4-fluorophenyl)-3-[3-methoxy-4-(4-methyl-1H-imidazol-1-yl)benzylidene]octahydroquinolizin-4-one LDA (1.5 M solution in THF, 1.75 mL) was added to a solution of (6S*,9aS*)-6-(4-fluorophenyl)octahydroquinolizin-4-one (500 mg) in THF (10 mL) at 0° C. The reaction solution was stirred at 0° C. for one hour, and then a solution of 3-methoxy-4-(4-methyl-1H-imidazol-1-yl)benzaldehyde (437 mg) in THF (1 mL) was added to the reaction solution. The reaction solution was further stirred at 0° C. for one hour. Water and ethyl acetate were added to the reaction solution, and the organic layer was separated. The resulting organic layer was dried over magnesium sulfate and then concentrated under reduced pressure to obtain 660 mg of a crude aldol adduct. A solution of the crude aldol adduct (660 mg) in methylene chloride (5.0 mL) was cooled to 0° C. Triethylamine (1.19 mL) and methanesulfonyl chloride (330 µL) were added to the reaction solution, which was then stirred at room temperature for three hours and 20 minutes. Sodium methoxide (28% solution in methanol, 1.64 g) and ethanol (1.0 mL) were added to the reaction solution, which was then stirred at room temperature for one hour and 50 minutes. Water and ethyl acetate were added to the reaction solution, and the organic layer was separated. The resulting organic layer was washed with brine, dried over anhydrous magnesium sulfate, and then concentrated under reduced pressure. The residue was purified by silica gel column chromatography (elution solvent: heptane-ethyl acetate system->ethyl acetate-methanol system) to obtain 445 mg of the title compound. The property values of the compound are as follows.

$^1$H-NMR (CDCl$_3$) δ(ppm): 1.54-2.07 (m, 7H), 2.31 (s, 3H), 2.40-2.43 (m, 1H), 2.66-2.76 (m, 1H), 2.86-2.94 (m, 1H), 3.42-3.50 (m, 1H), 3.88 (s, 3H), 6.19-6.20 (m, 1H), 6.94 (s, 1H), 7.00-7.08 (m, 4H), 7.21-7.30 (m, 3H), 7.75 (s, 1H), 7.84 (s, 1H).

Synthesis of (E)-(6S,9aS)-6-(4-fluorophenyl)-3-[3-methoxy-4-(4-methyl-1H-imidazol-1-yl)benzylidene]octahydroquinolizin-4-one and (E)-(6R, 9aR)-6-(4-fluorophenyl)-3-[3-methoxy-4-(4-methyl-1H-imidazol-1-yl)benzylidene]octahydroquinolizin-4-one The racemate (E)-(6S*,9aS*)-6-(4-fluorophenyl)-3-[3-methoxy-4-(4-methyl-1H-imidazol-1-yl)benzylidene]octahydroquinolizin-4-one obtained above (445 mg) was separated by CHIRALPAK™ AD-H manufactured by Daicel Chemical Industries, Ltd. (2 cm×25 cm; mobile phase: hexane:ethanol=50:50) to obtain the title optically active compound with a retention time of 9.3 minutes (139 mg; >99% ee) and the title optically active compound with a retention time of 11.2 minutes (139 mg; >97% ee).

The property values of the title optically active compound with a retention time of 9.3 minutes (Example 19) are as follows.

$^1$H-NMR (CDCl$_3$) δ(ppm): 1.50-1.61 (m, 1H), 1.68-1.90 (m, 3H), 1.98-2.12 (m, 1H), 2.34 (s, 3H), 2.56-2.64 (m, 1H), 2.72-2.80 (m, 1H), 2.88-3.00 (m, 1H), 3.45-3.51 (m, 1H), 3.81-3.96 (m, 1H), 3.89 (s, 3H), 6.26-6.30 (m, 1H), 6.88-6.92 (m, 2H), 6.96 (dd, J=1.2, 1.2 Hz, 1H), 7.03-7.06 (m, 2H), 7.28-7.30 (m, 1H), 7.83-7.85 (m, 2H).

The property values of the title optically active compound with a retention time of 11.2 minutes (Example 20) are as follows.

$^1$H-NMR (CDCl$_3$) δ(ppm): 1.50-1.61 (m, 1H), 1.68-1.90 (m, 3H), 1.98-2.12 (m, 1H), 2.34 (s, 3H), 2.56-2.64 (m, 1H), 2.72-2.80 (m, 1H), 2.88-3.00 (m, 1H), 3.45-3.51 (m, 1H), 3.81-3.96 (m, 1H), 3.89 (s, 3H), 6.26-6.30 (m, 1H), 6.88-6.92 (m, 2H), 6.96 (dd, J=1.2, 1.2 Hz, 1H), 7.03-7.06 (m, 2H), 7.28-7.30 (m, 1H), 7.83-7.85 (m, 2H).

Examples 21 and 22

Synthesis of (E)-(5S)-(4-fluorophenyl)-2-[3-methoxy-4-(4-methyl-1H-imidazol-1-yl)benzylidene]-(8aS)-hexahydroindolizin-3-one and (E)-(5R)-(4-fluorophenyl)-2-[3-methoxy-4-(4-methyl-1H-imidazol-1-yl)benzylidene]-(8aR)-hexahydroindolizin-3-one

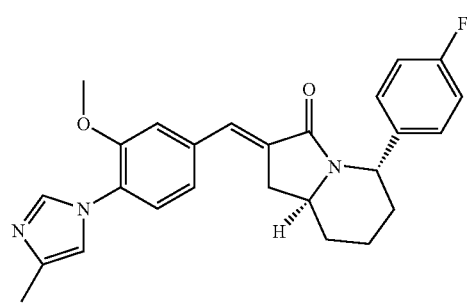

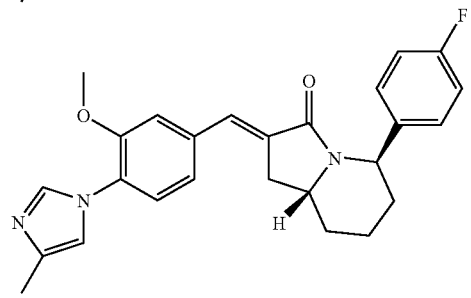

Synthesis of 1-(3-bromopropionyl)-2-(4-fluorophenyl)-2,3-dihydro-1H-pyridin-4-one To a solution of 4-methoxypyridine (3.0 g) in tetrahydrofuran (50 mL), 4-fluorophenylmagnesium bromide (1 M solution in tetrahydrofuran; 27.5 mL) was added dropwise at −40° C. to −20° C. over 10 minutes. To this solution, 3-bromopropionyl chloride (2.77 mL) was added dropwise at −40° C. to −20° C., and the reaction solution was stirred at −20° C. for 30 minutes. The reaction solution was poured into a 10% hydrochloric acid solution, and the mixture was stirred for 20 minutes, followed by extraction with ethyl acetate. The extract was washed with brine, dried over anhydrous magnesium sulfate, and then concentrated under reduced pressure. The residue was purified by silica gel column chromatography (heptane-ethyl acetate system) to obtain 2.9 g of the title compound. The property values of the compound are as follows.

ESI-MS; m/z 327 [M$^+$+H]. $^1$H-NMR (CDCl$_3$) δ(ppm): 2.86 (d, J=16.4 Hz, 2H), 3.00-3.30 (m, 2H), 3.67 (t, J=6.8 Hz, 2H), 3.84 (t, J=6.4 Hz, 1H), 5.49 (d, J=8.0 Hz, 1H), 6.90-7.10 (m, 3H), 7.10-7.30 (m, 2H).

Synthesis of 5-(4-fluorophenyl)hexahydroindolizine-3,7-dione

A solution of tributyltin hydride (3.88 mL) and 2,2'-azobis(isobutyronitrile) (0.56 g) in benzene (25 mL) was added dropwise to a solution of 1-(3-bromopropionyl)-2-(4-fluorophenyl)-2,3-dihydro-1H-pyridin-4-one obtained above (2.9 g) in benzene (60 mL) at 90° C. over four hours. The reaction solution was stirred at the same temperature for three hours. The reaction solution was returned to room temperature and poured into water, followed by extraction with ethyl acetate. The extract was washed with brine, dried over anhydrous magnesium sulfate, and then concentrated under reduced pressure. The residue was purified by silica gel column chromatography (heptane-ethyl acetate system) to obtain 600 mg of the title compound. The property values of the compound are as follows.

ESI-MS; m/z 248 [M$^+$+H]. $^1$H-NMR (CDCl$_3$) δ(ppm): 1.68-1.80 (m, 1H), 2.24-2.40 (m, 2H), 2.42-2.66 (m, 3H), 2.78-2.86 (m, 1H), 2.95 (td, J=2.0, 14.8 Hz, 1H), 3.70-3.80 (m, 1H), 5.83 (d, J=7.6 Hz, 1H), 6.98-7.05 (m, 2H), 7.22-7.30 (m, 2H).

Synthesis of 5-(4-fluorophenyl)-7-hydroxyhexahydroindolizin-3-one

Sodium borohydride (230 mg) was added to a solution of 5-(4-fluorophenyl)hexahydroindolizine-3,7-dione obtained above (500 mg) in ethanol (75 mL) at room temperature, and the reaction solution was stirred for one hour. The reaction solution was added to ice water, followed by extraction with ethyl acetate. The extract was washed with brine, dried over anhydrous magnesium sulfate, and then concentrated under reduced pressure to obtain 500 mg of the title compound. The property values of the compound are as follows.

ESI-MS; m/z 250 [M$^+$+H]. $^1$H-NMR (CDCl$_3$) δ(ppm): 1.20-2.60 (m, 9H), 3.60-3.90 (m, 1H), 4.10-4.30 (m, 1H), 5.35-5.55 (m, 1H), 6.90-7.10 (m, 2H), 7.10-7.35 (m, 2H).

Synthesis of 5-(4-fluorophenyl)hexahydroindolizin-3-one

Methanesulfonyl chloride (0.563 mL) was added to a solution of 5-(4-fluorophenyl)-7-hydroxyhexahydroindolizin-3-one obtained above (500 mg) and triethylamine (2.43 mL) in dichloromethane (90 mL) at 0° C., and the reaction solution was stirred at 0° C. for 30 minutes. The reaction solution was added to ice water, followed by extraction with ethyl acetate. The extract was washed with brine, dried over anhydrous magnesium sulfate, and then concentrated under reduced pressure to obtain 800 mg of a mesylate compound. The mesylate compound (800 mg) was dissolved in 1-methyl-2-pyrrolidinone (114 mL), and sodium borohydride (3.0 g) was added thereto. The reaction solution was stirred at 100° C. for 1.5 hours. The reaction solution was returned to room temperature and poured into water, followed by extraction with ethyl acetate. The extract was washed with brine, dried over anhydrous magnesium sulfate, and then concentrated under reduced pressure. The residue was purified by silica gel column chromatography (heptane-ethyl acetate system) to obtain 270 mg of the title compound. The property values of the compound are as follows.

ESI-MS; m/z 234 [M$^+$+H]. $^1$H-NMR (CDCl$_3$) δ(ppm): 1.20-1.32 (m, 1H), 1.48 (tq, J=3.2, 13.6 Hz, 1H), 1.56-1.90 (m, 4H), 2.20-2.34 (m, 2H), 2.40-2.54 (m, 2H), 3.52-3.64 (m, 1H), 5.41 (d, J=5.2 Hz, 1H), 6.96-7.06 (m, 2H), 7.12-7.22 (m, 2H).

Synthesis of diethyl [5-(4-fluorophenyl)-3-oxooctahydroindolizin-2-yl]phosphonate Iodotrimethylsilane (0.228 mL) was added to a solution of 5-(4-fluorophenyl)hexahydroindolizin-3-one obtained above (170 mg) and N,N,N',N'-tetramethylethylenediamine (0.544 mL) in dichloromethane (2.5 mL) at 0° C., and the reaction solution was stirred at 0° C. for 30 minutes. Iodine (367 mg) was added to the reaction solution at 0° C., and the reaction solution was stirred at the same temperature for 40 minutes. The reaction solution was added to ice-sodium thiosulfate solution, followed by extraction with ethyl acetate. The extract was washed with 1 N hydrochloric acid and brine, dried over anhydrous magnesium sulfate, and then concentrated under reduced pressure to obtain 270 mg of an iodine compound. A solution of the resulting iodine compound (270 mg) in triethyl phosphite (5.56 mL) was stirred at 130° C. for two hours. The reaction solution was returned to room temperature and concentrated under reduced pressure. The residue was purified by silica gel column chromatography (heptane-ethyl acetate system) to obtain 260 mg of the title compound. The property values of the compound are as follows.

ESI-MS; m/z 370 [M$^+$+H].

Synthesis of (E)-(5S)-(4-fluorophenyl)-2-[3-methoxy-4-(4-methyl-1H-imidazol-1-yl)benzylidene]-(8aS)-hexahydroindolizin-3-one and (E)-(5R)-(4-fluorophenyl)-2-[3-methoxy-4-(4-methyl-1H-imidazol-1-yl)benzylidene]-(8aR)-hexahydroindolizin-3-one Lithium hydroxide (26.7 mg) was added to a mixed solution of 3-methoxy-4-(4-methyl-1H-imidazol-1-yl)benzaldehyde (80 mg) and diethyl [5-(4-fluorophenyl)-3-oxooctahydroindolizin-2-yl]phosphonate obtained above (100 mg) in tetrahydrofuran (1 mL) and ethanol (4 mL), and the reaction solution was stirred at room temperature for 12 hours. The reaction solution was added to ice-sodium bicarbonate water, followed by extraction with ethyl acetate. The extract was washed with brine, dried over anhydrous magnesium sulfate, and then concentrated under reduced pressure. The residue was purified by silica gel column chromatography (heptane-ethyl acetate system) to obtain 20 mg of a racemate of the title compound. The resulting racemate (20 mg) was separated by CHIRALPAK™ AD-H manufactured by Daicel Chemical Industries, Ltd. (2 cm×25 cm; mobile phase: 50% ethanol-hexane) to obtain the title optically active compound with a retention time of 27 minutes (7.2 mg; >99% ee) and the title optically active compound with a retention time of 33 minutes (7.2 mg; >93% ee).

The property values of the title optically active compound with a retention time of 27 minutes (Example 21) are as follows.

ESI-MS; m/z 432 [M$^+$+H]. $^1$H-NMR (CDCl$_3$) δ(ppm): 1.33 (dq, J=3.6, 12.4 Hz, 1H), 1.55-1.70 (m, 1H), 1.70-2.00 (m, 3H), 2.32 (s, 3H), 2.41 (brd, J=12.8 Hz, 1H), 2.80 (td, J=3.2, 18 Hz, 1H), 3.30 (ddd, J=2.8, 8.0, 18 Hz, 1H), 3.60-3.75 (m, 1H), 3.90 (s, 3H), 5.63 (d, J=5.6 Hz, 1H), 6.95 (s, 1H), 7.04 (t, J=8.8 Hz, 2H), 7.14 (s, 1H), 7.17 (d, J=8.0 Hz, 1H), 7.20-7.32 (m, 3H), 7.45 (t, J=2.8 Hz, 1H), 7.77 (s, 1H).

The property values of the title optically active compound with a retention time of 33 minutes (Example 22) are as follows.

ESI-MS; m/z 432 [M$^+$+H]. $^1$H-NMR (CDCl$_3$) δ(ppm): 1.33 (dq, J=3.6, 12.4 Hz, 1H), 1.55-1.70 (m, 1H), 1.70-2.00 (m, 3H), 2.32 (s, 3H), 2.41 (brd, J=12.8 Hz, 1H), 2.80 (td, J=3.2, 18 Hz, 1H), 3.30 (ddd, J=2.8, 8.0, 18 Hz, 1H), 3.60-3.75 (m, 1H), 3.90 (s, 3H), 5.63 (d, J=5.6 Hz, 1H), 6.95 (s, 1H), 7.04 (t, J=8.8 Hz, 2H), 7.14 (s, 1H), 7.17 (d, J=8.0 Hz, 1H), 7.20-7.32 (m, 3H), 7.45 (t, J=2.8 Hz, 1H), 7.77 (s, 1H).

Examples 23, 24, 25, and 26

Synthesis of (E)-(5S)-(3,4-difluorophenyl)-2-[3-methoxy-4-(4-methyl-1H-imidazol-1-yl)benzylidene]-(8aS)-hexahydroindolizin-3-one, (E)-(5R)-(3,4-difluorophenyl)-2-[3-methoxy-4-(4-methyl-1H-imidazol-1-yl)benzylidene]-(8aR)-hexahydroindolizin-3-one, (Z)-(5S)-(3,4-difluorophenyl)-2-[3-methoxy-4-(4-methyl-1H-imidazol-1-yl)benzylidene]-(8aS)-hexahydroindolizin-3-one, and (Z)-(5R)-(3,4-difluorophenyl)-2-[3-methoxy-4-(4-methyl-1H-imidazol-1-yl)benzylidene]-(8aR)-hexahydroindolizin-3-one

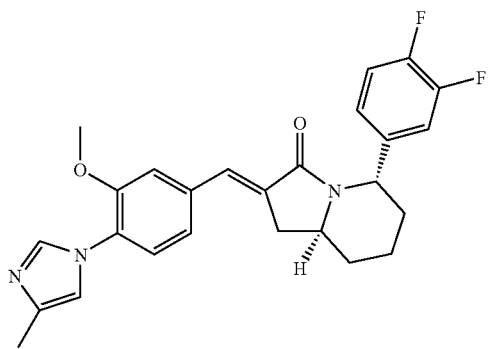

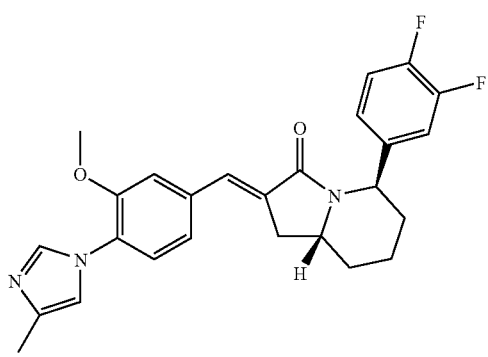

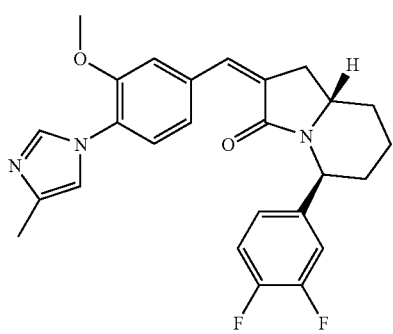

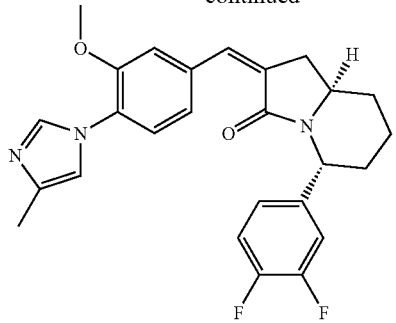

Synthesis of 5-(3,4-difluorophenyl)hexahydroindolizine-3,7-dione

To a solution of 4-methoxypyridine (2.7 g) in tetrahydrofuran (50 mL), 3,4-difluorophenylmagnesium bromide (0.5 M solution in tetrahydrofuran; 50 mL) was added dropwise at −40° C. to −20° C. over 10 minutes. To this solution, 3-bromopropionyl chloride (2.49 mL) was added dropwise at −40° C. to −20° C., and the reaction solution was stirred at −20° C. for 30 minutes. The reaction solution was poured into a 10% hydrochloric acid solution, and the mixture was stirred for 20 minutes, followed by extraction with ethyl acetate. The extract was washed with brine, dried over anhydrous magnesium sulfate, and then concentrated under reduced pressure. The residue was purified by silica gel column chromatography (heptane-ethyl acetate system) to obtain 3.4 g of 1-(3-bromopropionyl)-2-(3,4-difluorophenyl)-2,3-dihydro-1H-pyridin-4-one. A solution of tributyltin hydride (5.75 mL) and 2,2'-azobis(isobutyronitrile) (0.657 g) in benzene (50 mL) was added dropwise to a solution of 1-(3-bromopropionyl)-2-(3,4-difluorophenyl)-2,3-dihydro-1H-pyridin-4-one obtained above (3.4 g) in benzene (50 mL) at 90° C. over four hours. The reaction solution was stirred at the same temperature for three hours. The reaction solution was returned to room temperature and poured into water, followed by extraction with ethyl acetate. The extract was washed with brine, dried over anhydrous magnesium sulfate, and then concentrated under reduced pressure. The residue was purified by silica gel column chromatography (heptane-ethyl acetate system) to obtain 1.4 g of the title compound. The property value of the compound is as follows.
ESI-MS; m/z 266 [M$^+$+H].

Synthesis of 5-(3,4-difluorophenyl)-7-hydroxyhexahydroindolizin-3-one

Sodium borohydride (644 mg) was added to a solution of 5-(3,4-difluorophenyl)hexahydroindolizine-3,7-dione obtained above (1.4 g) in ethanol (20 mL) at room temperature, and the reaction solution was stirred for one hour. The reaction solution was added to ice water, followed by extraction with ethyl acetate. The extract was washed with brine, dried over anhydrous magnesium sulfate, and then concentrated under reduced pressure to obtain 1.5 g of the title compound. The property value of the compound is as follows.
ESI-MS; m/z 268 [M$^+$+H].

Synthesis of 5-(3,4-difluorophenyl)hexahydroindolizin-3-one

Methanesulfonyl chloride (1.58 mL) was added to a solution of 5-(3,4-difluorophenyl)-7-hydroxyhexahydroindolizin-3-one obtained above (1.4 g) and triethylamine (6.8 mL) in dichloromethane (25.2 mL) at 0° C., and the reaction solution was stirred at 0° C. for 30 minutes. The reaction solution was added to ice water, followed by extraction with ethyl acetate. The extract was washed with brine, dried over anhydrous magnesium sulfate, and then concentrated under reduced pressure to obtain 1.9 g of a mesylate compound. The resulting mesylate compound (1.9 g) was dissolved in 1-methyl-2-pyrrolidinone (271 mL), and sodium borohydride (7.13 g) was added thereto. The reaction solution was stirred at 100° C. for 1.5 hours. The reaction solution was returned to room temperature and poured into water, followed by extraction with ethyl acetate. The extract was washed with brine, dried over anhydrous magnesium sulfate, and then concentrated under reduced pressure. The residue was purified by silica gel column chromatography (heptane-ethyl acetate system) to obtain 500 mg of the title compound. The property values of the compound are as follows.

ESI-MS; m/z 252 [M$^+$+H]. $^1$H-NMR (CDCl$_3$) δ(ppm): 1.20-1.32 (m, 1H), 1.45 (tq, J=3.2, 13.6 Hz, 1H), 1.52-1.90 (m, 4H), 2.20-2.32 (m, 2H), 2.44-2.54 (m, 2H), 3.52-3.62 (m, 1H), 5.39 (d, J=5.2 Hz, 1H), 6.88-6.96 (m, 1H), 6.96-7.06 (m, 1H), 7.06-7.18 (m, 1H).

Synthesis of diethyl [5-(3,4-difluorophenyl)-3-oxooctahydroindolizin-2-yl]phosphonate Iodotrimethylsilane (0.227 mL) was added to a solution of 5-(3,4-difluorophenyl)hexahydroindolizin-3-one obtained above (200 mg) and N,N,N',N'-tetramethylethylenediamine (0.601 mL) in dichloromethane (5 mL) at 0° C., and the reaction solution was stirred at 0° C. for 30 minutes. Iodine (404 mg) was added to the reaction solution at 0° C., and the reaction solution was stirred at the same temperature for 40 minutes. The reaction solution was added to a mixture of ice with a sodium thiosulfate solution, followed by extraction with ethyl acetate. The extract was washed with 1 N hydrochloric acid and brine, dried over anhydrous magnesium sulfate, and then concentrated under reduced pressure to obtain 320 mg of an iodine compound. A solution of the iodine compound obtained above (320 mg) in triethyl phosphite (5 mL) was stirred at 130° C. for two hours. The reaction solution was returned to room temperature and concentrated under reduced pressure. The residue was purified by silica gel column chromatography (heptane-ethyl acetate system) to obtain 328 mg of the title compound. The property value of the compound is as follows.

ESI-MS; m/z 388 [M$^+$+H].

Synthesis of (E)-(5S)-(3,4-difluorophenyl)-2-[3-methoxy-4-(4-methyl-1H-imidazol-1-yl)benzylidene]-(8aS)-hexahydroindolizin-3-one, (E)-(5R)-(3,4-difluorophenyl)-2-[3-methoxy-4-(4-methyl-1H-imidazol-1-yl)benzylidene]-(8aR)-hexahydroindolizin-3-one, (Z)-(5S)-(3,4-difluorophenyl)-2-[3-methoxy-4-(4-methyl-1H-imidazol-1-yl)benzylidene]-(8aS)-hexahydroindolizin-3-one, and (Z)-(5R)-(3,4-difluorophenyl)-2-[3-methoxy-4-(4-methyl-1H-imidazol-1-yl)benzylidene]-(8aR)-hexahydroindolizin-3-one Lithium hydroxide (66.8 mg) was added to a mixed solution of 3-methoxy-4-(4-methyl-1H-imidazol-1-yl)benzaldehyde (200 mg) and diethyl [5-(3,4-difluorophenyl)-3-oxooctahydroindolizin-2-yl]phosphonate obtained above (328 mg) in tetrahydrofuran (1 mL) and ethanol (4 mL), and the reaction solution was stirred at room temperature for 12 hours. The reaction solution was added to a mixture of ice with sodium bicarbonate water, followed by extraction with ethyl acetate. The extract was washed with brine, dried over anhydrous magnesium sulfate, and then concentrated under reduced pressure. The residue was purified by silica gel column chromatography (heptane-ethyl acetate system) to obtain 60 mg of a racemate of the title compound E-isomer and 20 mg of a racemate of the title compound Z-isomer. The resulting racemate of E-isomer (20 mg) was separated by CHIRALPAK™ AD-H manufactured by Daicel Chemical Industries, Ltd. (2 cm×25 cm; mobile phase: 70% ethanol-hexane) to obtain the title optically active compound with a retention time of 23 minutes (6.3 mg; >99% ee) and the title optically active compound with a retention time of 30 minutes (6.1 mg; >99% ee). The resulting racemate of Z-isomer (20 mg) was separated by CHIRALPAK™ AD-H manufactured by Daicel Chemical Industries, Ltd. (2 cm×25 cm; mobile phase: 70% ethanol-hexane) to obtain the title optically active compound with a retention time of 19 minutes (3.0 mg; >99% ee) and the title optically active compound with a retention time of 25 minutes (3.0 mg; >99% ee). The property values of the compound are as follows.

The property values of the (E) title optically active compound with a retention time of 23 minutes (Example 23) are as follows.

ESI-MS; m/z 450 [M$^+$+H]. $^1$H-NMR (CDCl$_3$) δ(ppm): 1.33 (dq, J=3.6, 12.4 Hz, 1H), 1.55-1.70 (m, 1H), 1.70-2.05 (m, 3H), 2.32 (s, 3H), 2.36 (brd, J=14.4 Hz, 1H), 2.69 (td, J=3.2, 17.6 Hz, 1H), 3.25-3.38 (m, 1H), 3.60-3.70 (m, 1H), 3.90 (s, 3H), 5.61 (d, J=5.2 Hz, 1H), 6.96 (s, 1H), 6.92-7.02 (m, 1H), 7.02-7.20 (m, 4H), 7.30 (d, J=8.0 Hz, 1H), 7.45 (t, J=2.8 Hz, 1H), 7.77 (s, 1H).

The property values of the (E) title optically active compound with a retention time of 30 minutes (Example 24) are as follows.

ESI-MS; m/z 450 [M$^+$+H]. $^1$H-NMR (CDCl$_3$) δ(ppm): 1.33 (dq, J=3.6, 12.4 Hz, 1H), 1.55-1.70 (m, 1H), 1.70-2.05 (m, 3H), 2.32 (s, 3H), 2.36 (brd, J=14.4 Hz, 1H), 2.69 (td, J=3.2, 17.6 Hz, 1H), 3.25-3.38 (m, 1H), 3.60-3.70 (m, 1H), 3.90 (s, 3H), 5.61 (d, J=5.2 Hz, 1H), 6.96 (s, 1H), 6.92-7.02 (m, 1H), 7.02-7.20 (m, 4H), 7.30 (d, J=8.0 Hz, 1H), 7.45 (t, J=2.8 Hz, 1H), 7.77 (s, 1H).

The property values of the (Z) title optically active compound with a retention time of 19 minutes (Example 25) are as follows.

ESI-MS; m/z 450 [M$^+$+H]. $^1$H-NMR (CDCl$_3$) δ(ppm): 1.34 (dq, J=3.2, 12.8 Hz, 1H), 1.52 (tq, J=3.2, 12.8 Hz, 1H), 1.60-1.96 (m, 3H), 2.31 (s, 3H), 2.26-2.36 (m, 1H), 2.56-2.66 (m, 1H), 3.08-3.22 (m, 1H), 3.58-3.68 (m, 1H), 3.91 (s, 3H), 5.50 (d, J=5.6 Hz, 1H), 6.76 (t, J=2.4 Hz, 1H), 6.90-7.30 (m, 6H), 7.79 (s, 1H), 8.25 (s, 1H).

The property values of the (Z) title optically active compound with a retention time of 25 minutes (Example 26) are as follows.

ESI-MS; m/z 450 [M$^+$+H]. $^1$H-NMR (CDCl$_3$) δ(ppm): 1.34 (dq, J=3.2, 12.8 Hz, 1H), 1.52 (tq, J=3.2, 12.8 Hz, 1H), 1.60-1.96 (m, 3H), 2.31 (s, 3H), 2.26-2.36 (m, 1H), 2.56-2.66 (m, 1H), 3.08-3.22 (m, 1H), 3.58-3.68 (m, 1H), 3.91 (s, 3H), 5.50 (d, J=5.6 Hz, 1H), 6.76 (t, J=2.4 Hz, 1H), 6.90-7.30 (m, 6H), 7.79 (s, 1H), 8.25 (s, 1H).

Examples 27 and 28

Synthesis of (E)-(5R,8aS)-5-(4-fluorophenyl)-2-[3-methoxy-4-(4-methyl-1H-imidazol-1-yl)benzylidene]hexahydroindolizin-3-one and (E)-(5S,8aR)-5-(4-fluorophenyl)-2-[3-methoxy-4-(4-methyl-1H-imidazol-1-yl)benzylidene]hexahydroindolizin-3-one

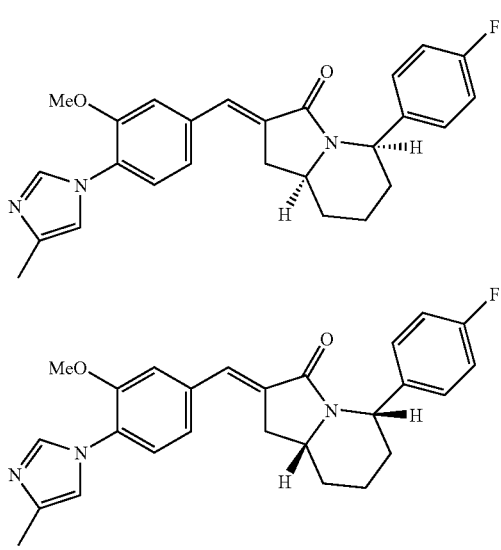

Synthesis of 1-[(2R*,6S*)-2-(4-fluorophenyl)-6-vinylpiperidin-1-yl]propenone

Acrylic chloride (0.31 mL) was added to a solution of (2R*,6S*)-2-(4-fluorophenyl)-6-vinylpiperidine (520 mg) and diisopropylamine (0.66 mL) in methylene chloride (10 mL), and the reaction solution was stirred at room temperature for five hours. Chloroform and 1 N aqueous hydrochloric acid were added to the reaction solution, and the organic layer was separated. The resulting organic layer was washed with saturated sodium bicarbonate water, dried over magnesium sulfate, and then concentrated under reduced pressure. The residue was purified by silica gel column chromatography (elution solvent:heptane->heptane:ethyl acetate=1:1) to obtain 201 mg of the title compound. The property values of the compound are as follows.

$^1$H-NMR (CDCl$_3$) δ(ppm): 1.59-1.70 (m, 1H), 1.78-1.96 (m, 4H), 2.40-2.47 (m, 1H), 4.85 (dt, J=10.4, 1.2 Hz, 1H), 4.93-5.01 (m, 1H), 5.03 (d, J=17.2 Hz, 1H), 5.50 (ddd, J=17.2, 10.4, 7.6 Hz, 1H), 5.67-5.72 (m, 2H), 6.36 (dd, J=17.2, 1.6 Hz, 1H), 6.60 (dd, J=17.2, 10.4 Hz, 1H), 6.98 (t, J=8.8 Hz, 2H), 7.26 (dd, J=8.8, 5.6 Hz, 2H).

(5R*,8aS*)-5-(4-fluorophenyl)-6,7,8,8a-tetrahydro-5H-indolizin-3-one

A solution of 1-[(2R*,6S*)-2-(4-fluorophenyl)-6-vinylpiperidin-1-yl]propenone (201 mg) and tricyclohexylphosphine[1,3-bis(2,4,6-trimethylphenyl)-4,5-dihydroimidazol-2-ylidene][benzylidene]ruthenium (IV) dichloride (33 mg) in methylene chloride (100 mL) was heated under reflux for 17 hours. The reaction solution was left to cool to room temperature and then concentrated. The residue was purified by silica gel column chromatography (elution solvent: heptane:ethyl acetate=4:1->ethyl acetate) to obtain 105 mg of the title compound. The property values of the compound are as follows.

$^1$H-NMR (CDCl$_3$) δ(ppm):
1.28-1.40 (m, 1H), 1.60-1.81 (m, 2H), 1.86-1.94 (m, 1H), 2.00-2.09 (m, 1H), 2.11-2.19 (m, 1H), 4.05 (brd, J=12.8 Hz, 1H), 4.50 (dd, J=9.2, 3.2 Hz, 1H), 6.03 (dd, J=6.0, 2.0 Hz, 1H), 6.98-7.04 (m, 3H), 7.25 (dd, J=7.2, 5.6 Hz, 2H).

Synthesis of (5R*,8aS*)-5-(4-fluorophenyl)hexahydroindolizin-3-one

Platinum oxide (10 mg) was added to a solution of (5R*,8aS*)-5-(4-fluorophenyl)-6,7,8,8a-tetrahydro-5H-indolizin-3-one (105 mg) in methanol (5 mL), and the reaction solution was stirred in a hydrogen stream at room temperature for three hours. The reaction solution was filtered through celite, and the filtrate was concentrated under reduced pressure to obtain 87 mg of the title compound. The property value of the compound is as follows.

ESI-MS; m/z 234 [M$^+$+H].

Synthesis of (5S*,8aR*)-5-(4-fluorophenyl)-2-iodohexahydroindolizin-3-one

Iodotrimethylsilane (0.08 mL) was added to a solution of (5R*,8aS*)-5-(4-fluorophenyl)hexahydroindolizin-3-one (87 mg) and N,N,N',N'-tetramethylethylenediamine (0.2 mL) in methylene chloride (5 mL) at 0° C., and the reaction solution was stirred at 0° C. for 20 minutes. Iodine (142 mg) was added to the reaction solution, which was then stirred at 0° C. for 40 minutes. Ethyl acetate and a saturated sodium thiosulfate solution were added to the reaction solution, and the organic layer was separated. The resulting organic layer was washed with brine, dried over magnesium sulfate, and then concentrated under reduced pressure to obtain 120 mg of the title compound. The property value of the compound is as follows.

ESI-MS; m/z 360 [M$^+$+H].

Synthesis of diethyl [(5S*,8aR*)-5-(4-fluorophenyl)-3-oxooctahydroindolizin-2-yl]phosphonate A mixture of (5S*,8aR*)-5-(4-fluorophenyl)-2-iodohexahydroindolizin-3-one (120 mg) with triethyl phosphite (2 mL) was stirred at 120° C. for 14 hours. The reaction solution was left to cool to room temperature and then concentrated under reduced pressure to obtain 123 mg of the title compound. The property value of the compound is as follows.

ESI-MS; m/z 370 [M$^+$+H].

Synthesis of (E)-(5R*,8aS*)-5-(4-fluorophenyl)-2-{1-[3-methoxy-4-(4-methyl-1H-imidazol-1-yl)benzylidene]hexahydroindolizin}-3-one Lithium hydroxide monohydrate (42 mg) was added to a mixed solution of diethyl [(5S*,8aR*)-5-(4-fluorophenyl)-3-oxooctahydroindolizin-2-yl]phosphonate (123 mg) and 3-methoxy-4-(4-methyl-1H-imidazol-1-yl)benzaldehyde (72 mg) in tetrahydrofuran (3 mL) and ethanol (1 mL), and the reaction solution was stirred at room temperature for one hour. Ethyl acetate and brine were added to the reaction solution, and the organic layer was separated. The resulting organic layer was dried over magnesium sulfate and then concentrated under reduced pressure. The residue was purified by silica gel column chromatography (carrier: Chromatorex NH; elution solvent: heptane:ethyl acetate=1:1->ethyl acetate) to obtain 80 mg of the title compound. The property values of the compound are as follows.

ESI-MS; m/z 432 [M++H]. ¹H-NMR (CDCl₃) δ(ppm): 1.34-1.45 (m, 1H), 1.42-1.54 (m, 1H), 1.57-1.80 (m, 2H), 1.91-2.15 (m, 3H), 2.63-2.71 (m, 1H), 3.25 (ddd, 16.8, 6.4, 1.6 Hz, 1H), 3.56-3.64 (m, 1H), 3.86 (s, 3H), 4.36 (dd, J=10.0, 3.2 Hz, 1H), 6.92 (brs, 1H), 7.00-7.05 (m, 3H), 7.08 (brd, J=9.2, 1H), 7.20 (brs, 1H), 7.24 (d, J=9.2 Hz, 1H), 7.28 (dd, J=8.8, 5.6 Hz, 2H), 7.72 (s, 1H).

Synthesis of (E)-(5R,8aS)-5-(4-fluorophenyl)-2-{1-[3-methoxy-4-(4-methyl-1H-imidazol-1-yl)benzylidene]hexahydroindolizin-3-one and (E)-(5S,8aR)-5-(4-fluorophenyl)-2-{1-[3-methoxy-4-(4-methyl-1H-imidazol-1-yl)benzylidene]hexahydroindolizin-3-one The racemate (E)-(1R*,8aS*)-5-(4-fluorophenyl)-2-{1-[3-methoxy-4-(4-methyl-1H-imidazol-1-yl)benzylidene]hexahydroindolizin-3-one obtained above (80 mg) was separated by CHIRALPAK™ IA manufactured by Daicel Chemical Industries, Ltd. (2 cm×25 cm; mobile phase: ethanol) to obtain the title optically active compound with a retention time of 23 minutes (28 mg; >99% ee) and the title optically active compound with a retention time of 26 minutes (26 mg; >99% ee).

The property values of the title optically active compound with a retention time of 23 minutes (Example 27) are as follows.

¹H-NMR (CDCl₃) δ(ppm): 1.34-1.45 (m, 1H), 1.42-1.54 (m, 1H), 1.57-1.80 (m, 2H), 1.91-2.15 (m, 3H) 2.30 (s, 3H), 2.63-2.71 (m, 1H), 3.25 (ddd, 16.8, 6.4, 1.6 Hz, 1H), 3.56-3.64 (m, 1H), 3.86 (s, 3H), 4.36 (dd, J=10.0, 3.2 Hz, 1H), 6.92 (brs, 1H), 7.00-7.05 (m, 3H), 7.08 (brd, J=9.2, 1H), 7.20 (brs, 1H), 7.24 (d, J=9.2 Hz, 1H), 7.28 (dd, J=8.8, 5.6 Hz, 2H), 7.72 (s, 1H).

The property values of the title optically active compound with a retention time of 26 minutes (Example 28) are as follows.

¹H-NMR (CDCl₃) δ(ppm) 1.34-1.45 (m, 1H), 1.42-1.54 (m, 1H), 1.57-1.80 (m, 2H), 1.91-2.15 (m, 3H) 2.30 (s, 3H), 2.63-2.71 (m, 1H), 3.25 (ddd, 16.8, 6.4, 1.6 Hz, 1H), 3.56-3.64 (m, 1H), 3.86 (s, 3H), 4.36 (dd, J=10.0, 3.2 Hz, 1H), 6.92 (brs, 1H), 7.00-7.05 (m, 3H), 7.08 (brd, J=9.2, 1H), 7.20 (brs, 1H), 7.24 (d, J=9.2 Hz, 1H), 7.28 (dd, J=8.8, 5.6 Hz, 2H), 7.72 (s, 1H).

Examples 29 and 30

Synthesis of (E)-(6R,9aS)-3-[3-methoxy-4-(4-methyl-1H-imidazol-1-yl)benzylidene]-6-(4-methoxyphenyl)octahydroquinolizin-4-one and (E)-(6S,9aR)-3-[3-methoxy-4-(4-methyl-1H-imidazol-1-yl)benzylidene]-6-(4-methoxyphenyl)octahydroquinolizin-4-one

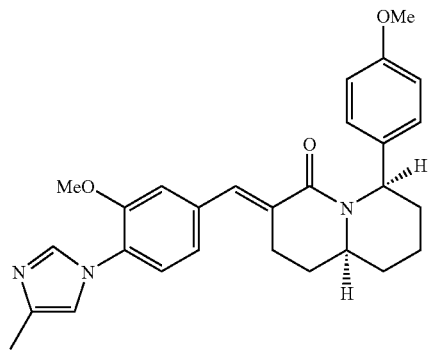

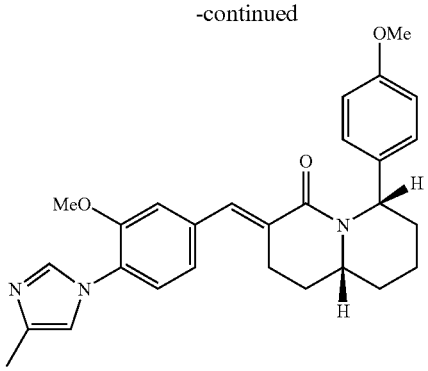

Synthesis of 1-(4-methoxyphenyl)hepta-5,6-dienyl-1-amine 462 mg of the title compound was obtained from (4-methoxybenzyl)-(4-methoxybenzylidene)amine (600 mg) and 6-iodohexa-1,2-diene (500 mg) according to the method described in Journal of the American Chemical Society, 2003, vol. 125, p. 11956. The property value of the compound is as follows.

ESI-MS; m/z 201 [M+—NH₃].

Synthesis of (2R*,6S*)-2-(4-methoxyphenyl)-6-vinylpiperidine

Acetic acid (0.12 mL) was added to a solution of an allylpalladium chloride dimer (78 mg) and 1,1'-bis(diphenylphosphino)ferrocene (236 mg) in THF (50 mL), and the reaction solution was stirred at room temperature for 10 minutes. A solution of 1-(4-methoxyphenyl)hepta-5,6-dienyl-1-amine (462 mg) in THF (10 mL) was added to the reaction solution, which was then stirred at 70° C. for 15 hours. The reaction solution was left to cool to room temperature. Then, diethyl ether and 1 N aqueous hydrochloric acid were added to the reaction solution, and the aqueous layer was separated. The resulting aqueous layer was washed with diethyl ether, and then a 5 N sodium hydroxide solution was added to the aqueous layer until the pH was adjusted to 11 or less. Chloroform was added to the aqueous layer, and the organic layer was separated. The resulting organic layer was dried over magnesium sulfate, and concentrated under reduced pressure to obtain 320 mg of the title compound. The property value of the compound is as follows.

ESI-MS; m/z 218 [M++H].

Synthesis of 1-[(2R*,6S*)-2-(4-methoxyphenyl)-6-vinylpiperidin-1-yl]-3-buten-1-one Diethyl cyanophosphonate (0.67 mL) was added to a solution of (2R*,6S*)-2-(4-methoxyphenyl)-6-vinylpiperidine (320 mg), vinylacetic acid (0.37 mL), and triethylamine (1.23 mL) in DMF (5 mL), and the reaction solution was stirred at room temperature for nine hours. Ethyl acetate and 1 N aqueous hydrochloric acid were added to the reaction solution, and the organic layer was separated. The resulting organic layer was washed with saturated sodium bicarbonate water, dried over magnesium sulfate, and then concentrated under reduced pressure. The residue was purified by silica gel column chromatography (elution solvent: heptane->heptane: ethyl acetate=1:1) to obtain 100 mg of the title compound. The property value of the compound is as follows.

ESI-MS; m/z 286 [M++H].

Synthesis of (6R*,9aS*)-6-(4-methoxyphenyl)-3,6,7,8,9,9a-hexahydroquinolizin-4-one A solution of 1-[(2R*,6S*)-2-(4-methoxyphenyl)-6-vinylpiperidin-1-yl]-3-buten-1-one (100 mg) and tricyclohexylphosphine[1,3-bis(2,4,6-trimethylphenyl)-4,5-dihydroimidazol-2-ylidene][benzylidene]ruthenium (IV) dichloride (30 mg) in methylene chloride (50 mL) was heated under reflux for 1.5 hours. The reaction solution was left to cool to room temperature and then concentrated. The residue was purified by silica gel column chromatography (elution solvent: heptane:ethyl acetate=4:1->ethyl acetate) to obtain 28 mg of the title compound. The property values of the compound are as follows.

$^1$H-NMR (CDCl$_3$) δ(ppm): 1.42-1.53 (m, 1H), 1.60-1.77 (m, 2H), 1.82-1.91 (m, 1H), 2.00-2.07 (m, 1H), 2.17-2.27 (m, 1H), 2.92-3.10 (m, 2H), 3.77 (s, 3H), 4.25-4.35 (m, 1H), 5.30 (t, J=4.4 Hz, 1H), 5.66 (brd, J=10.0 Hz, 1H), 5.82-5.88 (m, 1H), 6.82 (d, J=8.8 Hz, 2H), 7.11 (d, J=8.8 Hz, 2H).

Synthesis of (6R*,9aS*)-6-(4-methoxyphenyl)octahydroquinolizin-4-one

Platinum oxide (2 mg) was added to a solution of (6R*,9aS*)-6-(4-methoxyphenyl)-3,6,7,8,9,9a-hexahydroquinolizin-4-one (28 mg) in methanol (5 mL), and the reaction solution was stirred in a hydrogen stream at room temperature for 13 hours. The reaction solution was filtered through celite, and the filtrate was concentrated under reduced pressure to obtain 23 mg of the title compound. The property values of the compound are as follows.

$^1$H-NMR (CDCl$_3$) δ(ppm): 1.34-1.44 (m, 1H), 1.47-1.86 (m, 5H), 1.90-1.98 (m, 2H), 2.04-2.21 (m, 2H), 2.48-2.53 (m, 2H), 3.57-3.66 (m, 1H), 3.77 (s, 3H), 5.38 (t, J=3.2 Hz, 1H), 6.82 (d, J=8.8 Hz, 2H), 7.10 (d, J=8.8, 2H).

Synthesis of (6R*,9aS*)-3-iodo-6-(4-methoxyphenyl)octahydroquinolizin-4-one

Iodotrimethylsilane (0.02 mL) was added to a solution of (6R*,9aS*)-6-(4-methoxyphenyl)octahydroquinolizin-4-one (23 mg) and N,N,N',N'-tetramethylethylenediamine (0.05 mL) in methylene chloride (3 mL) at 0° C., and the reaction solution was stirred at 0° C. for 30 minutes. Iodine (34 mg) was added to the reaction solution, which was then stirred at 0° C. for one hour. Ethyl acetate and a saturated sodium thiosulfate solution were added to the reaction solution, and the organic layer was separated. The resulting organic layer was washed with brine, dried over magnesium sulfate, and then concentrated under reduced pressure to obtain 34 mg of the title compound. The property value of the compound is as follows.

ESI-MS; m/z 38 [M$^+$+H].

Synthesis of diethyl [(6S*,9aR*)-6-(4-methoxyphenyl)-4-oxooctahydroquinolizin-3-yl]phosphonate A mixture of (6R*,9aS*)-3-iodo-6-(4-methoxyphenyl)octahydroquinolizin-4-one (34 mg) with triethyl phosphite (1 mL) was stirred at 120° C. for five hours. The reaction solution was left to cool to room temperature and then concentrated under reduced pressure to obtain 35 mg of the title compound. The property value of the compound is as follows.

ESI-MS; m/z 396 [M$^+$+H].

Synthesis of (E)-(6R*,9aS*)-3-[3-methoxy-4-(4-methyl-1H-imidazol-1-yl)benzylidene]-6-(4-methoxyphenyl)octahydroquinolizin-4-one Lithium hydroxide monohydrate (11 mg) was added to a mixed solution of diethyl [(6S*,9aR*)-6-(4-methoxyphenyl)-4-oxooctahydroquinolizin-3-yl]phosphonate (35 mg) and 3-methoxy-4-(4-methyl-1H-imidazol-1-yl)benzaldehyde (19 mg) in tetrahydrofuran (2 mL) and ethanol (0.5 mL), and the reaction solution was stirred at room temperature for three hours. Ethyl acetate and brine were added to the reaction solution, and the organic layer was separated. The resulting organic layer was dried over magnesium sulfate and then concentrated under reduced pressure. The residue was purified by silica gel column chromatography (carrier: Chromatorex NH; elution solvent: heptane:ethyl acetate=1:1->ethyl acetate) to obtain 28 mg of the title compound. The property values of the compound are as follows.

ESI-MS; m/z 458 [M$^+$+H]. $^1$H-NMR (CDCl$_3$) δ(ppm): 1.39-1.49 (m, 1H), 1.52-1.76 (m, 4H), 1.98-2.05 (m, 1H), 2.18-2.24 (m, 2H) 2.32 (s, 3H), 2.66-2.76 (m, 1H), 3.09 (brd, J=16.0 Hz, 1H), 3.75-3.84 (m, 4H), 3.85 (s, 3H), 5.56 (brt, J=3.2 Hz, 1H), 6.85 (d, J=8.8 Hz, 2H), 6.94 (brs, 1H), 7.03 (brs, 1H), 7.04 (brd, J=8.0 Hz, 1H), 7.16 (d, J=8.8 Hz, 2H), 7.24 (d, J=8.0 Hz, 1H), 7.78 (s, 1H), 7.81 (brd, J=2.4 Hz, 1H).

Synthesis of (E)-(6R,9aS)-3-[3-methoxy-4-(4-methyl-1H-imidazol-1-yl)benzylidene]-6-(4-methoxyphenyl)octahydroquinolizin-4-one and (E)-(6S,9aR)-3-[3-methoxy-4-(4-methyl-1H-imidazol-1-yl)benzylidene]-6-(4-methoxyphenyl)octahydroquinolizin-4-one The racemate (E)-(6R*,9aS*)-3-[3-methoxy-4-(4-methyl-1H-imidazol-1-yl)benzylidene]-6-(4-methoxyphenyl)octahydroquinolizin-4-one obtained above (28 mg) was separated by CHIRALPAK™ AD-H manufactured by Daicel Chemical Industries, Ltd. (2 cm×25 cm; mobile phase: ethanol) to obtain the title optically active compound with a retention time of 19 minutes (9.8 mg; >99% ee) and the title optically active compound with a retention time of 32 minutes (8.6 mg; >99% ee).

The property values of the title optically active compound with a retention time of 19 minutes (Example 29) are as follows.

ESI-MS; m/z 458 [M$^+$+H]. $^1$H-NMR (CDCl$_3$) δ(ppm): 1.39-1.49 (m, 1H), 1.52-1.76 (m, 4H), 1.98-2.05 (m, 1H), 2.18-2.24 (m, 2H) 2.32 (s, 3H), 2.66-2.76 (m, 1H), 3.09 (brd, 16.0 Hz, 1H), 3.75-3.84 (m, 4H), 3.85 (s, 3H), 5.56 (brt, J=3.2 Hz, 1H), 6.85 (d, J=8.8 Hz, 2H), 6.94 (brs, 1H), 7.03 (brs, 1H), 7.04 (brd, J=8.0 Hz, 1H), 7.16 (d, J=8.8 Hz, 2H), 7.24 (d, J=8.0 Hz, 1H), 7.78 (s, 1H), 7.81 (brd, J=2.4 Hz, 1H).

The property values of the title optically active compound with a retention time of 32 minutes (Example 30) are as follows.

ESI-MS; m/z 458 [M$^+$+H]. $^1$H-NMR (CDCl$_3$) δ(ppm): 1.39-1.49 (m, 1H), 1.52-1.76 (m, 4H), 1.98-2.05 (m, 1H), 2.18-2.24 (m, 2H) 2.32 (s, 3H), 2.66-2.76 (m, 1H), 3.09 (brd, 16.0 Hz, 1H), 3.75-3.84 (m, 4H), 3.85 (s, 3H), 5.56 (brt, J=3.2 Hz, 1H), 6.85 (d, J=8.8 Hz, 2H), 6.94 (brs, 1H), 7.03 (brs, 1H), 7.04 (brd, J=8.0 Hz, 1H), 7.16 (d, J=8.8 Hz, 2H), 7.24 (d, J=8.0 Hz, 1H), 7.78 (s, 1H), 7.81 (brd, J=2.4 Hz, 1H).

Examples 31 and 32

Synthesis of (E)-(4S,10aS)-4-(4-fluorophenyl)-7-[3-methoxy-4-(4-methyl-1H-imidazol-1-yl)benzylidene]octahydropyrido[1,2-a]azepin-6-one and (E)-(4R,10aR)-4-(4-fluorophenyl)-7-[3-methoxy-4-(4-methyl-1H-imidazol-1-yl)benzylidene]octahydropyrido[1,2-a]azepin-6-one

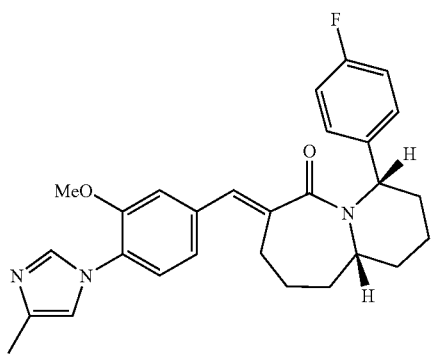

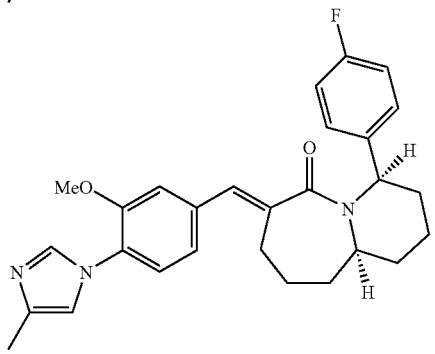

Synthesis of 1-[(2R*,6S*)-2-(4-fluorophenyl)-6-vinylpiperidin-1-yl]-4-penten-1-one To a solution of (2R*,6S*)-2-(4-fluorophenyl)-6-vinylpiperidine (460 mg) and diisopropylamine (0.59 mL) in methylene chloride (10 mL), 4-pentenoyl chloride (0.37 mL) was added, and the reaction solution was stirred at room temperature for 1.5 hours. Chloroform and 1 N aqueous hydrochloric acid were added to the reaction solution, and the organic layer was separated. The resulting organic layer was washed with saturated sodium bicarbonate water, dried over magnesium sulfate, and then concentrated under reduced pressure. The residue was purified by silica gel column chromatography (elution solvent: heptane->heptane:ethyl acetate=1:1) to obtain 307 mg of the title compound. The property value of the compound is as follows.

ESI-MS; m/z 288 [M$^+$+H].

Synthesis of (4R*,10aS*)-4-(4-fluorophenyl)-1,3,4,7,8,10a-hexahydro-2H-pyrido[1,2-a]azepin-6-one A solution of 1-[(2R*,6S*)-2-(4-fluorophenyl)-6-vinylpiperidin-1-yl]-4-penten-1-one (307 mg) and tricyclohexylphosphine[1,3-bis(2,4,6-trimethylphenyl)-4,5-dihydroimidazol-2-ylidene][benzylidene]ruthenium (IV) dichloride (64 mg) in methylene chloride (150 mL) was heated under reflux for 25 hours. The reaction solution was left to cool to room temperature and then concentrated. The residue was purified by silica gel column chromatography (elution solvent: heptane:ethyl acetate=4:1->ethyl acetate) to obtain 146 mg of the title compound. The property values of the compound are as follows.

ESI-MS; m/z 260 [M$^+$+H], $^1$H-NMR (CDCl$_3$) δ(ppm): 1.46-1.78 (m, 4H), 2.00-2.10 (m, 1H), 2.20-2.30 (m, 1H) 2.45-2.47 (m, 3H), 3.26 (td, J=12.8, 5.2 Hz, 1H), 4.68-4.76 (m, 1H), 5.39-5.45 (m, 1H), 5.71-5.80 (m, 2H), 6.95 (t, J=8.8 Hz, 2H), 7.25 (dd, J=8.8, 5.2 Hz, 2H).

Synthesis of (4R*,10aR*)-4-(4-fluorophenyl)octahydropyrido[1,2-a]azepin-6-one

Platinum oxide (10 mg) was added to a solution of (4R*,10aS*)-4-(4-fluorophenyl)-1,3,4,7,8,10a-hexahydro-2H-pyrido[1,2-a]azepin-6-one (146 mg) in methanol (5 mL), and the reaction solution was stirred in a hydrogen stream at room temperature for 25 hours. The reaction solution was filtered through celite, and the filtrate was concentrated under reduced pressure to obtain 140 mg of the title compound. The property values of the compound are as follows.

ESI-MS; m/z 262 [M$^+$+H]. $^1$H-NMR (CDCl$_3$) δ(ppm): 1.20-1.32 (m, 1H), 1.40-1.74 (m, 6H), 1.80-1.97 (m, 3H), 1.98-2.08 (m, 1H), 2.30-2.41 (m, 1H), 2.59-2.75 (m, 2H), 3.68 (td, J=10.0, 5.6 Hz, 1H), 5.87 (d, J=6.0 Hz, 1H), 6.97 (t, J=8.8 Hz, 2H), 7.32 (dd, J=8.8, 5.6 Hz, 2H).

Synthesis of (4R*,10aS*)-4-(4-fluorophenyl)-7-iodooctahydropyrido[1,2-a]azepin-6-one Iodotrimethylsilane (0.11 mL) was added to a solution of (4R*,10aR*)-4-(4-fluorophenyl)octahydropyrido[1,2-a]azepin-6-one (140 mg) and N,N,N',N'tetramethylethylenediamine (0.28 mL) in methylene chloride (15 mL) at 0° C., and the reaction solution was stirred at 0° C. for 30 minutes. Iodine (204 mg) was added to the reaction solution, which was then stirred at 0° C. for one hour. Ethyl acetate and a saturated sodium thiosulfate solution were added to the reaction solution, and the organic layer was separated. The resulting organic layer was washed with brine, dried over magnesium sulfate, and then concentrated under reduced pressure to obtain 208 mg of the title compound. The property value of the compound is as follows.

ESI-MS; m/z 388 [M$^+$+H].

Synthesis of diethyl [(4R*,10aS*)-4-(4-fluorophenyl)-6-oxodecahydropyrido[1,2-a]azepin-7-yl]phosphonate A mixture of (4R*,10aS*)-4-(4-fluorophenyl)-7-iodooctahydropyrido[1,2-a]azepin-6-one (208 mg) with triethyl phosphite (2 mL) was stirred at 120° C. for 1.5 hours. The reaction solution was left to cool to room temperature and then concentrated under reduced pressure to obtain 213 mg of the title compound. The property value of the compound is as follows.

ESI-MS; m/z 398 [M$^+$+H].

Synthesis of (E)-(4S*,10aS*)-4-(4-fluorophenyl)-7-[3-methoxy-4-(4-methyl-1H-imidazol-1-yl)benzylidene]octahydropyrido[1,2-a]azepin-6-one Lithium hydroxide monohydrate (68 mg) was added to a mixed solution of diethyl [(4R*,10aS*)-4-(4-fluorophenyl)-

6-oxodecahydropyrido[1,2-a]azepin-7-yl]phosphonate (213 mg) and 3-methoxy-4-(4-methyl-1H-imidazol-1-yl)benzaldehyde (116 mg) in tetrahydrofuran (6 mL) and ethanol (1.5 mL), and the reaction solution was stirred at room temperature for 25 hours. Ethyl acetate and brine were added to the reaction solution, and the organic layer was separated. The resulting organic layer was dried over magnesium sulfate and then concentrated under reduced pressure. The residue was purified by silica gel column chromatography (carrier: Chromatorex NH; elution solvent: heptane:ethyl acetate=1:1->ethyl acetate) to obtain 125 mg of the title compound. The property values of the compound are as follows.

ESI-MS; m/z 460 [M$^+$+H]. $^1$H-NMR (CDCl$_3$) δ(ppm): 1.37-1.46 (m, 1H), 1.49-1.75 (m, 4H), 1.84-1.98 (m, 2H), 1.99-2.10 (m, 1H), 2.24-2.31 (m, 2H), 2.33 (s, 3H), 2.59-2.65 (m, 2H), 3.85 (s, 3H), 3.88-3.97 (m, 1H), 5.84 (dd, J=7.2, 2.4 Hz, 1H), 6.93 (brs, 1H), 6.99 (t, J=8.8 Hz, 2H), 7.02 (brs, 1H), 7.04 (d, J=1.6 Hz, 1H), 7.08 (dd, J=8.4, 1.6 Hz, 1H), 7.23 (d, J=8.4 Hz, 1H), 7.49 (dd, J=8.8, 5.6 Hz, 2H), 7.81 (brs, 1H).

Synthesis of (E)-(4S,10aS)-4-(4-fluorophenyl)-7-[3-methoxy-4-(4-methyl-1H-imidazol-1-yl)benzylidene]octahydropyrido[1,2-a]azepin-6-one and (E)-(4R,10aR)-4-(4-fluorophenyl)-7-[3-methoxy-4-(4-methyl-1H-imidazol-1-yl)benzylidene]octahydropyrido[1,2-a]azepin-6-one The racemate (E)-(4S*,10aS*)-4-(4-fluorophenyl)-7-[3-methoxy-4-(4-methyl-1H-imidazol-1-yl)benzylidene]octahydropyrido[1,2-a]azepin-6-one obtained above (60 mg) was separated by CHIRALCEL™ OD-H manufactured by Daicel Chemical Industries, Ltd. (2 cm×25 cm; mobile phase: hexane:ethanol=8:2) to obtain the title optically active compound with a retention time of 12 minutes (7.9 mg; >99% ee) and the title optically active compound with a retention time of 15 minutes (7.7 mg; >94% ee).

The property values of the title optically active compound with a retention time of 12 minutes (Example 31) are as follows.

ESI-MS; m/z 460 [M$^+$+H]. $^1$H-NMR (CDCl$_3$) δ(ppm): 1.37-1.46 (m, 1H), 1.49-1.75 (m, 4H), 1.84-1.98 (m, 2H), 1.99-2.10 (m, 1H), 2.24-2.31 (m, 2H), 2.33 (s, 3H), 2.59-2.65 (m, 2H), 3.85 (s, 3H), 3.88-3.97 (m, 1H), 5.84 (dd, J=7.2, 2.4 Hz, 1H), 6.93 (brs, 1H), 6.99 (t, J=8.8 Hz, 2H), 7.02 (brs, 1H), 7.04 (d, J=1.6 Hz, 1H), 7.08 (dd, J=8.4, 1.6 Hz, 1H), 7.23 (d, J=8.4 Hz, 1H), 7.49 (dd, J=8.8, 5.6 Hz, 2H), 7.81 (brs, 1H).

The property values of the title optically active compound with a retention time of 15 minutes (Example 32) are as follows.

ESI-MS; m/z 460 [M$^+$+H]. $^1$H-NMR (CDCl$_3$) δ(ppm): 1.37-1.46 (m, 1H), 1.49-1.75 (m, 4H), 1.84-1.98 (m, 2H), 1.99-2.10 (m, 1H), 2.24-2.31 (m, 2H), 2.33 (s, 3H), 2.59-2.65 (m, 2H), 3.85 (s, 3H), 3.88-3.97 (m, 1H), 5.84 (dd, J=7.2, 2.4 Hz, 1H), 6.93 (brs, 1H), 6.99 (t, J=8.8 Hz, 2H), 7.02 (brs, 1H), 7.04 (d, J=1.6 Hz, 1H), 7.08 (dd, J=8.4, 1.6 Hz, 1H), 7.23 (d, J=8.4 Hz, 1H), 7.49 (dd, J=8.8, 5.6 Hz, 2H), 7.81 (brs, 1H).

Example 33

Synthesis of (E)-(5R,7aS)-5-(3,4-difluorophenyl)-2-[3-methoxy-4-(4-methyl-1H-imidazol-1-yl)benzylidene]hexahydropyrrolidin-3-one

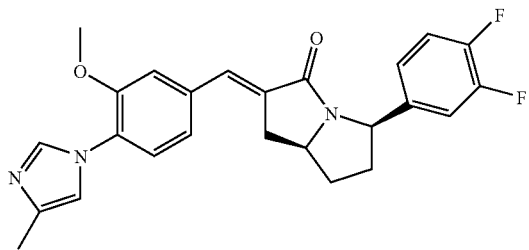

Synthesis of methyl (S)-2-tert-butoxycarbonylamino-5-(3,4-difluorophenyl)-5-oxopentanoate To a solution of (S)-5-oxopyrrolidine-1,2-dicarboxylic acid 1-tert-butyl ester 2-methyl ester (5.5 g) in tetrahydrofuran (100 mL), 3,4-difluorophenylmagnesium bromide (0.5 M solution in tetrahydrofuran; 50 mL) was added dropwise at −40° C. over 10 minutes, and the reaction solution was stirred at −40° C. to 0° C. for two hours. Water was added to the solution in small portions, followed by extraction with ethyl acetate. The extract was washed with brine, dried over anhydrous magnesium sulfate, and then concentrated under reduced pressure. The residue was purified by silica gel column chromatography (heptane-ethyl acetate system) to obtain 8.0 g of the title compound. The property values of the compound are as follows.

ESI-MS; m/z 380 [M$^+$+Na]. $^1$H-NMR (CDCl$_3$) δ(ppm): 1.41 (s, 9H), 1.75-2.12 (m, 1H), 2.20-2.50 (m, 1H), 2.92-3.16 (m, 2H), 3.76 (s, 3H), 4.38 (s, 1H), 5.16 (s, 1H), 6.90-7.85 (m, 3H).

Synthesis of (2S,5R)-5-(3,4-difluorophenyl)pyrrolidine-1,2-dicarboxylic acid 1-tert-butyl ester 2-methyl ester A solution of 4 N hydrochloric acid in ethyl acetate (92.3 mL) was added dropwise to a solution of methyl (S)-2-tert-butoxycarbonylamino-5-(3,4-difluorophenyl)-5-oxopentanoate (8.0 g) in ethyl acetate (90 mL) at room temperature, and the solution was stirred at room temperature for 12 hours. The reaction solution was concentrated under reduced pressure to obtain 5.4 g of a yellow oil. The crude product was dissolved in ethyl acetate (100 mL). Saturated sodium bicarbonate water (100 mL) was added dropwise thereto, and the reaction solution was stirred at room temperature for 20 minutes. The reaction solution was subjected to extraction with ethyl acetate. The extract was washed with brine, dried over anhydrous magnesium sulfate, and then concentrated under reduced pressure to obtain 4.8 g of a pale red oil. The resulting pale red oil (1 g) was dissolved in ethyl acetate (30 mL). Palladium-carbon (containing 50% water, 130 mg) was added to the solution, and the reaction solution was stirred in a hydrogen atmosphere for four hours. Palladium-carbon in the reaction solution was removed by filtration through celite, and the filtrate was concentrated under reduced pressure to obtain 1.0 g of a yellow oil. The resulting yellow oil was dissolved in DMF (20 mL). Triethylamine (1.87 mL) and di-tert-butyl dicarbonate (1.96 g) were added to the solution, and the reaction solution was stirred at room temperature for three days. The reaction solution was poured into water, followed by extraction with ethyl acetate. The extract was washed with brine, dried over anhydrous magnesium sulfate, and then concentrated under reduced pressure. The residue was purified by silica gel column chromatography (heptane-ethyl acetate system) to obtain 0.83 g of the title compound. The property values of the compound are as follows.

ESI-MS; m/z 364 [M$^+$+Na]. $^1$H-NMR (CD$_3$OD) δ(ppm): 1.18 and 1.40 (s, 9H), 1.80-1.90 (m, 1H), 1.90-2.10 (m, 1H), 2.20-2.30 (m, 1H), 2.30-2.45 (m, 1H), 3.80 (s, 3H), 4.20-4.50 (m, 1H), 4.73-4.95 (m, 1H), 7.10-7.28 (m, 1H), 7.28-7.40 (m, 1H), 7.52-7.70 (m, 1H).

Synthesis of tert-butyl (E)-(2R,5S)-2-(3,4-difluorophenyl)-5-(2-methoxycarbonylvinyl)pyrrolidine-1-carboxylate Lithium borohydride (212 mg) was added to a solution of (2S,5R)-5-(3,4-difluorophenyl)pyrrolidine-1,2-dicarboxylic acid 1-tert-butyl ester 2-methyl ester (0.83 g) in tetrahydrofuran (10 mL) at 0° C., and the reaction solution was stirred at room temperature for 12 hours. The reaction solution was added to ice water, followed by extraction with ethyl acetate. The extract was washed with brine, dried over anhydrous magnesium sulfate, and then concentrated under reduced pressure to obtain 1.0 g of an alcohol compound. DMSO (0.34 mL) was added dropwise to a solution of oxalyl chloride (0.41 mL) in dichloromethane (15 mL) at −70° C., and the reaction solution was stirred at the same temperature for three minutes. A solution of the above alcohol compound (1.0 g) in dichloromethane (10 mL) was added dropwise thereto at −60° C., and the reaction solution was stirred at the same temperature for 15 minutes. Triethylamine (3.11 mL) was added dropwise to the solution, and the reaction solution was stirred at −60° C. to 0° C. for 30 minutes. The reaction solution was poured into water, followed by extraction with ethyl acetate. The extract was washed with brine, dried over anhydrous magnesium sulfate, and then concentrated under reduced pressure to obtain 1.0 g of an aldehyde compound. Sodium hydride (60% oil, 0.272 g) was added to a solution of trimethyl phosphonoacetate (1.86 g) in DMF (20 mL) at room temperature, and the reaction solution was stirred for 20 minutes. This solution was added to a solution of the above aldehyde (1.0 g) in DMF (10 mL), and the reaction solution was stirred at room temperature for three hours. The reaction solution was poured into water, followed by extraction with ethyl acetate. The extract was washed with brine, dried over anhydrous magnesium sulfate, and then concentrated under reduced pressure. The residue was purified by silica gel column chromatography (heptane-ethyl acetate system) to obtain 0.95 g of the title compound. The property values of the compound are as follows.

ESI-MS; m/z 390 [M$^+$+Na]. $^1$H-NMR (CDCl$_3$) δ(ppm): 1.10-1.60 (m, 9H), 1.80-1.92 (m, 2H), 2.06-2.20 (m, 1H), 2.24-2.36 (m, 1H), 3.78 (s, 3H), 4.40-5.00 (m, 2H), 6.03 (d, J=14.8 Hz, 1H), 6.90-7.20 (m, 4H).

Synthesis of tert-butyl (2R,5S)-2-(3,4-difluorophenyl)-5-(2-methoxycarbonylethyl)pyrrolidine-1-carboxylate Palladium-carbon (containing 50% water, 124 mg) was added to a solution of tert-butyl (E)-(2R,5S)-2-(3,4-difluorophenyl)-5-(2-methoxycarbonylvinyl)pyrrolidine-1-carboxylate (0.95 g) in ethyl acetate (30 mL), and the reaction solution was stirred in a hydrogen atmosphere at room temperature for six hours. Palladium-carbon in the reaction solution was removed by filtration through celite, and the filtrate was concentrated under reduced pressure to obtain 0.90 g of the title compound. The property values of the compound are as follows.

ESI-MS; m/z 392 [M$^+$+Na]. $^1$H-NMR (CDCl$_3$) δ(ppm): 1.10-1.50 (m, 9H), 1.60-1.70 (m, 1H), 1.70-1.90 (m, 2H), 1.94-2.06 (m, 1H), 2.16-2.32 (m, 2H), 2.36-2.50 (m, 2H), 3.70 (s, 3H), 3.98 (s, 1H), 4.10-4.90 (m, 1H), 6.90-7.25 (m, 3H).

Synthesis of (5R,7aS)-5-(3,4-difluorophenyl)hexahydropyrrolidin-3-one tert-Butyl (2R,5S)-2-(3,4-difluorophenyl)-5-(2-methoxycarbonylethyl)pyrrolidine-1-carboxylate (0.95 g) was dissolved in ethyl acetate (10 mL). A solution of 4 N hydrochloric acid in ethyl acetate (10 mL) was added thereto, and the reaction solution was stirred at 50° C. for three hours. The reaction solution was concentrated under reduced pressure to obtain 1.2 g of a yellow oil. The resulting yellow oil was dissolved in ethanol (10 mL). A 5 N sodium hydroxide solution (10 mL) was added thereto, and the reaction solution was stirred at 50° C. for two hours. The reaction solution was cooled to 0° C. and neutralized with 5 N hydrochloric acid. The reaction solution was concentrated under reduced pressure, and the residue was suspended in dichloromethane (40 mL). Thionyl chloride (2.55 mL) was added thereto, and the reaction solution was stirred at 50° C. for one hour. The reaction solution was concentrated under reduced pressure, and the residue was suspended in dichloromethane (10 mL), followed by addition of a 5 N sodium hydroxide solution (10 mL). The reaction solution was stirred at room temperature for 30 minutes and then poured into ice water, followed by extraction with ethyl acetate. The extract was washed with brine, dried over anhydrous magnesium sulfate, and then concentrated under reduced pressure. The residue was purified by silica gel column chromatography (heptane-ethyl acetate system) to obtain 620 mg of the title compound. The property values of the compound are as follows.

ESI-MS; m/z 238 [M$^+$+H]. $^1$H-NMR (CDCl$_3$) δ(ppm): 1.55-1.70 (m, 1H), 1.85-2.05 (m, 3H), 2.30-2.40 (m, 1H), 2.50-2.70 (m, 2H), 2.70-2.85 (m, 1H), 4.03-4.17 (m, 1H), 4.61 (d, J=9.2 Hz, 1H), 6.89-7.02 (m, 2H), 7.07-7.15 (m, 1H).

Synthesis of diethyl [(5R,7aS)-5-(3,4-difluorophenyl)-3-oxohexahydropyrrolidin-2-yl]phosphonate Iodotrimethylsilane (0.17 mL) was added to a solution of (5R,7aS)-5-(3,4-difluorophenyl)hexahydropyrrolidin-3-one (210 mg) and N,N,N',N'-tetramethylethylenediamine (0.451 mL) in dichloromethane (5 mL) at 0° C., and the reaction solution was stirred at 0° C. for 30 minutes. Iodine (303 mg) was added to the reaction solution at 0° C., and the reaction solution was stirred at the same temperature for 40 minutes. The reaction solution was added to ice-sodium thiosulfate solution, followed by extraction with ethyl acetate. The extract was washed with 1 N hydrochloric acid and brine, dried over anhydrous magnesium sulfate, and then concentrated under reduced pressure to obtain 320 mg of an iodine compound. A solution of the resulting iodine compound (320 mg) in triethyl phosphite (5 mL) was stirred at 130° C. for two hours. The reaction solution was returned to room temperature and concentrated under reduced pressure. The residue was purified by silica gel column chromatography (heptane-ethyl acetate system) to obtain 328 mg of the title compound. The property values of the compound are as follows.

ESI-MS; m/z 374 [M$^+$+H]. $^1$H-NMR (CDCl$_3$) δ(ppm): 1.30-1.40 (m, 6H), 1.60-1.75 (m, 1H), 1.80-2.10 (m, 2H), 2.20-2.40 (m, 1H), 2.50-2.75 (m, 2H), 3.30-3.50 (m, 1H), 4.00-4.30 (m, 5H), 4.64 (d, J=8.8 Hz, 1H), 6.90-7.17 (m, 3H).

Synthesis of (E)-(5R,7aS)-5-(3,4-difluorophenyl)-2-[3-methoxy-4-(4-methyl-1H-imidazol-1-yl)benzylidene]hexahydropyrrolidin-3-one Lithium hydroxide (66.8 mg) was added to a mixed solution of 3-methoxy-4-(4-methyl-1H-imidazol-1-yl)benzaldehyde (200 mg) and diethyl [(5R,7aS)-5-(3,4-difluorophenyl)-3-oxohexahydropyrrolidin-2-yl]phosphonate (328 mg) in tetrahydrofuran (1 mL) and ethanol (4 mL), and the reaction solution was stirred at room temperature for 12 hours. The reaction solution was added to ice-sodium bicarbonate water, followed by extraction with ethyl acetate. The extract was washed with brine, dried over anhydrous magnesium sulfate, and then concentrated under reduced pressure. The residue was purified by silica gel column chromatography (heptane-ethyl acetate system) to obtain 300 mg of a crude product of the title compound. The crude product (15 mg) was re-refined by a preparative optical resolution column (CHIRALPAK™ IA manufactured by Daicel Chemical Industries, Ltd. (2 cm×25 cm), ethanol-hexane system) to obtain 6.0 mg of the title compound. The property values of the compound are as follows.

ESI-MS; m/z 436 [M$^+$+H]. $^1$H-NMR (CDCl$_3$) δ(ppm): 1.70-1.84 (m, 1H), 2.11 (dd, J=12.8, 7.2 Hz, 1H), 2.18 (quint, J=6.0 Hz, 1H), 2.32 (s, 3H), 2.60-2.76 (m, 1H), 2.93 (ddd, J=3.6, 6.8, 16.4 Hz, 1H), 3.40 (ddd, J=2.0, 5.4, 16.4 Hz, 1H), 3.89 (s, 3H), 4.11 (sext, J=6.0 Hz, 1H), 4.79 (d, J=9.2 Hz, 1H), 6.92-7.04 (m, 3H), 7.09 (d, J=1.2 Hz, 1H), 7.08-7.18 (m, 2H), 7.20-7.23 (m, 1H), 7.28 (d, J=8.0 Hz, 1H), 7.77 (d, J=1.2 Hz, 1H).

Example 34

Synthesis of (E)-(3R,9aR)-3-(3,4-difluorophenyl)-6-[3-methoxy-4-(4-methyl-1H-imidazol-1-yl)benzylidene]octahydropyrrolo[1,2-a]azepin-5-one

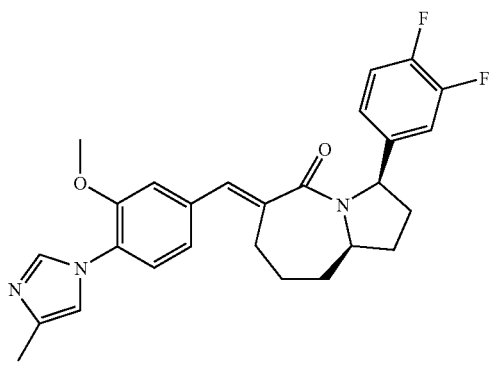

Synthesis of tert-butyl (2R,5R)-2-(3,4-difluorophenyl)-5-{(E)-4-methoxycarbonyl-3-butenyl}pyrrolidine-1-carboxylate A solution of tert-butyl (2R,5S)-2-(3,4-difluorophenyl)-5-(2-methoxycarbonylethyl)pyrrolidine-1-carboxylate (2.0 g) in tetrahydrofuran (50 mL) was added dropwise to a solution of lithium aluminum hydride (0.268 g) in tetrahydrofuran (75 mL) at 0° C., and the reaction solution was stirred at the same temperature for 30 minutes. Water (0.27 mL), a 15% sodium hydroxide solution (0.27 mL), and water (0.81 mL) were sequentially added to the reaction solution, which was then stirred for 20 minutes. Then, the inorganic salt precipitated in the reaction solution was removed by filtration through celite, and the filtrate was concentrated to obtain 1.8 g of an alcohol compound. DMSO (0.678 mL) was added dropwise to a solution of oxalyl chloride (0.819 mL) in dichloromethane (40 mL) at −70° C., and the reaction solution was stirred at the same temperature for three minutes. A solution of the alcohol compound obtained above (1.8 g) in dichloromethane (10 mL) was added dropwise to the reaction solution at −60° C., and the reaction solution was stirred at the same temperature for 15 minutes. Triethylamine (6.21 mL) was added dropwise to the solution, and the reaction solution was stirred at −60° C. to 0° C. for 30 minutes. The reaction solution was poured into water, followed by extraction with ethyl acetate. The extract was washed with brine, dried over anhydrous magnesium sulfate, and then concentrated under reduced pressure to obtain 2.0 g of an aldehyde compound. Sodium hydride (60% oil, 0.278 g) was added to a solution of trimethyl phosphonoacetate (1.27 g) in DMF (20 mL) at room temperature, and the reaction solution was stirred for 20 minutes. The reaction solution was added to a solution of the resulting aldehyde (1.8 g) in DMF (10 mL), and the mixture was stirred at room temperature for three hours. The reaction solution was poured into water, followed by extraction with ethyl acetate. The extract was washed with brine, dried over anhydrous magnesium sulfate, and then concentrated under reduced pressure. The residue was purified by silica gel column chromatography (heptane-ethyl acetate system) to obtain 1.3 g of the title compound. The property values of the compound are as follows.

ESI-MS; m/z 418 [M$^+$+Na]. $^1$H-NMR (CDCl$_3$) δ(ppm): 1.00-1.50 (m, 9H), 1.56-1.90 (m, 3H), 1.96-2.16 (m, 2H), 2.20-2.44 (m, 3H), 3.71 (s, 3H), 3.90-4.00 (m, 1H), 4.74 (s, 1H), 5.92 (d, J=15.6 Hz, 1H), 7.00-7.25 (m, 4H).

Synthesis of tert-butyl (2R,5R)-2-(3,4-difluorophenyl)-5-(4-methoxycarbonylbutyl)pyrrolidine-1-carboxylate Palladium-carbon (containing 50% water, 0.376 g) was added to a solution of tert-butyl (2R,5R)-2-(3,4-difluorophenyl)-5-{(E)-4-methoxycarbonyl-3-butenyl}pyrrolidine-1-carboxylate (1.3 g) in ethyl acetate (50 mL), and the reaction solution was stirred in a hydrogen atmosphere at room temperature for six hours. Palladium-carbon in the reaction solution was removed by filtration through celite, and the filtrate was concentrated under reduced pressure to obtain 1.3 g of the title compound.

ESI-MS; m/z 420 [M$^+$+Na]. $^1$H-NMR (CDCl$_3$) δ(ppm): 1.00-2.10 (m, 18H), 2.26-2.40 (m, 1H), 2.37 (t, J=7.2 Hz, 2H), 3.66 (s, 3H), 3.86-3.90 (m, 1H), 4.66-4.80 (m, 1H), 7.00-7.26 (m, 3H).

Synthesis of (3R,9aR)-3-(3,4-difluorophenyl)octahydropyrrolo[1,2-a]azepin-5-one

A solution of 4 N hydrochloric acid in ethyl acetate (3.16 mL) was added to a solution of tert-butyl (2R,5R)-2-(3,4-difluorophenyl)-5-(4-methoxycarbonylbutyl)pyrrolidine-1-carboxylate (0.30 g) in ethyl acetate (10 mL). The reaction solution was stirred at 50° C. for three hours and then concentrated under reduced pressure to obtain 0.24 g of a yellow oil. A 5 N sodium hydroxide solution (2.0 mL) was added to a solution of the resulting yellow oil (0.24 g) in ethanol (3.2 mL), and the reaction solution was stirred at 50° C. for two hours. The reaction solution was cooled to 0° C. and neutralized with 5 N hydrochloric acid. The reaction solution was concentrated under reduced pressure, and the residue was suspended in dichloromethane (13.5 mL). Thionyl chloride (0.86 mL) was added to the solution, and the reaction solution was stirred at 50° C. for one hour. The reaction solution was concentrated under reduced pressure, and the residue was suspended in dichloromethane (10 mL). A 5 N sodium hydroxide solution (5 mL) was added to the solution. The reaction solution was stirred at room temperature for 30 minutes and then poured into ice water, followed by extraction with ethyl acetate. The extract was washed with brine, dried over anhydrous magnesium sulfate, and then concentrated under reduced pressure. The residue was purified by silica gel column chromatography (heptane-ethyl acetate system) to obtain 0.62 g of the title compound. The property values of the compound are as follows.

ESI-MS; m/z 531 [2M$^+$+H]. $^1$H-NMR (CDCl$_3$) δ(ppm): 1.46-1.74 (m, 4H), 1.86-2.22 (m, 6H), 2.43-2.53 (m, 1H), 2.66 (dd, J=7.2, 14.4 Hz, 1H), 3.76-3.88 (m, 1H), 5.25 (d, J=7.6 Hz, 1H), 6.93-6.99 (m, 1H), 7.00-7.13 (m, 2H).

Synthesis of diethyl [(3R,9aR)-3-(3,4-difluorophenyl)-5-oxooctahydropyrrolo[1,2-a]azepin-6-yl]phosphonate Iodotrimethylsilane (0.109 mL) was added to a solution of (3R,9aR)-3-(3,4-difluorophenyl)octahydropyrrolo[1,2-a]azepin-5-one (0.15 g) and N,N,N',N'tetramethylethylenediamine (0.29 mL) in dichloromethane (3.57 mL) at 0° C., and the reaction solution was stirred at 0° C. for 30 minutes. Iodine (0.194 g) was added to the reaction solution at 0° C., and the reaction solution was stirred at the same temperature for 40 minutes. The reaction solution was added to ice-sodium thiosulfate solution, followed by extraction with ethyl acetate. The extract was washed with 1 N hydrochloric acid and brine, dried over anhydrous magnesium sulfate, and then concentrated under reduced pressure to obtain 0.25 g of an iodine compound. A solution of the resulting iodine compound (0.25 g) in triethyl phosphite (7 mL) was stirred at 130° C. for two hours. The reaction solution was returned to room temperature and concentrated under reduced pressure. The residue was purified by silica gel column chromatography (heptane-ethyl acetate system) to obtain 0.25 g of the title compound. The property values of the compound are as follows.

ESI-MS; m/z 402 [M$^+$+H].

Synthesis of (E)-(3R,9aR)-3-(3,4-difluorophenyl)-6-[3-methoxy-4-(4-methyl-1H-imidazol-1-yl)benzylidene]octahydropyrrolo[1,2-a]azepin-5-one Lithium hydroxide (0.0668 g) was added to a mixed solution of 3-methoxy-4-(4-methyl-1H-imidazol-1-yl)benzaldehyde (0.20 g) and diethyl [(3R,9aR)-3-(3,4-difluorophenyl)-5-oxooctahydropyrrolo[1,2-a]azepin-6-yl]phosphonate (0.25 g) in tetrahydrofuran (1 mL) and ethanol (4 mL), and the reaction solution was stirred at room temperature for 12 hours. The reaction solution was added to ice-sodium bicarbonate water, followed by extraction with ethyl acetate. The extract was washed with brine, dried over anhydrous magnesium sulfate, and then concentrated under reduced pressure. The residue was purified by silica gel column chromatography (heptane-ethyl acetate system) to obtain 0.20 g of the title compound. The property values of the compound are as follows.

ESI-MS; m/z 464 [M$^+$+H]. $^1$H-NMR (CDCl$_3$) δ(ppm): 1.70-2.40 (m, 9H), 2.31 (s, 3H), 2.90-3.00 (m, 1H), 3.85 (s, 3H), 3.84-3.98 (m, 1H), 5.28-5.34 (m, 1H), 6.94 (s, 1H), 6.98-7.18 (m, 6H), 7.22-7.30 (m, 1H), 7.74 (s, 1H).

Example 35

Synthesis of methyl (E)-4-{(4S*,9aR*)-7-[3-methoxy-4-(4-methyl-1H-imidazol-1-yl)benzylidene]-6-oxooctahydroquinolizin-4-yl}benzoate

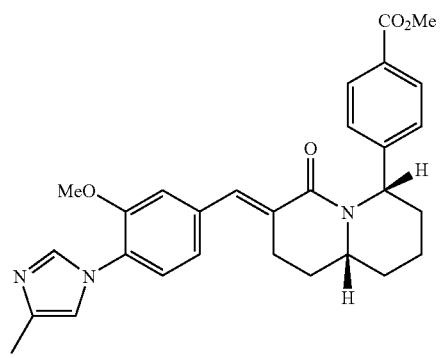

Synthesis of 1-(4-carbomethoxyphenyl)hepta-5,6-dienyl-1-amine 595 mg of the title compound was obtained from (4-carbomethoxybenzyl)-(4-carbomethoxybenzylidene)amine (985 mg) and 6-iodohexa-1,2-diene (723 mg) according to the method described in Journal of the American Chemical Society, 2003, vol. 125, p. 11956. The property value of the compound is as follows.

ESI-MS; m/z 229 [M$^+$-NH$_3$].

Synthesis of (2R*,6S*)-2-(4-carbomethoxyphenyl)-6-vinylpiperidine

Acetic acid (0.2 mL) was added to a solution of an allylpalladium chloride dimer (116 mg) and 1,1'-bis(diphenylphosphino)ferrocene (350 mg) in THF (50 mL), and the reaction solution was stirred at room temperature for 10 minutes. A solution of 1-(4-carbomethoxyphenyl)hepta-5,6-dienyl-1-amine (595 mg) in THF (10 mL) was added to the reaction solution, which was then stirred at 70° C. for 18 hours. The reaction solution was left to cool to room temperature. Then, diethyl ether and 1 N aqueous hydrochloric acid were added to the reaction solution, and the aqueous layer was separated. The resulting aqueous layer was washed with diethyl ether, and then a 5 N sodium hydroxide solution was added to the aqueous layer until the pH was adjusted to 11 or less. Chloroform was added to the aqueous layer, and the organic layer was separated. The resulting organic layer was dried over magnesium sulfate, and concentrated under reduced pressure to obtain 422 mg of the title compound. The property value of the compound is as follows.

ESI-MS; m/z 246 [M$^+$+H].

Synthesis of 1-[(2R*,6S*)-2-(4-carbomethoxyphenyl)-6-vinylpiperidin-1yl]-3-buten-1-one Diethyl cyanophosphonate (0.78 mL) was added to a solution of (2R*,6S*)-2-(4-carbomethoxyphenyl)-6-vinylpiperidine (422 mg), vinylacetic acid (0.44 mL), and triethylamine (1.44 mL) in DMF (5 mL), and the reaction solution was stirred at room temperature for one hour. Ethyl acetate and 1 N aqueous hydrochloric acid were added to the reaction solution, and the organic layer was separated. The resulting organic layer was washed with saturated sodium bicarbonate water, dried over magnesium sulfate, and then concentrated under reduced pressure. The residue was purified by silica gel column chromatography (elution solvent: heptane->heptane:ethyl acetate=1:1) to obtain 281 mg of the title compound. The property value of the compound is as follows.

ESI-MS; m/z 314 [M$^+$+H].

Synthesis of (6R*,9aS*)-6-(4-carbomethoxyphenyl)-3,6,7,8,9,9a-hexahydroquinolizin-4-one A solution of 1-[(2R*,6S*)-2-(4-carbomethoxyphenyl)-6-vinylpiperidin-1-yl]-3-buten-1-one (281 mg) and tricyclohexylphosphine[1,3-bis(2,4,6-trimethylphenyl)-4,5-dihydroimidazol-2-ylidene][benzylidene]ruthenium (IV) dichloride (53 mg) in methylene chloride (150 mL) was heated under reflux for 1.5 hours. The reaction solution was left to cool to room temperature and then concentrated. The residue was purified by silica gel column chromatography (elution solvent: heptane:ethyl acetate=4:1->ethyl acetate) to obtain 145 mg of the title compound. The property value of the compound is as follows.

ESI-MS; m/z 286 [M$^+$+H].

Synthesis of (6R*,9aS*)-6-(4-carbomethoxyphenyl) octahydroquinolizin-4-one

Platinum oxide (10 mg) was added to a solution of (6R*,9aS*)-6-(4-carbomethoxyphenyl)-3,6,7,8,9,9a-hexahydroquinolizin-4-one (145 mg) in methanol (5 mL), and the reaction solution was stirred in a hydrogen stream at room temperature for three hours. The reaction solution was filtered through celite, and the filtrate was concentrated under reduced pressure to obtain 125 mg of the title compound. The property values of the compound are as follows.
ESI-MS; m/z 288 [M$^+$+H]. $^1$H-NMR (CDCl$_3$) δ(ppm): 1.25-1.37 (m, 1H), 1.46-1.64 (m, 3H), 1.70-1.86 (m, 2H), 1.92-2.01 (m, 2H), 2.04-2.12 (m, 1H), 2.16-2.27 (m, 1H), 2.47-2.53 (m, 2H), 3.59-3.68 (m, 1H), 3.89 (s, 3H), 5.40 (t, J=3.6 Hz, 1H), 7.26 (d, J=8.4 Hz, 2H), 7.96 (d, J=8.4 Hz, 2H).

Synthesis of (6R*,9aS*)-6-(4-carbomethoxyphenyl)-3-iodooctahydroquinolizin-4-one Iodotrimethylsilane (0.1 mL) was added to a solution of (6R*,9aS*)-6-(4-carbomethoxyphenyl)octahydroquinolizin-4-one (125 mg) and N,N,N',N'-tetramethylethylenediamine (0.23 mL) in methylene chloride (10 mL) at 0° C., and the reaction solution was stirred at 0° C. for 30 minutes. Iodine (166 mg) was added to the reaction solution, which was then stirred at 0° C. for one hour. Ethyl acetate and a saturated sodium thiosulfate solution were added to the reaction solution, and the organic layer was separated. The resulting organic layer was washed with brine, dried over magnesium sulfate, and then concentrated under reduced pressure to obtain 180 mg of the title compound. The property value of the compound is as follows.
ESI-MS; m/z 414 [M$^+$+H].

Synthesis of diethyl [(6S*,9aR*)-6-(4-carbomethoxyphenyl)-4-oxooctahydroquinolizin-3-yl]phosphonate A mixture of (6R*,9aS*)-6-(4-carbomethoxyphenyl)-3-iodooctahydroquinolizin-4-one (180 mg) with triethyl phosphite (2 mL) was stirred at 120° C. for two hours. The reaction solution was left to cool to room temperature and then concentrated under reduced pressure to obtain 185 mg of the title compound. The property value of the compound is as follows.
ESI-MS; m/z 424 [M$^+$+H].

Synthesis of methyl (E)-4-{(4S*,9aR*)-7-[3-methoxy-4-(4-methyl-1H-imidazol-1-yl)benzylidene]-6-oxooctahydroquinolizin-4-yl}benzoate Lithium hydroxide monohydrate (55 mg) was added to a mixed solution of diethyl [(6S*,9aR*)-6-(4-carbomethoxyphenyl)-4-oxooctahydroquinolizin-3-yl]phosphonate (185 mg) and 3-methoxy-4-(4-methyl-1H-imidazol-1-yl)benzaldehyde (94 mg) in tetrahydrofuran (4 mL) and ethanol (1 mL), and the reaction solution was stirred at room temperature for two hours. Ethyl acetate and brine were added to the reaction solution, and the organic layer was separated. The resulting organic layer was dried over magnesium sulfate and then concentrated under reduced pressure. The residue was purified by silica gel column chromatography (carrier: Chromatorex NH; elution solvent: heptane:ethyl acetate=1:1->ethyl acetate) to obtain 191 mg of the title compound. The property values of the compound are as follows.
ESI-MS; m/z 486 [M$^+$+H]. $^1$H-NMR (CDCl$_3$) δ(ppm): 1.30-1.42 (m, 1H), 1.48-1.80 (m, 4H), 2.02-2.09 (m, 1H), 2.22-2.28 (m, 2H) 2.30 (s, 3H), 2.66-2.78 (m, 1H), 3.12 (brd, J=16.0 Hz, 1H), 3.78-3.86 (m, 4H), 3.90 (s, 3H), 5.56 (brt, J=3.6 Hz, 1H), 6.93 (brs, 1H), 7.02 (dd, J=1.2 Hz, 1H), 7.05 (dd, J=9.2, 1.2 Hz, 1H), 7.25 (d, J=9.2 Hz, 1H), 7.33 (d, J=8.0 Hz, 2H), 7.72 (d, J=0.8 Hz, 1H), 7.79 (d, J=2.8 Hz, 1H), 7.99 (d, J=8.0 Hz, 2H).

Example 36

Synthesis of (E)-(6S*,9aR*)-6-(4-hydroxymethylphenyl)-3-[3-methoxy-4-(4-methyl-1H-imidazol-1-yl)benzylidene]octahydroquinolizin-4-one

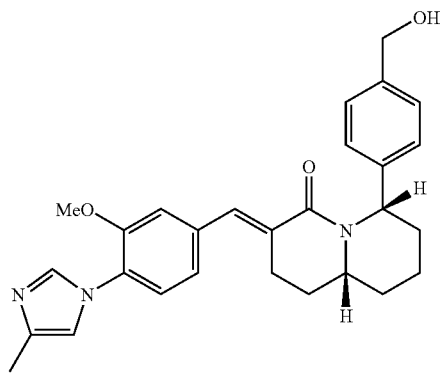

Lithium aluminum hydride (4 mg) was added to a solution of methyl (E)-4-{(4S*,9aR*)-7-[3-methoxy-4-(4-methyl-1H-imidazol-1-yl)benzylidene]-6-oxooctahydroquinolizin-4-yl}benzoate (50 mg) in THF (1 mL) at 0° C., and the reaction solution was stirred at 0° C. for two hours. A saturated ammonium chloride solution and ethyl acetate were added to the reaction solution, and the organic layer was separated. The resulting organic layer was dried over magnesium sulfate and then concentrated under reduced pressure. The residue was purified by silica gel column chromatography (carrier: Chromatorex NH; elution solvent: ethyl acetate->ethyl acetate:methanol=5:1) to obtain 24 mg of the title compound. The property values of the compound are as follows.
ESI-MS; m/z 458 [M$^+$+H]. $^1$H-NMR (CDCl$_3$) δ(ppm): 1.36-1.46 (m, 1H), 1.53-1.78 (m, 4H), 2.00-2.07 (m, 1H), 2.20-2.27 (m, 2H) 2.31 (s, 3H), 2.66-2.78 (m, 1H), 3.11 (brd, J=15.6 Hz, 1H), 3.76-3.85 (m, 1H), 3.86 (s, 3H), 4.67 (s, 2H), 5.55 (brs, 1H), 6.94 (brs, 1H), 7.04 (d, J=1.2 Hz, 1H), 7.05 (dd, J=8.0, 1.2 Hz, 1H), 7.26 (d, J=8.0 Hz, 3H), 7.33 (d, J=8.0 Hz, 2H), 7.74 (d, J=1.2 Hz, 1H), 7.81 (d, J=2.4 Hz, 1H).

Example 37

Synthesis of (E)-(6S*,9aR*)-6-(4-cyanophenyl)-3-[3-methoxy-4-(4-methyl-1H-imidazol-1-yl)benzylidene]octahydroquinolizin-4-one

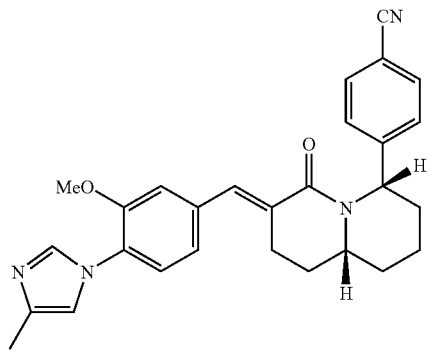

Dess-Martin periodinane (37 mg) was added to a solution of (E)-(6S*,9aR*)-6-(4-hydroxymethylphenyl)-3-[3-methoxy-4-(4-methyl-1H-imidazol-1-yl)benzylidene]octahydroquinolizin-4-one (20 mg) in methylene chloride (2 mL), and the reaction solution was stirred at room temperature for 30 minutes. Saturated sodium bicarbonate water and ethyl acetate were added to the reaction solution, and the organic layer was separated. The resulting organic layer was dried over magnesium sulfate and then concentrated under reduced pressure to obtain a crude aldehyde compound. Hydroxylamine hydrochloride (9 mg) and sodium acetate (11 mg) were added to a solution of the resulting crude aldehyde compound in ethanol (3 mL), and the reaction solution was stirred at room temperature for 12 hours. Saturated sodium bicarbonate water and ethyl acetate were added to the reaction solution, and the organic layer was separated. The resulting organic layer was dried over magnesium sulfate and then concentrated under reduced pressure to obtain a crude oxime compound. To a solution of the resulting crude oxime compound in THF (5 mL), 1,1'-carbonyldiimidazole (70 mg) was added, and the reaction solution was heated to reflux for five hours. The reaction solution was left to cool to room temperature. Then, ethyl acetate and water were added to the reaction solution, and the organic layer was separated. The resulting organic layer was dried over magnesium sulfate and then concentrated under reduced pressure. The residue was purified by silica gel column chromatography (carrier: Chromatorex NH; elution solvent: heptane:ethyl acetate=1:1->ethyl acetate) to obtain 6 mg of the title compound. The property values of the compound are as follows.

ESI-MS; m/z 453 [M++H]. $^1$H-NMR (CDCl$_3$) δ(ppm): 1.25-1.40 (m, 1H), 1.43-1.56 (m, 1H), 1.62-1.85 (m, 3H), 2.03-2.11 (m, 1H), 2.13-2.32 (m, 2H) 2.33 (s, 3H), 2.67-2.77 (m, 1H), 3.11 (brd, J=16.4 Hz, 1H), 3.76-3.85 (m, 1H), 3.86 (s, 3H), 5.50 (brs, 1H), 6.94 (brs, 1H), 7.02 (d, J=1.2 Hz, 1H), 7.04 (dd, J=8.0, 1.2 Hz, 1H), 7.26 (d, J=8.0 Hz, 1H), 7.36 (d, J=7.6 Hz, 2H), 7.62 (d, J=7.6 Hz, 2H), 7.77 (d, J=2.8 Hz, 1H), 7.81 (s, 1H).

Example 38

Synthesis of (E)-4-{(4S*,9aR*)-7-[3-methoxy-4-(4-methyl-1H-imidazol-1-yl)benzylidene]-6-oxooctahydroquinolizin-4-yl}benzoic acid

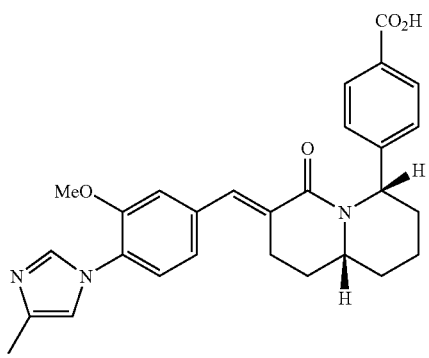

A 2 N sodium hydroxide solution (1 mL) was added to a solution of methyl (E)-4-{(4S*,9aR*)-7-[3-methoxy-4-(4-methyl-1H-imidazol-1-yl)benzylidene]-6-oxooctahydroquinolizin-4-yl}benzoate (80 mg) in methanol (2 mL), and the reaction solution was stirred at room temperature for 18 hours. 2 N hydrochloric acid (1 mL) was added to the reaction solution, and the solution was concentrated under reduced pressure. The resulting residue was purified by silica gel column chromatography (elution solvent: chloroform:methanol=5:1) to obtain 77 mg of the title compound. The property values of the compound are as follows.

ESI-MS; m/z 472 [M++H]. $^1$H-NMR (CDCl$_3$) δ(ppm): 1.33-1.44 (m, 1H), 1.52-1.84 (m, 4H), 2.02-2.11 (m, 1H), 2.22-2.32 (m, 2H) 2.40 (s, 3H), 2.67-2.78 (m, 1H), 3.11 (brd, J=16.0 Hz, 1H), 3.79-3.86 (m, 1H), 3.87 (s, 3H), 5.58 (brs, 1H), 6.97 (brs, 1H), 7.06 (brs, 1H), 7.07 (d, J=8.4 Hz, 1H), 7.28 (d, J=8.4 Hz, 1H), 7.33 (d, J=8.4 Hz, 2H), 7.81 (brs, 1H), 8.02 (d, J=8.4 Hz, 2H), 8.10 (brs, 1H).

Example 39

Synthesis of (E)-(6S*,9aR*)-6-(4-aminophenyl)-3-[3-methoxy-4-(4-methyl-1H-imidazol-1-yl)benzylidene]octahydroquinolizin-4-one

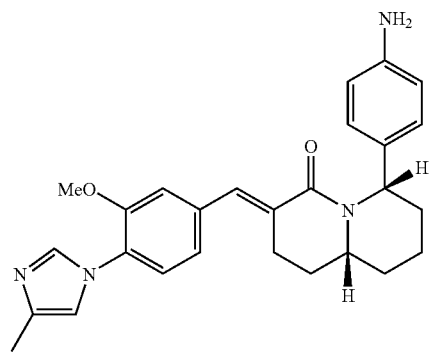

A solution of (E)-4-(4S*,9aR*)-7-[3-methoxy-4-(4-methyl-1H-imidazol-1-yl)benzylidene]-6-oxooctahydroquinolizin-4-yl)benzoic acid (58 mg), diphenylphosphoryl azide (51 mg), and triethylamine (0.026 mL) in toluene (3 mL) was heated under reflux for one hour. The reaction solution was left to cool to room temperature and concentrated under reduced pressure. 5 N hydrochloric acid (3 mL) was added to the residue, and the reaction solution was heated under reflux for one hour. The reaction solution was left to cool to room temperature and adjusted to pH 11 or less by a 5 N sodium hydroxide solution, followed by extraction with chloroform. The resulting organic layer was dried over magnesium sulfate and then concentrated under reduced pressure. The residue was purified by silica gel column chromatography (carrier: Chromatorex NH; elution solvent: ethyl acetate) to obtain 9 mg of the title compound. The property values of the compound are as follows.

ESI-MS; m/z 443 [M++H]. $^1$H-NMR (CDCl$_3$) δ(ppm): 1.22-1.32 (m, 1H), 1.47-1.78 (m, 4H), 1.82-2.01 (m, 2H), 2.34 (s, 3H), 2.35-2.44 (m, 1H), 2.64-2.72 (m, 1H), 2.84-2.91 (m, 1H), 3.42-3.50 (m, 1H), 3.87 (s, 3H), 6.13 (brd, J=3.2 Hz, 1H), 6.67 (d, J=8.4 Hz, 2H), 6.94 (brs, 1H), 7.01 (brs, 1H), 7.02 (d, J=8.4 Hz, 2H), 7.05 (brd, J=8.4 Hz, 1H), 7.25 (d, J=8.4 Hz, 1H), 7.81 (brs, 2H).

Example 40

Synthesis of (E)-4-{(4S*,9aR*)-7-[3-methoxy-4-(4-methyl-1H-imidazol-1-yl)benzylidene]-6-oxooctahydroquinolizin-4-yl}-N,N-dimethylbenzamide

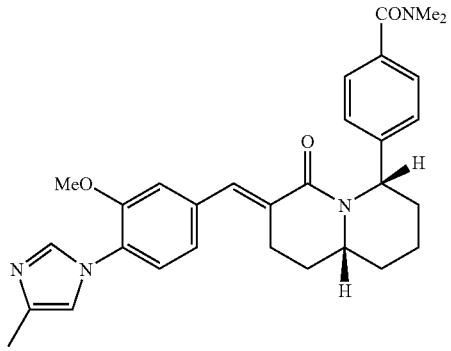

IPEA (0.03 mL), HOBT (10 mg), and EDC (14 mg) were sequentially added to a solution of (E)-4-{(4S*,9aR*)-7-[3-methoxy-4-(4-methyl-1H-imidazol-1-yl)benzylidene]-6-oxooctahydroquinolizin-4-yl}benzoic acid (22 mg) and dimethylamine (2 M solution in THF, 0.12 mL) in DMF (2 mL), and the reaction solution was stirred at room temperature for two hours. Then, the reaction solution was further stirred at 100° C. for six hours. The reaction solution was left to cool to room temperature. Ethyl acetate and saturated sodium bicarbonate water were added to the reaction solution, and the organic layer was separated. The resulting organic layer was dried over magnesium sulfate and then concentrated under reduced pressure. The residue was purified by silica gel column chromatography (carrier: Chromatorex NH; elution solvent: ethyl acetate:methanol=9:1) to obtain 19 mg of the title compound. The property values of the compound are as follows.

ESI-MS; m/z 499 [M$^+$+H]. $^1$H-NMR (CDCl$_3$) δ(ppm): 1.32-1.43 (m, 1H), 1.47-1.77 (m, 4H), 2.00-2.07 (m, 1H), 2.20-2.30 (m, 2H), 2.32 (s, 3H), 2.66-2.78 (m, 1H), 2.99 (brs, 3H), 3.05-3.16 (m, 4H), 3.76-3.85 (m, 1H), 3.86 (s, 3H), 5.58 (brs, 1H), 6.94 (brs, 1H), 7.04 (brs, 1H), 7.06 (brd, J=8.8 Hz, 1H), 7.26 (d, J=8.8 Hz, 1H), 7.29 (d, J=7.6 Hz, 2H), 7.38 (d, J=7.6 Hz, 2H), 7.75 (brs, 1H), 7.81 (d, J=2.4 Hz, 1H).

Examples 41 and 42

Synthesis of (E)-(6S,9aR)-6-(3-fluorophenyl)-3-[3-methoxy-4-(4-methyl-1H-imidazol-1-yl)benzylidene]octahydroquinolizin-4-one and (E)-(6R,9aS)-6-(3-fluorophenyl)-3-[3-methoxy-4-(4-methyl-1H-imidazol-1-yl)benzylidene]octahydroquinolizin-4-one

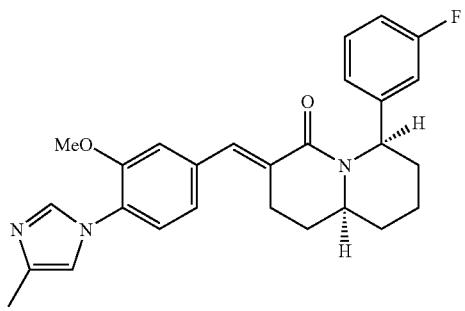

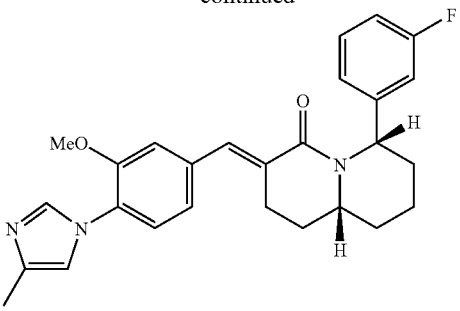

Synthesis of 1-(3-fluorophenyl)hepta-5,6-dienyl-1-amine 765 mg of the title compound was obtained from (3-fluorobenzyl)-(3-fluorobenzylidene)amine (913 mg) and 6-iodohexa-1,2-diene (904 mg) according to the method described in Journal of the American Chemical Society, 2003, vol. 125, p. 11956. The property values of the compound are as follows.

$^1$H-NMR (CDCl$_3$) δ(ppm): 1.27-1.52 (m, 2H), 1.65-1.80 (m, 2H), 1.95-2.05 (m, 2H), 3.92 (t, J=6.8 Hz, 1H), 4.65 (dt, J=6.8, 3.2 Hz, 2H), 5.05 (quintet, J=6.8 Hz, 1H), 6.91-6.97 (m, 1H), 7.02-7.07 (m, 1H), 7.09 (d, J=8.0 Hz, 1H), 7.26-7.30 (m, 1H).

Synthesis of (2R*,6S*)-2-(3-fluorophenyl)-6-vinylpiperidine

Acetic acid (0.22 mL) was added to a solution of an allylpalladium chloride dimer (136 mg) and 1,1'-bis(diphenylphosphino)ferrocene (426 mg) in THF (70 mL) in a nitrogen atmosphere, and the reaction solution was stirred at room temperature for 10 minutes. A solution of 1-(3-fluorophenyl)hepta-5,6-dienyl-1-amine (765 mg) in THF (40 mL) was added to the reaction solution at room temperature, and the reaction solution was stirred at 70° C. for 14 hours. The reaction solution was left to cool to room temperature. Then, diethyl ether and 2 N hydrochloric acid were added to the reaction solution, and the aqueous layer was separated. The resulting aqueous layer was washed with diethyl ether, and then a 5 N sodium hydroxide solution was added to the aqueous layer under ice-cooling until the pH was adjusted to 11 or less. Chloroform was added to the aqueous layer, and the organic layer was separated. The resulting organic layer was dried over magnesium sulfate, and concentrated under reduced pressure to obtain 748 mg of the title compound. The property values of the compound are as follows.

ESI-MS; m/z 206 [M$^+$+H]. $^1$H-NMR (CDCl$_3$) δ(ppm): 1.30-1.60 (m, 3H), 1.68-1.80 (m, 2H), 1.88-1.96 (m, 1H), 3.30-3.43 (m, 1H), 3.66-3.77 (m, 1H), 5.04 (brd, J=10.0 Hz, 1H), 5.20 (brd, J=17.2 Hz, 1H), 5.91 (ddd, J=17.2, 10.4, 6.8 Hz, 1H), 6.89-6.97 (m, 1H), 7.10-7.20 (m, 2H), 7.23-7.31 (m, 1H).

Synthesis of 1-[(2R*,6S*)-2-(3-fluorophenyl)-6-vinylpiperidin-1-yl]-3-buten-1-one Diethyl cyanophosphonate (1.78 mL) was added to a solution of (2R*,6S*)-2-(3-fluorophenyl)-6-vinylpiperidine (748 mg), vinylacetic acid (0.96 mL), and triethylamine (3.1 mL) in DMF (15 mL) at room temperature, and the reaction solution was stirred at room temperature for 27 hours. Ethyl acetate and 1 N hydrochloric acid were added to the reaction solution, and the organic layer was separated. The resulting organic layer was sequentially washed with saturated sodium bicarbonate water and brine, dried over magnesium sulfate, and then concentrated under reduced pressure. The residue was purified by silica gel column chromatography (elution solvent: heptane-ethyl acetate system) to obtain 587 mg of the title compound. The property values of the compound are as follows.

ESI-MS; m/z 274 [M$^+$+H]. $^1$H-NMR (CDCl$_3$) δ(ppm): 1.58-1.66 (m, 1H), 1.76-1.92 (m, 4H), 2.37-2.46 (m, 1H), 3.25 (d, J=6.4 Hz, 2H), 4.85 (d, J=10.4 Hz, 2H), 5.03 (d, J=17.2 Hz, 1H), 5.12-5.24 (m, 2H), 5.50 (ddd, J=17.2, 10.0, 7.2 Hz, 1H), 5.58-5.82 (m, 1H), 5.98-6.10 (m, 1H), 6.89-6.96 (m, 1H), 7.01 (d, J=10.4 Hz, 1H), 7.04-7.12 (m, 1H), 7.22-7.30 (m, 1H).

Synthesis of (6R*,9aS*)-6-(3-fluorophenyl)-3,6,7,8,9,9a-hexahydroquinolizin-4-one A solution of 1-[(2R*,6S*)-2-(3-fluorophenyl)-6-vinylpiperidin-1-yl]-3-buten-1-one (587 mg) and tricyclohexylphosphine[1,3-bis(2,4,6-trimethylphenyl)-4,5-dihydroimidazol-2-ylidene][benzylidene]ruthenium (IV) dichloride (92 mg) in methylene chloride (250 mL) was heated under reflux in a nitrogen atmosphere for two hours. The reaction solution was left to cool to room temperature. Then, triethylamine (0.5 mL) was added thereto, and the reaction solution was concentrated under reduced pressure. The residue was purified by silica gel column chromatography (elution solvent: heptane-ethyl acetate system) to obtain 460 mg of the title compound. The property values of the compound are as follows.

ESI-MS; m/z 246 [M$^+$+H]. $^1$H-NMR (CDCl$_3$) δ(ppm): 1.39-1.54 (m, 1H), 1.60-1.78 (m, 2H), 1.85-1.95 (m, 1H), 1.98-2.07 (m, 1H), 2.21-2.32 (m, 1H), 2.94-3.12 (m, 2H), 4.27-4.37 (m, 1H), 5.34 (t, J=4.0 Hz, 1H), 5.68 (brd, J=10.0 Hz, 1H), 5.84-5.90 (m, 1H), 6.85-6.93 (m, 2H), 6.98-7.02 (m, 1H), 7.22-7.29 (m, 1H).

Synthesis of (6R*,9aS*)-6-(3-fluorophenyl)octahydroquinolizin-4-one

Platinum oxide (20 mg) was added to a solution of (6R*,9aS*)-6-(3-fluorophenyl)-3,6,7,8,9,9a-hexahydroquinolizin-4-one (460 mg) in methanol (10 mL), and the reaction solution was stirred in a hydrogen stream at room temperature for three hours. The reaction solution was filtered through celite, and the filtrate was concentrated under reduced pressure. The residue was purified by silica gel column chromatography (elution solvent: heptane-ethyl acetate system) to obtain 383 mg of the title compound. The property values of the compound are as follows.

ESI-MS; m/z 248 [M$^+$+H]. $^1$H-NMR (CDCl$_3$) δ(ppm): 1.29-1.42 (m, 1H), 1.47-1.65 (m, 3H), 1.69-1.87 (m, 2H), 1.92-2.01 (m, 2H), 2.02-2.10 (m, 1H), 2.14-2.26 (m, 1H), 2.45-2.58 (m, 2H), 3.57-3.67 (m, 1H), 5.40 (brt, J=4.0 Hz, 1H), 6.84-6.93 (m, 2H), 6.97-7.02 (m, 1H), 7.23-7.29 (m, 1H).

Synthesis of (6R*,9aS*)-6-(3-fluorophenyl)-3-iodooctahydroquinolizin-4-one

Iodotrimethylsilane (0.34 mL) was added to a solution of (6R*,9aS*)-6-(3-fluorophenyl) octahydroquinolizin-4-one (383 mg) and N,N,N',N'-tetramethylethylenediamine (0.82 mL) in methylene chloride (15 mL) under ice-cooling in a nitrogen atmosphere, and the reaction solution was stirred under ice-cooling for 30 minutes. Iodine (590 mg) was added to the reaction solution under ice-cooling, and the reaction solution was stirred under ice-cooling for one hour. Ethyl acetate and a saturated sodium thiosulfate solution were added to the reaction solution, and the organic layer was separated. The resulting organic layer was washed with brine, dried over magnesium sulfate, and then concentrated under reduced pressure to obtain 597 mg of the title compound. The property value of the compound is as follows.

ESI-MS; m/z 374 [M$^+$+H].

Synthesis of diethyl [(6S*,9aR*)-6-(3-fluorophenyl)-4-oxooctahydroquinolizin-3-yl]phosphonate A mixture of (6R*,9aS*)-6-(3-fluorophenyl)-3-iodooctahydroquinolizin-4-one (597 mg) with triethyl phosphite (6 mL) was stirred at 120° C. for five hours. The reaction solution was left to cool to room temperature and then concentrated under reduced pressure to obtain 670 mg of the title compound. The property value of the compound is as follows.

ESI-MS; m/z 384 [M$^+$+H].

Synthesis of (E)-(6S*,9aR*)-6-(3-fluorophenyl)-3-[3-methoxy-4-(4-methyl-1H-imidazol-1-yl)benzylidene]octahydroquinolizin-4-one Lithium hydroxide monohydrate (220 mg) was added to a mixed solution of diethyl [(6S*,9aR*)-6-(3-fluorophenyl)-4-oxooctahydroquinolizin-3-yl]phosphonate (670 mg) and 3-methoxy-4-(4-methyl-1H-imidazol-1-yl)benzaldehyde (378 mg) in tetrahydrofuran (15 mL) and ethanol (5 mL) at room temperature, and the reaction solution was stirred at room temperature for one hour. Ethyl acetate was added to the reaction solution, which was then sequentially washed with saturated sodium bicarbonate water and brine. The resulting organic layer was dried over magnesium sulfate and then concentrated under reduced pressure. The residue was purified by silica gel column chromatography (carrier: Chromatorex NH; elution solvent: heptane-ethyl acetate system) to obtain 583 mg of the title compound. The property values of the compound are as follows.

ESI-MS; m/z 446 [M$^+$+H]. $^1$H-NMR (CDCl$_3$) δ(ppm): 1.34-1.47 (m, 1H), 1.52-1.80 (m, 4H), 2.01-2.08 (m, 1H), 2.17-2.28 (m, 2H), 2.37 (s, 3H), 2.67-2.78 (m, 1H), 3.06-3.14 (m, 1H), 3.77-3.87 (m, 1H), 3.87 (s, 3H), 5.54 (brs, 1H), 6.88-6.99 (m, 3H), 7.03-7.11 (m, 3H), 7.23-7.34 (m, 2H), 7.82 (brd, J=2.4 Hz, 1H), 7.91 (brs, 1H).

Synthesis of (E)-(6S,9aR)-6-(3-fluorophenyl)-3-[3-methoxy-4-(4-methyl-1H-imidazol-1-yl)benzylidene]octahydroquinolizin-4-one and (E)-(6R,9aS)-6-(3-fluorophenyl)-3-[3-methoxy-4-(4-methyl-1H-imidazol-1-yl)benzylidene]octahydroquinolizin-4-one The racemate (E)-(6S*,9aR*)-6-(3-fluorophenyl)-3-[3-methoxy-4-(4-methyl-1H-imidazol-1-yl)benzylidene]octahydroquinolizin-4-one obtained above (20 mg) was separated by CHIRALPAK™ IA manufactured by Daicel Chemical Industries, Ltd. (2 cm×25 cm; mobile phase: ethanol) to obtain the title optically active compound with a retention time of 26 minutes (7.3 mg; >99% ee) and the title optically active compound with a retention time of 34 minutes (6.7 mg; >99% ee).

The property values of the title optically active compound with a retention time of 26 minutes (Example 41) are as follows.

ESI-MS; m/z 446 [M++H]. ¹H-NMR (CDCl₃) δ(ppm): 1.34-1.47 (m, 1H), 1.52-1.80 (m, 4H), 2.01-2.08 (m, 1H), 2.17-2.28 (m, 2H), 2.37 (s, 3H), 2.67-2.78 (m, 1H), 3.06-3.14 (m, 1H), 3.77-3.87 (m, 1H), 3.87 (s, 3H), 5.54 (brs, 1H), 6.88-6.99 (m, 3H), 7.03-7.11 (m, 3H), 7.23-7.34 (m, 2H), 7.82 (brd, J=2.4 Hz, 1H), 7.91 (brs, 1H).

The property values of the title optically active compound with a retention time of 34 minutes (Example 42) are as follows.

ESI-MS; m/z 446 [M++H]. ¹H-NMR (CDCl₃) δ(ppm): 1.34-1.47 (m, 1H), 1.52-1.80 (m, 4H), 2.01-2.08 (m, 1H), 2.17-2.28 (m, 2H), 2.37 (s, 3H), 2.67-2.78 (m, 1H), 3.06-3.14 (m, 1H), 3.77-3.87 (m, 1H), 3.87 (s, 3H), 5.54 (brs, 1H), 6.88-6.99 (m, 3H), 7.03-7.11 (m, 3H), 7.23-7.34 (m, 2H), 7.82 (brd, J=2.4 Hz, 1H), 7.91 (brs, 1H).

Examples 43 and 44

Synthesis of (E)-(6S,9aR)-6-(2-fluorophenyl)-3-[3-methoxy-4-(4-methyl-1H-imidazol-1-yl)benzylidene]octahydroquinolizin-4-one and (E)-(6R,9aS)-6-(2-fluorophenyl)-3-[3-methoxy-4-(4-methyl-1H-imidazol-1-yl)benzylidene]octahydroquinolizin-4-one

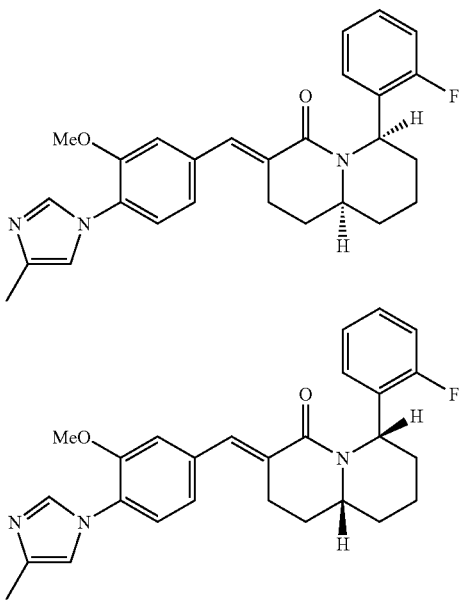

Synthesis of 1-(2-fluorophenyl)hepta-5,6-dienyl-1-amine 617 mg of the title compound was obtained from (2-fluorobenzyl)-(2-fluorobenzylidene)amine (890 mg) and 6-iodohexa-1,2-diene (881 mg) according to the method described in Journal of the American Chemical Society, 2003, vol. 125, p. 11956. The property values of the compound are as follows.

¹H-NMR (CDCl₃) δ(ppm): 1.31-1.43 (m, 1H), 1.44-1.57 (m, 1H), 1.68-1.84 (m, 2H), 1.97-2.06 (m, 2H), 4.21 (t, J=6.8 Hz, 1H), 4.64 (dt, J=6.8, 3.2 Hz, 2H), 5.06 (quintet, J=6.8 Hz, 1H), 6.98-7.06 (m, 1H), 7.10-7.15 (m, 1H), 7.18-7.26 (m, 1H), 7.35-7.42 (m, 1H).

Synthesis of (2R*,6S*)-2-(2-fluorophenyl)-6-vinylpiperidine

Acetic acid (0.17 mL) was added to a solution of an allylpalladium chloride dimer (110 mg) and 1,1'-bis(diphenylphosphino)ferrocene (344 mg) in THF (60 mL) in a nitrogen atmosphere, and the reaction solution was stirred at room temperature for 10 minutes. A solution of 1-(2-fluorophenyl)hepta-5,6-dienyl-1-amine (617 mg) in THF (30 mL) was added to the reaction solution at room temperature, and the reaction solution was stirred at 70° C. for 14 hours. The reaction solution was left to cool to room temperature. Then, diethyl ether and 2 N hydrochloric acid were added to the reaction solution, and the aqueous layer was separated. The resulting aqueous layer was washed with diethyl ether, and then a 5 N sodium hydroxide solution was added to the aqueous layer under ice-cooling until the pH was adjusted to 11 or less. Chloroform was added to the aqueous layer, and the organic layer was separated. The resulting organic layer was dried over magnesium sulfate, and concentrated under reduced pressure to obtain 518 mg of the title compound. The property values of the compound are as follows.

ESI-MS; m/z 206 [M++H]. ¹H-NMR (CDCl₃) δ(ppm): 1.28-1.68 (m, 3H), 1.70-1.79 (m, 1H), 1.79-1.88 (m, 1H), 1.88-1.98 (m, 1H), 3.26-3.38 (m, 1H), 4.09 (d, J=11.2 Hz, 1H), 5.04 (d, J=10.8 Hz, 1H), 5.20 (d, J=17.2 Hz, 1H), 5.85-5.97 (m, 1H), 6.97-7.05 (m, 1H), 7.08-7.15 (m, 1H), 7.16-7.26 (m, 1H), 7.54-7.63 (m, 1H).

Synthesis of 1-[(2R*,6S*)-2-(2-fluorophenyl)-6-vinylpiperidin-1-yl]-3-buten-1-one Diethyl cyanophosphonate (1.23 mL) was added to a solution of (2R*,6S*)-2-(2-fluorophenyl)-6-vinylpiperidine (518 mg), vinylacetic acid (0.66 mL), and triethylamine (2.1 mL) in DMF (10 mL) at room temperature, and the reaction solution was stirred at room temperature for 21 hours. Ethyl acetate and 1 N hydrochloric acid were added to the reaction solution, and the organic layer was separated. The resulting organic layer was sequentially washed with saturated sodium bicarbonate water and brine, dried over magnesium sulfate, and then concentrated under reduced pressure. The residue was purified by silica gel column chromatography (elution solvent: heptane-ethyl acetate system) to obtain 442 mg of the title compound. The property values of the compound are as follows.

ESI-MS; m/z 274 [M++H]. ¹H-NMR (CDCl₃) δ(ppm): 1.50-1.64 (m, 1H), 1.74-2.05 (m, 4H), 2.10-2.21 (m, 1H), 3.03 (brdd, J=16.4, 5.6 Hz, 1H), 3.16 (dd, J=16.0, 6.8 Hz, 1H), 5.01-5.16 (m, 4H), 5.20 (d, J=17.2 Hz, 1H), 5.46-5.57 (m, 1H), 5.82-6.02 (m, 2H), 6.97-7.10 (m, 2H), 7.19-7.24 (m, 1H), 7.29-7.36 (m, 1H).

Synthesis of (6R*,9aS*)-6-(2-fluorophenyl)-3,6,7,8,9,9a-hexahydroquinolizin-4-one A solution of 1-[(2R*,6S*)-2-(2-fluorophenyl)-6-vinylpiperidin-1-yl]-3-buten-1-one (442 mg) and tricyclohexylphosphine[1,3-bis(2,4,6-trimethylphenyl)-4,5-dihydroimidazol-2-ylidene][benzylidene]ruthenium (IV) dichloride (69 mg) in methylene chloride (180 mL) was heated under reflux in a nitrogen atmosphere for two hours. The reaction solution was left to cool to room temperature. Then, triethylamine (0.5 mL) was added thereto, and the reaction solution was concentrated under reduced pressure. The residue was purified by silica gel column chromatography (elution solvent: heptane-ethyl acetate system) to obtain 368 mg of the title compound. The property values of the compound are as follows.

ESI-MS; m/z 246 [M++H]. ¹H-NMR (CDCl₃) δ(ppm): 1.40-1.55 (m, 1H), 1.60-1.83 (m, 2H), 1.89-2.00 (m, 1H), 2.07-2.25 (m, 2H), 2.91-3.10 (m, 2H), 4.31-4.41 (m, 1H), 5.47 (brt, J=4.0 Hz, 1H), 5.68 (dd, J=10.0, 0.8 Hz, 1H), 5.80-5.88 (m, 1H), 6.97-7.08 (m, 2H), 7.12-7.22 (m, 2H).

Synthesis of (6R*,9aS*)-6-(2-fluorophenyl)octahydroquinolizin-4-one

Platinum oxide (16 mg) was added to a solution of (6R*,9aS*)-6-(2-fluorophenyl)-3,6,7,8,9,9a-hexahydroquinolizin-4-one (368 mg) in methanol (8 mL), and the reaction solution was stirred in a hydrogen stream at room temperature for two hours. The reaction solution was filtered through celite, and the filtrate was concentrated under reduced pressure. The residue was purified by silica gel column chromatography (elution solvent: heptane-ethyl acetate system) to obtain 309 mg of the title compound. The property values of the compound are as follows.

ESI-MS; m/z 248 [M$^+$+H]. $^1$H-NMR (CDCl$_3$) δ(ppm): 1.25-1.40 (m, 1H), 1.52-1.70 (m, 2H), 1.72-1.87 (m, 2H), 1.90-2.05 (m, 2H), 2.07-2.18 (m, 2H), 2.37-2.56 (m, 2H), 3.63-3.73 (m, 1), 5.53 (t, J=4.0 Hz, 1H), 6.96-7.08 (m, 2H), 7.10-7.22 (m, 2H).

Synthesis of (6R*,9aS*)-6-(2-fluorophenyl)-3-iodooctahydroquinolizin-4-one

Iodotrimethylsilane (0.28 mL) was added to a solution of (6R*,9aS*)-6-(2-fluorophenyl)octahydroquinolizin-4-one (309 mg) and N,N,N',N'-tetramethylethylenediamine (0.66 mL) in methylene chloride (12 mL) under ice-cooling in a nitrogen atmosphere, and the reaction solution was stirred under ice-cooling for 30 minutes. Iodine (476 mg) was added to the reaction solution under ice-cooling, and the reaction solution was stirred under ice-cooling for one hour. Ethyl acetate and a saturated sodium thiosulfate solution were added to the reaction solution, and the organic layer was separated. The resulting organic layer was washed with brine, dried over magnesium sulfate, and then concentrated under reduced pressure to obtain 500 mg of the title compound. The property value of the compound is as follows.

ESI-MS; m/z 374 [M$^+$+H].

Synthesis of diethyl [(6S*,9aR*)-6-(2-fluorophenyl)-4-oxooctahydroquinolizin-3-yl]phosphonate A mixture of (6R*,9aS*)-6-(2-fluorophenyl)-3-iodooctahydroquinolizin-4-one (500 mg) with triethyl phosphite (6 mL) was stirred at 120° C. for five hours. The reaction solution was left to cool to room temperature and then concentrated under reduced pressure to obtain 501 mg of the title compound. The property value of the compound is as follows.

ESI-MS; m/z 384 [M$^+$+H].

Synthesis of (E)-(6S*9aR*)-6-(2-fluorophenyl)-3-[3-methoxy-4-(4-methyl-1H-imidazol-1-yl)benzylidene]octahydroquinolizin-4-one Lithium hydroxide monohydrate (169 mg) was added to a mixed solution of diethyl [(6S*,9aR*)-6-(2-fluorophenyl)-4-oxooctahydroquinolizin-3-yl]phosphonate (501 mg) and 3-methoxy-4-(4-methyl-1H-imidazol-1-yl)benzaldehyde (290 mg) in tetrahydrofuran (12 mL) and ethanol (4 mL) at room temperature, and the reaction solution was stirred at room temperature for two hours. Ethyl acetate was added to the reaction solution, which was then sequentially washed with saturated sodium bicarbonate water and brine. The resulting organic layer was dried over magnesium sulfate and then concentrated under reduced pressure. The residue was purified by silica gel column chromatography (carrier: Chromatorex NH; elution solvent: heptane-ethyl acetate system) to obtain 483 mg of the title compound. The property values of the compound are as follows.

ESI-MS; m/z 446 [M$^+$+H]. $^1$H-NMR (CDCl$_3$) δ(ppm): 1.29-1.43 (m, 1H), 1.61-1.90 (m, 4H), 2.04-2.32 (m, 3H), 2.35 (s, 3H), 2.65-2.75 (m, 1H), 3.05-3.14 (m, 1H), 3.82-3.92 (m, 1H), 3.85 (s, 3H), 5.68 (brs, 1H), 6.94-6.96 (m, 1H), 7.01-7.10 (m, 4H), 7.16-7.23 (m, 2H), 7.24-7.28 (m, 1H), 7.76 (brd, J=2.8 Hz, 1H), 7.85 (brs, 1H).

Synthesis of (E)-(6S,9aR)-6-(2-fluorophenyl)-3-[3-methoxy-4-(4-methyl-1H-imidazol-1-yl)benzylidene]octahydroquinolizin-4-one and (E)-(6R,9aS)-6-(2-fluorophenyl)-3-[3-methoxy-4-(4-methyl-1H-imidazol-1-yl)benzylidene]octahydroquinolizin-4-one The racemate (E)-(6S*,9aR*)-6-(2-fluorophenyl)-3-[3-methoxy-4-(4-methyl-1H-imidazol-1-yl)benzylidene]octahydroquinolizin-4-one obtained above (20 mg) was separated by CHIRALPAK™ IA manufactured by Daicel Chemical Industries, Ltd. (2 cm×25 cm; mobile phase: ethanol) to obtain the title optically active compound with a retention time of 23 minutes (7.6 mg; >99% ee) and the title optically active compound with a retention time of 33 minutes (7.8 mg; >99% ee).

The property values of the title optically active compound with a retention time of 23 minutes (Example 43) are as follows.

ESI-MS; m/z 446 [M$^+$+H]. $^1$H-NMR (CDCl$_3$) δ(ppm): 1.29-1.43 (m, 1H), 1.61-1.90 (m, 4H), 2.04-2.32 (m, 3H), 2.35 (s, 3H), 2.65-2.75 (m, 1H), 3.05-3.14 (m, 1H), 3.82-3.92 (m, 1H), 3.85 (s, 3H), 5.68 (brs, 1H), 6.94-6.96 (m, 1H), 7.01-7.10 (m, 4H), 7.16-7.23 (m, 2H), 7.24-7.28 (m, 1H), 7.76 (brd, J=2.8 Hz, 1H), 7.85 (brs, 1H).

The property values of the title optically active compound with a retention time of 33 minutes (Example 44) are as follows.

ESI-MS; m/z 446 [M$^+$+H]. $^1$H-NMR (CDCl$_3$) δ(ppm): 1.29-1.43 (m, 1H), 1.61-1.90 (m, 4H), 2.04-2.32 (m, 3H), 2.35 (s, 3H), 2.65-2.75 (m, 1H), 3.05-3.14 (m, 1H), 3.82-3.92 (m, 1H), 3.85 (s, 3H), 5.68 (brs, 1H), 6.94-6.96 (m, 1H), 7.01-7.10 (m, 4H), 7.16-7.23 (m, 2H), 7.24-7.28 (m, 1H), 7.76 (brd, J=2.8 Hz, 1H), 7.85 (brs, 1H).

Examples 45 and 46

Synthesis of (E)-(6S,8R,9aR)-6-(4-fluorophenyl)-8-hydroxy-3-[3-methoxy-4-(4-methyl-1H-imidazol-1-yl)benzylidene]-8-methyloctahydroquinolizin-4-one and (E)-(6R,8S,9aS)-6-(4-fluorophenyl)-8-hydroxy-3-[3-methoxy-4-(4-methyl-1H-imidazol-1-yl)benzylidene]-8-methyloctahydroquinolizin-4-one

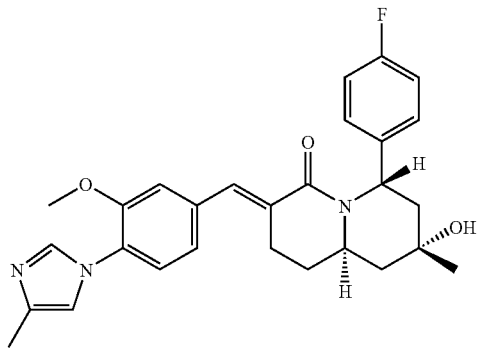

-continued

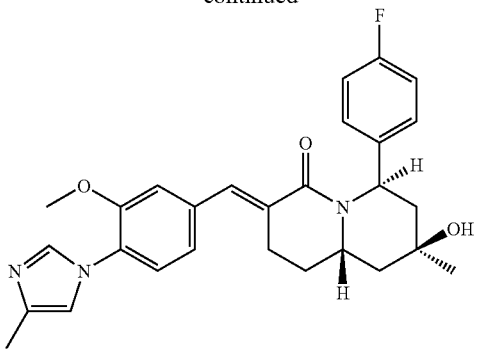

Synthesis of 1-(4-bromobutyryl)-2-(4-fluorophenyl)-2,3-dihydro-1H-pyridin-4-one 6.66 g of the title compound was obtained from 4-methoxypyridine (2.0 mL), 4-fluorophenylmagnesium bromide (1.0 M solution in THF, 20.7 mL), and 4-bromobutyryl chloride (2.4 mL) according to the method described in Tetrahedron Letters, 1986, vol. 27, p. 4549-4552. The property values of the compound are as follows.

$^1$H-NMR (CDCl$_3$) δ(ppm): 2.20-2.32 (m, 2H), 2.79-2.86 (m, 3H), 3.10-3.16 (m, 1H), 3.47-3.55 (m, 2H), 5.47 (brd, J=8.0 Hz, 1H), 6.00 (brs, 1H), 6.99-7.03 (m, 2H), 7.18-7.21 (m, 2H), 7.75 (brs, 1H).

Synthesis of (4S*,9aR*)-4-(4-fluorophenyl)hexahydroquinolizine-2,6-dione 1.05 g of the title compound was obtained from 1-(4-bromobutyryl)-2-(4-fluorophenyl)-2,3-dihydro-1H-pyridin-4-one (2.0 g), tributyltin hydride (1.87 mL), and AIBN (386 mg) according to the method described in The Journal of Organic Chemistry, 1993, vol. 58, p. 4198-4199. The property values of the compound are as follows.

$^1$H-NMR (CDCl$_3$) δ(ppm): 1.58-1.82 (m, 2H), 1.85-2.01 (m, 2H), 2.34-2.39 (m, 1H), 2.45-2.56 (m, 3H), 2.80 (dd, J=15.6, 7.2 Hz, 1H), 2.97-3.01 (m, 1H), 3.49-3.56 (m, 1H), 6.54 (brd, J=7.2 Hz, 1H), 6.99-7.03 (m, 2H), 7.21-7.24 (m, 2H).

Synthesis of (6S*,8R*,9aR*)-6-(4-fluorophenyl)-8-hydroxy-8-methyloctahydroquinolizin-4-one Methylmagnesium bromide (0.96 M solution in THF, 5.98 mL) was added to a solution of (4S*,9aR*)-4-(4-fluorophenyl)hexahydroquinolizine-2,6-dione (1.0 g) in THF (15 mL) under ice-cooling, and the reaction solution was stirred for 50 minutes. Because the starting material did not disappear, methylmagnesium bromide (0.96 M solution in THF, 5.98 mL) was further added to the reaction solution, which was then stirred for 30 minutes. A saturated ammonium chloride solution and ethyl acetate were added to the reaction solution, and the organic layer was separated. The resulting organic layer was washed with brine, dried over anhydrous magnesium sulfate, and then concentrated under reduced pressure. The residue was purified by silica gel column chromatography (elution solvent: heptane-ethyl acetate system->ethyl acetate-methanol system) to obtain a mixture of the starting material with the title compound. Methylmagnesium bromide (0.96 M solution in THF, 5.98 mL) was added to a solution of the resulting mixture in THF (15 mL) again under ice-cooling, and the reaction solution was stirred for one hour. A saturated ammonium chloride solution and ethyl acetate were added to the reaction solution, and the organic layer was separated. The resulting organic layer was washed with brine, dried over anhydrous magnesium sulfate, and then concentrated under reduced pressure. The residue was purified by silica gel column chromatography (elution solvent: heptane-ethyl acetate system->ethyl acetate-methanol system) to obtain a mixture of the starting material with the title compound. Methylmagnesium bromide (0.96 M solution in THF, 5.98 mL) was added to a solution of the mixture obtained again in THF (15 mL) again under ice-cooling, and the reaction solution was stirred for 1.5 hours. A saturated ammonium chloride solution and ethyl acetate were added to the reaction solution, and the organic layer was separated. The resulting organic layer was washed with brine, dried over anhydrous magnesium sulfate, and then concentrated under reduced pressure. The residue was purified by silica gel column chromatography (elution solvent: heptane-ethyl acetate system->ethyl acetate-methanol system) to obtain 760 mg of the title compound. The property values of the compound are as follows.

$^1$H-NMR (CDCl$_3$) δ(ppm): 1.26 (s, 3H), 1.56-1.68 (m, 3H), 1.80-2.01 (m, 3H), 2.01-2.12 (m, 1H), 2.42-2.64 (m, 3H), 3.79-3.85 (m, 1H), 6.06 (brd, J=6.8 Hz, 1H), 6.99-7.05 (m, 2H), 7.18-7.26 (m, 2H).

Synthesis of (6S*,8R*,9aR*)-8-(tert-butyldimethylsilanyloxy)-6-(4-fluorophenyl)-8-methyloctahydroquinolizin-4-one Triethylamine (201 µL) and TBSOTf (286 mg) were added to a solution of (6S*,8R*,9aR*)-6-(4-fluorophenyl)-8-hydroxy-8-methyloctahydroquinolizin-4-one (100 mg) in THF (1.0 mL) under ice-cooling, and the reaction solution was stirred for one hour and 50 minutes. Water and ethyl acetate were added to the reaction solution, and the organic layer was separated. The resulting organic layer was washed with brine, dried over anhydrous magnesium sulfate, and then concentrated under reduced pressure. The residue was purified by silica gel column chromatography (elution solvent: heptane-ethyl acetate system->ethyl acetate-methanol system) to obtain 116 mg of the title compound. The property values of the compound are as follows.

$^1$H-NMR (CDCl$_3$) δ(ppm): 0.00 (s, 3H), 0.12 (s, 3H), 0.72 (s, 9H), 1.48 (s, 3H), 1.68-1.89 (m, 3H), 1.98-2.12 (m, 3H), 2.20-2.28 (m, 1H), 2.58-2.68 (m, 2H), 2.70-2.78 (m, 1H), 4.00-4.06 (m, 1H), 6.11 (brd, J=6.8 Hz, 1H), 7.10-7.19 (m, 2H), 7.27-7.30 (m, 2H).

Synthesis of (E)-(6S*,8R*,9aR*)-8-(tert-butyldimethylsilanyloxy)-6-(4-fluorophenyl)-3-[3-methoxy-4-(4-methyl-1H-imidazol-1-yl)benzylidene]-8-methyloctahydroquinolizin-4-one LDA (1.5 M solution in THF, 434 µL) was added to a solution of (6S*,8R*,9aR*)-8-(tert-butyldimethylsilanyloxy)-6-(4-fluorophenyl)-8-methyloctahydroquinolizin-4-one (116 mg) in THF (2.0 mL) at 0° C. The reaction solution was stirred at 0° C. for one hour, and then a solution of 3-methoxy-4-(4-methyl-1H-imidazol-1-yl)benzaldehyde (83.2 mg) in THF (2.0 mL) was added to the reaction solution. The reaction solution was further stirred at 0° C. for 40 minutes. Water and ethyl acetate were added to the reaction solution, and the organic layer was separated. The resulting organic layer was dried over magnesium sulfate and then concentrated under reduced pressure to obtain 105.3 mg of a crude aldol adduct. A solution of the crude aldol adduct (105.3 mg) in methylene chloride (1.0 mL) was cooled to 0° C. Triethylamine (145 µL) and methanesulfonyl chloride (40 µL) were added to the reaction solution, which was then stirred at room temperature for one hour and 10 minutes.

Sodium methoxide (28% solution in methanol, 334 mg) and methanol (1.0 mL) were added to the reaction solution, which was then stirred at room temperature for one hour and 20 minutes. Water and ethyl acetate were added to the reaction solution, and the organic layer was separated. The resulting organic layer was washed with brine, dried over anhydrous magnesium sulfate, and then concentrated under reduced pressure. The residue was purified by silica gel column chromatography (carrier: Chromatorex NH; elution solvent: heptane-ethyl acetate system->ethyl acetate-methanol system) to obtain 102 mg of the title compound. The property values of the compound are as follows.

$^1$H-NMR (CDCl$_3$) δ(ppm): 0.00 (s, 3H), 0.10 (s, 3H), 0.71 (s, 9H), 1.48 (s, 3H), 1.78-1.92 (m, 3H), 2.08 (dd, J=7.2, 14.4, 1H), 2.20-2.30 (m, 1H), 2.45 (s, 3H), 2.60-2.65 (m, 1H), 2.94-3.10 (m, 2H), 4.00 (s, 3H), 4.10-4.16 (m, 1H), 6.15 (brd, J=6.4 Hz, 1H), 7.08-7.18 (m, 5H), 7.30-7.33 (m, 2H), 7.38-7.43 (m, 1H), 7.89 (s, 1H), 7.94 (s, 1H).

Synthesis of (E)-(6S*,8R*,9aR*)-6-(4-fluorophenyl)-8-hydroxy-3-[3-methoxy-4-(4-methyl-1H-imidazol-1-yl)benzylidene]-8-methyloctahydroquinolizin-4-one TBAF (1.0 M solution in THF, 404 µL) was added to a solution of (E)-(6S*,8R*,9aR*)-8-(tert-butyldimethylsilanyloxy)-6-(4-fluorophenyl)-3-[3-methoxy-4-(4-methyl-1H-imidazol-1-yl)benzylidene]-8-methyloctahydroquinolizin-4-one (102 mg) in THF (2.0 mL), and the reaction solution was stirred at room temperature overnight. A saturated ammonium chloride solution and ethyl acetate were added to the reaction solution, and the organic layer was separated. The resulting organic layer was washed with brine, dried over anhydrous magnesium sulfate, and then concentrated under reduced pressure. The residue was purified by silica gel column chromatography (carrier: Chromatorex NH; elution solvent: heptane-ethyl acetate system->ethyl acetate-methanol system) to obtain 66.4 mg of the title compound. The property values of the compound are as follows.

$^1$H-NMR (CDCl$_3$) δ(ppm): 1.64-1.78 (m, 3H), 2.05 (s, 3H), 2.07-2.16 (m, 2H), 2.32 (s, 3H), 2.45-2.52 (m, 1H), 2.76-2.85 (m, 1H), 2.90-2.99 (m, 1H), 3.87 (s, 3H), 3.94-4.02 (m, 1H), 6.16 (brd, J=6.4 Hz, 1H), 6.95 (t, J=1.2 Hz, 1H), 7.02-7.07 (m, 4H), 7.24-7.30 (m, 3H), 7.75 (d, J=1.2 Hz, 1H), 7.82 (s, 1H).

Synthesis of (E)-(6S,8R,9aR)-6-(4-fluorophenyl)-8-hydroxy-3-[3-methoxy-4-(4-methyl-1H-imidazol-1-yl)benzylidene]-8-methyloctahydroquinolizin-4-one and (E)-(6R,8S,9aS)-6-(4-fluorophenyl)-8-hydroxy-3-[3-methoxy-4-(4-methyl-1H-imidazol-1-yl)benzylidene]-8-methyloctahydroquinolizin-4-one The racemate (E)-(6S*,8R*,9aR*)-6-(4-fluorophenyl)-8-hydroxy-3-[3-methoxy-4-(4-methyl-1H-imidazol-1-yl)benzylidene]-8-methyloctahydroquinolizin-4-one obtained above (66.4 mg) was separated by CHIRALPAK™ IA manufactured by Daicel Chemical Industries, Ltd. (2 cm×25 cm; mobile phase: ethanol) to obtain the title optically active compound with a retention time of 5.7 minutes (27.2 mg; >99% ee) and the title optically active compound with a retention time of 6.9 minutes (28.5 mg; >99% ee).

The property values of the title optically active compound with a retention time of 5.7 minutes (Example 45) are as follows.

$^1$H-NMR (CDCl$_3$) δ(ppm): 1.64-1.78 (m, 3H), 2.05 (s, 3H), 2.07-2.16 (m, 2H), 2.32 (s, 3H), 2.45-2.52 (m, 1H), 2.76-2.85 (m, 1H), 2.90-2.99 (m, 1H), 3.87 (s, 3H), 3.94-4.02 (m, 1H), 6.16 (brd, J=6.4 Hz, 1H), 6.95 (t, J=1.2 Hz, 1H), 7.02-7.07 (m, 4H), 7.24-7.30 (m, 3H), 7.75 (d, J=1.2 Hz, 1H), 7.82 (s, 1H).

The property values of the title optically active compound with a retention time of 6.9 minutes (Example 46) are as follows.

$^1$H-NMR (CDCl$_3$) δ(ppm): 1.64-1.78 (m, 3H), 2.05 (s, 3H), 2.07-2.16 (m, 2H), 2.32 (s, 3H), 2.45-2.52 (m, 1H), 2.76-2.85 (m, 1H), 2.90-2.99 (m, 1H), 3.87 (s, 3H), 3.94-4.02 (m, 1H), 6.16 (brd, J=6.4 Hz, 1H), 6.95 (t, J=1.2 Hz, 1H), 7.02-7.07 (m, 4H), 7.24-7.30 (m, 3H), 7.75 (d, J=1.2 Hz, 1H), 7.82 (s, 1H).

Examples 47, 48, 49, 50, 51, and 52

Synthesis of (E)-(6S,8R,9aR)-6-(4-fluorophenyl)-8-hydroxy-3-[3-methoxy-4-(4-methyl-1H-imidazol-1-yl)benzylidene]-8-methyloctahydroquinolizin-4-one, (E)-(6R,8S,9aS)-6-(4-fluorophenyl)-8-hydroxy-3-[3-methoxy-4-(4-methyl-1H-imidazol-1-yl)benzylidene]-8-methyloctahydroquinolizin-4-one, (E)-(6S,9aR)-6-(4-fluorophenyl)-3-[3-methoxy-4-(4-methyl-1H-imidazol-1-yl)benzylidene]-8-methyl-1,2,3,6,9,9a-hexahydroquinolizin-4-one, (E)-(6R,9aS)-6-(4-fluorophenyl)-3-[3-methoxy-4-(4-methyl-1H-imidazol-1-yl)benzylidene]-8-methyl-1,2,3,6,9,9a-hexahydroquinolizin-4-one, (E)-(6S,8S,9aR)-6-(4-fluorophenyl)-8-hydroxy-3-[3-methoxy-4-(4-methyl-1H-imidazol-1-yl)benzylidene]-8-methyloctahydroquinolizin-4-one, and (E)-(6R,8R,9aS)-6-(4-fluorophenyl)-8-hydroxy-3-[3-methoxy-4-(4-methyl-1H-imidazol-1-yl)benzylidene]-8-methyloctahydroquinolizin-4-one

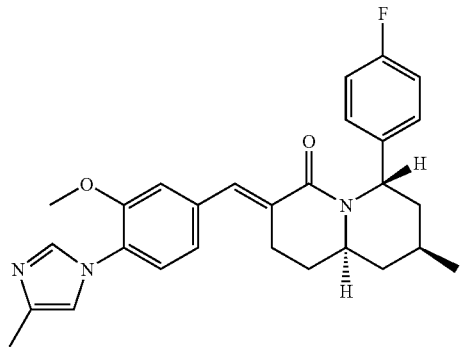

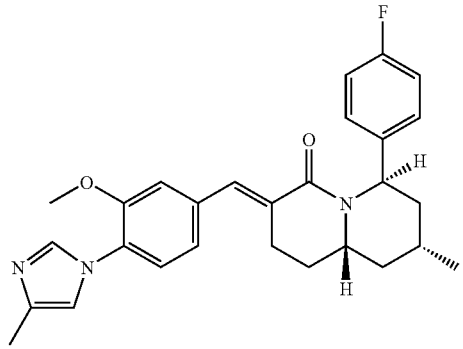

-continued

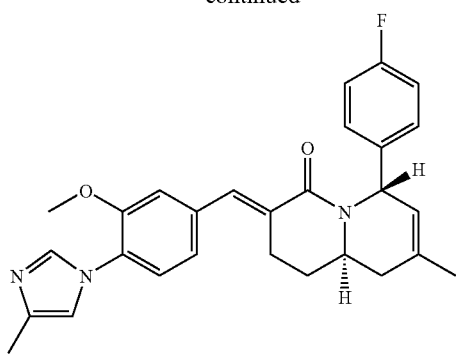

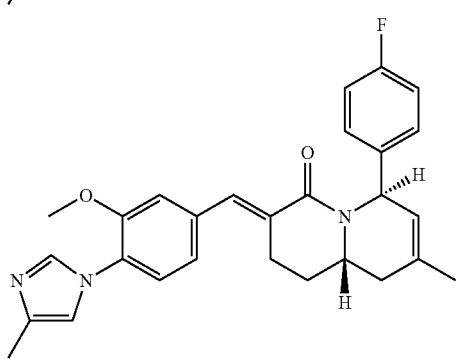

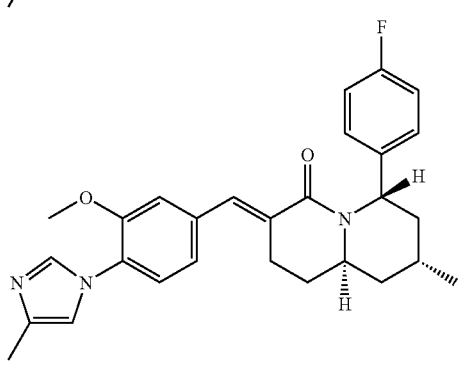

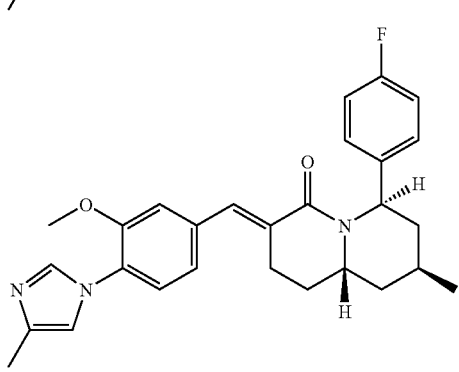

Synthesis of 1-(4-bromobutyryl)-2-(4-fluorophenyl)-2,3-dihydro-1H-pyridin-4-one 6.66 g of the title compound was obtained from 4-methoxypyridine (2.0 mL), 4-fluorophenylmagnesium bromide (1.0 M solution in THF, 20.7 mL), and 4-bromobutyryl chloride (2.4 mL) according to the method described in Tetrahedron Letters, 1986, vol. 27, p. 4549-4552. The property values of the compound are as follows.

$^1$H-NMR (CDCl$_3$) δ(ppm): 2.20-2.32 (m, 2H), 2.79-2.86 (m, 3H), 3.10-3.16 (m, 1H), 3.47-3.55 (m, 2H), 5.47 (brd, J=8.0 Hz, 1H), 6.00 (brs, 1H), 6.99-7.03 (m, 2H), 7.18-7.21 (m, 2H), 7.75 (brs, 1H).

Synthesis of (4S*,9aR*)-4-(4-fluorophenyl)hexahydroquinolizine-2,6-dione 1.05 g of the title compound was obtained from 1-(4-bromobutyryl)-2-(4-fluorophenyl)-2,3-dihydro-1H-pyridin-4-one (2.0 g), tributyltin hydride (1.87 mL), and AIBN (386 mg) according to the method described in The Journal of Organic Chemistry, 1993, vol. 58, p. 4198-4199. The property values of the compound are as follows.

$^1$H-NMR (CDCl$_3$) δ(ppm): 1.58-1.82 (m, 2H), 1.85-2.01 (m, 2H), 2.34-2.39 (m, 1H), 2.45-2.56 (m, 3H), 2.80 (dd, J=15.6, 7.2 Hz, 1H), 2.97-3.01 (m, 1H), 3.49-3.56 (m, 1H), 6.54 (brd, J=7.2 Hz, 1H), 6.99-7.03 (m, 2H), 7.21-7.24 (m, 2H).

Synthesis of (6S*,8R*,9aR*)-6-(4-fluorophenyl)-8-hydroxy-8-methyloctahydroquinolizin-4-one Methylmagnesium bromide (0.96 M solution in THF, 5.98 mL) was added to a solution of (4S*,9aR*)-4-(4-fluorophenyl)hexahydroquinolizine-2,6-dione (1.0 g) in THF (15 mL) under ice-cooling, and the reaction solution was stirred for 50 minutes. Because the starting material did not disappear, methylmagnesium bromide (0.96 M solution in THF, 5.98 mL) was further added to the reaction solution, which was then stirred for 30 minutes. A saturated ammonium chloride solution and ethyl acetate were added to the reaction solution, and the organic layer was separated. The resulting organic layer was washed with brine, dried over anhydrous magnesium sulfate, and then concentrated under reduced pressure. The residue was purified by silica gel column chromatography (elution solvent: heptane-ethyl acetate system->ethyl acetate-methanol system) to obtain a mixture of the starting material with the title compound. Methylmagnesium bromide (0.96 M solution in THF, 5.98 mL) was added to a solution of the resulting mixture in THF (15 mL) again under ice-cooling, and the reaction solution was stirred for one hour. A saturated ammonium chloride solution and ethyl acetate were added to the reaction solution, and the organic layer was separated. The resulting organic layer was washed with brine, dried over anhydrous magnesium sulfate, and then concentrated under reduced pressure. The residue was purified by silica gel column chromatography (elution solvent: heptane-ethyl acetate system->ethyl acetate-methanol system) to obtain a mixture of the starting material with the title compound. Methylmagnesium bromide (0.96 M solution in THF, 5.98 mL) was added to a solution of the mixture obtained again in THF (15 mL) again under ice-cooling, and the reaction solution was stirred for 1.5 hours. A saturated ammonium chloride solution and ethyl acetate were added to the reaction solution, and the organic layer was separated. The resulting organic layer was washed with brine, dried over anhydrous magnesium sulfate, and then concentrated under reduced pressure. The residue was purified by silica gel column chromatography (elution solvent: heptane-ethyl acetate system->ethyl acetate-methanol system) to obtain 760 mg of the title compound. The property values of the compound are as follows.

$^1$H-NMR (CDCl$_3$) δ(ppm): 1.26 (s, 3H), 1.56-1.68 (m, 3H), 1.80-2.01 (m, 3H), 2.01-2.12 (m, 1H), 2.42-2.64 (m, 3H), 3.79-3.85 (m, 1H), 6.06 (brd, J=6.8 Hz, 1H), 6.99-7.05 (m, 2H), 7.18-7.26 (m, 2H).

Synthesis of (E)-(6S,8R,9aR)-6-(4-fluorophenyl)-8-hydroxy-3-[3-methoxy-4-(4-methyl-1H-imidazol-1-yl)benzylidene]-8-methyloctahydroquinolizin-4-one, (E)-(6R,8S,9aS)-6-(4-fluorophenyl)-8-hydroxy-3-[3-methoxy-4-(4-methyl-1H-imidazol-1-yl)benzylidene]-8-methyloctahydroquinolizin-4-one, (E)-(6S,9aR)-6-(4-fluorophenyl)-3-[3-methoxy-4-(4-methyl-1H-imidazol-1-yl)benzylidene]-8-methyl-1,2,3,6,9,9a-hexahydroquinolizin-4-one, (E)-(6R,9aS)-6-(4-fluorophenyl)-3-[3-methoxy-4-(4-methyl-1H-imidazol-1-yl)benzylidene]-8-methyl-1,2,3,6,9,9a-hexahydroquinolizin-4-one, (E)-(6S,8S,9aR)-6-(4-fluorophenyl)-8-hydroxy-3-[3-methoxy-4-(4-methyl-1H-imidazol-1-yl)benzylidene]-8-methyloctahydroquinolizin-4-one, and (E)-(6R,8R,9aS)-6-(4-fluorophenyl)-8-hydroxy-3-[3-methoxy-4-(4-methyl-1H-imidazol-1-yl)benzylidene]-8-methyloctahydroquinolizin-4-one Triethylamine (302 μL) and methanesulfonyl chloride (84 μL) were added to a solution of (6S*,8R*,9aR*)-6-(4-fluorophenyl)-8-hydroxy-8-methyloctahydroquinolizin-4-one (100 mg) in methylene chloride (3.0 mL) under ice-cooling, and the reaction solution was stirred at room temperature overnight. Saturated sodium bicarbonate water and ethyl acetate were added to the reaction solution, and the organic layer was separated. The resulting organic layer was washed with brine, dried over anhydrous magnesium sulfate, and then concentrated under reduced pressure to obtain 72.0 mg of a crude olefin compound mixture. Platinum oxide (10.0 mg) was added to a solution of the resulting crude olefin compound mixture (72.0 mg) in methanol (5.0 mL), and the reaction solution was stirred in a hydrogen atmosphere at 0.4 MPa at room temperature for 31 hours. The reaction solution was filtered through celite, and the filtrate was concentrated under reduced pressure to obtain 70.6 mg of a mixture of a crude reduced compound with the starting material olefin compound. LDA (1.5 M solution in THF, 396 μL) was added to a solution of the resulting mixture of the crude reduced compound with the starting material olefin compound (70.6 mg) in THF (2.0 mL) at 0° C. The reaction solution was stirred at 0° C. for one hour, and then a solution of 3-methoxy-4-(4-methyl-1H-imidazol-1-yl)benzaldehyde (75.9 mg) in THF (2.0 mL) was added to the reaction solution. The reaction solution was further stirred at 0° C. for one hour and 10 minutes. Water and ethyl acetate were added to the reaction solution, and the organic layer was separated. The resulting organic layer was dried over magnesium sulfate and then concentrated under reduced pressure to obtain 39.5 mg of a crude aldol adduct. A solution of the resulting crude aldol adduct (39.5 mg) in methylene chloride (1.0 mL) was cooled to 0° C. Triethylamine (69 μL) and methanesulfonyl chloride (19.2 μL) were added to the reaction solution, which was then stirred at room temperature for two hours. Sodium methoxide (28% solution in methanol, 320 mg) and ethanol (1.0 mL) were added to the reaction solution, which was then stirred at room temperature for 50 minutes. Water and ethyl acetate were added to the reaction solution, and the organic layer was separated. The resulting organic layer was washed with brine, dried over anhydrous magnesium sulfate, and then concentrated under reduced pressure. The residue was purified by silica gel column chromatography (carrier: Chromatorex NH; elution solvent: heptane-ethyl acetate system->ethyl acetate-methanol system) to obtain 23.1 mg of a mixture of three racemates of the title compounds. The resulting racemate mixture was separated by CHIRALPAK™ AD-H manufactured by Daicel Chemical Industries, Ltd. (2 cm×25 cm; mobile phase: ethanol) to obtain an optically active compound of (E)-(6S*,8R*,9aR*)-6-(4-fluorophenyl)-8-hydroxy-3-[3-methoxy-4-(4-methyl-1H-imidazol-1-yl)benzylidene]-8-methyloctahydroquinolizin-4-one with a retention time of 5.9 minutes (2.1 mg; >99% ee) and an optically active compound thereof with a retention time of 8.8 minutes (1.6 mg; >99% ee).

The property values of the title optically active compound with a retention time of 5.9 minutes (Example 47) are as follows.

$^1$H-NMR (CDCl$_3$) δ(ppm): 0.98 (d, J=6.8 Hz, 3H), 1.50-1.65 (m, 4H), 1.77-1.90 (m, 1H), 1.96-2.04 (m, 1H), 2.33 (s, 3H), 2.36-2.43 (m, 1H), 2.65-2.74 (m, 1H), 2.84-2.94 (m, 1H), 3.42-3.48 (m, 1H), 3.87 (s, 3H), 6.21-6.26 (m, 1H), 6.95 (s, 1H), 7.02-7.07 (m, 4H), 7.19-7.29 (m, 3H), 7.80-7.84 (m, 1H), 7.84 (s, 1H).

The property values of the title optically active compound with a retention time of 8.8 minutes (Example 48) are as follows.

$^1$H-NMR (CDCl$_3$) δ(ppm): 0.98 (d, J=6.8 Hz, 3H), 1.50-1.65 (m, 4H), 1.77-1.90 (m, 1H), 1.96-2.04 (m, 1H), 2.33 (s, 3H), 2.36-2.43 (m, 1H), 2.65-2.74 (m, 1H), 2.84-2.94 (m, 1H), 3.42-3.48 (m, 1H), 3.87 (s, 3H), 6.21-6.26 (m, 1H), 6.95 (s, 1H), 7.02-7.07 (m, 4H), 7.19-7.29 (m, 3H), 7.80-7.84 (m, 1H), 7.84 (s, 1H).

Further, an optically active compound of (E)-(6S*,9aR*)-6-(4-fluorophenyl)-3-[3-methoxy-4-(4-methyl-1H-imidazol-1-yl)benzylidene]-8-methyl-1,2,3,6,9,9a-hexahydroquinolizin-4-one with a retention time of 9.8 minutes (3.6 mg; >99% ee) and an optically active compound with a retention time of 17.1 minutes (3.1 mg; >99% ee) were obtained.

The property values of the title optically active compound with a retention time of 9.8 minutes (Example 49) are as follows.

$^1$H-NMR (CDCl$_3$) δ(ppm): 1.71-1.78 (m, 1H), 1.85 (s, 3H), 1.88-1.95 (m, 1H), 1.95-2.03 (m, 1H), 2.32 (s, 3H), 2.38-2.48 (m, 1H), 2.68-2.80 (m, 2H), 3.60-3.72 (m, 1H), 3.85 (s, 3H), 5.60-5.64 (m, 1H), 6.27-6.32 (m, 1H), 6.93 (s, 1H), 6.98-7.06 (m, 4H), 7.24-7.28 (m, 1H), 7.45-7.50 (m, 2H), 7.76 (s, 1H), 7.80 (s, 1H).

The property values of the title optically active compound with a retention time of 17.1 minutes (Example 50) are as follows.

$^1$H-NMR (CDCl$_3$) δ(ppm): 1.71-1.78 (m, 1H), 1.85 (s, 3H), 1.88-1.95 (m, 1H), 1.95-2.03 (m, 1H), 2.32 (s, 3H), 2.38-2.48 (m, 1H), 2.68-2.80 (m, 2H), 3.60-3.72 (m, 1H), 3.85 (s, 3H), 5.60-5.64 (m, 1H), 6.27-6.32 (m, 1H), 6.93 (s, 1H), 6.98-7.06 (m, 4H), 7.24-7.28 (m, 1H), 7.45-7.50 (m, 2H), 7.76 (s, 1H), 7.80 (s, 1H).

(E)-(6S*,8S*,9aR*)-6-(4-fluorophenyl)-8-hydroxy-3-[3-methoxy-4-(4-methyl-1H-imidazol-1-yl)benzylidene]-8-methyloctahydroquinolizin-4-one that failed to be separated in the above operation was separated by CHIRALPAK™ IA manufactured by Daicel Chemical Industries, Ltd. (2 cm×25 cm; mobile phase: ethanol) to obtain an optically active compound with a retention time of 11.2 minutes (3.1 mg; >99% ee) and an optically active compound with a retention time of 16.8 minutes (1.1 mg; >99% ee).

The property values of the title optically active compound with a retention time of 11.2 minutes (Example 51) are as follows.

$^1$H-NMR (CDCl$_3$) δ(ppm): 1.01 (d, J=6.4 Hz, 3H), 1.23-1.36 (m, 3H), 1.65-1.80 (m, 2H), 1.82-2.18 (m, 3H), 2.31 (s, 3H), 2.76-2.92 (m, 2H), 3.82-3.91 (m, 1H), 3.85 (s, 3H), 5.55 (dd, J=10, 7.6 Hz, 1H), 6.93 (s, 1H), 6.99-7.04 (m, 4H), 7.22-7.26 (m, 3H), 7.74-7.77 (m, 1H).

The property values of the title optically active compound with a retention time of 16.8 minutes (Example 52) are as follows.

¹H-NMR (CDCl₃) δ(ppm): 1.01 (d, J=6.4 Hz, 3H), 1.23-1.36 (m, 3H), 1.65-1.80 (m, 2H), 1.82-2.18 (m, 3H), 2.31 (s, 3H), 2.76-2.92 (m, 2H), 3.82-3.91 (m, 1H), 3.85 (s, 3H), 5.55 (dd, J=10, 7.6 Hz, 1H), 6.93 (s, 1H), 6.99-7.04 (m, 4H), 7.22-7.26 (m, 3H), 7.74-7.77 (m, 1H).

Example 53

Synthesis of (E)-(4R,9aR)-7-[3-methoxy-4-(4-methyl-1H-imidazol-1-yl)benzylidene]-4-phenyl-hexahydropyrido[2,1-c][1,4]oxazin-6-one

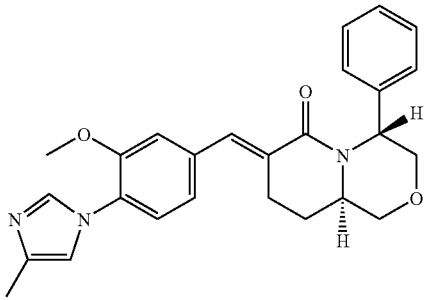

Synthesis of (4R,9aR)-4-phenylhexahydropyrido[2,1-c][1,4]oxazin-6-one

A solution of (S)-1-[(R)-2-hydroxy-1-phenylethyl]-6-oxopiperidine-2-carbonitrile (400 mg) that is a known compound described in a document (see European Journal of Organic Chemistry, 2004, vol. 23, p. 4823-4829) in saturated hydrochloric acid-ethanol (7 mL) was stirred at room temperature for two days. A saturated sodium bicarbonate solution and chloroform were added to the reaction solution, and the organic layer was separated. The resulting organic layer was washed with brine, dried over anhydrous magnesium sulfate, and then concentrated under reduced pressure to obtain 452 mg of a crude ester compound. Sodium borohydride (440 mg) was added to a solution of the resulting crude ester compound (452 mg) in methanol (10 mL) under ice-cooling, and the reaction solution was stirred at 0° C. for one hour and 50 minutes and then at room temperature for 30 minutes. Water and ethyl acetate were added to the reaction solution, and the organic layer was separated. The resulting organic layer was washed with brine, dried over anhydrous magnesium sulfate, and then concentrated under reduced pressure. The residue was purified by silica gel column chromatography (elution solvent: heptane-ethyl acetate system->ethyl acetate-methanol system) to obtain 166 mg of a diol compound. Triethylamine (145 μL) and p-toluenesulfonyl chloride (99.1 mg) were added to a solution of the resulting diol compound (108 mg) in methylene chloride (4.0 mL) under ice-cooling, and the reaction solution was stirred at room temperature overnight. The reaction solution was added dropwise to a solution of potassium tert-butoxide (97.2 mg) in THF (4.0 mL) under ice-cooling. Then, potassium tert-butoxide (194 mg) was added to the reaction solution, which was then stirred at room temperature for three hours and 40 minutes. Water and ethyl acetate were added to the reaction solution, and the organic layer was separated. The resulting organic layer was washed with brine, dried over anhydrous magnesium sulfate, and then concentrated under reduced pressure. The residue was purified by silica gel column chromatography (elution solvent: heptane-ethyl acetate system->ethyl acetate-methanol system) to obtain 23.3 mg of the title compound. The property values of the compound are as follows.

¹H-NMR (CDCl₃) δ(ppm): 1.28-1.38 (m, 1H), 1.57-1.68 (m, 1H), 1.79-1.87 (m, 2H), 2.36-2.46 (m, 1H), 2.51-2.58 (m, 1H), 3.27 (dd, J=11.2, 11.2 Hz, 1H), 3.57-3.64 (m, 1H), 3.83-3.87 (m, 2H), 4.49 (d, J=11.2 Hz, 1H), 5.80 (d, J=3.2 Hz, 1H), 7.24-7.36 (m, 3H), 7.51-7.53 (m, 2H).

Synthesis of (E)-(4R,9aR)-7-[3-methoxy-4-(4-methyl-1H-imidazol-1-yl)benzylidene]-4-phenyl-hexahydropyrido[2,1-c][1,4]oxazin-6-one LDA (1.5 M solution in THF, 118 μL) was added to a solution of (4R,9aR)-4-phenylhexahydropyrido[2,1-c][1,4]oxazin-6-one (27.3 mg) in THF (2.0 mL) at 0° C. The reaction solution was stirred at 0° C. for 30 minutes, and then a solution of 3-methoxy-4-(4-methyl-1H-imidazol-1-yl)benzaldehyde (38.3 mg) in THF (1.0 mL) was added to the reaction solution. The reaction solution was stirred at 0° C. for 35 minutes. Water and ethyl acetate were added to the reaction solution, and the organic layer was separated. The resulting organic layer was dried over magnesium sulfate and then concentrated under reduced pressure. The residue was purified by silica gel column chromatography (elution solvent: heptane-ethyl acetate system->ethyl acetate-methanol system) to obtain 37.1 mg of an alcohol compound. A solution of the resulting alcohol compound (37.1 mg) in methylene chloride (2.0 mL) was cooled to 0° C. Triethylamine (69.3 μL) and methanesulfonyl chloride (19.2 μL) were added to the reaction solution, which was then stirred at room temperature for 45 minutes. Sodium methoxide (28% solution in methanol, 160 mg) and methanol (1.0 mL) were added to the reaction solution, which was then stirred at room temperature for 30 minutes. Water and ethyl acetate were added to the reaction solution, and the organic layer was separated. The resulting organic layer was washed with brine, dried over anhydrous magnesium sulfate, and then concentrated under reduced pressure. The residue was purified by silica gel column chromatography (carrier: Chromatorex NH; elution solvent: heptane-ethyl acetate system->ethyl acetate-methanol system) to obtain 14.5 mg of the title compound. The property values of the compound are as follows.

¹H-NMR (CDCl₃) δ(ppm): 1.39-1.49 (m, 1H), 1.88-1.94 (m, 1H), 2.31 (s, 3H), 2.42-2.50 (m, 1H), 2.97-3.03 (m, 1H), 3.31 (t, J=11.2 Hz, 1H), 3.74-3.82 (m, 1H), 3.85 (s, 3H), 3.86-3.95 (m, 2H), 4.54 (d, J=11.2 Hz, 1H), 5.92 (brd, J=3.2 Hz, 1H), 6.91-7.01 (m, 3H), 7.21-7.39 (m, 4H), 7.58-7.61 (m, 2H), 7.71-7.74 (m, 1H), 7.83 (m, 1H).

Example 54

Synthesis of (E)-(5S,7aR)-5-(3,4-difluorophenyl)-2-[3-methoxy-4-(4-methyl-1H-imidazol-1-yl)benzylidene]hexahydropyrrolidin-3-one

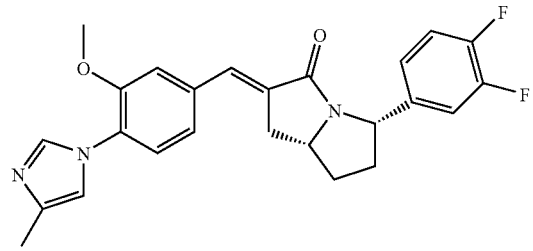

Synthesis of ethyl (R)-2-tert-butoxycarbonylamino-5-(3,4-difluorophenyl)-5-oxopentanoate To a solution of (R)-5-oxopyrrolidine-1,2-dicarboxylic acid 1-tert-butyl ester 2-ethyl ester (6.0 g) in tetrahydrofuran (100 mL), 3,4-difluorophenylmagnesium bromide (0.5 M solution in tetrahydrofuran; 50 mL) was added dropwise at −40° C. over 10 minutes, and the reaction solution was stirred at −40° C. to 0° C. for two hours. Water was added to the solution in small portions, followed by extraction with ethyl acetate. The extract was washed with brine, dried over anhydrous magnesium sulfate, and then concentrated under reduced pressure. The residue was purified by silica gel column chromatography (heptane-ethyl acetate system) to obtain 8.3 g of the title compound. The property values of the compound are as follows.

ESI-MS; m/z 394 [M$^+$+Na].

$^1$H-NMR (CDCl$_3$) δ(ppm): 1.28 (t, J=7.6 Hz, 3H), 1.42 (s, 9H), 2.00-2.13 (m, 1H), 2.25-2.40 (m, 1H), 2.95-3.15 (m, 2H), 4.21 (q, J=7.6 Hz, 2H), 4.30-4.45 (m, 1H), 5.10-5.20 (m, 1H), 7.20-7.30 (m, 1H), 7.70-7.83 (m, 2H).

Synthesis of (2R,5S)-5-(3,4-difluorophenyl)pyrrolidine-1,2-dicarboxylic acid 1-tert-butyl ester 2-ethyl ester A solution of 4 N hydrochloric acid in ethyl acetate (95.8 mL) was added dropwise to a solution of ethyl (R)-2-tert-butoxycarbonylamino-5-(3,4-difluorophenyl)-5-oxopentanoate (8.3 g) in ethyl acetate (93.4 mL) at room temperature, and the solution was stirred at room temperature for four hours. The reaction solution was concentrated under reduced pressure to obtain 7.5 g of a yellow oil. The crude product was dissolved in ethyl acetate (100 mL). Saturated sodium bicarbonate water (100 mL) was added dropwise thereto, and the reaction solution was stirred at room temperature for 20 minutes. The reaction solution was subjected to extraction with ethyl acetate. The extract was washed with brine, dried over anhydrous magnesium sulfate, and then concentrated under reduced pressure to obtain 5.1 g of a pale red oil. Palladium-carbon (containing 50% water, 900 mg) was added to a solution of the resulting pale red oil in ethyl acetate (70 mL), and the reaction solution was stirred in a hydrogen atmosphere for four hours. Palladium-carbon in the reaction solution was removed by filtration through celite, and the filtrate was concentrated under reduced pressure to obtain 5.1 g of a yellow oil. Triethylamine (7.48 mL) and di-tert-butyl dicarbonate (7.84 g) were added to a solution of the resulting yellow oil in DMF (80 mL), and the reaction solution was stirred at room temperature for one hour. The reaction solution was poured into water, followed by extraction with ethyl acetate. The extract was washed with brine, dried over anhydrous magnesium sulfate, and then concentrated under reduced pressure. The residue was purified by silica gel column chromatography (heptane-ethyl acetate system) to obtain 5.9 g of the title compound. The property values of the compound are as follows.

ESI-MS; m/z 378 [M$^+$+Na].

$^1$H-NMR (CDCl$_3$) δ(ppm): 1.19 and 1.41 (s, 9H), 1.30-1.49 (m, 3H), 1.80-1.95 (m, 1H), 1.95-2.10 (m, 1H), 2.15-2.40 (m, 2H), 4.27 (q, J=7.6 Hz, 2H), 4.34 and 4.71 (t, J=7.6 Hz, 1H), 4.40-4.50 and 4.85-4.97 (m, 1H), 7.05-7.15 (m, 1H), 7.20-7.30 (m, 1H), 7.46-7.55 (m, 1H).

Synthesis of tert-butyl (E)-(2S,5R)-2-(3,4-difluorophenyl)-5-(2-methoxycarbonylvinyl)pyrrolidine-1-carboxylate Lithium borohydride (1.45 g) was added to a solution of (2R,5S)-5-(3,4-difluorophenyl)pyrrolidine-1,2-dicarboxylic acid 1-tert-butyl ester 2-ethyl ester (5.9 g) in tetrahydrofuran (50 mL) at 0° C., and the reaction solution was stirred at room temperature for 12 hours. The reaction solution was added to ice water, followed by extraction with ethyl acetate. The extract was washed with brine, dried over anhydrous magnesium sulfate, and then concentrated under reduced pressure to obtain 3.9 g of an alcohol compound. DMSO (1.32 mL) was added dropwise to a solution of oxalyl chloride (1.6 mL) in dichloromethane (50 mL) at −70° C., and the reaction solution was stirred at the same temperature for three minutes. A solution of the above alcohol compound (3.9 g) in dichloromethane (20 mL) was added dropwise to the solution at −60° C., and the reaction solution was stirred at the same temperature for 15 minutes. Triethylamine (13 mL) was added dropwise to the solution, and the reaction solution was stirred at −60° C. to 0° C. for 30 minutes. The reaction solution was poured into water, followed by extraction with ethyl acetate. The extract was washed with brine, dried over anhydrous magnesium sulfate, and then concentrated under reduced pressure to obtain 3.9 g of an aldehyde compound. Sodium hydride (60% oil, 0.754 g) was added to a solution of trimethyl phosphonoacetate (3.43 g) in DMF (20 mL) at room temperature, and the reaction solution was stirred for 20 minutes. The reaction solution was added to a solution of the above aldehyde (3.9 g) in DMF (10 mL), and the reaction solution was stirred at room temperature for two hours. The reaction solution was poured into water, followed by extraction with ethyl acetate. The extract was washed with brine, dried over anhydrous magnesium sulfate, and then concentrated under reduced pressure. The residue was purified by silica gel column chromatography (heptane-ethyl acetate system) to obtain 4.5 g of the title compound. The property values of the compound are as follows.

ESI-MS; m/z 390 [M$^+$+Na].

$^1$H-NMR (CDCl$_3$) δ(ppm): 1.10-1.50 (m, 9H), 1.77-1.93 (m, 2H), 2.08-2.20 (m, 1H), 2.22-2.36 (m, 1H), 3.78 (s, 3H), 4.40-4.66 (m, 1H), 4.66-4.94 (m, 1H), 6.03 (d, J=14.4 Hz, 1H), 6.90-7.16 (m, 4H).

Synthesis of tert-butyl (2S,5R)-2-(3,4-difluorophenyl)-5-(2-methoxycarbonylethyl)pyrrolidine-1-carboxylate Palladium-carbon (containing 50% water, 900 mg) was added to a solution of tert-butyl (E)-(2S,5R)-2-(3,4-difluorophenyl)-5-(2-methoxycarbonylvinyl)pyrrolidine-1-carboxylate (4.5 g) in ethyl acetate (100 mL), and the reaction solution was stirred in a hydrogen atmosphere at room temperature for 2.5 hours. Palladium-carbon in the reaction solution was removed by filtration through celite, and the filtrate was concentrated under reduced pressure to obtain 4.1 g of the title compound. The property values of the compound are as follows.

ESI-MS; m/z 392 [M$^+$+Na].

$^1$H-NMR (CDCl$_3$) δ(ppm): 1.10-1.50 (m, 9H), 1.60-1.70 (m, 1H), 1.70-1.90 (m, 2H), 1.94-2.06 (m, 1H), 2.16-2.32 (m, 2H), 2.36-2.50 (m, 2H), 3.70 (s, 3H), 3.98 (s, 1H), 4.60-4.90 (m, 1H), 6.90-7.14 (m, 3H).

Synthesis of (5S,7aR)-5-(3,4-difluorophenyl)hexahydropyrrolidin-3-one

A solution of 4 N hydrochloric acid in ethyl acetate (10 mL) was added to a solution of tert-butyl (2S,5R)-2-(3,4-difluorophenyl)-5-(2-methoxycarbonylethyl)pyrrolidine-1-carboxylate (1.5 g) in ethyl acetate (10 mL), and the reaction solution was stirred at 50° C. for 30 minutes. The reaction solution was concentrated under reduced pressure to obtain 1.5 g of a yellow oil. The crude product was dissolved in ethanol (10 mL). A 5 N sodium hydroxide solution (10 mL) was added thereto, and the reaction solution was stirred at 50° C. for one hour. The reaction solution was cooled to 0° C. and neutralized with 5 N hydrochloric acid. The solution was concentrated under reduced pressure, and the residue was suspended in dichloromethane (20 mL). Thionyl chloride (2.5 mL) was added thereto, and the reaction solution was stirred at 50° C. for one hour. The reaction solution was concentrated under reduced pressure, and the residue was suspended in dichloromethane (10 mL), followed by addition of a 5 N sodium hydroxide solution (15 mL). The reaction solution was stirred at room temperature for 30 minutes and then poured into ice water, followed by extraction with ethyl acetate. The extract was washed with brine, dried over anhydrous magnesium sulfate, and then concentrated under reduced pressure. The residue was purified by silica gel column chromatography (heptane-ethyl acetate system) to obtain 770 mg of the title compound.

The property values of the compound are as follows.
ESI-MS; m/z 238 [M$^+$+H].
$^1$H-NMR (CDCl$_3$) δ(ppm): 1.55-1.70 (m, 1H), 1.85-2.10 (m, 3H), 2.30-2.40 (m, 1H), 2.50-2.70 (m, 1H), 2.57 (dd, J=8.8, 16.8 Hz, 1H), 2.70-2.85 (m, 1H), 4.03-4.18 (m, 1H), 4.61 (d, J=9.2 Hz, 1H), 6.89-7.02 (m, 2H), 7.07-7.15 (m, 1H).

Synthesis of diethyl [(5S,7aR)-5-(3,4-difluorophenyl)-3-oxohexahydropyrrolidin-2-yl]phosphonate Iodotrimethylsilane (0.162 mL) was added to a solution of (5S,7aR)-5-(3,4-difluorophenyl)hexahydropyrrolidin-3-one (200 mg) and N,N,N',N'-tetramethylethylenediamine (0.430 mL) in dichloromethane (5 mL) at 0° C., and the reaction solution was stirred at 0° C. for 30 minutes. Iodine (289 mg) was added to the reaction solution at 0° C., and the reaction solution was stirred at the same temperature for 40 minutes. The reaction solution was added to ice-sodium thiosulfate solution, followed by extraction with ethyl acetate. The extract was washed with 1 N hydrochloric acid and brine, dried over anhydrous magnesium sulfate, and then concentrated under reduced pressure to obtain 320 mg of an iodine compound. A solution of the resulting iodine compound (320 mg) in triethyl phosphite (5 mL) was stirred at 130° C. for two hours. The reaction solution was returned to room temperature and concentrated under reduced pressure to obtain 400 mg of the title compound. The property value of the compound is as follows.
ESI-MS; m/z 374 [M$^+$+H].

Synthesis of (E)-(5S,7aR)-5-(3,4-difluorophenyl)-2-[3-methoxy-4-(4-methyl-1H-imidazol-1-yl)benzylidene]hexahydropyrrolidin-3-one Lithium hydroxide (56.8 mg) was added to a mixed solution of 3-methoxy-4-(4-methyl-1H-imidazol-1-yl)benzaldehyde (170 mg) and diethyl [(5S,7aR)-5-(3,4-difluorophenyl)-3-oxohexahydropyrrolidin-2-yl]phosphonate obtained above (400 mg) in tetrahydrofuran (1 mL)-ethanol (4 mL), and the reaction solution was stirred at room temperature for 12 hours. The reaction solution was added to ice-sodium bicarbonate water, followed by extraction with ethyl acetate. The extract was washed with brine, dried over anhydrous magnesium sulfate, and then concentrated under reduced pressure. The residue was purified by silica gel column chromatography (heptane-ethyl acetate system) to obtain 250 mg of a crude product of the title compound. The resulting crude product (20 mg) was re-refined by a preparative optical resolution column (CHIRALPAK™ AD-H manufactured by Daicel Chemical Industries, Ltd. (2 cm×25 cm), ethanol-hexane system) to obtain 8.4 mg of the title compound. The property values of the compound are as follows.
ESI-MS; m/z 436 [M$^+$+H].
$^1$H-NMR (CDCl$_3$) δ(ppm): 1.70-1.84 (m, 1H), 2.11 (dd, J=7.2, 12.8 Hz, 1H), 2.18 (quint, J=6.0 Hz, 1H), 2.32 (s, 3H), 2.60-2.76 (m, 1H), 2.93 (ddd, J=3.6, 6.8, 16.4 Hz, 1H), 3.40 (ddd, J=2.0, 5.6, 16.4 Hz, 1H), 3.89 (s, 3H), 4.06-4.16 (m, 1H), 4.79 (d, J=9.2 Hz, 1H), 6.92-7.04 (m, 3H), 7.09 (d, J=1.2 Hz, 1H), 7.10-7.18 (m, 2H), 7.20-7.24 (m, 1H), 7.28 (d, J=8.0 Hz, 1H), 7.76 (d, J=1.2 Hz, 1H).

Example 55

Synthesis of (E)-(3S,9aS)-3-(3,4-difluorophenyl)-6-[3-methoxy-4-(4-methyl-1H-imidazol-1-yl)benzylidene]octahydropyrrolo[1,2-a]azepin-5-one

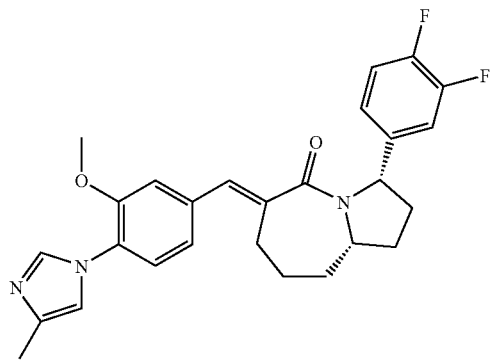

Synthesis of tert-butyl (2S,5S)-2-(3,4-difluorophenyl)-5-[(E)-4-methoxycarbonyl-3-butenyl]pyrrolidine-1-carboxylate A solution of tert-butyl (2S,5R)-2-(3,4-difluorophenyl)-5-(2-methoxycarbonylethyl)pyrrolidine-1-carboxylate (2.2 g) in tetrahydrofuran (20 mL) was added dropwise to a solution of lithium aluminum hydride (0.295 g) in tetrahydrofuran (20 mL) at 0° C., and the reaction solution was stirred at the same temperature for 30 minutes. Water (0.3 mL), a 15% sodium hydroxide solution (0.3 mL), and water (0.9 mL) were sequentially added to the reaction solution, which was then stirred for 20 minutes. Then, the inorganic salt was removed by filtration, and the filtrate was concentrated to obtain 2.0 g of an alcohol compound. DMSO (0.753 mL) was added dropwise to a solution of oxalyl chloride (0.91 mL) in dichloromethane (30 mL) at −70° C., and the reaction solution was stirred at the same temperature for three minutes. A solution of the resulting alcohol compound (2.0 g) in dichloromethane (10 mL) was added dropwise to the reaction solution at −60° C., and the reaction solution was stirred at the same temperature for 15 minutes. Triethylamine (6.9 mL) was added dropwise to the reaction solution, which was then stirred at −60° C. to 0° C. for 30 minutes. The reaction solution was poured into water, followed by extraction with ethyl acetate. The extract was washed with brine, dried over anhydrous magnesium sulfate, and then concentrated under reduced pressure to obtain 2.0 g of an aldehyde compound. Sodium hydride (60% oil, 0.306 g) was added to a solution of trimethyl phosphonoacetate (1.39 g) in DMF (20 mL) at room temperature, and the reaction solution was stirred for 20 minutes. The reaction solution was added to a solution of the resulting aldehyde compound (2.0 g) in DMF (10 mL), and the reaction solution was stirred at room temperature for 12 hours. The reaction solution was poured into water, followed by extraction with ethyl acetate. The extract was washed with brine, dried over anhydrous magnesium sulfate, and then concentrated under reduced pressure. The residue was purified by silica gel column chromatography (heptane-ethyl acetate system) to obtain 1.7 g of the title compound. The property value of the compound is as follows.

ESI-MS; m/z 418 [M$^+$+Na].

Synthesis of tert-butyl (2S,5S)-2-(3,4-difluorophenyl)-5-(4-methoxycarbonylbutyl)pyrrolidine-1-carboxylate Palladium-carbon (containing 50% water, 0.492 g) was added to a solution of tert-butyl (2S,5S)-2-(3,4-difluorophenyl)-5-[(E)-4-methoxycarbonyl-3-butenyl]pyrrolidine-1-carboxylate (1.7 g) in ethyl acetate (60 mL), and the reaction solution was stirred in a hydrogen atmosphere at room temperature for two hours. Palladium-carbon in the reaction solution was removed by filtration, and the filtrate was concentrated under reduced pressure to obtain 1.7 g of the title compound. The property values of the compound are as follows.

ESI-MS; m/z 420 [M$^+$+Na]. $^1$H-NMR (CDCl$_3$) δ(ppm): 1.00-1.88 (m, 16H), 1.90-2.10 (m, 2H), 2.20-2.30 (m, 1H), 2.36 (t, J=7.2 Hz, 2H), 3.67 (s, 3H), 3.80-4.00 (m, 1H), 4.50-4.90 (m, 1H), 6.89-6.96 (m, 1H), 6.97-7.13 (m, 3H).

Synthesis of (3S,9aS)-3-(3,4-difluorophenyl)octahydropyrrolo[1,2-a]azepin-5-one tert-Butyl (2S,5S)-2-(3,4-difluorophenyl)-5-(4-methoxycarbonylbutyl)pyrrolidine-1-carboxylate (1.7 g) was dissolved in ethyl acetate (10 mL). A solution of 4 N hydrochloric acid in ethyl acetate (17 mL) was added thereto, and the reaction solution was stirred at 50° C. for 30 minutes. The reaction solution was concentrated under reduced pressure to obtain 1.5 g of a yellow oil. The property value of the compound is as follows.

ESI-MS; m/z 298 [M$^+$+H].

The crude product (1.5 g) was dissolved in ethanol (10 mL). A 5 N sodium hydroxide solution (20 mL) was added thereto, and the reaction solution was stirred at 50° C. for one hour. The reaction solution was cooled to 0° C. and neutralized with 5 N hydrochloric acid. The solution was concentrated under reduced pressure, and the residue was suspended in dichloromethane (20 mL). Thionyl chloride (4.0 mL) was added thereto, and the reaction solution was stirred at 50° C. for 30 minutes. The reaction solution was concentrated under reduced pressure, and the residue was suspended in dichloromethane (10 mL), followed by addition of a 5 N sodium hydroxide solution (15 mL). The reaction solution was stirred at room temperature for 30 minutes and then poured into ice water, followed by extraction with ethyl acetate. The extract was washed with brine, dried over anhydrous magnesium sulfate, and then concentrated under reduced pressure. The residue was purified by silica gel column chromatography (heptane-ethyl acetate system) to obtain 0.75 g of the title compound. The property values of the compound are as follows.

ESI-MS; m/z 266 [M$^+$+H].
$^1$H-NMR (CDCl$_3$) δ(ppm): 1.46-1.74 (m, 4H), 1.86-2.22 (m, 6H), 2.43-2.53 (m, 1H), 2.66 (dd, J=7.2, 14.4 Hz, 1H), 3.76-3.88 (m, 1H), 5.25 (d, J=7.6 Hz, 1H), 6.93-6.99 (m, 1H), 7.00-7.13 (m, 2H).

Synthesis of diethyl [(3S,9aS)-3-(3,4-difluorophenyl)-5-oxooctahydropyrrolo[1,2-a]azepin-6-yl]phosphonate Iodotrimethylsilane (0.164 mL) was added to a solution of (3S,9aS)-3-(3,4-difluorophenyl)octahydropyrrolo[1,2-a]azepin-5-one (0.225 g) and N,N,N',N'-tetramethylethylenediamine (0.435 mL) in dichloromethane (5.36 mL) at 0° C., and the reaction solution was stirred at 0° C. for 30 minutes. Iodine (0.291 g) was added to the reaction solution at 0° C., and the reaction solution was stirred at the same temperature for 40 minutes. The reaction solution was added to ice-sodium thiosulfate solution, followed by extraction with ethyl acetate. The extract was washed with 1 N hydrochloric acid and brine, dried over anhydrous magnesium sulfate, and then concentrated under reduced pressure to obtain 0.33 g of an iodine compound. A solution of the resulting iodine compound (0.33 g) in triethyl phosphite (7 mL) was stirred at 130° C. for two hours. The reaction solution was returned to room temperature and concentrated under reduced pressure to obtain 0.52 g of the title compound. The property value of the compound is as follows.

ESI-MS; m/z 402 [M$^+$+H].

Synthesis of (E)-(3S,9aS)-3-(3,4-difluorophenyl)-6-[3-methoxy-4-(4-methyl-1H-imidazol-1-yl)benzylidene]octahydropyrrolo[1,2-a]azepin-5-one Lithium hydroxide (0.0668 g) was added to a mixed solution of 3-methoxy-4-(4-methyl-1H-imidazol-1-yl)benzaldehyde (0.20 g) and diethyl [(3S,9aS)-3-(3,4-difluorophenyl)-5-oxooctahydropyrrolo[1,2-a]azepin-6-yl]phosphonate obtained above (0.52 g) in tetrahydrofuran (1 mL)-ethanol (4 mL), and the reaction solution was stirred at room temperature for 12 hours. The reaction solution was added to ice-sodium bicarbonate water, followed by extraction with ethyl acetate. The extract was washed with brine, dried over anhydrous magnesium sulfate, and then concentrated under reduced pressure. The residue was purified by silica gel column chromatography (heptane-ethyl acetate system) to obtain 0.223 g of the title compound. The property values of the compound are as follows.

ESI-MS; m/z 464 [M$^+$+H]. $^1$H-NMR (CDCl$_3$) δ(ppm): 1.70-2.40 (m, 9H), 2.31 (s, 3H), 2.90-3.00 (m, 1H), 3.85 (s, 3H), 3.84-3.98 (m, 1H), 5.28-5.34 (m, 1H), 6.92-6.96 (m, 1H), 6.98-7.18 (m, 6H), 7.25 (d, J=7.6 Hz, 1H), 7.71 (d, J=1.6 Hz, 1H).

Example 56

Synthesis of (E)-(3S,8aS)-3-(4-chlorophenyl)-6-[3-methoxy-4-(4-methyl-1H-imidazol-1-yl)benzylidene]hexahydroindolizin-5-one

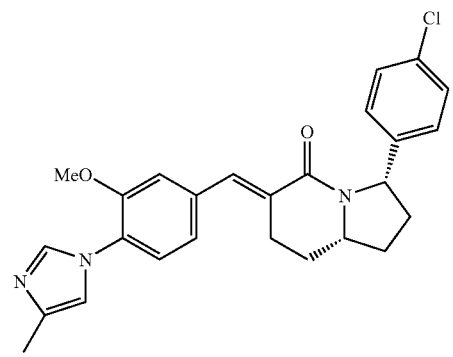

Synthesis of ethyl (R)-2-tert-butoxycarbonylamino-5-(4-chlorophenyl)-5-oxopentanoate To a solution of (R)-5-oxopyrrolidine-1,2-dicarboxylic acid 1-tert-butyl ester 2-ethyl ester (CAS No. 128811-48-3; 4.0 g) in tetrahydrofuran (100 mL), 4-chlorophenylmagnesium bromide (1.0 M solution in diethyl ether; 17.1 mL) was added dropwise at −40° C. over 20 minutes, and the reaction solution was stirred at −40° C. to 0° C. for one hour. Water was added to the solution in small portions at 0° C., followed by extraction with ethyl acetate. The extract was washed with brine, dried over anhydrous magnesium sulfate, and then concentrated under reduced pressure. The residue was purified by silica gel column chromatography (heptane-ethyl acetate system) to obtain 5.6 g of the title compound as a colorless oil. The property values of the compound are as follows.

ESI-MS; m/z 392 [M$^+$+Na]. $^1$H-NMR (CDCl$_3$)$_6$(ppm): 1.28 (t, J=7.2 Hz, 3H), 1.42 (s, 9H), 2.00-2.50 (m, 2H), 2.95-3.20 (m, 2H), 4.10-4.50 (m, 2H), 4.10-5.20 (m, 2H), 7.41-7.47 (m, 2H), 7.86-7.92 (m, 2H).

Synthesis of ethyl (R)-5-(4-chlorophenyl)-3,4-dihydro-2H-pyrrole-2-carboxylate A solution of 4 N hydrochloric acid in ethyl acetate (30 mL) was added dropwise to a solution of ethyl (R)-2-tert-butoxycarbonylamino-5-(4-chlorophenyl)-5-oxopentanoate (5.6 g) in ethyl acetate (30 mL) at room temperature, and the reaction solution was stirred at room temperature for two hours. The reaction solution was concentrated under reduced pressure to obtain 5.0 g of a yellow oil. Saturated sodium bicarbonate water (100 mL) was added dropwise to a solution of the crude product in ethyl acetate (100 mL), and the reaction solution was stirred at room temperature for 20 minutes. The reaction solution was subjected to extraction with ethyl acetate. The extract was washed with brine, dried over anhydrous magnesium sulfate, and then concentrated under reduced pressure to obtain 3.5 g of the title compound as a pale yellow oil. The property values of the compound are as follows.

ESI-MS; m/z 525 [2M$^+$+Na]. $^1$H-NMR (CDCl$_3$) δ(ppm): 1.32 (t, J=7.2 Hz, 3H), 2.18-2.43 (m, 2H), 2.90-3.03 (m, 1H), 3.05-3.20 (m, 1H), 4.25 (q, J=7.2 Hz, 2H), 4.85-4.95 (m, 1H), 7.36-7.41 (m, 2H), 7.79-7.85 (m, 2H).

Synthesis of (2R,5S)-5-(4-chlorophenyl)pyrrolidine-1,2-dicarboxylic acid 1-tert-butyl ester 2-ethyl ester Sodium borohydride (1.05 g) was added to a solution of ethyl (R)-5-(4-chlorophenyl)-3,4-dihydro-2H-pyrrole-2-carboxylate (3.5 g) in methanol (80 mL)-acetic acid (20 mL) at −45° C. over five minutes. The reaction solution was stirred at −45° C. to 0° C. for three hours. A disodium hydrogen phosphate solution was added to the reaction solution. The reaction solution was stirred at room temperature for 20 minutes, and the organic solvent was evaporated under reduced pressure. The residue was subjected to extraction with ethyl acetate. The organic layer was washed with sodium bicarbonate water, dried over anhydrous magnesium sulfate, and then concentrated under reduced pressure to obtain 3.6 g of a yellow oil. Triethylamine (7.49 mL) and di-tert-butyl dicarbonate (3.76 g) were added to a solution of the resulting oil in dichloromethane (50 mL), and the reaction solution was stirred at room temperature for one hour. The reaction solution was poured into ice water, followed by extraction with ethyl acetate. The extract was washed with brine, dried over anhydrous magnesium sulfate, and then concentrated under reduced pressure. The residue was purified by silica gel column chromatography (heptane-ethyl acetate system) to obtain 3.3 g of the title compound as a yellow oil. The property values of the compound are as follows.

ESI-MS; m/z 376 [M$^+$+Na]. $^1$H-NMR (CDCl$_3$) δ(ppm): 1.17 and 1.41 (s, 9H), 1.26-1.38 (m, 3H), 1.84-2.10 (m, 2H), 2.16-2.36 (m, 2H), 4.20-4.30 (m, 2H), 4.30-5.00 (m, 2H), 7.25-7.35 (m, 2H), 7.45-7.60 (m, 2H).

Synthesis of tert-butyl (2S,5R)-2-(4-chlorophenyl)-5-((E)-2-methoxycarbonylvinyl)pyrrolidine-1-carboxylate Lithium borohydride (813 mg) was added to a solution of (2R,5S)-5-(4-chlorophenyl)pyrrolidine-1,2-dicarboxylic acid 1-tert-butyl ester 2-ethyl ester (3.3 g) in tetrahydrofuran (50 mL) at 0° C., and the reaction solution was stirred at room temperature for 12 hours. The reaction solution was added to ice water, followed by extraction with ethyl acetate. The extract was washed with brine, dried over anhydrous magnesium sulfate, and then concentrated under reduced pressure to obtain 3.0 g of an alcohol compound as a yellow oil. DMSO (1.09 mL) was added dropwise to a solution of oxalyl chloride (1.24 mL) in dichloromethane (40 mL) at −70° C., and the reaction solution was stirred at the same temperature for three minutes. A solution of the above alcohol compound (3.0 g) in dichloromethane (20 mL) was added dropwise thereto at −60° C., and the reaction solution was stirred at the same temperature for 15 minutes. Triethylamine (10.7 mL) was added dropwise to the solution, and the reaction solution was stirred at −60° C. to 0° C. for 30 minutes. The reaction solution was poured into water, followed by extraction with ethyl acetate. The extract was washed with brine, dried over anhydrous magnesium sulfate, and then concentrated under reduced pressure to obtain 3.0 g of an aldehyde compound as a pale yellow oil. Sodium hydride (60% oil, 0.579 g) was added to a solution of trimethyl phosphonoacetate (2.63 g) in DMF (20 mL) at room temperature, and the reaction solution was stirred for 20 minutes. This solution was added to a solution of the above aldehyde (3.0 g) in DMF (10 mL) at room temperature, and the reaction solution was stirred at room temperature for one hour. The reaction solution was poured into water, followed by extraction with ethyl acetate. The extract was washed with brine, dried over anhydrous magnesium sulfate, and then concentrated under reduced pressure. The residue was purified by silica gel column chromatography (heptane-ethyl acetate system) to obtain 2.8 g of the title compound as a yellow oil. The property values of the compound are as follows.

ESI-MS; m/z 388 [M$^+$+Na]. $^1$H-NMR (CDCl$_3$) δ(ppm): 1.00-1.50 (m, 9H), 1.75-1.95 (m, 2H), 2.05-2.20 (m, 1H), 2.20-2.35 (m, 1H), 3.77 (s, 3H), 4.30-5.00 (m, 2H), 5.95-6.10 (m, 1H), 6.95-7.05 (m, 1H), 7.18 (d, J=8.4 Hz, 2H), 7.30 (d, J=8.4 Hz, 2H).

Synthesis of methyl (E)-3-[(2R,5S)-1-(3-butenoyl)-5-(4-chlorophenyl)pyrrolidin-2-yl]acrylate A solution of 4 N hydrochloric acid in ethyl acetate (19.4 mL) was added dropwise to a solution of tert-butyl (2S,5R)-2-(4-chlorophenyl)-5-((E)-2-methoxycarbonylvinyl)pyrrolidine-1-carboxylate (2.8 g) in ethyl acetate (5 mL) at room temperature, and the reaction solution was stirred at 50° C. for 30 minutes. The reaction solution was concentrated under reduced pressure to obtain 2.5 g of a yellow solid. Diethyl cyanophosphonate (1.97 mL) was added dropwise to a solution of the resulting yellow solid (2.5 g), vinylacetic acid (1.1 mL), and triethylamine (3.63 mL) in DMF (40 mL) at 0° C., and the reaction solution was stirred at the same temperature for two hours. The reaction solution was poured into ice water, followed by extraction with ethyl acetate. The extract was sequentially washed with a 1 N hydrochloric acid solution, saturated sodium bicarbonate water, and brine, and then dried over anhydrous magnesium sulfate and concentrated under reduced pressure. The residue was purified by silica gel column chromatography (heptane-ethyl acetate system) to obtain 2.2 g of the title compound as a yellow oil. The property values of the compound are as follows.

ESI-MS; m/z 334 [M$^+$+H]. $^1$H-NMR (CDCl$_3$) δ(ppm): 1.30-3.20 (m, 6H), 3.76 and 3.79 (s, 3H), 4.60-5.20 (m, 4H), 5.70-6.20 (m, 2H), 6.90-7.40 (m, 5H).

Synthesis of (3S,8aR)-3-(4-chlorophenyl)-2,3,6,8a-tetrahydro-1H-indolizin-3-one

Grubbs catalyst 2nd generation (559 mg) was added to a solution of methyl (E)-3-[(2R,5S)-1-(3-butenoyl)-5-(4-chlorophenyl)pyrrolidin-2-yl]acrylate (2.2 g) in dichloromethane (100 mL), and the reaction solution was heated under reflux in a nitrogen atmosphere for five hours. The reaction solution was returned to room temperature. Triethylamine (4 mL) was added to the reaction solution, which was then stirred for 20 minutes. The reaction solution was concentrated under reduced pressure, and the residue was purified by silica gel column chromatography (heptane-ethyl acetate system) to obtain 1.3 g of the title compound as a brown oil. The property values of the compound are as follows.

ESI-MS; m/z 248 [M$^+$+H]. $^1$H-NMR (CDCl$_3$) δ(ppm): 1.70-1.90 (m, 2H), 2.05-2.15 (m, 1H), 2.25-2.45 (m, 1H), 2.90-3.05 (m, 2H), 4.20-4.35 (m, 1H), 5.10 (d, J=8.8 Hz, 1H), 5.98-6.04 (m, 1H), 6.06-6.12 (m, 1H), 7.00-7.08 (m, 2H), 7.20-7.28 (m, 2H).

Synthesis of (3S,8aS)-3-(4-chlorophenyl)hexahydroindolizin-5-one

Platinum oxide (151 mg) was added to a solution of (3S,8aR)-3-(4-chlorophenyl)-2,3,6,8a-tetrahydro-1H-indolizin-3-one (1.3 g) in methanol (50 mL), and the reaction solution was stirred in a hydrogen atmosphere at room temperature for five hours. Platinum oxide was removed from the reaction solution by filtration, and the filtrate was concentrated under reduced pressure. The residue was purified by silica gel column chromatography (heptane-ethyl acetate system) to obtain 1.0 g of the title compound as a pale brown solid. The property values of the compound are as follows.

ESI-MS; m/z 250 [M$^+$+H]. $^1$H-NMR (CDCl$_3$) δ(ppm): 1.50-1.90 (m, 4H), 1.90-2.10 (m, 2H), 2.15-2.50 (m, 4H), 3.52-3.65 (m, 1H), 5.08 (d, J=8.8 Hz, 1H), 7.06 (d, J=8.4 Hz, 2H), 7.25 (d, J=8.4 Hz, 2H).

Synthesis of diethyl [(3S,8aR)-3-(4-chlorophenyl)-5-oxooctahydroindolizin-6-yl]phosphonate Iodotrimethylsilane (0.763 mL) was added dropwise to a solution of (3S,8aS)-3-(4-chlorophenyl)hexahydroindolizin-5-one (1.0 g) and N,N,N',N'-tetramethylethylenediamine (2.05 mL) in dichloromethane (40 mL) at 0° C., and the reaction solution was stirred at 0° C. for 30 minutes. Iodine (1.36 g) was added to the reaction solution at 0° C., and the reaction solution was stirred at the same temperature for 40 minutes. The reaction solution was added to ice-sodium thiosulfate solution, followed by extraction with ethyl acetate. The extract was washed with 1 N hydrochloric acid and brine, dried over anhydrous magnesium sulfate, and then concentrated under reduced pressure to obtain an iodine compound.

A solution of the resulting iodine compound in triethyl phosphite (20 mL) was stirred at 130° C. for two hours. The reaction solution was returned to room temperature and concentrated under reduced pressure to obtain 2.5 g of the title compound. The property value of the compound is as follows.

ESI-MS; m/z 386 [M$^+$+H].

Synthesis of (E)-(3S,8aS)-3-(4-chlorophenyl)-6-[3-methoxy-4-(4-methyl-1H-imidazol-1-yl)benzylidene]hexahydroindolizin-5-one Lithium hydroxide (355 mg) was added to a mixed solution of 3-methoxy-4-(4-methyl-1H-imidazol-1-yl)benzaldehyde (875 mg) and diethyl [(3S,8aR)-3-(4-chlorophenyl)-5-oxooctahydroindolizin-6-yl]phosphonate (2.5 g) in tetrahydrofuran (8 mL)-ethanol (30 mL), and the reaction solution was stirred under shading at room temperature for five hours. The reaction solution was poured into ice water, followed by extraction with ethyl acetate. The extract was washed with brine, dried over anhydrous magnesium sulfate, and then concentrated under reduced pressure. The residue was purified by silica gel column chromatography (heptane-ethyl acetate system) to obtain 1.43 g of the title compound as a colorless solid. The property values of the compound are as follows.

ESI-MS; m/z 448 [M$^+$+H]. $^1$H-NMR (CDCl$_3$) δ(ppm): 1.66-1.88 (m, 3H), 2.02-2.12 (m, 1H), 2.26-2.40 (m, 2H), 2.30 (s, 3H), 2.68-2.82 (m, 1H), 3.10-3.20 (m, 1H), 3.76-3.90 (m, 1H), 3.85 (s, 3H), 5.20 (d, J=8.8 Hz, 1H), 6.94 (s, 1H), 7.02-7.16 (m, 2H), 7.12 (d, J=8.4 Hz, 2H), 7.20-7.34 (m, 1H), 7.28 (d, J=8.4 Hz, 2H), 7.72 (d, J=1.6 Hz, 1H), 7.76 (d, J=2.0 Hz, 1H).

Example 57

Synthesis of (E)-(3S,8aS)-3-(2,4,5-trifluorophenyl)-6-[3-methoxy-4-(4-methyl-1H-imidazol-1-yl)benzylidene]hexahydroindolizin-5-one

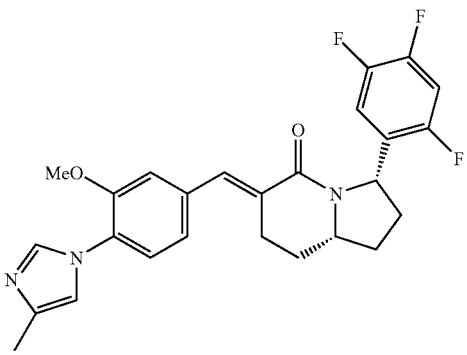

Synthesis of ethyl (R)-2-tert-butoxycarbonylamino-5-(2,4,5-trifluorophenyl)-5-oxopentanoate To a suspension of magnesium (0.452 g) in tetrahydrofuran (20 mL), 1-bromo-2,4,5-trifluorobenzene (2.2 mL) was added dropwise at 55° C. over 15 minutes, and the reaction solution was stirred at room temperature for 30 minutes. This solution was added dropwise to a solution of (R)-5-oxopyrrolidine-1,2-dicarboxylic acid 1-tert-butyl ester 2-ethyl ester (4.0 g) in tetrahydrofuran (25 mL) at −40° C. over 10 minutes, and the reaction solution was stirred at −40° C. to 0° C. for one hour. Water was added to the solution in small portions at 0° C., followed by extraction with ethyl acetate. The extract was washed with brine, dried over anhydrous magnesium sulfate, and then concentrated under reduced pressure. The residue was purified by silica gel column chromatography (heptane-ethyl acetate system) to obtain 4.5 g of the title compound as a colorless oil. The property values of the compound are as follows.

$^1$H-NMR (CDCl$_3$) δ(ppm): 1.29 (t, J=7.2 Hz, 3H), 1.42 (s, 9H), 1.90-2.10 (m, 1H), 2.20-2.40 (m, 1H), 2.90-3.20 (m, 2H), 4.21 (q, J=7.2 Hz, 2H), 4.20-4.50 (m, 1H), 5.00-5.20 (m, 1H), 6.95-7.05 (m, 1H), 7.70-7.80 (m, 1H).

Synthesis of ethyl (R)-5-(2,4,5-trifluorophenyl)-3,4-dihydro-2H-pyrrole-2-carboxylate A solution of 4 N hydrochloric acid in ethyl acetate (20 mL) was added dropwise to a solution of ethyl (R)-2-tert-butoxycarbonylamino-5-(2,4,5-trifluorophenyl)-5-oxopentanoate (4.5 g) in ethyl acetate (20 mL) at room temperature, and the reaction solution was stirred for one hour at room temperature. The reaction solution was concentrated under reduced pressure to obtain 4.0 g of a yellow oil. Saturated sodium bicarbonate water (30 mL) was added dropwise to a solution of the crude product in ethyl acetate (20 mL). The reaction solution was stirred at room temperature for 20 minutes, and the organic layer was separated. The resulting organic layer was washed with brine, dried over anhydrous magnesium sulfate, and then concentrated under reduced pressure to obtain 2.8 g of the title compound as a pale yellow oil. The property value of the compound is as follows.

ESI-MS; m/z 272 [M$^+$+H].

Synthesis of (2R,5S)-5-(2,4,5-trifluorophenyl)pyrrolidine-1,2-dicarboxylic acid 1-tert-butyl ester 2-ethyl ester 10% palladium-carbon (containing 50% water, 0.95 g) was added to a solution of ethyl (R)-5-(2,4,5-trifluorophenyl)-3,4-dihydro-2H-pyrrole-2-carboxylate (2.8 g) in ethyl acetate (50 mL), and the reaction solution was stirred in a hydrogen atmosphere at room temperature for six hours. Palladium-carbon in the reaction solution was removed by filtration, and then the filtrate was concentrated under reduced pressure to obtain 2.8 g of a reduced compound. Triethylamine (2.13 mL) and di-tert-butyl dicarbonate (2.67 g) were added to a solution of the resulting reduced compound in DMF (30 mL), and the reaction solution was stirred at room temperature for six hours. The reaction solution was poured into ice water, followed by extraction with ethyl acetate. The extract was washed with brine, dried over anhydrous magnesium sulfate, and then concentrated under reduced pressure. The residue was purified by silica gel column chromatography (heptane-ethyl acetate system) to obtain 4.2 g of the title compound as a yellow oil. The property values of the compound are as follows.

$^1$H-NMR (CDCl$_3$) δ(ppm): 1.23 and 1.43 (s, 9H), 1.20-1.50 (m, 3H), 1.82-2.08 (m, 2H), 2.18-2.44 (m, 2H), 4.15-4.40 (m, 2H), 4.15-5.30 (m, 2H), 6.80-6.95 (m, 1H), 7.85-8.05 (m, 1H).

Synthesis of tert-butyl (2S,5R)-2-(2,4,5-trifluorophenyl)-5-((E)-2-methoxycarbonylvinyl)pyrrolidine-1-carboxylate Lithium borohydride (0.863 g) was added to a solution of (2R,5S)-5-(2,4,5-trifluorophenyl)pyrrolidine-1,2-dicarboxylic acid 1-tert-butyl ester 2-ethyl ester (4.2 g) in tetrahydrofuran (40 mL) at 0° C., and the reaction solution was stirred at room temperature for 12 hours. The reaction solution was added to ice water, followed by extraction with ethyl acetate. The extract was washed with brine, dried over anhydrous magnesium sulfate, and then concentrated under reduced pressure to obtain 3.3 g of an alcohol compound as a yellow oil. DMSO (1.35 mL) was added dropwise to a solution of oxalyl chloride (1.63 mL) in dichloromethane (40 mL) at −70° C., and the reaction solution was stirred at the same temperature for three minutes. A solution of the above alcohol compound (3.3 g) in dichloromethane (10 mL) was added dropwise thereto at −60° C., and the reaction solution was stirred at the same temperature for 15 minutes. Triethylamine (11.2 mL) was added dropwise to the solution, and the reaction solution was stirred at −60° C. to 0° C. for 30 minutes. The reaction solution was poured into water, followed by extraction with ethyl acetate. The extract was washed with brine, dried over anhydrous magnesium sulfate, and then concentrated under reduced pressure to obtain 3.3 g of an aldehyde compound as a pale yellow oil. Sodium hydride (60% oil, 0.460 g) was added to a solution of trimethyl phosphonoacetate (2.19 g) in DMF (30 mL) at room temperature, and the reaction solution was stirred for 20 minutes. This solution was added to a solution of the above aldehyde (3.3 g) in DMF (20 mL) at room temperature, and the reaction solution was stirred at room temperature for one hour. The reaction solution was poured into water, followed by extraction with ethyl acetate. The extract was washed with brine, dried over anhydrous magnesium sulfate, and then concentrated under reduced pressure. The residue was purified by silica gel column chromatography (heptane-ethyl acetate system) to obtain 3.3 g of the title compound as a yellow oil. The property values of the compound are as follows.

$^1$H-NMR (CDCl$_3$) δ(ppm): 1.00-1.50 (m, 9H), 1.80-1.90 (m, 2H), 2.10-2.20 (m, 1H), 2.30-2.45 (m, 1H), 3.78 (s, 3H), 4.30-5.20 (m, 2H), 5.95-6.15 (m, 1H), 6.85-7.15 (m, 3H).

Synthesis of methyl (E)-3-[(2R,5S)-1-(3-butenoyl)-5-(2,4,5-trifluorophenyl)pyrrolidin-2-yl]acrylate A solution of 4 N hydrochloric acid in ethyl acetate (17.8 mL) was added dropwise to a solution of tert-butyl (2S,5R)-2-(2,4,5-trifluorophenyl)-5-((E)-2-methoxycarbonylvinyl)pyrrolidine-1-carboxylate (3.3 g) in ethyl acetate (20 mL) at the same temperature, and the reaction solution was stirred at 50° C. for 30 minutes. The reaction solution was concentrated under reduced pressure to obtain 2.7 g of a yellow solid. Diethyl cyanophosphonate (2.22 mL) was added dropwise to a solution of the resulting yellow solid (2.7 g), vinylacetic acid (1.23 mL), and triethylamine (4.07 mL) in DMF (30 mL) at 0° C., and the reaction solution was stirred at the same temperature for two hours. The reaction solution was poured into ice water, followed by extraction with ethyl acetate. The extract was washed with a 1 N hydrochloric acid solution, saturated sodium bicarbonate water, and brine, and then dried over anhydrous magnesium sulfate and concentrated under reduced pressure. The residue was purified by silica gel column chromatography (heptane-ethyl acetate system) to obtain 2.2 g of the title compound as a yellow oil. The property value of the compound is as follows.

ESI-MS; m/z 354 [M$^+$+H].

Synthesis of (3S,8aR)-3-(2,4,5-trifluorophenyl)-2,3,6,8a-tetrahydro-1H-indolizin-3-one Grubbs catalyst 2nd generation (0.424 g) was added to a solution of methyl (E)-3-[(2R,5S)-1-(3-butenoyl)-5-(2,4,5- trifluorophenyl)pyrrolidin-2-yl]acrylate (2.2 g) in dichloromethane (40 mL), and the reaction solution was heated under reflux in a nitrogen atmosphere for five hours. The reaction solution was returned to room temperature. Triethylamine (8 mL) was added to the reaction solution, which was then stirred for 20 minutes. The reaction solution was concentrated under reduced pressure, and the residue was purified by silica gel column chromatography (heptane-ethyl acetate system) to obtain 1.0 g of the title compound as a brown oil. The property values of the compound are as follows.

ESI-MS; m/z 268 [M$^+$+H]. $^1$H-NMR (CDCl$_3$) δ(ppm): 1.68-1.82 (m, 1H), 1.86 (dd, J=6.0, 12.8 Hz, 1H), 2.10-2.20 (m, 1H), 2.30-2.43 (m, 1H), 2.90-3.08 (m, 2H), 4.20-4.35 (m, 1H), 5.31 (d, J=9.2 Hz, 1H), 6.00-6.15 (m, 2H), 6.65-6.75 (m, 1H), 6.85-6.95 (m, 1H).

Synthesis of (3S,8aS)-3-(2,4,5-trifluorophenyl) hexahydroindolizin-5-one

Platinum oxide (84.9 mg) was added to a solution of (3S,8aR)-3-(2,4,5-trifluorophenyl)-2,3,6,8a-tetrahydro-1H-indolizin-3-one (1.0 g) in methanol (30 mL), and the reaction solution was stirred in a hydrogen atmosphere at room temperature for four hours. Platinum oxide in the reaction solution was removed by filtration, and the filtrate was concentrated under reduced pressure. The residue was purified by silica gel column chromatography (heptane-ethyl acetate system) to obtain 0.75 g of the title compound as a pale brown solid. The property value of the compound is as follows.

ESI-MS; m/z 270 [M$^+$+H].

Synthesis of diethyl [(3S,8aR)-3-(2,4,5-trifluorophenyl)-5-oxooctahydroindolizin-6-yl]phosphonate Iodotrimethylsilane (0.476 mL) was added dropwise to a solution of (3S,8aS)-3-(2,4,5-trifluorophenyl)hexahydroindolizin-5-one (0.75 g) and N,N,N',N'-tetramethylethylenediamine (1.39 mL) in dichloromethane (20 mL) at 0° C., and the reaction solution was stirred at 0° C. for 30 minutes. Iodine (0.85 g) was added to the reaction solution at 0° C., and the reaction solution was stirred at the same temperature for 40 minutes. The reaction solution was added to ice-sodium thiosulfate solution, followed by extraction with ethyl acetate. The extract was washed with 1 N hydrochloric acid and brine, dried over anhydrous magnesium sulfate, and then concentrated under reduced pressure to obtain 1.1 g of an iodine compound.

A solution of the iodine compound (1.1 g) in triethyl phosphite (6 mL) was stirred at 130° C. for one hour. The reaction solution was returned to room temperature and concentrated under reduced pressure to obtain 2.0 g of the title compound. The property value of the compound is as follows.

ESI-MS; m/z 406 [M$^+$+H].

Synthesis of (E)-(3S,8aS)-3-(2,4,5-trifluorophenyl)-6-[3-methoxy-4-(4-methyl-1H-imidazol-1-yl)benzylidene]hexahydroindolizin-5-one Lithium hydroxide (0.265 g) was added to a mixed solution of 3-methoxy-4-(4-methyl-1H-imidazol-1-yl)benzaldehyde (0.60 g) and diethyl [(3S,8aR)-3-(2,4,5-trifluorophenyl)-5-oxooctahydroindolizin-6-yl]phosphonate (2.0 g) in tetrahydrofuran (4 mL)-ethanol (16 mL), and the reaction solution was stirred under shading at room temperature for 12 hours. The reaction solution was poured into ice water, followed by extraction with ethyl acetate. The extract was washed with brine, dried over anhydrous magnesium sulfate, and then concentrated under reduced pressure. The residue was purified by silica gel column chromatography (heptane-ethyl acetate system) to obtain 0.97 g of the title compound as a colorless solid. The property values of the compound are as follows.

ESI-MS; m/z 468 [M$^+$+H]. $^1$H-NMR (CDCl$_3$) δ(ppm): 1.60-1.83 (m, 2H), 1.83-1.94 (m, 1H), 2.00-2.18 (m, 1H), 2.25-2.40 (m, 2H), 2.31 (s, 3H), 2.68-2.84 (m, 1H), 3.12-3.23 (m, 1H), 3.74-3.90 (m, 1H), 3.86 (s, 3H), 5.39 (d, J=8.8 Hz, 1H), 6.74-6.88 (m, 1H), 6.88-7.00 (m, 2H), 7.06 (s, 1H), 7.09 (d, J=8.0 Hz, 1H), 7.24-7.34 (m, 1H), 7.73 (s, 1H), 7.70 (s, 1H).

Example 58

Synthesis of (E)-(3S,8aS)-3-(2,3,4-trifluorophenyl)-6-[3-methoxy-4-(4-methyl-1H-imidazol-1-yl)benzylidene]hexahydroindolizin-5-one

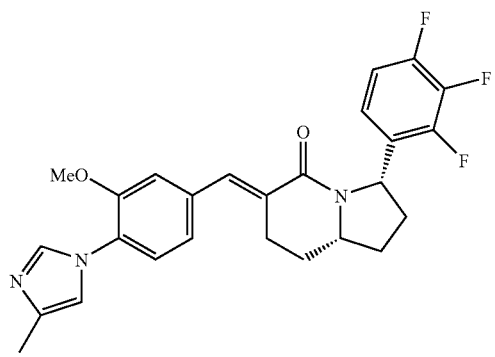

Synthesis of ethyl (R)-2-tert-butoxycarbonylamino-5-(2,3,4-trifluorophenyl)-5-oxopentanoate To a suspension of magnesium (0.452 g) in tetrahydrofuran (20 mL), 1-bromo-2,3,4-trifluorobenzene (2.21 mL) was added dropwise at 55° C. over 15 minutes, and the reaction solution was stirred at room temperature for 30 minutes. This solution was added dropwise to a solution of (R)-5-oxopyrrolidine-1,2-dicarboxylic acid 1-tert-butyl ester 2-ethyl ester (4.0 g) in tetrahydrofuran (25 mL) at −40° C. over 10 minutes, and the reaction solution was stirred at −40° C. to 0° C. for one hour. Water was added to the solution in small portions at 0° C., followed by extraction with ethyl acetate. The extract was washed with brine, dried over anhydrous magnesium sulfate, and then concentrated under reduced pressure. The residue was purified by silica gel column chromatography (heptane-ethyl acetate system) to obtain 4.2 g of the title compound as a colorless oil. The property values of the compound are as follows.

$^1$H-NMR (CDCl$_3$) δ(ppm): 1.29 (t, J=7.2 Hz, 3H), 1.42 (s, 9H), 1.95-2.20 (m, 1H), 2.20-2.40 (m, 1H), 2.95-3.20 (m, 2H), 4.22 (q, J=7.2 Hz, 2H), 4.20-4.50 (m, 1H), 5.05-5.25 (m, 1H), 7.00-7.15 (m, 1H), 7.60-7.75 (m, 1H).

Synthesis of ethyl (R)-5-(2,3,4-trifluorophenyl)-3,4-dihydro-2H-pyrrole-2-carboxylate A solution of 4 N hydrochloric acid in ethyl acetate (20 mL) was added dropwise to a solution of ethyl (R)-2-tertbutoxycarbonylamino-5-(2,3,4-trifluorophenyl)-5-oxopentanoate (4.2 g) in ethyl acetate (15 mL) at room temperature, and the reaction solution was stirred for one hour at room temperature. The reaction solution was concentrated under reduced pressure to obtain 4.5 g of a yellow oil. Saturated sodium bicarbonate water (30 mL) was added dropwise to a solution of the crude product in ethyl acetate (20 mL), and the reaction solution was stirred at room temperature for 20 minutes. The reaction solution was subjected to extraction with ethyl acetate. The extract was washed with brine, dried over anhydrous magnesium sulfate, and then concentrated under reduced pressure to obtain 2.7 g of the title compound as a pale yellow oil. The property values of the compound are as follows.

ESI-MS; m/z 272 [M$^+$+H]. $^1$H-NMR (CDCl$_3$) δ(ppm): 1.32 (t, J=7.2 Hz, 3H), 2.18-2.30 (m, 1H), 2.32-2.44 (m, 1H), 2.98-3.10 (m, 1H), 3.12-3.24 (m, 1H), 4.25 (q, J=7.2 Hz, 2H), 4.85-4.90 (m, 1H), 6.95-7.05 (m, 1H), 7.25-7.85 (m, 1H).

Synthesis of (2R,5S)-5-(2,3,4-trifluorophenyl)pyrrolidine-1,2-dicarboxylic acid 1-tert-butyl ester 2-ethyl ester Palladium-carbon (containing 50% water, 0.44 g) was added to a solution of ethyl (R)-5-(2,3,4-trifluorophenyl)-3,4-dihydro-2H-pyrrole-2-carboxylate (2.2 g) in ethyl acetate (132 mL), and the reaction solution was stirred in a hydrogen atmosphere at room temperature for 12 hours. Palladium-carbon in the reaction solution was removed by filtration, and then the filtrate was concentrated under reduced pressure to obtain 2.20 g of a reduced compound. Triethylamine (5.23 mL) and di-tert-butyl dicarbonate (2.80 g) were added to a solution of the resulting reduced compound in DMF (30.3 mL), and the reaction solution was stirred at room temperature for six hours. The reaction solution was poured into ice water, followed by extraction with ethyl acetate. The extract was washed with brine, dried over anhydrous magnesium sulfate, and then concentrated under reduced pressure. The residue was purified by silica gel column chromatography (heptane-ethyl acetate system) to obtain 4.2 g of the title compound as a yellow oil. The property values of the compound are as follows.

$^1$H-NMR (CDCl$_3$) δ(ppm): 1.22 and 1.53 (s, 9H), 1.18-1.48 (m, 3H), 1.85-2.08 (m, 2H), 2.20-2.44 (m, 2H), 4.26 (q, J=7.2 Hz, 2H), 4.25-5.25 (m, 2H), 6.90-7.05 (m, 1H), 7.70-7.90 (m, 1H).

Synthesis of methyl (E)-3-[(2R,5S)-1-(3-butenoyl)-5-(2,3,4-trifluorophenyl)pyrrolidin-2-yl]acrylate Lithium borohydride (0.863 g) was added to a solution of (2R,5S)-5-(2,3,4-trifluorophenyl)pyrrolidine-1,2-dicarboxylic acid 1-tert-butyl ester 2-ethyl ester (4.2 g) in tetrahydrofuran (40 mL) at 0° C., and the reaction solution was stirred at room temperature for 4 hours. The reaction solution was added to ice water, followed by extraction with ethyl acetate. The extract was washed with brine, dried over anhydrous magnesium sulfate, and then concentrated under reduced pressure to obtain 3.3 g of an alcohol compound as a yellow oil. DMSO (1.12 mL) was added dropwise to a solution of oxalyl chloride (1.26 mL) in dichloromethane (40 mL) at −70° C., and the reaction solution was stirred at the same temperature for three minutes. A solution of the above alcohol compound (3.3 g) in dichloromethane (10 mL) was added dropwise thereto at −60° C., and the reaction solution was stirred at the same temperature for 15 minutes. Triethylamine (8.78 mL) was added dropwise to the solution, and the reaction solution was stirred at −60° C. to 0° C. for 30 minutes. The reaction solution was poured into water, followed by extraction with ethyl acetate. The extract was washed with brine, dried over anhydrous magnesium sulfate, and then concentrated under reduced pressure to obtain 3.3 g of an aldehyde compound as a pale yellow oil. Sodium hydride (60% oil, 0.460 g) was added to a solution of trimethyl phosphonoacetate (2.19 g) in DMF (30 mL) at room temperature, and the reaction solution was stirred for 20 minutes. This solution was added to a solution of the above aldehyde (3.3 g) in DMF (20 mL) at room temperature, and the reaction solution was stirred at room temperature for one hour. The reaction solution was poured into water, followed by extraction with ethyl acetate. The extract was washed with brine, dried over anhydrous magnesium sulfate, and then concentrated under reduced pressure. The residue was purified by silica gel column chromatography (heptane-ethyl acetate system) to obtain 1.8 g of tert-butyl (2S,5R)-2-(2,3,4-trifluorophenyl)-5-[(E)-(2-methoxycarbonylvinyl)]pyrrolidine-1-carboxylate as a yellow oil.

A solution of 4 N hydrochloric acid in ethyl acetate (9.73 mL) was added dropwise to a solution of tert-butyl (2S,5R)-2-(2,3,4-trifluorophenyl)-5-[(E)-(2-methoxycarbonylvinyl)]pyrrolidine-1-carboxylate (1.8 g) in ethyl acetate (20 mL) at room temperature, and the reaction solution was stirred at 50° C. for 30 minutes. The reaction solution was concentrated under reduced pressure to obtain 1.8 g of a yellow solid. Diethyl cyanophosphonate (1.21 mL) was added dropwise to a solution of the resulting yellow solid (1.8 g), vinylacetic acid (0.671 mL), and triethylamine (2.22 mL) in DMF (30 mL) at 0° C., and the reaction solution was stirred at room temperature for two hours. The reaction solution was poured into ice water, followed by extraction with ethyl acetate. The extract was sequentially washed with a 1 N hydrochloric acid solution, saturated sodium bicarbonate water, and brine, and then dried over anhydrous magnesium sulfate and concentrated under reduced pressure. The residue was purified by silica gel column chromatography (heptane-ethyl acetate system) to obtain 1.2 g of the title compound as a yellow oil. The property value of the compound is as follows.

ESI-MS; m/z 354 [M$^+$+H].

Synthesis of (3S,8aR)-3-(2,3,4-trifluorophenyl)-2,3,6,8a-tetrahydro-1H-indolizin-3-one Grubbs catalyst 2nd generation (0.231 g) was added to a solution of methyl (E)-3-[(2R,5S)-1-(3-butenoyl)-5-(2,3,4-trifluorophenyl)pyrrolidin-2-yl]acrylate (1.2 g) in dichloromethane (20 mL), and the reaction solution was heated under reflux in a nitrogen atmosphere for five hours. The reaction solution was returned to room temperature. Triethylamine (4 mL) was added to the reaction solution, which was then stirred for 20 minutes. The reaction solution was concentrated under reduced pressure, and the residue was purified by silica gel column chromatography (heptane-ethyl acetate system) to obtain 0.61 g of the title compound as a brown oil. The property values of the compound are as follows.

ESI-MS; m/z 268 [M$^+$+H]. $^1$H-NMR (CDCl$_3$) δ(ppm): 1.68-1.82 (m, 1H), 1.87 (dd, J=6.0, 12.8 Hz, 1H), 2.10-2.18 (m, 1H), 2.32-2.45 (m, 1H), 2.90-3.10 (m, 2H), 4.24-4.34 (m, 1H), 5.33 (d, J=8.8 Hz, 1H), 5.96-6.06 (m, 1H), 6.06-6.14 (m, 1H), 6.56-6.65 (m, 1H), 6.78-6.90 (m, 1H).

Synthesis of (3S,8aS)-3-(2,3,4-trifluorophenyl)hexahydroindolizin-5-one

Platinum oxide (0.0596 g) was added to a solution of (3S,8aR)-3-(2,3,4-trifluorophenyl)-2,3,6,8a-tetrahydro-1H-indolizin-3-one (0.61 g) in methanol (30.5 mL), and the reaction solution was stirred in a hydrogen atmosphere at room temperature for five hours. Platinum oxide in the reaction solution was removed by filtration, and the filtrate was concentrated under reduced pressure. The residue was purified by silica gel column chromatography (heptane-ethyl acetate system) to obtain 0.46 g of the title compound as a pale brown solid. The property values of the compound are as follows.

ESI-MS; m/z 270 [M$^+$+H]. $^1$H-NMR (CDCl$_3$) δ(ppm): 1.50-1.70 (m, 2H), 1.74-1.90 (m, 2H), 1.95-2.10 (m, 2H), 2.16-2.50 (m, 4H), 3.55-3.70 (m, 1H), 5.28 (d, J=9.2 Hz, 1H), 6.60-6.70 (m, 1H), 6.70-6.95 (m, 1H).

Synthesis of diethyl [(3S,8aR)-3-(2,3,4-trifluorophenyl)-5-oxooctahydroindolizin-6-yl]phosphonate Iodotrimethylsilane (0.316 mL) was added dropwise to a solution of (3S,8aS)-3-(2,3,4-trifluorophenyl)hexahydroindolizin-5-one (0.46 g) and N,N,N',N'-tetramethylethylenediamine (0.877 mL) in dichloromethane (11.5 mL) at 0° C., and the reaction solution was stirred at 0° C. for 30 minutes. Iodine (0.563 g) was added to the reaction solution at 0° C., and the reaction solution was stirred at the same temperature for 40 minutes. The reaction solution was added to ice-sodium thiosulfate solution, followed by extraction with ethyl acetate. The extract was washed with 1 N hydrochloric acid and brine, dried over anhydrous magnesium sulfate, and then concentrated under reduced pressure to obtain 0.71 g of an iodine compound.

A solution of the resulting iodine compound (0.71 g) in triethyl phosphite (4 mL) was stirred at 130° C. for two hours. The reaction solution was returned to room temperature and concentrated under reduced pressure to obtain 2.0 g of the title compound. The property value of the compound is as follows.

ESI-MS; m/z 406 [M$^+$+H].

Synthesis of (E)-(3S,8aS)-3-(2,3,4-trifluorophenyl)-6-[3-methoxy-4-(4-methyl-1H-imidazol-1-yl)benzylidene]hexahydroindolizin-5-one Lithium hydroxide (0.177 g) was added to a mixed solution of 3-methoxy-4-(4-methyl-1H-imidazol-1-yl)benzaldehyde (0.40 g) and diethyl [(3S,8aR)-3-(2,3,4-trifluorophenyl)-5-oxooctahydroindolizin-6-yl]phosphonate (2.0 g) in tetrahydrofuran (4 mL)-ethanol (16 mL), and the reaction solution was stirred under shading at room temperature for 12 hours. The reaction solution was poured into ice water, followed by extraction with ethyl acetate. The extract was washed with brine, dried over anhydrous magnesium sulfate, and then concentrated under reduced pressure. The residue was purified by silica gel column chromatography (heptane-ethyl acetate system) to obtain 0.506 g of the title compound as a colorless solid. The property values of the compound are as follows.

ESI-MS; m/z 468 [M$^+$+H]. $^1$H-NMR (CDCl$_3$) δ(ppm): 1.64-1.82 (m, 2H), 1.86-1.94 (m, 1H), 2.08-2.16 (m, 1H), 2.26-2.44 (m, 2H), 2.30 (s, 3H), 2.70-2.83 (m, 1H), 3.12-3.20 (m, 1H), 3.76-3.88 (m, 1H), 3.85 (s, 3H), 5.41 (d, J=8.8 Hz, 1H), 6.70-6.80 (m, 1H), 6.84-6.96 (m, 2H), 7.02-7.12 (m, 2H), 7.20-7.30 (m, 1H), 7.72 (s, 1H), 7.76 (d, J=2.4 Hz, 1H).

Example 59

Synthesis of (E)-(3S 0.8aS)-3-(2,5-difluorophenyl)-6-[3-methoxy-4-(4-methyl-1H-imidazol-1-yl)benzylidene]hexahydroindolizin-5-one

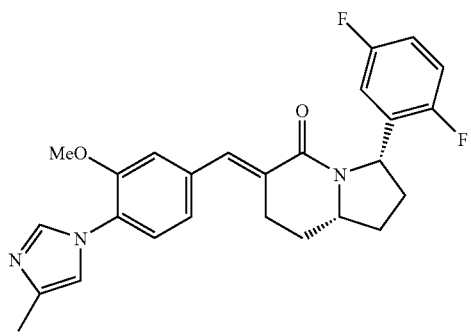

Synthesis of ethyl (R)-2-tert-butoxycarbonylamino-5-(2,5-difluorophenyl)-5-oxopentanoate To a suspension of magnesium (0.569 g) in tetrahydrofuran (20 mL), 1-bromo-2,5-difluorobenzene (2.64 mL) was added dropwise at 55° C. over 15 minutes, and the reaction solution was stirred at room temperature for one hour. This solution was added dropwise to a solution of (R)-5-oxopyrrolidine-1,2-dicarboxylic acid 1-tert-butyl ester 2-ethyl ester (5.0 g) in tetrahydrofuran (25 mL) at −40° C. over 20 minutes, and the reaction solution was stirred at −40° C. to 0° C. for one hour. Water was added to the solution in small portions at 0° C., followed by extraction with ethyl acetate. The extract was washed with brine, dried over anhydrous magnesium sulfate, and then concentrated under reduced pressure. The residue was purified by silica gel column chromatography (heptane-ethyl acetate system) to obtain 5.7 g of the title compound as a colorless oil. The property values of the compound are as follows.

$^1$H-NMR (CDCl$_3$) δ(ppm): 1.20-1.46 (m, 12H), 1.96-2.40 (m, 2H), 2.95-3.20 (m, 2H), 4.10-5.40 (m, 4H), 6.80-7.60 (m, 3H).

Synthesis of ethyl (R)-5-(2,5-difluorophenyl)-3,4-dihydro-2H-pyrrole-2-carboxylate A solution of 4 N hydrochloric acid in ethyl acetate (25.9 mL) was added dropwise to a solution of ethyl (R)-2-tert-butoxycarbonylamino-5-(2,5-difluorophenyl)-5-oxopentanoate (5.7 g) in ethyl acetate (20.7 mL) at room temperature, and the reaction solution was stirred for one hour at room temperature. The reaction solution was concentrated under reduced pressure to obtain 6.0 g of a yellow oil. Saturated sodium bicarbonate water (30 mL) was added dropwise to a solution of the crude product in ethyl acetate (20 mL), and the reaction solution was stirred at room temperature for 20 minutes. The reaction solution was subjected to extraction with ethyl acetate. The extract was washed with brine, dried over anhydrous magnesium sulfate, and then concentrated under reduced pressure to obtain 4.2 g of the title compound as a pale yellow oil. The property values of the compound are as follows.

ESI-MS; m/z 254 [M$^+$+H]. $^1$H-NMR (CDCl$_3$) δ(ppm): 1.32 (t, J=7.2 Hz, 3H), 2.16-2.30 (m, 1H), 2.30-2.44 (m, 1H), 2.98-3.12 (m, 1H), 3.14-3.26 (m, 1H), 4.25 (q, J=7.2 Hz, 2H), 4.85-4.95 (m, 1H), 7.00-7.15 (m, 2H), 7.70-7.80 (m, 1H).

Synthesis of methyl (E)-3-[(2R,5S)-1-(3-butenoyl)-5-(2,5-difluorophenyl)pyrrolidin-2-yl]acrylate Sodium borohydride (0.99 g) was added to a solution of ethyl (R)-5-(2,5-difluorophenyl)-3,4-dihydro-2H-pyrrole-2-carboxylate (3.3 g) in methanol (40 mL)-acetic acid (10 mL) at −60° C. over 15 minutes. The reaction solution was stirred at −60° C. to 0° C. for one hour. A sodium bicarbonate solution was added to the reaction solution. The mixture was stirred at room temperature for 20 minutes, and the organic solvent was evaporated under reduced pressure. The residue was subjected to extraction with ethyl acetate, washed with sodium bicarbonate water, and then dried over anhydrous magnesium sulfate. The residue was concentrated under reduced pressure to obtain 3.3 g of a yellow oil. Triethylamine (7.06 mL) and di-tert-butyl dicarbonate (3.55 g) were added to a solution of the resulting oil in dichloromethane (50 mL), and the reaction solution was stirred at room temperature for 12 hours. The reaction solution was poured into ice water, followed by extraction with ethyl acetate. The extract was washed with brine, dried over anhydrous magnesium sulfate, and then concentrated under reduced pressure. The residue was purified by silica gel column chromatography (heptane-ethyl acetate system) to obtain 4.2 g of (2R,5S)-5-(2,5-difluorophenyl)pyrrolidine-1,2-dicarboxylic acid 1-tert-butyl ester 2-ethyl ester as a yellow oil.

Lithium borohydride (1.03 g) was added to a solution of (2R,5S)-5-(2,5-difluorophenyl)pyrrolidine-1,2-dicarboxylic acid 1-tert-butyl ester 2-ethyl ester (4.2 g) in tetrahydrofuran (40 mL) at 0° C., and the reaction solution was stirred at room temperature for 12 hours. The reaction solution was added to ice water, followed by extraction with ethyl acetate. The extract was washed with brine, dried over anhydrous magnesium sulfate, and then concentrated under reduced pressure to obtain 3.3 g of an alcohol compound as a yellow oil. DMSO (1.24 mL) was added dropwise to a solution of oxalyl chloride (1.4 mL) in dichloromethane (50 mL) at −70° C., and the reaction solution was stirred at the same temperature for three minutes. A solution of the above alcohol compound (3.3 g) in dichloromethane (10 mL) was added dropwise thereto at −60° C., and the reaction solution was stirred at the same temperature for 15 minutes. Triethylamine (9.12 mL) was added dropwise to the solution, and the reaction solution was stirred at −60° C. to 0° C. for 30 minutes. The reaction solution was poured into water, followed by extraction with ethyl acetate. The extract was washed with brine, dried over anhydrous magnesium sulfate, and then concentrated under reduced pressure to obtain 3.4 g of an aldehyde compound as a pale yellow oil. Sodium hydride (60% oil, 0.524 g) was added to a solution of trimethyl phosphonoacetate (2.58 g) in DMF (30 mL) at room temperature, and the reaction solution was stirred for 20 minutes. This solution was added to a solution of the above aldehyde (3.4 g) in DMF (20 mL) at room temperature, and the reaction solution was stirred at room temperature for one hour. The reaction solution was poured into water, followed by extraction with ethyl acetate. The extract was washed with brine, dried over anhydrous magnesium sulfate, and then concentrated under reduced pressure. The residue was purified by silica gel column chromatography (heptane-ethyl acetate system) to obtain 3.7 g of tert-butyl (2S,5R)-2-(2,5-difluorophenyl)-5-[(E)-(2-methoxycarbonylvinyl)]pyrrolidine-1-carboxylate as a yellow oil.

A solution of 4 N hydrochloric acid in ethyl acetate (20 mL) was added dropwise to a solution of the resulting ester (3.7 g) in ethyl acetate (20 mL) at room temperature, and the reaction solution was stirred at 50° C. for 30 minutes. The reaction solution was concentrated under reduced pressure to obtain 3.8 g of a yellow solid. Diethyl cyanophosphonate (2.48 mL) was added dropwise to a solution of the resulting yellow solid (3.8 g), vinylacetic acid (1.38 mL), and triethylamine (4.56 mL) in DMF (37 mL) at 0° C., and the reaction solution was stirred at room temperature for two hours. The reaction solution was poured into ice water, followed by extraction with ethyl acetate. The extract was sequentially washed with a 1 N hydrochloric acid solution, saturated sodium bicarbonate water, and brine, and then dried over anhydrous magnesium sulfate and concentrated under reduced pressure. The residue was purified by silica gel column chromatography (heptane-ethyl acetate system) to obtain 4.6 g of the title compound as a yellow oil. The property value of the compound is as follows.

ESI-MS; m/z 336 [M$^+$+H].

Synthesis of (3S,8aR)-3-(2,5-difluorophenyl)-2,3,6,8a-tetrahydro-1H-indolizin-3-one Grubbs catalyst 2nd generation (0.594 g) was added to a solution of methyl (E)-3-[(2R,5S)-1-(3-butenoyl)-5-(2,5-difluorophenyl)pyrrolidin-2-yl]acrylate (4.6 g) in dichloromethane (60 mL), and the reaction solution was heated under reflux in a nitrogen atmosphere for five hours. The reaction solution was returned to room temperature. Triethylamine (8 mL) was added to the reaction solution, which was then stirred for 20 minutes. The reaction solution was concentrated under reduced pressure, and the residue was purified by silica gel column chromatography (heptane-ethyl acetate system) to obtain 1.3 g of the title compound as a brown oil. The property values of the compound are as follows.

ESI-MS; m/z 250 [M$^+$+H]. $^1$H-NMR (CDCl$_3$) δ(ppm): 1.68-1.83 (m, 1H), 1.88 (dd, J=6.0, 12.8 Hz, 1H), 2.06-2.20 (m, 1H), 2.10-2.44 (m, 1H), 2.90-3.10 (m, 2H), 4.20-4.35 (m, 1H), 5.36 (d, J=8.8 Hz, 1H), 6.00-6.20 (m, 2H), 6.53-6.65 (m, 1H), 7.80-6.90 (m, 1H), 6.90-7.05 (m, 1H).

Synthesis of (3S,8aS)-3-(2,5-difluorophenyl)hexahydroindolizin-5-one

Platinum oxide (0.127 g) was added to a solution of (3S,8aR)-3-(2,5-difluorophenyl)-2,3,6,8a-tetrahydro-1H-indolizin-3-one (1.3 g) in methanol (65 mL), and the reaction solution was stirred in a hydrogen atmosphere at room temperature for five hours. Platinum oxide in the reaction solution was removed by filtration, and the filtrate was concentrated under reduced pressure. The residue was purified by silica gel column chromatography (heptane-ethyl acetate system) to obtain 1.2 g of the title compound as a pale brown solid. The property values of the compound are as follows.

ESI-MS; m/z 252 [M$^+$+H]. $^1$H-NMR (CDCl$_3$) δ(ppm): 1.54-1.70 (m, 2H), 1.74-1.90 (m, 2H), 1.96-2.12 (m, 2H), 2.12-2.50 (m, 4H), 3.50-3.70 (m, 1H), 5.31 (d, J=9.6 Hz, 1H), 6.55-6.70 (m, 1H), 6.80-6.90 (m, 1H), 6.90-7.05 (m, 1H).

Synthesis of diethyl [(3S,8aR)-3-(2,5-difluorophenyl)-5-oxooctahydroindolizin-6-yl]phosphonate Iodotrimethylsilane (0.884 mL) was added dropwise to a solution of (3S,8aS)-3-(2,5-difluorophenyl)hexahydroindolizin-5-one (1.2 g) and N,N,N',N'-tetramethylethylenediamine (2.46 mL) in dichloromethane (30 mL) at 0° C., and the reaction solution was stirred at 0° C. for 30 minutes. Iodine (1.58 g) was added to the reaction solution at 0° C., and the reaction solution was stirred at the same temperature for 40 minutes. The reaction solution was added to ice-sodium thiosulfate solution, followed by extraction with ethyl acetate. The extract was washed with 1 N hydrochloric acid and brine, dried over anhydrous magnesium sulfate, and then concentrated under reduced pressure to obtain 1.8 g of an iodine compound.

A solution of the resulting iodine compound (1.8 g) in triethyl phosphite (9.0 mL) was stirred at 130° C. for one hour. The reaction solution was returned to room temperature and concentrated under reduced pressure to obtain 4.1 g of the title compound. The property value of the compound is as follows.

ESI-MS; m/z 388 [M$^+$+H].

Synthesis of (E)-(3S,8aS)-3-(2,5-difluorophenyl)-6-[3-methoxy-4-(4-methyl-1H-imidazol-1-yl)benzylidene]hexahydroindolizin-5-one Lithium hydroxide (0.443 g) was added to a mixed solution of 3-methoxy-4-(4-methyl-1H-imidazol-1-yl)benzaldehyde (1.0 g) and diethyl [(3S,8aR)-3-(2,5-difluorophenyl)-5-oxooctahydroindolizin-6-yl]phosphonate (4.1 g) in tetrahydrofuran (4 mL)-ethanol (16 mL), and the reaction solution was stirred under shading at room temperature for 12 hours. The reaction solution was poured into ice water, followed by extraction with ethyl acetate. The extract was washed with brine, dried over anhydrous magnesium sulfate, and then concentrated under reduced pressure. The residue was purified by silica gel column chromatography (heptane-ethyl acetate system) to obtain 1.85 g of the title compound as a colorless oil. The property values of the compound are as follows.

ESI-MS; m/z 450 [M$^+$+H]. $^1$H-NMR (CDCl$_3$) δ(ppm): 1.64-1.94 (m, 3H), 2.02-2.14 (m, 1H), 2.28-2.42 (m, 2H), 2.31 (s, 3H), 2.70-2.84 (m, 1H), 3.12-3.24 (m, 1H), 3.76-3.90 (m, 1H), 3.87 (s, 3H), 5.44 (d, J=8.8 Hz, 1H), 6.66-6.74 (m, 1H), 6.84-6.94 (m, 1H), 6.95 (s, 1H), 6.97-7.08 (m, 1H), 7.07 (s, 1H), 7.08 (d, J=8.0 Hz, 1H), 7.27 (d, J=8.0 Hz, 1H), 7.73 (s, 1H), 7.78 (s, 1H).

Example 60

Synthesis of (E)-(3S,8aS)-3-(3-fluorophenyl)-6-[3-methoxy-4-(4-methyl-1H-imidazol-1-yl)benzylidene]hexahydroindolizin-5-one

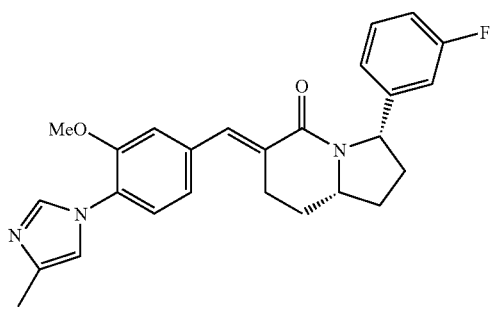

Synthesis of ethyl (R)-2-tert-butoxycarbonylamino-5-(3-fluorophenyl)-5-oxopentanoate To a solution of (R)-5-oxopyrrolidine-1,2-dicarboxylic acid 1-tert-butyl ester 2-ethyl ester (4.0 g) in tetrahydrofuran (100 mL), 3-fluorophenylmagnesium bromide (1.0 M solution in tetrahydrofuran; 17.1 mL) was added dropwise at −40° C. over 10 minutes, and the reaction solution was stirred at −40° C. to 0° C. for one hour. Water was added to the solution in small portions at 0° C., followed by extraction from the reaction solution with ethyl acetate. The extract was washed with brine, dried over anhydrous magnesium sulfate, and then concentrated under reduced pressure. The residue was purified by silica gel column chromatography (heptane-ethyl acetate system) to obtain 5.5 g of the title compound as a colorless oil. The property values of the compound are as follows.

$^1$H-NMR (CDCl$_3$) δ(ppm): 1.24-1.36 (m, 3H), 1.38-1.46 (s, 9H), 2.00-2.50 (m, 2H), 2.95-3.20 (m, 2H), 4.15-5.20 (m, 4H), 6.90-7.80 (m, 4H).

Synthesis of ethyl (R)-5-(3-fluorophenyl)-3,4-dihydro-2H-pyrrole-2-carboxylate

A solution of 4 N hydrochloric acid in ethyl acetate (25 mL) was added dropwise to a solution of ethyl (R)-2-tert-butoxycarbonylamino-5-(3-fluorophenyl)-5-oxopentanoate (5.5 g) in ethyl acetate (20 mL) at room temperature, and the reaction solution was stirred at room temperature for one hour. The reaction solution was concentrated under reduced pressure to obtain 5.0 g of a yellow oil. Saturated sodium bicarbonate water (30 mL) was added dropwise to a solution of the crude product in ethyl acetate (20 mL), and the reaction solution was stirred at room temperature for 20 minutes. The reaction solution was subjected to extraction with ethyl acetate. The extract was washed with brine, dried over anhydrous magnesium sulfate, and then concentrated under reduced pressure to obtain 3.5 g of the title compound as a pale yellow oil. The property values of the compound are as follows.

ESI-MS; m/z 236 [M$^+$+H]. $^1$H-NMR (CDCl$_3$) δ(ppm): 1.32 (t, J=7.2 Hz, 3H), 2.18-2.43 (m, 2H), 2.90-3.03 (m, 1H), 3.08-3.20 (m, 1H), 4.25 (q, J=7.2 Hz, 2H), 4.85-4.95 (m, 1H), 7.10-7.20 (m, 1H), 7.38 (dd, J=8.0, 14.0 Hz, 1H), 7.55-7.70 (m, 2H).

Synthesis of (2R,5S)-5-(3-fluorophenyl)pyrrolidine-1,2-dicarboxylic acid 1-tert-butyl ester 2-ethyl ester Palladium-carbon (containing 50% water, 0.50 g) was added to a solution of ethyl (R)-5-(3-fluorophenyl)-3,4-dihydro-2H-pyrrole-2-carboxylate (3.5 g) in ethyl acetate (50 mL), and the reaction solution was stirred in a hydrogen atmosphere at room temperature for four hours. Palladium-carbon in the reaction solution was removed by filtration, and then the filtrate was concentrated under reduced pressure to obtain 3.5 g of a reduced compound. Triethylamine (7.51 mL) and di-tert-butyl dicarbonate (4.47 g) were added to a solution of the resulting reduced compound in DMF (50 mL), and the reaction solution was stirred at room temperature for 12 hours. The reaction solution was poured into ice water, followed by extraction with ethyl acetate. The extract was washed with brine, dried over anhydrous magnesium sulfate, and then concentrated under reduced pressure. The residue was purified by silica gel column chromatography (heptane-ethyl acetate system) to obtain 4.2 g of the title compound as a yellow oil. The property values of the compound are as follows.

$^1$H-NMR (CDCl$_3$) δ(ppm): 1.17 and 1.42 (s, 9H), 1.20-1.48 (m, 3H), 1.86-2.21 (m, 2H), 2.16-2.38 (m, 2H), 4.10-4.40 (m, 2H), 4.25-5.05 (m, 2H), 6.80-7.00 (m, 1H), 7.20-7.40 (m, 3H).

Synthesis of tert-butyl (2S,5R)-2-(3-fluorophenyl)-5-[(E)-(2-methoxycarbonylvinyl)]pyrrolidine-1-carboxylate Lithium borohydride (1.03 g) was added to a solution of (2R,5S)-5-(3-fluorophenyl)pyrrolidine-1,2-dicarboxylic acid 1-tert-butyl ester 2-ethyl ester (4.2 g) in tetrahydrofuran (40 mL) at 0° C., and the reaction solution was stirred at room temperature for 12 hours. The reaction solution was added to ice water, followed by extraction with ethyl acetate. The extract was washed with brine, dried over anhydrous magnesium sulfate, and then concentrated under reduced pressure to obtain 3.7 g of an alcohol compound as a yellow oil. DMSO (1.42 mL) was added dropwise to a solution of oxalyl chloride (1.61 mL) in dichloromethane (80 mL) at −70° C., and the reaction solution was stirred at the same temperature for three minutes. A solution of the above alcohol compound (3.7 g) in dichloromethane (10 mL) was added dropwise thereto at −60° C., and the reaction solution was stirred at the same temperature for 15 minutes. Triethylamine (10.5 mL) was added dropwise to the solution, and the reaction solution was stirred at −60° C. to 0° C. for 30 minutes. The reaction solution was poured into water, followed by extraction with ethyl acetate. The extract was washed with brine, dried over anhydrous magnesium sulfate, and then concentrated under reduced pressure to obtain 3.8 g of an aldehyde compound as a pale yellow oil. Sodium hydride (60% oil, 0.524 g) was added to a solution of trimethyl phosphonoacetate (2.82 g) in DMF (25 mL) at room temperature, and the reaction solution was stirred for 20 minutes. This solution was added to a solution of the above aldehyde (3.8 g) in DMF (25 mL) at room temperature, and the reaction solution was stirred at room temperature for one hour. The reaction solution was poured into water, followed by extraction with ethyl acetate. The extract was washed with brine, dried over anhydrous magnesium sulfate, and then concentrated under reduced pressure. The residue was purified by silica gel column chromatography (heptane-ethyl acetate system) to obtain 4.0 g of the title compound as a yellow oil. The property values of the compound are as follows.

$^1$H-NMR (CDCl$_3$) δ(ppm): 1.00-1.50 (m, 9H), 1.80-1.94 (m, 2H), 2.08-2.20 (m, 1H), 2.26-2.36 (m, 1H), 3.78 (s, 3H), 4.20-5.00 (m, 2H), 5.95-6.15 (m, 1H), 6.80-7.35 (m, 5H).

Synthesis of methyl (E)-3-[(2R,5S)-1-(3-butenoyl)-5-(3-fluorophenyl)pyrrolidin-2-yl]acrylate A solution of 4 N hydrochloric acid in ethyl acetate (32.1 mL) was added dropwise to a solution of tert-butyl (2S,5R)-2-(3-fluorophenyl)-5-[(E)-(2-methoxycarbonylvinyl)]pyrrolidine-1-carboxylate (4.0 g) in ethyl acetate (20 mL) at room temperature, and the reaction solution was stirred at 50° C. for 30 minutes. The reaction solution was concentrated under reduced pressure to obtain 3.8 g of a yellow solid. Diethyl cyanophosphonate (2.81 mL) was added dropwise to a solution of the resulting yellow solid (3.8 g), vinylacetic acid (1.56 mL), and triethylamine (5.17 mL) in DMF (40 mL) at 0° C., and the reaction solution was stirred at the same temperature for two hours. The reaction solution was poured into ice water, followed by extraction with ethyl acetate. The extract was sequentially washed with a 1 N hydrochloric acid solution, saturated sodium bicarbonate water, and brine, and then dried over anhydrous magnesium sulfate and concentrated under reduced pressure. The residue was purified by silica gel column chromatography (heptane-ethyl acetate system) to obtain 2.7 g of the title compound as a yellow oil. The property value of the compound is as follows.

ESI-MS; m/z 318 [M$^+$+H].

Synthesis of (3S,8aR)-3-(3-fluorophenyl)-2,3,6,8a-tetrahydro-1H-indolizin-3-one Grubbs catalyst 2nd generation (0.304 g) was added to a solution of methyl (E)-3-[(2R,5S)-1-(3-butenoyl)-5-(3-fluorophenyl)pyrrolidin-2-yl]acrylate (1.2 g) in dichloromethane (40 mL), and the reaction solution was heated under reflux in a nitrogen atmosphere for five hours. The reaction solution was returned to room temperature. Triethylamine (4 mL) was added to the reaction solution, which was then stirred for 20 minutes. The reaction solution was concentrated under reduced pressure, and the residue was purified by silica gel column chromatography (heptane-ethyl acetate system) to obtain 0.60 g of the title compound as a brown oil. The property values of the compound are as follows.

ESI-MS; m/z 232 [M$^+$+H]. $^1$H-NMR (CDCl$_3$) δ(ppm): 1.78-1.92 (m, 2H), 2.04-2.14 (m, 1H), 2.30-2.43 (m, 1H), 2.94-3.02 (m, 2H), 4.25-4.35 (m, 1H), 5.12 (d, J=8.8 Hz, 1H), 5.95-6.08 (m, 1H), 6.06-6.15 (m, 1H), 6.75-6.85 (m, 1H), 6.85-6.95 (m, 2H), 7.20-7.30 (m, 1H).

Synthesis of (3S,8aS)-3-(3-fluorophenyl)hexahydroindolizin-5-one

Platinum oxide (0.0786 g) was added to a solution of (3S,8aR)-3-(3-fluorophenyl)-2,3,6,8a-tetrahydro-1H-indolizin-3-one (0.60 g) in methanol (30 mL), and the reaction solution was stirred in a hydrogen atmosphere at room temperature for five hours. Platinum oxide in the reaction solution was removed by filtration, and the filtrate was concentrated under reduced pressure. The residue was purified by silica gel column chromatography (heptane-ethyl acetate system) to obtain 0.560 g of the title compound as a pale brown solid. The property values of the compound are as follows.

ESI-MS; m/z 234 [M$^+$+H]. $^1$H-NMR (CDCl$_3$) δ(ppm): 1.54-1.88 (m, 4H), 1.94-2.10 (m, 2H), 2.14-2.50 (m, 4H), 3.54-3.66 (m, 1H), 5.00 (d, J=9.2 Hz, 1H), 6.76-6.84 (m, 1H), 6.84-6.96 (m, 2H), 7.20-7.30 (m, 1H).

Synthesis of diethyl [(3S,8aR)-3-(3-fluorophenyl)-5-oxooctahydroindolizin-6-yl]phosphonate Iodotrimethylsilane (0.444 mL) was added dropwise to a solution of (3S,8aS)-3-(3-fluorophenyl)hexahydroindolizin-5-one (0.539 g) and N,N,N',N'-tetramethylethylenediamine (1.20 mL) in dichloromethane (27 mL) at 0° C., and the reaction solution was stirred at 0° C. for 30 minutes. Iodine (0.792 g) was added to the reaction solution at 0° C., and the reaction solution was stirred at the same temperature for 40 minutes. The reaction solution was added to ice-sodium thiosulfate solution, followed by extraction with ethyl acetate. The extract was washed with 1 N hydrochloric acid and brine, dried over anhydrous magnesium sulfate, and then concentrated under reduced pressure to obtain 0.85 g of an iodine compound.

A solution of the resulting iodine compound (0.85 g) in triethyl phosphite (10 mL) was stirred at 130° C. for one hour.

The reaction solution was returned to room temperature and concentrated under reduced pressure to obtain 1.9 g of the title compound. The property value of the compound is as follows.

ESI-MS; m/z 370 [M$^+$+H].

Synthesis of (E)-(3S,8aS)-3-(3-fluorophenyl)-6-[3-methoxy-4-(4-methyl-1H-imidazol-1-yl)benzylidene]hexahydroindolizin-5-one Lithium hydroxide (0.217 g) was added to a mixed solution of 3-methoxy-4-(4-methyl-1H-imidazol-1-yl)benzaldehyde (0.49 g) and diethyl [(3S,8aR)-3-(3-fluorophenyl)-5-oxooctahydroindolizin-6-yl]phosphonate (1.9 g) in tetrahydrofuran (4 mL)-ethanol (16 mL), and the reaction solution was stirred under shading at room temperature for 12 hours. The reaction solution was poured into ice water, followed by extraction with ethyl acetate. The extract was washed with brine, dried over anhydrous magnesium sulfate, and then concentrated under reduced pressure. The residue was purified by silica gel column chromatography (heptane-ethyl acetate system) to obtain 0.76 g of the title compound as a colorless solid. The property values of the compound are as follows.

ESI-MS; m/z 432 [M$^+$+H]. $^1$H-NMR (CDCl$_3$) δ(ppm): 1.70-1.90 (m, 3H), 2.02-2.12 (m, 1H), 2.26-2.40 (m, 2H), 2.30 (s, 3H), 2.70-2.82 (m, 1H), 3.12-3.22 (m, 1H), 3.76-3.90 (m, 1H), 3.85 (s, 3H), 5.22 (d, J=8.8 Hz, 1H), 6.84-7.00 (m, 2H), 6.94 (s, 1H), 6.99 (d, J=8.0 Hz, 1H), 7.05 (s, 1H), 7.08 (d, J=8.0 Hz, 1H), 7.24-7.36 (m, 2H), 7.72 (d, J=1.6 Hz, 1H), 7.77 (d, J=2.4 Hz, 1H).

Example 61

Synthesis of (E)-(3S,8aS)-3-(2,6-difluoropyridin-3-yl)-6-[3-methoxy-4-(4-methyl-1H-imidazol-1-yl)benzylidene]hexahydroindolizin-5-one

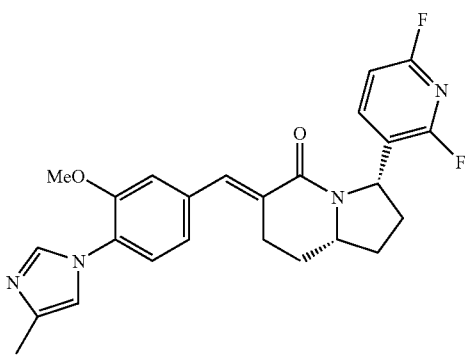

Synthesis of ethyl (R)-2-tert-butoxycarbonylamino-5-(2,6-difluoropyridin-3-yl)-5-oxopentanoate To a solution of diisopropylamine (0.653 mL) in tetrahydrofuran (30 mL), n-butyl lithium (1.57 M solution in hexane, 2.97 mL) was added at −78° C. over five minutes, and the reaction solution was stirred at the same temperature for 20 minutes. 2,6-Difluoropyridine (0.388 mL) was added dropwise to the solution at −78° C., and the reaction solution was stirred at −78° C. for three hours. A solution of (R)-5-oxopyrrolidine-1,2-dicarboxylic acid 1-tert-butyl ester 2-ethyl ester (1.0 g) in tetrahydrofuran (5.0 mL) was added dropwise to this solution at −78° C., and the reaction solution was stirred at 0° C. for one hour. Water was added to the solution in small portions at 0° C., followed by extraction with ethyl acetate. The extract was washed with brine, dried over anhydrous magnesium sulfate, and then concentrated under reduced pressure. The residue was purified by silica gel column chromatography (heptane-ethyl acetate system) to obtain 1.2 g of the title compound as a pale yellow oil. The property values of the compound are as follows.

$^1$H-NMR (CDCl$_3$) δ(ppm): 1.30 (t, J=7.2 Hz, 3H), 1.41 (s, 9H), 1.94-2.08 (m, 1H), 2.28-2.40 (m, 1H), 2.98-3.22 (m, 2H), 4.22 (q, J=7.2 Hz, 2H), 4.30-4.45 (m, 1H), 5.05-5.20 (m, 1H), 6.95 (dd, J=2.4, 8.0 Hz, 1H), 8.50 (q, J=8.0 Hz, 1H).

Synthesis of ethyl (R)-5-(2,6-difluoropyridin-3-yl)-3,4-dihydro-2H-pyrrole-2-carboxylate A solution of 4 N hydrochloric acid in ethyl acetate (6.0 mL) was added dropwise to a solution of ethyl (R)-2-tert-butoxycarbonylamino-5-(2,6-difluoropyridin-3-yl)-5-oxopentanoate (1.2 g) in ethyl acetate (50 mL) at room temperature, and the reaction solution was stirred for one hour at room temperature. The reaction solution was concentrated under reduced pressure to obtain 1.0 g of a yellow oil. Saturated sodium bicarbonate water (30 mL) was added dropwise to a solution of the crude product in ethyl acetate (20 mL), and the reaction solution was stirred at room temperature for 20 minutes. The reaction solution was subjected to extraction with ethyl acetate. The extract was washed with brine, dried over anhydrous magnesium sulfate, and then concentrated under reduced pressure to obtain 1.0 g of the title compound as a pale yellow oil. The property values of the compound are as follows.

ESI-MS; m/z 255 [M$^+$+H]. $^1$H-NMR (CDCl$_3$) δ(ppm): 1.32 (t, J=7.2 Hz, 3H), 2.19-2.31 (m, 1H), 2.33-2.45 (m, 1H), 3.00-3.12 (m, 1H), 3.14-3.28 (m, 1H), 4.25 (q, J=7.2 Hz, 2H), 4.85 (t, J=8.0 Hz, 1H), 6.90 (dd, J=2.8, 8.0 Hz, 1H), 8.67 (q, J=8.0 Hz, 1H).

Synthesis of (2R,5S)-5-(2,6-difluoropyridin-3-yl)pyrrolidine-1,2-dicarboxylic acid 1-tert-butyl ester 2-ethyl ester 10% palladium-carbon (containing 50% water, 0.10 g) was added to a solution of ethyl (R)-5-(2,6-difluoropyridin-3-yl)-3,4-dihydro-2H-pyrrole-2-carboxylate (0.90 g) in ethyl acetate (50 mL), and the reaction solution was stirred in a hydrogen atmosphere at room temperature for six hours. Palladium-carbon in the reaction solution was removed by filtration, and then the filtrate was concentrated under reduced pressure to obtain 0.90 g of a reduced compound.

Triethylamine (1.93 mL) and di-tert-butyl dicarbonate (1.15 g) were added to a solution of the resulting reduced compound in DMF (50 mL), and the reaction solution was stirred at room temperature for 12 hours. The reaction solution was poured into ice water, followed by extraction with ethyl acetate. The extract was washed with brine, dried over anhydrous magnesium sulfate, and then concentrated under reduced pressure. The residue was purified by silica gel column chromatography (heptane-ethyl acetate system) to obtain 0.68 g of the title compound as a yellow oil. The property values of the compound are as follows.

$^1$H-NMR (CDCl$_3$) δ(ppm): 1.22 and 1.42 (s, 9H), 1.28-1.40 (m, 3H), 1.84-2.18 (m, 2H), 2.22-2.48 (m, 2H), 4.26 (q, J=7.2 Hz, 2H), 4.20-5.40 (m, 2H), 6.75-6.90 (m, 1H), 8.50-8.75 (m, 1H).

Synthesis of tert-butyl (2S,5R)-2-(2,6-difluoropyridin-3-yl)-5-[(E)-(2-methoxycarbonylvinyl)]pyrrolidine-1-carboxylate Lithium aluminum hydride (43.6 mg) was added to a solution of (2R,5S)-5-(2,6-difluoropyridin-3-yl)pyrrolidine-1,2-dicarboxylic acid 1-tert-butyl ester 2-ethyl ester (0.68 g) in tetrahydrofuran (30 mL) at −40° C., and the reaction solution was stirred at −40° C. to 0° C. for 30 minutes. The reaction solution was cooled to −40° C. again. Lithium aluminum hydride (66 mg) was added to the reaction solution, which was then stirred at −40° C. to 0° C. for 30 minutes. Water (0.13 mL), a 15% sodium hydroxide solution (0.15 mL), and water (0.39 mL) were sequentially added to the reaction solution at 0° C., and the mixture was stirred at room temperature for 20 minutes. The insoluble matter in the mixture was removed by filtration, and then the filtrate was concentrated under reduced pressure to obtain 0.63 g of an alcohol compound as a yellow oil.

DMSO (0.399 mL) was added dropwise to a solution of oxalyl chloride (0.455 mL) in dichloromethane (20 mL) at −70° C., and the reaction solution was stirred at the same temperature for three minutes. A solution of the alcohol compound (0.75 g) in dichloromethane (5 mL) was added dropwise thereto at −60° C., and the reaction solution was stirred at the same temperature for 15 minutes. Triethylamine (3.93 mL) was added dropwise to the solution, and the reaction solution was stirred at −60° C. to 0° C. for 30 minutes. The reaction solution was poured into water, followed by extraction with ethyl acetate. The extract was washed with brine, dried over anhydrous magnesium sulfate, and then concentrated under reduced pressure to obtain 0.80 g of an aldehyde compound as a pale yellow oil. Sodium hydride (60% oil, 0.113 g) was added to a solution of trimethyl phosphonoacetate (0.609 g) in DMF (5 mL) at room temperature, and the reaction solution was stirred for 20 minutes. This solution was added to a solution of the above aldehyde (0.80 g) in DMF (5 mL) at room temperature, and the reaction solution was stirred at room temperature for one hour. The reaction solution was poured into water, followed by extraction with ethyl acetate. The extract was washed with brine, dried over anhydrous magnesium sulfate, and then concentrated under reduced pressure. The residue was purified by silica gel column chromatography (heptane-ethyl acetate system) to obtain 0.85 g of the title compound as a yellow oil. The property values of the compound are as follows.

$^1$H-NMR (CDCl$_3$) δ(ppm): 1.00-1.50 (m, 9H), 1.75-2.00 (m, 2H), 2.10-2.25 (m, 1H), 2.30-2.50 (m, 1H), 3.78 (s, 3H), 4.40-4.75 (m, 1H), 4.85-5.20 (m, 1H), 6.04 (d, J=15.2 Hz, 1H), 6.84 (d, J=7.2 Hz, 1H), 6.85-7.10 (m, 1H), 7.65-7.90 (m, 1H).

Synthesis of methyl (E)-3-[(2R,5S)-1-(3-butenoyl)-5-(2,6-difluoropyridin-3-yl)pyrrolidin-2-yl]acrylate A solution of 4 N hydrochloric acid in ethyl acetate (6.07 mL) was added dropwise to a solution of tert-butyl (2S,5R)-2-(2,6-difluoropyridin-3-yl)-5-[(E)-(2-methoxycarbonylvinyl)]pyrrolidine-1-carboxylate (0.85 g) in ethyl acetate (20 mL) at room temperature, and the reaction solution was stirred at 50° C. for 30 minutes. The reaction solution was concentrated under reduced pressure to obtain 0.85 g of a yellow solid. Diethyl cyanophosphonate (0.598 mL) was added dropwise to a solution of the resulting yellow solid (0.85 g), vinylacetic acid (0.334 mL), and triethylamine (1.1 mL) in DMF (20 mL) at 0° C., and the reaction solution was stirred at room temperature for two hours. The reaction solution was poured into ice water, followed by extraction with ethyl acetate. The extract was washed with brine, and then dried over anhydrous magnesium sulfate and concentrated under reduced pressure. The residue was purified by silica gel column chromatography (heptane-ethyl acetate system) to obtain 0.58 g of the title compound as a yellow oil. The property value of the compound is as follows. ESI-MS; m/z 337 [M$^+$+H].

Synthesis of (3S,8aR)-3-(2,6-difluoropyridin-3-yl)-2,3,6,8a-tetrahydro-1H-indolizin-3-one Grubbs catalyst 2nd generation (0.147 g) was added to a solution of methyl (E)-3-[(2R,5S)-1-(3-butenoyl)-5-(2,6-difluoropyridin-3-yl)pyrrolidin-2-yl]acrylate (0.58 g) in dichloromethane (20 mL), and the reaction solution was heated under reflux in a nitrogen atmosphere for five hours. The reaction solution was returned to room temperature. Triethylamine (4 mL) was added to the reaction solution, which was then stirred for 20 minutes. The reaction solution was concentrated under reduced pressure, and the residue was purified by silica gel column chromatography (heptane-ethyl acetate system) to obtain 0.314 g of the title compound as a brown solid. The property values of the compound are as follows.

ESI-MS; m/z 251 [M$^+$+H]. $^1$H-NMR (CDCl$_3$) δ(ppm): 1.62-1.78 (m, 1H), 1.86-1.94 (m, 1H), 2.13-2.22 (m, 1H), 2.34-2.47 (m, 1H), 2.96-3.04 (m, 2H), 4.25-4.35 (m, 1H), 5.27 (d, J=8.8 Hz, 1H), 6.00-6.15 (m, 2H), 6.71 (dd, J=2.8, 8.0 Hz, 1H), 7.39 (dd, J=8.0, 17.6 Hz, 1H).

Synthesis of (3S,8aS)-3-(2,6-difluoropyridin-3-yl)hexahydroindolizin-5-one

Platinum oxide (35.1 mg) was added to a solution of (3S,8aR)-3-(2,6-difluoropyridin-3-yl)-2,3,6,8a-tetrahydro-1H-indolizin-3-one (0.314 g) in methanol (20 mL), and the reaction solution was stirred in a hydrogen atmosphere at room temperature for five hours. Platinum oxide was removed from the reaction solution by filtration, and the filtrate was concentrated under reduced pressure. The residue was purified by silica gel column chromatography (heptane-ethyl acetate system) to obtain 0.30 g of the title compound as a pale brown solid. The property values of the compound are as follows.

ESI-MS; m/z 253 [M$^+$+H]. $^1$H-NMR (CDCl$_3$) δ(ppm): 1.48-1.68 (m, 4H), 1.75-1.90 (m, 1H), 2.00-2.12 (m, 1H), 2.16-2.52 (m, 4H), 3.53-3.70 (m, 1H), 5.21 (d, J=9.2 Hz, 1H), 6.74 (dd, J=3.2, 8.0 Hz, 1H), 7.47 (dd, J=8.0, 17.6 Hz, 1H).

Synthesis of diethyl [(3S,8aR)-3-(2,6-difluoropyridin-3-yl)-5-oxooctahydroindolizin-6-yl]phosphonate Iodotrimethylsilane (0.23 mL) was added dropwise to a solution of (3S,8aS)-3-(2,6-difluoropyridin-3-yl)hexahydroindolizin-5-one (0.30 g) and N,N,N',N'-tetramethylethylenediamine (0.617 mL) in dichloromethane (15 mL) at 0° C., and the reaction solution was stirred at 0° C. for 30 minutes. Iodine (0.409 g) was added to the reaction solution at 0° C., and the reaction solution was stirred at the same temperature for 40 minutes. The reaction solution was added to ice-sodium thiosulfate solution, followed by extraction with ethyl acetate. The extract was washed with 1 N hydrochloric acid and brine, dried over anhydrous magnesium sulfate, and then concentrated under reduced pressure to obtain 0.45 g of an iodine compound.

A solution of the resulting iodine compound (0.45 g) in triethyl phosphite (10 mL) was stirred at 130° C. for one hour.

The reaction solution was returned to room temperature and concentrated under reduced pressure to obtain 1.0 g of the title compound. The property value of the compound is as follows.

ESI-MS; m/z 389 [M$^+$+H].

Synthesis of (E)-(3S,8aS)-3-(2,6-difluoropyridin-3-yl)-6-[3-methoxy-4-(4-methyl-1H-imidazol-1-yl)benzylidene]hexahydroindolizin-5-one Lithium hydroxide (0.106 g) was added to a mixed solution of 3-methoxy-4-(4-methyl-1H-imidazol-1-yl)benzaldehyde (0.24 g) and diethyl [(3S,8aR)-3-(2,6-difluoropyridin-3-yl)-5-oxooctahydroindolizin-6-yl]phosphonate (1.0 g) in tetrahydrofuran (4 mL)-ethanol (16 mL), and the reaction solution was stirred under shading at room temperature for 12 hours. The reaction solution was poured into ice water, followed by extraction with ethyl acetate. The extract was washed with brine, dried over anhydrous magnesium sulfate, and then concentrated under reduced pressure. The residue was purified by silica gel column chromatography (heptane-ethyl acetate system) to obtain 0.42 g of the title compound as a colorless solid. The property values of the compound are as follows.

ESI-MS; m/z 451 [M$^+$+H]. $^1$H-NMR (CDCl$_3$) δ(ppm): 1.56-1.82 (m, 2H), 1.82-2.00 (m, 1H), 2.10-2.20 (m, 1H), 2.24-2.48 (m, 2H), 2.30 (s, 3H), 2.70-2.84 (m, 1H), 3.12-3.22 (m, 1H), 3.76-3.90 (m, 1H), 3.86 (s, 3H), 5.34 (d, J=9.2 Hz, 1H), 6.77 (d, J=8.0 Hz, 1H), 6.94 (s, 1H), 7.06 (s, 1H), 7.10 (d, J=8.0 Hz, 1H), 7.20-7.35 (m, 1H), 7.54 (dd, J=8.0, 8.0 Hz, 1H), 7.73 (s, 1H), 7.75 (s, 1H).

Example 62

Synthesis of (E)-(3S,8aS)-3-(2,4-difluorophenyl)-6-[3-methoxy-4-(4-methyl-1H-imidazol-1-yl)benzylidene]hexahydroindolizin-5-one

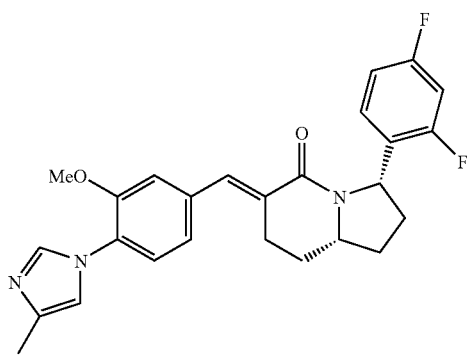

Synthesis of ethyl (R)-2-tert-butoxycarbonylamino-5-(2,4-difluorophenyl)-5-oxopentanoate To a suspension of magnesium (736 mg) in tetrahydrofuran (20 mL), 1-bromo-2,4-difluorobenzene (3.42 mL) was added dropwise at 45° C. over five minutes, and the reaction solution was stirred at room temperature for one hour. This solution was added dropwise to a solution of (R)-5-oxopyrrolidine-1,2-dicarboxylic acid 1-tert-butyl ester 2-ethyl ester (6.0 g) in tetrahydrofuran (50 mL) at −40° C. over 20 minutes, and the reaction solution was stirred at −40° C. to 0° C. for one hour. Water was added to the solution in small portions at 0° C., followed by extraction with ethyl acetate. The extract was washed with brine, dried over anhydrous magnesium sulfate, and then concentrated under reduced pressure. The residue was purified by silica gel column chromatography (heptane-ethyl acetate system) to obtain 7.5 g of the title compound as a colorless oil.

$^1$H-NMR (CDCl$_3$) δ(ppm): 1.29 (t, J=7.2 Hz, 3H), 1.42 (s, 9H), 1.95-2.10 (m, 1H), 2.20-2.35 (m, 1H), 2.95-3.20 (m, 2H), 4.21 (q, J=7.2 Hz, 2H), 4.30-4.45 (m, 1H), 5.05-5.20 (m, 1H), 6.82-6.92 (m, 1H), 6.92-7.02 (m, 1H), 7.90-8.00 (m, 1H).

Synthesis of ethyl (R)-5-(2,4-difluorophenyl)-3,4-dihydro-2H-pyrrole-2-carboxylate A solution of 4 N hydrochloric acid in ethyl acetate (42.9 mL) was added dropwise to a solution of ethyl (R)-2-tert-butoxycarbonylamino-5-(2,4-difluorophenyl)-5-oxopentanoate (8.1 g) in ethyl acetate (20 mL) at room temperature, and the reaction solution was stirred at room temperature for 12 hours. The reaction solution was concentrated under reduced pressure to obtain 7.0 g of a yellow oil. Saturated sodium bicarbonate water (100 mL) was added dropwise to a solution of the crude product in ethyl acetate (100 mL), and the reaction solution was stirred at room temperature for 20 minutes. The reaction solution was subjected to extraction with ethyl acetate. The extract was washed with brine, dried over anhydrous magnesium sulfate, and then concentrated under reduced pressure to obtain 5.1 g of the title compound as a pale yellow oil. The property values of the compound are as follows.

ESI-MS; m/z 254 [M$^+$+H]. $^1$H-NMR (CDCl$_3$) δ(ppm): 1.32 (t, J=7.2 Hz, 3H), 2.15-2.29 (m, 1H), 2.30-2.40 (m, 1H), 2.95-3.10 (m, 1H), 3.10-3.25 (m, 1H), 4.25 (q, J=7.2 Hz, 2H), 4.80-4.90 (m, 1H), 6.80-6.89 (m, 1H), 6.89-6.98 (m, 1H), 8.04-8.12 (m, 1H).

Synthesis of (2R,5S)-5-(2,4-difluorophenyl)pyrrolidine-1,2-dicarboxylic acid 1-tert-butyl ester 2-ethyl ester 10% palladium-carbon (containing 50% water, 800 mg) was added to a solution of ethyl (R)-5-(2,4-difluorophenyl)-3,4-dihydro-2H-pyrrole-2-carboxylate (5.1 g) in ethyl acetate (100 mL), and the reaction solution was stirred in a hydrogen atmosphere at room temperature for eight hours. Palladium-carbon in the reaction solution was removed by filtration, and then the filtrate was concentrated under reduced pressure to obtain 5.0 g of a reduced compound.

Triethylamine (10.7 mL) and di-tert-butyl dicarbonate (6.42 g) were added to a solution of the resulting reduced compound in DMF (50 mL) at 0° C., and the reaction solution was stirred at room temperature for 12 hours. The reaction solution was poured into ice water, followed by extraction with ethyl acetate. The extract was washed with brine, dried over anhydrous magnesium sulfate, and then concentrated under reduced pressure. The residue was purified by silica gel column chromatography (heptane-ethyl acetate system) to obtain 7.4 g of the title compound as a yellow oil. The property values of the compound are as follows.

$^1$H-NMR (CDCl$_3$) δ(ppm): 1.20 and 1.42 (s, 9H), 1.20-1.40 (m, 3H), 1.84-2.10 (m, 2H), 2.16-2.42 (m, 2H), 4.26 (q, J=7.2 Hz, 2H), 4.20-5.30 (m, 2H), 6.70-6.80 (m, 1H), 6.80-6.95 (m, 1H), 7.90-8.10 (m, 1H).

Synthesis of tert-butyl (2S,5R)-2-(2,4-difluorophenyl)-5-[(E)-(2-methoxycarbonylvinyl)]pyrrolidine-1-carboxylate Lithium borohydride (1.82 g) was added to a solution of (2R,5S)-5-(2,4-difluorophenyl)pyrrolidine-1,2-dicarboxylic acid 1-tert-butyl ester 2-ethyl ester (7.4 g) in tetrahydrofuran (100 mL) at 0° C., and the reaction solution was stirred at room temperature for five hours. The reaction solution was added to ice water, followed by extraction with ethyl acetate. The extract was washed with brine, dried over anhydrous magnesium sulfate, and then concentrated under reduced pressure to obtain 6.5 g of an alcohol compound as a yellow oil. DMSO (2.36 mL) was added dropwise to a solution of oxalyl chloride (2.69 mL) in dichloromethane (100 mL) at −70° C., and the reaction solution was stirred at the same temperature for three minutes. A solution of the above alcohol compound (6.5 g) in dichloromethane (20 mL) was added dropwise thereto at −60° C., and the reaction solution was stirred at the same temperature for 15 minutes. Triethylamine (23.2 mL) was added dropwise to the solution, and the reaction solution was stirred at −60° C. to 0° C. for 30 minutes. The reaction solution was poured into water, followed by extraction with ethyl acetate. The extract was washed with brine, dried over anhydrous magnesium sulfate, and then concentrated under reduced pressure to obtain 6.5 g of an aldehyde compound as a pale yellow oil. Sodium hydride (60% oil, 0.92 g) was added to a solution of trimethyl phosphonoacetate (4.95 g) in DMF (50 mL) at room temperature, and the reaction solution was stirred for 20 minutes. This solution was added to a solution of the above aldehyde (6.5 g) in DMF (20 mL) at room temperature, and the reaction solution was stirred at room temperature for one hour. The reaction solution was poured into water, followed by extraction with ethyl acetate. The extract was washed with brine, dried over anhydrous magnesium sulfate, and then concentrated under reduced pressure. The residue was purified by silica gel column chromatography (heptane-ethyl acetate system) to obtain 4.74 g of the title compound as a yellow oil. The property values of the compound are as follows.

$^1$H-NMR (CDCl$_3$) δ(ppm): 1.10-1.50 (m, 9H), 1.78-1.92 (m, 2H), 2.06-2.22 (m, 1H), 2.28-2.40 (m, 1H), 3.78 (s, 3H), 4.40-4.70 (m, 1H), 4.90-5.30 (m, 1H), 5.95-6.15 (m, 1H), 6.78 (t, J=9.6 Hz, 1H), 6.87 (t, J=8.4 Hz, 1H), 6.95-7.10 (m, 1H), 7.15-7.30 (m, 1H).

Synthesis of methyl (E)-3-[(2R,5S)-1-(3-butenoyl)-5-(2,4-difluorophenyl)pyrrolidin-2-yl]acrylate A solution of 4 N hydrochloric acid in ethyl acetate (20 mL) was added dropwise to a solution of tert-butyl (2S,5R)-2-(2,4-difluorophenyl)-5-[(E)-(2-methoxycarbonylvinyl)]pyrrolidine-1-carboxylate (2.8 g) in ethyl acetate (20 mL) at room temperature, and the reaction solution was stirred at 50° C. for 30 minutes. The reaction solution was concentrated under reduced pressure to obtain 2.5 g of a yellow solid. Diethyl cyanophosphonate (1.97 mL) was added dropwise to a solution of the resulting yellow solid (2.5 g), vinylacetic acid (1.1 mL), and triethylamine (3.63 mL) in DMF (40 mL) at 0° C., and the reaction solution was stirred at the same temperature for two hours. The reaction solution was poured into ice water, followed by extraction with ethyl acetate. The extract was sequentially washed with a 1 N hydrochloric acid solution, saturated sodium bicarbonate water, and brine, and then dried over anhydrous magnesium sulfate and concentrated under reduced pressure. The residue was purified by silica gel column chromatography (heptane-ethyl acetate system) to obtain 1.9 g of the title compound as a yellow oil. The property values of the compound are as follows.

ESI-MS; m/z 336 [M$^+$+H]. $^1$H-NMR (CDCl$_3$) δ(ppm): 1.66-3.20 (m, 6H), 3.76 and 3.80 (s, 3H), 4.20-5.40 (m, 4H), 5.80-6.00 (m, 1H), 6.09 (d, J=15.6 Hz, 1H), 6.70-7.30 (m, 4H).

Synthesis of (3S,8aR)-3-(2,4-difluorophenyl)-2,3,6,8a-tetrahydro-1H-indolizin-3-one Grubbs catalyst 2nd generation (481 mg) was added to a solution of methyl (E)-3-[(2R,5S)-1-(3-butenoyl)-5-(2,4-difluorophenyl)pyrrolidin-2-yl]acrylate (1.9 g) in dichloromethane (50 mL), and the reaction solution was heated under reflux in a nitrogen atmosphere for five hours. The reaction solution was returned to room temperature. Triethylamine (4 mL) was added to the reaction solution, which was then stirred for 20 minutes. The reaction solution was concentrated under reduced pressure, and the residue was purified by silica gel column chromatography (heptane-ethyl acetate system) to obtain 0.85 g of the title compound as a brown oil. The property values of the compound are as follows.

ESI-MS; m/z 250 [M$^+$+H]. $^1$H-NMR (CDCl$_3$) δ(ppm): 1.68-1.84 (m, 1H), 1.86 (dd, J=6.4, 12.8 Hz, 1H), 2.06-2.18 (m, 1H), 2.30-2.42 (m, 1H), 2.90-3.08 (m, 2H), 4.20-4.34 (m, 1H), 5.34 (d, J=8.8 Hz, 1H), 5.98-6.14 (m, 2H), 6.70-6.90 (m, 3H).

Synthesis of (3S,8aS)-3-(2,4-difluorophenyl)hexahydroindolizin-5-one

Platinum oxide (95 mg) was added to a solution of (3S,8aR)-3-(2,4-difluorophenyl)-2,3,6,8a-tetrahydro-1H-indolizin-3-one (0.85 g) in methanol (40 mL), and the reaction solution was stirred in a hydrogen atmosphere at room temperature for five hours. Platinum oxide in the reaction solution was removed by filtration, and the filtrate was concentrated under reduced pressure. The residue was purified by silica gel column chromatography (heptane-ethyl acetate system) to obtain 0.72 g of the title compound as a pale brown solid. The property values of the compound are as follows.

ESI-MS; m/z 252 [M$^+$+H]. $^1$H-NMR (CDCl$_3$) δ(ppm): 1.52-1.68 (m, 2H), 1.74-1.90 (m, 2H), 1.96-2.10 (m, 2H), 2.14-2.52 (m, 4H), 3.50-3.65 (m, 1H), 5.30 (d, J=9.2 Hz, 1H), 6.70-6.90 (m, 2H), 6.91 (dd, J=8.8, 14.4 Hz, 1H).

Synthesis of diethyl [(3S,8aR)-3-(2,4-difluorophenyl)-5-oxooctahydroindolizin-6-yl]phosphonate Iodotrimethylsilane (0.551 mL) was added dropwise to a solution of (3S,8aS)-3-(2,4-difluorophenyl)hexahydroindolizin-5-one (0.72 g) and N,N,N',N'-tetramethylethylenediamine (1.48 mL) in dichloromethane (30 mL) at 0° C., and the reaction solution was stirred at 0° C. for 30 minutes. Iodine (0.982 g) was added to the reaction solution at 0° C., and the reaction solution was stirred at the same temperature for 40 minutes. The reaction solution was added to ice-sodium thiosulfate solution, followed by extraction with ethyl acetate. The extract was washed with 1 N hydrochloric acid and brine, dried over anhydrous magnesium sulfate, and then concentrated under reduced pressure to obtain 1.3 g of an iodine compound.

A solution of the resulting iodine compound (1.3 g) in triethyl phosphite (23.2 mL) was stirred at 130° C. for one hour. The reaction solution was returned to room temperature and concentrated under reduced pressure to obtain 1.8 g of the title compound. The property value of the compound is as follows.

ESI-MS; m/z 388 [M++H].

Synthesis of (E)-(3S,8aS)-3-(2,4-difluorophenyl)-6-[3-methoxy-4-(4-methyl-1H-imidazol-1-yl)benzylidene]hexahydroindolizin-5-one Lithium hydroxide (406 mg) was added to a mixed solution of 3-methoxy-4-(4-methyl-1H-imidazol-1-yl)benzaldehyde (550 mg) and diethyl [(3S,8aR)-3-(2,4-difluorophenyl)-5-oxooctahydroindolizin-6-yl]phosphonate (1.8 g) in tetrahydrofuran (5 mL)-ethanol (20 mL), and the reaction solution was stirred under shading at room temperature for 12 hours. The reaction solution was poured into ice water, followed by extraction with ethyl acetate. The extract was washed with brine, dried over anhydrous magnesium sulfate, and then concentrated under reduced pressure. The residue was purified by silica gel column chromatography (heptane-ethyl acetate system) to obtain 0.76 g of the title compound as a colorless solid. The property values of the compound are as follows.

ESI-MS; m/z 450 [M++H]. $^1$H-NMR (CDCl$_3$) δ(ppm): 1.60-1.83 (m, 2H), 1.84-1.93 (m, 1H), 2.04-2.13 (m, 1H), 2.28-2.40 (m, 2H), 2.30 (s, 3H), 2.70-2.83 (m, 1H), 3.12-3.20 (m, 1H), 3.76-3.88 (m, 1H), 3.86 (s, 3H), 5.42 (d, J=8.8 Hz, 1H), 6.74-6.88 (m, 2H), 6.94 (s, 1H), 6.90-7.04 (m, 1H), 7.06 (s, 1H), 7.09 (d, J=8.0 Hz, 1H), 7.26 (d, J=8.0 Hz, 1H), 7.72 (s, 1H), 7.77 (d, J=2.4 Hz, 1H).

Example 63

Synthesis of (E)-(3S,8aS)-3-(3-chlorophenyl)-6-[3-methoxy-4-(4-methyl-1H-imidazol-1-yl)benzylidene]hexahydroindolizin-5-one

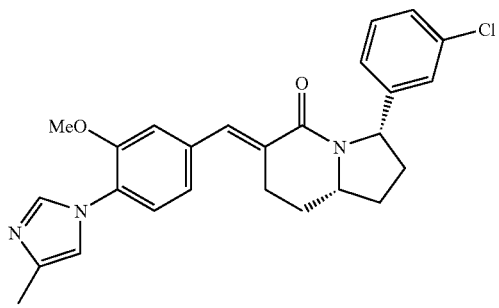

Synthesis of ethyl (R)-2-tert-butoxycarbonylamino-5-(3-chlorophenyl)-5-oxopentanoate To a solution of (R)-5-oxopyrrolidine-1,2-dicarboxylic acid 1-tert-butyl ester 2-ethyl ester (2.0 g) in tetrahydrofuran (100 mL), 3-chlorophenylmagnesium bromide (0.5 M solution in tetrahydrofuran; 17.1 mL) was added dropwise at −40° C. over 20 minutes, and the reaction solution was stirred at −40° C. to 0° C. for one hour. Water was added to the solution in small portions at 0° C., followed by extraction with ethyl acetate. The extract was washed with brine, dried over anhydrous magnesium sulfate, and then concentrated under reduced pressure. The residue was purified by silica gel column chromatography (heptane-ethyl acetate system) to obtain 2.5 g of the title compound as a colorless oil. The property values of the compound are as follows.

$^1$H-NMR (CDCl$_3$) δ(ppm): 1.28 (t, J=7.2 Hz, 3H), 1.42 (s, 9H), 2.00-2.20 (m, 1H), 2.20-2.40 (m, 1H), 2.95-3.20 (m, 2H), 4.21 (d, J=7.2 Hz, 2H), 4.30-4.45 (m, 1H), 5.20-5.30 (m, 1H), 7.41 (t, J=8.0 Hz, 1H), 7.54 (d, J=8.0 Hz, 1H), 7.82 (d, J=8.0 Hz, 1H), 7.92 (t, J=2.0 Hz, 1H).

Synthesis of ethyl (R)-5-(4-chlorophenyl)-3,4-dihydro-2H-pyrrole-2-carboxylate

A solution of 4 N hydrochloric acid in ethyl acetate (20 mL) was added dropwise to a solution of ethyl (R)-2-tert-butoxycarbonylamino-5-(3-chlorophenyl)-5-oxopentanoate (2.5 g) in ethyl acetate (20 mL) at room temperature, and the reaction solution was stirred at room temperature for 12 hours. The reaction solution was concentrated under reduced pressure to obtain 2.0 g of a yellow oil. Saturated sodium bicarbonate water (100 mL) was added dropwise to a solution of the crude product in ethyl acetate (100 mL), and the reaction solution was stirred at room temperature for 20 minutes. The reaction solution was subjected to extraction with ethyl acetate. The extract was washed with brine, dried over anhydrous magnesium sulfate, and then concentrated under reduced pressure to obtain 1.5 g of the title compound as a pale yellow oil. The property values of the compound are as follows.

ESI-MS; m/z 252 [M++H]. $^1$H-NMR (CDCl$_3$) δ(ppm): 1.32 (t, J=7.2 Hz, 3H), 2.15-2.45 (m, 2H), 2.90-3.05 (m, 1H), 3.05-3.20 (m, 1H), 4.25 (q, J=7.2 Hz, 2H), 4.85-4.95 (m, 1H), 7.35 (t, J=8.0 Hz, 1H), 7.40-7.45 (m, 1H), 7.74 (td, J=1.6, 8.0 Hz, 1H), 7.90 (t, J=1.6 Hz, 1H).

Synthesis of (2R,5S)-5-(3-chlorophenyl)pyrrolidine-1,2-dicarboxylic acid 1-tert-butyl ester 2-ethyl ester Sodium borohydride (0.451 g) was added to a solution of ethyl (R)-5-(3-chlorophenyl)-3,4-dihydro-2H-pyrrole-2-carboxylate (1.5 g) in methanol (40 mL)-acetic acid (10 mL) at −45° C. over five minutes. The reaction solution was stirred at −45° C. to 0° C. for three hours. A disodium hydrogen phosphate solution was added to the reaction solution. The mixture was stirred at room temperature for 20 minutes, and the organic solvent was evaporated under reduced pressure. The residue was subjected to extraction with dichloromethane, and the extract was dried over anhydrous magnesium sulfate. The extract was concentrated to obtain 1.4 g of a reduced compound. Triethylamine (3.21 mL) and di-tert-butyl dicarbonate (1.61 g) were added to a solution of the reduced compound (1.4 g) in dichloromethane (20 mL), and the reaction solution was stirred at room temperature for 12 hours. The reaction solution was poured into ice water, followed by extraction with ethyl acetate. The extract was washed with brine, dried over anhydrous magnesium sulfate, and then concentrated under reduced pressure. The residue was purified by silica gel column chromatography (heptane-ethyl acetate system) to obtain 1.7 g of the title compound as a yellow oil. The property values of the compound are as follows.

$^1$H-NMR (CDCl$_3$) δ(ppm): 1.17 and 1.42 (s, 9H), 1.20-1.44 (m, 3H), 1.80-2.14 (m, 2H), 2.14-2.38 (m, 2H), 4.10-5.20 (m, 4H), 7.12-7.28 (m, 2H), 7.38-7.50 (m, 1H), 7.54-7.61 (m, 1H).

Synthesis of tert-butyl (2S,5R)-2-(3-chlorophenyl)-5-[(E)-(2-methoxycarbonylvinyl)]pyrrolidine-1-carboxylate Lithium borohydride (394 mg) was added to a solution of (2R,5S)-5-(3-chlorophenyl)pyrrolidine-1,2-dicarboxylic acid 1-tert-butyl ester 2-ethyl ester (1.6 g) in tetrahydrofuran (30 mL) at 0° C., and the reaction solution was stirred at room temperature for 12 hours. The reaction solution was added to ice water, followed by extraction with ethyl acetate. The extract was washed with brine, dried over anhydrous magnesium sulfate, and then concentrated under reduced pressure to obtain 1.6 g of an alcohol compound as a yellow oil. DMSO (0.619 mL) was added dropwise to a solution of oxalyl chloride (0.66 mL) in dichloromethane (40 mL) at −70° C., and the reaction solution was stirred at the same temperature for three minutes. A solution of the above alcohol compound (1.6 g) in dichloromethane (20 mL) was added dropwise thereto at −60° C., and the reaction solution was stirred at the same temperature for 15 minutes. Triethylamine (5.72 mL) was added dropwise to the solution, and the reaction solution was stirred at −60° C. to 0° C. for 30 minutes. The reaction solution was poured into water, followed by extraction with ethyl acetate. The extract was washed with brine, dried over anhydrous magnesium sulfate, and then concentrated under reduced pressure to obtain 1.6 g of an aldehyde compound as a pale yellow oil. Sodium hydride (60% oil, 0.309 g) was added to a solution of trimethyl phosphonoacetate (1.4 g) in DMF (20 mL) at room temperature, and the reaction solution was stirred for 20 minutes. This solution was added to a solution of the above aldehyde (1.6 g) in DMF (10 mL) at room temperature, and the reaction solution was stirred at room temperature for one hour. The reaction solution was poured into water, followed by extraction with ethyl acetate. The extract was washed with brine, dried over anhydrous magnesium sulfate, and then concentrated under reduced pressure. The residue was purified by silica gel column chromatography (heptane-ethyl acetate system) to obtain 1.34 g of the title compound as a yellow oil. The property values of the compound are as follows.

ESI-MS; m/z 388 [M$^+$+Na]. $^1$H-NMR (CDCl$_3$) δ(ppm): 1.00-1.50 (m, 9H), 1.60-1.95 (m, 2H), 2.05-2.45 (m, 2H), 3.73 and 3.78 (s, 3H), 4.30-5.10 (m, 2H), 5.95-6.15 (m, 1H), 6.90-7.10 (m, 1H), 7.13 (d, J=7.6 Hz, 1H), 7.15-7.30 (m, 3H).

Synthesis of methyl (E)-3-[(2R,5S)-1-(3-butenoyl)-5-(3-chlorophenyl)pyrrolidin-2-yl]acrylate A solution of 4 N hydrochloric acid in ethyl acetate (10 mL) was added dropwise to a solution of tert-butyl (2S,5R)-2-(3-chlorophenyl)-5-[(E)-(2-methoxycarbonylvinyl)]pyrrolidine-1-carboxylate (1.34 g) in ethyl acetate (5 mL) at room temperature, and the reaction solution was stirred at 50° C. for one hour. The reaction solution was concentrated under reduced pressure to obtain 1.0 g of a yellow solid. Diethyl cyanophosphonate (2.29 mL) was added dropwise to a solution of the resulting yellow solid (1.0 g), vinylacetic acid (1.27 mL), and triethylamine (4.22 mL) in DMF (30 mL) at 0° C., and the reaction solution was stirred at room temperature for two hours. The reaction solution was poured into ice water, followed by extraction with ethyl acetate. The extract was sequentially washed with a 1 N hydrochloric acid solution, saturated sodium bicarbonate water, and brine, and then dried over anhydrous magnesium sulfate and concentrated under reduced pressure. The residue was purified by silica gel column chromatography (heptane-ethyl acetate system) to obtain 0.72 g of the title compound as a yellow oil. The property values of the compound are as follows.

ESI-MS; m/z 334 [M$^+$+H]. $^1$H-NMR (CDCl$_3$) δ(ppm): 1.20-3.20 (m, 6H), 3.76 and 3.80 (s, 3H), 4.22-4.36 (m, 1H), 4.54-5.22 (m, 3H), 5.78-6.00 (m, 1H), 6.00-6.16 (m, 1H), 6.90-7.40 (m, 5H).

Synthesis of (3S,8aR)-3-(3-chlorophenyl)-2,3,6,8a-tetrahydro-1H-indolizin-3-one

Grubbs catalyst 2nd generation (0.45 g) was added to a solution of methyl (E)-3-[(2R,5S)-1-(3-butenoyl)-5-(3-chlorophenyl)pyrrolidin-2-yl]acrylate (0.72 g) in dichloromethane (40 mL), and the reaction solution was heated under reflux in a nitrogen atmosphere for three hours. The reaction solution was returned to room temperature. Triethylamine (1 mL) was added to the reaction solution, which was then stirred for 20 minutes. The reaction solution was concentrated under reduced pressure, and the residue was purified by silica gel column chromatography (heptane-ethyl acetate system) to obtain 0.36 g of the title compound as a brown oil. The property values of the compound are as follows.

ESI-MS; m/z 248 [M$^+$+H]. $^1$H-NMR (CDCl$_3$) δ(ppm): 1.76-1.92 (m, 2H), 2.02-2.14 (m, 1H), 2.29-2.42 (m, 1H), 2.94-3.02 (m, 2H), 4.24-4.34 (m, 1H), 5.09 (d, J=8.8 Hz, 1H), 5.96-6.06 (m, 1H), 6.06-6.14 (m, 1H), 6.98 (d, J=7.2 Hz, 1H), 7.08 (s, 1H), 7.17 (d, J=7.2 Hz, 1H), 7.21 (d, J=7.2 Hz, 1H).

Synthesis of (3S,8aS)-3-(3-chlorophenyl)hexahydroindolizin-5-one

Platinum oxide (42.4 mg) was added to a solution of (3S,8aR)-3-(3-chlorophenyl)-2,3,6,8a-tetrahydro-1H-indolizin-3-one (0.36 g) in methanol (30 mL), and the reaction solution was stirred in a hydrogen atmosphere at room temperature for five hours. Platinum oxide in the reaction solution was removed by filtration, and the filtrate was concentrated under reduced pressure. The residue was purified by silica gel column chromatography (heptane-ethyl acetate system) to obtain 0.32 g of the title compound as a pale yellow solid. The property values of the compound are as follows.

ESI-MS; m/z 250 [M$^+$+H]. $^1$H-NMR (CDCl$_3$) δ(ppm): 1.55-1.90 (m, 4H), 1.95-2.10 (m, 2H), 2.15-2.50 (m, 4H), 3.55-3.68 (m, 1H), 5.08 (d, J=8.8 Hz, 1H), 6.99-7.04 (m, 1H), 7.08-7.11 (m, 1H), 7.15-7.19 (m, 1H), 7.22 (t, J=8.0 Hz, 1H).

Synthesis of diethyl [(3S,8aR)-3-(3-chlorophenyl)-5-oxooctahydroindolizin-6-yl]phosphonate Iodotrimethylsilane (0.244 mL) was added dropwise to a solution of (3S,8aS)-3-(3-chlorophenyl)hexahydroindolizin-5-one (0.32 g) and N,N,N',N'-tetramethylethylenediamine (0.657 mL) in dichloromethane (20 mL) at 0° C., and the reaction solution was stirred at 0° C. for 30 minutes. Iodine (0.435 g) was added to the reaction solution at 0° C., and the reaction solution was stirred at the same temperature for 40 minutes. The reaction solution was added to ice-sodium thiosulfate solution, followed by extraction with ethyl acetate. The extract was washed with 1 N hydrochloric acid and brine, dried over anhydrous magnesium sulfate, and then concentrated under reduced pressure to obtain 0.50 g of an iodine compound.

A solution of the resulting iodine compound (0.50 g) in triethyl phosphite (6.0 mL) was stirred at 130° C. for two hours. The reaction solution was returned to room temperature and concentrated under reduced pressure to obtain 0.52 g of the title compound. The property value of the compound is as follows.

ESI-MS; m/z 386 [M$^+$+H].

Synthesis of (E)-(3S,8aS)-3-(3-chlorophenyl)-6-[3-methoxy-4-(4-methyl-1H-imidazol-1-yl)benzylidene]hexahydroindolizin-5-one Lithium hydroxide (0.142 g) was added to a mixed solution of 3-methoxy-4-(4-methyl-1H-imidazol-1-yl)benzaldehyde (0.28 g) and diethyl [(3S,8aR)-3-(3-chlorophenyl)-5-oxooctahydroindolizin-6-yl]phosphonate (0.52 g) in tetrahydrofuran (1 mL)-ethanol (4 mL), and the reaction solution was stirred under shading at room temperature for three hours. The reaction solution was poured into ice water, followed by extraction with ethyl acetate. The extract was washed with brine, dried over anhydrous magnesium sulfate, and then concentrated under reduced pressure. The residue was purified by silica gel column chromatography (heptane-ethyl acetate system) to obtain 0.438 g of the title compound as a colorless oil. The property values of the compound are as follows.

ESI-MS; m/z 448 [M$^+$+H]. $^1$H-NMR (CDCl$_3$) δ(ppm): 1.70-1.90 (m, 3H), 2.02-2.14 (m, 1H), 2.25-2.40 (m, 2H), 2.30 (s, 3H), 2.70-2.83 (m, 1H), 3.10-3.20 (m, 1H), 3.75-3.90 (m, 1H), 3.85 (s, 3H), 5.19 (d, J=8.8 Hz, 1H), 6.92-6.96 (m, 1H), 7.02-7.12 (m, 3H), 7.13-7.29 (m, 4H), 7.72 (d, J=1.6 Hz, 1H), 7.76 (d, J=2.0 Hz, 1H).

Example 64

Synthesis of (E)-(3S,8aS)-3-(3,5-difluorophenyl)-6-[3-methoxy-4-(4-methyl-1H-imidazol-1-yl)benzylidene]hexahydroindolizin-5-one

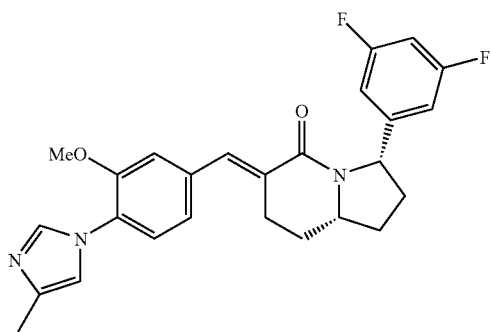

Synthesis of ethyl (R)-2-tert-butoxycarbonylamino-5-(3,5-difluorophenyl)-5-oxopentanoate To a solution of (R)-5-oxopyrrolidine-1,2-dicarboxylic acid 1-tert-butyl ester 2-ethyl ester (3.0 g) in tetrahydrofuran (70 mL), 3,5-difluorophenylmagnesium bromide (0.5 M solution in tetrahydrofuran; 25.7 mL) was added dropwise at −40° C. over 10 minutes, and the reaction solution was stirred at −40° C. to 0° C. for one hour. Water was added to the solution in small portions at 0° C., followed by extraction with ethyl acetate. The extract was washed with brine, dried over anhydrous magnesium sulfate, and then concentrated under reduced pressure. The residue was purified by silica gel column chromatography (heptane-ethyl acetate system) to obtain 3.0 g of the title compound as a pale yellow oil. The property values of the compound are as follows.

$^1$H-NMR (CDCl$_3$) δ(ppm): 1.20-1.42 (m, 3H), 1.42 (s, 9H), 1.95-2.50 (m, 2H), 2.90-3.20 (m, 2H), 4.22 (q, J=7.2 Hz, 2H), 4.10-5.30 (m, 2H), 6.90-7.06 (m, 1H), 7.40-7.50 (m, 2H).

Synthesis of ethyl (R)-5-(3,5-difluorophenyl)-3,4-dihydro-2H-pyrrole-2-carboxylate A solution of 4 N hydrochloric acid in ethyl acetate (20 mL) was added dropwise to a solution of ethyl (R)-2-tert-butoxycarbonylamino-5-(3,5-difluorophenyl)-5-oxopentanoate (3.0 g) in ethyl acetate (20 mL) at room temperature, and the reaction solution was stirred at room temperature for 12 hours. The reaction solution was concentrated under reduced pressure to obtain 2.0 g of a yellow oil. Saturated sodium bicarbonate water (50 mL) was added dropwise to a solution of the crude product in ethyl acetate (20 mL), and the reaction solution was stirred at room temperature for 20 minutes, followed by extraction with ethyl acetate. The extract was washed with brine, dried over anhydrous magnesium sulfate, and then concentrated under reduced pressure to obtain 2.0 g of the title compound as a pale red oil. The property values of the compound are as follows.

ESI-MS; m/z 254 [M$^+$+H]. $^1$H-NMR (CDCl$_3$) δ(ppm): 1.32 (t, J=7.2 Hz, 3H), 2.22-2.44 (m, 2H), 2.88-3.00 (m, 1H), 3.05-3.16 (m, 1H), 4.25 (q, J=7.2 Hz, 2H), 4.86-4.98 (m, 1H), 6.85-6.95 (m, 1H), 7.35-7.45 (m, 2H).

Synthesis of (2R,5S)-5-(3,5-difluorophenyl)pyrrolidine-1,2-dicarboxylic acid 1-tert-butyl ester 2-ethyl ester 10% palladium-carbon (containing 50% water, 0.441 g) was added to a solution of ethyl (R)-5-(3,5-difluorophenyl)-3,4-dihydro-2H-pyrrole-2-carboxylate (2.0 g) in ethyl acetate (50 mL), and the reaction solution was stirred in a hydrogen atmosphere at room temperature for four hours. Palladium-carbon in the reaction solution was removed by filtration, and then the filtrate was concentrated under reduced pressure to obtain 2.0 g of a reduced compound as a yellow oil.

Triethylamine (2.93 mL) and di-tert-butyl dicarbonate (3.07 g) were added to a solution of the resulting reduced compound in DMF (20 mL), and the reaction solution was stirred at room temperature for one hour. The reaction solution was poured into ice water, followed by extraction with ethyl acetate. The extract was washed with brine, dried over anhydrous magnesium sulfate, and then concentrated under reduced pressure. The residue was purified by silica gel column chromatography (heptane-ethyl acetate system) to obtain 2.7 g of the title compound as a yellow oil. The property values of the compound are as follows.

$^1$H-NMR (CDCl$_3$) δ(ppm): 1.20 and 1.42 (s, 9H), 1.16-1.50 (m, 3H), 1.84-2.12 (m, 2H), 2.16-2.40 (m, 2H), 4.28 (q, J=7.2 Hz, 2H), 4.20-5.00 (m, 2H), 6.60-6.72 (m, 1H), 7.06-7.24 (m, 2H).

Synthesis of tert-butyl (2S,5R)-2-(3,5-difluorophenyl)-5-((E)-2-methoxycarbonylvinyl)pyrrolidine-1-carboxylate Lithium borohydride (0.687 g) was added to a solution of (2R,5S)-5-(3,5-difluorophenyl)pyrrolidine-1,2-dicarboxylic acid 1-tert-butyl ester 2-ethyl ester (2.7 g) in tetrahydrofuran (30 mL) at 0° C., and the reaction solution was stirred at room temperature for 12 hours. The reaction solution was poured into ice water, followed by extraction with ethyl acetate. The extract was washed with brine, dried over anhydrous magnesium sulfate, and then concentrated under reduced pressure to obtain 2.7 g of an alcohol compound as a yellow oil. DMSO (1.14 mL) was added dropwise to a solution of oxalyl chloride (1.39 mL) in dichloromethane (40 mL) at −70° C., and the reaction solution was stirred at the same temperature for three minutes. A solution of the above alcohol compound (2.7 g) in dichloromethane (20 mL) was added dropwise thereto at −60° C., and the reaction solution was stirred at the same temperature for 15 minutes. Triethylamine (11.3 mL) was added dropwise to the solution, and the reaction solution was stirred at −60° C. to 0° C. for 30 minutes. The reaction solution was poured into water, followed by extraction with ethyl acetate. The extract was washed with brine, dried over anhydrous magnesium sulfate, and then concentrated under reduced pressure to obtain 2.7 g of an aldehyde compound as a pale yellow oil. Sodium hydride (60% oil, 0.521 g) was added to a solution of trimethyl phosphonoacetate (2.37 g) in DMF (20 mL) at room temperature, and the reaction solution was stirred for 20 minutes. This solution was added to a solution of the above aldehyde (2.7 g) in DMF (10 mL) at room temperature, and the reaction solution was stirred at room temperature for one hour. The reaction solution was poured into water, followed by extraction with ethyl acetate. The extract was washed with brine, dried over anhydrous magnesium sulfate, and then concentrated under reduced pressure. The residue was purified by silica gel column chromatography (heptane-ethyl acetate system) to obtain 2.4 g of the title compound as a yellow oil. The property values of the compound are as follows.

$^1$H-NMR (CDCl$_3$) δ(ppm): 1.10-1.60 (m, 9H), 1.75-1.95 (m, 2H), 2.05-2.20 (m, 1H), 2.25-2.40 (m, 1H), 3.78 (s, 3H), 4.40-5.10 (m, 2H), 5.96-6.14 (m, 1H), 6.62-6.72 (m, 1H), 6.72-6.82 (m, 2H), 6.90-7.06 (m, 1H).

Synthesis of methyl (E)-3-[(2R,5S)-1-(3-butenoyl)-5-(3,5-difluorophenyl)pyrrolidin-2-yl]acrylate A solution of 4 N hydrochloric acid in ethyl acetate (30 mL) was added dropwise to a solution of tert-butyl (2S,5R)-2-(3,5-difluorophenyl)-5-((E)-2-methoxycarbonylvinyl)pyrrolidine-1-carboxylate (1.2 g) in ethyl acetate (5 mL) at room temperature, and the reaction solution was stirred at 50° C. for one hour. The reaction solution was concentrated under reduced pressure to obtain 1.0 g of a yellow solid. Diethyl cyanophosphonate (2.05 mL) was added dropwise to a solution of the resulting yellow solid (1.0 g), vinylacetic acid (1.14 mL), and triethylamine (3.78 mL) in DMF (30 mL) at 0° C., and the reaction solution was stirred at the same temperature for one hour. The reaction solution was poured into ice water, followed by extraction with ethyl acetate. The extract was sequentially washed with a 1 N hydrochloric acid solution, saturated sodium bicarbonate water, and brine, and then dried over anhydrous magnesium sulfate and concentrated under reduced pressure. The residue was purified by silica gel column chromatography (heptane-ethyl acetate system) to obtain 0.78 g of the title compound as a yellow oil. The property values of the compound are as follows.

ESI-MS; m/z 336 [M$^+$+H]. $^1$H-NMR (CDCl$_3$) δ(ppm): 1.20-3.16 (m, 6H), 3.76 and 3.80 (s, 3H), 4.56-5.24 (m, 4H), 5.78-6.00 (m, 1H), 6.00-6.14 (m, 1H), 6.60-6.86 (m, 3H), 6.90-7.10 (m, 1H).

Synthesis of (3S,8aR)-3-(3,5-difluorophenyl)-2,3,6,8a-tetrahydro-1H-indolizin-3-one Grubbs catalyst 2nd generation (0.487 g) was added to a solution of methyl (E)-3-[(2R,5S)-1-(3-butenoyl)-5-(3,5-difluorophenyl)pyrrolidin-2-yl]acrylate (0.78 g) in dichloromethane (70 mL), and the reaction solution was heated under reflux in a nitrogen atmosphere for three hours. The reaction solution was returned to room temperature. Triethylamine (1.0 mL) was added to the reaction solution, which was then stirred for 20 minutes. The reaction solution was concentrated under reduced pressure, and the residue was purified by silica gel column chromatography (heptane-ethyl acetate system) to obtain 0.44 g of the title compound as a brown oil. The property values of the compound are as follows.

ESI-MS; m/z 250 [M$^+$+H]. $^1$H-NMR (CDCl$_3$) δ(ppm): 1.76-1.90 (m, 2H), 2.03-2.16 (m, 1H), 2.28-2.44 (m, 1H), 2.90-3.06 (m, 2H), 4.24-4.34 (m, 1H), 5.08 (d, J=9.2 Hz, 1H), 5.98-6.06 (m, 1H), 6.06-6.14 (m, 1H), 6.58-6.68 (m, 3H).

Synthesis of (3S,8aS)-3-(3,5-difluorophenyl)hexahydroindolizin-5-one

Platinum oxide (20 mg) was added to a solution of (3S,8aR)-3-(3,5-difluorophenyl)-2,3,6,8a-tetrahydro-1H-indolizin-3-one (0.17 g) in methanol (25 mL), and the reaction solution was stirred in a hydrogen atmosphere at room temperature for 2.5 hours. Platinum oxide in the reaction solution was removed by filtration, and the filtrate was concentrated under reduced pressure. The residue was purified by silica gel column chromatography (heptane-ethyl acetate system) to obtain 0.167 g of the title compound as a yellow oil. The property values of the compound are as follows.

ESI-MS; m/z 252 [M$^+$+H]. $^1$H-NMR (CDCl$_3$) δ(ppm): 1.52-1.90 (m, 4H), 1.96-2.12 (m, 2H), 2.14-2.50 (m, 4H), 3.53-3.65 (m, 1H), 5.05 (d, J=9.2 Hz, 1H), 6.55-6.70 (m, 3H).

Synthesis of diethyl [(3S,8aR)-3-(3,5-difluorophenyl)-5-oxooctahydroindolizin-6-yl]phosphonate Iodotrimethylsilane (0.128 mL) was added dropwise to a solution of (3S,8aS)-3-(3,5-difluorophenyl)hexahydroindolizin-5-one (0.167 g) and N,N,N',N'-tetramethylethylenediamine (0.341 mL) in dichloromethane (20 mL) at 0° C., and the reaction solution was stirred at 0° C. for 30 minutes. Iodine (0.228 g) was added to the reaction solution at 0° C., and the reaction solution was stirred at the same temperature for 40 minutes. The reaction solution was added to ice-sodium thiosulfate solution, followed by extraction with ethyl acetate. The extract was washed with brine, dried over anhydrous magnesium sulfate, and then concentrated under reduced pressure to obtain 0.25 g of an iodine compound.

A solution of the resulting iodine compound (0.25 g) in triethyl phosphite (6.25 mL) was stirred at 130° C. for two hours. The reaction solution was returned to room temperature and concentrated under reduced pressure to obtain 0.40 g of the title compound. The property value of the compound is as follows.

ESI-MS m/z 388 [M$^+$+H].

Synthesis of (E)-(3S,8aS)-3-(3,5-difluorophenyl)-6-[3-methoxy-4-(4-methyl-1H-imidazol-1-yl)benzylidene]hexahydroindolizin-5-one Lithium hydroxide (56.8 mg) was added to a mixed solution of 3-methoxy-4-(4-methyl-1H-imidazol-1-yl)benzaldehyde (0.12 g) and diethyl [(3S,8aR)-3-(3,5-difluorophenyl)-5-oxooctahydroindolizin-6-yl]phosphonate (0.25 g) in tetrahydrofuran (1.0 mL)-ethanol (4.0 mL), and the reaction solution was stirred under shading at room temperature for 12 hours. The reaction solution was poured into ice water, followed by extraction with ethyl acetate. The extract was washed with brine, dried over anhydrous magnesium sulfate, and then concentrated under reduced pressure. The residue was purified by silica gel column chromatography (heptane-ethyl acetate system) to obtain 0.22 g of the title compound as a colorless oil. The property values of the compound are as follows.

ESI-MS; m/z 450 [M⁺+H]. ¹H-NMR (CDCl₃) δ(ppm): 1.70-1.90 (m, 3H), 2.04-2.14 (m, 1H), 2.26-2.40 (m, 2H), 2.30 (s, 3H), 2.68-2.82 (m, 1H), 3.12-3.22 (m, 1H), 3.76-3.90 (m, 1H), 3.86 (s, 3H), 5.17 (d, J=9.2 Hz, 1H), 6.62-6.76 (m, 3H), 6.94 (s, 1H), 7.06 (s, 1H), 7.08 (d, J=8.0 Hz, 1H), 7.26 (d, J=8.0 Hz, 1H), 7.72 (d, J=1.2 Hz, 1H), 7.76 (d, J=2.0 Hz, 1H).

Examples 65 and 66

Synthesis of (E)-(6S,9aS)-6-(3,4-difluorophenyl)-3-[3-methoxy-4-(4-methyl-1H-imidazol-1-yl)ben-zylidene]octahydroquinolizin-4-one and (E)-(6R,9aR)-6-(3,4-difluorophenyl)-3-[3-methoxy-4-(4-methyl-1H-imidazol-1-yl)benzylidene] octahydroquinolizin-4-one

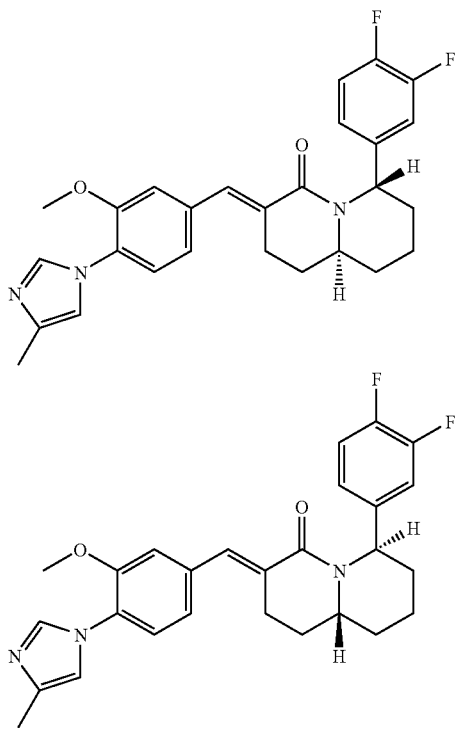

Synthesis of 1-(4-bromobutyryl)-2-(3,4-difluorophe-nyl)-2,3-dihydro-1H-pyridin-4-one To a suspension of magnesium (1.38 g) and a small amount of an iodine piece in anhydrous diethyl ether (70 mL), 1-bromo-3,4-difluorobenzene (10 g) was added dropwise in a nitrogen atmosphere while heating under reflux. When the reaction started, the reaction vessel was removed from the oil bath. The remaining 1-bromo-3,4-difluorobenzene was added dropwise such that the reaction mixture was mildly refluxed, followed by stirring at room temperature for three hours. A solution of 4-methoxypyridine (6.8 mL) in THF (50 mL) was added to the reaction mixture. To the reaction mixture, 4-bromobutyryl chloride (6 mL) was added dropwise at −25° C. over 15 minutes, and the reaction mixture was further stirred for one hour. 5 N aqueous hydrochloric acid (30 mL) was added to the reaction mixture, and the reaction mixture was stirred at room temperature for 10 minutes, followed by extraction with ethyl acetate. The organic layer was washed with brine, dried over magnesium sulfate, and then concentrated under reduced pressure. The residue was purified by silica gel column chromatography (elution solvent: heptane-ethyl acetate system) to obtain 11.1 g of the title compound. The property values of the compound are as follows.

¹H-NMR (CDCl₃) δ(ppm): 2.22-2.32 (m, 2H), 2.68-2.88 (m, 3H), 3.08-3.18 (m, 1H), 3.51-3.55 (m, 2H), 5.48 (d, J=8.4 Hz, 1H), 6.00 (brs, 1H), 6.90-7.15 (m, 2H), 7.70 (brs, 1H).

Synthesis of (6S*,9aS*)-4-(3,4-difluorophenyl) hexahydroquinolizine-2,6-dione 5.46 g of the title compound was obtained from 1-(4-bromobutyryl)-2-(3,4-difluorophenyl)-2,3-dihydro-1H-pyridin-4-one (11.1 g) in the same manner as in Examples 13 and 14. The property values of the compound are as follows.

¹H-NMR (CDCl₃) δ(ppm): 1.58-1.67 (m, 1H), 1.70-1.80 (m, 1H), 1.86-1.94 (m, 1H), 1.94-2.04 (m, 1H), 2.35-2.41 (m, 1H), 2.45-2.57 (m, 3H), 2.80 (dd, J=15.2 Hz, 7.2 Hz, 1H), 2.93-2.99 (m, 1H), 3.50-3.57 (m, 1H), 6.50 (d, J=7.2 Hz, 1H), 6.96-7.00 (m, 1H), 7.07-7.13 (m, 1H).

Synthesis of (6S*,9aS*)-6-(3,4-difluorophenyl)oc-tahydroquinolizin-4-one 2.11 g of the title compound was obtained from (6S*,9aS*)-4-(3,4-difluorophenyl)hexahydroquinolizine-2,6-di-one (3 g) in the same manner as in Examples 13 and 14. The property values of the compound are as follows.

¹H-NMR (CDCl₃) δ(ppm): 1.38-2.00 (m, 8H), 2.28-2.35 (m, 1H), 2.42-2.60 (m, 2H), 3.24-3.32 (m, 1H), 6.06 (brd, J=4.4 Hz, 1H), 6.89-6.94 (m, 1H) 6.97-7.03 (m, 1H), 7.08-7.16 (m, 1H).

Synthesis of (E)-(6S,9aS)-6-(3,4-difluorophenyl)-3-[3-methoxy-4-(4-methyl-1H-imidazol-1-yl)ben-zylidene]octahydroquinolizin-4-one and (E)-(6R,9aR)-6-(3,4-difluorophenyl)-3-[3-methoxy-4-(4-methyl-1H-imidazol-1-yl)benzylidene] octahydroquinolizin-4-one 2.59 g of a racemate mixture of the title compound was obtained from (6S*,9aS*)-6-(3,4-difluorophenyl)octahydro-quinolizin-4-one (2.11 g) in the same manner as in Examples 21 and 22. The racemate was separated by CHIRALPAK™ AD-H manufactured by Daicel Chemical Industries, Ltd. (2 cm×25 cm; mobile phase: hexane:ethanol=55:45; flow rate: 10 mL/min) to obtain the title optically active compound with a retention time of 24 minutes (835 mg) and the title optically active compound with a retention time of 29 minutes (823 mg).

The property values of the title optically active compound with a retention time of 24 minutes (Example 65) are as follows.

¹H-NMR (CDCl₃) δ(ppm): 1.54-1.79 (m, 4H), 1.90-2.05 (m, 3H), 2.31 (s, 3H), 2.33-2.40 (m, 1H), 2.68-2.76 (m, 1H), 2.87-2.95 (m, 1H), 3.41-3.48 (m, 1H), 3.88 (s, 3H), 6.17 (brd, J=4.4 Hz, 1H), 6.94 (s, 1H), 6.98-7.28 (m, 6H), 7.30 (d, J=1.2 Hz, 1H), 7.84 (s, 1H).

The property values of the title optically active compound with a retention time of 29 minutes (Example 66) are as follows.

¹H-NMR (CDCl₃) δ(ppm): 1.54-1.79 (m, 4H), 1.90-2.05 (m, 3H), 2.31 (s, 3H), 2.33-2.40 (m, 1H), 2.68-2.76 (m, 1H), 2.87-2.95 (m, 1H), 3.41-3.48 (m, 1H), 3.88 (s, 3H), 6.17 (brd, J=4.4 Hz, 1H), 6.94 (s, 1H), 6.98-7.28 (m, 6H), 7.30 (d, J=1.2 Hz, 1H), 7.84 (s, 1H).

Examples 67 and 68

Synthesis of (E)-(6S,9aS)-6-(4-chlorophenyl)-3-[3-methoxy-4-(4-methyl-1H-imidazol-1-yl)benzylidene]octahydroquinolizin-4-one and (E)-(6R,9aR)-6-(4-chlorophenyl)-3-[3-methoxy-4-(4-methyl-1H-imidazol-1-yl)benzylidene]octahydroquinolizin-4-one

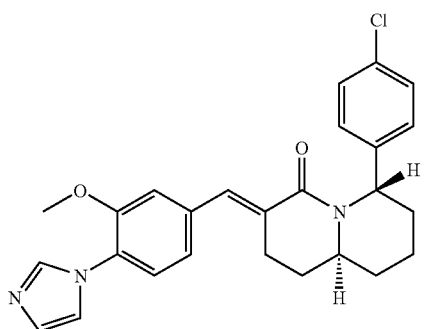

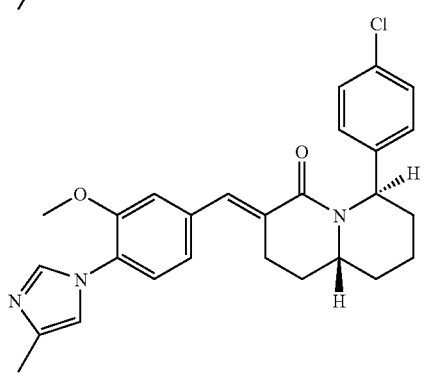

Synthesis of (6S*,9aS*)-6-(4-chlorophenyl)octahydroquinolizin-4-one (6S*,9aS*)-4-(4-chlorophenyl)hexahydroquinolizin-2,6-dione (15.8 g) was obtained from 4-methoxypyridine (14.2 mL) in the same manner as in Examples 13 and 14. 2.26 g of the title compound was obtained from 3 g of the resulting compound in the same manner as in Examples 13 and 14. The property values of the compound are as follows.
$^1$H-NMR (CDCl$_3$) δ(ppm): 1.22-1.98 (m, 9H), 2.32-2.60 (m, 3H), 3.34-3.31 (m, 1H), 6.09 (brd, J=4.4 Hz, 1H), 7.12-7.16 (m, 2H), 7.29-7.32 (m, 2H).

Synthesis of (E)-(6S,9aS)-6-(4-chlorophenyl)-3-[3-methoxy-4-(4-methyl-1H-imidazol-1-yl)benzylidene]octahydroquinolizin-4-one and (E)-(6R,9aR)-6-(4-chlorophenyl)-3-[3-methoxy-4-(4-methyl-1H-imidazol-1-yl)benzylidene]octahydroquinolizin-4-one 3.1 g of a racemate mixture of the title compound was obtained from (6S*,9aS*)-6-(4-chlorophenyl)octahydroquinolizin-4-one (2.26 g) in the same manner as in Examples 21 and 22. The racemate was separated by CHIRALPAK™ AD-H manufactured by Daicel Chemical Industries, Ltd. (2 cm×25 cm; mobile phase: hexane:ethanol=50:50; flow rate: 10 mL/min) to obtain the title optically active compound with a retention time of 25 minutes (1.02 g) and the title optically active compound with a retention time of 32 minutes (1.13 g).

The property values of the title optically active compound with a retention time of 25 minutes (Example 67) are as follows.
$^1$H-NMR (CDCl$_3$) δ(ppm): 1.54-1.79 (m, 4H), 1.84-2.04 (m, 3H), 2.31 (s, 3H), 2.37-2.44 (m, 1H), 2.67-2.76 (m, 1H), 2.86-2.94 (m, 1H), 3.40-3.46 (m, 1H), 3.87 (s, 3H), 6.19 (brd, J=4 Hz, 1H), 6.94 (s, 1H), 7.01-7.04 (m, 2H), 7.19-7.34 (m, 4H), 7.72 (d, J=1.6 Hz, 1H), 7.83 (s, 1H).

The property values of the title optically active compound with a retention time of 32 minutes (Example 68) are as follows.
$^1$H-NMR (CDCl$_3$) δ(ppm): 1.54-1.79 (m, 4H), 1.84-2.04 (m, 3H), 2.31 (s, 3H), 2.37-2.44 (m, 1H), 2.67-2.76 (m, 1H), 2.86-2.94 (m, 1H), 3.40-3.46 (m, 1H), 3.87 (s, 3H), 6.19 (brd, J=4 Hz, 1H), 6.94 (s, 1H), 7.01-7.04 (m, 2H), 7.19-7.34 (m, 4H), 7.72 (d, J=1.6 Hz, 1H), 7.83 (s, 1H).

Examples 69 and 70

Synthesis of (E)-(S)-6-(3,4,5-trifluorophenyl)-3-[3-methoxy-4-(4-methyl-1H-imidazol-1-yl)benzylidene]-1,2,3,8,9,9a-hexahydroquinolizin-4-one and (E)-(R)-6-(3,4,5-trifluorophenyl)-3-[3-methoxy-4-(4-methyl-1H-imidazol-1-yl)benzylidene]-1,2,3,8,9,9a-hexahydroquinolizin-4-one

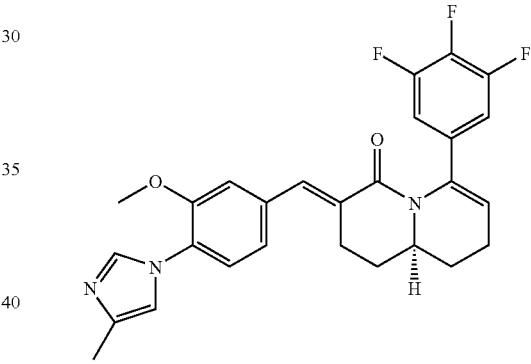

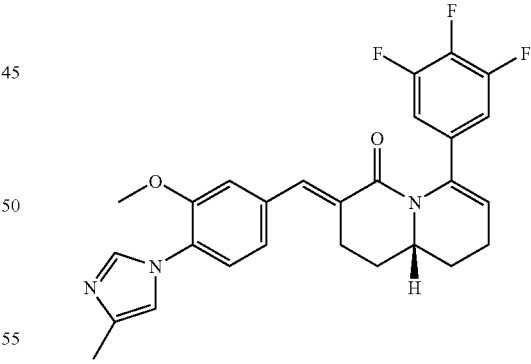

Synthesis of (S*)-6-(3,4,5-trifluorophenyl)-1,2,3,8,9,9a-hexahydroquinolizin-4-one A solution of (6S*,9aS*)-8-hydroxy-6-(3,4,5-trifluorophenyl)octahydroquinolizin-4-one obtained in Examples 13 and 14 (3.57 g) in THF (30 mL) was cooled to 0° C. Triethylamine (3.2 mL) and methanesulfonyl chloride (1.3 mL) were added to the reaction solution, which was then stirred at room temperature for 30 minutes. Potassium tert-butoxide (3.9 g) and THF (60 mL) were added to the reaction mixture, and the reaction mixture was heated under reflux for 80 minutes and left to cool. Then, water and ethyl acetate were added to the reaction solution, and the organic layer was separated. The resulting organic layer was washed with brine, dried over anhydrous magnesium sulfate, and then concentrated under reduced pressure. The residue was purified by silica gel column chromatography (elution solvent: heptane-ethyl acetate system) to obtain 1.65 g of the title compound. The property values of the compound are as follows.
$^1$H-NMR (CDCl$_3$) δ(ppm): 1.60-1.68 (m, 1H), 1.76-2.00 (m, 4H), 2.22-2.38 (m, 4H), 2.47-2.55 (m, 1H), 3.62-3.69 (m, 1H), 5.15 (t, J=4 Hz, 1H), 6.80-6.84 (m, 2H).

Synthesis of (E)-(S)-6-(3,4,5-trifluorophenyl)-3-[3-methoxy-4-(4-methyl-1H-imidazol-1-yl)benzylidene]-1,2,3,8,9,9a-hexahydroquinolizin-4-one and (E)-(R)-6-(3,4,5-trifluorophenyl)-3-[3-methoxy-4-(4-methyl-1H-imidazol-1-yl)benzylidene]-1,2,3,8,9,9a-hexahydroquinolizin-4-one 1.1 g of a racemate mixture of the title compound was obtained from (S*)-6-(3,4,5-trifluorophenyl)-1,2,3,8,9,9a-hexahydroquinolizin-4-one (1.02 g) in the same manner as in Examples 21 and 22. The racemate was separated by CHIRALPAK™ AD-H manufactured by Daicel Chemical Industries, Ltd. (2 cm×25 cm; mobile phase: hexane:ethanol=50:50; flow rate: 10 mL/min) to obtain the title optically active compound with a retention time of 18 minutes (202 mg) and the title optically active compound with a retention time of 25 minutes (216 mg).

The property values of the title optically active compound with a retention time of 18 minutes (Example 69) are as follows.
$^1$H-NMR (CDCl$_3$) δ(ppm): 1.55-1.65 (m, 1H), 1.71-1.82 (m, 2H), 2.06-2.13 (m, 1H), 2.30 (s, 3H), 2.32-2.42 (m, 2H), 2.63-2.73 (m, 1H), 3.03-3.10 (m, 1H), 3.74-3.82 (m, 1H), 3.86 (s, 3H), 5.54 (t, J=3.6 Hz, 1H), 6.84-7.03 (m, 5H), 7.26 (d, J=8 Hz, 1H), 7.62 (s, 1H), 7.72 (s, J=1.2 Hz, 1H).

The property values of the title optically active compound with a retention time of 25 minutes (Example 70) are as follows.
$^1$H-NMR (CDCl$_3$) δ(ppm): 1.55-1.65 (m, 1H), 1.71-1.82 (m, 2H), 2.06-2.13 (m, 1H), 2.30 (s, 3H), 2.32-2.42 (m, 2H), 2.63-2.73 (m, 1H), 3.03-3.10 (m, 1H), 3.74-3.82 (m, 1H), 3.86 (s, 3H), 5.54 (t, J=3.6 Hz, 1H), 6.84-7.03 (m, 5H), 7.26 (d, J=8 Hz, 1H), 7.62 (s, 1H), 7.72 (s, J=1.2 Hz, 1H).

Example 71

Synthesis of (E)-(6S,8S,9aR)-8-fluoro-3-[3-methoxy-4-(4-methyl-1H-imidazol-1-yl)benzylidene]-6-(3,4,5-trifluorophenyl)octahydroquinolizin-4-one

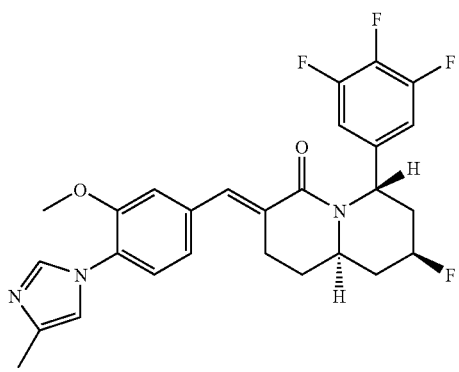

Synthesis of 1-(4-bromobutyryl)-2-(3,4,5-trifluorophenyl)-2,3-dihydro-1H-pyridin-4-one 1.02 g of the title compound was obtained from 4-methoxypyridine (1.52 mL), 3,4,5-trifluorophenylmagnesium bromide (0.3 M solution in THF, 50 mL), and 4-bromobutyryl chloride (1.74 mL) according to the method described in Tetrahedron Letters, 1986, vol. 27, p. 4549-4552. The property values of the compound are as follows.
$^1$H-NMR (CDCl$_3$) δ(ppm): 2.24-2.31 (m, 2H), 2.77-2.88 (m, 3H), 3.06-3.18 (m, 1H), 3.51-3.55 (m, 2H), 5.48 (brd, J=8.0 Hz, 1H), 5.98 (brs, 1H), 6.82-6.90 (m, 2H), 7.72 (brs, 1H).

Synthesis of (6S*,9aR*)-4-(3,4,5-trifluorophenyl) hexahydroquinolizine-2,6-dione 331 mg of the title compound was obtained from 1-(4-bromobutyryl)-2-(3,4,5-trifluorophenyl)-2,3-dihydro-1H-pyridin-4-one (1.15 g), tributyltin hydride (973 μL), and AIBN (201 mg) according to the method described in The Journal of Organic Chemistry, 1993, vol. 58, p. 4198-4199. The property values of the compound are as follows.
$^1$H-NMR (CDCl$_3$) δ(ppm): 1.61-1.69 (m, 1H), 1.72-1.82 (m, 1H), 1.87-1.97 (m, 1H), 1.99-2.07 (m, 1H), 2.23-2.31 (m, 1H), 2.39 (ddd, J=14.8, 3.2, 1.6 Hz, 1H), 2.47-2.57 (m, 2H), 2.81 (ddd, J=15.2, 7.2, 0.8 Hz, 1H), 2.92 (ddd, J=15.2, 2.4, 1.6 Hz, 1H), 3.52-3.59 (m, 1H), 6.45 (brd, J=7.2 Hz, 1H), 6.88-6.92 (m, 2H).

Synthesis of (6S*,9aR*)-8-hydroxy-6-(3,4,5-trifluorophenyl)octahydroquinolizin-4-one A solution of (6S*,9aR*)-4-(3,4,5-trifluorophenyl) hexahydroquinolizine-2,6-dione (331 mg) in methanol (10 mL) was cooled to 0° C. Sodium borohydride (64.1 mg) was added to the reaction solution, which was then stirred for one hour. Water and ethyl acetate were added to the reaction solution, and the organic layer was separated. The resulting organic layer was washed with brine, dried over anhydrous magnesium sulfate, and then concentrated under reduced pressure to obtain 340 mg of a crude alcohol compound. The property values of the compound are as follows.
$^1$H-NMR (CDCl$_3$) δ(ppm): 1.57-1.64 (m, 1H), 1.70-2.00 (m, 3H), 2.00-2.12 (m, 1H), 2.20-2.60 (m, 5H), 3.28-3.35 (m, ½H), 3.81-3.89 (m, 1H), 4.23-4.26 (m, ½H), 5.91 (brd, J=6.4 Hz, ½H), 6.15 (brd, J=4.8 Hz, ½H), 6.80-6.94 (m, 2H).

Synthesis of (6S*,8S*,9aR*)-8-(tert-butyldimethylsilanyloxy)-6-(3,4,5-fluorophenyl)octahydroquinolizin-4-one and (6S*,8R*,9aR*)-8-(tert-butyldimethylsilanyloxy)-6-(3,4,5-fluorophenyl) octahydroquinolizin-4-one A solution of (6S*,9aR*)-8-hydroxy-6-(3,4,5-trifluorophenyl)octahydroquinolizin-4-one (171 mg) in DMF (5.0 mL) was cooled to 0° C. Imidazole (233 mg), TBSCl (258 mg), and DMAP (6.98 mg) were sequentially added to the reaction solution, which was then stirred at room temperature for 4.5 hours. Water and ethyl acetate were added to the reaction solution, and the organic layer was separated. The resulting organic layer was washed with brine, dried over anhydrous magnesium sulfate, and then concentrated under reduced pressure. The residue was purified by silica gel column chromatography (elution solvent: heptane-ethyl acetate system) to obtain (6S*,8S*,9aR*)-8-(tert-butyldimethylsilanyloxy)-6-(3,4,5-fluorophenyl)octahydroquinolizin-4-one (103 mg) and (6S*,8R*,9aR*)-8-(tert-butyldimethylsilanyloxy)-6-(3,4,5-fluorophenyl)octahydroquinolizin-4-one (60.5 mg).

The property values of (6S*,8S*,9aR*)-8-(tert-butyldimethylsilanyloxy)-6-(3,4,5-fluorophenyl)octahydroquinolizin-4-one are as follows.

$^1$H-NMR (CDCl$_3$) δ(ppm): 0.00 (s, 3H), 0.03 (s, 3H), 0.75 (s, 9H), 1.61-1.74 (m, 2H), 1.74-1.80 (m, 1H), 1.82-2.02 (m, 2H), 2.07-2.14 (m, 2H), 2.35-2.40 (m, 1H), 2.53 (ddd, J=12.4, 8.8, 5.6 Hz, 1H), 2.60-2.67 (m, 1H), 3.90-3.96 (m, 1H), 4.23-4.26 (m, 1H), 5.99 (brd, J=7.2 Hz, 1H), 6.84-6.93 (m, 2H)

The property values of (6S*,8R*,9aR*)-8-(tert-butyldimethylsilanyloxy)-6-(3,4,5-fluorophenyl)octahydroquinolizin-4-one are as follows.

$^1$H-NMR (CDCl$_3$) δ(ppm): 0.00 (s, 3H), 0.03 (s, 3H), 0.84 (s, 9H), 1.38-1.47 (m, 1H), 1.53-1.60 (m, 2H), 1.67-1.80 (m, 2H), 1.82-1.99 (m, 2H), 2.33-2.38 (m, 1H), 2.40-2.48 (m, 1H), 2.48-2.56 (m, 1H), 3.22-3.29 (m, 1H), 3.68-3.76 (m, 1H), 6.06 (brs, 1H), 6.72-6.76 (m, 2H).

Synthesis of (E)-(6S*,8R*,9aR*)-8-(tert-butyldimethylsilanyloxy)-6-(3,45-trifluorophenyl)-3-[3-methoxy-4-(4-methyl-1H-imidazol-1-yl)benzylidene]octahydroquinolizin-4-one LDA (1.5 M solution in THF, 153 μL) was added to a solution of (6S*,8R*,9aR*)-8-(tert-butyldimethylsilanyloxy)-6-(3,4,5-fluorophenyl)octahydroquinolizin-4-one (47.7 mg) in THF (2.0 mL) at 0° C. The reaction solution was stirred at 0° C. for one hour, and then a solution of 3-methoxy-4-(4-methyl-1H-imidazol-1-yl)benzaldehyde (24.9 mg) in THF (1 mL) was added to the reaction solution. The reaction solution was further stirred at 0° C. for 30 minutes. Water and ethyl acetate were added to the reaction solution, and the organic layer was separated. The resulting organic layer was dried over magnesium sulfate and then concentrated under reduced pressure to obtain 27.2 mg of a crude aldol adduct.

A solution of the crude aldol adduct (27.2 mg) in methylene chloride (1.0 mL) was cooled to 0° C. Triethylamine (48.2 μL) and methanesulfonyl chloride (13.4 μL) were added to the reaction solution, which was then stirred at room temperature for five hours. Sodium methoxide (28% solution in methanol, 50 mg) and ethanol (1.0 mL) were added to the reaction solution, which was then stirred at room temperature for 1.5 hours. Water and ethyl acetate were added to the reaction solution, and the organic layer was separated. The resulting organic layer was washed with brine, dried over anhydrous magnesium sulfate, and then concentrated under reduced pressure. The residue was purified by silica gel column chromatography (elution solvent: heptane-ethyl acetate system->ethyl acetate-methanol system) to obtain 21.0 mg of the title compound. The property values of the compound are as follows.

$^1$H-NMR (CDCl$_3$) δ(ppm): 0.06 (s, 3H), 0.09 (s, 3H), 0.89 (s, 9H), 1.54-1.64 (m, 1H), 1.64-1.74 (m, 1H), 1.80-1.92 (m, 2H), 2.00-2.10 (m, 1H), 2.33 (s, 3H), 2.42-2.50 (m, 1H), 2.72-2.80 (m, 1H), 2.88-2.98 (m, 1H), 3.41-3.48 (m, 1H), 3.81-3.90 (m, 1H), 3.88 (s, 3H), 6.20-6.23 (m, 1H), 6.82-6.90 (m, 2H), 6.95 (brs, 1H), 7.02-7.06 (m, 2H), 7.26-7.30 (m, 1H), 7.81 (brs, 1H), 7.84 (s, 1H).

Synthesis of (E)-(6S*,8R*,9aR*)-6-(3,4,5-trifluorophenyl)-8-hydroxy-3-[3-methoxy-4-(4-methyl-1H-imidazol-1-yl)benzylidene]octahydroquinolizin-4-one TBAF (1.0 M solution in THF, 68.6 μL) was added to a solution of (E)-(6S*,8R*,9aR*)-8-(tert-butyldimethylsilanyloxy)-6-(3,4,5-trifluorophenyl)-3-[3-methoxy-4-(4-methyl-1H-imidazol-1-yl)benzylidene]octahydroquinolizin-4-one (21.0 mg) in THF (1.0 mL), and the reaction solution was stirred at room temperature overnight. A saturated ammonium chloride solution and ethyl acetate were added to the reaction solution, and the organic layer was separated. The resulting organic layer was washed with brine, dried over anhydrous magnesium sulfate, and then concentrated under reduced pressure. The residue was purified by silica gel column chromatography (carrier: Chromatorex NH; elution solvent: heptane-ethyl acetate system->ethyl acetate-methanol system) to obtain 11.5 mg of the title compound. The property values of the compound are as follows.

$^1$H-NMR (CDCl$_3$) δ(ppm): 1.50-1.61 (m, 1H), 1.68-1.90 (m, 3H), 1.98-2.12 (m, 1H), 2.34 (s, 3H), 2.56-2.64 (m, 1H), 2.72-2.80 (m, 1H), 2.88-3.00 (m, 1H), 3.45-3.51 (m, 1H), 3.81-3.96 (m, 1H), 3.89 (s, 3H), 6.26-6.30 (m, 1H), 6.88-6.92 (m, 2H), 6.96 (dd, J=1.2, 1.2 Hz, 1H), 7.03-7.06 (m, 2H), 7.28-7.30 (m, 1H), 7.83-7.85 (m, 2H).

Synthesis of (E)-(6S,8R,9aR)-6-(3,4,5-trifluorophenyl)-8-hydroxy-3-[3-methoxy-4-(4-methyl-1H-imidazol-1-yl)benzylidene]octahydroquinolizin-4-one and (E)-(6R,8S,9aS)-6-(3,4,5-trifluorophenyl)-8-hydroxy-3-[3-methoxy-4-(4-methyl-1H-imidazol-1-yl)benzylidene]octahydroquinolizin-4-one The racemate (E)-(6S*,8R*,9aR*)-6-(3,4,5-trifluorophenyl)-8-hydroxy-3-[3-methoxy-4-(4-methyl-1H-imidazol-1-yl)benzylidene]octahydroquinolizin-4-one obtained above (11.5 mg) was separated by CHIRALPAK™ AD-H manufactured by Daicel Chemical Industries, Ltd. (2 cm×25 cm; mobile phase: ethanol) to obtain the title optically active compound with a retention time of 4.8 minutes (4.9 mg; >99% ee) and the title optically active compound with a retention time of 6.0 minutes (4.4 mg; >99% ee).

The property values of the title optically active compound with a retention time of 4.8 minutes are as follows.

$^1$H-NMR (CDCl$_3$) δ(ppm): 1.50-1.61 (m, 1H), 1.68-1.90 (m, 3H), 1.98-2.12 (m, 1H), 2.34 (s, 3H), 2.56-2.64 (m, 1H), 2.72-2.80 (m, 1H), 2.88-3.00 (m, 1H), 3.45-3.51 (m, 1H), 3.81-3.96 (m, 1H), 3.89 (s, 3H), 6.26-6.30 (m, 1H), 6.88-6.92 (m, 2H), 6.96 (dd, J=1.2, 1.2 Hz, 1H), 7.03-7.06 (m, 2H), 7.28-7.30 (m, 1H), 7.83-7.85 (m, 2H).

The property values of the title optically active compound with a retention time of 6.0 minutes are as follows.

$^1$H-NMR (CDCl$_3$) δ(ppm): 1.50-1.61 (m, 1H), 1.68-1.90 (m, 3H), 1.98-2.12 (m, 1H), 2.34 (s, 3H), 2.56-2.64 (m, 1H), 2.72-2.80 (m, 1H), 2.88-3.00 (m, 1H), 3.45-3.51 (m, 1H), 3.81-3.96 (m, 1H), 3.89 (s, 3H), 6.26-6.30 (m, 1H), 6.88-6.92 (m, 2H), 6.96 (dd, J=1.2, 1.2 Hz, 1H), 7.03-7.06 (m, 2H), 7.28-7.30 (m, 1H), 7.83-7.85 (m, 2H).

Synthesis of (E)-(6S,8S,9aR)-8-fluoro-3-[3-methoxy-4-(4-methyl-1H-imidazol-1-yl)benzylidene]-6-(3,4,5-trifluorophenyl)octahydroquinolizin-4-one Diethylaminosulfur trifluoride (13.2 μL) was added to a solution of (E)-(6S,8R,9aR)-6-(3,4,5-trifluorophenyl)-8-hydroxy-3-[3-methoxy-4-(4-methyl-1H-imidazol-1-yl)benzylidene]octahydroquinolizin-4-one that is an optically active compound obtained above with a retention time of 4.8 minutes (10 mg) in dichloromethane (2.0 mL) under ice-cooling, and the reaction solution was stirred for two hours. Crushed ice, water, and ethyl acetate were added to the reaction solution, and the organic layer was separated. The resulting organic layer was washed with brine, dried over anhydrous magnesium sulfate, and then concentrated under reduced pressure. The residue was purified by silica gel column chromatography (elution solvent: heptane-ethyl acetate system->ethyl acetate-methanol system) to obtain 5.9 mg of the title optically active compound. The property values of the optically active compound are as follows.

$^1$H-NMR (CDCl$_3$) δ(ppm): 1.70-2.20 (m, 5H), 2.34 (s, 3H), 2.70-2.80 (m, 1H), 2.80-2.90 (m, 2H), 3.80-3.90 (m, 1H), 3.89 (s, 3H), 5.04-5.19 (m, 1H), 6.18 (d, J=7.6 Hz, 1H), 6.94-7.06 (m, 5H), 7.29 (d, J=8.0 Hz, H), 7.85 (s, 1H), 7.90 (s, 1H).

Example 72

Synthesis of (E)-(6S,8R,9aR)-8-methoxy-3-[3-methoxy-4-(4-methyl-1H-imidazol-1-yl)benzylidene]-6-(3,4,5-trifluorophenyl)octahydroquinolizin-4-one

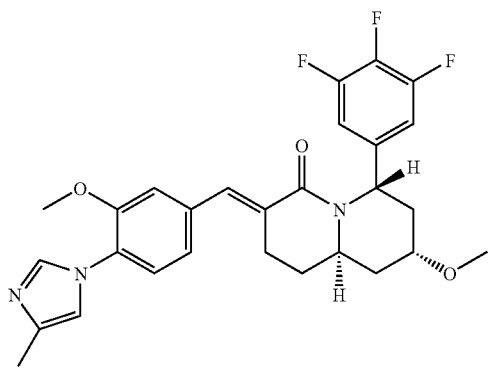

Sodium hydride (4.0 mg) and iodomethane (6.3 μL) were added to a solution of (E)-(6S,8R,9aR)-6-(3,4,5-trifluorophenyl)-8-hydroxy-3-[3-methoxy-4-(4-methyl-1H-imidazol-1-yl)benzylidene]octahydroquinolizin-4-one that is an optically active compound obtained in Example 71 with a retention time of 4.8 minutes (10 mg) in THF (2.0 mL) under ice-cooling, and the reaction solution was stirred at room temperature overnight. Water and ethyl acetate were added to the reaction solution, and the organic layer was separated. The resulting organic layer was washed with brine, dried over anhydrous magnesium sulfate, and then concentrated under reduced pressure. The residue was purified by silica gel column chromatography (carrier: Chromatorex NH; elution solvent: heptane-ethyl acetate system->ethyl acetate-methanol system) to obtain 3.05 mg of the title optically active compound. The property values of the optically active compound are as follows.

$^1$H-NMR (CDCl$_3$) δ(ppm): 1.43-1.51 (m, 1H), 1.70-1.86 (m, 2H), 2.04-2.14 (m, 2H), 2.31 (s, 3H), 2.58-2.66 (m, 1H), 2.72-2.82 (m, 1H), 2.88-2.98 (m, 1H), 3.38 (s, 3H), 3.38-3.50 (m, 2H), 3.88 (s, 3H), 6.25-6.30 (br, 1H), 6.85-6.96 (m, 3H), 7.00-7.06 (m, 2H), 7.24-7.30 (m, 1H), 7.73 (s, 1H), 7.84 (s, 1H).

Examples 73 and 74

Synthesis of (E)-(R)-4-(4-fluorophenyl)-7-[3-methoxy-4-(4-methyl-1H-imidazol-1-yl)benzylidene]-3,4,8,9-tetrahydro-7H-pyrido[2,1-c][1,4]oxazin-6-one and (E)-(S)-4-(4-fluorophenyl)-7-[3-methoxy-4-(4-methyl-1H-imidazol-1-yl)benzylidene]-3,4,8,9-tetrahydro-7H-pyrido[2,1-c][1,4]oxazin-6-one

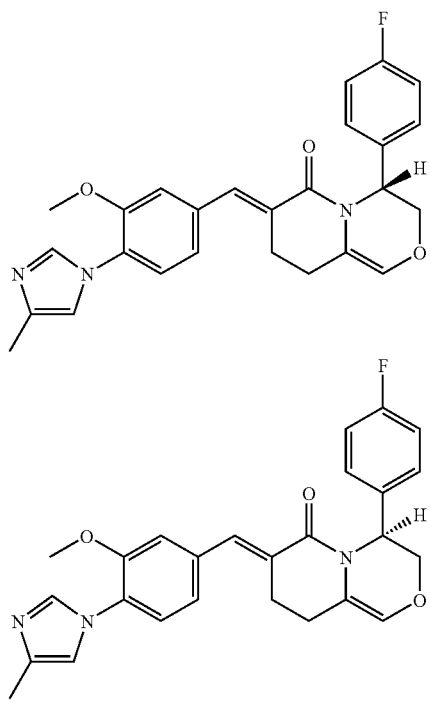

Synthesis of 2-amino-2-(4-fluorophenyl)ethanol 6.90 g of the title compound was obtained from 4-fluoro-DL-phenylglycine (10.0 g) according to the method described in The Journal of Organic Chemistry, 1993, vol. 58(13), p. 3568-3571. The property values of the compound are as follows.

$^1$H-NMR (CDCl$_3$) δ(ppm): 1.91 (brs, 2H), 3.53 (dd, J=4.4, 10.8 Hz, 1H), 3.71 (dd, J=4.4, 10.8 Hz, 1H), 4.05 (dd, J=4.4, 8.4 Hz, 1H), 7.01-7.07 (m, 2H), 7.27-7.33 (m, 2H).

Synthesis of (3R*,5S*,8aR*)-3-(4-fluorophenyl)hexahydrooxazolo[3,2-a]pyridine-5-carbonitrile 4.09 g of the title compound was obtained from 2-amino-2-(4-fluorophenyl)ethanol obtained above (6.9 g) according to the method described in Organic Synthesis, 1992, vol. 70, p. 54. The property values of the compound are as follows.

$^1$H-NMR (CDCl$_3$) δ(ppm): 1.49-1.58 (m, 1H), 1.64-1.84 (m, 2H), 1.88-1.97 (m, 2H), 2.10-2.16 (m, 1H), 3.70 (t, J=8.0 Hz, 1H), 3.80-3.81 (m, 1H), 3.88 (t, J=8.0 Hz, 1H), 4.11 (dd, J=2.8, 9.6 Hz, 1H), 4.24 (t, J=8.0 Hz, 1H), 7.03-7.08 (m, 2H), 7.33-7.37 (m, 2H).

Synthesis of (S*)-1-[(R*)-1-(4-fluorophenyl)-2-hydroxyethyl]-6-oxopiperidine-2-carbonitrile 1.17 g of the title compound was obtained from (3R*,5S*,8aR*)-3-(4-fluorophenyl)hexahydrooxazolo[3,2-a]pyridine-5-carbonitrile obtained above (4.09 g) according to the method described in European Journal of Organic Chemistry, 2004, vol. 23, p. 4823-4829. The property values of the compound are as follows.

$^1$H-NMR (CDCl$_3$) δ(ppm): 1.96-2.06 (m, 2H), 2.08-2.20 (m, 2H), 2.50-2.65 (m, 2H), 2.69-2.76 (m, 1H), 4.10-4.20 (m, 2H), 4.41-4.43 (m, 1H), 5.41-5.44 (m, 1H), 7.07-7.11 (m, 2H), 7.36-7.39 (m, 2H).

Synthesis of ethyl (R*)-1-[(R*)-1-(4-fluorophenyl)-2-hydroxyethyl]-6-oxopiperidine-2-carboxylate A solution of (S*)-1-[(R*)-1-(4-fluorophenyl)-2-hydroxyethyl]-6-oxopiperidine-2-carbonitrile (1.17 g) in saturated hydrochloric acid-ethanol (20 mL) was stirred at room temperature for two days. A saturated sodium bicarbonate solution and chloroform were added to the reaction solution, and the organic layer was separated. The resulting organic layer was washed with brine, dried over anhydrous magnesium sulfate, and then concentrated under reduced pressure. The residue was purified by silica gel column chromatography (elution solvent: heptane-ethyl acetate system->ethyl acetate-methanol system) to obtain 290 mg of the title compound. The property values of the compound are as follows.

$^1$H-NMR (CDCl$_3$) δ(ppm): 1.30 (t, J=7.2 Hz, 3H), 1.56-1.84 (m, 3H), 2.06-2.14 (m, 1H), 2.48-2.57 (m, 1H), 2.61-2.68 (m, 1H), 3.08-3.12 (m, 1H), 3.82-3.88 (m, 2H), 4.02-4.08 (m, 1H), 4.24 (q, J=7.2 Hz, 2H), 6.08 (dd, J=3.6, 9.2 Hz, 1H), 7.02-7.08 (m, 2H), 7.20-7.23 (m, 2H).

Synthesis of (R*)-4-(4-fluorophenyl)-1-hydroxyhexahydropyrido[2,1-c][1,4]oxazin-6-one Sodium borohydride (70.9 mg) was added to a solution of ethyl (R*)-1-[(R*)-1-(4-fluorophenyl)-2-hydroxyethyl]-6-oxopiperidine-2-carboxylate (290 mg) in methanol (5.0 mL) under ice-cooling, and the reaction solution was stirred for one hour and 40 minutes. Water and ethyl acetate were added to the reaction solution, and the organic layer was separated. The resulting organic layer was washed with brine, dried over anhydrous magnesium sulfate, and then concentrated under reduced pressure. The residue was purified by silica gel column chromatography (elution solvent: heptane-ethyl acetate system->ethyl acetate-methanol system) to obtain 183 mg of the title compound. The property values of the compound are as follows.

$^1$H-NMR (CDCl$_3$) δ(ppm): 1.46-1.68 (m, 2H), 1.76-1.90 (m, 1H), 1.90-2.00 (m, ⅓H), 2.08-2.18 (m, ⅔H), 2.36-2.56 (m, 2H), 2.89 (brs, ⅓H), 3.25-3.33 (m, ⅔H), 3.54 (t, 7.6 Hz, ⅓H), 3.99 (dd, J=4.4, 12.4 Hz, ⅔H), 4.12 (d, J=12 Hz, ⅓H), 4.39 (dd, J=2.4, 12.4 Hz, ⅔H), 4.48 (dd, J=3.6, J=12 Hz, ⅓H), 4.61 (dd, J=5.2, 8.0 Hz, ⅔H), 4.94-4.97 (m, ⅓H), 5.71-5.74 (m, ⅔H), 5.82 (brs, J=3.6 Hz, ⅓H), 6.99-7.05 (m, 2H), 7.47-7.53 (m, 2H).

Synthesis of (R*)-4-(4-fluorophenyl)-3,4,8,9-tetrahydro-7H-pyrido[2,1-c][1,4]oxazin-6-one and (4R*,9aR*)-4-(4-fluorophenyl)hexahydropyrido[2,1-c][1,4]oxazin-6-one Triethylsilane (5.5 mL) and trimethylsilyl trifluoromethanesulfonate (442 μL) were added to a solution of (R*)-4-(4-fluorophenyl)-1-hydroxyhexahydropyrido[2,1-c][1,4]oxazin-6-one (324 mg) in dichloromethane (10 mL), and the reaction solution was reacted at room temperature for 1.5 hours. Then, the reaction solution was heated to 60° C. and stirred for two hours. Water and ethyl acetate were added to the reaction solution, and the organic layer was separated. The resulting organic layer was washed with brine, dried over anhydrous magnesium sulfate, and then concentrated under reduced pressure. The residue was purified by silica gel column chromatography (elution solvent: heptane-ethyl acetate system->ethyl acetate-methanol system) to obtain 69.2 mg of (R*)-4-(4-fluorophenyl)-3,4,8,9-tetrahydro-7H-pyrido[2,1-c][1,4]oxazin-6-one and 52.8 mg of (4R*,9aR*)-4-(4-fluorophenyl)hexahydropyrido[2,1-c][1,4]oxazin-6-one. The physical properties of (R*)-4-(4-fluorophenyl)-3,4,8,9-tetrahydro-7H-pyrido[2,1-c][1,4]oxazin-6-one are as follows.

$^1$H-NMR (CDCl$_3$) δ(ppm): 1.86-1.93 (m, 2H), 2.38-2.42 (m, 2H), 2.54-2.59 (m, 2H), 4.05 (dd, J=2.8, 11.2 Hz, 1H), 4.33 (dd, J=1.2, 11.2 Hz, 1H), 5.65 (brs, 1H), 5.85 (s, 1H), 6.98-7.04 (m, 2H), 7.26-7.32 (m, 2H).

The physical properties of (4R*,9aR*)-4-(4-fluorophenyl)hexahydropyrido[2,1-c][1,4]oxazin-6-one are as follows.

$^1$H-NMR (CDCl$_3$) δ(ppm): 1.28-1.37 (m, 1H), 1.54-1.63 (m, 1H), 1.75-1.86 (m, 2H), 2.33-2.42 (m, 1H), 2.47-2.54 (m, 1H), 3.26 (t, J=10.8 Hz, 1H), 3.48-3.58 (m, 1H), 3.81-3.87 (m, 2H), 4.42 (d, J=12.4 Hz, 1H), 5.74 (d, J=3.2 Hz, 1H), 6.98-7.04 (m, 2H), 7.51-7.55 (m, 2H).

Synthesis of (E)-(R*)-4-(4-fluorophenyl)-7-[3-methoxy-4-(4-methyl-1H-imidazol-1-yl)benzylidene]-3,4,8,9-tetrahydro-7H-pyrido[2,1-c][1,4]oxazin-6-one LDA (1.5 M solution in THF, 212 μL) was added to a solution of (R*)-4-(4-fluorophenyl)-3,4,8,9-tetrahydro-7H-pyrido[2,1-c][1,4]oxazin-6-one (39.2 mg) in THF (2.0 mL) under ice-cooling. The reaction solution was stirred at 0° C. for 50 minutes, and then a solution of 3-methoxy-4-(4-methyl-1H-imidazol-1-yl)benzaldehyde (68.8 mg) in THF (1.0 mL) was added to the reaction solution. The reaction solution was further stirred at 0° C. for 50 minutes. Water and ethyl acetate were added to the reaction solution, and the organic layer was separated. The resulting organic layer was dried over magnesium sulfate and then concentrated under reduced pressure. The residue was purified by silica gel column chromatography (elution solvent: heptane-ethyl acetate system->ethyl acetate-methanol system) to obtain 56.5 mg of an alcohol compound. A solution of the resulting alcohol compound (56.5 mg) in methylene chloride (2.0 mL) was cooled to 0° C. Triethylamine (102 μL) and methanesulfonyl chloride (28.3 μL) were added to the reaction solution, which was then stirred at room temperature for one hour. The solvent in the reaction solution was removed by an evaporator. Then, methanol (2.0 mL) and sodium methoxide (28% solution in methanol, 118 mg) were added to the residue, and the reaction solution was stirred at room temperature overnight. Water and ethyl acetate were added to the reaction solution, and the organic layer was separated. The resulting organic layer was washed with brine, dried over anhydrous magnesium sulfate, and then concentrated under reduced pressure. The residue was purified by silica gel column chromatography (elution solvent: heptane-ethyl acetate system->ethyl acetate-methanol system) to obtain 39.0 mg of the title compound. The property values of the compound are as follows.

¹H-NMR (CDCl₃) δ(ppm): 2.30 (s, 3H), 2.39-2.48 (m, 2H), 2.73-2.81 (m, 1H), 3.02-3.07 (m, 1H), 3.86 (s, 3H), 4.18 (dd, J=2.4, 11.2 Hz, 1H), 4.45 (d, J=11.2 Hz, 1H), 5.73 (brs, 1H), 5.94 (s, 1H), 6.90-7.05 (m, 6H), 7.36-7.39 (m, 2H), 7.72 (d, J=0.8 Hz, 1H), 7.83 (s, 1H).

Synthesis of (E)-(R)-4-(4-fluorophenyl)-7-[3-methoxy-4-(4-methyl-1H-imidazol-1-yl)benzylidene]-3,4,8,9-tetrahydro-7H-pyrido[2,1-c][1,4]oxazin-6-one and (E)-(S)-4-(4-fluorophenyl)-7-[3-methoxy-4-(4-methyl-1H-imidazol-1-yl)benzylidene]-3,4,8,9-tetrahydro-7H-pyrido[2,1-c][1,4]oxazin-6-one The racemate (E)-(R*)-4-(4-fluorophenyl)-7-[3-methoxy-4-(4-methyl-1H-imidazol-1-yl)benzylidene]-3,4,8,9-tetrahydro-7H-pyrido[2,1-c][1,4]oxazin-6-one obtained above (39.0 mg) was separated by CHIRALCEL™ OJ-H manufactured by Daicel Chemical Industries, Ltd. (2 cm×25 cm; mobile phase: ethanol) to obtain the title optically active compound with a retention time of 7.1 minutes (12.9 mg; >99% ee) and the title optically active compound with a retention time of 13.7 minutes (12.2 mg; >99% ee). The property values of the title optically active compound with a retention time of 7.1 minutes (Example 73) are as follows.

¹H-NMR (CDCl₃) δ(ppm): 2.30 (s, 3H), 2.39-2.48 (m, 2H), 2.73-2.81 (m, 1H), 3.02-3.07 (m, 1H), 3.86 (s, 3H), 4.18 (dd, J=2.4, 11.2 Hz, 1H), 4.45 (d, J=11.2 Hz, 1H), 5.73 (brs, 1H), 5.94 (s, 1H), 6.90-7.05 (m, 6H), 7.36-7.39 (m, 2H), 7.72 (d, J=0.8 Hz, 1H), 7.83 (s, 1H).

The property values of the title optically active compound with a retention time of 13.7 minutes (Example 74) are as follows.

¹H-NMR (CDCl₃) δ(ppm): 2.30 (s, 3H), 2.39-2.48 (m, 2H), 2.73-2.81 (m, 1H), 3.02-3.07 (m, 1H), 3.86 (s, 3H), 4.18 (dd, J=2.4, 11.2 Hz, 1H), 4.45 (d, J=11.2 Hz, 1H), 5.73 (brs, 1H), 5.94 (s, 1H), 6.90-7.05 (m, 6H), 7.36-7.39 (m, 2H), 7.72 (d, J=0.8 Hz, 1H), 7.83 (s, 1H).

Examples 75 and 76

Synthesis of (E)-(4R,9aR)-4-(4-fluorophenyl)-7-[3-methoxy-4-(4-methyl-1H-imidazol-1-yl)benzylidene]hexahydropyrido[2,1-c][1,4]oxazin-6-one and (E)-(4S,9aS)-4-(4-fluorophenyl)-7-[3-methoxy-4-(4-methyl-1H-imidazol-1-yl)benzylidene]hexahydropyrido[2,1-c][1,4]oxazin-6-one

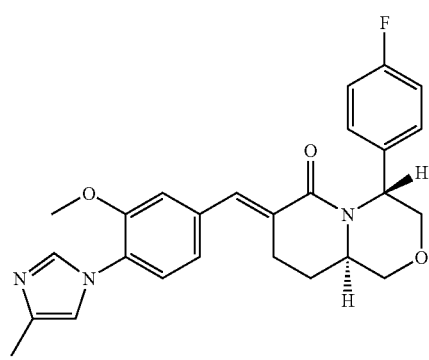

-continued

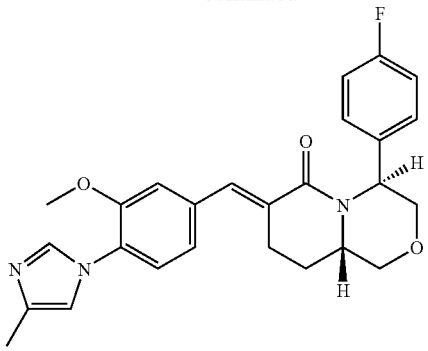

Synthesis of (4R*,9aR*)-4-(4-fluorophenyl)-7-[3-methoxy-4-(4-methyl-1H-imidazol-1-yl)benzylidene]hexahydropyrido[2,1-c][1,4]oxazin-6-one LDA (1.5 M solution in THF, 137 μL) was added to a solution of (4R*,9aR*)-4-(4-fluorophenyl)hexahydropyrido[2,1-c][1,4]oxazin-6-one (25.6 mg) in THF (2.0 mL) under ice-cooling. The reaction solution was stirred at 0° C. for 40 minutes, and then a solution of 3-methoxy-4-(4-methyl-1H-imidazol-1-yl)benzaldehyde (44.5 mg) in THF (1.0 mL) was added to the reaction solution. The reaction solution was further stirred at 0° C. for 40 minutes. Water and ethyl acetate were added to the reaction solution, and the organic layer was separated. The resulting organic layer was dried over magnesium sulfate and then concentrated under reduced pressure. The residue was purified by silica gel column chromatography (elution solvent: heptane-ethyl acetate system->ethyl acetate-methanol system) to obtain 38.5 mg of an alcohol compound. A solution of the resulting alcohol compound (38.5 mg) in methylene chloride (2.0 mL) was cooled to 0° C. Triethylamine (69.2 μL) and methanesulfonyl chloride (19.2 μL) were added to the reaction solution, which was then stirred at room temperature for two hours and 20 minutes. Methanol (1.0 mL) and sodium methoxide (28% solution in methanol, 160 mg) were added to the reaction solution, which was then stirred at room temperature for 40 minutes. Water and ethyl acetate were added to the reaction solution, and the organic layer was separated. The resulting organic layer was washed with brine, dried over anhydrous magnesium sulfate, and then concentrated under reduced pressure. The residue was purified by silica gel column chromatography (elution solvent: heptane-ethyl acetate system->ethyl acetate-methanol system) to obtain 19.2 mg of the title compound. The property values of the compound are as follows.

¹H-NMR (CDCl₃) δ(ppm): 1.39-1.49 (m, 1H), 1.87-1.94 (m, 1H), 2.03 (s, 3H), 2.39-2.48 (m, 1H), 2.96-3.01 (m, 1H), 3.30 (t, J=11.2 Hz, 1H), 3.70-3.78 (m, 1H), 3.84 (s, 3H), 3.84-3.96 (m, 2H), 4.57 (d, J=11.2 Hz, 1H), 5.88 (d, J=3.2 Hz, 1H), 6.93-7.08 (m, 5H), 7.24-7.28 (m, 1H), 7.59-7.63 (m, 2H), 7.72 (brs, 1H), 7.81 (d, J=1.6 Hz, 1H).

Synthesis of (4R,9aR)-4-(4-fluorophenyl)-7-[3-methoxy-4-(4-methyl-1H-imidazol-1-yl)benzylidene]hexahydropyrido[2,1-c][1,4]oxazin-6-one and (4S,9aS)-4-(4-fluorophenyl)-7-[3-methoxy-4-(4-methyl-1H-imidazol-1-yl)benzylidene]hexahydropyrido[2,1-c][1,4]oxazin-6-one The racemate (4R*,9aR*)-4-(4-fluorophenyl)-7-[3-methoxy-4-(4-methyl-1H-imidazol-1-yl)benzylidene]hexahydropyrido[2,1-c][1,4]oxazin-6-one obtained above (19.0 mg) was separated by CHIRALPAK™ AD-H manufactured by Daicel Chemical Industries, Ltd. (2 cm×25 cm; mobile phase: ethanol) to obtain the title optically active compound with a retention time of 7.3 minutes (7.3 mg; >99% ee) and the title optically active compound with a retention time of 8.9 minutes (7.1 mg; >97% ee).

The property values of the title optically active compound with a retention time of 7.3 minutes (Example 75) are as follows.

$^1$H-NMR (CDCl$_3$) δ(ppm): 1.39-1.49 (m, 1H), 1.87-1.94 (m, 1H), 2.03 (s, 3H), 2.39-2.48 (m, 1H), 2.96-3.01 (m, 1H), 3.30 (t, J=11.2 Hz, 1H), 3.70-3.78 (m, 1H), 3.84 (s, 3H), 3.84-3.96 (m, 2H), 4.57 (d, J=11.2 Hz, 1H), 5.88 (d, J=3.2 Hz, 1H), 6.93-7.08 (m, 5H), 7.24-7.28 (m, 1H), 7.59-7.63 (m, 2H), 7.72 (brs, 1H), 7.81 (d, J=1.6 Hz, 1H).

The property values of the title optically active compound with a retention time of 8.9 minutes (Example 76) are as follows.

$^1$H-NMR (CDCl$_3$) δ(ppm): 1.39-1.49 (m, 1H), 1.87-1.94 (m, 1H), 2.03 (s, 3H), 2.39-2.48 (m, 1H), 2.96-3.01 (m, 1H), 3.30 (t, J=11.2 Hz, 1H), 3.70-3.78 (m, 1H), 3.84 (s, 3H), 3.84-3.96 (m, 2H), 4.57 (d, J=11.2 Hz, 1H), 5.88 (d, J=3.2 Hz, 1H), 6.93-7.08 (m, 5H), 7.24-7.28 (m, 1H), 7.59-7.63 (m, 2H), 7.72 (brs, 1H), 7.81 (d, J=1.6 Hz, 1H).

Examples 77, 78, and 79

Synthesis of (E)-(6S,8R,9aR)-8-fluoro-3-[3-methoxy-4-(4-methyl-1H-imidazol-1-yl)benzylidene]-6-(3,4,5-trifluorophenyl)octahydroquinolizin-4-one, (E)-(6S,9aR)-3-[3-methoxy-4-(4-methyl-1H-imidazol-1-yl)benzylidene]-6-(3,4,5-trifluorophenyl)-1,2,3,6,9,9a-hexahydroquinolizin-4-one, and (E)-(6S,9aR)-3-[3-methoxy-4-(4-methyl-1H-imidazol-1-yl)benzylidene]-6-(3,4,5-trifluorophenyl)-1,2,3,6,7,9a-hexahydroquinolizin-4-one

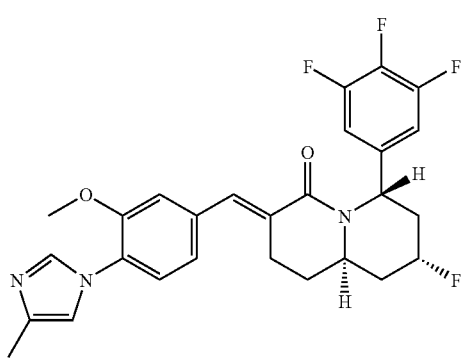

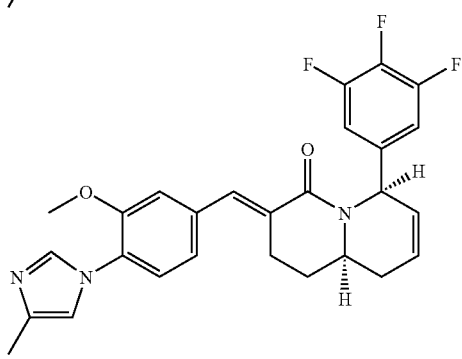

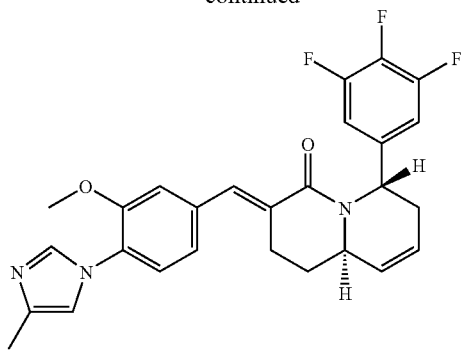

Synthesis of (E)-(6S*,8S*,9aR*)-8-(tert-butyldimethylsilanyloxy)-6-(3,4,5-trifluorophenyl)-3-[3-methoxy-4-(4-methyl-1H-imidazol-1-yl)benzylidene]octahydroquinolizin-4-one LDA (1.5 M solution in THF, 332 μL) was added to a solution of (6S*,8S*,9aR*)-8-(tert-butyldimethylsilanyloxy)-6-(3,4,5-fluorophenyl)octahydroquinolizin-4-one obtained in Example 71 (59.2 mg) in THF (2.0 mL) at 0° C. The reaction solution was stirred at 0° C. for one hour, and then a solution of 3-methoxy-4-(4-methyl-1H-imidazol-1-yl)benzaldehyde (59.2 mg) in THF (1 mL) was added to the reaction solution. The reaction solution was further stirred at 0° C. for 30 minutes. Water and ethyl acetate were added to the reaction solution, and the organic layer was separated. The resulting organic layer was dried over magnesium sulfate and then concentrated under reduced pressure to obtain 139 mg of a crude aldol adduct.

A solution of the crude aldol adduct (139 mg) in methylene chloride (3.0 mL) was cooled to 0° C. Triethylamine (185 μL) and methanesulfonyl chloride (51.3 μL) were added to the reaction solution, which was then stirred at room temperature for two hours and 10 minutes. Sodium methoxide (28% solution in methanol, 128 mg) and ethanol (1.0 mL) were added to the reaction solution, which was then stirred at room temperature for 40 minutes. Water and ethyl acetate were added to the reaction solution, and the organic layer was separated. The resulting organic layer was washed with brine, dried over anhydrous magnesium sulfate, and then concentrated under reduced pressure. The residue was purified by silica gel column chromatography (elution solvent: heptane-ethyl acetate system->ethyl acetate-methanol system) to obtain 61 mg of a mixture of the aldol adduct with the title compound. 61 mg of the resulting mixture was re-dissolved in methylene chloride (3.0 mL), and the reaction solution was cooled to 0° C. Triethylamine (147 μL) and methanesulfonyl chloride (51.3 μL) were added to the reaction solution, which was then stirred at room temperature for four hours and 15 minutes. Sodium methoxide (28% solution in methanol, 128 mg) and ethanol (1.0 mL) were added to the reaction solution, which was then stirred at room temperature for two hours and 15 minutes. Water and ethyl acetate were added to the reaction solution, and the organic layer was separated. The resulting organic layer was washed with brine, dried over anhydrous magnesium sulfate, and then concentrated under reduced pressure. The residue was purified by silica gel column chromatography (elution solvent: heptane-ethyl acetate system->ethyl acetate-methanol system) to obtain 44.1 mg of the title compound. The property values of the compound are as follows.

¹H-NMR (CDCl₃) δ(ppm): 0.00 (s, 3H), 0.03 (s, 3H), 0.75 (s, 9H), 1.68-1.78 (m, 2H), 1.78-1.87 (m, 1H), 2.08-2.20 (m, 2H), 2.38 (s, 3H), 2.38-2.41 (m, 1H), 2.82-2.88 (m, 1H), 2.93-3.00 (m, 1H), 3.92 (s, 3H), 4.02-4.07 (m, 1H), 4.25-4.29 (m, 1H), 6.05 (brd, J=7.2 Hz, 1H), 6.95-7.00 (m, 3H), 7.04-7.09 (m, 2H), 7.30-7.36 (m, 1H), 7.80-7.88 (m, 2H).

Synthesis of (E)-(6S*,8S*,9aR*)-6-(3,4,5-trifluorophenyl)-8-hydroxy-3-[3-methoxy-4-(4-methyl-1H-imidazol-1-yl)benzylidene]octahydroquinolizin-4-one TBAF (1.0 M solution in THF, 144 μL) was added to a solution of (E)-(6S*,8S*,9aR*)-8-(tert-butyldimethylsilanyloxy)-6-(3,4,5-trifluorophenyl)-3-[3-methoxy-4-(4-methyl-1H-imidazol-1-yl)benzylidene]octahydroquinolizin-4-one (44.1 mg) in THF (1.0 mL), and the reaction solution was stirred at room temperature overnight. A saturated ammonium chloride solution and ethyl acetate were added to the reaction solution, and the organic layer was separated. The resulting organic layer was washed with brine, dried over anhydrous magnesium sulfate, and then concentrated under reduced pressure. The residue was purified by silica gel column chromatography (carrier: Chromatorex NH; elution solvent: heptane-ethyl acetate system->ethyl acetate-methanol system) to obtain 25.4 mg of the title compound. The property values of the compound are as follows.

¹H-NMR (CDCl₃) δ(ppm): 1.67-1.84 (m, 2H), 1.84-1.94 (m, 1H), 2.07-2.20 (m, 2H), 2.41 (s, 3H), 2.41-2.48 (m, 1H), 2.76-2.86 (m, 1H), 2.86-2.96 (m, 1H), 3.88 (s, 3H), 3.97-4.05 (m, 1H), 4.29-4.34 (m, 1H), 5.98-6.04 (m, 1H), 6.94-7.06 (m, 5H), 7.26-7.30 (m, 1H), 7.78 (s, 1H), 7.81 (s, 1H).

Synthesis of (E)-(6S,8S,9aR)-6-(3,4,5-trifluorophenyl)-8-hydroxy-3-[3-methoxy-4-(4-methyl-1H-imidazol-1-yl)benzylidene]octahydroquinolizin-4-one and (E)-(6R,8R,9aS)-6-(3,4,5-trifluorophenyl)-8-hydroxy-3-[3-methoxy-4-(4-methyl-1H-imidazol-1-yl)benzylidene]octahydroquinolizin-4-one The racemate (E)-(6S*,8S*,9aR*)-6-(3,4,5-trifluorophenyl)-8-hydroxy-3-[3-methoxy-4-(4-methyl-1H-imidazol-1-yl)benzylidene]octahydroquinolizin-4-one obtained above (25.4 mg) was separated by CHIRALPAK™ AD-H manufactured by Daicel Chemical Industries, Ltd. (2 cm×25 cm; mobile phase: ethanol) to obtain the title optically active compound with a retention time of 4.4 minutes (13.3 mg; >99% ee) and the title optically active compound with a retention time of 5.2 minutes (12.1 mg; >97% ee).

The property values of the title optically active compound with a retention time of 4.4 minutes are as follows.

¹H-NMR (CDCl₃) δ(ppm): 1.67-1.84 (m, 2H), 1.84-1.94 (m, 1H), 2.07-2.20 (m, 2H), 2.41 (s, 3H), 2.41-2.48 (m, 1H), 2.76-2.86 (m, 1H), 2.86-2.96 (m, 1H), 3.88 (s, 3H), 3.97-4.05 (m, 1H), 4.29-4.34 (m, 1H), 5.98-6.04 (m, 1H), 6.94-7.06 (m, 5H), 7.26-7.30 (m, 1H), 7.78 (s, 1H), 7.81 (s, 1H).

The property values of the title optically active compound with a retention time of 5.2 minutes are as follows.

¹H-NMR (CDCl₃) δ(ppm): 1.67-1.84 (m, 2H), 1.84-1.94 (m, 1H), 2.07-2.20 (m, 2H), 2.41 (s, 3H), 2.41-2.48 (m, 1H), 2.76-2.86 (m, 1H), 2.86-2.96 (m, 1H), 3.88 (s, 3H), 3.97-4.05 (m, 1H), 4.29-4.34 (m, 1H), 5.98-6.04 (m, 1H), 6.94-7.06 (m, 5H), 7.26-7.30 (m, 1H), 7.78 (s, 1H), 7.81 (s, 1H).

Synthesis of (E)-(6S,8R,9aR)-8-fluoro-3-[3-methoxy-4-(4-methyl-1H-imidazol-1-yl)benzylidene]-6-(3,4,5-trifluorophenyl)octahydroquinolizin-4-one, (E)-(6S,9aR)-3-[3-methoxy-4-(4-methyl-1H-imidazol-1-yl)benzylidene]-6-(3,4,5-trifluorophenyl)-1,2,3,6,9,9a-hexahydroquinolizin-4-one, and (E)-(6S,9aR)-3-[3-methoxy-4-(4-methyl-1H-imidazol-1-yl)benzylidene]-6-(3,4,5-trifluorophenyl)-1,2,3,6,7,9a-hexahydroquinolizin-4-one Diethylaminosulfur trifluoride (301 μL) was added to a solution of (E)-(6S,8S,9aR)-6-(3,4,5-trifluorophenyl)-8-hydroxy-3-[3-methoxy-4-(4-methyl-1H-imidazol-1-yl)benzylidene]octahydroquinolizin-4-one that is an optically active compound obtained above with a retention time of 4.4 minutes (228 mg) in dichloromethane (20 mL) under ice-cooling, and the reaction solution was stirred at room temperature overnight. Crushed ice, water, and ethyl acetate were added to the reaction solution, and the organic layer was separated. The resulting organic layer was washed with brine, dried over anhydrous magnesium sulfate, and then concentrated under reduced pressure. The residue was purified by silica gel column chromatography (elution solvent: heptane-ethyl acetate system->ethyl acetate-methanol system) and CHIRALPAK™ AD-H manufactured by Daicel Chemical Industries, Ltd. (2 cm×25 cm; mobile phase: ethanol-hexane system) to obtain (E)-(6S,8R,9aR)-8-fluoro-3-[3-methoxy-4-(4-methyl-1H-imidazol-1-yl)benzylidene]-6-(3,4,5-trifluorophenyl)octahydroquinolizin-4-one (69 mg), (E)-(6S,9aR)-3-[3-methoxy-4-(4-methyl-1H-imidazol-1-yl)benzylidene]-6-(3,4,5-trifluorophenyl)-1,2,3,6,9,9a-hexahydroquinolizin-4-one (125 mg), and (E)-(6S,9aR)-3-[3-methoxy-4-(4-methyl-1H-imidazol-1-yl)benzylidene]-6-(3,4,5-trifluorophenyl)-1,2,3,6,7,9a-hexahydroquinolizin-4-one (1.8 mg). The property values of (E)-(6S,8R,9aR)-8-fluoro-3-[3-methoxy-4-(4-methyl-1H-imidazol-1-yl)benzylidene]-6-(3,4,5-trifluorophenyl)octahydroquinolizin-4-one are as follows.

¹H-NMR (CDCl₃) δ(ppm): 1.75-1.85 (m, 2H), 2.02-2.20 (m, 3H), 2.31 (s, 3H), 2.66-2.84 (m, 2H), 2.88-2.98 (m, 1H), 3.44-3.53 (m, 1H), 3.88 (s, 3H), 4.70-4.92 (m, 1H), 6.30 (brs, 1H), 6.87-6.96 (m, 3H), 7.00-7.05 (m, 2H), 7.28 (d, J=7.6 Hz, 1H), 7.74 (s, 1H), 7.85 (s, 1H).

The property values of (E)-(6S,9aR)-3-[3-methoxy-4-(4-methyl-1H-imidazol-1-yl)benzylidene]-6-(3,4,5-trifluorophenyl)-1,2,3,6,9,9a-hexahydroquinolizin-4-one are as follows.

¹H-NMR (CDCl₃) δ(ppm): 1.74-1.82 (m, 1H), 1.90-2.00 (m, 1H), 2.11-2.20 (m, 1H), 2.30 (s, 3H), 2.45-2.53 (m, 1H), 2.69-2.86 (m, 2H), 3.61-3.67 (m, 1H), 3.86 (s, 3H), 5.83-5.87 (m, 1H), 6.10-6.14 (m, 1H), 6.20 (brs, 1H), 6.93 (s, 1H), 6.98-7.06 (m, 2H), 7.16-7.21 (m, 2H), 7.24-7.28 (m, 1H), 7.73 (s, 1H), 7.80 (s, 1H).

The property values of (E)-(6S,9aR)-3-[3-methoxy-4-(4-methyl-1H-imidazol-1-yl)benzylidene]-6-(3,4,5-trifluorophenyl)-1,2,3,6,7,9a-hexahydroquinolizin-4-one are as follows.

¹H-NMR (CDCl₃) δ(ppm): 1.50-1.68 (m, 2H), 2.06-2.12 (m, 1H), 2.52-2.62 (m, 2H), 2.70-2.80 (m, 1H), 3.02-3.08 (m, 1H), 3.76-3.82 (m, 1H), 3.87 (s, 3H), 5.53-5.58 (m, 1H), 5.98-6.05 (m, 1H), 6.35 (d, J=6.8 Hz, 1H), 6.94 (s, 1H), 7.00-7.06 (m, 4H), 7.25-7.30 (m, 1H), 7.73 (s, 1H), 7.89 (s, 1H).

Examples 80 and 81

Synthesis of (E)-(4R,9aR)-7-[3-methoxy-4-(4-methyl-1H-imidazol-1-yl)benzylidene]-4-(3,4,5-trifluorophenyl)hexahydropyrido[2,1-c][1,4]oxazin-6-one and (E)-(4S,9aS)-7-[3-methoxy-4-(4-methyl-1H-imidazol-1-yl)benzylidene]-4-(3,4,5-trifluorophenyl) hexahydropyrido[2,1-c][1,4]oxazin-6-one

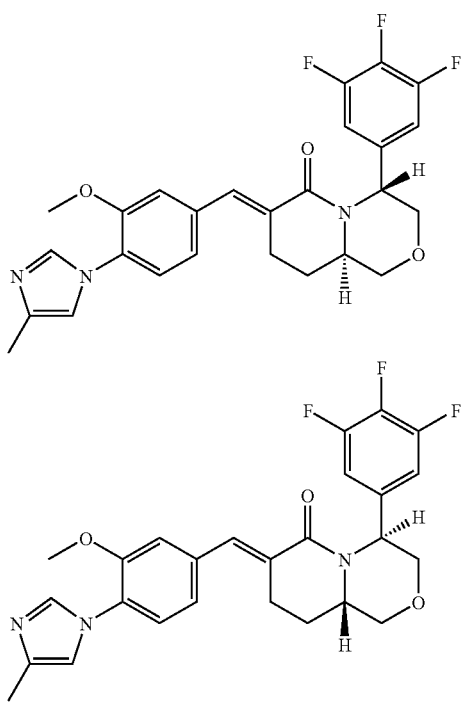

Synthesis of 2-amino-2-(3,4,5-trifluorophenyl)ethanol 9.31 g of the title compound was obtained from 3,4,5-trifluoro-DL-phenylglycine (12.4 g) according to the method described in The Journal of Organic Chemistry, 1993, vol. 58(13), p. 3568-3571. The property values of the compound are as follows.

$^1$H-NMR (CDCl$_3$) δ(ppm): 1.83 (brs, 2H), 3.50 (dd, J=7.6, 10.8 Hz, 1H), 3.72 (dd, J=4.0, 10.8 Hz, 1H), 4.04 (dd, J=4.0, 7.6 Hz, 1H), 6.96-7.06 (m, 2H).

Synthesis of (3R*,5S*,8aR*)-3-(3,4,5-trifluorophenyl)hexahydrooxazolo[3,2-a]pyridine-5-carbonitrile 6.6 g of the title compound was obtained from 2-amino-2-(3,4,5-trifluorophenyl)ethanol obtained above (9.3 g) according to the method described in Organic Synthesis, 1992, vol. 70, p. 54. The property values of the compound are as follows.

$^1$H-NMR (CDCl$_3$) δ(ppm): 1.48-1.59 (m, 1H), 1.64-1.76 (m, 1H), 1.78-1.87 (m, 1H), 1.92-1.98 (m, 2H), 2.11-2.16 (m, 1H), 3.65 (dd, J=7.2, 8.0 Hz, 1H), 3.83-3.87 (m, 2H), 4.11 (dd, J=2.8, 10.0 Hz, 1H), 4.24 (t, J=8.0 Hz, 1H), 6.99-7.06 (m, 2H).

Synthesis of (S*)-1-[(R*)-1-(3,4,5-trifluorophenyl)-2-hydroxyethyl]-6-oxopiperidine-2-carbonitrile 2.0 g of the title compound was obtained from (3R*,5S*,8aR*)-3-(3,4,5-trifluorophenyl)hexahydrooxazolo[3,2-a] pyridine-5-carbonitrile obtained above (6.6 g) according to the method described in European Journal of Organic Chemistry, 2004, vol. 23, p. 4823-4829. The property values of the compound are as follows.

$^1$H-NMR (CDCl$_3$) δ(ppm): 1.98-2.33 (m, 4H), 2.50-2.61 (m, 1H), 2.62-2.78 (m, 1H), 4.16 (brs, 2H), 4.50-4.52 (m, 1H), 5.32-5.34 (m, 1H), 7.05-7.98 (m, 2H).

Synthesis of ethyl 1-[2-hydroxy-1-(3,4,5-trifluorophenyl)ethyl]-6-oxopiperidine-2-carboxylate A solution of (S*) 1-[(R*)-1-(3,4,5-trifluorophenyl)-2-hydroxyethyl]-6-oxopiperidine-2-carbonitrile (2.0 g) in saturated hydrochloric acid-ethanol (30 mL) was stirred at room temperature for nine days. A saturated sodium bicarbonate solution and chloroform were added to the reaction solution, and the organic layer was separated. The resulting organic layer was washed with brine, dried over anhydrous magnesium sulfate, and then concentrated under reduced pressure. The residue was purified by silica gel column chromatography (elution solvent: heptane-ethyl acetate system->ethyl acetate-methanol system) to obtain 1.48 g of the title compound. The property values of the compound are as follows.

$^1$H-NMR (CDCl$_3$) δ(ppm): 1.30 (t, J=7.2 Hz, 3H), 1.68-1.88 (m, 3H), 2.12-2.18 (m, 1H), 2.46-2.58 (m, 1H), 3.03 (brs, 1H), 3.83-3.91 (m, 2H), 3.98-4.05 (m, 1H), 4.24 (q, J=7.2 Hz, 2H), 5.88-5.93 (m, 1H), 6.89-6.98 (m, 2H).

Synthesis of (4R*,9aR*)-4-(3,4,5-trifluorophenyl)hexahydropyrido[2,1-c][1,4]oxazin-6-one (166 mg) and (4R*,9aS*)-4-(3,4,5-trifluorophenyl)hexahydropyrido[2,1-c][1,4]oxazin-6-one Sodium borohydride (325 mg) was added to absolution of ethyl 1-[2-hydroxy-1-(3,4,5-trifluorophenyl)ethyl]-6-oxopiperidine-2-carboxylate (1.48 g) in methanol (20 mL) under ice-cooling, and the reaction solution was stirred for one hour and 20 minutes. Water and ethyl acetate were added to the reaction solution, and the organic layer was separated. The resulting organic layer was washed with brine, dried over anhydrous magnesium sulfate, and then concentrated under reduced pressure to obtain 1.22 g of a crude lactol compound. A mixture of the resulting crude lactol compound (1.22 g), (1S)-(+)-10-camphorsulfonic acid (94.1 mg), and trimethyl orthoformate (10 mL) was stirred at room temperature for 1.5 hours. Water and ethyl acetate were added to the reaction solution, and the organic layer was separated. The resulting organic layer was washed with brine, dried over anhydrous magnesium sulfate, and then concentrated under reduced pressure. Because the starting material remained, (1S)-(+)-10-camphorsulfonic acid (94.1 mg) and trimethyl orthoformate (10 mL) were added to the residue, and the reaction solution was stirred at room temperature overnight. Water and ethyl acetate were added to the reaction solution, and the organic layer was separated. The resulting organic layer was washed with brine, dried over anhydrous magnesium sulfate, and then concentrated under reduced pressure to obtain 1.27 g of a crude methoxy compound. A mixture of the resulting crude methoxy compound (950 mg), triethylsilane (4.84 mL), and TFA (10 mL) was stirred at 70° C. for 15.5 hours. Water and ethyl acetate were added to the reaction solution, and the organic layer was separated. The resulting organic layer was washed with brine, dried over anhydrous magnesium sulfate, and then concentrated under reduced pressure. The residue was purified by silica gel column chromatography (elution solvent: heptane-ethyl acetate system->ethyl acetate-methanol system) to obtain (4R*,9aR*)-4-(3,4,5-trifluorophenyl) hexahydropyrido[2,1-c][1,4]oxazin-6-one (166 mg) and (4R*,9aS*)-4-(3,4,5-trifluorophenyl)hexahydropyrido[2,1-c][1,4]oxazin-6-one (64 mg). The physical properties of (4R*,9aR*)-4-(3,4,5-trifluorophenyl)hexahydropyrido[2,1-c][1,4]oxazin-6-one are as follows.

$^1$H-NMR (CDCl$_3$) δ(ppm): 1.30-1.40 (m, 1H), 1.56-1.68 (m, 1H), 1.84-1.92 (m, 2H), 2.35-2.44 (m, 1H), 2.51-2.56 (m, 1H), 3.26 (t, J=11.2 Hz, 1H), 3.48-3.55 (m, 1H), 3.82 (dd, J=3.6, 12.4 Hz, 1H), 3.89 (dd, J=2.8, 11.2 Hz, 1H), 4.35 (d, J=12.4 Hz, 1H), 5.68 (d, J=2.8 Hz, 1H), 7.23-7.26 (m, 2H).

The physical properties of (4R*,9aS*)-4-(3,4,5-trifluorophenyl)hexahydropyrido[2,1-c][1,4]oxazin-6-one are as follows.

$^1$H-NMR (CDCl$_3$) δ(ppm): 1.50-1.60 (m, 1H), 1.80-1.94 (m, 2H), 1.98-2.08 (m, 1H), 2.42-2.46 (m, 2H), 3.56 (t, J=11.2 Hz, 1H), 3.63 (dd, J=6.4, 12.0 Hz, 1H), 3.80-3.84 (m, 1H), 3.94 (dd, J=4.0, 11.2 Hz, 1H), 4.16 (dd, J=4.0, 12 Hz, 1H), 4.71-4.74 (m, 1H), 6.87-6.91 (m, 2H).

Synthesis of (E)-(4R*,9aR*)-7-[3-methoxy-4-(4-methyl-1H-imidazol-1-yl)benzylidene]-4-(3,4,5-trifluorophenyl)hexahydropyrido[2,1-c][1,4]oxazin-6-one TMSI (327 µL) was added to a solution of (4R*,9aR*)-4-(3,4,5-trifluorophenyl)hexahydropyrido[2,1-c][1,4]oxazin-6-one (437 mg) and TMED (693 µL) in methylene chloride (15 mL) under ice-cooling. The reaction solution was stirred at 0° C. for one hour. Then, iodine (582 mg) was added to the reaction solution, which was then stirred at 0° C. for one hour and 10 minutes. A saturated sodium thiosulfate solution and ethyl acetate were added to the reaction solution, and the organic layer was separated. The resulting organic layer was washed with brine, dried over anhydrous magnesium sulfate, and then concentrated under reduced pressure to obtain an iodine compound. A mixture of the resulting iodine compound with triethyl phosphite (2.6 mL) was stirred at 120° C. for five hours. The solvent was removed by an evaporator. Then, 3-methoxy-4-(4-methyl-1H-imidazol-1-yl)benzaldehyde (430 mg) and lithium hydroxide (193 mg) were added to a solution of the resulting residue in THF-ethanol (10:1, 16.5 mL), and the reaction solution was stirred at room temperature overnight. Water and ethyl acetate were added to the reaction solution, and the organic layer was separated. The resulting organic layer was washed with brine, dried over anhydrous magnesium sulfate, and then concentrated under reduced pressure. The residue was purified by silica gel column chromatography (elution solvent: heptane-ethyl acetate system->ethyl acetate-methanol system) to obtain the title compound.

$^1$H-NMR (CDCl$_3$) δ(ppm): 1.41-1.51 (m, 1H), 1.90-1.98 (m, 1H), 2.30 (s, 3H), 2.42-2.52 (m, 1H), 2.98-3.06 (m, 1H), 3.29 (t, J=10.8 Hz, 1H), 3.68-3.77 (m, 1H), 3.86 (s, 3H), 3.88-3.98 (m, 2H), 4.41 (d, J=12 Hz, 1H), 5.81 (d, J=2.4 Hz, 1H), 6.93 (s, 1H), 6.97-6.99 (m, 2H), 7.24-7.34 (m, 3H), 7.72 (s, 1H), 7.82 (s, 1H).

Synthesis of (E)-(4R,9aR)-7-[3-methoxy-4-(4-methyl-1H-imidazol-1-yl)benzylidene]-4-(3,4,5-trifluorophenyl)hexahydropyrido[2,1-c][1,4]oxazin-6-one and (E)-(4S,9aS)-7-[3-methoxy-4-(4-methyl-1H-imidazol-1-yl)benzylidene]-4-(3,4,5-trifluorophenyl)hexahydropyrido[2,1-c][1,4]oxazin-6-one The racemate (E)-(4R*,9aR*)-7-[3-methoxy-4-(4-methyl-1H-imidazol-1-yl)benzylidene]-4-(3,4,5-trifluorophenyl)hexahydropyrido[2,1-c][1,4]oxazin-6-one obtained above was separated by CHIRALPAK™ IA-H manufactured by Daicel Chemical Industries, Ltd. (2 cm×25 cm; mobile phase: ethanol-hexane system) to obtain the title optically active compound with a retention time of 9.0 minutes (209 mg; >99% ee) and the title optically active compound with a retention time of 12.5 minutes (203 mg; >99% ee).

The property values of the title optically active compound with a retention time of 9.0 minutes (Example 80) are as follows.

$^1$H-NMR (CDCl$_3$) δ(ppm): 1.41-1.51 (m, 1H), 1.90-1.98 (m, 1H), 2.30 (s, 3H), 2.42-2.52 (m, 1H), 2.98-3.06 (m, 1H), 3.29 (t, J=10.8 Hz, 1H), 3.68-3.77 (m, 1H), 3.86 (s, 3H), 3.88-3.98 (m, 2H), 4.41 (d, J=12 Hz, 1H), 5.81 (d, J=2.4 Hz, 1H), 6.93 (s, 1H), 6.97-6.99 (m, 2H), 7.24-7.34 (m, 3H), 7.72 (s, 1H), 7.82 (s, 1H).

The property values of the title optically active compound with a retention time of 12.5 minutes (Example 81) are as follows.

$^1$H-NMR (CDCl$_3$) δ(ppm): 1.41-1.51 (m, 1H), 1.90-1.98 (m, 1H), 2.30 (s, 3H), 2.42-2.52 (m, 1H), 2.98-3.06 (m, 1H), 3.29 (t, J=10.8 Hz, 1H), 3.68-3.77 (m, 1H), 3.86 (s, 3H), 3.88-3.98 (m, 2H), 4.41 (d, J=12 Hz, 1H), 5.81 (d, J=2.4 Hz, 1H), 6.93 (s, 1H), 6.97-6.99 (m, 2H), 7.24-7.34 (m, 3H), 7.72 (s, 1H), 7.82 (s, 1H).

Examples 82 and 83

Synthesis of (E)-(4S,9aR)-7-[3-methoxy-4-(4-methyl-1H-imidazol-1-yl)benzylidene]-4-(3,4,5-trifluorophenyl)hexahydropyrido[2,1-c][1,4]oxazin-6-one and (E)-(4R,9aS)-7-[3-methoxy-4-(4-methyl-1H-imidazol-1-yl)benzylidene]-4-(3,4,5-trifluorophenyl)hexahydropyrido[2,1-c][1,4]oxazin-6-one

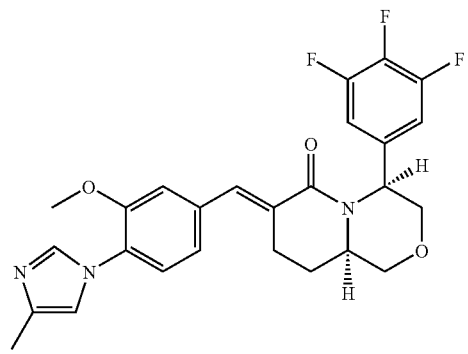

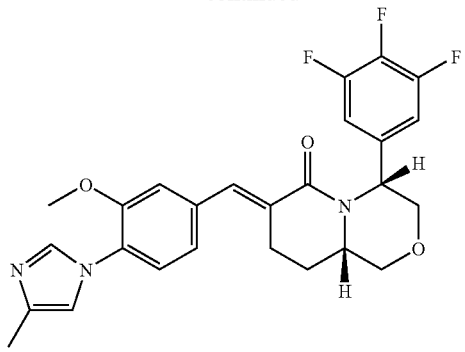

Synthesis of (E)-(4R*,9aS*)-7-[3-methoxy-4-(4-methyl-1H-imidazol-1-yl)benzylidene]-4-(3,4,5-trifluorophenyl)hexahydropyrido[2,1-c][1,4]oxazin-6-one TMSI (152 μL) was added to a solution of (4R*,9aS*)-4-(3,4,5-trifluorophenyl)hexahydropyrido[2,1-c][1,4]oxazin-6-one synthesized by the method of Examples 80 and 81 (204 mg) and TMED (377 μL) in methylene chloride (7.0 mL) under ice-cooling. The reaction solution was stirred at 0° C. for one hour. Then, iodine (272 mg) was added to the reaction solution, which was then stirred at 0° C. for one hour. A saturated sodium thiosulfate solution and ethyl acetate were added to the reaction solution, and the organic layer was separated. The resulting organic layer was washed with brine, dried over anhydrous magnesium sulfate, and then concentrated under reduced pressure to obtain an iodine compound. A mixture of the resulting iodine compound with triethyl phosphite (2.0 mL) was stirred at 120° C. for seven hours. The solvent was removed by an evaporator. Then, 3-methoxy-4-(4-methyl-1H-imidazol-1-yl)benzaldehyde (301 mg) and lithium hydroxide monohydrate (89.9 mg) were added to a solution of the resulting residue in THF-ethanol (10:1, 7.7 mL), and the reaction solution was stirred at room temperature for two hours and 20 minutes. Water and ethyl acetate were added to the reaction solution, and the organic layer was separated. The resulting organic layer was washed with brine, dried over anhydrous magnesium sulfate, and then concentrated under reduced pressure. The residue was purified by silica gel column chromatography (elution solvent: heptane-ethyl acetate system->ethyl acetate-methanol system) to obtain 300 mg of the title compound. The property values of the compound are as follows.

¹H-NMR (CDCl₃) δ(ppm): 1.60-1.75 (m, 1H), 1.96-2.02 (m, 1H), 2.30 (s, 3H), 2.72-2.83 (m, 1H), 3.12-3.20 (m, 1H), 3.62 (t, J=11.6 Hz, 1H), 3.86 (s, 3H), 3.86 (dd, J=4.8, 12.4 Hz, 1H), 3.96 (dd, J=4.0, 11.6 Hz, 1H), 4.10-4.17 (m, 1H), 4.32 (dd, J=3.6, 12.4 Hz, 1H), 5.02 (dd, J=3.6, 4.8 Hz, 1H), 6.93-6.94 (m, 1H), 6.96-7.05 (m, 4H), 7.26-7.29 (m, 1H), 7.73 (d, J=1.6 Hz, 1H), 7.76 (d, J=2.4 Hz, 1H).

Synthesis of (E)-(4S,9aR)-7-[3-methoxy-4-(4-methyl-1H-imidazol-1-yl)benzylidene]-4-(3,4,5-trifluorophenyl)hexahydropyrido[2,1-c][1,4]oxazin-6-one and (E)-(4R,9aS)-7-[3-methoxy-4-(4-methyl-1H-imidazol-1-yl)benzylidene]-4-(3,4,5-trifluorophenyl)hexahydropyrido[2,1-c][1,4]oxazin-6-one The racemate (E)-(4R*,9aS*)-7-[3-methoxy-4-(4-methyl-1H-imidazol-1-yl)benzylidene]-4-(3,4,5-trifluorophenyl)hexahydropyrido[2,1-c][1,4]oxazin-6-one obtained above was separated by CHIRALPAK™ IA manufactured by Daicel Chemical Industries, Ltd. (2 cm×25 cm; mobile phase: isopropyl alcohol) to obtain the title optically active compound with a retention time of 22.0 minutes (69.6 mg; >99% ee) and the title optically active compound with a retention time of 26.2 minutes (61 mg; >95% ee).

The property values of the title optically active compound with a retention time of 22.0 minutes (Example 82) are as follows.

¹H-NMR (CDCl₃) δ(ppm): 1.60-1.75 (m, 1H), 1.96-2.02 (m, 1H), 2.30 (s, 3H), 2.72-2.83 (m, 1H), 3.12-3.20 (m, 1H), 3.62 (t, J=11.6 Hz, 1H), 3.86 (s, 3H), 3.86 (dd, J=4.8, 12.4 Hz, 1H), 3.96 (dd, J=4.0, 11.6 Hz, 1H), 4.10-4.17 (m, 1H), 4.32 (dd, J=3.6, 12.4 Hz, 1H), 5.02 (dd, J=3.6, 4.8 Hz, 1H), 6.93-6.94 (m, 1H), 6.96-7.05 (m, 4H), 7.26-7.29 (m, 1H), 7.73 (d, J=1.6 Hz, 1H), 7.76 (d, J=2.4 Hz, 1H).

The property values of the title optically active compound with a retention time of 26.2 minutes (Example 83) are as follows.

¹H-NMR (CDCl₃) δ(ppm): 1.60-1.75 (m, 1H), 1.96-2.02 (m, 1H), 2.30 (s, 3H), 2.72-2.83 (m, 1H), 3.12-3.20 (m, 1H), 3.62 (t, J=11.6 Hz, 1H), 3.86 (s, 3H), 3.86 (dd, J=4.8, 12.4 Hz, 1H), 3.96 (dd, J=4.0, 11.6 Hz, 1H), 4.10-4.17 (m, 1H), 4.32 (dd, J=3.6, 12.4 Hz, 1H), 5.02 (dd, J=3.6, 4.8 Hz, 1H), 6.93-6.94 (m, 1H), 6.96-7.05 (m, 4H), 7.26-7.29 (m, 1H), 7.73 (d, J=1.6 Hz, 1H), 7.76 (d, J=2.4 Hz, 1H).

(E)-(4R,9aS)-7-[3-methoxy-4-(4-methyl-1H-imidazol-1-yl)benzylidene]-4-(3,4,5-trifluorophenyl)hexahydropyrido[2,1-c][1,4]oxazin-6-one was also separately synthesized by the following method.

Synthesis of (S)-5-benzyloxymethylmorpholin-3-one

Bromoacetyl chloride (5.06 mL) was added to a mixed solution of (R)-(+)-2-amino-3-benzyloxy-1-propanol (10 g) in toluene (100 mL) and a 2 N sodium hydroxide solution (100 mL) under ice-cooling. The reaction solution was stirred at 0° C. for 30 minutes and then at 60° C. for one hour. The reaction solution was returned to room temperature. Then, a toluene-THF (1:1) mixed solution was added to the reaction solution, and the organic layer was separated. The resulting organic layer was dried over anhydrous magnesium sulfate and then concentrated under reduced pressure. The residue was purified by silica gel column chromatography (elution solvent: heptane-ethyl acetate system) to obtain 1.36 g of the title compound. The property values of the compound are as follows.

¹H-NMR (CDCl₃) δ(ppm): 3.42 (t, J=9.2 Hz, 1H), 3.54 (dd, J=9.2, 5.2 Hz, 1H), 3.62 (dd, J=12.0, 6.0 Hz, 1H), 3.75 (m, 1H), 3.86 (dd, J=12.0, 4.0 Hz, 1H), 4.12 (d, J=16.8 Hz, 1H), 4.18 (d, J=16.8 Hz, 1H), 4.53 (s, 2H), 6.29 (bs, 1H), 7.28-7.40 (m, 5H).

Synthesis of tert-butyl (S)-3-benzyloxymethyl-5-oxomorpholine-4-carboxylate

TEA (1.72 mL), 4-dimethylaminopyridine (189 mg), and di-tert-butyl dicarbonate (2.02 g) were added to a solution of (S)-5-benzyloxymethylmorpholin-3-one (1.36 g) in acetonitrile (25 mL). The reaction solution was stirred at room temperature for two hours. Then, brine and ethyl acetate were added to the reaction solution, and the organic layer was separated. The resulting organic layer was dried over anhydrous magnesium sulfate and then concentrated under reduced pressure. The residue was purified by silica gel column chromatography (elution solvent: heptane-ethyl acetate system) to obtain 1.65 g of the title compound. The property values of the compound are as follows.

¹H-NMR (CDCl₃) δ(ppm): 1.50 (s, 9H), 3.57 (dd, J=8.8, 4.8 Hz, 1H), 3.68-3.75 (m, 2H), 4.08-4.28 (m, 4H), 4.53 (d, J=12.0 Hz, 1H), 4.58 (d, J=12.0 Hz, 1H), 7.25-7.36 (m, 5H).

Synthesis of tert-butyl {(S)-1-benzyloxymethyl-2-[2-oxo-2-(3,4,5-trifluorophenyl)ethoxy]ethyl}carbamate To a suspension of magnesium (249 mg) in diethyl ether (5 mL), 1-bromo-3,4,5-trifluorobenzene (446 μL) was added dropwise at 40° C. over 10 minutes, and the reaction solution was stirred at 40° C. for one hour. This solution was added dropwise to a solution of tert-butyl (S)-3-benzyloxymethyl-5-oxomorpholine-4-carboxylate (1.1 g) in tetrahydrofuran (30 mL) at −40° C. over 10 minutes, and the reaction solution was stirred at −40° C. for one hour. A saturated ammonium chloride solution was added to the solution in small portions at −40° C., and the reaction solution was returned to room temperature. Ethyl acetate was added to the reaction solution, and the organic layer was separated. The resulting organic layer was washed with brine, and then dried over anhydrous magnesium sulfate and concentrated under reduced pressure. The residue was purified by silica gel column chromatography (heptane-ethyl acetate system) to obtain 952 mg of the title compound. The property values of the compound are as follows.

¹H-NMR (CDCl₃) δ(ppm): 1.43 (s, 9H), 3.54 (dd, J=9.2, 6.0 Hz, 1H), 3.61-3.71 (m, 3H), 3.96 (m, 1H), 4.51 (s, 2H), 4.61 (s, 2H), 5.02 (m, 1H), 7.21-7.35 (m, 5H), 7.50-7.62 (m, 2H).

Synthesis of [(3S,5R)-5-(3,4,5-trifluorophenyl)morpholin-3-yl]methanol

A solution of 4 N hydrochloric acid in ethyl acetate (30 mL) was added to a solution of tert-butyl {(S)-1-benzyloxymethyl-2-[2-oxo-2-(3,4,5-trifluorophenyl)ethoxy]ethyl}carbamate (3.55 g) in ethyl acetate (30 mL) at room temperature. The reaction solution was stirred at room temperature for one hour and then concentrated under reduced pressure. 10% palladium-carbon (containing 50% water, 167 mg) was added to a solution of the resulting residue in methanol (50 mL), and the reaction solution was stirred in a hydrogen atmosphere at room temperature for 18 hours. Palladium-carbon in the reaction solution was removed by filtration, and then the filtrate was concentrated under reduced pressure. A saturated sodium bicarbonate solution and ethyl acetate were added to the resulting residue, and the organic layer was separated. The organic layer was washed with brine. The resulting organic layer was dried over anhydrous magnesium sulfate and then concentrated under reduced pressure. The residue was purified by silica gel column chromatography (elution solvent: heptane-ethyl acetate system) to obtain 1.52 g of the title compound. The property values of the compound are as follows.

¹H-NMR (CDCl₃) δ(ppm): 3.13-3.22 (m, 2H), 3.34 (dd, J=10.8, 10.4 Hz, 1H), 3.53 (dd, J=10.8, 6.4 Hz, 1H), 3.67 (dd, J=10.8, 4.0 Hz, 1H), 3.77 (dd, J=10.8, 3.2 Hz, 1H), 3.85 (dd, J=10.8, 3.2 Hz, 1H), 3.96 (dd, J=10.4, 3.2 Hz, 1H), 7.02-7.25 (m, 2H).

Synthesis of 1-[(3S,5R)-3-hydroxymethyl-5-(3,4,5-trifluorophenyl)morpholin-4-yl]-(3-buten)-1-one Vinylacetic acid (0.784 mL), bis(2-oxo-3-oxazolidinyl)phosphinic chloride (2.35 g), and TEA (1.71 mL) were sequentially added to a solution of [(3S,5R)-5-(3,4,5-trifluorophenyl)morpholin-3-yl]methanol (1.52 g) in THF (50 mL) at room temperature. The reaction solution was stirred at room temperature for two hours. Then, a 1 N hydrochloric acid solution and ethyl acetate were added to the reaction solution, and the organic layer was separated. The resulting organic layer was washed with a 1 N sodium hydroxide solution and brine, dried over anhydrous magnesium sulfate, and then concentrated under reduced pressure. The residue was purified by silica gel column chromatography (elution solvent: heptane-ethyl acetate system) to obtain 1.66 g of the title compound. The property values of the compound are as follows.

ESI-MS; m/z 316 [M⁺+H]. ¹H-NMR (CDCl₃) δ(ppm): 3.30 (m, 3H), 3.46 (m, 1H), 3.65 (dd, J=12.0, 4.0 Hz, 1H), 3.76 (dd, J=12.8, 4.0 Hz, 1H), 3.80 (m, 1H), 3.99 (d, J=12.0 Hz, 1H), 4.48 (d, J=12.8 Hz, 1H), 5.15-5.29 (m, 2H), 5.64 (m, 1H), 6.01 (m, 1H), 7.25-7.30 (m, 2H).

Synthesis of methyl (E)-3-[(3S,5R)-4-(3-butenoyl)-5-(3,4,5-trifluorophenyl)morpholin-3-yl]acrylate Oxalyl chloride (0.664 mL) was added dropwise to a solution of DMSO (0.576 mL) in dichloromethane (40 mL) at −78° C., and the reaction solution was stirred at the same temperature for 20 minutes. A solution of 1-[(3S,5R)-3-hydroxymethyl-5-(3,4,5-trifluorophenyl)morpholin-4-yl]-(3-buten)-1-one (1.6 g) in dichloromethane (10 mL) was added dropwise to the reaction solution at −78° C., and the reaction solution was stirred at the same temperature for 30 minutes. Triethylamine (3.54 mL) was added dropwise to the reaction solution, which was then stirred at −78° C. for 30 minutes. A saturated ammonium chloride solution was added to the reaction solution, and then the reaction solution was heated to room temperature. Ethyl acetate was added to the reaction solution, and the organic layer was separated. The organic layer was washed with brine, dried over anhydrous magnesium sulfate, and then concentrated under reduced pressure to obtain an aldehyde compound. Sodium hydride (60% oil, 0.304 g) was added to a mixed solution of trimethyl phosphonoacetate (1.46 mL) in THF (35 mL) and DMF (8 mL) at 0° C., and the reaction solution was stirred at room temperature for 30 minutes. A solution of the aldehyde compound obtained above in THF (5 mL) was added to the reaction solution at 0° C., and the reaction solution was stirred at room temperature for 30 minutes. A saturated ammonium chloride solution and ethyl acetate were added to the reaction solution, and the organic layer was separated. The resulting organic layer was dried over anhydrous magnesium sulfate and then concentrated under reduced pressure. The residue was purified by silica gel column chromatography (elution solvent: heptane-ethyl acetate system) to obtain 1.24 g of the title compound. The property value of the compound is as follows.
ESI-MS; m/z 370 [M⁺+H].

Synthesis of (4R,9aS)-4-(3,4,5-trifluorophenyl)-3,4,7,9a-tetrahydro-1H-pyrido[2,1-c][1,4]oxazin-6-one Grubbs catalyst 2nd generation (285 mg) was added to a solution of methyl (E)-3-[(3S,5R)-4-(3-butenoyl)-5-(3,4,5-trifluorophenyl)morpholin-3-yl]acrylate (1.24 g) in dichloromethane (100 mL), and the reaction solution was heated under reflux in a nitrogen atmosphere for 1.5 hours. The reaction solution was returned to room temperature. Triethylamine (3 mL) was added to the reaction solution, which was then stirred for 10 minutes. The reaction solution was concentrated under reduced pressure, and the residue was purified by silica gel column chromatography (heptane-ethyl acetate system) to obtain 250 mg of the title compound. The property values of the compound are as follows.

ESI-MS; m/z 284 [M$^+$+H]. $^1$H-NMR (CDCl$_3$) δ(ppm): 2.91-3.11 (m, 2H), 3.62-3.69 (m, 2H), 4.06 (dd, J=11.2, 4.0 Hz, 1H), 4.22 (dd, J=12.0, 3.2 Hz, 1H), 4.50-4.60 (m, 1H), 4.76-4.80 (m, 1H), 5.57-5.61 (m, 1H), 5.93-6.01 (m, 1H), 6.83-6.95 (m, 2H).

Synthesis of (4R,9aS)-4-(3,4,5-trifluorophenyl) hexahydropyrido[2,1-c][1,4]oxazin-6-one Platinum oxide (20.1 mg) was added to a solution of (4R, 9aS)-4-(3,4,5-trifluorophenyl)-3,4,7,9a-tetrahydro-1H-pyrido[2,1-c][1,4]oxazin-6-one (250 mg) in methanol (6 mL), and the reaction solution was stirred in a hydrogen atmosphere at room temperature for two hours. The reaction solution was filtered through celite, and the filtrate was concentrated under reduced pressure to obtain 252 mg of the title compound. The property value of the compound is as follows.

ESI-MS; m/z 286 [M$^+$+H].

Synthesis of diethyl [(4R,9aS)-6-oxo-4-(3,4,5-trifluorophenyl)octahydropyrido[2,1-c][1,4]oxazin-7-yl] phosphonate Iodotrimethylsilane (0.188 mL) was added to a solution of (4R,9aS)-4-(3,4,5-trifluorophenyl)hexahydropyrido[2,1-c][1,4]oxazin-6-one (252 mg) and N,N,N',N'-tetramethylethylenediamine (0.466 mL) in methylene chloride (6 mL) in a nitrogen atmosphere at 0° C., and the reaction solution was stirred under ice-cooling for 30 minutes. Iodine (336 mg) was added to the reaction solution under ice-cooling, and the reaction solution was stirred under ice-cooling for one hour. Ethyl acetate and a saturated sodium thiosulfate solution were added to the reaction solution, and the organic layer was separated. The resulting organic layer was washed with brine, dried over magnesium sulfate, and then concentrated under reduced pressure to obtain an iodide compound. Triethyl phosphite (3 mL) was added to the resulting iodide compound, and the mixture was stirred at 120° C. for two hours. The reaction solution was left to cool to room temperature and then concentrated under reduced pressure to obtain 372 mg of the title compound. The property value of the compound is as follows.

ESI-MS; m/z 422 [M$^+$+H].

Synthesis of (E)-(4R,9aS)-7-[3-methoxy-4-(4-methyl-1H-imidazol-1-yl)benzylidene]-4-(3,4,5-trifluorophenyl)hexahydropyrido[2,1-c][1,4]oxazin-6-one Lithium hydroxide monohydrate (63.4 mg) was added to a mixed solution of diethyl [(4R,9aS)-6-oxo-4-(3,4,5-trifluorophenyl)octahydropyrido[2,1-c][1,4]oxazin-7-yl]phosphonate (372 mg) and 3-methoxy-4-(4-methyl-1H-imidazol-1-yl)benzaldehyde (229 mg) in tetrahydrofuran (6 mL) and ethanol (2 mL) at room temperature, and the reaction solution was stirred at room temperature for two hours. Ethyl acetate and water were added to the reaction solution, and the organic layer was separated. The organic layer was washed with brine. The resulting organic layer was dried over magnesium sulfate and then concentrated under reduced pressure. The residue was purified by silica gel column chromatography (carrier: Chromatorex NH; elution solvent: heptane-ethyl acetate system) to obtain 163.2 mg of the title compound.

(4R,9aS)-4-(3,4,5-trifluorophenyl)-3,4,7,9a-tetrahydro-1H-pyrido[2,1-c][1,4]oxazin-6-one as an intermediate for synthesizing (E)-(4R,9aS)-7-[3-methoxy-4-(4-methyl-1H-imidazol-1-yl)benzylidene]-4-(3,4,5-trifluorophenyl) hexahydropyrido[2,1-c][1,4]oxazin-6-one was also separately synthesized by the following method.

Synthesis of 9H-fluoren-9-ylmethyl (3S,5R)-3-hydroxymethyl-5-(3,4,5-trifluorophenyl)morpholine-4-carboxylate 9-Fluorenylmethyl chloroformate (327 mg) was added to a mixed solution of [(3S,5R)-5-(3,4,5-trifluorophenyl)morpholin-3-yl]methanol (250 mg) in dichloromethane (5 mL) and a saturated sodium bicarbonate solution (5 mL), and the reaction solution was stirred at room temperature for six hours. Dichloromethane and a saturated ammonium chloride solution were added to the reaction solution, and the organic layer was separated. The resulting organic layer was dried over magnesium sulfate and then concentrated under reduced pressure. The residue was purified by silica gel chromatography (elution solvent: heptane->heptane:ethyl acetate=2:1) to obtain 470 mg of the title compound. The property values of the compound are as follows.

ESI-MS; m/z 470 [M$^+$+H]. $^1$H-NMR (CDCl$_3$) δ(ppm): 2.79 (brs, 1H), 3.15 (brm, 1H), 3.43-3.47 (dd, J=3.6, 11.6 Hz, 1H), 3.50-3.63 (m, 2H), 3.90 (d, J=12.0 Hz, 1H), 4.22-4.26 (m, 2H), 4.65-4.73 (m, 2H), 4.86-4.90 (dd, J=4.8 Hz, 6.4 Hz, 1H), 6.99 (brt, 2H), 7.30-7.40 (m, 4H), 7.55-7.57 (brd, 2H), 7.71-7.73 (d, J=7.2 Hz, 2H).

Synthesis of methyl 3-[(3S,5R)-5-(3,4,5-trifluorophenyl)morpholin-3-yl]acrylate

DMSO (0.14 mL) was added to a solution of oxalyl chloride (0.16 mL) in dichloromethane (10 mL) in a nitrogen atmosphere at −78° C. over five minutes, and the reaction solution was stirred at −78° C. for five minutes. A solution of 9H-fluoren-9-ylmethyl (3S,5R)-3-hydroxymethyl-5-(3,4,5-trifluorophenyl)morpholine-4-carboxylate (470 mg) in dichloromethane (2 mL) was added to the reaction solution at −78° C., and the reaction solution was stirred at −78° C. for 30 minutes. Triethylamine (0.86 mL) was added to the reaction solution at −78° C., and the reaction solution was stirred at −78° C. for 20 minutes. A saturated ammonium chloride solution was added to the reaction solution at −78° C., and the reaction solution was heated to room temperature. Then, dichloromethane was added to the reaction solution, and the organic layer was separated. The resulting organic layer was dried over magnesium sulfate and then concentrated under reduced pressure. Trimethyl phosphonoacetate (0.28 mL) was added to a mixed solution of sodium hydride (containing 60% mineral oil, 58 mg) in THF (10 mL)-DMF (2 mL) at 0° C., and the reaction solution was stirred at 0° C. for 30 minutes. A solution of the residue obtained above in THF (2 ml) was added to the reaction solution at 0° C., and the reaction solution was stirred at 0° C. for 30 minutes. A saturated ammonium chloride solution and ethyl acetate were added to the reaction solution, and the organic layer was separated. The resulting organic layer was dried over magnesium sulfate and then concentrated under reduced pressure. Diethylamine (1 mL) was added to a solution of the residue in acetonitrile (4 mL), and the reaction solution was stirred for 30 minutes. Toluene was added to the reaction solution, which was then concentrated under reduced pressure. The residue was purified by silica gel chromatography (elution solvent: heptane->heptane:ethyl acetate=1:1) to obtain 227 mg of an E/Z isomer mixture of the title compound. The property values of the compound are as follows.

ESI-MS; m/z 302 [M++H]. ¹H-NMR (CDCl₃) δ(ppm): 3.10-3.30 (brm, 2H), 3.73-4.02 (brm, 6H), 4.45-4.62 (brm, 1H), 5.91-6.17 (m, 1H), 6.82-6.88 (m, 1H), 6.02-7.10 (mbr, 2H)

Synthesis of methyl (E)-3-[(3S,5R)-4-(3-butenoyl)-5-(3,4,5-trifluorophenyl)morpholin-3-yl]acrylate and methyl (Z)-3-[(3S,5R)-4-(3-butenoyl)-5-(3,4,5-trifluorophenyl)morpholin-3-yl]acrylate Triethylamine (0.2 mL), vinylacetic acid (0.09 mL), and BOPCl (275 mg) were sequentially added to a solution of methyl 3-[(3S,5R)-5-(3,4,5-trifluorophenyl)morpholin-3-yl] acrylate (217 mg) in THF (5 mL) at 0° C., and the reaction solution was stirred at room temperature for two hours. Ethyl acetate and 0.5 N hydrochloric acid were added to the reaction solution, and the organic layer was separated. The resulting organic layer was sequentially washed with a 0.5 N sodium hydroxide solution and brine, dried over magnesium sulfate, and then concentrated under reduced pressure. The residue was purified by silica gel chromatography (elution solvent: heptane->heptane:ethyl acetate=1:1) to obtain 110 mg of methyl (E)-3-[(3S,5R)-4-(3-butenoyl)-5-(3,4,5-trifluorophenyl)morpholin-3-yl]acrylate and 132 mg of methyl (Z)-3-[(3S,5R)-4-(3-butenoyl)-5-(3,4,5-trifluorophenyl) morpholin-3-yl]acrylate. The property values of the isomers are as follows.

Methyl (E)-3-[(3S,5R)-4-(3-butenoyl)-5-(3,4,5-trifluorophenyl)morpholin-3-yl]acrylate ESI-MS; m/z 370 [M++H]. ¹H-NMR (CDCl₃) δ(ppm): 3.11-3.23 (m, 2H), 3.65 (s, 3H), 3.77-3.84 (ddd, J=4.0, 12.0, 13.4 Hz, 2H) 4.10-4.15 (m, 2H), 4.51-4.48 (brd, 2H), 5.13-5.26 (m, 2H), 5.51-5.64 (m, 2H), 6.50-6.55 (dd, J=4.8, 16.0 Hz, 1H), 7.23 (brt, 2H).

Methyl (Z)-3-[(3S,5R)-4-(3-butenoyl)-5-(3,4,5-trifluorophenyl)morpholin-3-yl]acrylate ESI-MS; m/z 370 [M++H]. ¹H-NMR (CDCl₃) δ(ppm): 3.01-3.08 (m, 1H), 3.20-3.26 (m, 1H), 3.72 (s, 3H), 3.78-4.02 (m, 2H), 4.01-4.05 (d, J=12.0 Hz, 1H), 4.50-4.53 (d, J=12.8 Hz, 1H), 5.14-5.23 (m, 2H), 5.63-5.70 (m, 3H), 5.90-6.00 (m, 2H), 7.34-7.37 (m, 2H).

Synthesis of (4R,9aS)-4-(3,4,5-trifluorophenyl)-3,4,7,9a-tetrahydro-1H-pyrido[2,1-c][1,4]oxazin-6-one Grubbs catalyst 2nd generation (27.7 mg) was added to a solution of methyl (E)-3-[(3S,5R)-4-(3-butenoyl)-5-(3,4,5-trifluorophenyl)morpholin-3-yl]acrylate (109.8 mg) and methyl (Z)-3-[(3S,5R)-4-(3-butenoyl)-5-(3,4,5-trifluorophenyl)morpholin-3-yl]acrylate (132.5 mg) in dichloromethane (12 mL), and the reaction solution was heated under reflux in a nitrogen atmosphere for one hour. The reaction solution was returned to room temperature. Triethylamine (0.5 mL) was added to the reaction solution, which was then stirred for 10 minutes. The reaction solution was concentrated under reduced pressure, and the residue was purified by silica gel column chromatography (elution solvent: heptane:ethyl acetate=4:1->ethyl acetate) to obtain 96.6 mg of the title compound.

Examples 84 and 85

Synthesis of (E)-(6R,7S,9aR)-7-hydroxy-3-[3-methoxy-4-(4-methyl-1H-imidazol-1-yl)benzylidene]-6-(3,4,5-trifluorophenyl)octahydroquinolizin-4-one and (E)-(6S,7R,9aS)-7-hydroxy-3-[3-methoxy-4-(4-methyl-1H-imidazol-1-yl)benzylidene]-6-(3,4,5-trifluorophenyl)octahydroquinolizin-4-one

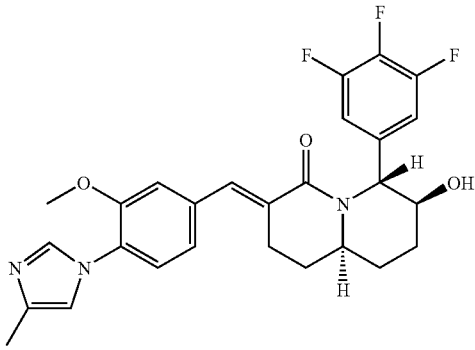

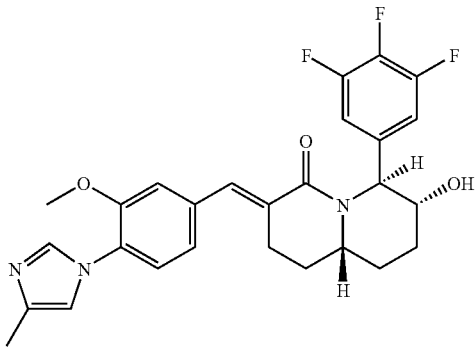

Synthesis of (6S*,8S*,9aR*)-8-hydroxy-6-(3,4,5-trifluorophenyl)octahydroquinolizin-4-one TBAF (1M THF solution, 7.26 mL) was added to a solution of (6S*,8S*,9aR*)-8-(tert-butyldimethylsilanyloxy)-6-(3,4,5-fluorophenyl)octahydroquinolizin-4-one (1.50 g) in THF (20 mL), and the reaction solution was stirred at room temperature overnight. A saturated ammonium chloride solution and ethyl acetate were added to the reaction solution, and the organic layer was separated. The resulting organic layer was washed with brine, dried over anhydrous magnesium sulfate, and then concentrated under reduced pressure. The residue was purified by silica gel column chromatography (elution solvent: heptane-ethyl acetate system->ethyl acetate-methanol system) to obtain 1.06 g of the title compound. The property values of the compound are as follows.

¹H-NMR (CDCl₃) δ(ppm): 1.56-1.65 (m, 1H), 1.65-1.77 (m, 2H), 1.77-1.87 (m, 1H), 1.87-1.96 (m, 1H), 2.01-2.12 (m, 2H), 2.35-2.42 (m, 1H), 2.42-2.59 (m, 2H), 3.81-3.99 (m, 1H), 4.21-4.26 (m, 1H), 5.90 (d, J=6.8 Hz, 1H), 6.86-6.94 (m, 2H).

Synthesis of (6S*,9aR*)-6-(3,4,5-trifluorophenyl)-1,2,3,6,9,9a-hexahydroquinolizin-4-one Methanesulfonyl chloride (776 μL) and triethylamine (2.79 mL) were added to a solution of (6S*,8S*,9aR*)-8-hydroxy-6-(3,4,5-trifluorophenyl)octahydroquinolizin-4-one (1.0 g) in methylene chloride (20 mL) under ice-cooling, and the reaction solution was stirred at room temperature for two hours. The solvent was removed by an evaporator. Then, sodium methoxide (28% solution in methanol, 3.22 g) was added to a mixed solution of the resulting residue in THF-ethanol (17 mL), and the reaction solution was stirred at room temperature for four hours. To make the starting material disappear, sodium methoxide (28% solution in methanol, 5.0 mL) was added to the reaction solution, which was then stirred at room temperature overnight. Water and ethyl acetate were added to the reaction solution, and the organic layer was separated. The resulting organic layer was washed with brine, dried over anhydrous magnesium sulfate, and then concentrated under reduced pressure. The residue was purified by silica gel column chromatography (elution solvent: heptane-ethyl acetate system->ethyl acetate-methanol system) to obtain 681 mg of the title compound. The property values of the compound are as follows.
$^1$H-NMR (CDCl$_3$) δ(ppm): 1.64-1.73 (m, 2H), 1.74-1.98 (m, 2H), 2.06-2.14 (m, 1H), 2.28-2.42 (m, 2H), 2.44-2.52 (m, 1H), 3.50-3.58 (m, 1H), 5.74-5.80 (m, 1H), 6.03-6.08 (m, 1H), 6.20 (brs, 1H), 7.06-7.14 (m, 2H).

Synthesis of (1aR*,2R*,6aR*,7aS*)-2-(3,4,5-trifluorophenyl)octahydro-1-oxa-2a-aza-cyclopropa[b]naphthalen-3-one and (1aS*,2R*,6aR*,7aR*)-2-(3,4,5-trifluorophenyl)octahydro-1-oxa-2a-aza-cyclopropa[b]naphthalen-3-one mCPBA (1.04 g) was added to a solution of (6S*,9aR*)-6-(3,4,5-trifluorophenyl)-1,2,3,6,9,9a-hexahydroquinolizin-4-one (681 mg) in methylene chloride (30 mL), and the reaction solution was stirred at room temperature for three days. Water and ethyl acetate were added to the reaction solution, and the organic layer was separated. The resulting organic layer was washed with brine, dried over anhydrous magnesium sulfate, and then concentrated under reduced pressure. The residue was purified by silica gel column chromatography (elution solvent: heptane-ethyl acetate system->ethyl acetate-methanol system) to obtain (1aR*,2R*,6aR*,7aS*)-2-(3,4,5-trifluorophenyl)octahydro-1-oxa-2a-aza-cyclopropa[b]naphthalen-3-one (283 mg) and (1aS*,2R*,6aR*,7aR*)-2-(3,4,5-trifluorophenyl)octahydro-1-oxa-2a-aza-cyclopropa[b]naphthalen-3-one (235 mg). The physical properties of (1aR*,2R*,6aR*,7aS*)-2-(3,4,5-trifluorophenyl)octahydro-1-oxa-2a-aza-cyclopropa[b]naphthalen-3-one are as follows.
$^1$H-NMR (CDCl$_3$) δ(ppm): 1.54-1.60 (m, 1H), 1.63-1.86 (m, 3H), 1.92 (td, J=5.6, 15.2 Hz, 1H), 2.10 (dd, J=12, 15.2 Hz, 1H), 2.27-2.36 (m, 1H), 2.44-2.51 (m, 1H), 3.27-3.35 (m, 1H), 3.39-3.41 (m, 1H), 3.50-3.52 (m, 1H), 6.34 (brs, 1H), 7.06-7.10 (m, 2H).

The physical properties of (1aS*,2R*,6aR*,7aR*)-2-(3,4,5-trifluorophenyl)octahydro-1-oxa-2a-aza-cyclopropa[b]naphthalen-3-one are as follows.
$^1$H-NMR (CDCl$_3$) δ(ppm): 1.60-1.68 (m, 2H), 1.72-1.80 (m, 1H), 1.80-1.92 (m, 1H), 1.94-2.02 (m, 1H), 2.10-2.16 (m, 1H), 2.36-2.50 (m, 2H), 3.49-3.52 (m, 1H), 3.59 (t, J=4.4 Hz, 1H), 3.60-3.66 (m, 1H), 5.94 (d, J=4.4 Hz, 1H), 7.00-7.10 (m, 2H).

Synthesis of (6R*,7S*,9aR*)-7-hydroxy-6-(3,4,5-trifluorophenyl)octahydroquinolizin-4-one A solution of (1aR*,2R*,6aR*,7aS*)-2-(3,4,5-trifluorophenyl)octahydro-1-oxa-2a-aza-cyclopropa[b]naphthalen-3-one (123 mg) in THF (4.0 mL) was cooled to −78° C. Lithium triethyl borohydride (1 M solution in THF, 620 μL) was added to the reaction solution, which was then stirred at 0° C. for one hour. Water and ethyl acetate were added to the reaction solution, and the organic layer was separated. The resulting organic layer was washed with brine, dried over anhydrous magnesium sulfate, and then concentrated under reduced pressure. The residue was purified by silica gel column chromatography (elution solvent: heptane-ethyl acetate system->ethyl acetate-methanol system) to obtain 125 mg of the title compound. The property values of the compound are as follows.
$^1$H-NMR (CDCl$_3$) δ(ppm): 1.42-1.48 (m, 1H), 1.60-1.82 (m, 4H), 1.82-2.06 (m, 3H), 2.47-2.62 (m, 2H), 2.81 (brs, 1H), 3.32-3.40 (m, 1H), 4.48-4.52 (m, 1H), 5.97 (brs, 1H), 6.76-6.84 (m, 2H).

Synthesis of (6R*,7S*,9aR*)-7-(tert-butyldimethylsilanyloxy)-6-(3,4,5-trifluorophenyl)octahydroquinolizin-4-one A solution of (6R*,7S*,9aR*)-7-hydroxy-6-(3,4,5-trifluorophenyl)octahydroquinolizin-4-one (164 mg), TBSCl (165 mg), imidazole (149 mg), and DMAP (6.7 mg) in DMF (5.0 mL) was stirred at room temperature overnight. To make the starting material disappear, TBSCl (165 mg) was added to the reaction solution, which was then stirred at room temperature overnight. Water and ethyl acetate were added to the reaction solution, and the organic layer was separated. The resulting organic layer was washed with brine, dried over anhydrous magnesium sulfate, and then concentrated under reduced pressure. The residue was purified by silica gel column chromatography (elution solvent: heptane-ethyl acetate system->ethyl acetate-methanol system) to obtain 227 mg of the title compound. The property values of the compound are as follows.
$^1$H-NMR (CDCl$_3$) δ(ppm): 0.01 (s, 3H), 0.02 (s, 3H), 0.81 (s, 9H), 1.25-1.32 (m, 1H), 1.48-1.70 (m, 4H), 1.70-1.97 (m, 3H), 2.34-2.50 (m, 2H), 3.22-3.32 (m, 1H), 4.29 (brs, 1H), 5.73 (brs, 1H), 6.66-6.76 (m, 2H).

(E)-(6R*,7S*,9aR*)-7-(tert-butyldimethlsilanyloxy)-3-[3-methoxy-4-(4-methyl-1H-imidazol-1-yl)benzylidene]-6-(3,4,5-trifluorophenyl)octahydroquinolizin-4-one 336 mg of the title compound was obtained from (6R*,7S*,9aR*)-7-(tert-butyldimethylsilanyloxy)-6-(3,4,5-trifluorophenyl)octahydroquinolizin-4-one (227 mg) in the same manner as in Examples 80 and 81. The property values of the compound are as follows.
$^1$H-NMR (CDCl$_3$) δ(ppm): 0.13 (s, 3H), 0.14 (s, 3H), 0.91 (s, 9H), 1.40-1.50 (m, 1H), 1.68-1.80 (m, 1H), 1.82-1.96 (m, 2H), 2.00-2.16 (m, 2H), 2.31 (s, 3H), 2.72-2.82 (m, 1H), 2.90-2.98 (m, 1H), 3.50-3.58 (m, 1H), 3.87 (s, 3H), 4.39-4.41 (m, 1H), 5.89 (brs, 1H), 6.84-6.90 (m, 2H), 6.94-6.95 (m, 1H), 7.02-7.05 (m, 2H), 7.25-7.27 (m, 1H), 7.72 (d, J=1.6 Hz, 1H), 7.80 (s, 1H).

Synthesis of (E)-(6R*,7S*,9aR*)-7-hydroxy-3-[3-methoxy-4-(4-methyl-1H-imidazol-1-yl)benzylidene]-6-(3,4,5-trifluorophenyl)octahydroquinolizin-4-one 100 mg of the title compound was obtained from (E)-(6R*,7S*,9aR*)-7-(tert-butyldimethylsilanyloxy)-3-[3-methoxy-4-(4-methyl-1H-imidazol-1-yl)benzylidene]-6-(3,4,5-trifluorophenyl)octahydroquinolizin-4-one (336 mg) in the same manner as in Example 71. The property values of the compound are as follows.

$^1$H-NMR (CDCl$_3$) δ(ppm): 1.45-1.54 (m, 1H), 1.66-1.80 (m, 3H), 1.90-1.96 (m, 1H), 2.00-2.12 (m, 1H), 2.31 (s, 3H), 2.72-2.82 (m, 1H), 2.90-3.00 (m, 1H), 3.46-3.56 (m, 1H), 3.88 (s, 3H), 4.54-4.58 (m, 1H), 6.09 (s, 1H), 6.86-6.90 (m, 2H), 6.94-6.95 (m, 1H), 7.01-7.04 (m, 2H), 7.26-7.28 (m, 1H), 7.73 (d, J=1.2 Hz, 1H), 7.82 (s, 1H).

Synthesis of (E)-(6R,7S,9aR)-7-hydroxy-3-[3-methoxy-4-(4-methyl-1H-imidazol-1-yl)benzylidene]-6-(3,4,5-trifluorophenyl)octahydroquinolizin-4-one and (E)-(6S,7R,9aS)-7-hydroxy-3-[3-methoxy-4-(4-methyl-1H-imidazol-1-yl)benzylidene]-6-(3,4,5-trifluorophenyl)octahydroquinolizin-4-one The racemate (E)-(6R*,7S*,9aR*)-7-hydroxy-3-[3-methoxy-4-(4-methyl-1H-imidazol-1-yl)benzylidene]-6-(3,4,5-trifluorophenyl)octahydroquinolizin-4-one obtained above was separated by CHIRALPAK™ AD-H manufactured by Daicel Chemical Industries, Ltd. (2 cm×25 cm; mobile phase: ethanol) to obtain the title optically active compound with a retention time of 5.4 minutes (35 mg; >99% ee) and the title optically active compound with a retention time of 11.9 minutes (30 mg; >99% ee).

The property values of the title optically active compound with a retention time of 5.4 minutes (Example 84) are as follows.
$^1$H-NMR (CDCl$_3$) δ(ppm): 1.45-1.54 (m, 1H), 1.66-1.80 (m, 3H), 1.90-1.96 (m, 1H), 2.00-2.12 (m, 1H), 2.31 (s, 3H), 2.72-2.82 (m, 1H), 2.90-3.00 (m, 1H), 3.46-3.56 (m, 1H), 3.88 (s, 3H), 4.54-4.58 (m, 1H), 6.09 (s, 1H), 6.86-6.90 (m, 2H), 6.94-6.95 (m, 1H), 7.01-7.04 (m, 2H), 7.26-7.28 (m, 1H), 7.73 (d, J=1.2 Hz, 1H), 7.82 (s, 1H).

The property values of the title optically active compound with a retention time of 11.9 minutes (Example 85) are as follows.
$^1$H-NMR (CDCl$_3$) δ(ppm): 1.45-1.54 (m, 1H), 1.66-1.80 (m, 3H), 1.90-1.96 (m, 1H), 2.00-2.12 (m, 1H), 2.31 (s, 3H), 2.72-2.82 (m, 1H), 2.90-3.00 (m, 1H), 3.46-3.56 (m, 1H), 3.88 (s, 3H), 4.54-4.58 (m, 1H), 6.09 (s, 1H), 6.86-6.90 (m, 2H), 6.94-6.95 (m, 1H), 7.01-7.04 (m, 2H), 7.26-7.28 (m, 1H), 7.73 (d, J=1.2 Hz, 1H), 7.82 (s, 1H).

Examples 86 and 87

Synthesis of (E)-(6R,7R,9aR)-7-hydroxy-3-[3-methoxy-4-(4-methyl-1H-imidazol-1-yl)benzylidene]-6-(3,4,5-trifluorophenyl)octahydroquinolizin-4-one and (E)-(6S,7S,9aS)-7-hydroxy-3-[3-methoxy-4-(4-methyl-1H-imidazol-1-yl)benzylidene]-6-(3,4,5-trifluorophenyl)octahydroquinolizin-4-one

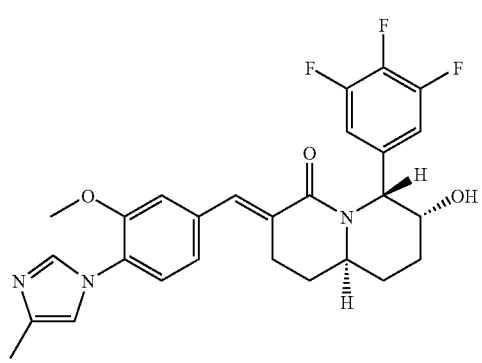

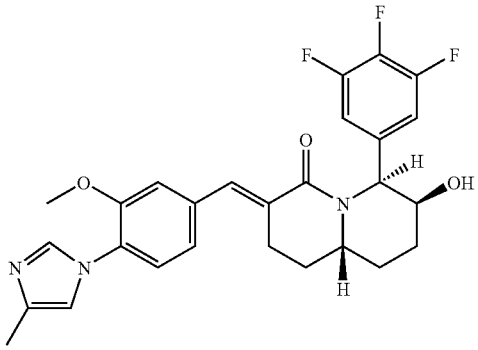

Synthesis of (6R*,7R*,9aR*)-7-hydroxy-6-(3,4,5-trifluorophenyl)octahydroquinolizin-4-one 45 mg of the title compound (purity: 50%) was obtained from (1aS*,2R*,6aR*,7aR*)-2-(3,4,5-trifluorophenyl)octahydro-1-oxa-2a-aza-cyclopropa[b]naphthalen-3-one in the same manner as in Examples 84 and 85. The property values of the compound are as follows.
$^1$H-NMR (CDCl$_3$) δ(ppm):
1.50-2.18 (m, 8H), 2.36-2.50 (m, 2H), 3.02 (brs, 1H), 3.26-3.36 (m, 1H), 4.00-4.06 (m, 1H), 6.06 (d, J=4.8 Hz, 1H), 7.18-7.26 (m, 2H).

Synthesis of (6R*,7R*,9aR*)-7-(tert-butyldimethylsilanyloxy)-6-(3,4,5-trifluorophenyl)octahydroquinolizin-4-one 28 mg of the title compound was obtained from (6R*,7R*,9aR*)-7-hydroxy-6-(3,4,5-trifluorophenyl)octahydroquinolizin-4-one (45 mg, purity: 50%) in the same manner as in Examples 84 and 85. The property values of the compound are as follows.
$^1$H-NMR (CDCl$_3$) δ(ppm):
0.06 (s, 3H) 0.11 (s, 3H), 0.88 (s, 9H), 1.50-1.64 (m, 2H), 1.66-1.76 (m, 2H), 1.78-1.90 (m, 2H), 1.90-2.00 (m, 2H), 2.38-2.56 (m, 2H), 3.22-3.30 (m, 1H), 3.95-4.01 (m, 1H), 5.96 (d, J=5.6 Hz, 1H), 7.19-7.26 (m, 2H).

Synthesis of (E)-(6R*,7R*,9aR*)-7-(tert-butyldimethylsilanyloxy)-3-[3-methoxy-4-(4-methyl-1H-imidazol-1-yl)benzylidene]-6-(3,4,5-trifluorophenyl) octahydroquinolizin-4-one 29 mg of the title compound was obtained from (6R*,7R*,9aR*)-7-(tert-butyldimethylsilanyloxy)-6-(3,4,5-trifluorophenyl)octahydroquinolizin-4-one (28 mg) in the same manner as in Examples 80 and 81. The property values of the compound are as follows.
$^1$H-NMR (CDCl$_3$) δ(ppm): 1.26-1.40 (m, 1H), 1.60-1.80 (m, 2H), 1.84-1.92 (m, 1H), 1.94-2.06 (m, 2H), 2.30 (s, 3H), 2.70-2.88 (m, 2H), 3.41-3.47 (m, 1H), 3.87 (s, 3H), 4.02-4.18 (m, 1H), 6.03 (d, J=5.2 Hz, 1H), 6.94 (s, 1H), 7.00-7.02 (m, 2H), 7.22-7.32 (s, 3H), 7.72 (s, 1H), 7.82 (s, 1H).

Synthesis of (E)-(6R,7R,9aR)-7-hydroxy-3-[3-methoxy-4-(4-methyl-1H-imidazol-1-yl)benzylidene]-6-(3,4,5-trifluorophenyl)octahydroquinolizin-4-one and (E)-(6S,7S,9aS)-7-hydroxy-3-[3-methoxy-4-(4-methyl-1H-imidazol-1-yl)benzylidene]-6-(3,4,5-trifluorophenyl)octahydroquinolizin-4-one A racemate (E)-(6R*,7R*,9aR*)-7-hydroxy-3-[3-methoxy-4-(4-methyl-1H-imidazol-1-yl)benzylidene]-6-(3,4,5-trifluorophenyl)octahydroquinolizin-4-one was obtained from (E)-(6R*,7R*,9aR*)-7-(tert-butyldimethylsilanyloxy)-3-[3-methoxy-4-(4-methyl-1H-imidazol-1-yl)benzylidene]-6-(3,4,5-trifluorophenyl)octahydroquinolizin-4-one (29 mg) in the same manner as in Example 71. Then, the racemate was separated by CHIRALPAK™ AD-H manufactured by Daicel Chemical Industries, Ltd. (2 cm×25 cm; mobile phase: ethanol) to obtain the title optically active compound with a retention time of 5.0 minutes (3.7 mg; >80% ee) and the title optically active compound with a retention time of 5.7 minutes (5.2 mg; >71% ee).

The property values of the title optically active compound with a retention time of 5.0 minutes (Example 86) are as follows.

$^1$H-NMR (CDCl$_3$) δ(ppm): 1.34-1.38 (m, 1H), 1.50-1.78 (m, 2H), 1.78-1.88 (m, 1H), 1.96-2.08 (m, 2H), 2.30 (s, 3H), 2.68-2.78 (m, 1H), 2.80-2.90 (m, 1H), 3.49-3.56 (m, 1H), 3.87 (s, 3H), 4.12-4.20 (m, 1H), 6.12 (d, J=5.6 Hz, 1H), 6.94-6.95 (m, 1H), 7.00-7.02 (m, 2H), 7.22-7.29 (m, 3H), 7.72 (d, J=1.2 Hz, 1H), 7.79 (s, 1H).

The property values of the title optically active compound with a retention time of 5.7 minutes (Example 87) are as follows.

$^1$H-NMR (CDCl$_3$) δ(ppm): 1.34-1.38 (m, 1H), 1.50-1.78 (m, 2H), 1.78-1.88 (m, 1H), 1.96-2.08 (m, 2H), 2.30 (s, 3H), 2.68-2.78 (m, 1H), 2.80-2.90 (m, 1H), 3.49-3.56 (m, 1H), 3.87 (s, 3H), 4.12-4.20 (m, 1H), 6.12 (d, J=5.6 Hz, 1H), 6.94-6.95 (m, 1H), 7.00-7.02 (m, 2H), 7.22-7.29 (m, 3H), 7.72 (d, J=1.2 Hz, 1H), 7.79 (s, 1H).

Example 88

Synthesis of (E)-(6S,9aR)-6-(4-fluorophenyl)-3-[3-methoxy-4-(4-methyl-1H-imidazol-1-yl)benzylidene]-1,2,3,6,9,9a-hexahydroquinolizin-4-one

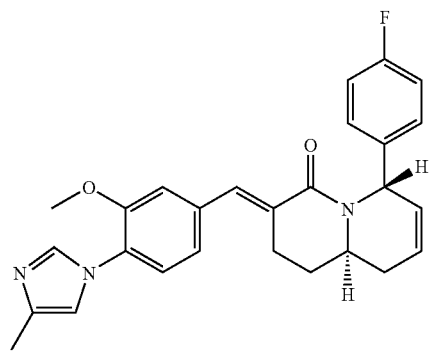

Synthesis of 1-(4-bromobutyryl)-2-(4-fluorophenyl)-2,3-dihydro-1H-pyridin-4-one 6.66 g of the title compound was obtained from 4-methoxypyridine (2.0 mL), 4-fluorophenylmagnesium bromide (1.0 M solution in THF, 20.7 mL), and 4-bromobutyryl chloride (2.4 mL) according to the method described in Tetrahedron Letters, 1986, vol. 27, p. 4549-4552. The property values of the compound are as follows.

$^1$H-NMR (CDCl$_3$) δ(ppm): 2.20-2.32 (m, 2H), 2.79-2.86 (m, 3H), 3.10-3.16 (m, 1H), 3.47-3.55 (m, 2H), 5.47 (brd, J=8.0 Hz, 1H), 6.00 (brs, 1H), 6.99-7.03 (m, 2H), 7.18-7.21 (m, 2H), 7.75 (brs, 1H).

Synthesis of (4S*,9aR*)-4-(4-fluorophenyl)hexahydroquinolizine-2,6-dione 1.05 g of the title compound was obtained from 1-(4-bromobutyryl)-2-(4-fluorophenyl)-2,3-dihydro-1H-pyridin-4-one (2.0 g), tributyltin hydride (1.87 mL), and AIBN (386 mg) according to the method described in The Journal of Organic Chemistry, 1993, vol. 58, p. 4198-4199. The property values of the compound are as follows.

$^1$H-NMR (CDCl$_3$) δ(ppm): 1.58-1.82 (m, 2H), 1.85-2.01 (m, 2H), 2.34-2.39 (m, 1H), 2.45-2.56 (m, 3H), 2.80 (dd, J=15.6, 7.2 Hz, 1H), 2.97-3.01 (m, 1H), 3.49-3.56 (m, 1H), 6.54 (brd, J=7.2 Hz, 1H), 6.99-7.03 (m, 2H), 7.21-7.24 (m, 2H).

Synthesis of (6S*,9aR*)-6-(4-fluorophenyl)-8-hydroxyoctahydroquinolizin-4-one

A solution of (4S*,9aR*)-4-(4-fluorophenyl)hexahydroquinolizine-2,6-dione (790 mg) in methanol (20 mL) was cooled to 0° C. Sodium borohydride (149 mg) was added to the reaction solution, which was then stirred for two hours and 15 minutes. Water and ethyl acetate were added to the reaction solution, and the organic layer was separated. The resulting organic layer was washed with brine, dried over anhydrous magnesium sulfate, and then concentrated under reduced pressure to obtain 760 mg of a crude alcohol compound. The property values of the compound are as follows.

$^1$H-NMR (CDCl$_3$) δ(ppm): 1.52-2.15 (m, 7H), 2.44-2.69 (m, 3H), 3.30-3.36 (m, ⅓H), 3.86-3.94 (m, 1H), 4.22 (brs, ⅔H), 5.99-6.00 (brd, J=6.4 Hz, ⅔H), 6.22-6.23 (brd, J=6.4 Hz, ⅓H), 7.00-7.04 (m, ⁴⁄₃H), 7.15-7.18 (m, ⅔H), 7.22-7.27 (m, 2H).

Synthesis of (6S*,8S*,9aR*)-8-(tert-butyldimethylsilanyloxy)-6-(4-fluorophenyl)octahydroquinolizin-4-one and (6S*,8R*,9aR*)-8-(tert-butyldimethylsilanyloxy)-6-(4-fluorophenyl)octahydroquinolizin-4-one A solution of (6S*,9aR*)-6-(4-fluorophenyl)-8-hydroxyoctahydroquinolizin-4-one (203 mg) in DMF (5.0 mL) was cooled to 0° C. Imidazole (262 mg), TBSCl (291 mg), and DMAP (9.42 mg) were sequentially added to the reaction solution, which was then stirred at room temperature for two hours. Saturated sodium bicarbonate water and ethyl acetate were added to the reaction solution, and the organic layer was separated. The resulting organic layer was washed with brine, dried over anhydrous magnesium sulfate, and then concentrated under reduced pressure. The residue was purified by silica gel column chromatography (elution solvent: heptane-ethyl acetate system) to obtain 183 mg of (6S*,8S*,9aR*)-8-(tert-butyldimethylsilanyloxy)-6-(4-fluorophenyl)octahydroquinolizin-4-one and 31.8 mg of (6S*,8R*,9aR*)-8-(tert-butyldimethylsilanyloxy)-6-(4-fluorophenyl)octahydroquinolizin-4-one. The property values of (6S*,8S*,9aR*)-8-(tert-butyldimethylsilanyloxy)-6-(4-fluorophenyl)octahydroquinolizin-4-one are as follows.

$^1$H-NMR (CDCl$_3$) δ(ppm): 0.00 (s, 3H), 0.05 (s, 3H), 0.76 (s, 9H), 1.65-1.75 (m, 2H), 1.75-1.85 (m, 1H), 1.85-2.08 (m, 2H), 2.08-2.20 (m, 2H), 2.41-2.52 (m, 1H), 2.52-2.70 (m, 2H), 4.01-4.06 (m, 1H), 4.26-4.27 (m, 1H), 6.04 (brd, J=6.4 Hz, 1H), 7.03-7.08 (m, 2H), 7.27-7.31 (m, 2H).

The property values of (6S*,8R*,9aR*)-8-(tert-butyldimethylsilanyloxy)-6-(4-fluorophenyl)octahydroquinolizin-4-one are as follows.

¹H-NMR (CDCl₃) δ(ppm): 0.04 (s, 3H), 0.07 (s, 3H), 0.88 (s, 9H), 1.57-1.63 (m, 1H), 1.70-1.82 (m, 4H), 1.86-1.99 (m, 2H), 2.43-2.60 (m, 3H), 3.29-3.35 (m, 1H), 3.80-3.88 (m, 1), 6.17-6.19 (m, 1H), 7.01-7.06 (m, 2H), 7.13-7.16 (m, 2H).

Synthesis of (E)-(6S*,8S*,9aR*)-8-(tert-butyldimethylsilanyloxy)-6-(4-fluorophenyl)-3-[3-methoxy-4-(4-methyl-1H-imidazol-1-yl)benzylidene]octahydroquinolizin-4-one LDA (1.5 M solution in THF, 1.11 mL) was added to a solution of (6S*,8S*,9aR*)-8-(tert-butyldimethylsilanyloxy)-6-(4-fluorophenyl)octahydroquinolizin-4-one (298 mg) in THF (5.0 mL) at 0° C. The reaction solution was stirred at 0° C. for one hour, and then a solution of 3-methoxy-4-(4-methyl-1H-imidazol-1-yl)benzaldehyde (179 mg) in THF (3 mL) was added to the reaction solution. The reaction solution was further stirred at 0° C. for 40 minutes. Water and ethyl acetate were added to the reaction solution, and the organic layer was separated. The resulting organic layer was dried over magnesium sulfate and then concentrated under reduced pressure to obtain 443 mg of a crude aldol adduct.

A solution of the crude aldol adduct (443 mg) in methylene chloride (7 mL) was cooled to 0° C. Triethylamine (416 µL) and methanesulfonyl chloride (115 µL) were added to the reaction solution, which was then stirred at room temperature for 5.5 hours. Saturated sodium bicarbonate water and ethyl acetate were added to the reaction solution, and the organic layer was separated. The resulting organic layer was washed with brine and then dried over magnesium sulfate and concentrated under reduced pressure to obtain a crude mesyl compound. Sodium methoxide (121 mg) and methanol (1.0 mL) were added to a solution of the crude mesyl compound in THF, and the reaction solution was stirred at room temperature for two hours. Water and ethyl acetate were added to the reaction solution, and the organic layer was separated. The resulting organic layer was washed with brine, dried over anhydrous magnesium sulfate, and then concentrated under reduced pressure. The residue was purified by silica gel column chromatography (carrier: Chromatorex NH; elution solvent: heptane-ethyl acetate system->ethyl acetate-methanol system) to obtain 330 mg of the title compound. The property values of the compound are as follows.

¹H-NMR (CDCl₃) δ(ppm): 0.00 (s, 3H), 0.05 (s, 3H), 0.77 (s, 9H), 1.75-1.96 (m, 3H), 2.12 (s, 3H), 2.12-2.24 (m, 2H), 2.44-2.52 (m, 1H), 2.84-3.02 (m, 2H), 3.97 (s, 3H), 4.11-4.20 (m, 1H), 4.26-4.32 (m, 1H), 6.08-6.12 (m, 1H), 7.03-7.18 (m, 7H), 7.22-7.40 (m, 2H), 7.87 (s, 1H).

Synthesis of (E)-(6S*,8S*,9aR*)-6-(4-fluorophenyl)-8-hydroxy-3-[3-methoxy-4-(4-methyl-1H-imidazol-1-yl)benzylidene]octahydroquinolizin-4-one TBAF (1.0 M solution in THF, 1.15 mL) was added to a solution of (E)-(6S*,8S*,9aR*)-8-(tert-butyldimethylsilanyloxy)-6-(4-fluorophenyl)-3-[3-methoxy-4-(4-methyl-1H-imidazol-1-yl)benzylidene]octahydroquinolizin-4-one (330 mg) in THF (5.0 mL), and the reaction solution was stirred at room temperature overnight. A saturated ammonium chloride solution and ethyl acetate were added to the reaction solution, and the organic layer was separated. The resulting organic layer was washed with brine, dried over anhydrous magnesium sulfate, and then concentrated under reduced pressure. The residue was purified by silica gel column chromatography (carrier: Chromatorex NH; elution solvent: heptane-ethyl acetate system->ethyl acetate-methanol system) to obtain 232 mg of the title compound. The property values of the compound are as follows.

¹H-NMR (CDCl₃) δ(ppm): 1.75-1.96 (m, 3H), 2.07-2.15 (m, 1H), 2.17-2.27 (m, 1H), 2.34 (s, 3H), 2.52-2.56 (m, 1H), 2.78-2.84 (m, 1H), 2.88-2.96 (m, 1H), 3.88 (s, 3H), 4.01-4.08 (m, 1H), 4.26-4.30 (m, 1H), 6.04-6.10 (m, 1H), 6.96 (s, 1H), 7.00-7.06 (m, 4H), 7.16-7.34 (m, 3H), 7.82 (s, 1H), 7.82-7.84 (m, 1H).

Synthesis of (E)-(6S,8S,9aR)-6-(4-fluorophenyl)-8-hydroxy-3-[3-methoxy-4-(4-methyl-1H-imidazol-1-yl)benzylidene]octahydroquinolizin-4-one and (E)-(6R,8R,9aS)-6-(4-fluorophenyl)-8-hydroxy-3-[3-methoxy-4-(4-methyl-1H-imidazol-1-yl)benzylidene]octahydroquinolizin-4-one The racemate (E)-(6S*,8S*,9aR*)-6-(4-fluorophenyl)-8-hydroxy-3-[3-methoxy-4-(4-methyl-1H-imidazol-1-yl)benzylidene]octahydroquinolizin-4-one obtained above (232 mg) was separated by CHIRALPAK™ AD-H manufactured by Daicel Chemical Industries, Ltd. (2 cm×25 cm; mobile phase: ethanol) to obtain the title optically active compound with a retention time of 5.0 minutes (89 mg; >99% ee) and the title optically active compound with a retention time of 9.7 minutes (89 mg; >99% ee).

The property values of the title optically active compound with a retention time of 5.0 minutes are as follows.

¹H-NMR (CDCl₃) δ(ppm): 1.75-1.96 (m, 3H), 2.07-2.15 (m, 1H), 2.17-2.27 (m, 1H), 2.34 (s, 3H), 2.52-2.56 (m, 1H), 2.78-2.84 (m, 1H), 2.88-2.96 (m, 1H), 3.88 (s, 3H), 4.01-4.08 (m, 1H), 4.26-4.30 (m, 1H), 6.04-6.10 (m, 1H), 6.96 (s, 1H), 7.00-7.06 (m, 4H), 7.16-7.34 (m, 3H), 7.82 (s, 1H), 7.82-7.84 (m, 1H).

The property values of the title optically active compound with a retention time of 9.7 minutes are as follows.

¹H-NMR (CDCl₃) δ(ppm): 1.75-1.96 (m, 3H), 2.07-2.15 (m, 1H), 2.17-2.27 (m, 1H), 2.34 (s, 3H), 2.52-2.56 (m, 1H), 2.78-2.84 (m, 1H), 2.88-2.96 (m, 1H), 3.88 (s, 3H), 4.01-4.08 (m, 1H), 4.26-4.30 (m, 1H), 6.04-6.10 (m, 1H), 6.96 (s, 1H), 7.00-7.06 (m, 4H), 7.16-7.34 (m, 3H), 7.82 (s, 1H), 7.82-7.84 (m, 1H).

Synthesis of (E)-(6S,9aR)-6-(4-fluorophenyl)-3-[3-methoxy-4-(4-methyl-1H-imidazol-1-yl)benzylidene]-1,2,3,6,9,9a-hexahydroquinolizin-4-one 784 mg of the title compound was obtained from (E)-(6S,8S,9aR)-6-(4-fluorophenyl)-8-hydroxy-3-[3-methoxy-4-(4-methyl-1H-imidazol-1-yl)benzylidene]octahydroquinolizin-4-one (884 mg) in the same manner as in Example 71. The property values of the compound are as follows.

¹H-NMR (CDCl₃) δ(ppm): 1.70-1.80 (m, 1H), 1.85-1.98 (m, 1H), 2.10-2.19 (m, 1H), 2.31 (s, 3H), 2.42-2.55 (m, 1H), 2.70-2.82 (m, 2H), 3.62-3.75 (m, 1H), 3.88 (s, 3H), 5.88-5.94 (m, 1H), 6.04-6.10 (m, 1H), 6.34 (brs, 1H), 6.93 (s, 1H), 6.96-7.07 (m, 4H), 7.22-7.28 (m, 1H), 7.49-7.52 (m, 2H), 7.71 (s, 1H), 7.80 (s, 1H).

Example 89

Synthesis of (3S,8aS)-6-{1-[3-methoxy-4-(4-methyl-1H-imidazol-1-yl)phenyl]-(E)-methylidene}-3-(2,4,6-trifluorophenyl)hexahydroindolizin-5-one

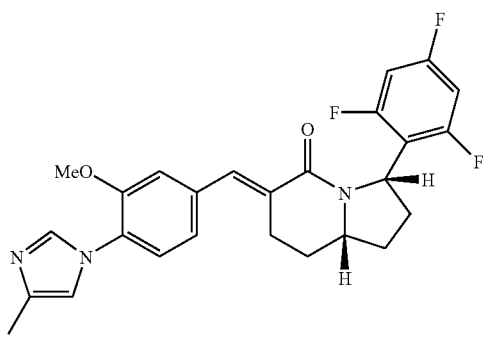

Synthesis of ethyl (2R,5S)-5-(3,4,5-trifluorophenyl)pyrrolidine-2-carboxylate To a solution of (R)-5-oxopyrrolidine-1,2-dicarboxylic acid 1-tert-butyl ester 2-ethyl ester (CAS No. 128811-48-3; 5.7 g) in tetrahydrofuran (30 mL), 2,4,6-trifluorophenylmagnesium bromide (0.24 M solution in THF; 100 mL) was added dropwise at −40° C. over one hour, and the reaction solution was stirred at −40° C. for 12 hours. Saturated aqueous ammonium chloride and ethyl acetate were added to the solution. The reaction solution was heated to room temperature, and the organic layer was separated. The resulting organic layer was washed with brine, dried over anhydrous magnesium sulfate, and then concentrated under reduced pressure. The residue was purified by silica gel column chromatography (heptane->heptane:ethyl acetate=1:1) to obtain 6.2 g of ethyl (R)-2-tert-butoxycarbonylamino-5-oxo-5-(2,4,6-trifluorophenyl)pentanoate. A solution of 4 N hydrochloric acid in ethyl acetate (30 mL) was added to a solution of the resulting ethyl (R)-2-tert-butoxycarbonylamino-5-oxo-5-(2,4,6-trifluorophenyl)pentanoate in ethyl acetate (30 mL), and the solution was stirred for 12 hours. The reaction solution was concentrated under reduced pressure. Ethyl acetate and saturated sodium bicarbonate water were added to the residue, and the organic layer was separated. The resulting organic layer was dried over anhydrous magnesium sulfate and then concentrated under reduced pressure. 10% palladium-carbon (100 mg) was added to a solution of the residue in ethyl acetate (20 mL) and ethanol (10 mL), and the reaction solution was stirred in a hydrogen atmosphere at 1 atm for 21 hours. The reaction solution was filtered through celite, and the filtrate was concentrated under reduced pressure to obtain 4.34 g of the title compound. The property value of the compound is as follows.

ESI-MS; m/z 274 [M$^+$+H].

Synthesis of [(2R,5S)-5-(2,4,6-trifluorophenyl)pyrrolidin-2-yl]methanol

LAH (724 mg) was added to a solution of ethyl (2R,5S)-5-(2,4,6-trifluorophenyl)pyrrolidine-2-carboxylate (4.34 g) in THF (100 mL) at −15° C. over one hour. The reaction solution was stirred at −15° C. for 19 hours. Water (0.8 mL), a 5 N sodium hydroxide solution (0.8 mL), and water (2.5 mL) were sequentially added to the reaction solution, and the mixture was stirred at room temperature for 30 minutes. The reaction solution was filtered through celite, and the filtrate was concentrated under reduced pressure to obtain 3.68 g of the title compound. The property values of the compound are as follows.

ESI-MS; m/z 232 [M$^+$+H].

Synthesis of tert-butyl (2R,5S)-2-hydroxymethyl-5-(2,4,6-trifluorophenyl)pyrrolidine-1-carboxylate Di-tert-butyl dicarbonate (5.21 g) was added to a solution of [(2R,5S)-5-(2,4,6-trifluorophenyl)pyrrolidin-2-yl]methanol (3.68 g) and triethylamine (4.4 mL) in DMF, and the reaction solution was stirred at room temperature for six hours. Imidazole (1 g) was added to the reaction solution, and the mixture was stirred for one hour. Then, ethyl acetate and ice-cooled 1 N aqueous hydrochloric acid were added to the solution, and the organic layer was separated. The resulting organic layer was washed with saturated sodium bicarbonate water, dried over anhydrous magnesium sulfate, and then concentrated under reduced pressure. The residue was purified by silica gel column chromatography (heptane->heptane:ethyl acetate=1:1) to obtain 2.82 g of the title compound. The property value of the compound is as follows.

ESI-MS; m/z 332 [M$^+$+H].

Synthesis of tert-butyl (2R,5S)-2-((E)-2-ethoxycarbonylvinyl)-5-(2,4,6-trifluorophenyl)pyrrolidine-1-carboxylate A solution of DMSO (1.62 g) in methylene chloride (5 mL) was added dropwise to a solution of oxalyl chloride (1.62 g) in methylene chloride (5 mL) at −78° C., and the reaction solution was stirred at the same temperature for 10 minutes. A solution of tert-butyl (2R,5S)-2-hydroxymethyl-5-(2,4,6-trifluorophenyl)pyrrolidine-1-carboxylate (2.82 g) in dichloromethane (5 mL) was added dropwise to the reaction solution at −78° C., and the reaction solution was stirred at the same temperature for 70 minutes. Triethylamine (5.94 mL) was added dropwise to the solution, and the reaction solution was stirred at −78° C. for 40 minutes. A toluene-THF (1:1) mixed solution and a saturated ammonium chloride solution were added to the reaction solution. The mixture was returned to room temperature, and the organic layer was separated. The resulting organic layer was sequentially washed with 1 N aqueous hydrochloric acid, saturated sodium bicarbonate water, and brine, dried over anhydrous magnesium sulfate, and then concentrated under reduced pressure.

Triethylphosphonoacetate (2.5 mL) was added to a suspension of sodium hydride (containing 60% mineral oil, 511 mg) in THF (70 mL) at 0° C., and the reaction solution was stirred at the same temperature for one hour. A solution of the above residue in THF (30 mL) was added to the reaction solution, which was then stirred at 0° C. for 30 minutes and at room temperature for one hour. Ethyl acetate and a saturated ammonium chloride solution were added to the reaction solution, and the organic layer was separated. The resulting organic layer was dried over anhydrous magnesium sulfate and then concentrated under reduced pressure. The residue was purified by silica gel column chromatography (heptane->heptane:ethyl acetate=1:1) to obtain 2.23 g of the title compound. The property value of the compound is as follows.

ESI-MS; m/z 400 [M$^+$+H].

Synthesis of ethyl (E)-3-[(2R,5S)-1-(3-butenoyl)-5-(2,4,6-trifluorophenyl)pyrrolidin-2-yl]acrylate A solution of 4 N hydrochloric acid in ethyl acetate (10 mL) was added to a solution of tert-butyl (2R,5S)-2-((E)-2- ethoxycarbonylvinyl)-5-(2,4,6-trifluorophenyl)pyrrolidine-1-carboxylate (2.23 g) in ethyl acetate (10 mL), and the reaction solution was stirred at room temperature for two hours and then concentrated under reduced pressure. Ethyl acetate and saturated sodium bicarbonate water were added to the residue, and the organic layer was separated. The organic layer was dried over anhydrous magnesium sulfate and then concentrated under reduced pressure. Triethylamine (1.1 mL), vinylacetic acid (0.38 mL), and BOPCl (1.58 g) were sequentially added to a solution of the residue in THF (30 mL), and the reaction solution was stirred at room temperature for 20 hours. A toluene-THF (1:1) mixed solution and 1 N aqueous hydrochloric acid were added to the reaction solution, and the organic layer was separated. The resulting organic layer was washed with a 1 N sodium hydroxide solution, dried over anhydrous magnesium sulfate, and then concentrated under reduced pressure to obtain 1.35 g of the title compound. The property value of the compound is as follows.

ESI-MS; m/z 368[M$^+$+H].

Synthesis of (3S,8aR)-3-(2,4,6-trifluorophenyl)-2,3,6,8a-tetrahydro-1H-indolizin-5-one A solution of ethyl (E)-3-[(2R,5S)-1-(3-butenoyl)-5-(2,4,6-trifluorophenyl)pyrrolidin-2-yl]acrylate (1.35 g) and Grubbs catalyst 2nd generation (155 mg) in methylene chloride (70 mL) was heated under reflux for two hours. The reaction solution was left to cool to room temperature. Then, triethylamine (0.5 mL) was added to the reaction solution, and the mixture was stirred for one hour. The reaction solution was concentrated under reduced pressure, and the residue was purified by silica gel column chromatography (heptane->heptane:ethyl acetate=1:1->ethyl acetate) to obtain 548 mg of the title compound. The property value of the compound is as follows.

ESI-MS; m/z 268 [M$^+$+H].

Synthesis of (3S,8aR)-3-(2,4,6-trifluorophenyl)hexahydroindolizin-5-one

Platinum oxide (25 mg) was added to a solution of (3S,8aR)-3-(2,4,6-trifluorophenyl)-2,3,6,8a-tetrahydro-1H-indolizin-5-one (548 mg) in methanol (5 mL), and the reaction solution was stirred in a hydrogen atmosphere at 1 atm at room temperature for one hour. The reaction solution was filtered through celite, and the filtrate was concentrated under reduced pressure to obtain 550 mg of the title compound. The property value of the compound is as follows.

ESI-MS; m/z 270 [M$^+$+H].

Synthesis of (3S,8aS)-6-{1-[3-methoxy-4-(4-methyl-1H-imidazol-1-yl)phenyl]-(E)-methylidene}-3-(2,4,6-trifluorophenyl)hexahydroindolizin-5-one Iodotrimethylsilane (0.44 mL) was added dropwise to a solution of (3S,8aR)-3-(2,4,6-trifluorophenyl)hexahydroindolizin-5-one (550 mg) and N,N,N',N'-tetramethylethylenediamine (1.08 mL) in methylene chloride (10 mL) at 0° C., and the reaction solution was stirred at 0° C. for 30 minutes. Iodine (777 mg) was added to the reaction solution at 0° C., and the reaction solution was stirred at 0° C. for one hour. A saturated sodium thiosulfate solution and ethyl acetate were added to the reaction solution. The mixture was returned to room temperature, and then the organic layer was separated. The resulting organic layer was washed with brine, dried over anhydrous magnesium sulfate, and then concentrated under reduced pressure. A solution of the residue in triethyl phosphite (2 mL) was stirred at 120° C. for two hours. The reaction solution was left to cool to room temperature and concentrated under reduced pressure. To a solution of the residue in THF (20 mL) and ethanol (5 mL), 3-methoxy-4-(4-methyl-1H-imidazol-1-yl)benzaldehyde (443 mg) and lithium hydroxide monohydrate (258 mg) were added, and the reaction solution was stirred at room temperature for 3.5 hours. Ethyl acetate and brine were added to the reaction solution, and the organic layer was separated. The resulting organic layer was dried over anhydrous magnesium sulfate and then concentrated under reduced pressure. The residue was purified by silica gel column chromatography (carrier: Chromatorex NH; elution solvent: heptane:ethyl acetate=1:1->ethyl acetate->ethyl acetate:methanol=9:1) to obtain 523 mg of the title compound. The property values of the compound are as follows.

ESI-MS; m/z 468 [M$^+$+H]. $^1$H-NMR (CDCl$_3$) δ(ppm): 1.68-1.83 (m, 1H), 1.93-2.10 (m, 2H), 2.12-2.25 (m, 2H), 2.30 (s, 3H), 2.34-2.47 (m, 1H), 2.64-2.75 (m, 1H), 3.10 (brd, J=16.4 Hz, 1H), 3.74-3.82 (m, 1H), 3.83 (s, 3H), 5.39 (d, J=10.0 Hz, 1H), 6.61 (t, J=8.8 Hz, 2H), 6.91 (s, 1H), 7.02 (brs, 1H), 7.05 (brd, J=8.4 Hz, 1H), 7.23 (d, J=8.4 Hz, 1H), 7.70 (s, 1H), 7.72 (brs, 1H).

Example 90

Synthesis of (6S,9aR)-6-(3,4-difluorophenyl)-3-{1-[3-methoxy-4-(4-methyl-1H-imidazol-1-yl)phenyl]-(E)-methylidene}octahydroquinolizin-4-one

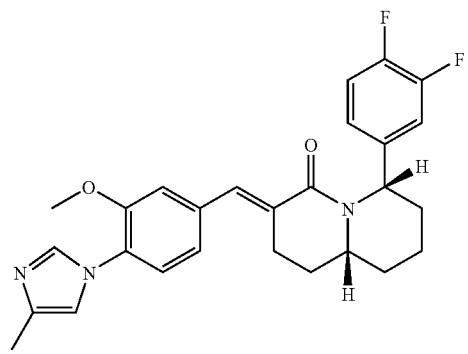

Synthesis of (R)-6-oxopiperidine-1,2-dicarboxylic acid 1-tert-butyl ester 2-methyl ester Thionyl chloride (206 mL) was added to methanol (750 mL) at −20° C. over one hour, and the reaction solution was stirred at −20° C. for 15 minutes. (R)-6-oxopiperidine-2-carboxylic acid (CAS #72002-30-3) (26.0 g) was added to the reaction solution at −20° C. The reaction solution was stirred at room temperature for 13 hours and then concentrated under reduced pressure. Triethylamine (62.2 mL), DMAP (13.6 g), and di-tert-butyl dicarbonate (146 g) were added to a solution of the residue in acetonitrile (700 mL) at 0° C., and the reaction solution was stirred at room temperature for two days. The reaction solution was concentrated under reduced pressure. Ethyl acetate and a saturated sodium bicarbonate solution were added to the residue, and the organic layer was separated. Further, the organic layer was washed with brine. The resulting organic layer was dried over magnesium sulfate and then concentrated under reduced pressure. The residue was purified by silica gel column chromatography (elution solvent: heptane-ethyl acetate system) to obtain 32.5 g of the title compound. The property values of the compound are as follows.

$^1$H-NMR (CDCl$_3$) δ(ppm): 1.50 (s, 9H), 1.65-1.85 (m, 2H), 2.00-2.09 (m, 1H), 2.12-2.21 (m, 1H), 2.45-2.63 (m, 2H), 3.77 (s, 3H), 4.68-4.74 (s, 1H).

Synthesis of methyl (2R,6S)-6-(3,4-difluorophenyl) piperidine-2-carboxylate

To a solution of (R)-6-oxopiperidine-1,2-dicarboxylic acid 1-tert-butyl ester 2-methyl ester (820 mg) in THF (12 mL), 3,4-difluorophenylmagnesium bromide (0.5 M solution in THF, 7.0 mL) was added in a nitrogen atmosphere at −78° C. over 20 minutes. The reaction solution was stirred at −78° C. to −10° C. for two hours, and then quenched with a saturated ammonium chloride solution at −10° C. Water was added to the reaction solution, followed by extraction with ethyl acetate. The resulting extract was dried over magnesium sulfate and then concentrated under reduced pressure. The residue was purified by silica gel column chromatography (elution solvent: heptane-ethyl acetate system) to obtain methyl (R)-2-tert-butoxycarbonylamino-6-(3,4-difluorophenyl)-6-oxohexanoate (850 mg). A solution of 4 N hydrochloric acid in ethyl acetate (25 mL) was added to a solution of methyl (R)-2-tert-butoxycarbonylamino-6-(3,4-difluorophenyl)-6-oxohexanoate (2.45 g) in ethyl acetate (25 mL) at room temperature, and the reaction solution was stirred at room temperature for 12 hours. The reaction solution was concentrated under reduced pressure, and the residue was made basic with a saturated sodium bicarbonate solution. Then, chloroform was added to the residue, and the mixture was stirred at room temperature for two hours. The organic layer was separated, dried over magnesium sulfate, and then concentrated under reduced pressure. 10% palladium-carbon (150 mg) was added to a solution of the residue in methanol (30 mL), and the reaction solution was stirred in a hydrogen atmosphere at room temperature for two hours. The reaction solution was filtered through celite, and the filtrate was concentrated under reduced pressure. The residue was purified by silica gel column chromatography (elution solvent: heptane-ethyl acetate system) to obtain 1.25 g of the title compound. The property values of the compound are as follows.

ESI-MS; m/z 256[M$^+$+H]. $^1$H-NMR (CDCl$_3$) δ(ppm): 1.33-1.47 (m, 1H), 1.48-1.60 (m, 2H), 1.72-1.80 (m, 1H), 1.95-2.03 (m, 1H), 2.04-2.12 (m, 1H), 2.16 (brs, 1H), 3.48 (dd, J=11.2, 2.8 Hz, 1H), 3.63 (dd, J=11.2, 2.8 Hz, 1H), 3.74 (s, 3H), 7.06-7; 12(m, 2H), 7.21-7.28 (m, 1H).

Synthesis of (6S,9aR)-6-(3,4-difluorophenyl)-3,6,7,8,9,9a-hexahydroquinolizin-4-one Diethyl cyanophosphonate (3.14 mL) was added to a solution of methyl (2R,6S)-6-(3,4-difluorophenyl)piperidine-2-carboxylate (1.61 g), vinylacetic acid (1.78 mL), and triethylamine (5.27 mL) in DMF (40 mL) at 0° C., and the reaction solution was stirred at room temperature for five hours. Ethyl acetate and 0.5 N hydrochloric acid were added to the reaction solution, and the organic layer was separated. The resulting organic layer was sequentially washed with saturated sodium bicarbonate water and brine, dried over magnesium sulfate, and then concentrated under reduced pressure. The residue was purified by silica gel column chromatography (elution solvent: heptane-ethyl acetate system) to obtain methyl (2R,6S)-1-(3-butenoyl)-6-(3,4-difluorophenyl)piperidine-2-carboxylate. Lithium borohydride (315 mg) was added to a solution of methyl (2R,6S)-1-(3-butenoyl)-6-(3,4-difluorophenyl)piperidine-2-carboxylate in THF (40 mL) at 0° C., and the reaction solution was stirred at 0° C. for one hour and at room temperature for 5.5 hours. The reaction solution was added to a mixed solution of a cooled ammonium chloride solution in ethyl acetate, and the mixture was stirred at room temperature for 20 minutes. The organic layer was separated, dried over magnesium sulfate, and then concentrated under reduced pressure. The residue was purified by silica gel column chromatography (elution solvent: heptane-ethyl acetate system) to obtain 1-[(2S,6R)-2-(3,4-difluorophenyl)-6-(hydroxymethyl)piperidin-1-yl]-(3-buten)-1-one. DMSO (0.92 mL) was added to a solution of oxalyl chloride (0.56 mL) in dichloromethane (30 mL) in a nitrogen atmosphere at −78° C. over five minutes, and the reaction solution was stirred at −78° C. for 10 minutes. A solution of 1-[(2S,6R)-2-(3,4-difluorophenyl)-6-(hydroxymethyl)piperidin-1-yl]-(3-buten)-1-one in dichloromethane (7 mL) was added to the reaction solution at −78° C. over 20 minutes, and the reaction solution was stirred at −78° C. for 20 minutes. Triethylamine (2.7 mL) was added to the reaction solution at −78° C. over 10 minutes, and then the reaction solution was stirred at −60° C. for 30 minutes. The reaction solution was quenched with a saturated ammonium chloride solution at −60° C. and heated to room temperature. Then, ethyl acetate and 0.5 N hydrochloric acid were added to the reaction solution, and the organic layer was separated. The resulting organic layer was sequentially washed with water and brine, dried over magnesium sulfate, and then concentrated under reduced pressure. Trimethyl phosphonoacetate (1.06 mL) was added to a mixed solution of 60% sodium hydride (161 mg) in THF (20 mL)-DMF (4 mL) at 0° C., and the reaction solution was stirred at room temperature for 30 minutes. A solution of the residue obtained above in THF (3 mL) was added to the reaction solution at 0° C., and the reaction solution was stirred at room temperature for 30 minutes. The reaction solution was added to a cooled ammonium chloride solution, followed by extraction with ethyl acetate. The resulting extract was dried over magnesium sulfate and then concentrated under reduced pressure. The residue was purified by silica gel column chromatography (elution solvent: heptane-ethyl acetate system) to obtain methyl (E)-3-[(2R,6S)-1-(3-butenoyl)-6-(3,4-difluorophenyl)piperidin-2-yl]acrylate and methyl (Z)-3-[(2R,6S)-1-(3-butenoyl)-6-(3,4-difluorophenyl)piperidin-2-yl]acrylate. A solution of a mixture of methyl (E)-3-[(2R,6S)-1-(3-butenoyl)-6-(3,4-difluorophenyl)piperidin-2-yl]acrylate with methyl (Z)-3-[(2R,6S)-1-(3-butenoyl)-6-(3,4-difluorophenyl)piperidin-2-yl] acrylate and Grubbs catalyst 2nd generation (187 mg) in methylene chloride (140 mL) was heated under reflux in a nitrogen atmosphere for three hours. The reaction solution was left to cool to room temperature. Then, triethylamine (0.30 mL) was added to the reaction solution, and the mixture was stirred at room temperature for 10 minutes and concentrated under reduced pressure. The residue was purified by silica gel column chromatography (elution solvent: heptane-ethyl acetate system) to obtain 418 mg of the title compound. The property value of the compound is as follows.

ESI-MS; m/z 264 [M$^+$+H].

Synthesis of (6S,9aR)-6-(3,4-difluorophenyl)octahydroquinolizin-4-one

Platinum oxide (48 mg) was added to a solution of (6S,9aR)-6-(3,4-difluorophenyl)-3,6,7,8,9,9a-hexahydroquinolizin-4-one (558 mg) in methanol (15 mL), and the reaction solution was stirred in a hydrogen stream at room temperature for three hours. The reaction solution was filtered through celite, and the filtrate was concentrated under reduced pressure. The residue was purified by silica gel column chromatography (elution solvent: heptane-ethyl acetate system) to obtain 400 mg of the title compound. The property value of the compound is as follows.

ESI-MS; m/z 266 [M$^+$+H].

Synthesis of (6S,9aR)-6-(3,4-difluorophenyl)-3-{1-[3-methoxy-4-(4-methyl-1H-imidazol-1-yl)phenyl]-(E)-methylidene}octahydroquinolizin-4-one Iodotrimethylsilane (0.34 mL) was added to a solution of (6S,9aR)-6-(3,4-difluorophenyl) octahydroquinolizin-4-one (400 mg) and N,N,N',N'-tetramethylethylenediamine (0.80 mL) in methylene chloride (13 mL) in a nitrogen atmosphere at 0° C., and the reaction solution was stirred at 0° C. for 30 minutes. Iodine (575 mg) was added to the reaction solution at 0° C., and the reaction solution was stirred at 0° C. for one hour. Ethyl acetate and a saturated sodium thiosulfate solution were added to the reaction solution, and the organic layer was separated. The resulting organic layer was washed with brine, dried over magnesium sulfate, and then concentrated under reduced pressure to obtain an iodide compound. A mixture of the resulting iodide compound with triethyl phosphite (6 mL) was stirred at 120° C. for five hours. The reaction solution was left to cool to room temperature, and then the reaction solution was concentrated under reduced pressure. Lithium hydroxide monohydrate (190 mg) was added to a mixed solution of the residue and 3-methoxy-4-(4-methyl-1H-imidazol-1-yl)benzaldehyde (392 mg) in tetrahydrofuran (15 mL) and ethanol (5 mL) at room temperature, and the reaction solution was stirred at room temperature for six hours. Ethyl acetate was added to the reaction solution, which was then sequentially washed with saturated sodium bicarbonate water and brine. The resulting organic layer was dried over magnesium sulfate and then concentrated under reduced pressure. The residue was purified by silica gel column chromatography (carrier: Chromatorex NH; elution solvent: heptane-ethyl acetate system) and then by silica gel column chromatography (elution solvent: heptane-ethyl acetate system) to obtain 490 mg of the title compound. The property values of the compound are as follows.

ESI-MS; m/z 464[M$^+$+H]. $^1$H-NMR (CDCl$_3$) δ(ppm): 1.33-1.82 (m, 5H), 2.00-2.10 (m, 1H), 2.10-2.30 (m, 2H), 2.31 (s, 3H), 2.66-2.77 (m, 1H), 3.07-3.16 (m, 1H), 3.75-3.85 (m, 1H), 3.86 (s, 3H), 5.48 (brs, 1H), 6.92-6.95 (m, 1H), 6.96-7.01 (m, 1H), 7.02-7.16 (m, 4H), 7.24-7.30 (m, 1H), 7.72 (d, J=1.2 Hz, 1H), 7.81 (brd, J=2.4 Hz, 1H).

Example 91

Synthesis of (6S,9aR)-6-(3,4,5-trifluorophenyl)-3-{1-[3-methoxy-4-(4-methyl-1H-imidazol-1-yl)phenyl]-(E)-methylidene}octahydroquinolizin-4-one

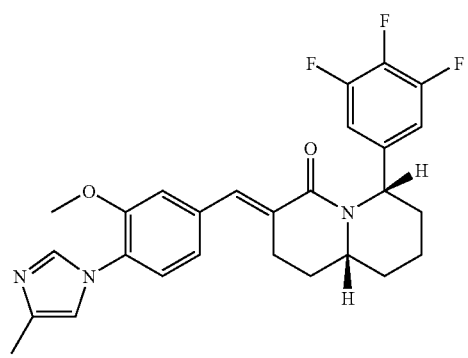

Synthesis of methyl (2R,6S)-6-(3,4,5-trifluorophenyl)piperidine-2-carboxylate

To a solution of (R)-6-oxopiperidine-1,2-dicarboxylic acid 1-tert-butyl ester 2-methyl ester (13.0 g) in THF (140 mL), 3,4,5-trifluorophenylmagnesium bromide (prepared from 1-bromo-3,4,5-trifluorobenzene (11.7 g) and magnesium (1.48 g) by the method described in Org. Synth., 2001, 79, 176) was added in a nitrogen atmosphere at −78° C. over 30 minutes. The reaction solution was stirred at −78° C. to −10° C. for two hours, and then quenched with a saturated ammonium chloride solution at −10° C. Water was added to the reaction solution, followed by extraction with ethyl acetate. The resulting extract was dried over magnesium sulfate and then concentrated under reduced pressure. A solution of 4 N hydrochloric acid in ethyl acetate (150 mL) was added to a solution of the residue in ethyl acetate (150 mL) at room temperature, and the reaction solution was stirred at room temperature for nine hours. The reaction solution was concentrated under reduced pressure, and the residue was made basic with a saturated sodium bicarbonate solution. Then, chloroform was added to the residue, and the mixture was stirred at room temperature for two hours. The organic layer was separated, dried over magnesium sulfate, and then concentrated under reduced pressure. 10% palladium-carbon (700 mg) was added to a solution of the residue in methanol (200 mL), and the reaction solution was stirred in a hydrogen atmosphere at room temperature for nine hours. The reaction solution was filtered through celite, and the filtrate was concentrated under reduced pressure. The residue was purified by silica gel column chromatography (elution solvent: heptane-ethyl acetate system) to obtain 5.47 g of the title compound. The property value of the compound is as follows.

ESI-MS; m/z 274 [M$^+$+H].

Synthesis of (6S,9aR)-6-(3,4,5-trifluorophenyl)-3,6,7,8,9,9a-hexahydroquinolizin-4-one Diethyl cyanophosphonate (10.0 mL) was added to a solution of methyl (2R,6S)-6-(3,4,5-difluorophenyl)piperidine-2-carboxylate (5.47 g), vinylacetic acid (5.67 mL), and triethylamine (16.8 mL) in DMF (140 mL) at 0° C., and the reaction solution was stirred at 0° C. for five hours. Ethyl acetate and saturated sodium bicarbonate water were added to the reaction solution, and the organic layer was separated. The resulting organic layer was washed with brine, dried over magnesium sulfate, and then concentrated under reduced pressure. The residue was purified by silica gel column chromatography (elution solvent: heptane-ethyl acetate system) to obtain methyl (2R,6S)-1-(3-butenoyl)-6-(3,4,5-trifluorophenyl)piperidine-2-carboxylate. Methyl (2R,6S)-1-(3-butenoyl)-6-(3,4,5-trifluorophenyl)piperidine-2-carboxylate was dissolved in THF (120 mL). Lithium borohydride (826 mg) was added to the reaction solution at 0° C., and the reaction solution was stirred at room temperature for three hours. The reaction solution was added to a mixed solution of a cooled ammonium chloride solution in ethyl acetate, and the mixture was stirred at room temperature for 20 minutes. The organic layer was separated, dried over magnesium sulfate, and then concentrated under reduced pressure. The residue was purified by silica gel column chromatography (elution solvent: heptane-ethyl acetate system) to obtain 1-[(2S,6R)-2-(3,4,5-trifluorophenyl)-6-(hydroxymethyl)piperidin-1-yl]-(3-buten)-1-one. DMSO (1.18 mL) was added to a solution of oxalyl chloride (1.36 mL) in dichloromethane (90 mL) in a nitrogen atmosphere at −78° C. over five minutes, and the reaction solution was stirred at −78° C. for 10 minutes. A solution of 1-[(2S,6R)-2-(3,4,5-trifluorophenyl)-6-(hydroxymethyl)piperidin-1-yl]-(3-buten)-1-one in dichloromethane (10 mL) was added to the reaction solution at −78° C. over 20 minutes, and the reaction solution was stirred at −78° C. for 20 minutes. Triethylamine (8.65 mL) was added to the reaction solution at −78° C. over 10 minutes, and then the reaction solution was stirred at −50° C. for one hour. Water and ethyl acetate were added to the reaction solution, and the organic layer was separated. The resulting organic layer was washed with brine, dried over magnesium sulfate, and then concentrated under reduced pressure to obtain a residue. Trimethyl phosphonoacetate (3.44 mL) was added to a mixed solution of 60% sodium hydride (520 mg) in THF (70 mL)-DMF (14 mL) at 0° C., and the reaction solution was stirred at room temperature for 30 minutes. A solution of the residue obtained above in THF (10 mL) was added to the reaction solution at 0° C., and the mixture was stirred at room temperature for 30 minutes. The reaction solution was added to a cooled ammonium chloride solution, followed by extraction with ethyl acetate. The resulting extract was dried over magnesium sulfate and then concentrated under reduced pressure. The residue was purified by silica gel column chromatography (elution solvent: heptane-ethyl acetate system) to obtain methyl (E)-3-[(2R,6S)-1-(3-butenoyl)-6-(3,4,5-trifluorophenyl)piperidin-2-yl]acrylate and methyl (Z)-3-[(2R,6S)-1-(3-butenoyl)-6-(3,4,5-trifluorophenyl)piperidin-2-yl]acrylate.

A solution of a mixture of methyl (E)-3-[(2R,6S)-1-(3-butenoyl)-6-(3,4,5-trifluorophenyl)piperidin-2-yl]acrylate with methyl (Z)-3-[(2R,6S)-1-(3-butenoyl)-6-(3,4,5-trifluorophenyl)piperidin-2-yl]acrylate and Grubbs catalyst 2nd generation (707 mg) in methylene chloride (300 mL) was heated under reflux in a nitrogen atmosphere for three hours. The reaction solution was left to cool to room temperature. Then, triethylamine (1.15 mL) was added to the reaction solution, and the mixture was stirred at room temperature for 10 minutes and concentrated under reduced pressure. The residue was purified by silica gel column chromatography (elution solvent: heptane-ethyl acetate system) to obtain 2.01 g of the title compound. The property value of the compound is as follows.

ESI-MS; m/z 282 [M$^+$+H].

Synthesis of (6S,9aR)-6-(3,4,5-trifluorophenyl)octahydroquinolizin-4-one

Platinum oxide (162 mg) was added to a solution of (6S,9aR)-6-(3,4,5-trifluorophenyl)-3,6,7,8,9,9a-hexahydroquinolizin-4-one (2.01 g) in methanol (50 mL), and the reaction solution was stirred in a hydrogen stream at room temperature for seven hours. The reaction solution was filtered through celite, and the filtrate was concentrated under reduced pressure. The residue was purified by silica gel column chromatography (elution solvent: heptane-ethyl acetate system) to obtain 1.79 g of the title compound. The property value of the compound is as follows.

ESI-MS; m/z 284 [M$^+$+H].

Synthesis of (6S,9aR)-6-(3,4,5-trifluorophenyl)-3-{1-[3-methoxy-4-(4-methyl-1H-imidazol-1-yl)phenyl]-(E)-methylidene}octahydroquinolizin-4-one Iodotrimethylsilane (1.41 mL) was added to a solution of (6S,9aR)-6-(3,4,5-trifluorophenyl)octahydroquinolizin-4-one (1.79 g) and N,N,N',N'tetramethylethylenediamine (3.34 mL) in methylene chloride (50 mL) in a nitrogen atmosphere at at 0° C., and the reaction solution was stirred at 0° C. for 30 minutes. Iodine (2.41 g) was added to the reaction solution at 0° C., and the reaction solution was stirred at 0° C. for one hour. Ethyl acetate and a saturated sodium thiosulfate solution were added to the reaction solution, and the organic layer was separated. The resulting organic layer was washed with brine, dried over magnesium sulfate, and then concentrated under reduced pressure to obtain (6S,9aR)-6-(3,4,5-trifluorophenyl)-3-iodooctahydroquinolizin-4-one. A mixture of (6S,9aR)-6-(3,4,5-trifluorophenyl)-3-iodooctahydroquinolizin-4-one with triethyl phosphite (20 mL) was stirred at 120° C. for three hours. The reaction solution was left to cool to room temperature, and then the reaction solution was concentrated under reduced pressure. Lithium hydroxide monohydrate (792 mg) was added to a mixed solution of the residue and 3-methoxy-4-(4-methyl-1H-imidazol-1-yl)benzaldehyde (1.64 g) in tetrahydrofuran (45 mL) and ethanol (15 mL) at room temperature, and the reaction solution was stirred at room temperature for four hours. Ethyl acetate was added to the reaction solution, which was then sequentially washed with saturated sodium bicarbonate water and brine. The resulting organic layer was dried over magnesium sulfate and then concentrated under reduced pressure. The residue was purified by silica gel column chromatography (carrier: Chromatorex NH; elution solvent: heptane-ethyl acetate system) and then by silica gel column chromatography (elution solvent: heptane-ethyl acetate system->ethyl acetate-methanol system) to obtain 2.46 g of the title compound. The property values of the compound are as follows.

ESI-MS; m/z 482 [M$^+$+H]. $^1$H-NMR (CDCl$_3$) δ(ppm): 1.34-1.85 (m, 5H), 2.05-2.30 (m, 3H), 2.30 (s, 3H), 2.65-2.76 (m, 1H), 3.12 (brd, J=16.0 Hz, 1H), 3.79 (brt, J=11.2 Hz, 1H), 3.86 (s, 3H), 5.43 (brs, 1H), 6.84-6.92 (m, 2H), 6.94 (brs, 1H), 7.02-7.07 (m, 2H), 7.24-7.28 (m, 1H), 7.72 (brs, 1H), 7.79 (brs, 1H).

Example 92

Synthesis of (6S,9aR)-6-(4-chlorophenyl)-3-{1-[3-methoxy-4-(4-methyl-1H-imidazol-1-yl)phenyl]-(E)-methylidene}octahydroquinolizin-4-one

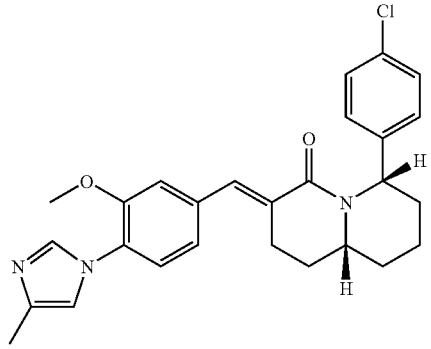

Synthesis of methyl (2R,6S)-6-(4-chlorophenyl)piperidine-2-carboxylate

To a solution of (R)-6-oxopiperidine-1,2-dicarboxylic acid 1-tert-butyl ester 2-methyl ester (9.00 g) in THF (120 mL), 4-chlorophenylmagnesium bromide (1.0 M solution in diethyl ether, 42 mL) was added in a nitrogen atmosphere at −78° C. over 20 minutes. The reaction solution was heated from −78° C. to −40° C. over 1.5 hours while stirring, and then quenched with a saturated ammonium chloride solution at −40° C. Water was added to the reaction solution, followed by extraction with ethyl acetate. The resulting extract was dried over magnesium sulfate and then concentrated under reduced pressure. The residue was purified by silica gel column chromatography (elution solvent: heptane-ethyl acetate system) to obtain methyl (R)-2-tert-butoxycarbonylamino-6-(4-chlorophenyl)-6-oxohexanoate (9.53 g). A solution of 4 N hydrochloric acid in ethyl acetate (90 mL) was added to a solution of methyl (R)-2-tert-butoxycarbonylamino-6-(4-chlorophenyl)-6-oxohexanoate (9.53 g) in ethyl acetate (90 mL) at room temperature, and the reaction solution was stirred at room temperature for 12 hours. The reaction solution was concentrated under reduced pressure, and the residue was made basic with a saturated sodium bicarbonate solution. Then, chloroform was added to the residue, and the mixture was stirred at room temperature for two hours. The organic layer was separated, dried over magnesium sulfate, and then concentrated under reduced pressure. Sodium cyanoborohydride (3.29 g) and then acetic acid (4.27 mL) were added to a solution of the residue in methanol (150 mL) at 0° C., and the reaction solution was stirred at 0° C. for one hour and at room temperature for one hour. A saturated sodium bicarbonate solution was added to the reaction solution, followed by extraction with chloroform. The resulting extract was dried over magnesium sulfate and then concentrated under reduced pressure. The residue was purified by silica gel column chromatography (elution solvent: heptane-ethyl acetate system) and solidified with a heptane-diisopropyl ether system to obtain 2.47 g of the title compound. The property values of the compound are as follows.

ESI-MS; m/z 254 [M$^+$+H]. 1H-NMR (CDCl$_3$) δ(ppm): 1.38-1.60 (m, 3H), 1.72-1.78 (m, 1H), 1.96-2.03 (m, 1H), 2.05-2.12 (m, 1H), 2.17 (brs, 1H), 3.49 (dd, J=10.8, 2.8 Hz, 1H), 3.63 (dd, J=11.2, 2.8 Hz, 1H), 3.73 (s, 3H), 7.25-7.34 (m, 4H).

Synthesis of [(2R,6S)-6-(4-chlorophenyl)piperidin-2-yl]methanol

Methyl (2R,6S)-6-(4-chlorophenyl)piperidine-2-carboxylate (2.47 g) was added to a suspension of lithium aluminum hydride (508 mg) in THF (50 mL) in a nitrogen atmosphere at −20° C., and the reaction solution was stirred at −20° C. for one hour. Water (0.51 mL), a 5 N sodium hydroxide solution (0.51 mL), and water (1.53 mL) were sequentially added to the reaction solution at −20° C., and the reaction solution was stirred at room temperature for 15 minutes. Ethyl acetate was added to the reaction solution. Then, the reaction solution was filtered through celite, and the filtrate was concentrated under reduced pressure. The residue was purified by silica gel column chromatography (carrier: Chromatorex NH; elution solvent: heptane-ethyl acetate system) to obtain 1.90 g of the title compound. The property value of the compound is as follows.

ESI-MS; m/z 226[M$^+$+H].

Synthesis of (6S,9aR)-6-(4-chlorophenyl)-3,6,7,8,9,9a-hexahydroquinolizin-4-one

Triethylamine (2.20 mL), vinylacetic acid (1.16 mL), and BOPCl (3.47 g) were sequentially added to a solution of [(2R,6S)-6-(4-chlorophenyl)piperidin-2-yl]methanol (2.36 g) in THF at 0° C., and the reaction solution was stirred at room temperature for five hours. An ethyl acetate-toluene (1:1) mixed solution and 0.5 N hydrochloric acid were added to the reaction solution, and the organic layer was separated. The resulting organic layer was sequentially washed with a 0.5 N sodium hydroxide solution, a saturated sodium bicarbonate solution, and brine, dried over magnesium sulfate, and then concentrated under reduced pressure to obtain 1-[(2S,6R)-2-(4-chlorophenyl)-6-(hydroxymethyl)piperidin-1-yl]-(3-buten)-1-one. DMSO (1.04 mL) was added to a solution of oxalyl chloride (1.20 mL) in dichloromethane (70 mL) in a nitrogen atmosphere at −78° C. over five minutes, and the reaction solution was stirred at −78° C. for 10 minutes. A solution of 1-[(2S,6R)-2-(4-chlorophenyl)-6-(hydroxymethyl)piperidin-1-yl]-(3-buten)-1-one in dichloromethane (10 mL) was added to the reaction solution at −78° C. over 20 minutes, and the reaction solution was stirred at −78° C. for 20 minutes. Triethylamine (7.64 mL) was added to the reaction solution at −78° C. over 10 minutes, and then the reaction solution was stirred at −50° C. for one hour. The reaction solution was added to water, followed by extraction with ethyl acetate. The resulting extract was washed with brine, dried over magnesium sulfate, and then concentrated under reduced pressure to obtain a crude aldehyde compound (2.68 g). Trimethyl phosphonoacetate (2.73 mL) was added to a mixed solution of 60% sodium hydride (413 mg) in THF (50 mL)-DMF (10 mL) at 0° C., and the reaction solution was stirred at room temperature for 30 minutes. A solution of the crude aldehyde compound obtained above (2.41 g) in THF (10 mL) was added to the reaction solution at 0° C., and the reaction solution was stirred at room temperature for 30 minutes. The reaction solution was added to a cooled ammonium chloride solution, followed by extraction with ethyl acetate. The resulting extract was dried over magnesium sulfate and then concentrated under reduced pressure. The residue was purified by silica gel column chromatography (elution solvent: heptane-ethyl acetate system) to obtain a low-polar isomer of methyl 3-[(2R,6S)-1-(3-butenoyl)-6-(4-chlorophenyl)piperidin-2-yl]acrylate (0.65 g) and a high-polar isomer of methyl 3-[(2R,6S)-1-(3-butenoyl)-6-(4-chlorophenyl)piperidin-2-yl]acrylate (1.10 g). A solution of the low-polar isomer of methyl 3-[(2R,6S)-1-(3-butenoyl)-6-(4-chlorophenyl)piperidin-2-yl]acrylate (0.65 g) and Grubbs catalyst 2nd generation (158 mg) in methylene chloride (60 mL) was heated under reflux in a nitrogen atmosphere for three hours. The reaction solution was left to cool to room temperature. Then, triethylamine (0.26 mL) was added to the reaction solution, which was then stirred at room temperature for 10 minutes and concentrated under reduced pressure. Likewise, a solution of the high-polar isomer of methyl 3-[(2R,6S)-1-(3-butenoyl)-6-(4-chlorophenyl)piperidin-2-yl]acrylate (1.10 g) and Grubbs catalyst 2nd generation (268 mg) in methylene chloride (100 mL) was heated under reflux in a nitrogen atmosphere for three hours. The reaction solution was left to cool to room temperature. Then, triethylamine (0.44 mL) was added to the reaction solution, which was then stirred at room temperature for 10 minutes and concentrated under reduced pressure. The residues obtained from both isomers were combined and purified by silica gel column chromatography (elution solvent: heptane-ethyl acetate system) to obtain 1.09 g of the title compound. The property value of the compound is as follows.

ESI-MS; m/z 262 [M$^+$+H].

Synthesis of (6S,9aR)-6-(4-chlorophenyl)octahydroquinolizin-4-one

Platinum oxide (95 mg) was added to a solution of (6S,9aR)-6-(4-chlorophenyl)-3,6,7,8,9,9a-hexahydroquinolizin-4-one (1.09 g) in methanol (50 mL), and the reaction solution was stirred in a hydrogen atmosphere at room temperature for one hour. The reaction solution was filtered through celite, and the filtrate was concentrated under reduced pressure. The residue was purified by silica gel column chromatography (elution solvent: heptane-ethyl acetate system) to obtain 877 mg of the title compound. The property value of the compound is as follows.

ESI-MS; m/z 264 [M$^+$+H].

Synthesis of (6S,9aR)-6-(4-chlorophenyl)-3-{1-[3-methoxy-4-(4-methyl-1H-imidazol-1-yl)phenyl]-(E)-methylidene}octahydroquinolizin-4-one Iodotrimethylsilane (0.74 mL) was added to a solution of (6S,9aR)-6-(4-chlorophenyl)octahydroquinolizin-4-one (877 mg) and N,N,N',N'-tetramethylethylenediamine (1.76 mL) in methylene chloride (25 mL) in a nitrogen atmosphere at 0° C., and the reaction solution was stirred at 0° C. for 30 minutes. Iodine (1.26 g) was added to the reaction solution at 0° C., and the reaction solution was stirred at 0° C. for one hour. A sodium thiosulfate solution and ethyl acetate were added to the reaction solution, and the organic layer was separated. The resulting organic layer was washed with brine, dried over magnesium sulfate, and then concentrated under reduced pressure to obtain (6S,9aR)-6-(4-chlorophenyl)-3-iodooctahydroquinolizin-4-one. A mixture of (6S,9aR)-6-(4-chlorophenyl)-3-iodooctahydroquinolizin-4-one with triethyl phosphite (10 mL) was stirred at 120° C. for two hours. The reaction solution was left to cool to room temperature and concentrated under reduced pressure to obtain diethyl [(6S,9aR)-6-(4-chlorophenyl)-4-oxooctahydroquinolizin-3-yl]phosphonate. Lithium hydroxide monohydrate (422 mg) was added to a mixed solution of diethyl [(6S,9aR)-6-(4-chlorophenyl)-4-oxooctahydroquinolizin-3-yl]phosphonate and 3-methoxy-4-(4-methyl-1H-imidazol-1-yl)benzaldehyde (869 mg) in tetrahydrofuran (21 mL) and ethanol (7 mL) at room temperature, and the reaction solution was stirred at room temperature for two hours. Ethyl acetate and saturated sodium bicarbonate water were added to the reaction solution, and the organic layer was separated. The resulting organic layer was washed with brine, dried over magnesium sulfate, and then concentrated under reduced pressure. The residue was purified by silica gel column chromatography (carrier: Chromatorex NH; elution solvent: heptane-ethyl acetate system) and then by silica gel column chromatography (elution solvent: heptane-ethyl acetate system->ethyl acetate-methanol system) to obtain 1.07 g of the title compound. The property values of the compound are as follows.

ESI-MS; m/z 462[M++H]. 1H-NMR (CDCl3) δ(ppm): 1.33-1.80 (m, 5H), 2.00-2.09 (m, 1H), 2.11-2.30 (m, 2H), 2.31 (s, 3H), 2.66-2.78 (m, 1H), 3.07-3.17 (m, 1H), 3.76-3.87 (m, 1H), 3.86 (s, 3H), 5.51 (brs, 1H), 6.92-6.95 (m, 1H), 7.02-7.07 (m, 2H), 7.20 (brd, J=8.4 Hz, 2H), 7.24-7.32 (m, 3H), 7.72 (d, J=1.6 Hz, 1H), 7.81 (brd, J=2.8 Hz, 1H)

Example 93

Synthesis of (E)-(3S,8aS)-3-(2,3-difluorophenyl)-6-[3-methoxy-4-(4-methyl-1H-imidazol-1-yl)benzylidene]hexahydroindolizin-5-one

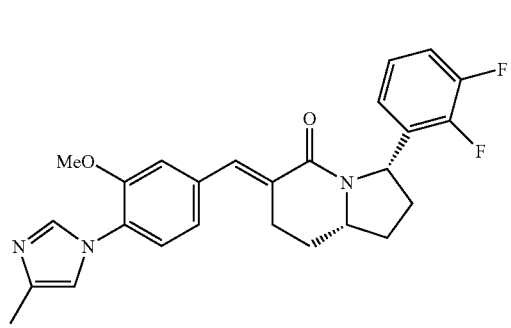

The title compound was obtained in the same manner as in Example 56.

ESI-MS; m/z 450 [M++H]. 1H-NMR (CDCl3) δ(ppm): 1.62-1.88 (m, 2H), 1.86-1.96 (m, 1H), 2.02-2.14 (m, 1H), 2.26-2.45 (m, 2H), 2.30 (s, 3H), 2.68-2.82 (m, 1H), 3.10-3.20 (m, 1H), 3.76-3.90 (m, 1H), 3.85 (s, 3H), 5.48 (d, J=9.2 Hz, 1H), 6.74-6.82 (m, 1H), 6.81 (s, 1H), 6.90-7.12 (m, 4H), 7.20-7.30 (m, 1H), 7.72 (d, J=1.6 Hz, 1H), 7.77 (d, J=2.4 Hz, 1H).

Example 94

Synthesis of (4R,9aS)-4-(4-fluorophenyl)-7-{1-[3-methoxy-4-(4-methyl-1H-imidazol-1-yl)phenyl]-(E)-methylidene}hexahydropyrido[2,1-c][1,4]oxazin-6-one

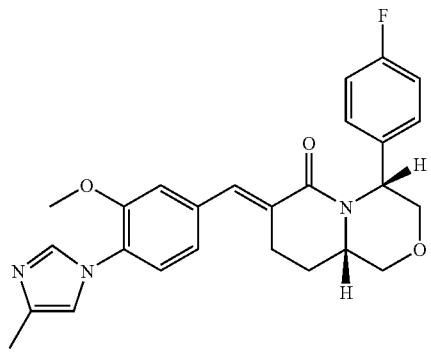

18.9 mg of the title compound was obtained from [(3S,5R)-5-(4-fluorophenyl)morpholin-3-yl]methanol (250 mg) in the same manner as in Examples 82 and 83. The property values of the compound are as follows.

ESI-MS; m/z 448 [M++H]. 1H-NMR (CDCl3) δ(ppm): 1.62-1.73 (m, 1H), 1.94-1.99 (m, 1H), 2.31 (s, 3H), 2.75-2.84 (m, 1H), 3.12-3.17 (m, 1H), 3.66 (dd, J=11.2, 11.2 Hz, 1H), 3.85 (s, 3H), 3.91-3.99 (m, 2H), 4.11-4.20 (m, 1H), 4.35 (dd, J=12.0, 3.6 Hz, 1H), 5.14 (t, J=4.0 Hz, 1H), 6.94 (s, 1H), 7.01-7.07 (m, 4H), 7.25-7.27 (m, 1H), 7.31-7.34 (m, 2H), 7.72 (s, 1H), 7.78 (s, 1H).

Example 95

Synthesis of (4R,9aS)-4-(3,4-difluorophenyl)-7-{1-[3-methoxy-4-(4-methyl-1H-imidazol-1-yl)phenyl]-(E)-methylidene}hexahydropyrido[2,1-c][1,4]oxazin-6-one

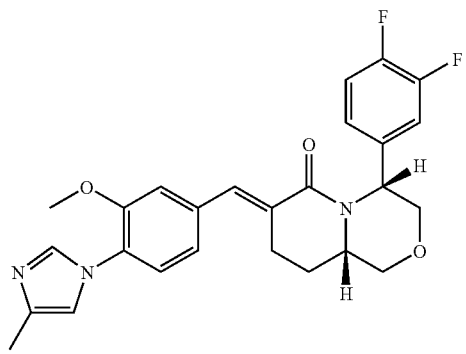

Synthesis of (4R,9aS)-4-(3,4-difluorophenyl)hexahydropyrido[2,1-c][1,4]oxazin-6-one 18 mg of the title compound was obtained from [(3S,5R)-5-(3,4-difluorophenyl)morpholin-3-yl]methanol (779 mg) in the same manner as in the other method in Examples 82 and 83. The property values of the compound are as follows.

ESI-MS; m/z 268 [M$^+$+H]. $^1$H-NMR (CDCl$_3$) δ(ppm): 1.50-1.70 (m, 1H), 1.80-1.92 (m, 2H), 1.98-2.06 (m, 1H), 2.42-2.46 (m, 2H), 3.57 (dd, J=11.6, 11.6 Hz, 1H), 3.67 (dd, J=12.0, 6.4 Hz, 1H), 3.80-3.88 (m, 1H), 3.92 (dd, J=12.0, 4.0 Hz, 1H), 4.17 (dd, J=12.4 Hz, 4.0 Hz, 1H), 4.78 (dd, J=6.0 Hz, 4.0 Hz, 1H), 6.98-7.03 (m, 1H), 7.04-7.13 (m, 2H).

Synthesis of (4R,9aS)-4-(3,4-difluorophenyl)-7-{1-[3-methoxy-4-(4-methyl-1H-imidazol-1-yl)phenyl]-(E)-methylidene}hexahydropyrido[2,1-c][1,4]oxazin-6-one 1.5 mg of the title compound was obtained from [(4R,9aS)-4-(3,4-difluorophenyl)hexahydropyrido[2,1-c][1,4]oxazin-6-one (8 mg) and 3-methoxy-4-(4-methyl-1H-imidazol-1-yl)benzaldehyde (39 mg) in the same manner as in Examples 75 and 76. The property values of the compound are as follows.

ESI-MS; m/z 466 [M$^+$+H]. $^1$H-NMR (CDCl$_3$) δ(ppm): 1.65-1.80 (m, 1H), 1.96-2.01 (m, 1H), 2.30 (s, 3H), 2.74-2.84 (m, 1H), 3.12-3.19 (m, 1H), 3.65 (dd, J=11.2, 11.2 Hz, 1H), 3.86 (s, 3H), 3.90-3.97 (m, 2H), 4.09-4.18 (m, 1H), 4.34 (dd, J=12.4, 3.6 Hz, 1H), 5.09 (t, J=4.0 Hz, 1H), 6.93 (s, 1H), 7.01-7.19 (m, 5H), 7.26-7.28 (m, 1H), 7.74 (s, 1H), 7.78 (brd, J=2.8 Hz, 1H).

Example 96

Synthesis of (4R,9aS)-4-(4-chlorophenyl)-7-{1-[3-methoxy-4-(4-methyl-1H-imidazol-1-yl)phenyl]-(E)-methylidene}hexahydropyrido[2,1-c][1,4]oxazin-6-one

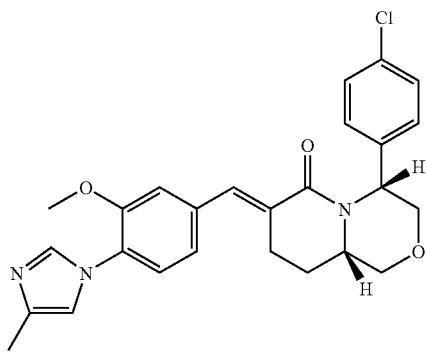

Synthesis of (S)-5-benzyloxymethylmorpholin-3-one

Chloroacetyl chloride (0.242 mL) was added to a mixed solution of (R)-(+)-2-amino-3-benzyloxy-1-propanol (500 g) in toluene (7 mL) and a 2 N sodium hydroxide solution (7 mL) under ice-cooling. The reaction solution was stirred at room temperature for one hour. Then, THF and brine were added to the reaction solution, and the organic layer was separated. The resulting organic layer was washed with brine, and then dried over anhydrous magnesium sulfate and concentrated under reduced pressure. Sodium iodide (82.7 mg) and potassium tert-butoxide (681 mg) were added to a solution of the resulting residue in THF (15 mL) under ice-cooling. The reaction solution was stirred at room temperature for one hour. Then, a saturated ammonium chloride solution and ethyl acetate were added to the reaction solution, and the organic layer was separated. The resulting organic layer was washed with brine, and then dried over anhydrous magnesium sulfate and concentrated under reduced pressure. The residue was purified by silica gel column chromatography (eluent solvent: heptane-ethyl acetate system) to obtain 387 mg of the title compound. The property values of the compound are as follows.

$^1$H-NMR (CDCl$_3$) δ(ppm): 3.42 (t, J=9.2 Hz, 1H), 3.54 (dd, J=9.2, 5.2 Hz, 1H), 3.62 (dd, J=12.0, 6.0 Hz, 1H), 3.75 (m, 1H), 3.86 (dd, J=12.0, 4.0 Hz, 1H), 4.12 (d, J=16.8 Hz, 1H), 4.18 (d, J=16.8 Hz, 1H), 4.53 (s, 2H), 6.29 (bs, 1H), 7.28-7.40 (m, 5H).

Synthesis of tert-butyl (S)-3-benzyloxymethyl-5-oxomorpholine-4-carboxylate

Dimethylaminopyridine (224 mg) and di-tert-butyl dicarbonate (1.2 g) were added to a solution of (S)-5-benzyloxymethylmorpholin-3-one (810 mg) in acetonitrile (20 mL). The reaction solution was stirred at room temperature for three hours. Then, water and ethyl acetate were added to the reaction solution, and the organic layer was separated. The organic layer was washed with brine, and then dried over anhydrous sodium sulfate and concentrated under reduced pressure. The residue was purified by silica gel column chromatography (elution solvent: heptane-ethyl acetate system) to obtain 1.1 g of the title compound. The property values of the compound are as follows.

$^1$H-NMR (CDCl$_3$) δ(ppm): 1.50 (s, 9H), 3.57 (dd, J=8.8, 4.8 Hz, 1H), 3.68-3.75 (m, 2H), 4.08-4.28 (m, 4H), 4.53 (d, J=12.0 Hz, 1H), 4.58 (d, J=12.0 Hz, 1H), 7.25-7.36 (m, 5H).

Synthesis of tert-butyl (R)-3-(tert-butyldiphenylsilanyloxymethyl)-5-oxomorpholine-4-carboxylate Palladium hydroxide (873 mg) and a catalytic amount of acetic acid were added to a solution of tert-butyl (S)-3-benzyloxymethyl-5-oxomorpholine-4-carboxylate (2 g) in ethyl acetate (30 mL). The reaction solution was stirred in a hydrogen atmosphere for 12 hours and then filtered through celite. Ethyl acetate was added to the filtrate. The resulting solution was sequentially washed with a saturated sodium bicarbonate solution and brine, dried over anhydrous magnesium sulfate, and then concentrated under reduced pressure. Imidazole (1.06 g) and tert-butyldiphenylchlorosilane (2.03 mL) were added to a solution of the resulting residue in DMF (15 mL), and the reaction solution was stirred at room temperature for 12 hours. Water and ethyl acetate were added to the reaction solution, and the organic layer was separated. The resulting organic layer was washed with brine, dried over anhydrous magnesium sulfate, and then concentrated under reduced pressure. The residue was purified by silica gel column chromatography (heptane-ethyl acetate system) to obtain 1.47 g of the title compound. The property values of the compound are as follows.

$^1$H-NMR (CDCl$_3$) δ(ppm): 1.06 (s, 9H), 1.44 (s, 9H), 3.68 (dd, J=9.6, 4.0 Hz, 1H), 3.77 (dd, J=12.0, 2.4 Hz, 1H), 3.85 (t, J=9.6 Hz, 1H), 4.09-4.25 (m, 3H), 4.37 (dd, J=12.8, 1.2 Hz, 1H), 7.35-7.45 (m, 6H), 7.62-7.66 (m, 4H).

Synthesis of tert-butyl {(R)-1-(tert-butyldiphenylsilanyloxymethyl)-2-[2-(4-chlorophenyl)-2-oxoethoxy]ethyl}carbamate 4-Chlorophenylmagnesium bromide (1 M solution in diethyl ether, 3.44 mL) was added dropwise to a solution of tert-butyl (R)-3-(tert-butyldiphenylsilanyloxymethyl)-5-oxomorpholine-4-carboxylate (1.47 g) in THF (35 mL) at −50° C. over five minutes, and the reaction solution was stirred at −40° C. for one hour. A saturated ammonium chloride solution was added to the solution in small portions at −40° C., and the reaction solution was returned to room temperature. Ethyl acetate was added to the reaction solution, and the organic layer was separated. The resulting organic layer was washed with brine, and then dried over anhydrous magnesium sulfate and concentrated under reduced pressure. The residue was purified by silica gel column chromatography (heptane-ethyl acetate system) to obtain 1.48 g of the title compound. The property value of the compound is as follows.
ESI-MS; m/z 604 [M$^+$+Na].

Synthesis of [(3S,5R)-5-(4-chlorophenyl)morpholin-3-yl]methanol

A solution of 4 N hydrochloric acid in ethyl acetate (18 mL) was added to tert-butyl {(R)-1-(tert-butyldiphenylsilanyloxymethyl)-2-[2-(4-chlorophenyl)-2-oxoethoxy]ethyl}carbamate (960 mg) under ice-cooling. The reaction solution was stirred under ice-cooling for 30 minutes and subsequently at room temperature for 30 minutes, and then concentrated under reduced pressure. Platinum oxide (37.4 mg) was added to a solution of the resulting residue in methanol (18 mL), and the reaction solution was stirred in a hydrogen atmosphere at room temperature for one hour. The reaction solution was filtered through celite. A saturated sodium bicarbonate solution and ethyl acetate were added to the filtrate, and the organic layer was separated. The organic layer was sequentially washed with a saturated sodium bicarbonate solution and brine. The resulting organic layer was dried over anhydrous magnesium sulfate and then concentrated under reduced pressure. The residue was purified by silica gel column chromatography (eluent solvent: heptane-ethyl acetate system) to obtain a crude product. A 1 M solution of tetrabutylammonium fluoride in THF (0.947 mL) was added to a solution of the resulting crude product in THF (5 mL), and the reaction solution was stirred at room temperature for one hour. A saturated ammonium chloride solution and ethyl acetate were added to the reaction solution, and the organic layer was separated. The resulting organic layer was washed with brine, and then dried over anhydrous magnesium sulfate and concentrated under reduced pressure. The residue was purified by silica gel column chromatography (eluent solvent: heptane-ethyl acetate system) to obtain 86 mg of the title compound. The property values of the compound are as follows.
$^1$H-NMR (CDCl$_3$) δ(ppm): 3.16-3.26 (m, 2H), 3.39 (dd, J=10.8, 10.4 Hz, 1H), 3.53 (dd, J=10.8, 5.6 Hz, 1H), 3.67 (dd, J=10.8, 4.0 Hz, 1H), 3.78 (dd, J=11.6, 3.2 Hz, 1H), 3.86 (dd, J=10.8, 3.2 Hz, 1H), 4.00 (dd, J=10.4, 3.2 Hz, 1H), 7.29 (dd, J=8.4, 2.4 Hz, 2H), 7.34 (dd, J=8.4, 2.4 Hz, 2H).

Synthesis of 9H-fluoren-9-ylmethyl (3R,5S)-3-(4-chlorophenyl)-5-hydroxymethylmorpholine-4-carboxylate 9-Fluorenylmethyl chloroformate (122 mg) was added to a mixed solution of [(3S,5R)-5-(4-chlorophenyl)morpholin-3-yl]methanol (86 mg) in methylene chloride (3 mL) and a saturated sodium bicarbonate solution (3 mL). The reaction solution was stirred at room temperature for eight hours. Then, chloroform and a saturated ammonium chloride solution were added to the reaction solution, and the organic layer was separated. The resulting organic layer was washed with brine, and then dried over anhydrous magnesium sulfate and concentrated under reduced pressure. The residue was purified by silica gel column chromatography (eluent solvent: heptane-ethyl acetate system) to obtain 153 mg of the title compound. The property value of the compound is as follows.
ESI-MS; m/z 472[M$^+$+Na].

Synthesis of methyl 3-[(3S,5R)-5-(4-chlorophenyl)morpholin-3-yl]acrylate

Oxalyl chloride (0.148 mL) was added dropwise to a solution of DMSO (0.145 mL) in dichloromethane (4 mL) at −78° C., and the reaction solution was stirred at the same temperature for 20 minutes. A solution of 9H-fluoren-9-ylmethyl (3R,5S)-3-(4-chlorophenyl)-5-hydroxymethylmorpholine-4-carboxylate (153 mg) in dichloromethane (3 mL) was added dropwise to the reaction solution at −78° C., and the reaction solution was stirred at the same temperature for 30 minutes. Triethylamine (0.474 mL) was added dropwise to the reaction solution, which was then stirred at −78° C. for 30 minutes. A saturated ammonium chloride solution was added to the reaction solution, and the reaction solution was heated to room temperature. Ethyl acetate was added to the reaction solution, and the organic layer was separated. The organic layer was washed with brine, dried over anhydrous magnesium sulfate, and then concentrated under reduced pressure to obtain a crude aldehyde compound. Trimethyl phosphonoacetate (0.098 mL) was added to a mixed solution of sodium hydride (containing 60% mineral oil, 23.1 mg) in THF (3 mL) and DMF (1 mL) at 0° C., and the reaction solution was stirred at room temperature for 30 minutes. A solution of the resulting crude aldehyde compound in THF (2 mL) was added to the reaction solution at 0° C., and the reaction solution was stirred at room temperature for 30 minutes. A saturated ammonium chloride solution and ethyl acetate were added to the reaction solution, and the organic layer was separated. The resulting organic layer was washed with brine, and then dried over anhydrous magnesium sulfate and concentrated under reduced pressure. Diethylamine (0.6 mL) was added to a solution of the resulting residue in acetonitrile (3 mL), and the reaction solution was stirred at room temperature for 30 minutes. The reaction solution was diluted with toluene and concentrated under reduced pressure. The residue was purified by silica gel column chromatography (eluent solvent: heptane-ethyl acetate system) to obtain 89 mg of an E/Z isomer mixture of the title compound. The property value of the compound is as follows.
ESI-MS; m/z 282[M$^+$+H].

Synthesis of methyl 3-[(3S,5R)-4-(3-butenoyl)-5-(4-chlorophenyl)morpholin-3-yl]-(E)-acrylate and methyl 3-[(3S,5R)-4-(3-butenoyl)-5-(4-chlorophenyl)morpholin-3-yl]-(Z)-acrylate TEA (88.4 μL) was added to a solution of methyl 3-[(3S,5R)-5-(4-chlorophenyl)morpholin-3-yl]acrylate (89 mg), vinylacetic acid (40.4 μL), and bis(2-oxo-3-oxazolidinyl)phosphinic chloride (121 mg) in THF (4 mL) at room temperature. The reaction solution was stirred at room temperature for two hours. Then, a 1 N hydrochloric acid solution and ethyl acetate were added to the reaction solution, and the organic layer was separated. The resulting organic layer was sequentially washed with a 1 N sodium hydroxide solution and brine, dried over anhydrous magnesium sulfate, and then concentrated under reduced pressure. The residue was purified by silica gel column chromatography (elution solvent: heptane-ethyl acetate system) to obtain 52.8 mg of methyl 3-[(3S,5R)-4-(3-butenoyl)-5-(4-chlorophenyl)morpholin-3-yl]-(E)-acrylate and 35.1 mg of methyl 3-[(3S,5R)-4-(3-butenoyl)-5-(4-chlorophenyl)morpholin-3-yl]-(Z)-acrylate. The property values of the isomers are as follows.

Methyl 3-[(3S,5R)-4-(3-butenoyl)-5-(4-chlorophenyl)morpholin-3-yl]-(E)-acrylate $^1$H-NMR (CDCl$_3$) δ(ppm): 3.13-3.20 (m, 2H), 3.61 (s, 3H), 3.76-3.85 (m, 2H), 4.09 (d, J=11.6 Hz, 1H), 4.55 (d, J=8.0 Hz, 1H), 4.57 (m, 1H), 5.16 (d, J=16.8 Hz, 1H), 5.23 (d, J=10.4 Hz, 1H), 5.49 (bs, 1H), 5.59 (d, J=16.0 Hz, 1H), 5.94-6.04 (m, 1H), 6.49 (dd, J=16.8, 6.0 Hz, 1H), 7.25 (d, J=8.4 Hz, 2H), 7.44 (d, J=8.4 Hz, 2H).

Methyl 3-[(3S,5R)-4-(3-butenoyl)-5-(4-chlorophenyl)morpholin-3-yl]-(Z)-acrylate $^1$H-NMR (CDCl$_3$) δ(ppm): 3.05 (dd, J=15.6, 5.6 Hz, 1H), 3.23 (dd, J=15.6, 6.8 Hz, 1H), 3.71 (s, 3H), 3.79-3.88 (m, 2H), 4.02 (d, J=11.6 Hz, 1H), 4.60 (d, J=12.4 Hz, 1H), 5.13-5.21 (m, 2H), 5.62 (d, J=11.6 Hz, 1H), 5.65-5.69 (m, 2H), 5.91-6.02 (m, 2H), 7.27 (d, J=8.4 Hz, 2H), 7.60 (d, J=8.4 Hz, 2H).

Synthesis of (4R,9aS)-4-(4-chlorophenyl)hexahydropyrido[2,1-c][1,4]oxazin-6-one

Grubbs catalyst 2nd generation (21.3 mg) was added to a solution of methyl 3-[(3S,5R)-4-but-3-enoyl-5-(4-chlorophenyl)morpholin-3-yl]-(E)-acrylate and methyl 3-[(3S,5R)-4-but-3-enoyl-5-(4-chlorophenyl)morpholin-3-yl]-(Z)-acrylate (87.9 mg) in dichloromethane (10 mL), and the reaction solution was heated under reflux in a nitrogen atmosphere for 1.5 hours. The reaction solution was returned to room temperature. Triethylamine (500 µL) was added to the reaction solution, which was then stirred for 10 minutes. The reaction solution was concentrated under reduced pressure, and the residue was purified by silica gel column chromatography (heptane-ethyl acetate system) to obtain a crude product. Platinum oxide (6.02 mg) was added to a solution of the crude product in methanol (3 mL), and the reaction solution was stirred in a hydrogen atmosphere at room temperature for one hour. The reaction solution was filtered under celite, and the filtrate was concentrated under reduced pressure. The residue was purified by silica gel column chromatography (eluent solvent: heptane-ethyl acetate system) to obtain 48.7 mg of the title compound. The property values of the compound are as follows.
ESI-MS; m/z 266[M$^+$+H]. $^1$H-NMR (CDCl$_3$) δ(ppm): 1.50-1.59 (m, 1H), 1.81-1.90 (m, 2H), 1.97-2.03 (m, 1H), 2.41-2.45 (m, 2H), 3.56 (t, J=10.8 Hz, 1H) 3.67 (dd, J=12.0, 6.4 Hz, 1H), 3.79-3.85 (m, 1H), 3.90 (dd, J=10.4, 3.6 Hz, 1H), 4.15 (dd, J=12.0, 4.0 Hz, 1H), 4.78 (dd, J=10.4, 4.0 Hz, 1H), 7.19 (d, J=8.4 Hz, 2H), 7.26 (d, J=8.4 Hz, 2H).

Synthesis of diethyl [(4R,9aS)-4-(4-chlorophenyl)-6-oxooctahydropyrido[2,1-c][1.4]oxazin-7-yl]phosphonate Iodotrimethylsilane (52.1 µL) was added to a solution of (4R,9aS)-4-(4-chlorophenyl)hexahydropyrido[2,1-c][1,4]oxazin-6-one (48.7 mg) and N,N,N',N'-tetramethylethylenediamine (96.7 µL) in dichloromethane (2 mL) in a nitrogen atmosphere at 0° C., and the reaction solution was stirred under ice-cooling for 30 minutes. Iodine (55.7 mg) was added to the reaction solution under ice-cooling, and the reaction solution was stirred under ice-cooling for 30 minutes. Ethyl acetate and a saturated sodium thiosulfate solution were added to the reaction solution, and the organic layer was separated. The resulting organic layer was washed with brine, dried over magnesium sulfate, and then concentrated under reduced pressure to obtain a crude iodide compound. Triethyl phosphite (1 mL) was added to the resulting crude iodide compound, and the mixture was stirred at 120° C. for one hour. The reaction solution was left to cool to room temperature and then concentrated under reduced pressure to obtain 73.5 mg of the title compound. The property values of the compound are as follows.
ESI-MS; m/z 402 [M$^+$+H].

Synthesis of (4R,9aS)-4-(4-chlorophenyl)-7-[1-[3-methoxy-4-(4-methyl-1H-imidazol-1-yl)phenyl]-(E)-methylidene]hexahydropyrido[2,1-c][1,4]oxazin-6-one Lithium hydroxide monohydrate (13.1 mg) was added to a mixed solution of diethyl [(4R,9aS)-4-(4-chlorophenyl)-6-oxooctahydropyrido[2,1-c][1,4]oxazin-7-yl]phosphonate (73.5 mg) and 3-methoxy-4-(4-methyl-1H-imidazol-1-yl)benzaldehyde (47.5 mg) in THF (1.5 mL) and ethanol (0.5 mL) at room temperature, and the reaction solution was stirred at room temperature for 1.5 hours. Ethyl acetate and water were added to the reaction solution, and the organic layer was separated. The resulting organic layer was washed with brine, dried over magnesium sulfate, and then concentrated under reduced pressure. The residue was purified by silica gel column chromatography (carrier: Chromatorex NH; elution solvent: heptane-ethyl acetate system) to obtain 68.4 mg of the title compound. The property values of the compound are as follows.
ESI-MS; m/z 464[M$^+$+H]. $^1$H-NMR (CDCl$_3$) δ(ppm): 1.65-1.73 (m, 1H), 1.92-2.03 (m, 1H), 2.30 (s, 3H), 2.73-2.83 (m, 1H), 3.10-3.20 (m, 1H), 3.64 (t, J=11.2 Hz, 1H), 3.84 (s, 3H), 3.93 (dd, J=12.0, 4.8 Hz, 2H), 4.10-4.17 (m, 1H), 4.33 (dd, J=12.0, 4.0 Hz, 1H), 5.10 (t, J=4.0 Hz, 1H), 6.92 (t, J=1.2 Hz, 1H), 7.00-7.04 (m, 2H), 7.24-7.33 (m, 5H), 7.70 (d, J=1.6 Hz, 1H), 7.76 (d, J=2.4 Hz, 1H).

Examples 97 and 98

Synthesis of methyl (4S,9aR)-7-{1-[3-methoxy-4-(4-methyl-1H-imidazol-1-yl)phenyl]-(E)-methylidene}-6-oxo-4-(3,4,5-trifluorophenyl)octahydropyrido[1,2-a]pyrazine-2-carboxylate and methyl (4R,9aS)-7-{1-[3-methoxy-4-(4-methyl-1H-imidazol-1-yl)phenyl]-(E)-methylidene}-6-oxo-4-(3,4,5-trifluorophenyl)octahydropyrido[1,2-a]pyrazine-2-carboxylate

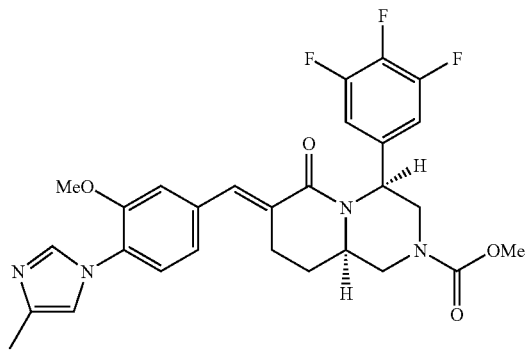

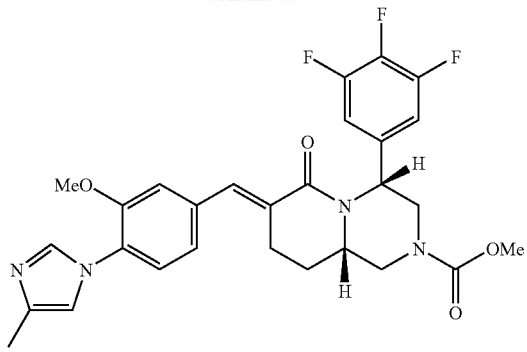

Synthesis of 1,2,3-trifluoro-5-((E)-2-nitrovinyl)benzene

Ammonium acetate (7.3 g) was added to a solution of 3,4,5-trifluorobenzaldehyde (12.6 g) and nitromethane (17.1 mL) in acetic acid (50 mL), and the reaction solution was stirred at 100° C. for three hours. The reaction solution was left to cool to room temperature and then concentrated under reduced pressure. Ethyl acetate and saturated sodium bicarbonate water were added to the residue, and the organic layer was separated. The resulting organic layer was dried over anhydrous magnesium sulfate and then concentrated under reduced pressure. The residue was purified by silica gel column chromatography (heptane->heptane:ethyl acetate=9:1) to obtain 10.5 g of the title compound. The property values of the compound are as follows.

$^1$H-NMR (CDCl$_3$) δ(ppm): 7.19 (dd, J=7.2, 6.0 Hz, 2H), 7.48 (d, J=13.6 Hz, 1H), 7.85 (d, J=13.6 Hz, 1H).

Synthesis of N1-allyl-1-(3,4,5-trifluorophenyl)ethane-1,2-diamine

Allylamine (9.8 mL) was added to a solution of 1,2,3-trifluoro-5-((E)-2-nitrovinyl)benzene (6.6 g) in THF (30 mL). The reaction solution was stirred at room temperature for 2.5 hours and then concentrated under reduced pressure. Zinc powder (10.6 g) was added to a solution of the residue in ethanol (35 mL) and concentrated hydrochloric acid (35 mL) at 0° C., and the reaction solution was stirred at 0° C. for 30 minutes and at room temperature for 15 hours. The reaction solution was added to ice-cold aqueous ammonia, and the reaction mixture was subjected to extraction with chloroform. The resulting organic layer was dried over anhydrous magnesium sulfate and then concentrated under reduced pressure to obtain 7.52 g of a crude product of the title compound. The property values of the compound are as follows.

ESI-MS; m/z 231 [M$^+$+H]. $^1$H-NMR (CDCl$_3$) δ(ppm): 2.71 (dd, J=12.8, 7.2 Hz, 1H), 2.88 (dd, J=12.8, 4.8 Hz, 1H), 3.02 (dd, J=14.0, 8.0 Hz, 1H), 3.14 (dd, J=14.0, 5.2 Hz, 1H), 3.58 (dd, J=7.2, 4.8 Hz, 1H), 5.06-5.18 (m, 2H), 5.80-5.91 (m, 1H), 6.98 (dd, J=8.8, 6.8 Hz, 2H).

Synthesis of ethyl (S*)-1-[(R*)-2-allylamino-2-(3,4,5-trifluorophenyl)ethyl]aziridine-2-carboxylate and ethyl (S*)-1-[(S*)-2-allylamino-2-(3,4,5-trifluorophenyl)ethyl]aziridine-2-carboxylate IPEA (17 mL) and ethyl 2,3-dibromopropionate (7.1 mL) were added to a solution of N1-allyl-1-(3,4,5-trifluorophenyl)ethane-1,2-diamine (7.52 g) in 1,2-dichloroethane (70 mL), and the reaction solution was stirred at room temperature for 18 hours. Saturated sodium bicarbonate water was added to the reaction solution, and the organic layer was separated. The resulting organic layer was dried over anhydrous magnesium sulfate and then concentrated under reduced pressure. The residue was purified by silica gel column chromatography (heptane->ethyl acetate) to obtain 3.0 g of a low-polar isomer of the title compound and 2.7 g of a high-polar isomer of the title compound. The property values of the isomers are as follows.

Low-Polar Isomer

ESI-MS; m/z 329 [M$^+$+H]. $^1$H-NMR (CDCl$_3$) δ(ppm): 1.28 (t, J=7.2 Hz, 3H), 1.50 (d, J=6.4 Hz, 1H), 2.01 (dd, J=6.4, 3.2 Hz, 1H), 2.14 (d, J=3.2 Hz, 1H), 2.22 (dd, J=12.0, 4.8 Hz, 1H), 2.67 (dd, J=12.0, 8.0 Hz, 1H), 3.02 (dd, J=14.4, 6.8 Hz, 1H), 3.13 (dd, J=14.4, 5.2 Hz, 1H), 3.83 (dd, J=8.0, 4.8 Hz, 1H), 4.14-4.25 (m, 2H), 5.06-5.19 (m, 2H), 5.79-5.90 (m, 1H), 6.95-7.02 (m, 2H).

High-Polar Isomer

ESI-MS; m/z 329[M$^+$+H]. $^1$H-NMR (CDCl$_3$) δ(ppm): 1.28 (t, J=7.2 Hz, 3H), 1.63 (dd, J=6.4, 0.8 Hz, 1H), 1.84 (dd, J=6.8, 3.2 Hz, 1H), 1.97 (dd, J=12.0, 5.2 Hz, 1H), 2.20 (dd, J=3.2, 0.8 Hz, 1H), 2.87 (dd, J=12.0, 8.4 Hz, 1H), 2.96-3.03 (m, 1H), 3.10-3.17 (m, 1H), 3.90 (dd, J=8.4, 5.2 Hz, 1H), 4.17 (q, J=7.2 Hz, 2H), 5.05-5.15 (m, 2H), 5.77-5.86 (m, 1H), 6.96-7.06 (m, 2H).

Synthesis of ethyl 1-[2-tert-butoxycarbonylamino-2-(3,4,5-trifluorophenyl)ethyl]aziridine-2-carboxylate 1,3-Dimethylbarbituric acid (4.28 g) and tetrakis(triphenylphosphine)palladium (0) (1.05 g) were added to a solution of the low-polar isomer of ethyl 1-[2-allylamino-2-(3,4,5-trifluorophenyl)ethyl]aziridine-2-carboxylate (3.0 g) in methylene chloride (50 mL), and the reaction solution was stirred at room temperature for two hours. A 1 N sodium hydroxide solution was added to the reaction solution, and the organic layer was separated. The resulting organic layer was dried over anhydrous magnesium sulfate and then concentrated under reduced pressure. Triethylamine (5.1 mL) and di-tert-butyl dicarbonate (3.99 g) were added to a solution of the residue in methylene chloride (50 mL), and the reaction solution was stirred at room temperature for 19 hours. The reaction solution was concentrated under reduced pressure, and the residue was purified by silica gel column chromatography (heptane->heptane:ethyl acetate=1:1) to obtain 1.96 g of the title compound. The property values of the compound are as follows.

ESI-MS; m/z 389 [M$^+$+H]. $^1$H-NMR (CDCl$_3$) δ(ppm): 1.29 (t, J=7.2 Hz, 3H), 1.54-1.57 (m, 1H), 1.95-2.01 (m, 1H), 2.06 (d, J=2.8 Hz, 1H), 2.49 (dd, J=12.0, 5.2 Hz, 1H), 2.74-2.84 (m, 1H), 4.14-4.23 (m, 2H), 4.70-4.77 (m, 1H), 5.67-5.78 (m, 1H), 6.69 (dd, J=8.0, 6.8 Hz, 2H).

Synthesis of ethyl 3-{[2-tert-butoxycarbonylamino-2-(3,4,5-trifluorophenyl)ethyl]methoxycarbonylamino}-2-chloropropionate Methyl chloroformate (0.58 mL) was added to a solution of ethyl 1-[2-tert-butoxycarbonylamino-2-(3,4,5-trifluorophenyl)ethyl]aziridine-2-carboxylate (1.96 g) in toluene (30 mL), and the reaction solution was heated under reflux for one hour. The reaction solution was left to cool to room temperature and then concentrated under reduced pressure. The residue was purified by silica gel column chromatography (heptane->heptane:ethyl acetate=1:1) to obtain 2.16 g of the title compound. The property value of the compound is as follows.

ESI-MS; m/z 505 [M$^+$+Na].

Synthesis of ethyl 3-{[2-amino-2-(3,4,5-trifluorophenyl)ethyl]methoxycarbonylamino}-2-chloropropionate A solution of 4 N hydrochloric acid in ethyl acetate (20 mL) was added to a solution of ethyl 3-{[2-tert-butoxycarbonylamino-2-(3,4,5-trifluorophenyl)ethyl]methoxycarbonylamino}-2-chloropropionate (2.16 g) in ethyl acetate (20 mL), and the reaction solution was stirred at room temperature for 15.5 hours. The reaction solution was concentrated under reduced pressure. Ethyl acetate and saturated sodium bicarbonate water were added to the residue, and the organic layer was separated. The resulting organic layer was dried over anhydrous magnesium sulfate and then concentrated under reduced pressure to obtain 2.03 g of a crude product of the title compound. The property value of the compound is as follows.

ESI-MS; m/z 383[M$^+$+H].

Synthesis of 5-(3,4,5-trifluorophenyl)piperazine-1,3-dicarboxylic acid 3-ethyl ester 1-methyl ester IPEA (1.85 mL) and sodium iodide (795 mg) were added to a solution of ethyl 3-{[2-amino-2-(3,4,5-trifluorophenyl)ethyl]methoxycarbonylamino}-2-chloropropionate (2.03 g) in THF (20 mL), and the reaction solution was stirred at 80° C. for four hours. The reaction solution was left to cool to room temperature. Then, ethyl acetate and saturated sodium bicarbonate water were added to the reaction solution, and the organic layer was separated. The resulting organic layer was dried over anhydrous magnesium sulfate and then concentrated under reduced pressure. The residue was purified by silica gel column chromatography (heptane->heptane:ethyl acetate=2:1) to obtain 991 mg of the title compound. The property value of the compound is as follows.

ESI-MS; m/z 347 [M$^+$+H].

Synthesis of methyl 3-hydroxymethyl-5-(3,4,5-trifluorophenyl)piperazine-1-carboxylate Lithium borohydride (187 mg) was added to a solution of 5-(3,4,5-trifluorophenyl)piperazine-1,3-dicarboxylic acid 3-ethyl ester 1-methyl ester (991 mg) in THF (20 mL), and the reaction solution was stirred at room temperature for two hours. A saturated ammonium chloride solution and ethyl acetate were added to the reaction solution, and the organic layer was separated. The resulting organic layer was dried over anhydrous magnesium sulfate and then concentrated under reduced pressure to obtain 867 mg of a crude product of the title compound. The property value of the compound is as follows.

ESI-MS; m/z 305 [M$^+$+H].

Synthesis of 2-hydroxymethyl-6-(3,4,5-trifluorophenyl)piperazine-1,4-dicarboxylic acid 1-(9H-fluoren-9-ylmethyl) ester 4-methyl ester 9-Fluorenylmethyl chloroformate (958 mg) was added to a mixed solution of methyl 3-hydroxymethyl-5-(3,4,5-trifluorophenyl)piperazine-1-carboxylate (867 mg) in methylene chloride (20 mL) and saturated sodium bicarbonate water (20 mL), and the reaction solution was stirred at room temperature for 14 hours. The organic layer was separated from the reaction solution. The resulting organic layer was dried over anhydrous magnesium sulfate and then concentrated under reduced pressure. The residue was purified by silica gel column chromatography (heptane->ethyl acetate) to obtain 916 mg of the title compound. The property value of the compound is as follows.

ESI-MS; m/z 527 [M$^+$+H].

Synthesis of 2-(2-ethoxycarbonylvinyl)-6-(3,4,5-trifluorophenyl)piperazine-1,4-dicarboxylic acid 1-(9H-fluoren-9-ylmethyl) ester 4-methyl ester A solution of DMSO (406 mg) in methylene chloride (5 mL) was added to a solution of oxalyl chloride (440 mg) in methylene chloride (10 mL) in a nitrogen stream at −78° C., and the reaction solution was stirred at −78° C. for 15 minutes. A solution of 2-hydroxymethyl-6-(3,4,5-trifluorophenyl)piperazine-1,4-dicarboxylic acid 1-(9H-fluoren-9-ylmethyl) ester 4-methyl ester (916 mg) in methylene chloride (5 mL) was added to the reaction solution, which was then stirred at −78° C. for 45 minutes. Triethylamine (1.21 mL) was added to the reaction solution, which was then stirred at −78° C. for 20 minutes and at room temperature for 40 minutes. A saturated ammonium chloride solution and ethyl acetate were added to the reaction solution, and the organic layer was separated. The resulting organic layer was dried over anhydrous magnesium sulfate and then concentrated under reduced pressure to obtain a crude aldehyde compound.

Triethyl phosphonoacetate (778 mg) was added to a suspension of sodium hydride (containing 60% mineral oil, 104 mg) in THF (15 mL), and the reaction solution was stirred at room temperature for one hour. A solution of the crude aldehyde compound synthesized above in THF (5 mL) was added to the reaction solution, which was then stirred at room temperature for one hour. A saturated ammonium chloride solution and ethyl acetate were added to the reaction solution, and the organic layer was separated. The resulting organic layer was dried over anhydrous magnesium sulfate and then concentrated under reduced pressure. The residue was purified by silica gel column chromatography (heptane->heptane:ethyl acetate=1:1) to obtain 1.03 g of an E/Z isomer mixture of the title compound. The property value of the compound is as follows.

ESI-MS; m/z 617 [M$^+$+Na].

Synthesis of methyl 3-(2-ethoxycarbonylvinyl)-5-(3,4,5-trifluorophenyl)piperazine-1-carboxylate Diethylamine (2 mL) was added to a solution of 2-(2-ethoxycarbonylvinyl)-6-(3,4,5-trifluorophenyl)piperazine-1,4-dicarboxylic acid 1-(9H-fluoren-9-ylmethyl) ester 4-methyl ester (1.03 g) in acetonitrile (10 mL), and the reaction solution was stirred at room temperature for one hour. The reaction solution was concentrated, and the residue was purified by silica gel column chromatography (heptane->ethyl acetate) to obtain 422 mg of an E/Z isomer mixture of the title compound. The property value of the compound is as follows.

ESI-MS; m/z 373 [M$^+$+H].

Synthesis of methyl 4-(3-butenoyl)-3-(2-ethoxycarbonylvinyl)-5-(3,4,5-trifluorophenyl)piperazine-1-carboxylate BOPCl (557 mg) was added to a solution of methyl 3-(2-ethoxycarbonylvinyl)-5-(3,4,5-trifluorophenyl)piperazine-1-carboxylate (422 mg), triethylamine (0.61 mL), and vinylacetic acid (0.19 mL) in THF (15 mL), and the reaction solution was stirred at room temperature for 20 hours. 1 N aqueous hydrochloric acid and ethyl acetate were added to the reaction solution, and the organic layer was separated. The resulting organic layer was washed with saturated sodium bicarbonate water, dried over anhydrous magnesium sulfate, and then concentrated under reduced pressure to obtain 643 mg of an E/Z isomer mixture crude product of the title compound. The property value of the compound is as follows.

ESI-MS; m/z 441 [M$^+$+H].

Synthesis of methyl (4R*,9aS*)-6-oxo-4-(3,4,5-trifluorophenyl)-1,3,4,6,7,9a-hexahydropyrido[1,2-a]pyrazine-2-carboxylate Grubbs catalyst 2nd generation (124 mg) was added to a solution of methyl 4-(3-butenoyl)-3-(2-ethoxycarbonylvinyl)-5-(3,4,5-trifluorophenyl)piperazine-1-carboxylate (643 mg) in methylene chloride (50 mL), and the reaction solution was heated under reflux for one hour. The reaction solution was left to cool to room temperature. Then, triethylamine (0.2 mL) was added to the reaction solution, which was then stirred at room temperature for 20 minutes. The reaction solution was concentrated under reduced pressure, and the residue was purified by silica gel column chromatography (ethyl acetate) to obtain 174 mg of the title compound. The property values of the compound are as follows.

ESI-MS; m/z 341 [M$^+$+H]. $^1$H-NMR (CDCl$_3$) δ(ppm): 2.98-3.18 (m, 2H), 3.35 (t, J=6.0 Hz, 0.5H), 3.37 (t, J=6.0 Hz, 0.5H), 3.60 (brs, 1.5H), 3.64 (brs, 1.5H), 3.76-3.89 (m, 2H), 4.10 (dd, J=14.0, 2.0 Hz, 0.5H), 4.26 (dd, J=14.0, 2.0 Hz, 0.5H), 4.63-4.73 (m, 1H), 5.32 (brd, J=12.4 Hz, 1H), 5.69 (dd, J=16.8, 12.4 Hz, 1H), 6.00-6.07 (m, 1H), 6.82 (t, J=6.8 Hz, 2H).

Synthesis of methyl (4R*,9aS*)-6-oxo-4-(3,4,5-trifluorophenyl)octahydropyrido[1,2-a]pyrazine-2-carboxylate Platinum oxide (10 mg) was added to a solution of methyl (4R*,9aS*)-6-oxo-4-(3,4,5-trifluorophenyl)-1,3,4,6,7,9a-hexahydropyrido[1,2-a]pyrazine-2-carboxylate obtained by performing the above method again (292 mg) in methanol (5 mL), and the reaction solution was stirred in a hydrogen atmosphere at room temperature for three hours. The reaction solution was filtered through celite, and the filtrate was concentrated under reduced pressure to obtain 255 mg of the title compound. The property values of the compound are as follows.

ESI-MS; m/z 343[M$^+$+H]. $^1$H-NMR (CDCl$_3$) δ(ppm): 1.53-1.77 (m, 2H), 1.79-1.95 (m, 2H), 2.05 (brs, 3H), 2.45-2.63 (m, 2H), 3.18 (t, J=12.8 Hz, 0.5H), 3.19 (t, J=12.8 Hz, 0.5H), 3.61 (s, 1.5H), 3.63 (s, 1.5H), 3.64-3.83 (m, 3H), 3.93-4.02 (m, 1H), 4.14 (brd, J=14.0 Hz, 0.5H), 4.28 (brd, J=14.0 Hz, 0.5H), 5.34 (brd, J=15.2 Hz, 1H), 6.82 (t, J=6.4 Hz, 2H).

Synthesis of methyl (4S,9aR)-7-{1-[3-methoxy-4-(4-methyl-1H-imidazol-1-yl)phenyl]-(E)-methylidene}-6-oxo-4-(3,4,5-trifluorophenyl)octahydropyrido[1,2-a]pyrazine-2-carboxylate and methyl (4R,9aS)-7-{1-[3-methoxy-4-(4-methyl-1H-imidazol-1-yl)phenyl]-(E)-methylidene}-6-oxo-4-(3,4,5-trifluorophenyl)octahydropyrido[1,2-a]pyrazine-2-carboxylate Iodotrimethylsilane (0.05 mL) was added to a solution of methyl (4R*,9aS*)-6-oxo-4-(3,4,5-trifluorophenyl)octahydropyrido[1,2-a]pyrazine-2-carboxylate (37 mg) and TMED (0.06 mL) in methylene chloride (5 mL) at 0° C., and the reaction solution was stirred at 0° C. for 30 minutes. Iodine (41 mg) was added to the reaction solution, which was then stirred at 0° C. for two hours. Ethyl acetate and a saturated sodium thiosulfate solution were added to the reaction solution, and the organic layer was separated. The resulting organic layer was dried over anhydrous magnesium sulfate and then concentrated under reduced pressure to obtain a crude iodide compound. Triethyl phosphite (1 mL) was added to the resulting crude iodide compound, and the reaction solution was stirred at 120° C. for 40 minutes. The reaction solution was left to cool to room temperature and then concentrated under reduced pressure. To a mixed solution of the residue in THF (3 mL) and ethanol (1 mL), 3-methoxy-4-(4-methyl-1H-imidazol-1-yl)benzaldehyde (23 mg) and lithium hydroxide monohydrate (14 mg) were added, and the reaction solution was stirred at room temperature for one hour. Ethyl acetate and brine were added to the reaction solution, and the organic layer was separated. The resulting organic layer was dried over anhydrous magnesium sulfate and then concentrated under reduced pressure. The residue was purified by silica gel column chromatography (heptane:ethyl acetate=1:1->ethyl acetate->ethyl acetate:methanol=9:1) to obtain 20 mg of a racemate of the title compound. The resulting racemate (20 mg) was separated by CHIRALPAK™ AD-H manufactured by Daicel Chemical Industries, Ltd. (2 cm×25 cm; mobile phase: ethanol) to obtain the title optically active compound with a retention time of 18 minutes (7.8 mg; >99% ee) and the title optically active compound with a retention time of 41 minutes (6.3 mg; >99% ee).

The property values of the title optically active compound with a retention time of 18 minutes (Example 97) are as follows.

ESI-MS; m/z 541 [M$^+$+Na]. $^1$H-NMR (CDCl$_3$) δ(ppm): 1.70-1.83 (m, 1H), 2.08-2.18 (m, 1H), 2.31 (s, 3H), 2.71-2.82 (m, 1H), 3.12-3.24 (m, 2H), 3.65 (s, 1.5H), 3.66 (s, 1.5H), 3.68-3.84 (m, 2H), 3.87 (s, 3H), 4.11-4.20 (m, 1H), 4.28 (dd, J=14.0, 1.6 Hz, 0.5H), 4.42 (dd, J=14.0, 1.6 Hz, 0.5H), 5.50 (brd, J=12.8 Hz, 1H), 6.86-6.92 (m, 2H), 6.94 (brs, 1H), 7.03 (brs, 1H), 7.05 (brd, J=8.0 Hz, 1H), 7.28 (d, J=8.0 Hz, 1H), 7.74 (d, J=1.2 Hz, 1H), 7.83 (brs, 1H).

The property values of the title optically active compound with a retention time of 41 minutes (Example 98) are as follows.

ESI-MS; m/z 541 [M$^+$+H]. $^1$H-NMR (CDCl$_3$) δ(ppm): 1.70-1.83 (m, 1H), 2.08-2.18 (m, 1H), 2.31 (s, 3H), 2.71-2.82 (m, 1H), 3.12-3.24 (m, 2H), 3.65 (s, 1.5H), 3.66 (s, 1.5H), 3.68-3.84 (m, 2H), 3.87 (s, 3H), 4.11-4.20 (m, 1H), 4.28 (dd, J=14.0, 1.6 Hz, 0.5H), 4.42 (dd, J=14.0, 1.6 Hz, 0.5H), 5.50 (brd, J=12.8 Hz, 1H), 6.86-6.92 (m, 2H), 6.94 (brs, 1H), 7.03 (brs, 1H), 7.05 (brd, J=8.0 Hz, 1H), 7.28 (d, J=8.0 Hz, 1H), 7.74 (d, J=1.2 Hz, 1H), 7.83 (brs, 1H).

Examples 99 and 100

Synthesis of methyl (4R,9aR)-7-{1-[3-methoxy-4-(4-methyl-1H-imidazol-1-yl)phenyl]-(E)-methylidene}-6-oxo-4-(3,4,5-trifluorophenyl)octahydropyrido[1,2-a]pyrazine-2-carboxylate and methyl (4S,9aS)-7-{1-[3-methoxy-4-(4-methyl-1H-imidazol-1-yl)phenyl]-(E)-methylidene}-6-oxo-4-(3,4,5-trifluorophenyl)octahydropyrido[1,2-a]pyrazine-2-carboxylate

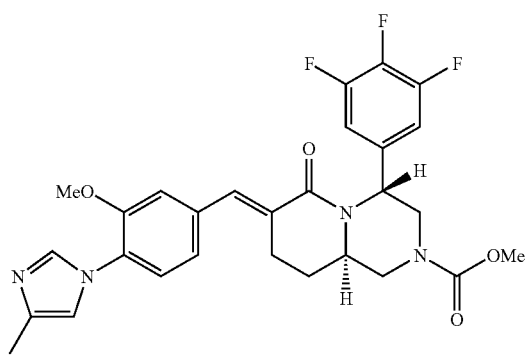

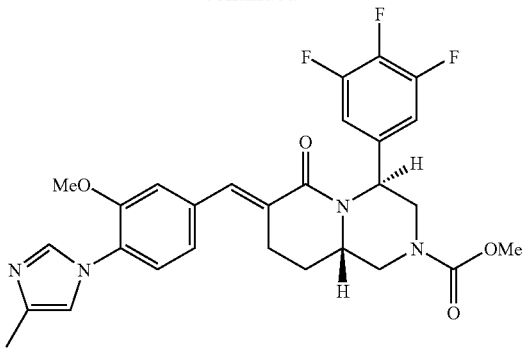

Synthesis of methyl (4R*,9aR*)-6-oxo-4-(3,4,5-trifluorophenyl)octahydropyrido[1,2-a]pyrazine-2-carboxylate 100 mg of the title compound was obtained from an isomer mixture of ethyl 1-[2-allylamino-2-(3,4,5-trifluorophenyl)ethyl]aziridine-2-carboxylate (5.7 g) in the same manner as Examples 97 and 98. The property values of the compound are as follows.

ESI-MS; m/z 343 [M⁺+H]. ¹H-NMR (CDCl₃) δ(ppm): 1.46-1.57 (m, 1H), 1.65-1.76 (m, 1H), 1.86-1.94 (m, 1H), 1.95-2.04 (m, 1H), 2.43 (dd, J=10.4, 5.2 Hz, 0.3H), 2.47 (dd, J=10.4, 5.2 Hz, 0.7H), 2.56 (td, J=6.4, 1.6 Hz, 0.7H), 2.61 (td, J=6.4, 1.6 Hz, 0.3H), 2.64-2.80 (m, 1H), 3.14-3.29 (m, 1H), 3.30-3.39 (m, 1H), 3.76 (brs, 3H), 3.90-4.17 (m, 1H), 4.47-4.72 (m, 1H), 5.91-5.99 (m, 1H), 6.89-7.01 (m, 2H).

Synthesis of methyl (4R,9aR)-7-{1'-[3-methoxy-4-(4-methyl-1H-imidazol-1-yl)phenyl]-(E)-methylidene}-6-oxo-4-(3,4,5-trifluorophenyl)octahydropyrido[1,2-a]pyrazine-2-carboxylate and methyl (4S,9aS)-7-{1-[3-methoxy-4-(4-methyl-1H-imidazol-1-yl)phenyl]-(E)-methylidene}-6-oxo-4-(3,4,5-trifluorophenyl)octahydropyrido[1,2-a]pyrazine-2-carboxylate Iodotrimethylsilane (0.13 mL) was added to a solution of methyl (4R*,9aR*)-6-oxo-4-(3,4,5-trifluorophenyl)octahydropyrido[1,2-a]pyrazine-2-carboxylate (100 mg) and TMED (0.26 mL) in methylene chloride (5 mL) at 0° C., and the reaction solution was stirred at 0° C. for one hour. Iodine (111 mg) was added to the reaction solution, which was then stirred at 0° C. for 30 minutes. Ethyl acetate and a saturated sodium thiosulfate solution were added to the reaction solution, and the organic layer was separated. The resulting organic layer was dried over anhydrous magnesium sulfate and then concentrated under reduced pressure to obtain a crude iodine compound. Triethyl phosphite (1 mL) was added to the resulting crude iodine compound, and the reaction solution was stirred at 120° C. for two hours. The reaction solution was left to cool to room temperature and then concentrated under reduced pressure. To a mixed solution of the residue in THF (4 mL) and ethanol (1 mL), 3-methoxy-4-(4-methyl-1H-imidazol-1-yl)benzaldehyde (63 mg) and lithium hydroxide monohydrate (37 mg) were added, and the reaction solution was stirred at room temperature for six hours. Ethyl acetate and brine were added to the reaction solution, and the organic layer was separated. The resulting organic layer was dried over anhydrous magnesium sulfate and then concentrated under reduced pressure. The residue was purified by silica gel column chromatography (carrier: Chromatorex NH; elution solvent: heptane:ethyl acetate 1:1->ethyl acetate) to obtain 112 mg of a racemate of the title compound. 25 mg of the resulting racemate was separated by CHIRALPAK™ IA manufactured by Daicel Chemical Industries, Ltd. (2 cm×25 cm; mobile phase: ethanol) to obtain the title optically active compound with a retention time of 21 minutes (7.1 mg; >99% ee) and the title optically active compound with a retention time of 31 minutes (7.2 mg; >99% ee).

The property values of the title optically active compound with a retention time of 21 minutes (Example 99) are as follows.

ESI-MS; m/z 541 [M⁺+H]. ¹H-NMR (CDCl₃) δ(ppm): 1.55-1.67 (m, 1H), 2.00-2.09 (m, 1H), 2.29 (s, 3H), 2.56-2.66 (m, 1H), 2.74-2.88 (m, 1H), 2.94-3.02 (m, 1H), 3.24-3.40 (m, 1H), 3.47-3.59 (m, 1H), 3.77 (brs, 3H), 3.86 (s, 3H), 3.92-4.20 (m, 1H), 4.49-4.73 (m, 1H), 6.00-6.09 (m, 1H), 6.93 (s, 1H), 6.96-7.05 (m, 4H), 7.26 (d, J=8.4 Hz, 1H), 7.71 (d, J=1.2 Hz, 1H), 7.82 (brs, 1H).

The property values of the title optically active compound with a retention time of 31 minutes (Example 100) are as follows.

ESI-MS; m/z 541 [M⁺+H]. ¹H-NMR (CDCl₃) δ(ppm): 1.55-1.67 (m, 1), 2.00-2.09 (m, 1H), 2.29 (s, 3H), 2.56-2.66 (m, 1H), 2.74-2.88 (m, 1H), 2.94-3.02 (m, 1H), 3.24-3.40 (m, 1H), 3.47-3.59 (m, 1H), 3.77 (brs, 3H), 3.86 (s, 3H), 3.92-4.20 (m, 1H), 4.49-4.73 (m, 1H), 6.00-6.09 (m, 1H), 6.93 (s, 1H), 6.96-7.05 (m, 4H), 7.26 (d, J=8.4 Hz, 1H), 7.71 (d, J=1.2 Hz, 1H), 7.82 (brs, 1H).

Examples 101 and 102

Synthesis of (4R,9aS)-7-{1-[3-methoxy-4-(4-methyl-1H-imidazol-1-yl)phenyl]-(E)-methylidene}-4-(3,4,5-trifluorophenyl)octahydropyrido[1,2-a]pyrazin-6-one and (4S,9aR)-7-{1-[3-methoxy-4-(4-methyl-1H-imidazol-1-yl)phenyl]-(E)-methylidene}-4-(3,4,5-trifluorophenyl)octahydropyrido[1,2-a]pyrazin-6-one

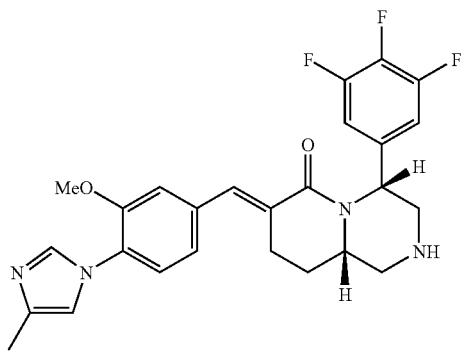

253
-continued

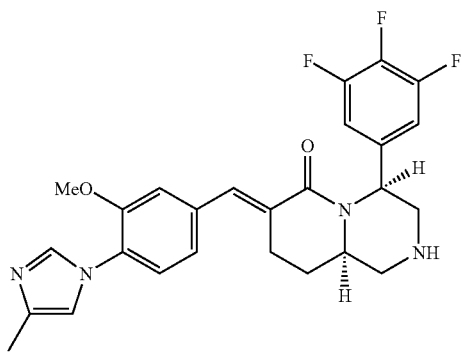

Iodotrimethylsilane (0.91 mL) was added to a solution of methyl (4R*,9aS*)-7-{1-[3-methoxy-4-(4-methyl-1H-imidazol-1-yl)phenyl]-(E)-methylidene}-6-oxo-4-(3,4,5-trifluorophenyl)octahydropyrido[1,2-a]pyrazine-2-carboxylate (175 mg) in methylene chloride (20 mL), and the reaction solution was heated under reflux for three hours. The reaction solution was left to cool to room temperature. Then, methanol and a 1 N sodium hydroxide solution were sequentially added to the reaction solution, and the organic layer was separated. The resulting organic layer was dried over anhydrous magnesium sulfate and then concentrated under reduced pressure. The residue was purified by silica gel column chromatography (elution solvent: chloroform:methanol 9:1) to obtain 163 mg of a racemate of the title compound. 25 mg of the resulting racemate was separated by CHIRALPAK™ AD-H manufactured by Daicel Chemical Industries, Ltd. (2 cm×25 cm; mobile phase: ethanol) to obtain the title optically active compound with a retention time of 7.7 minutes (5.2 mg; >99% ee) and the title optically active compound with a retention time of 9.5 minutes (3.0 mg; >99% ee).

The property values of the title optically active compound with a retention time of 7.7 minutes (Example 101) are as follows.

ESI-MS; m/z 483 [M$^+$+H]. $^1$H-NMR (CDCl$_3$) δ(ppm): 1.65-1.77 (m, 1H), 2.02-2.09 (m, 1H) 2.31 (s, 3H), 2.70-2.82 (m, 1H), 2.89 (t, J=12.0 Hz, 1H), 3.10-3.19 (m, 2H), 3.62 (dd, J=12.0, 3.6 Hz, 1H), 3.64-3.70 (m, 2H), 3.86 (s, 3H), 4.00-4.08 (m, 1H), 5.13 (t, J=4.0 Hz, 1H), 6.90-6.95 (m, 3H), 7.02 (d, J=1.2 Hz, 1H), 7.04 (dd, J=8.4, 1.2 Hz, 1H), 7.26 (d, J=8.4 Hz, 1H), 7.75 (d, J=1.2 Hz, 1H), 7.76 (brs, 1H).

The property values of the title optically active compound with a retention time of 9.5 minutes (Example 102) are as follows.

ESI-MS; m/z 483 [M$^+$+H]. $^1$H-NMR (CDCl$_3$) δ(ppm): 1.65-1.77 (m, 1H), 2.02-2.09 (m, 1H), 2.31 (s, 3H), 2.70-2.82 (m, 1H), 2.89 (t, J=12.0 Hz, 1H), 3.10-3.19 (m, 2H), 3.62 (dd, J=12.0, 3.6 Hz, 1H), 3.64-3.70 (m, 2H), 3.86 (s, 3H), 4.00-4.08 (m, 1H), 5.13 (t, J=4.0 Hz, 1H), 6.90-6.95 (m, 3H), 7.02 (d, J=1.2 Hz, 1H), 7.04 (dd, J=8.4, 1.2 Hz, 1H), 7.26 (d, J=8.4 Hz, 1H), 7.75 (d, J=1.2 Hz, 1H), 7.76 (brs, 1H).

254

Examples 103 and 104

Synthesis of (4S,9aS)-7-{1-[3-methoxy-4-(4-methyl-1H-imidazol-1-yl)phenyl]-(E)-methylidene}-4-(3,4,5-trifluorophenyl)octahydropyrido[1,2-a]pyrazin-6-one and (4R,9aR)-7-{1-[3-methoxy-4-(4-methyl-1H-imidazol-1-yl)phenyl]-(E)-methylidene}-4-(3,4,5-trifluorophenyl)octahydropyrido[1,2-a]pyrazin-6-one

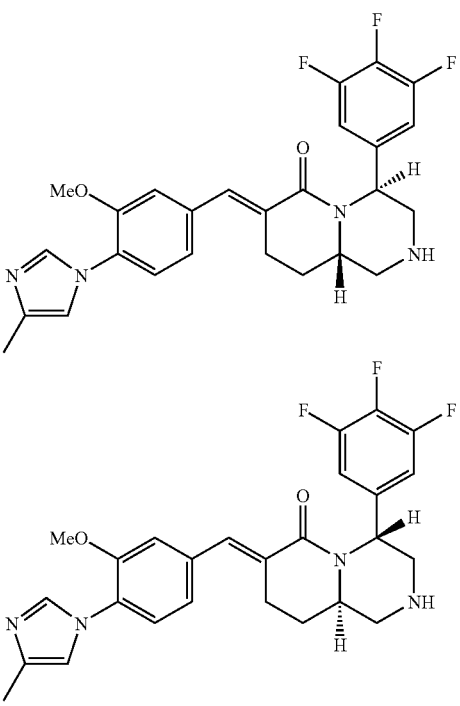

78 mg of a racemate of the title compound was obtained from methyl (4R*,9aR*)-7-{1-[3-methoxy-4-(4-methyl-1H-imidazol-1-yl)phenyl]-(E)-methylidene}-6-oxo-4-(3,4,5-trifluorophenyl)octahydropyrido[1,2-a]pyrazine-2-carboxylate (81 mg) in the same manner as in Examples 101 and 102. 78 mg of the resulting racemate was separated by CHIRALPAK™ AD-H manufactured by Daicel Chemical Industries, Ltd. (2 cm×25 cm; mobile phase: hexane:ethanol 1:1) to obtain the title optically active compound with a retention time of 14 minutes (23 mg; >99% ee) and the title optically active compound with a retention time of 25 minutes (23 mg; >99% ee).

The property values of the title optically active compound with a retention time of 14 minutes (Example 103) are as follows.

ESI-MS; m/z 483 [M$^+$+H]. $^1$H-NMR (CDCl$_3$) δ(ppm): 1.50-1.63 (m, 1H), 1.94-2.02 (m, 1H), 2.30 (s, 3H), 2.50-2.60 (m, 1H), 2.63 (t, J=11.2 Hz, 1H), 2.95-3.03 (m, 1H), 3.08 (dd, J=11.6, 2.4 Hz, 1H), 3.19 (dd, J=12.8, 4.4 Hz, 1H), 3.54 (d, J=12.8 Hz, 1H), 3.58-3.67 (m, 1H), 3.86 (s, 3H), 5.89 (d, J=3.2 Hz, 1H), 6.92 (s, 1H), 6.97 (s, 1H), 6.99 (dd, J=9.6, 1.2 Hz, 1H), 7.23-7.28 (m, 3H), 7.71 (d, J=0.8 Hz, 1H), 7.80 (s, 1H).

The property values of the title optically active compound with a retention time of 25 minutes (Example 104) are as follows.

ESI-MS; m/z 483 [M$^+$+H]. $^1$H-NMR (CDCl$_3$) δ(ppm): 1.50-1.63 (m, 1H), 1.94-2.02 (m, 1H), 2.30 (s, 3H), 2.50-2.60 (m, 1H), 2.63 (t, J=11.2 Hz, 1H), 2.95-3.03 (m, 1H), 3.08 (dd, J=111.6, 2.4 Hz, 1H), 3.19 (dd, J=12.8, 4.4 Hz, 1H), 3.54 (d, J=12.8 Hz, 1H), 3.58-3.67 (m, 1H), 3.86 (s, 3H), 5.89 (d, J=3.2 Hz, 1H), 6.92 (s, 1H), 6.97 (s, 1H), 6.99 (dd, J=9.6, 1.2 Hz, 1H), 7.23-7.28 (m, 3H), 7.71 (d, J=0.8 Hz, 1H), 7.80 (s, 1H).

Examples 105 and 106

Synthesis of (4S,9aR)-2-ethyl-7-{1-[3-methoxy-4-(4-methyl-1H-imidazol-1-yl)phenyl]-(E)-methylidene}-4-(3,45-trifluorophenyl)octahydropyrido[1,2-a]pyrazin-6-one and (4R,9aS)-2-ethyl-7-{1-[3-methoxy-4-(4-methyl-1H-imidazol-1-yl)phenyl]-(E)-methylidene}-4-(3,4,5-trifluorophenyl)octahydropyrido[1,2-a]pyrazin-6-one

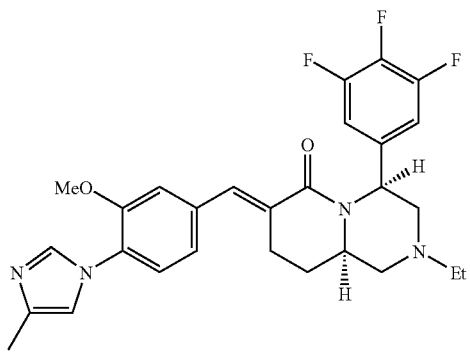

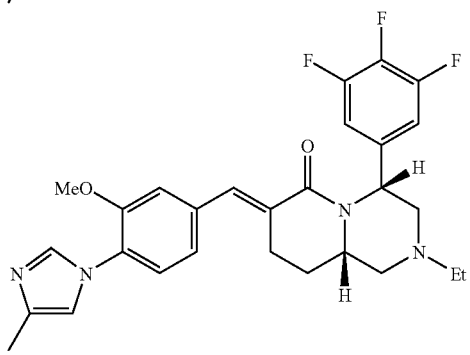

1 N aqueous hydrochloric acid (0.29 mL) and sodium cyanoborohydride (18 mg) were sequentially added to a solution of (4R*,9aS*)-7-{1-[3-methoxy-4-(4-methyl-1H-imidazol-1-yl)phenyl]-(E)-methylidene}-4-(3,4,5-trifluorophenyl)octahydropyrido[1,2-a]pyrazin-6-one (47 mg) and acetaldehyde (13 mg) in ethanol (5 mL) at 0° C., and the reaction solution was stirred at 0° C. for 30 minutes and at room temperature for two hours. Saturated sodium bicarbonate water and ethyl acetate were added to the reaction solution, and the organic layer was separated. The resulting organic layer was dried over anhydrous magnesium sulfate and then concentrated under reduced pressure. The residue was purified by silica gel column chromatography (elution solvent: ethyl acetate->ethyl acetate:methanol 4:1) to obtain 37 mg of a racemate of the title compound. 37 mg of the resulting racemate was separated by CHIRALPAK™ IA manufactured by Daicel Chemical Industries, Ltd. (2 cm×25 cm; mobile phase: ethanol) to obtain the title optically active compound with a retention time of 23 minutes (8 mg; >99% ee) and the title optically active compound with a retention time of 42 minutes (6 mg; >99% ee).

The property values of the title optically active compound with a retention time of 23 minutes (Example 105) are as follows.

ESI-MS; m/z 511 [M$^+$+H]. $^1$H-NMR (CDCl$_3$) δ(ppm): 1.08 (t, J=7.2 Hz, 3H), 1.75-1.87 (m, 1H), 1.98-2.05 (m, 1H), 2.26 (t, J=11.2 Hz, 1H), 2.30 (s, 3H), 2.32 (dd, J=12.4, 8.8 Hz, 1H), 2.44 (q, J=7.2 Hz, 2H), 2.70-2.82 (m, 1H), 2.94-3.00 (m, 1H), 3.05-3.18 (m, 2H), 3.80-3.88 (m, 4H), 4.77 (dd, J=8.8, 4.8 Hz, 1H), 6.89-6.93 (m, 3H), 6.99 (d, J=1.6 Hz, 1H), 7.02 (dd, J=8.0, 1.6 Hz, 1H), 7.24 (d, J=8.0 Hz, 1H), 7.64 (brs, 1H), 7.71 (d, J=1.2 Hz, 1H).

The property values of the title optically active compound with a retention time of 42 minutes (Example 106) are as follows.

ESI-MS; m/z 511 [M$^+$+H]. $^1$H-NMR (CDCl$_3$) δ(ppm): 1.08 (t, J=7.2 Hz, 3H), 1.75-1.87 (m, 1H), 1.98-2.05 (m, 1H), 2.26 (t, J=11.2 Hz, 1H), 2.30 (s, 3H), 2.32 (dd, J=12.4, 8.8 Hz, 1H), 2.44 (q, J=7.2 Hz, 2H), 2.70-2.82 (m, 1H), 2.94-3.00 (m, 1H), 3.05-3.18 (m, 2H), 3.80-3.88 (m, 4H), 4.77 (dd, J=8.8, 4.8 Hz, 1H), 6.89-6.93 (m, 3H), 6.99 (d, J=1.6 Hz, 1H), 7.02 (dd, J=8.0, 1.6 Hz, 1H), 7.24 (d, J=8.0 Hz, 1H), 7.64 (brs, 1H), 7.71 (d, J=1.2 Hz, 1H).

Example 107

Synthesis of (4R,9aR)-2-ethyl-7-{1-[3-methoxy-4-(4-methyl-1H-imidazol-1-yl)phenyl]-(E)-methylidene}-4-(3,4,5-trifluorophenyl)octahydropyrido[1,2-a]pyrazin-6-one

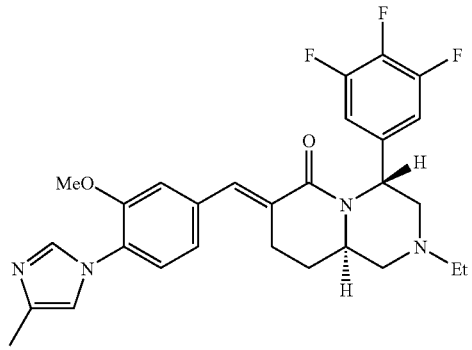

15 mg of the title compound was obtained in the same manner as in Examples 105 and 106 from (4R,9aR)-7-{1-[3-methoxy-4-(4-methyl-1H-imidazol-1-yl)phenyl]-(E)-methylidene}-4-(3,4,5-trifluorophenyl)octahydropyrido[1,2-a]pyrazin-6-one (20 mg) obtained in Examples 103 and 104. The property values of the compound are as follows.

$^1$H-NMR (CDCl$_3$) δ(ppm): 1.15 (t, J=7.2 Hz, 3H), 1.50-1.63 (m, 1H), 1.90-2.01 (m, 2H), 2.30 (s, 3H), 2.36-2.53 (m, 4H), 2.71-3.00 (m, 2H), 3.35 (d, J=12.4 Hz, 1H), 3.60-3.69 (m, 1H), 3.84 (s, 3H), 5.94 (d, J=3.6 Hz, 1H), 6.92 (s, 1H), 6.96 (s, 1H), 6.97 (brd, J=7.2 Hz, 1H), 7.24 (d, J=7.2 Hz, 1H), 7.36-7.44 (m, 2H), 7.71 (s, 1H), 7.78 (brs, 1H).

Example 108

Synthesis of (4S,9aS)-2-ethyl-7-{1-[3-methoxy-4-(4-methyl-1H-imidazol-1-yl)phenyl]-(E)-methylidene}-4-(3,4,5-trifluorophenyl)octahydropyrido[1,2-a]pyrazin-6-one

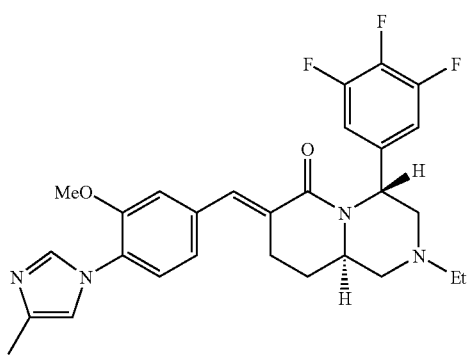

13 mg of the title compound was obtained in the same manner as in Examples 105 and 106 from (4S,9aS)-7-{1-[3-methoxy-4-(4-methyl-1H-imidazol-1-yl)phenyl]-(E)-methylidene}-4-(3,4,5-trifluorophenyl)octahydropyrido[1,2-a]pyrazin-6-one (20 mg) obtained in Examples 103 and 104. The property values of the compound are as follows.

$^1$H-NMR (CDCl$_3$) δ(ppm): 1.15 (t, J=7.2 Hz, 3H), 1.50-1.63 (m, 1H), 1.90-2.01 (m, 2H), 2.30 (s, 3H), 2.36-2.53 (m, 4H), 2.71-3.00 (m, 2H), 3.35 (d, J=12.4 Hz, 1H), 3.60-3.69 (m, 1H), 3.84 (s, 3H), 5.94 (d, J=3.6 Hz, 1H), 6.92 (s, 1H), 6.96 (s, 1H), 6.97 (brd, J=7.2 Hz, 1H), 7.24 (d, J=7.2 Hz, 1H), 7.36-7.44 (m, 2H), 7.71 (s, 1H), 7.78 (brs, 1H).

Examples 109 and 110

Synthesis of (4S,9aR)-7-{1-[3-methoxy-4-(4-methyl-1H-imidazol-1-yl)phenyl]-(E)-methylidene}-2-methyl-4-(3,4,5-trifluorophenyl)octahydropyrido[1,2-a]pyrazin-6-one and (4R,9aS)-7-{1-[3-methoxy-4-(4-methyl-1H-imidazol-1-yl)phenyl]-(E)-methylidene}-2-methyl-4-(3,4,5-trifluorophenyl)octahydropyrido[1,2-a]pyrazin-6-one

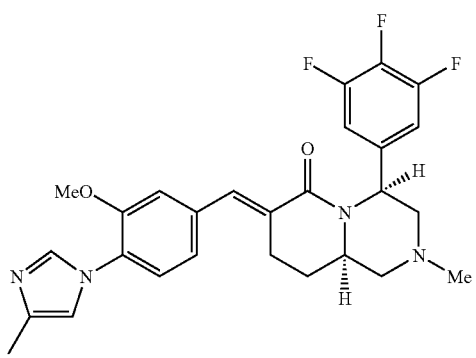

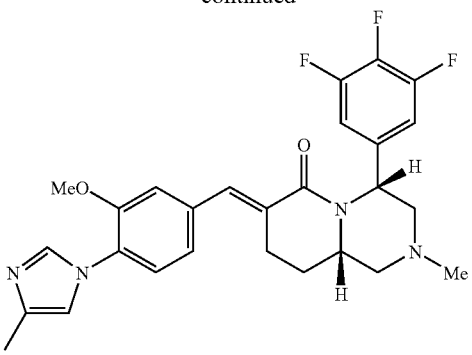

A racemate of the title compound was obtained from (4R*,9aS*)-7-{1-[3-methoxy-4-(4-methyl-1H-imidazol-1-yl)phenyl]-(E)-methylidene}-4-(3,4,5-trifluorophenyl)octahydropyrido[1,2-a]pyrazin-6-one (20 mg) and formaldehyde (6 mg) in the same manner as in Examples 105 and 106. The resulting racemate was separated by CHIRALPAK™ IA manufactured by Daicel Chemical Industries, Ltd. (2 cm×25 cm; mobile phase: ethanol) to obtain the title optically active compound with a retention time of 24 minutes (5.3 mg; >99% ee) and the title optically active compound with a retention time of 38 minutes (4.8 mg; >99% ee).

The property values of the title optically active compound with a retention time of 24 minutes (Example 109) are as follows.

ESI-MS; m/z 497 [M$^+$+H]. $^1$H-NMR (CDCl$_3$) δ(ppm): 1.75-1.87 (m, 1H), 1.97-2.05 (m, 1H), 2.24-2.29 (m, 1H), 2.30 (s, 3H), 2.32 (s, 3H), 2.72-2.82 (m, 1H), 2.84-2.90 (m, 1H), 3.02-3.11 (m, 2H), 3.80-3.88 (m, 5H), 4.75 (dd, J=9.2, 4.8 Hz, 1H), 6.88-6.94 (m, 3H), 7.00 (brs, 1H), 7.03 (brd, J=8.4 Hz, 1H), 7.25 (d, J=8.4 Hz, 1H), 7.65 (brs, 1H), 7.72 (s, 1H).

The property values of the title optically active compound with a retention time of 38 minutes (Example 110) are as follows.

ESI-MS; m/z 497 [M$^+$+H]. $^1$H-NMR (CDCl$_3$) δ(ppm): 1.75-1.87 (m, 1H), 1.97-2.05 (m, 1H), 2.24-2.29 (m, 1H), 2.30 (s, 3H), 2.32 (s, 3H), 2.72-2.82 (m, 1H), 2.84-2.90 (m, 1H), 3.02-3.11 (m, 2H), 3.80-3.88 (m, 5H), 4.75 (dd, J=9.2, 4.8 Hz, 1H), 6.88-6.94 (m, 3H), 7.00 (brs, 1H), 7.03 (brd, J=8.4 Hz, 1H), 7.25 (d, J=8.4 Hz, 1H), 7.65 (brs, 1H), 7.72 (s, 1H).

Examples 111 and 112

Synthesis of (4S,9aR)-7-{1-[3-methoxy-4-(4-methyl-1H-imidazol-1-yl)phenyl]-(E)-methylidene}-2-propyl-4-(3,4,5-trifluorophenyl)octahydropyrido[1,2-a]pyrazin-6-one and (4R,9aS)-7-{1-[3-methoxy-4-(4-methyl-1H-imidazol-1-yl)phenyl]-(E)-methylidene}-2-propyl-4-(3,4,5-trifluorophenyl)octahydropyrido[1,2-a]pyrazin-6-one

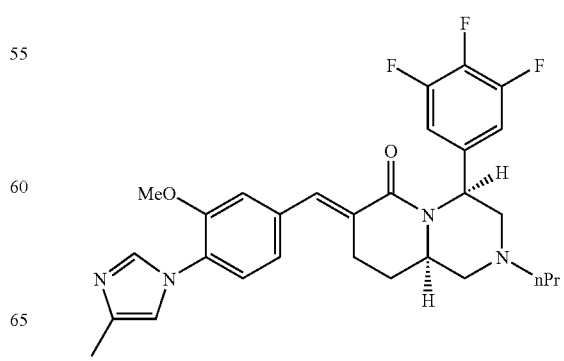

-continued

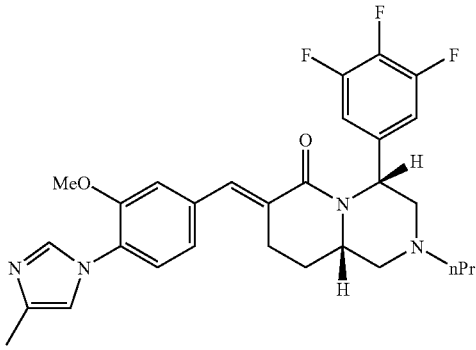

A racemate of the title compound was obtained from (4R*, 9aS*)-7-{1-[3-methoxy-4-(4-methyl-1H-imidazol-1-yl)phenyl]-(E)-methylidene}-4-(3,4,5-trifluorophenyl)octahydropyrido[1,2-a]pyrazin-6-one (20 mg) and propionaldehyde (0.009 mL) in the same manner as in Examples 105 and 106. The resulting racemate was separated by CHIRALPAK™ IA manufactured by Daicel Chemical Industries, Ltd. (2 cm×25 cm; mobile phase: ethanol) to obtain the title optically active compound with a retention time of 26 minutes (6.3 mg; >99% ee) and the title optically active compound with a retention time of 38 minutes (6.58 mg; >99% ee).

The property values of the title optically active compound with a retention time of 26 minutes (Example 111) are as follows.

ESI-MS; m/z 525 [M$^+$+H]. $^1$H-NMR (CDCl$_3$) δ(ppm): 0.88 (t, J=7.6 Hz, 3H), 1.42-1.52 (m, 2H), 1.74-1.85 (m, 1H), 1.97-2.04 (m, 1H), 2.29 (s, 3H), 2.30-2.38 (m, 4H), 2.70-2.81 (m, 1H), 2.90-2.95 (m, 1H), 3.04-3.16 (m, 2H), 3.80-3.88 (m, 4H), 4.78 (dd, J=8.0, 4.4 Hz, 1H), 6.88-6.94 (m, 3H), 6.98 (brs, 1H), 7.01 (brd, J=8.0 Hz, 1H), 7.24 (d, J=8.4 Hz, 1H), 7.64 (brs, 1H), 7.70 (d, J=0.8 Hz, 1H).

The property values of the title optically active compound with a retention time of 38 minutes (Example 112) are as follows.

ESI-MS; m/z 525[M$^+$+H]. $^1$H-NMR (CDCl$_3$) δ(ppm): 0.88 (t, J=7.6 Hz, 3H), 1.42-1.52 (m, 2H), 1.74-1.85 (m, 1H), 1.97-2.04 (m, 1H), 2.29 (s, 3H), 2.30-2.38 (m, 4H), 2.70-2.81 (m, 1H), 2.90-2.95 (m, 1H), 3.04-3.16 (m, 2H), 3.80-3.88 (m, 4H), 4.78 (dd, J=8.0, 4.4 Hz, 1H), 6.88-6.94 (m, 3H), 6.98 (brs, 1H), 7.01 (brd, J=8.0 Hz, 1H), 7.24 (d, J=8.4 Hz, 1H), 7.64 (brs, 1H), 7.70 (d, J=0.8 Hz, 1H).

Example 113

Synthesis of (4R*,9aS*)-2-acetyl-7-{-[3-methoxy-4-(4-methyl-1H-imidazol-1-yl)phenyl]-(E)-methylidene}-4-(3,4,5-trifluorophenyl)octahydropyrido[1,2-a]pyrazin-6-one

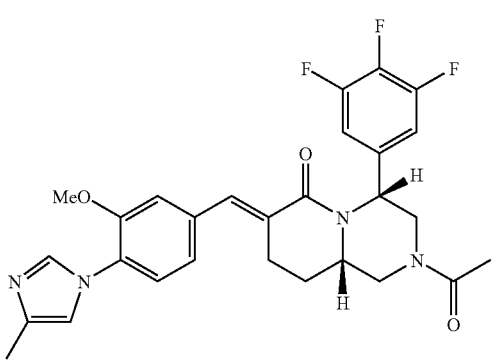

Acetic anhydride (0.5 mL) was added to a solution of (4R*,9aS*)-7-{1-[3-methoxy-4-(4-methyl-1H-imidazol-1-yl)phenyl]-(E)-methylidene}-4-(3,4,5-trifluorophenyl)octahydropyrido[1,2-a]pyrazin-6-one (20 mg) in pyridine (1 mL), and the reaction solution was stirred at room temperature for 12 hours. The reaction solution was concentrated under reduced pressure. The residue was purified by silica gel column chromatography (carrier: Chromatorex NH; elution solvent: ethyl acetate->ethyl acetate:methanol 4:1) to obtain 10.2 mg of the title compound. The property values of the compound are as follows.

ESI-MS; m/z 525[M$^+$+H]. $^1$H-NMR (CDCl$_3$) δ(ppm): 1.74-1.87 (m, 1H), 1.93 (s, 1.5H), 1.96 (s, 1.5H), 2.10-2.22 (m, 1H), 2.31 (s, 3H), 2.70-2.86 (m, 1H), 3.23 (t, J=12.4 Hz, 0.5H), 3.32 (t, J=12.4 Hz, 0.5H), 3.57-3.68 (m, 2H), 3.76-3.80 (m, 1H), 3.87 (s, 1.5H), 3.88 (s, 1.5H), 3.92-4.00 (m, 1H), 4.13-4.28 (m, 1H), 5.46-5.50 (m, 0.5H), 5.56-5.60 (m, 0.5H), 6.85-6.93 (m, 2H), 6.95 (brs, 1H), 7.03 (brs, 0.5H), 7.04 (brd, J=8.0 Hz, 0.5H), 7.05 (brs, 0.5H), 7.07 (brd, J=8.0 Hz, 0.5H), 7.28 (d, J=8.0 Hz, 0.5H), 7.30 (d, J=8.0 Hz, 0.5H), 7.74 (brs, 1H), 7.81 (d, J=2.4 Hz, 0.5H), 7.87 (d, J=2.4 Hz, 0.5H).

Example 114

Synthesis of (4R*,9aS*)-2-methanesulfonyl-7-{1-[3-methoxy-4-(4-methyl-1H-imidazol-1-yl)phenyl]-(E)-methylidene}-4-(3,4,5-trifluorophenyl)octahydropyrido[1,2-a]pyrazin-6-one

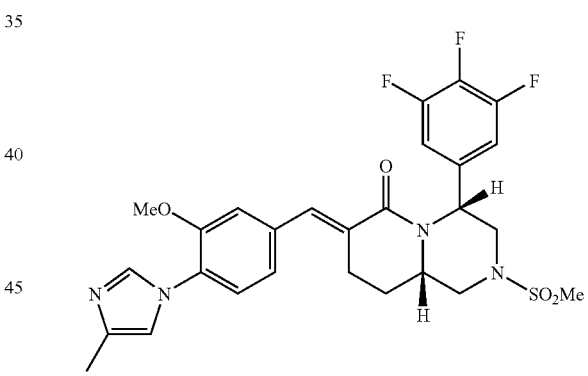

IPEA (0.02 mL) and methanesulfonyl chloride (0.004 mL) were sequentially added to a solution of (4R*,9aS*)-7-{1-[3-methoxy-4-(4-methyl-1H-imidazol-1-yl)phenyl]-(E)-methylidene}-4-(3,4,5-trifluorophenyl)octahydropyrido[1,2-a]pyrazin-6-one (20 mg) in methylene chloride (3 mL), and the reaction solution was stirred at 0° C. for one hour. Ethyl acetate and saturated sodium bicarbonate water were added to the reaction solution, and the organic layer was separated. The resulting organic layer was dried over anhydrous magnesium sulfate and then concentrated under reduced pressure. The residue was purified by silica gel column chromatography (carrier: Chromatorex NH; elution solvent: heptane:ethyl acetate 1:1->ethyl acetate->ethyl acetate:methanol 4:1) to obtain 24 mg of the title compound. The property values of the compound are as follows.

ESI-MS; m/z 561 [M++H]. ¹H-NMR (CDCl₃) δ(ppm): 1.74-1.85 (m, 1H), 2.12-2.18 (m, 1H), 2.30 (s, 3H), 2.48 (s, 3H), 2.74-2.84 (m, 1H), 3.15 (t, J=12.0 Hz, 1H), 3.18-3.26 (m, 1H), 3.76 (dd, J=12.0, 3.2 Hz, 1H), 3.87 (s, 3H), 3.95 (dd, J=14.0, 3.2 Hz, 1H), 4.02 (dd, J=14.0, 2.8 Hz, 1H), 4.18-4.27 (m, 1H), 5.49 (brs, 1H), 6.92-6.97 (m, 3H), 7.02 (brs, 1H), 7.04 (dd, J=8.0, 1.6 Hz, 1H), 7.27 (d, J=8.0 Hz, 1H), 7.73 (d, J=1.2 Hz, 1H), 7.81 (d, J=2.4 Hz, 1H).

Example 115

Synthesis of (4R*,9aS*)-7-{1-[3-methoxy-4-(4-methyl-1H-imidazol-1-yl)phenyl]-(E)-methylidene}-6-oxo-4-(3,4,5-trifluorophenyl)octahydropyrido[1,2-a]pyrazine-2-carboxylic acid dimethylamide

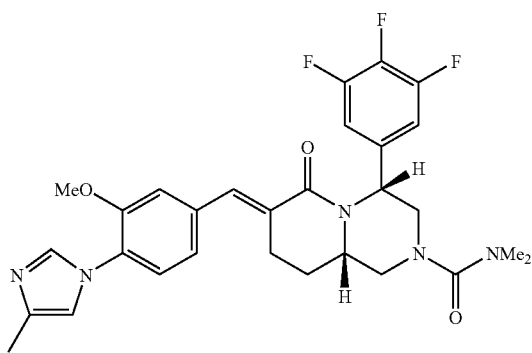

IPEA (0.02 mL) and dimethylcarbamyl chloride (0.006 mL) were sequentially added to a solution of (4R*,9aS*)-7-{1-[3-methoxy-4-(4-methyl-1H-imidazol-1-yl)phenyl]-(E)-methylidene}-4-(3,4,5-trifluorophenyl)octahydropyrido[1,2-a]pyrazin-6-one (20 mg) in methylene chloride (3 mL), and the reaction solution was stirred at 0° C. for one hour and at room temperature for five hours. Ethyl acetate and saturated sodium bicarbonate water were added to the reaction solution, and the organic layer was separated. The resulting organic layer was dried over anhydrous magnesium sulfate and then concentrated under reduced pressure. The residue was purified by silica gel column chromatography (carrier: Chromatorex NH; elution solvent: heptane:ethyl acetate 1:1->ethyl acetate->ethyl acetate:methanol 4:1) to obtain 17 mg of the title compound. The property values of the compound are as follows.

ESI-MS; m/z 554 [M++H]. ¹H-NMR (CDCl₃) δ(ppm): 1.78-1.80 (m, 1H), 2.02-2.10 (m, 1H), 2.30 (s, 3H), 2.71 (s, 6H), 2.72-2.83 (m, 1H), 3.16-3.23 (m, 1H), 3.26 (t, J=12.0 Hz, 1H), 3.39 (dd, J=12.0, 3.2 Hz, 1H), 3.87 (s, 3H), 3.91 (dd, J=13.6, 3.2 Hz, 1H), 3.95 (dd, J=13.6, 3.2 Hz, 1H), 4.01-4.20 (m, 1H), 5.54 (brs, 1H), 6.86-6.95 (m, 3H), 7.04 (brs, 1H), 7.06 (dd, J=8.0, 1.2 Hz, 1H), 7.27 (d, J=8.0 Hz, 1H), 7.73 (d, J=1.2 Hz, 1H), 7.85 (d, J=2.4 Hz, 1H).

Test Example 1

Quantification of Aβ Peptide in Culture of Neurons from Rat Fetus Brain (1) Rat Primary Neuronal Culture Primary neuronal cultures were prepared from the cerebral cortex of embryonic day 18 Wistar rats (Charles River Japan, Yokohama, Japan). Specifically, the embryos were aseptically removed from pregnant rats under ether anesthesia. The brain was isolated from the embryo and immersed in an ice-cold L-15 medium (Invitrogen Corp. Cat #11415-064, Carlsbad, Calif., USA, or SIGMA L1518, for example). The cerebral cortex was collected from the isolated brain under a stereoscopic microscope. The cerebral cortex fragments collected were enzymatically treated in an enzyme solution containing 0.25% trypsin (Invitrogen Corp. Cat #15050-065, Carlsbad, Calif., USA) and 0.01% DNase (Sigma D5025, St. Louis, Mo., USA) at 37° C. for 30 minutes to disperse the cells. Here, the enzymatic reaction was stopped by adding inactivated horse serum to the solution. The enzymatically treated solution was centrifuged at 1,500 rpm for five minutes to remove the supernatant. 5 to 10 mL of a medium was added to the resulting cell mass. Neurobasal medium (Invitrogen Corp. Cat #21103-049, Carlsbad, Calif., USA) supplemented with 2% B27 supplement (Invitrogen Corp. Cat #17504-044, Carlsbad, Calif., USA), 25 μM 2-mercaptoethanol (2-ME, WAKO Cat #139-06861, Osaka, Japan), 0.5 mM L-glutamine (Invitrogen Corp. Cat #25030-081, Carlsbad, Calif., USA), and Antibiotics-Antimycotics (Invitrogen Corp. Cat #15240-062, Carlsbad, Calif., USA) was used as the medium (Neurobasal/B27/2-ME). However, the above Neurobasal medium not supplemented with 2-ME (Neurobasal/B27) was used for the assay. The cells were redispersed by mild pipetting of the cell mass to which the medium was added. The cell dispersion was filtered through a 40-μm nylon mesh (Cell Strainer, Cat #35-2340, Becton Dickinson Labware, Franklin Lakes, N.J., USA) to remove the remaining cell mass, and thus a neuronal cell suspension was obtained. The neuronal cell suspension was diluted with the medium and then plated in a volume of 100 μl/well at an initial cell density of 5×10⁵ cells/cm² in a 96-well polystyrene culture plate pre-coated with poly-L or D-lysine (Falcon Cat #35-3075, Becton Dickinson Labware, Franklin Lakes, N.J., USA coated with poly-L-lysine using the method shown below, or BIOCOAT™ cell environments Poly-D-lysine cell ware 96-well plate, Cat #35-6461, Becton Dickinson Labware, Franklin Lakes, N.J., USA). Poly-L-lysine coating was carried out as follows. 100 μg/ml of a poly-L-lysine (SIGMA P2636, St. Louis, Mo., USA) solution was aseptically prepared with a 0.15 M borate buffer (pH 8.5). 100 μl/well of the solution was added to the 96-well polystyrene culture plate and incubated at room temperature for one or more hours or at 4° C. overnight or longer. The coated 96-well polystyrene culture plate was washed with sterile water four or more times, and then dried or rinsed with, for example, sterile PBS or medium, and used for cell plating. The plated cells were cultured in the culture plate at 37° C. in 5% CO₂-95% air for one day. Then, the total amount of the medium was replaced with a fresh Neurobasal/B27/2-ME medium, and then the cells were cultured for further three days.

(2) Addition of Compound

The drug was added to the culture plate on Day 4 of culture as follows. The total amount of the medium was removed from the wells, and 180 μl/well of Neurobasal medium not containing 2-ME and containing 2% B-27 (Neurobasal/B27) was added thereto. A solution of the test compound in dimethyl sulfoxide (hereinafter abbreviated as DMSO) was diluted with Neurobasal/B27 at 10-fold of the final concentration. 20 μl/well of the dilution was added to and sufficiently mixed with the medium. The final DMSO concentration was 1% or less. Only DMSO was added to the control group.

(3) Sampling

The cells were cultured for three days after addition of the compound, and the total amount of the medium was collected. The resulting medium was used as an ELISA sample. The sample was not diluted for ELISA measurement of Aβx-42 and diluted to 5-fold with a diluent supplied with an ELISA kit for ELISA measurement of Aβx-40.

(4) Evaluation of Cell Survival

Cell survival was evaluated by an MTT assay according to the following procedure. After collecting the medium, 100 μl/well of a pre-warmed medium was added to the wells. Further, 8 μl/well of a solution of 8 mg/ml of MTT (SIGMA M2128, St. Louis, Mo., USA) in D-PBS(−) (Dulbecco's phosphate buffered Saline, SIGMA D8537, St. Louis, Mo., USA) was added to the wells. The 96-well polystyrene culture plate was incubated in an incubator at 37° C. in 5% $CO_2$-95% air for 20 minutes. 100 μl/well of an MTT lysis buffer was added thereto, and MTT formazan crystals were sufficiently dissolved in the buffer in the incubator at 37° C. in 5% $CO_2$-95% air. Then, the absorbance at 550 nm in each well was measured. The MTT lysis buffer was prepared as follows. 100 g of SDS (sodium dodecyl sulfate (sodium lauryl sulfate), WAKO 191-07145, Osaka, Japan) was dissolved in a mixed solution of 250 mL of N,N'-dimethylformamide (WAKO 045-02916, Osaka, Japan) with 250 mL of distilled water. 350 μl each of concentrated hydrochloric acid and concentrated acetic acid were further added to the solution to allow the solution to have a final pH of about 4.7.

Upon measurement, wells having no cells plated and containing only the medium and MTT solution were set as background (bkg). The measured values were respectively applied to the following formula including subtracting bkg values from them. Thus, the proportion against the control group (group not treated with the drug, CTRL) (% of CTRL) was calculated to compare and evaluate cell survival activities.

% of CTRL=($A550$_sample−$A550$_$bkg$)/ ($A550$_CTRL−$A550$_$bkg$)×100

($A550$_sample: absorbance at 550 nm of sample well, $A550$_bkg: absorbance at 550 nm of background well, $A550$_CTRL: absorbance at 550 nm of control group well)

(5) Aβ ELISA

For Aβ ELISA, Human/Rat β Amyloid (42) ELISA Kit Wako (#290-62601) and Human/Rat β Amyloid (40) ELISA Kit Wako (#294-62501) from Wako Pure Chemical Industries, Ltd., or Human Amyloid beta (1-42) Assay Kit (#27711) and Human Amyloid beta (1-40) Assay Kit (#27713) from Immuno-Biological Laboratories, Co., Ltd. (IBL Co., Ltd.) were used. Aβ ELISA was carried out according to the protocols recommended by the manufacturers (methods described in the attached documents). However, the Aβ calibration curve was created using beta-amyloid peptide 1-42, rat and beta-amyloid peptide 1-40, rat (Calbiochem, #171596 [Aβ$_{42}$], #171593 [Aα$_{40}$]). The results are shown in Tables 1 and 2 as percentage to the Aβ concentration in the medium of the control group (% of CTRL).

TABLE 1

| Test Compound | Activity for reducing Aβ 42 Production IC50 (nM) |
|---|---|
| Example 3 | 63 |
| Example 6 | 120 |
| Example 8 | 73 |
| Example 11 | 97 |
| Example 13 | 91 |
| Example 15 | 80 |
| Example 17 | 68 |
| Example 19 | 129 |
| Example 30 | 109 |
| Example 41 | 47 |

TABLE 1-continued

| Test Compound | Activity for reducing Aβ 42 Production IC50 (nM) |
|---|---|
| Example 43 | 66 |
| Example 44 | 94 |
| Example 45 | 160 |
| Example 47 | 220 |
| Example 49 | 210 |
| Example 54 | 254 |

TABLE 2

| Test Compound | Activity for reducing Aβ 42 Production IC50 (nM) |
|---|---|
| Example 56 | 55 |
| Example 57 | 62 |
| Example 58 | 73 |
| Example 64 | 67 |
| Example 65 | 68 |
| Example 83 | 37 |
| Example 89 | 88 |
| Example 90 | 39 |
| Example 91 | 33 |
| Example 92 | 40 |

TABLE 3

| Test Compound | Activity for reducing Aβ 42 Production IC50 (nM) |
|---|---|
| Example 95 | 87 |
| Example 96 | 65 |
| Example 110 | 29 |

From the results of Tables 1 to 3, it was confirmed that the compound of the present invention has an activity for reducing Aβ42 production.

Test Example 2

Effect on Amyloid β Production in Cerebrospinal Fluid, Brain, and Plasma of Rats Animals were moved to a laboratory on the previous day of the start of experiment (Day 0). Provisional individual numbers were assigned to the tail of animals with an oil pen. Their body weights were measured, and allocation of treatment was performed. Thereafter, individual numbers were assigned to the animals again. A vehicle or sample was forcibly orally administered to the rats once a day over three days since the start of experiment (Day 1) (5 mL/kg). Six hours after the final oral administration, Nembutal (Dainippon Pharmaceutical Co., Ltd., Osaka) was intraperitoneally administered to the rats (50 mg/kg). Under anesthesia, the posterior region of neck was incised, and a 25 G needle was inserted into the cerebellomedullary cistern to collect about 100 μL of cerebrospinal fluid. The collected cerebrospinal fluid was put in a tube containing 1 μL of 100 mmol/L p-ABSF (4-(2-aminoethyl)benzenesulfofuloride) and preserved in ice in order to prevent decomposition of Aβ. Thereafter, the abdominal cavity was opened, and about 2.5 mL of blood was collected from the abdominal aorta using a heparin syringe and preserved in ice. Finally, the rats were decapitated, the brain was removed and lightly washed with ice cold saline, the wet weight of each half of the brain was then measured, and each half of the brain was put in a 15 mL tube and frozen with liquid nitrogen. The removed brain sample was cryopreserved until measurement. The cerebrospinal fluid was centrifuged at 4° C. at 7,000 rpm for five minutes, and then the supernatant was collected to measure Aβ. The blood was centrifuged at 4° C. at 3,000 rpm for five minutes, and then the plasma was collected to measure Aβ.

For Aβ40 and Aβ42 measurement, the cerebrospinal fluid or plasma was diluted with a diluent supplied with an Aβ measurement kit. 70% formic acid was added to the brain tissue (right brain) at 1 mL per 100 mg (wet weight) of the tissue, and the brain tissue was sonicated. Immediately after the sonication, the mixture was 20-fold diluted with a 0.9 mol/L Tris (Tris(hydroxymethyl)aminomethene) buffer (pH 12) and neutralized. The neutralized liquid was directly used for Aβ measurement.

Aβ was measured according to the instruction attached to the measurement kit. Specifically, 100 μL each of the diluted cerebrospinal fluid, the diluted plasma sample, or the original brain liquid before neutralization were added to a microplate having Aβ40 and Aβ42 antibodies solid-phased. 100 μL each of various concentrations of Aβ standard solutions were added to the microplate, and reaction was carried out at 4° C. overnight. The microplate was washed with a wash solution supplied with the measurement kit five times. Then, an HRP-labeled secondary antibody was added to the microplate, and reaction was carried out at 4° C. for one hour. After this reaction, the microplate was washed with the same wash solution five times and colored with a TMB solution, and the coloring reaction was stopped by a stop solution. Then, the absorbance at 450 nm was measured by SPECTRA MAX 190 (Molecular Devices, Sunnyvale, Calif., USA). The Aβ40 and Aβ42 concentrations in each sample were calculated from the standard. curve.

The compound of the general formula (I) or (II) or pharmacologically acceptable salt thereof according to the present invention has an effect of reducing production of Aβ42 or the like. Accordingly, the present invention can particularly provide a therapeutic or prophylactic agent for a neurodegenerative disease caused by Aβ such as Alzheimer's disease or Down's syndrome.

The compound of the general formula (I) of the present invention has an effect of reducing Aβ40 and Aβ42 production, and thus is particularly useful as a prophylactic or therapeutic agent for a neurodegenerative disease caused by Aβ such as Alzheimer's disease or Down's syndrome.

The invention claimed is:
1. A compound represented by the formula (1):

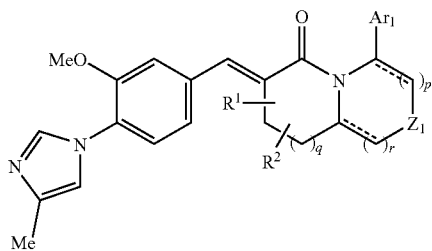

or a pharmacologically acceptable salt thereof,
wherein ----represents a single bond or a double bond;
$Ar_1$ represents a phenyl group that is optionally substituted with 1 to 3 substituents selected from Substituent Group A1 or a pyridinyl group that is optionally substituted with 1 to 3 substituents selected from Substituent Group A1;
$R^1$ and $R^2$ are the same or different and each represent a group selected from the following Substituent Group A1;
$Z_1$ represents a methylene group or vinylene group, which n optionally substituted with 1 or 2 substituents selected from Substituent Group A1, an oxygen atom, or an imino group that is optionally substituted with a substituent selected from Substituent Group A1; and
p, q, and r are each an integer of 1; Substituent Group A1: (1) a halogen atom, (2) a hydroxyl group, (3) a cyano group, (4) a C3-8 cycloalkyl group, (5) a C3-8 cycloalkoxy group, (6) a C1-6 alkyl group, wherein the C1-6 alkyl group may be substituted with 1 to 3 substituents selected from the group consisting of a halogen atom, hydroxyl group, cyano group, C3-8 cycloalkyl group, C1-6 alkoxy group, and C3-8 cycloalkoxy group, (7) a C1-6 alkoxy group, wherein the C1-6-alkoxy group is optionally substituted with 1 to 3 substituents selected from the group consisting of a halogen atom, hydroxyl group, cyano group, C3-8 cycloalkyl group, and C3-8 cycloalkoxy group, (8) an amino group that is optionally substituted with one or two C1-6 alkyl groups, wherein the C1-6 alkyl groups is optionally substituted with 1 to 3 halogen atoms, (9) a carbamoyl group that is optionally substituted with one of two C1-6 alkyl groups, wherein the C1-6 alkyl groups is optionally substituted with 1 to 3 halogen atoms, (10) a carboxyl group, (11) a C1-6 alkoxycarbonyl group, wherein the C1-6 alkoxy group is optionally substituted with 1 to 3 substituents selected from the group consisting of a halogen atom, hydroxyl group, cyano group, C3-8 cycloalkyl group, and C3-8 cycloalkoxy group, (12) a C1-6 alkyl group (13) a C1-6 alkylsulfonyl group, and (14) a hydrogen atom.

2. The compound or pharmacologically acceptable salt thereof accordion to claim 1, wherein the compound is represented by the formula (II):

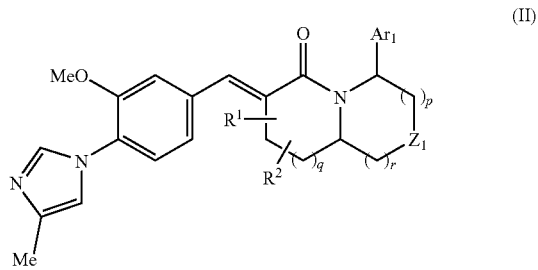

wherein $Ar_1$ represents a phenyl group that is optionally substituted with 1 to 3 substituents selected from Substituent Group A1 or a pyridinyl group that is optionally substituted with 1 to 3 substituents selected from Substituent Group A1;
$R^1$ and $R^2$ are the same or different and each represent a group selected from the following Substituent Group A1;
$Z_1$ represents a methylene group or vinylene group, which is optionally substituted with 1 or 2 substituents selected from Substituent Group A1, an oxygen atom, or an imino group that is optionally substituted with a substituent selected from Substituent Group A1 and p, q, and r are each an integer of 1; Substituent Group A1: (1) a halogen atom, (2) a hydroxyl group, (3) a cyano group, (4) a C3-8 cycloalkyl group, (5) a C3-8 cycloalkoxy group, (6) a C1-6 alkyl group, wherein the C1-6 alkyl group is optionally substituted with 1 to 3 substituents selected from the group consisting of a halogen atom, group, cyano group, C3-8 cycloalkyl group, C1-6 alkoxy group, and C3-8 cycloalkoxy group, (7) a C1-6 alkoxy group, wherein the C1-6 alkoxy group is optionally substituted with 1 to 3 substituents selected from the group consisting of a halogen atom, hydroxyl group, cyano group, C3-8 cycloalkyl group, and C3-8 cycloalkoxy group, (8) an amino group that is optionally substituted with one or two C1-6 alkyl groups, wherein the C1-6 alkyl groups is optionally substituted with 1 to 3 halogen atoms, (9) a carbamoyl group that is optionally substituted with one or two C1-6 alkyl groups, wherein the C1-6 alkyl groups is optionally substituted with 1 to 3 halogen atoms, (10) a carboxyl group, (11) a C1-6 alkoxycarbonyl group, wherein the C1-6 alkoxy group is optionally substituted with 1 to 3 substituents selected from the group consisting of a halogen atom, hydroxyl group, cyano group, C3-8 cycloalkyl group, and C3-8 cycloalkoxy group, (12) a C1-6 alkyl group, (13) a C1-6 alkylsulfonyl, and (14) a hydrogen atom.

3. The compound or pharmacologically acceptable salt thereof according to claim 1, wherein $Z_1$ represents a methylene group, wherein the methylene group is optionally substituted with 1 or 2 substituents selected from the group consisting of a C1-6 alkyl group, hydroxyl group, and halogen atom.

4. The compound or pharmacologically acceptable salt thereof according to claim 1, wherein $Z_1$ represents a methylene group that is optionally substituted with 1 or 2 halogen atoms.

5. The compound or pharmacologically acceptable salt thereof according to claim 1, wherein $Z_1$ represents a methylene group, wherein the methylene group is optionally substituted with 1 or 2 substituents selected from the group consisting of a C1-6 alkyl group, hydroxyl group, and halogen atom.

6. The compound or pharmacologically acceptable salt thereof according to claim 5, wherein $Z_1$ represents a methylene group, wherein the methylene group is optionally substituted with 1 or 2 substituents selected from the group consisting of is C1-6 alkyl group and hydroxyl group.

7. The compound or pharmacologically acceptable salt thereof according to claim 1, wherein $Z_1$ represents an oxygen atom.

8. The compound or pharmacologically acceptable salt thereof according to claim 1, wherein $Ar_1$ represents a phenyl group substituted with 1 to 3 halogen atoms.

9. The compound or pharmacologically acceptable salt thereof according to claim 1, wherein $Ar_1$ represents a phenyl group substituted with 1 to 3 fluorine atoms or chlorine atoms.

10. The compound or pharmacologically acceptable salt thereof according to claim 2, $Ar_1$ represents a phenyl group substituted with a fluorine atom.

11. The compound or pharmacologically acceptable salt thereof according to claim 1, wherein $R^1$ and $R^2$ are the same or different and each represent a substituent selected from the group consisting of a C1-6 alkyl group, halogen atom, hydroxyl group, and a hydrogen atom.

12. The compound or pharmacologically acceptable salt thereof according to claim 1, wherein the compound is selected from the following group:

7) (E)-(6R,9aS)-6-(4-fluorophenyl)-3-[3-methoxy-4-(4-methyl-1H-imidazol-1-yl)benzylidene]octahydroquinolizin-4-one, 8) (E)-(6S,9aR)-6-(4-fluorophenyl)-3-[3-methoxy-4-(4-methyl-1H-imidazol-1-yl)benzylidene]octahydroquinolizin-4-one, 9) (E)-(6S,8S,9aR)-6-phenyl-8-hydroxy-3-[3-methoxy-4-(4-methyl-1H-imidazol-1-yl)benzylidene]octahydroquinolizin-4-one, 10) (E)-(6R,8R,9aS)-6-phenyl-8-hydroxy-3-[3-methoxy-4-(4-methyl-1H-imidazol-1-yl)benzylidene]octahydroquinolizin-4-one, 11) (E)-(6S,8S,9aS)-6-(4-fluorophenyl)-8-hydroxy-3-[3-methoxy-4-(4-methyl-1H-imidazol-1-yl)benzylidene]octahydroquinolizin-4-one, 12) (E)-(6R,8R,9aS)-6-(4-fluorophenyl)-1-hydroxy-3-[3-methoxy-4-(4-methyl-1H-imidazol-1-yl)benzylidene]octahydroquinolizin-4-one, 13) (E)-(6S,9aS)-6-(3,4,5-trifluorophenyl)-3-[3-methoxy-4-(4-methyl-1H-imidazol-1-yl)benzylidene]octahydroquinolizin-4-one, 14) (E)-(6R,9aR)-6-(3,4,5-trifluorophenyl)-3-[3-methoxy-4-(4-methyl-1H-imidazol-1-yl)benzylidene]octahydroquinolizin-4-one, 15) (E)-(6S,8S,9aR)-6-(3,4,5-trifluorophenyl)-8-hydroxy-3-[3-methoxy-4-(4-methyl-1H-imidazol-1-yl)benzylidene]octahydroquinolizin-4-one, 16) (E)-(6R,8R,9aR)-6-(3,4,5-trifluorophenyl)-8-hydroxy-3-methoxy-4-(4-methyl-1H-imidazol-1-yl)benzylidene]octahydroquinolizin-4-one, 17) (E)-(6S,8R,9aR)-6-(3,4,5-trifluorophenyl)-8-hydroxy-3-[3-methoxy-4-(4-methyl-1H-imidazol-1-yl)benzylidene]octahydroquinolizin-4-one, 18) (E)-(6R,8R,9aS)-6-(3,4,5-trifluorophenyl)-8-hydroxy-3-[3-methoxy-4-(4-methyl-1H-imidazol-1-yl)benzylidene]octahydroquinolizin-4-one, 19) (E)-(6S,9aS)-6-(4-fluorophenyl)-3-[3-methoxy-4-(4-methyl-1H-imidazol-1-yl)benzylidene]octahydroquinolizin-4-one, 20) (E)-(6R,9aR)-6-(4-fluorophenyl)-3-[3-methoxy-4-(4-methyl-1H-imidazol-1-yl)benzylidene]octahydroquinolizin-4-one, 29) (E)-(6R,9aS)-3-[3-methoxy-4-(4-methyl-1H-imidazol-1-yl)benzylidene]-6-(4-methoxyphenyl)octahydroquinolizin-4-one, 30) (E)-(6S,9aR)-3-[3-methoxy-4-(4-methyl-1H-imidazol-1-yl)benzylidene]-6-(4-methoxyphenyl)octahydroquinolizin-4-one, 35) methyl (E)-4-{(4S*,9aR*)-7-[3-methoxy-4-(4-methyl-1H-imidazol-1-yl)benzylidene]-6-oxooctahydroquinolizin-4-yl}benzoate, 36) (E)-(6S*,9aR*)-6-(4-hydroxymethylphenyl)-3-[3-methoxy-4-(4-methyl-1H-imidazol-1-yl)benzylidene]octahydroquinolizin-4-one, 37) (E)-(6S*,9aR*)-6-(4-cyanophenyl)-3-[3-methoxy-4-(4-methyl-1H-imidazol-1-yl)benzylidene]octahydroquinolizin-4-one, 38) (E)-4-{(4S*,9aR*)-7-[3-methoxy-4-(4-methyl-1H-imidazol-1-yl)benzylidene]-6-oxooctahydroquinolizin-4-yl}benzoic acid, 39) (E)-(6S*,9aR*)-6-(4-aminophenyl)-3-[3-methoxy-4-(4-methyl-1H-imidazol-1-yl)benzylidene]octahydroquinolizin-4-one, 40) (E)-4-{(4S*,9aR*)-7-[3-methoxy-4-(4-methyl-1H-imidazol-1-yl)benzylidene]-6-oxooctahydroquinolizin-4-yl}-N,N-dimethylbenzamide, 41) (E)-(6S,9aR)-6-(3-fluorophenyl)-3-[3-methoxy-4-(4-methyl-1H-imidazol-1-yl)benzylidene]octahydroquinolizin-4-one,
42) (E)-(6R,9aS)-6-(3-fluorophenyl)-3-[3-methoxy-4-(4-methyl-1H-imidazol-1-yl)benzylidene]octahydroquinolizin-4-one,
43) (E)-(6S,9aR)-6-(2-fluorophenyl)-3-[3-methoxy-4-(4-methyl-1H-imidazol-1-yl)benzylidene]octahydroquinolizin-4-one,
44) (E)-(6R,9aS)-6-(2-fluorophenyl)-3-[3-methoxy-4-(4-methyl-1H-imidazol-1-yl)benzylidene]octahydroquinolizin-4-one,
45) (E)-(6S,8R,9aR)-6-(4-fluorophenyl)-8-hydroxy-3-[3-methoxy-4-(4-methyl-1H-imidazol-1-yl)benzylidene]-8-methyl-octahydroquinolizin-4-one,
46) (E)-(6R,8S,9aS)-6-(4-fluorophenyl)-8-hydroxy-3-[3-methoxy-4-(4-methyl-1H-imidazol-1-yl)benzylidene]-8-methyl-octahydroquinolizin-4-one,
47) (E)-(6S,8R,9aR)-6-(4-fluorophenyl)-8-hydroxy-3-[3-methoxy-4-(4-methyl-1H-imidazol-1-yl)benzylidene]-8-methyloctahydroquinolizin-4-one,
48) (E)-(6R,8S,9aS)-6-(4-fluorophenyl)-8-hydroxy-3-[3-methoxy-4-(4-methyl-1H-imidazol-1-yl)benzylidene]-8-methyloctahydroquinolizin-4-one,
51) (E)-(6R,8R,9aS)-6-(4fluorophenyl)-8-hydroxy-3-[3-methoxy-4-(4-methyl-1H-imidazol-1-yl)benzylidene]-8-methyloctahydroquinolizin-4-one,
52) (E)-(6R,8R,9aS)-6-(4-fluorophenyl)-8-hydroxy-3-[3-methoxy-4-(4-methyl-1H-imidazol-1-yl)benzylidene]-8-methyloctahydroquinolizin-4-one,
53) (E)-(4R,9aS)-7-[3-methoxy-4-(4-methylimidazol-1-yl)benzylidene]-4-phenylhexahydropyrido[2,1-c][1,4]oxazin-6-one,
65) (E)-(6S,9a S)-6-(3,4-difluorophenyl)-3-[3-methoxy-4-(4-methyl-1H-imidazol-1-yl)benzylidene]octahydroquinolizin-4-one,
66) (E)-(6R,9aR)-6-(3,4-difluorophenyl)-3-[3-methoxy-4-(4-methyl-1H-imidazol-1-yl)benzylidene]octahydroquinolizin-4-one,
67) (E)-(6S,9aS)-6-(4-chlorophenyl)-3-[3-methoxy-4-(4-methyl-1H-imidazol-1-yl)benzylidene]octahydroquinolizin-4-one,
68) (E)-(6R,9aR)-6-(4-chlorophenyl)-3-[3-methoxy-4-(4-methyl-1H-imidazol-1-yl)benzylidene]octahydroquinolizin-4-one,
69) (E)-(S)-6-(3,4,5-trifluorophenyl)-3-[3-methoxy-4-(4-methyl-1H-imidazol-1-yl)-benzylidene]-1,2,3,8,9,9a-hexahydroquinolizin-4-one,
70) (E)-(R)-6-(3,4,5-trifluorophenyl)-3-[3-methoxy-4-(4-methyl-1H-imidazol-1-yl)benzylidene]-1,2,3,8,9,9a-hexahydroquinolizin-4-one,
71) (E)-(6S,8S,9aR)-8-fluoro-3-[3-methoxy-4-(4-methyl-1H-imidazol-1-yl)benzylidene]-6-(3,4,5-trifluorophenyl)octahydroquinolizin-4-one,
72) (E)-(6S,8R,9aR)-8-methoxy-3-[3-methoxy-4-(4-methyl-1H-imidazol-1-yl)benzylidene]-(3,4,5-trifluorophenyl)octahydroquinolizin-4-one,
73) (E)-(R)-4-(4-fluorophenyl)-7-[3-methoxy-4-(4-methyl-1H-imidazol-1-yl)benzylidene]-3,4,8,9-tetrahydro-7H-pyrido[2,1-c][1,4]oxazin-6-one,
74) (E)-(S)-4-(4-fluorophenyl)-7-[3-methoxy-4-(4-methyl-1H-imidazol-1-yl)benzylidene]-3,4,8,9-tetrahydro-7H-pyrido[2,1-c][1,4]oxazin-6-one,
75) (E)-(4R,9aS)-4-(4-fluorophenyl)-7-[3-methoxy-4-(4-methyl-1H-imidazol-1-yl)benzylidene]hexahydropyrido[2,1-c][1,4]oxazin-6-one,
76) (E)-(4S,9aS)-4-(4-fluorophenyl)-7-[3-methoxy-4-(4-methyl-1H-imidazol-1-yl)benzylidene]hexahydropyrido[2,1-c][1,4]oxazin-6-one,
77) (E)-(6S,8R,9aR)-8-fluoro-3-[3-methoxy-4-(4-methyl-1H-imidazol-1-yl)benzylidene]-6-(3,4,5-trifluorophenyl)octahydroquinolizin-4-one,
80) (E)-(4R,9aR)-7-[3-methoxy-4-(4-methyl-1H-imidazol-1-yl)benzylidene]-4-(3,4,5-trifluorophenyl)hexahydropyrido[2,1-c][1,4]oxazin-6-one,
81) (E)-(4S,9aS)-7-[3-methoxy-4-(4-methyl-1H-yl)benzylidene]-4-(3,4,5-trifluorophenyl)hexahydropyrido[2,1-c][1,4]oxazin-6-one,
82 (E)-(4S,9aR)-7-[3-methoxy-4-(4-methyl-1H-imidazol-1-yl)benzylidene]-4-(3,4,5-trifluorophenyl)hexahydropyrido[2,1-c][1,4]oxazin-6-one,
83) (E)-(4R,9aS)-7-[3-methoxy-4-(4-methyl-1H-imidazol-1-yl)benzylidene]-4-(3,4,5-trifluorophenyl)hexahydropyrido[2,1-c][1,4]oxazin-6-one,
84) (E)-(6R,7S,9aR)-7-hydroxy-3-[3-methoxy-4-(4-methyl-1H-imidazol-1-yl)benzylidene]-6-(3,4,5-trifluorophenyl)octahydroquinolizin-4-one,
85) (E)-(6S,7R,9aS)-7-hydroxy-3-[3-methoxy-4-(4-methyl-1H-imidazol-1-yl)benzylidene]-6-(3,4,5-trifluorophenyl)octahydroquinolizin-4-one,
86) (E)-(6R,7R,9aR)-7-hydroxy-3-[3-methoxy-4-(4-methyl-imidazol-1-yl)benzylidene]-6-(3,4,5-trifluorophenyl)octahydroquinolizin-4-one,
87) (E)-(6S,7S,9aS)-7-hydroxy-3-[3-methoxy-4-(4-methyl-1H-imidazol-1-yl)benzylidene]-6-(3,4,5-trifluorophenyl)octahydroquinolizin-4-one,
90) (6S,9aR)-6-(3,4-fluorophenyl)-3-{1-[3-methoxy-4-(4-methyl-1H-imidazol-1-yl)phenyl]-(E)-methylidene}octahydroquinolizin-4-one,
91) (6S,9aR)-6-(3,4,5-trifluorophenyl)-3-{1-[3-methoxy-4-(4-methyl-1H-imidazol-1-yl)phenyl]-(E)-methylidene}octahydroquinolizin-4-one,
92) (6S,9aR)-6-(4-chlorophenyl)-3-{1-[3-methoxy-4-(4-methyl-1H-imidazol-1-yl)phenyl]-(E)-methylidene}octahydroquinolizin-4-one,
94) (4R,9aS)-4-(4-fluorophenyl)-7-{1-[3-methoxy-4-(4-methyl-1H-imidazol-1-yl)phenyl]-(E)-methylidene)hexahydropyrido[2,1-c][1,4]oxazin-6-one,
95) (4R,9aS)-4-(3,4-fluorophenyl)-7-{1-[3-methoxy-4-(4-methyl-1H-imidazol-1-yl)phenyl]-(E)-methylidene}hexahydropyrido[2,1-c][1,4]oxazin-6-one,
96) (4R,9aS)-4-(4-chlorophenyl)-7-{1-[3-methoxy-4-(4-methyl-1H-imidazol-1-yl)phenyl]-(E)-methylidene}hexahydropyrido[2,1-c][1,4]oxazin-6-one,
97) methyl (4S,9aR)-7-{1-[3-methoxy-4-(4-methyl-1H-imidazol-1-yl)phenyl]-(E)-methylidene}-6-oxo-4-(3,4,5-trifluorophenyl)octahydropyrido[1,2-a]pyrazine-2-carboxylate,
98) methyl (4R,9aS)-7-{1-[3-methoxy-4-(4-methyl-1H-imidazol-1-yl)phenyl]-(E)-methylidene}-6-oxo-4-(3,4,5-trifluorophenyl)octahydropyrido[1,2-a]pyrazine-2-carboxylate,
99) methyl (4R,9aR)-7-{1-[3-methoxy-4-(4-methyl-1H-imidazol-1-yl)phenyl]-(E)-methylidene}-6-oxo-4-(3,4,5-trifluorophenyl)octahydropyrido[1,2-a]pyrazine-2-carboxylate,
100) methyl (4S,9aS)-7-{1-[3-methoxy-4-(4-methyl-1H-imidazol-1-yl)phenyl]-(E)-methylidene-6-oxo-4-(3,4,5-trifluorophenyl)octahydropyrido[1,2-a]pyrazine-2-carboxylate, 101) (4R,9aS)-7-{1-[3-methoxy-4-(4-methyl-1H-imidazol-1-yl)phenyl]-(E)-methylidene}-4-(3,4,5-trifluorophenyl)octahydropyrido[1,2-a]pyrazin-6-one, 102) (4S,9aR)-7-{1-[3-methoxy-4-(4-methyl-1H-imidazol-1-yl)phenyl]-(E)-methylidene}-(3,4,5-trifluorophenyl)octahydropyrido[1,2-a]pyrazin-6-one, 103) (4S,9aS)-7-{1-[3-methoxy-4-(4-methyl-1H-imidazol-1-yl)phenyl]-(E)-methylidene}-4-(3,4,5-trifluorophenyl)octahydropyrido[1,2-a]pyrazin-6-one, 104) (4R,9aR)-7-{1-[3-methoxy-4-(4-methyl-1H-imidazol-1-yl)phenyl]-(E)-methylidene}-4-(3,4,5-trifluorophenyl)octahydropyrido[1,2-a]pyrazin-6-one, 105) (4S,9aR)-2-ethyl-7-{1-[3-methoxy-4-(4-methyl-1H-imidazol-1-yl)phenyl]-(E)-methylidene}-4-(3,4,5-trifluorophenyl)octahydropyrido[1,2-a]pyrazin-6-one, 106) (4R,9aS)-2-ethyl-7-{1-[1-methoxy-4-(4-methyl-1H-imidazol-1-yl)phenyl]-(E)-methylidene}-4-(3,4,5-trifluorophenyl)octahydropyrido[1,2-a]pyrazin-6-one, 107) (4R,9aR)-2-ethyl-7-{1-[3-methoxy-4-(4-methyl-1H-imidazol-1-yl)phenyl]-(E)-methylidene}-4-(3,4,5-trifluorophenyl)octahydropyrido[1,2-a]pyrazin-6-one, 108) (4S,9aS)-2-ethyl-7-{1-[3-methoxy-4-(4-methyl-1H-imidazol-1-yl)phenyl]-(E)-methylidene}-4-(3,4,5-trifluorophenyl)octahydropyrido[1,2-a]pyrazin-6-one, 109) (4S,9aR)-7-{1-[3-methoxy-4-(4-methyl-1H-imidazol-1-yl)phenyl]-(E)-methyl-4-(3,4,5-trifluorophenyl)octahydropyrido[1,2-a]pyrazin-6-one, 110) (4R,9aS)-7-{1-[3-methoxy-4-(4-methyl-1H-imidazol-1-yl)phenyl]-(E)-methylidene}-2-methyl-4-(3,4,5-trifluorophenyl)octahydropyrido[1,2-a]pyrazin-6-one, 111) (4S,9aR)-7-{1-[3-methoxy-4-(4-methyl-1H-imidazol-1-yl)phenyl]-(E)-methylidene}-2-propyl-4-(3,4,5-trifluorophenyl)octahydropyrido[1,2-a]pyrazin-6-one, 112) (4R,9aS)-7-{1-[3-methoxy-4-(4-methyl-1H-imidazol-1-yl)phenyl]-(E)-methylidene}-2-propyl-4-(3,4,5-trifluorophenyl)octahydropyrido[1,2-a]pyrazin-6-one, 113) (4R*,9aS*)-2-acetyl-7-{1-[3-methoxy-4-(4-methyl-1H-imidazol-1-yl)phenyl]-(E)-methylidene}-4-(3,4,5-trifluorophenyl)octahydropyrido[1,2-a]pyrazin-6-one, 114) (4R*,9aS*)-2-methanesulfonyl-7-{1-[3-methoxy-4-(4-methyl-1H-imidazol-1-yl)phenyl]-(E)-methylidene}-4-(3,4,5-trifluorophenyl)octahydropyrido[1,2-a]pyrazin-6-one, and 115) (4R*,9aS*)-7-{1-[3-methoxy-4-(4-methyl-1H-imidazol-1-yl)phenyl]-(E)-methylidene}-6-oxo-4-(3,4,5-trifluorophenyl)octahydropyrido[1,2-a]pyrazine-2-carboxylic acid dimethylamine.

13. A pharmaceutical composition comprising:
the compound or pharmacologically acceptable salt thereof according to claim 1 as an active ingredient; and
a pharmaceutically acceptable carrier.

14. The compound or pharmacologically acceptable salt thereof according to claim 1, wherein:
----representing a single bond;
$Ar_1$ represents a phenyl group that is optionally substituted with 1 to 3 substituents selected from substituent Group A1;
each of $R^1$ and $R^2$ is a hydrogen atom; and
$Z_1$ represents an oxygen atom that is optionally substituted with a substituent selected from Substituent Group A1.

* * * * *